(12) United States Patent
Albrecht et al.

(10) Patent No.: US 9,206,128 B2
(45) Date of Patent: Dec. 8, 2015

(54) MODULATORS OF METHYL MODIFYING ENZYMES, COMPOSITIONS AND USES THEREOF

(71) Applicant: Constellation Pharmaceuticals, Inc., Cambridge, MA (US)

(72) Inventors: Brian K. Albrecht, Cambridge, MA (US); James Edmund Audia, Cambridge, MA (US); Andrew S. Cook, Stow, MA (US); Alexandre Gagnon, Beaconsfield (CA); Jean-Christophe Harmange, Andover, MA (US); Christopher G. Nasveschuk, Stoneham, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/358,558

(22) PCT Filed: Nov. 19, 2012

(86) PCT No.: PCT/US2012/065796
§ 371 (c)(1),
(2) Date: May 15, 2014

(87) PCT Pub. No.: WO2013/075083
PCT Pub. Date: May 23, 2013

(65) Prior Publication Data
US 2014/0288123 A1  Sep. 25, 2014

Related U.S. Application Data

(60) Provisional application No. 61/561,822, filed on Nov. 18, 2011, provisional application No. 61/593,809, filed on Feb. 1, 2012.

(51) Int. Cl.
| | |
|---|---|
| C07D 213/61 | (2006.01) |
| C07D 213/64 | (2006.01) |
| C07D 221/18 | (2006.01) |
| C07D 401/12 | (2006.01) |
| C07D 405/12 | (2006.01) |
| C07D 413/12 | (2006.01) |

(52) U.S. Cl.
CPC ............ *C07D 213/64* (2013.01); *C07D 221/18* (2013.01); *C07D 401/12* (2013.01); *C07D 405/12* (2013.01); *C07D 413/12* (2013.01)

(58) Field of Classification Search
CPC .. C07D 213/30; C07D 221/18; C07D 401/12; C07D 405/12; C07D 413/12; A01B 12/006
See application file for complete search history.

(56) References Cited

U.S. PATENT DOCUMENTS

| | | | |
|---|---|---|---|
| 4,738,971 A | 4/1988 | Eriksoo et al. | |
| 5,308,854 A | 5/1994 | Hoffman, Jr. et al. | |
| 7,838,520 B2 | 11/2010 | Delorme et al. | |
| 2003/0207875 A1 | 11/2003 | Gymer et al. | |
| 2003/0229081 A1 | 12/2003 | Maduskuie | |
| 2005/0266473 A1 | 12/2005 | Zhang et al. | |
| 2006/0035938 A1 | 2/2006 | Bladh et al. | |
| 2007/0155744 A1* | 7/2007 | Jones et al. | 514/235.2 |
| 2008/0027050 A1 | 1/2008 | Terauchi et al. | |
| 2008/0227826 A1 | 9/2008 | Frechette et al. | |
| 2008/0280917 A1* | 11/2008 | Albrecht et al. | 514/252.04 |
| 2009/0029991 A1 | 1/2009 | Stokes et al. | |
| 2009/0075833 A1 | 3/2009 | Chinnaiyan et al. | |
| 2010/0069630 A1 | 3/2010 | Lee et al. | |
| 2010/0222420 A1 | 9/2010 | Chinnaiyan et al. | |
| 2010/0261743 A1 | 10/2010 | Londregan et al. | |
| 2010/0298270 A1* | 11/2010 | Keana et al. | 514/89 |
| 2011/0105509 A1 | 5/2011 | Kaila et al. | |
| 2011/0212946 A1* | 9/2011 | Barrow et al. | 514/217.07 |
| 2012/0071418 A1 | 3/2012 | Copeland et al. | |

FOREIGN PATENT DOCUMENTS

| | | | |
|---|---|---|---|
| WO | 03/020722 A1 | 3/2003 | |
| WO | 03/079986 A2 | 10/2003 | |
| WO | 2007/014838 A1 | 2/2007 | |
| WO | 2007/067968 A2 | 6/2007 | |
| WO | 2009/006577 A2 | 1/2009 | |
| WO | 2009/087285 A1 | 7/2009 | |
| WO | 2009/153721 A1 | 12/2009 | |
| WO | 2011/131741 A1 | 10/2011 | |
| WO | WO 2011/131741 | * 10/2011 | |
| WO | 2011/140324 A1 | 11/2011 | |
| WO | 2011/140325 A1 | 11/2011 | |
| WO | 2012/005805 A1 | 1/2012 | |
| WO | 2012/024543 A1 | 2/2012 | |
| WO | 2012/051492 A2 | 4/2012 | |
| WO | 2012/068589 A2 | 5/2012 | |
| WO | 2012/075080 A1 | 6/2012 | |
| WO | 2012/115885 A1 | 8/2012 | |
| WO | 2012/118812 A2 | 9/2012 | |

OTHER PUBLICATIONS

PubChem Compound Summary for CID 73087, Aug. 1, 2005, 2 pages.
PubChem Compound Summary for CID 50961558, Mar. 29, 2011, 2 pages.
PubChem Compound Summary for CID 40170690, May 30, 2009, 2 pages.
Yap, et al., "Somatic mutations at EZH2 Y641 act dominantly through a mechanism of selectively altered PRC2 catalytic activity, to increase H3K27 trimethylation," Blood, vol. 117, No. 8, Feb. 24, 2011, pp. 2451-2459.
PubChem Compound Summary for CID 6918837, Jul. 28, 2006, 2 pages.

(Continued)

*Primary Examiner* — D M Seaman
(74) *Attorney, Agent, or Firm* — McCarter & English LLP; Steven G. Davis; Michael J. DeGrazia

(57) ABSTRACT

Agents for modulating methyl modifying enzymes, compositions and uses thereof are provided herein.

17 Claims, No Drawings

(56) References Cited

OTHER PUBLICATIONS

Fiskus, et al., "Histone Deacetylase Inhibitors Deplete Enhancer of Zeste 2 and Associated Polycomb Repressive Complex 2 Proteins in Human Acute Leukemia Cells," Molecular Cancer Therapeutics, 2006;5:3096-3104.

Qi, et al., "Selective Inhibition of Ezh2 by a Small Molecule Inhibitor Blocks Tumor Cells Proliferation," Proceedings of the National Academy of Sciences of the United States of America, 109(52), 2012, 21360-21365.

Verma, et al., "Identification of Potent, Selective, Cell-Active Inhibitors of the Histone Lysine Methyltransferase EZH2," ACS Medicinal Chemistry Letters, 3(12), 2012, 1091-1096.

McCabe, et al., "EZH2 Inhibition as a Therapeutic Strategy for Lymphoma with EZH2-Activating Mutations," Nature, 492(7427), 2012, 108-112.

Knutson, et al., "A Selective Inhibitor of EZH2 Blocks H3K27 Methylation and Kills Mutant Lymphoma Cells," Nature Chemical Biology, 8(11), 2012, 890-896.

Fiskus, et al., "Combined Epigenetic Therapy with the Histone Methyltransferase EZH2 Inhibitor 3-Deazaneplanocin A and the Histone Deacetylase Inhibitor Panobinostat Against Human AML Cells," Blood, Sep. 24, 2009, 114:13, pp. 2733-2743.

Spannhoff, et al., "The Emerging Therapeutic Potential of Histone Methyltransferase and Demethylase Inhibitors," CHEMMEDCHEM, vol. 4, No. 10, Oct. 5, 2009, pp. 1568-1582, XP002610580.

\* cited by examiner

MODULATORS OF METHYL MODIFYING ENZYMES, COMPOSITIONS AND USES THEREOF

CROSS-REFERENCE TO RELATED APPLICATIONS

This application is a 35 U.S.C. §371 national stage filing of International Application No. PCT/US2012/065796, filed Nov. 19, 2012, which claims the benefit of U.S. Provisional Ser. No. 61/561,822, filed Nov. 18, 2011, and 61/593,809, filed Feb. 1, 2012. The entire contents of each of the aforementioned applications are incorporated herein by reference.

BACKGROUND OF THE INVENTION

Eukaryotic chromatin is composed of macromolecular complexes called nucleosomes. A nucleosome has 147 base pairs of DNA wrapped around a protein octamer having two subunits of each of histone protein H2A, H2B, H3, and H4. Histone proteins are subject to post-translational modifications which in turn affect chromatin structure and gene expression. One type of post-translational modification found on histones is methylation of lysine and arginine residues. Histone methylation plays a critical role in the regulation of gene expression in eukaryotes. Methylation affects chromatin structure and has been linked to both activation and repression of transcription (Zhang and Reinberg, Genes Dev. 15:2343-2360, 2001). Enzymes that catalyze attachment and removal of methyl groups from histones are implicated in gene silencing, embryonic development, cell proliferation, and other processes.

SUMMARY OF THE INVENTION

The present disclosure encompasses the recognition that methyl modifying enzymes are an attractive target for modulation, given their role in the regulation of diverse biological processes. It has now been found that compounds of this invention, and pharmaceutically acceptable compositions thereof, are effective as agents that stimulate activity of histone methyl modifying enzymes, including histone methylases and histone demethylases. Such compounds have the general formula I:

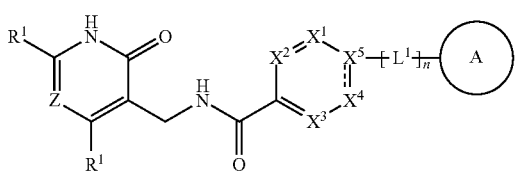

or a pharmaceutically acceptable salt thereof, wherein each variable is as defined herein.

Compounds of the present invention, and pharmaceutically acceptable compositions thereof, are useful for treating a variety of diseases, disorders or conditions, associated with a methyl modifying enzyme. Such diseases, disorders, or conditions include those described herein.

Compounds provided by this invention are also useful for the study of methyl modifying enzymes in biological and pathological phenomena; the study of intracellular signal transduction pathways mediated by methyl modifying enzymes and the comparative evaluation of new methyl modifying enzyme modulators.

DETAILED DESCRIPTION OF CERTAIN EMBODIMENTS

1. General Description of Compounds of the Invention

In certain embodiments, the present invention provides a compound of formula I:

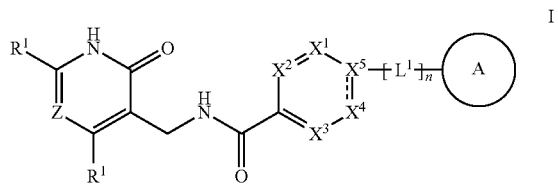

or a pharmaceutically acceptable salt thereof, wherein:

Z is =C($R^2$)— or =N—;

each of $X^1$, $X^2$ and $X^3$ is independently selected from =N— and =C($R^3$)—;

$X^4$ is selected from =N—, —C(=O)— and =C($R^3$)—;

$X^5$ is =C— or

no more than two of $X^1$, $X^2$, $X^3$, $X^4$, and $X^5$ are =N— or

ring A is phenyl, a monocyclic 5-6 membered heteroaryl comprising 1 to 3 hetero ring atoms independently selected from N, O and S, a carbocyclic comprising 4 or more ring atoms, or a heterocyclic, wherein ring A is optionally substituted with one or more $R^6$;

each $R^1$ and $R^2$ is independently selected from hydrogen, halo, —OH, —CN, $C_1$-$C_4$ alkyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, or —O—($C_0$-$C_4$ alkylene)-carbocyclyl; or one $R^1$ and $R^2$ are taken together with atoms to which they are bound to form an aryl, heteroaryl, heterocyclyl, or carbocyclyl;

each $R^3$ is independently selected from hydrogen, halo, —OH, —CN, $C_1$-$C_4$ alkyl, $C_2$-$C_4$ alkenyl or alkynyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)O$R^9$, —C(O)N($R^9$)$_2$, —S(O)$R^8$, —S(O)$_2R^8$ and —S(O)$_2$N($R^9$)$_2$;

each $L^1$, if $L^1$ is present, is independently selected from —C($R^4$)$_2$—, —C($R^4$)=C($R^4$)—, —C≡C—, —O—, —S—, —S(O)—, —S(O)$_2$, or —N($R^5$)—; or any $L^1$ is optionally taken together with $X^1$ or $X^4$ and any intervening atoms to form an aryl, heteroaryl, heterocyclyl or carbocyclyl fused to the ring comprising $X^1$, $X^2$, $X^3$, $X^4$ and $X^5$;

wherein when ring A is phenyl, a 5-6 membered heteroaryl, or a heterocyclyl bound to $L^1$ through a ring nitrogen atom, then n is an integer from 1 to 6;

each $R^4$ is independently selected from hydrogen, halo, $C_1$-$C_4$ alkyl, —$CH_2OH$, —OH, —($C_0$-$C_4$ alkylene)-O—($C_1$-$C_4$ alkyl), —($C_0$-$C_4$ alkylene)-N($R^7$)$_2$, or —CN; or two $R^4$ are taken together with a common carbon atom to which they are both bound to form a carbocyclic, heterocyclic, or =O; or two $R^4$ bound to different carbon atoms are taken together with the different carbon atoms and any intervening atoms to form a carbocyclic, or heterocyclic;

$R^5$ is selected from hydrogen, $C_1$-$C_4$ alkyl, and $C_2$-$C_4$ haloalkyl; or $R^4$ and $R^5$ are taken together with the atoms to which they are bound and any intervening atoms to form a heterocyclic;

each $R^6$ is independently selected from halo, —CN, =O, —($C_1$-$C_4$ alkylene)-O—$R^8$, —($C_0$-$C_4$ alkylene)-O—($C_0$-$C_4$ alkylene)-$R^9$, —($C_0$-$C_4$ alkylene)-N($R^7$)$_2$, —($C_0$-$C_4$ alkylene)-$R^8$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^9$)$_2$, —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—N($R^9$)$_2$; or two $R^6$ bound to adjacent atoms in ring A are taken together with the atoms to which they are bound to form a monocyclic aryl, heteroaryl, heterocyclyl, or carbocyclyl;

each $R^7$ is independently selected from hydrogen, —($C_0$-$C_4$ alkylene)-$R^9$, —($C_2$-$C_4$ alkylene)-O—$R^8$, —$C_2$-$C_4$ haloalkyl, —S(O)$_2$—$R^8$, —C(=O)—$R^8$, —C(=O)—N($R^9$)($R^9$), —($C_2$-$C_4$ alkylene)-O—C(=O)—$R^8$ and —($C_0$-$C_4$ alkylene)-C(=O)—O—$R^9$; or two $R^7$ are taken together with the nitrogen atom to which they are commonly bound to form an optionally substituted heterocyclyl or heteroaryl;

$R^8$ is selected from $C_1$-$C_4$ alkyl, aryl, heteroaryl, carbocyclyl and heterocyclyl;

each $R^9$ is independently selected from hydrogen or $R^8$;

=== represents a single or double bond;

n is 0 or an integer from 1 to 6;

wherein any portion of the compound designated as alkyl, alkylene, alkenyl, alkynyl, aryl, heteroaryl, heterocyclyl or carbocyclyl is optionally substituted; and each ring of any aryl, heteroaryl, heterocyclyl or carbocyclyl has not more than three substituents per ring.

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in *Organic Chemistry,* Thomas Sorrell, University Science Books, Sausalito, 1999; Smith and March *March's Advanced Organic Chemistry,* 5$^{th}$ Edition, John Wiley & Sons, Inc., New York, 2001; Larock, *Comprehensive Organic Transformations,* VCH Publishers, Inc., New York, 1989; Carruthers, Some *Modern Methods of Organic Synthesis,* 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$(as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "Co alkylene" as used herein means a bond. Thus, a moiety defined herein as "—($C_0$-$C_6$ alkylene)-aryl" includes both -aryl (i.e., —$C_0$ alkylene-aryl) and —($C_1$-$C_6$ alkylene)-aryl.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group.

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "carbocyclyl" (also referred to herein as "carbocycle" "cycloaliphatic" or "cycloalkyl"), as used herein, means a monocyclic hydrocarbon or bicyclic hydrocarbon that is completely saturated or that contains one or more units of unsaturation, but where there is no ring is aromatic.

The term "aryl" used alone or as part of a larger moiety as in "aralkyl", "aralkoxy", or "aryloxyalkyl", refers to monocyclic and bicyclic carbon ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic carbon ring is fused to one or more carbocyclyl rings regardless of whether the aromatic carbon ring or the carbocyclic ring is the pendant ring, or a group in which an aromatic carbon ring is fused to one or more heteroaryl or heterocyclyl rings, such as indanyl, phthalimidyl, naphthimidyl, phenantriidinyl, or tetrahydronaphthyl, and the like, wherein the pendant ring of the fused ring system is the aromatic carbon ring.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, wherein the pendant ring of the fused ring system is heteroaromatic. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, 5,6,7,8-tetrahydroquinolinyl, 5,6,7,8-tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. The term "heteroarylene" refers to a bivalent mono- or bicyclic heteroaryl ring.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. In certain embodiments, a "heterocycle", group is a 1,1'-heterocyclylene group (i.e., a spiro-fused ring). When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, 1,2,3,4-tetrahydroquinolinyl, 1,2,3,4-tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, wherein the pendant ring of the fused ring system is heterocyclyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

As used herein, the terms "carbocyclylene" or "cycloalkylene" are used interchangeably and refer to a bivalent carbocyclyl or cycloalkyl group. In certain embodiments, a carbocyclylene or cycloalkylene group is a 1,1-cycloalkylene group (i.e., a spiro-fused ring). Exemplary 1,1-cycloalkylene groups include

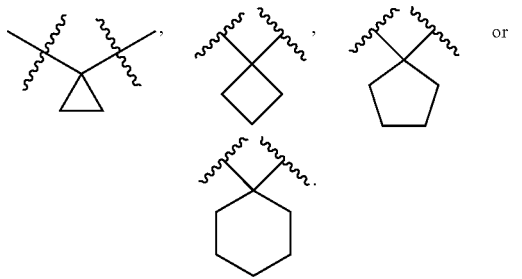

In other embodiments, a cycloalkylene group is a 1,2-cycloalkylene group or a 1,3-cycloalkylene group. Exemplary 1,2-cycloalkylene groups include

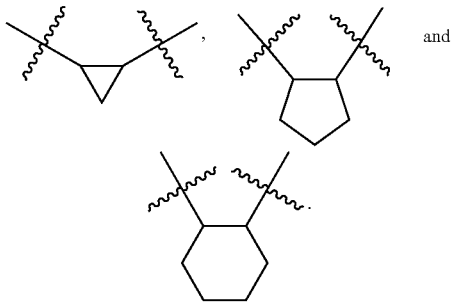

Exemplary 1,3-cycloalkylene groups include

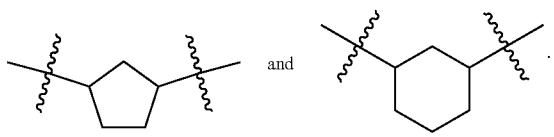 [SMILES: *C1CCC(*)C1 ; *C1CCCC(*)C1]

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "inhibitor" is defined as a compound that binds to and/or inhibits a target S-adenosylmethionine (SAM) utilizing enzyme with measurable affinity. In certain embodiments, an inhibitor has an IC$_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in activity of at least one SAM utilizing enzyme between a sample comprising a provided compound, or composition thereof, and at least one SAM dependent enzyme, and an equivalent sample comprising at least one SAM dependent enzyme, in the absence of said compound, or composition thereof.

3. Description of Exemplary Compounds

In certain embodiments, the present invention provides a compound having structural formula I:

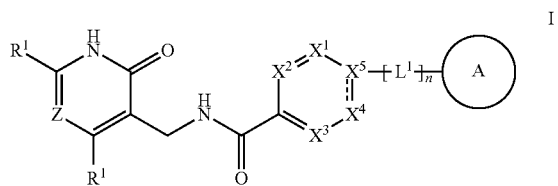

or a pharmaceutically acceptable salt thereof, wherein each variable is as defined above and described herein.

In some embodiments, $X^4$ is —C(=O)—, each of $X^1$, $X^2$, $X^3$ is =C(R$^3$)—, and $X^5$ is

wherein R$^3$ is as defined above and described herein resulting in a compound of Formula II:

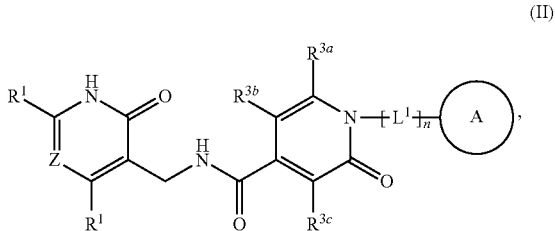

wherein each of R$^{3a}$, R$^{3b}$ and R$^{3c}$ are defined the same as R$^3$, and R$^1$, Z, R$^3$, L$^1$, ring A and Z are defined as throughout the specification.

Unless specified, each of the embodiments, set forth below is an embodiment of Formula I or Formula II.

As defined generally above and herein, each R$^1$ and R$^2$ is independently selected from hydrogen, halo, —OH, —CN, C$_1$-C$_4$ alkyl, —O—(C$_1$-C$_4$ alkyl), N(R$^7$)$_2$, —(C$_0$-C$_4$ alkylene)-aryl, —(C$_0$-C$_4$ alkylene)-heteroaryl, —(C$_0$-C$_4$ alkylene)-heterocyclyl, —(C$_0$-C$_4$ alkylene)-carbocyclyl, —O—(C$_0$-C$_4$ alkylene)-aryl, —O—(C$_0$-C$_4$ alkylene)-heteroaryl, —O—(C$_0$-C$_4$ alkylene)-heterocyclyl, or —O—(C$_0$-C$_4$ alkylene)-carbocyclyl; or one R$^1$ and R$^2$ are taken together with atoms to which they are bound to form an aryl, heteroaryl, heterocyclyl, or carbocyclyl;

wherein each R$^7$ is as defined above and described herein.

In one embodiment, each R$^1$ and R$^2$ is independently selected from hydrogen, halo, —OH, —CN, C$_1$-C$_4$ alkyl, C$_1$-C$_4$ haloalkyl, —O—(C$_1$-C$_4$ alkyl), N(R$^7$)$_2$, —(C$_0$-C$_4$ alkylene)-aryl, —(C$_0$-C$_4$ alkylene)-heteroaryl, —(C$_0$-C$_4$ alkylene)-heterocyclyl, or —(C$_0$-C$_4$ alkylene)-carbocyclyl; or one R$^1$ and R$^2$ are taken together with atoms to which they are bound to form an aryl, heteroaryl, heterocyclyl, or carbocyclyl;

wherein each R$^7$ is as defined above and described herein.

In some embodiments, each R$^1$ is hydrogen. In some embodiments, each R$^1$ is independently selected from halo, —OH, —CN, $C_1$-$C_4$ alkyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, or —O—($C_0$-$C_4$ alkylene)-carbocyclyl, wherein each $R^7$ is as defined above and described herein.

In some embodiments, each $R^1$ is independently selected from halo, —OH, —CN, $C_1$-$C_4$ alkyl, $C_1$-$C_4$ haloalkyl, —O—$C_1$-$C_4$ alkyl, N($R^7$)$_2$, —($C_0$-$C_4$ alkylene)-aryl, —($C_0$-$C_4$ alkylene)-heteroaryl, —($C_0$-$C_4$ alkylene)-heterocyclyl, or —($C_0$-$C_4$ alkylene)-carbocyclyl, wherein each $R^7$ is as defined above and described herein.

In some embodiments, each $R^1$ is independently selected from hydrogen and —CH$_3$. In some embodiments, each $R^1$ is hydrogen. In some embodiments, each $R^1$ is —CH$_3$. In some embodiments, one $R^1$ is hydrogen. In some embodiments, one $R^1$ is —CH$_3$. In some embodiments, one $R^1$ is —CH$_3$ and the other $R^1$ is —OCH$_3$ or —NHCH$_3$.

In some embodiments, each of $R^1$ and $R^2$ is hydrogen. In some embodiments, each $R^1$ is —CH$_3$ and $R^2$ is hydrogen.

In some embodiments, one $R^1$ is —CH$_3$; the other $R^1$ is —O—CH$_3$ or —NH—CH$_3$; and $R^2$ is hydrogen.

In some embodiments, $R^2$ is hydrogen.

As defined generally above and herein, Z is =C($R^2$)— or =N—, wherein $R^2$ as defined above and described herein. In some embodiments, Z is =C($R^2$)— wherein $R^2$ is as defined above and described herein. In some embodiments, Z is =N—. In some embodiments, Z is =CH—.

As defined generally above and herein, each $R^3$ is independently selected from hydrogen, halo, —OH, —CN, $C_1$-$C_4$ alkyl, $C_2$-$C_4$ alkenyl or alkynyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)O$R^9$, —C(O)N($R^9$)$_2$, —S(O)$R^8$, —S(O)$_2R^8$ and —S(O)$_2$N($R^9$)$_2$, wherein each of $R^7$, $R^8$ and $R^9$ is independently as defined above and described herein.

In some embodiments, each $R^3$ is independently selected from halo, —OH, —CN, $C_1$-$C_4$ alkyl, $C_2$-$C_4$ alkenyl or alkynyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)O$R^9$, —C(O)N($R^9$)$_2$, —S(O)$R^8$, —S(O)$_2R^8$ and —S(O)$_2$N($R^9$)$_2$, wherein each of $R^7$, $R^8$ and $R^9$ is independently as defined above and described herein.

In some embodiments, each $R^3$ is independently selected from hydrogen, halo, —OH, —CN, $C_1$-$C_4$ alkyl, $C_1$-$C_4$ haloalkyl, —O—$C_1$-$C_4$ alkyl, N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, wherein each $R^7$ is independently as defined above and described herein.

In some embodiments, each $R^3$ is hydrogen.

In some embodiments, each $R^3$ is independently selected from halo, —OH, —CN, $C_1$-$C_4$ alkyl, $C_1$-$C_4$ haloalkyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, wherein each $R^7$ is as defined above and described herein. In some embodiments, each $R^3$ is independently selected from hydrogen, halo, $C_1$-$C_4$ alkyl and —O-phenyl. In some embodiments, each $R^3$ is independently selected from hydrogen, chloro, —CH$_3$ and —O-phenyl.

In some embodiments, each $R^3$ is independently selected from hydrogen, halo, $C_1$-$C_4$ alkyl and —O—($C_1$-$C_4$ alkyl). In some embodiments, each $R^3$ is independently selected from hydrogen, fluoro, chloro, —CH$_3$ and —OCH$_3$.

As defined generally above for Formula I and herein, each of $X^1$, $X^2$ and $X^3$ is independently selected from =N— and =C($R^3$)—, wherein $R^3$ is as defined above and described herein. In some embodiments, each of $X^1$, $X^2$ and $X^3$ is independently =N—. In some embodiments, each of $X^1$, $X^2$ and $X^3$ is independently =C($R^3$)—, wherein $R^3$ is as defined above and described herein.

As defined generally above for Formula I and herein, $X^4$ is selected from =N—, —C(=O)— and =C($R^3$), wherein $R^3$ is as defined above and described herein. In some embodiments, $X^4$ is =N—. In some embodiments, $X^4$ is —C(=O)—. In some embodiments, $X^4$ is =C($R^3$)—, wherein $R^3$ is as defined above and described herein.

As defined generally above and herein for Formula I, $X^5$ is =C—, =N—, or

In some embodiments, $X^5$ is =C—. In some embodiments, $X^5$ is =N—. In some embodiments, $X^5$ is

In some embodiments of Formula I, each of $X^1$, $X^2$, $X^3$ and $X^4$ is =C($R^3$)—, and $X^5$ is =C—, wherein $R^3$ is as defined above and described herein.

In some embodiments of Formula I, each of $X^1$, $X^2$, $X^3$ and $X^4$ is =CH—, and $X^5$ is =C—.

As defined generally above and herein for Formula I, no more than two of $X^1$, $X^2$, $X^3$, $X^4$, and $X^5$ are =N— or

As defined generally above and herein, ring A is phenyl, a monocyclic 5-6 membered heteroaryl comprising 1 to 3 hetero ring atoms independently selected from N, O and S, a carbocyclic comprising 4 or more ring atoms, or a heterocyclic, wherein ring A is optionally substituted with one or more $R^6$, and wherein $R^6$ is independently as defined above and described herein.

In some embodiments, ring A is selected from phenyl, cyclopentyl, cyclohexyl, pyrimidin-2-yl, 2,3-dihydrobenzofuran-2-yl, pyridin-2-yl, pyridin-4-yl, piperidin-1-yl, piperidin-4-yl, pyrrolidin-3-yl, pyrrolidin-2-yl, tetrahydrofuran-3-yl, tetrahydrofuran-2-yl, 3-oxopiperazin-1-yl, morpholin-4-yl, morpholin-2-yl, tetrahydro-2H-pyran-4-yl, and tetrahydro-2H-pyran-3-yl, wherein ring A is optionally substituted with one or more $R^6$, and wherein $R^6$ is independently as defined above and described herein.

In some embodiments, ring A is selected from cyclopentyl, cyclohexyl, tetrahydrofuran-3-yl, tetrahydrofuran-2-yl, piperidin-1-yl, phenyl, pyrimidinyl, 2,3-dihydrobenzofuran-2- yl, pyridinyl, or 2-oxo-1H-pyridin-1-yl, wherein ring A is optionally substituted with up to two substituents independently selected from —CN, —CH$_2$CH$_3$, —CH$_3$, —OCH$_3$, =O, fluoro, pyridinyl, pyridazinyl, 1H-pyrazolyl, 1H-pyrrolyl, and pyrimidinyl.

In some embodiments, ring A is selected from cyclopentyl, cyclohexyl, tetrahydrofuran-3-yl, tetrahydrofuran-2-yl, piperidin-1-yl, phenyl, pyrimidinyl, 2,3-dihydrobenzofuran-2-yl, pyridinyl, or 2-oxo-1H-pyridin-1-yl, wherein ring A is optionally substituted with up to two R$^6$ independently selected from —CN, —CH$_2$CH$_3$, —CH$_3$, —OCH$_3$, =O, fluoro, pyridinyl, pyridazinyl, 1H-pyrazolyl, 1H-pyrrolyl, and pyrimidinyl.

In some embodiments, ring A is selected from cyclopentyl, cyclohexyl, tetrahydrofuran-3-yl, tetrahydrofuran-2-yl, piperidin-1-yl, phenyl, pyrimidinyl, 2,3-dihydrobenzofuran-2-yl, pyridinyl, or 2-oxo-1H-pyridin-1-yl, wherein ring A is optionally substituted with up to two R$^6$ independently selected from hydrogen, fluoro, —CH$_3$, —CH$_2$CH$_3$, —CF$_3$, —OCH$_3$, —CN, pyridin-4-yl, 1H-pyrrol-4-yl, pyridazin-4-yl, pyrimidin-4-yl, and 6-aminopyridin-3-yl.

In some embodiments, ring A is selected from cyclopentyl, cyclohexyl, tetrahydrofuran-3-yl, tetrahydrofuran-2-yl, piperidin-1-yl, phenyl, pyrimidinyl, 2,3-dihydrobenzofuran-2-yl, pyridinyl, or 2-oxo-1H-pyridin-1-yl, wherein ring A is optionally substituted with up to two substituents independently selected from hydrogen, fluoro, —CH$_3$, —CH$_2$CH$_3$, —CF$_3$, —OCH$_3$, —CN, pyridin-4-yl, 1H-pyrrol-4-yl, pyridazin-4-yl, pyrimidin-4-yl, and 6-aminopyridin-3-yl.

As defined generally above and herein, each L$^1$, if L$^1$ is present, is independently selected from —C(R$^4$)$_2$—, —C(R$^4$)=C(R$^4$)—, —C≡C—, —O—, —S—, —S(O)—, —S(O)$_2$, or —N(R$^5$)— where valency allows; or
  (a) for Formula I, any L$^1$ is optionally taken together with X$^1$ or X$^4$ and any intervening atoms to form an aryl, heteroaryl, heterocyclyl or carbocyclyl fused to the ring comprising X$^1$, X$^2$, X$^3$, X$^4$ and X$^5$; or
  (b) for Formula II, any L$^1$ is optionally taken together with R$^{3a}$ and any intervening atoms to form a fused aryl, heteroaryl, heterocyclyl or carbocyclyl ring,
wherein for Formula I, each of R$^4$, R$^5$, X$^1$, X$^2$, X$^3$, X$^4$ and X$^5$ is defined above and described herein and for Formula II, each of R$^4$, R$^5$, and R$^{3a}$ is defined above and described herein.

It will be understood by those of skill in the art that because the compounds of the invention are limited to compounds that are stable, compounds comprising certain combinations of L$^1$ units are not within the scope of the present invention. For example, when one L$^1$ unit is —O—, —S—, —S(O)—, —S(O)$_2$, or —N(R$^5$)—, an adjacent L$^1$ unit cannot be —O—, —S—, —S(O)—, —S(O)$_2$, or —N(R$^5$)—, except when one L$^1$ unit is —S(O)$_2$— and an adjacent L$_1$ unit is —N(R$^5$)—. In addition, the combination of L$^1$ units should not comprise —O—C(R$^4$)$_2$—O—, —N—C(R$^4$)$_2$—O—, or —O—C(R$^4$)$_2$—N—, except when the two R$^4$ bound to the same carbon atom are taken together to form =O.

In some embodiments, each L$^1$ is independently selected from —C(R$^4$)$_2$—, —C(R$^4$)=C(R$^4$)—, —C≡C—, —O—, —S—, —S(O)—, —S(O)$_2$, or —N(R$^5$)— where valency allows;
wherein each of R$^4$ and R$^5$ is independently as defined above and described herein.

In some embodiments, each L$^1$ is independently selected from —C(R$^4$)$_2$—, —O—, —S—, —S(O)—, —S(O)$_2$, or —N(R$^5$); or any L$^1$ is optionally taken together with X$^1$ or X$^4$ and any intervening atoms to form an aryl, heteroaryl, heterocyclyl or carbocyclyl fused to the ring comprising X$^1$, X$^2$, X$^3$, X$^4$ and X$^5$;
wherein each of R$^4$, R$^5$, X$^1$, X$^2$, X$^3$, X$^4$ and X$^5$ is independently as defined above and described herein.

In some embodiments, each L$^1$ is independently selected from —C(R$^4$)$_2$—, —O—, —S—, —S(O)—, —S(O)$_2$, or —N(R$^5$), wherein each of R$^4$ and R$^5$ is independently as defined above and described herein.

In some embodiments, no more than two consecutive L$^1$ are replaced by —O— or —S—. In some embodiments, no more than three consecutive L$^1$ are replaced by —O— or —S—.

In some embodiments of Formula I, any L$^1$ is optionally taken together with X$^1$ or X$^4$ and any intervening atoms to form an aryl, heteroaryl, heterocyclyl or carbocyclyl fused to the ring comprising X$^1$, X$^2$, X$^3$, X$^4$ and X$^5$, wherein each of X$^1$, X$^2$, X$^3$, X$^4$ and X$^5$ is independently as defined above and described herein.

In some embodiments of Formula II, any L$^1$ is optionally taken together with R$^{3a}$ and any intervening atoms to form a fused aryl, heteroaryl, heterocyclyl or carbocyclyl ring, wherein R$^{3a}$ is as defined above and described herein.

In some embodiments of Formula I, one L$^1$ is optionally taken together with X$^1$ or X$^4$ and any intervening atoms to form:

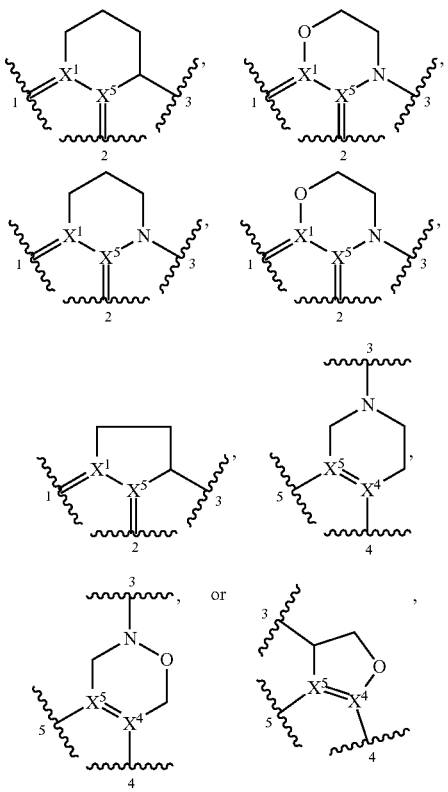

wherein:
⌐$^1$ represents a point of attachment to X$^2$; and
⌐$^2$ represents a point of attachment to X$^4$
⌐$^3$ represents a point of attachment to another L$^1$;
⌐$^4$ represents a point of attachment to X$^3$;
⌐$^5$ represents a point of attachment to X$^1$;
and each of X$^1$, X$^4$ and X$^5$ is independently as defined above and described herein.

As defined generally above and herein, when ring A is a heterocyclyl bound to $L^1$ through a ring nitrogen atom, phenyl, or a 5-6 membered heteroaryl, then n is an integer from 1 to 6.

In some embodiments, when Z is =C($R^2$)—, $X^4$ is =N— or =C($R^3$)—, $X^1$ is =C($R^3$)—, and ring A is a heterocyclyl, then the portion of the compound represented by -[$L^1$]$_n$- is other than a bond, —O— or —C(=O)—O—.

In some embodiments, when Z is =C($R^2$)—, $X^4$ is =C($R^3$)—, $X^1$ is =C($R^3$)—, n is 0, and ring A is a carbocyclyl or heterocyclyl, then the $R^3$ portion of each of $X^1$ and $X^4$ is independently selected from hydrogen, halo, —OH, —CN, $C_1$-$C_4$ alkyl, $C_2$-$C_4$ alkenyl or alkynyl, —O—($C_1$-$C_4$ alkyl), N($R^7$)$_2$, —($C_1$-$C_4$ alkylene)-aryl, —($C_1$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)O$R^9$, —C(O)N($R^9$)$_2$, —S(O)$R^8$, —S(O)$_2$$R^8$ and —S(O)$_2$N($R^9$)$_2$, wherein each of $R^7$, $R^8$ and $R^9$ is independently as defined above and described herein.

As defined generally above and herein, each $R^4$ is independently selected from hydrogen, halo, $C_1$-$C_4$ alkyl, —CH$_2$OH, —OH, —($C_0$-$C_4$ alkylene)-O—($C_1$-$C_4$ alkyl), —($C_0$-$C_4$ alkylene)-N($R^7$)$_2$, or —CN; or
two $R^4$ are taken together with a common carbon atom to which they are both bound to form a carbocyclic, heterocyclic, or =O; or
two $R^4$ bound to different carbon atoms are taken together with the different carbon atoms and any intervening atoms to form a carbocyclic or heterocyclic;
wherein each $R^7$ is independently as defined above and described herein.

In some embodiments, each $R^4$ is independently selected from hydrogen, halo, $C_1$-$C_4$ alkyl, $C_1$-$C_4$ haloalkyl, —CH$_2$OH, —OH, —($C_1$-$C_4$ alkylene)-O—($C_1$-$C_4$ alkyl), N($R^7$)$_2$, —O—($C_1$-$C_4$ alkyl), —CN; or
two $R^4$ are taken together with the atom or atoms to which they are bound and any intervening atoms to form a carbocyclic, heterocyclic, or =O;
wherein each $R^7$ is independently as defined above and described herein.

As defined generally above and herein, $R^5$ is selected from hydrogen, $C_1$-$C_4$ alkyl, and $C_2$-$C_4$ haloalkyl; or
$R^4$ and $R^5$ are taken together with the atoms to which they are bound and any intervening atoms to form a heterocyclic.

In certain embodiments, $R^5$ is selected from hydrogen, $C_1$-$C_4$ alkyl, and $C_2$-$C_4$ haloalkyl; or
$R^4$ and $R^5$ are taken together with the atoms to which they are bound and any intervening atoms to form a heterocyclic.

As defined generally above and herein, each $R^6$ can be any suitable substituent.

In some embodiments, each $R^6$ is independently selected from halo, —CN, =O, —($C_1$-$C_4$ alkylene)-O—$R^8$, —($C_0$-$C_4$ alkylene)-O—($C_0$-$C_4$ alkylene)-$R^9$, —($C_0$-$C_4$ alkylene)-N($R^7$)$_2$, —($C_0$-$C_4$ alkylene)-$R^8$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^9$)$_2$, —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—N($R^9$)$_2$; or
two $R^6$ bound to adjacent atoms in ring A are taken together with the atoms to which they are bound to form a monocyclic aryl, heteroaryl, heterocyclyl, or carbocyclyl;

wherein each of $R^7$, $R^8$ and $R^9$ is independently as defined above and described herein.

In some embodiments, each $R^6$ is independently selected from —($C_1$-$C_4$ alkyl), —($C_0$-$C_4$ alkylene)-Q, —($C_0$-$C_2$ alkylene)-N($R^{10}$)—($C_0$-$C_2$ alkylene)-Q, —O—($C_0$-$C_2$ alkylene)-Q, —($C_1$-$C_2$ alkylene)-O—($C_0$-$C_2$ alkylene)-Q, —C(O)-Q, —S(O)$_{1-2}$-Q, —N($R^{10}$)—($C_1$-$C_4$ alkylene)-O—C(O)—($C_1$-$C_4$ alkyl), —N($R^{10}$)—($C_1$-$C_4$ alkylene)-C(O)—O—($C_1$-$C_4$ alkyl), —($C_0$-$C_2$ alkylene)-N($R^{10}$)—($C_1$-$C_{10}$alkyl), —($C_0$-$C_2$ alkylene)-N($R^{10}$)—($C_2$-$C_{10}$ alkynyl), —($C_0$-$C_2$ alkylene)-N($R^{10}$)—($C_2$-$C_{10}$ alkenyl), —($C_0$-$C_2$ alkylene)-N($R^{10}$)—($C_0$-$C_2$ alkylene)-O—($C_1$-$C_4$ alkyl), —($C_0$-$C_2$ alkylene)-C(O)—N($R^{10}$)$_2$, —($C_1$-$C_4$ alkylene)-C(O)C(O)N($R^{10}$)($C_1$-$C_4$ alkyl), —O—($C_1$-$C_4$ alkylene)-O—($C_1$-$C_4$ alkyl), —($C_0$-$C_4$ alkylene)-O—C(O)—($C_1$-$C_4$ alkyl), —($C_0$-$C_4$ alkylene)-C(O)—O—($C_1$-$C_4$ alkyl), —($C_0$-$C_4$ alkylene)-O—($C_1$-$C_4$ alkyl), —($C_1$-$C_2$ alkylene)-S(O)$_{1-2}$—($C_1$-$C_4$ alkyl), —S(O)$_{1-2}$—($C_1$-$C_4$ alkyl), —($C_1$-$C_4$ alkylene)-N($R^{10}$)S(O)$_{1-2}$—($C_1$-$C_{10}$ alkyl), or —($C_1$-$C_4$ alkylene)-N($R^{10}$)—S(O)$_{1-2}$-Q, wherein:
any terminal methyl moiety present in $R^6$ is optionally replaced with —CH$_2$OH, CF$_3$, —CH$_2$F, —CH$_2$Cl, C(O)CH$_3$, C(O)CF$_3$, CN, or CO$_2$H;
each $R^{10}$ is independently selected from hydrogen and methyl; and
Q is selected from aryl, heteroaryl, carbocyclyl and heterocyclyl.

In some embodiments, each $R^6$ is independently selected from halo, —OH, —CN, =O, $C_1$-$C_4$ alkyl, $C_1$-$C_4$ haloalkyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl; or
two $R^6$ bound to adjacent atoms in ring A are taken together with the atoms to which they are bound to form a monocyclic aryl, heteroaryl, heterocyclyl, or carbocyclyl;
wherein each $R^7$ is independently as defined above and described herein.

In some embodiments, each $R^6$ is independently selected from =O, halo, —CN, —$C_1$-$C_4$ alkyl, —$C_1$-$C_4$ haloalkyl, —O—($C_1$-$C_4$ alkyl), optionally substituted heterocyclyl, and optionally substituted heteroaryl.

In some embodiments, ring A is selected from phenyl, cyclopentyl, cyclohexyl, pyrimidin-2-yl, 2,3-dihydrobenzofuran-2-yl, pyridin-2-yl, pyridin-4-yl, piperidin-1-yl, piperidin-4-yl, pyrrolidin-3-yl, pyrrolidin-2-yl, tetrahydrofuran-3-yl, tetrahydrofuran-2-yl, 3-oxopiperazin-1-yl, morpholin-4-yl, morpholin-2-yl, tetrahydro-2H-pyran-4-yl, and tetrahydro-2H-pyran-3-yl, wherein ring A is optionally substituted with one or more $R^6$ independently selected from =O, halo, —CN, —$C_1$-$C_4$ alkyl, $C_1$-$C_4$ haloalkyl, —O—(C1-C4 alkyl), optionally substituted heterocyclyl, and optionally substituted heteroaryl.

In some embodiments, each $R^6$ is independently selected from fluoro, —CH$_3$, —CH$_2$CH$_3$, —CF$_3$, —OCH$_3$, —CN, pyridin-4-yl, 1H-pyrrol-4-yl, pyridazin-4-yl, pyrimidin-4-yl, and 6-aminopyridin-3-yl.

In some embodiments, one $R^6$ is 2-aminopyrazol-5-yl.

As defined generally above and herein, each $R^7$ is independently selected from hydrogen, —($C_0$-$C_4$ alkylene)-$R^9$, —($C_2$-$C_4$ alkylene)-O—$R^8$, $C_2$-$C_4$ haloalkyl, —S(O)$_2$—$R^8$, —C(=O)—$R^8$, —C(=O)—N($R^9$)($R^9$), —($C_2$-$C_4$ alkylene)-O—C(=O)—$R^8$ and —($C_0$-$C_4$ alkylene)-C(=O)—O—R; or
two $R^7$ are taken together with the nitrogen atom to which they are commonly bound to form an optionally substituted heterocyclyl or heteroaryl;

wherein each of $R^8$ and $R^9$ is independently as defined above and described herein.

In some embodiments, each $R^7$ is independently selected from hydrogen, $C_1$-$C_4$ alkyl, $C_1$-$C_4$ haloalkyl, —S(O)$_2$—$R^8$, —C(=O)—$R^8$, —C(=O)—N($R^8$)($R^9$), and —C(=O)—O—$R^8$; or two $R^7$ are taken together with the nitrogen atom to which they are commonly bound to form an optionally substituted heterocyclyl;

wherein each of $R^8$ and $R^9$ is independently as defined above and described herein.

As defined generally above and herein, $R^8$ is selected from $C_1$-$C_4$ alkyl, $C_1$-$C_4$ haloalkyl, aryl, heteroaryl, carbocyclyl and heterocyclyl.

As defined generally above and herein, each $R^9$ is independently selected from hydrogen or $R^8$, wherein $R^8$ is independently as defined above and described herein.

As defined generally above and herein, === represents a single or double bond. In some embodiments, === represents a single bond. In some embodiments, === represents a double bond. In some embodiments, the bond between $X^4$ and $X^5$ is a single bond. In some embodiments, the bond between $X^4$ and $X^5$ is a double bond.

As defined generally above and herein, n is 0 or an integer from 1 to 6. In some embodiments, when ring A is a heterocyclyl bound to $L^1$ through a ring nitrogen atom, phenyl, or a 5-6 membered heteroaryl, then n is an integer from 1 to 6.

In some embodiments, -[$L^1$]$_n$- is selected from —O—, —S(O)—, —S(O)$_2$, —C($R^4$)$_2$—, —N($R^7$)—, —C($R^4$)$_2$—C($R^4$)$_2$—, —C($R^4$)$_2$—O-†, —C($R^4$)$_2$—C($R^4$)$_2$—O-†, —C($R^4$)$_2$—N($R^7$)-† and —O—C($R^4$)$_2$-†, wherein each of $R^4$ and $R^7$ is independently as defined above and described herein, and wherein † represents the portion of -[$L^1$]$_n$- bound to ring A.

In some embodiments, -[$L^1$]$_n$- is selected from —O—, —S(O)—, —S(O)$_2$, —CH$_2$—, —CH$_2$—O-†, —CH(CH$_3$)—O-†, —N(CH$_3$)-†, —N(CH$_2$CH$_3$)-†, —N(CH(CH$_3$)$_2$)-†, —N(CH$_2$CH(CH$_3$)$_2$)-†, —NH-†, —CH$_2$—N(CH$_3$)-†, —CH$_2$—NH-†, —CH(OH)—, —C(CH$_3$)—, —O—CH$_2$-†, —CH$_2$—CH$_2$—, —CH(CH$_3$)—CH$_2$-†, —CH(CH$_3$)—CH$_2$—O-†, —C((CH$_3$)$_2$)—, —C(CH$_3$)(OCH$_3$)—, —CH(OCH$_3$)—, —CH(CH$_2$OH)—, —C(CH$_3$)(OH)—, —CH(CH$_2$CH$_3$)—O-†, —CH(CH(CH$_3$)$_2$)—O-† and —CH(CH$_2$OCH$_3$)—, wherein † represents the portion of -[$L^1$]$_n$- bound to ring A.

In some embodiments, -[$L^1$]$_n$- is selected from —O—, —S(O)—, —S(O)$_2$, —CH$_2$—O-†, —CH(CH$_3$)—O-†, —N(CH$_3$)-†, —NH-†, —CH(OCH$_3$)—, —CH$_2$—N(CH$_3$)-†, —CH$_2$—NH-†, —CH(OH)—, —CH(CH$_3$)—, —CH$_2$—, —CH$_2$—CH$_2$—, —C(CH$_3$)(OH)—, —CH(CH$_2$CH$_3$)—O-†, —CH(CH(CH$_3$)$_2$)—O-† and —O—CH$_2$-†, wherein † represents the portion of -[$L^1$]$_n$- bound to ring A. In some aspects of these embodiments, -[$L^1$]$_n$- is selected from —CH((S)—CH$_3$)—O-†, —CH((S)—CH$_3$)—, —C((S)—CH$_3$)((R)—OH)—, —CH((S)—CH$_2$CH$_3$)—O-†, and —CH((S)—CH(CH$_3$)$_2$)—O-†. In other aspects of these embodiments, —[$L^1$]$_n$— is selected from —CH((R)—CH$_3$)—O-†, —CH((R)—CH$_3$)—, —C((R)—CH$_3$)((S)—OH)—, —CH((R)—CH$_2$CH$_3$)—O-†, and —CH((R)—CH(CH$_3$)$_2$)—O-†.

Any portion of the compound designated as alkyl, alkylene, alkenyl, alkynyl, aryl, heteroaryl, heterocyclyl or carbocyclyl is optionally substituted; and each ring of any aryl, heteroaryl, heterocyclyl or carbocyclyl has not more than three substituents per ring.

In some embodiments, the present invention provides a compound of formula I-i:

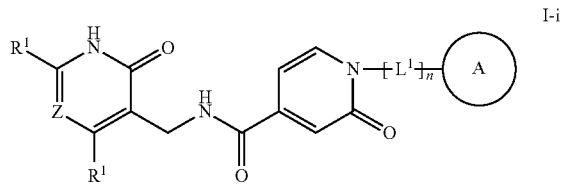

I-i or a pharmaceutically acceptable salt thereof, wherein each variable is defined above and described in classes and subclasses above and herein.

In some embodiments, the present invention provides a compound of formula I-i:

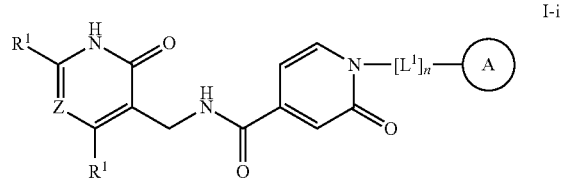

I-i or a pharmaceutically acceptable salt thereof, wherein:
-[$L^1$]$_n$- is —CH(CH$_3$)—CH$_2$-†;
ring A is phenyl optionally substituted with one or more $R^6$;
† represents the portion of -[$L^1$]$_n$- bound to ring A; and
each of $R^1$ and Z is independently as defined above and described herein. In one aspect of these embodiments, -[$L^1$]$_n$- is —CH((S)—CH$_3$)—CH$_2$-†. In another aspect of these embodiments, -[$L^1$]$_n$— is —CH((R)—CH$_3$)—CH$_2$-†.

In some embodiments, the present invention provides a compound of formula I-i:

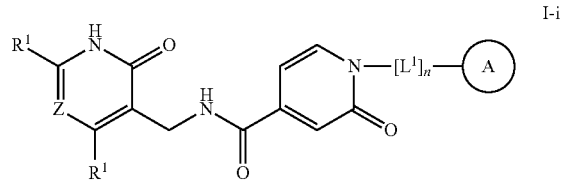

I-i or a pharmaceutically acceptable salt thereof, wherein:
-[$L^1$]$_n$- is —CH(CH$_3$)-†;
ring A is phenyl optionally substituted with one or more $R^6$;
† represents the portion of -[$L^1$]$_n$- bound to ring A; and
each of $R^1$ and Z is independently as defined above and described herein. In one aspect of these embodiments, -[$L^1$]$_n$- is —CH((S)—CH$_3$)-†. In another aspect of these embodiments, -[$L^1$]— is —CH((R)—CH$_3$)-†.

In certain embodiments, the present invention provides a compound of formula I:

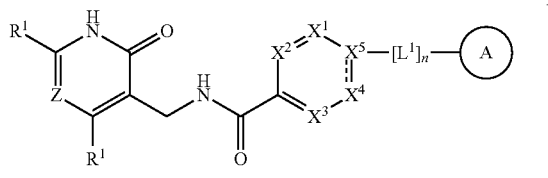

I or a pharmaceutically acceptable salt thereof, wherein:
Z is =C($R^2$)— or =N—;
each of $X^1$, $X^2$ and $X^3$ is independently selected from =N— and =C($R^3$)—;

$X^4$ is selected from =N—, —C(=O)— and =C($R^3$)—;
$X^5$ is =C— or

no more than two of $X^1$, $X^2$, $X^3$, $X^4$, and $X^5$ are =N— or

ring A is phenyl, a monocyclic 5-6 membered heteroaryl comprising 1 to 3 hetero ring atoms independently selected from N, O and S, a carbocyclic comprising 4 or more ring atoms, or a heterocyclic, wherein ring A is optionally substituted with one or more $R^6$;

each $R^1$ and $R^2$ is independently selected from hydrogen, halo, —OH, —CN, $C_1$-$C_4$ alkyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, or —O—($C_0$-$C_4$ alkylene)-carbocyclyl; or one $R^1$ and $R^2$ are taken together with atoms to which they are bound to form an aryl, heteroaryl, heterocyclyl, or carbocyclyl;

each $R^3$ is independently selected from hydrogen, halo, —OH, —CN, $C_1$-$C_4$ alkyl, $C_2$-$C_4$ alkenyl or alkynyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)O$R^9$, —C(O)N($R^9$)$_2$, —S(O)$R^8$, —S(O)$_2R^8$ and —S(O)$_2$N($R^9$)$_2$;

each $L^1$ is independently selected from —C($R^4$)$_2$—, —C($R^4$)=C($R^4$)—, —C≡C—, —O—, —S—, —S(O)—, —S(O)$_2$, or —N($R^5$)—; or any $L^1$ is optionally taken together with $X^1$ or $X^4$ and any intervening atoms to form an aryl, heteroaryl, heterocyclyl or carbocyclyl fused to the ring comprising $X^1$, $X^2$, $X^3$, $X^4$ and $X^5$;

wherein when ring A is phenyl, a 5-6 membered heteroaryl, or a heterocyclyl bound to $L^1$ through a ring nitrogen atom, then n is an integer from 1 to 6;

each $R^4$ is independently selected from hydrogen, halo, $C_1$-$C_4$ alkyl, —CH$_2$OH, —OH, —($C_0$-$C_4$ alkylene)-O—($C_1$-$C_4$ alkyl), —($C_0$-$C_4$ alkylene)-N($R^7$)$_2$, or —CN; or two $R^4$ are taken together with a common carbon atom to which they are both bound to form a carbocyclic, heterocyclic, or =O; or two $R^4$ bound to different carbon atoms are taken together with the different carbon atoms and any intervening atoms to form a carbocyclic, or heterocyclic;

$R^5$ is selected from hydrogen, $C_1$-$C_4$ alkyl, and $C_2$-$C_4$ haloalkyl; or $R^4$ and $R^5$ are taken together with the atoms to which they are bound and any intervening atoms to form a heterocyclic;

each $R^6$ is independently selected from halo, —CN, =O, —($C_1$-$C_4$ alkylene)-O—$R^8$, —($C_0$-$C_4$ alkylene)-O—($C_0$-$C_4$ alkylene)-$R^9$, —($C_0$-$C_4$ alkylene)-N($R^7$)$_2$, —($C_0$-$C_4$ alkylene)-$R^8$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^9$)$_2$, —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—N($R^9$)$_2$; or two $R^6$ bound to adjacent atoms in ring A are taken together with the atoms to which they are bound to form a monocyclic aryl, heteroaryl, heterocyclyl, or carbocyclyl;

each $R^7$ is independently selected from hydrogen, —($C_0$-$C_4$ alkylene)-$R^9$, —($C_2$-$C_4$ alkylene)-O—$R^8$, $C_2$-$C_4$ haloalkyl, —S(O)$_2$—$R^8$, —C(=O)—$R^8$, —C(=O)—N($R^9$)($R^9$), —($C_2$-$C_4$ alkylene)-O—C(=O)—$R^8$ and —($C_0$-$C_4$ alkylene)-C(=O)—O—$R^9$; or two $R^7$ are taken together with the nitrogen atom to which they are commonly bound to form an optionally substituted heterocyclyl or heteroaryl;

$R^8$ is selected from $C_1$-$C_4$ alkyl, aryl, heteroaryl, carbocyclyl and heterocyclyl;

each $R^9$ is independently selected from hydrogen or $R^8$;

═ represents a single or double bond;

n is 0 or an integer from 1 to 6;

wherein any portion of the compound designated as alkyl, alkylene, alkenyl, alkynyl, aryl, heteroaryl, heterocyclyl or carbocyclyl is optionally substituted; and each ring of any aryl, heteroaryl, heterocyclyl or carbocyclyl has not more than three substituents per ring; and wherein:

when each of $X^1$, $X^2$, $X^3$ and $X^4$ is =CH—, $X^5$ is =C—, and -[$L^1$]$_n$- is —S(O)$_2$—, then ring A is not an N-linked heterocyclyl;

when each of $X^1$, $X^2$, $X^3$ and $X^4$ is =CH—, $X^5$ is =C—, and -[$L^1$]$_n$- is —CH$_2$—, then ring A is other than piperidin-1-yl, 2,5-dioxo-1-imidazolidin-1-yl, or 2-oxo-1-pyrrolidin-1-yl;

when each of $X^1$, $X^2$, $X^3$ and $X^4$ is =CH—, $X^5$ is =C—, and -[$L^1$]$_n$- is —S(O)$_2$—NH-†, then ring A is other than pyridin-4-yl, 2,3-dimethylphenyl, or 4-chlorophenyl;

when each of $X^1$, $X^2$, $X^3$ and $X^4$ is =CH—, $X^5$ is =C—, and -[$L^1$]$_n$- is —S(O)$_2$—NH—CH$_2$-† or —NH—C(O)-†, then ring A is other than furan-2-yl or thiophen-2-yl;

when each of $X^1$, $X^2$, $X^3$ and $X^4$ is =CH—, $X^5$ is =C—, and -[$L^1$]$_n$- is —NH—S(O)$_2$-†, then ring A is other than benzodioxepin-7-yl, or benzodioxin-6-yl;

when each of $X^1$, $X^2$, $X^3$ and $X^4$ is =CH—, $X^5$ is =C—, and -[$L^1$]$_n$- is —O—CH$_2$-†, then ring A is other than 8-methylimidazo[1,2-a]pyridin-2-yl, 2-methylthiazol-4-yl, or 5-methyl-1,2,4-oxadiazol-3-yl;

† represents the portion of -[$L^1$]$_n$- bound to ring A; and the compound is other than:

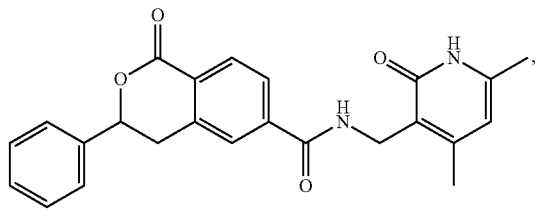

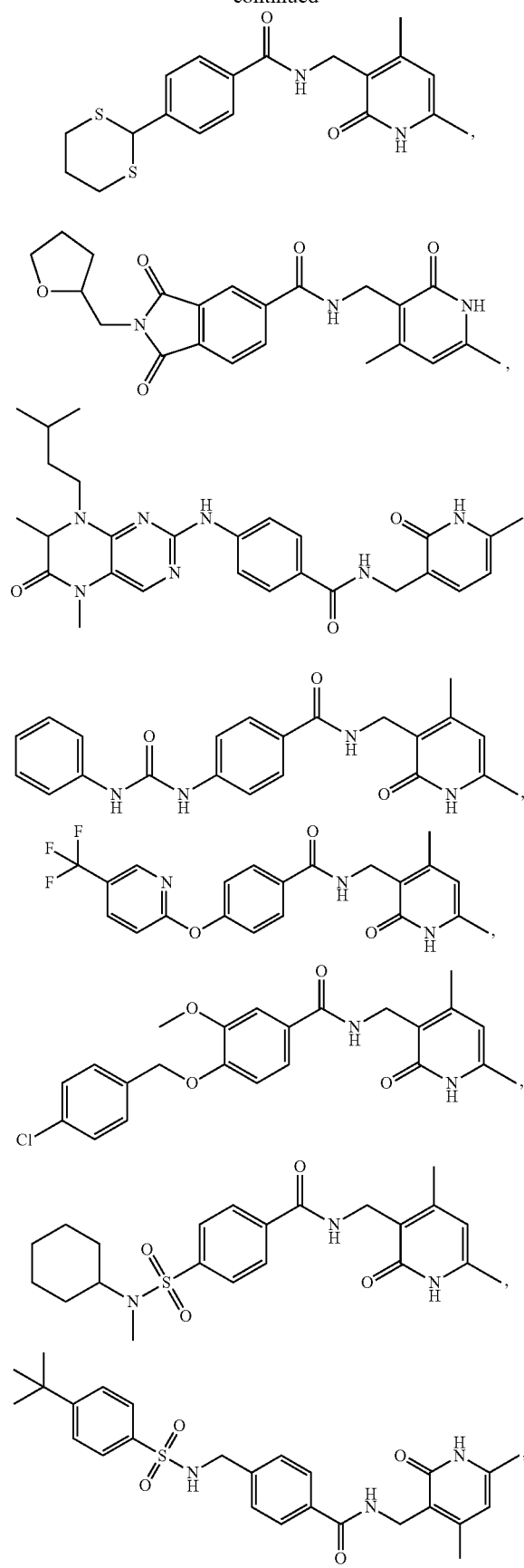
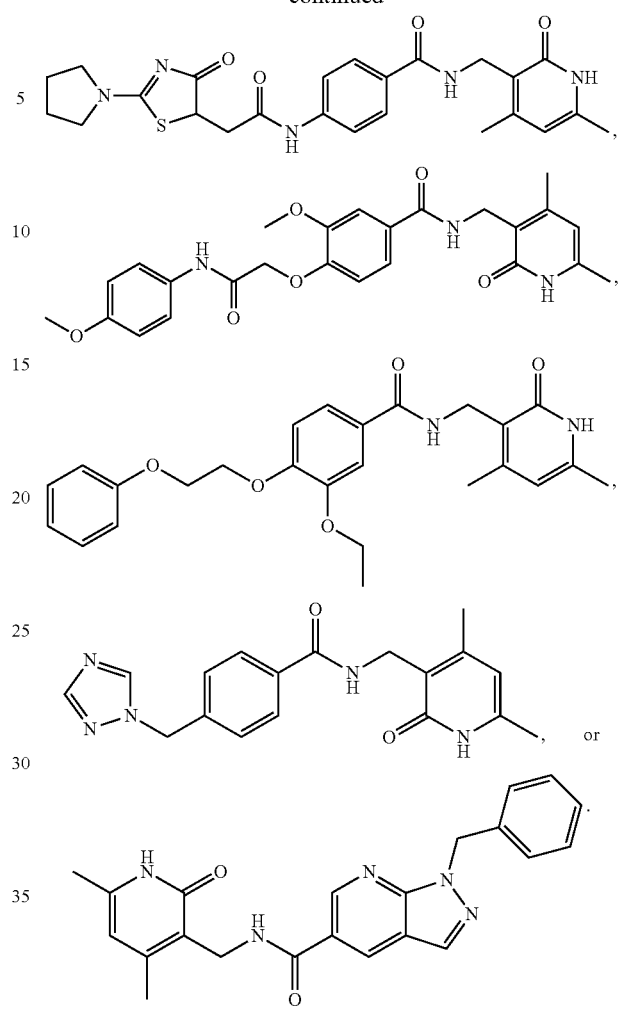
In certain embodiments, the present invention provides a compound of formula I:
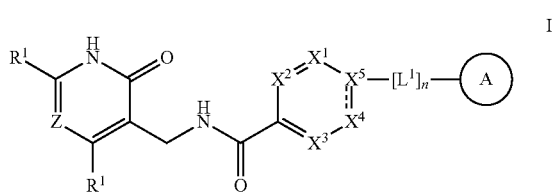
or a pharmaceutically acceptable salt thereof, wherein:
Z is =C(R$^2$)— or =N—;
each of X$^1$, X$^2$ and X$^3$ is independently selected from =N— and =C(R$^3$)—;
X$^4$ is selected from =N—, —C(=O)— and =C(R$^3$)—;
X$^5$ is =C— or

no more than two of $X^1$, $X^2$, $X^3$, $X^4$, and $X^5$ are =N— or

ring A is phenyl, a monocyclic 5-6 membered heteroaryl comprising 1 to 3 hetero ring atoms independently selected from N, O and S, a carbocyclic comprising 4 or more ring atoms, or a heterocyclic, wherein ring A is optionally substituted with one or more $R^6$;

each $R^1$ and $R^2$ is independently selected from hydrogen, halo, —OH, —CN, $C_1$-$C_4$ alkyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, or —O—($C_0$-$C_4$ alkylene)-carbocyclyl; or one $R^1$ and $R^2$ are taken together with atoms to which they are bound to form an aryl, heteroaryl, heterocyclyl, or carbocyclyl;

each $R^3$ is independently selected from hydrogen, halo, —OH, —CN, $C_1$-$C_4$ alkyl, $C_2$-$C_4$ alkenyl or alkynyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)O$R^9$, —C(O)N($R^9$)$_2$, —S(O)$R^8$, —S(O)$_2R^8$ and —S(O)$_2$N($R^9$)$_2$;

each $L^1$ is independently selected from —C($R^4$)$_2$—, —C($R^4$)=C($R^4$)—, —C≡C—, —O—, —S—, —S(O)—, —S(O)$_2$, or —N($R^5$)—; or any $L^1$ is optionally taken together with $X^1$ or $X^4$ and any intervening atoms to form an aryl, heteroaryl, heterocyclyl or carbocyclyl fused to the ring comprising $X^1$, $X^2$, $X^3$, $X^4$ and $X^5$;

wherein when ring A is phenyl, a 5-6 membered heteroaryl, or a heterocyclyl bound to $L^1$ through a ring nitrogen atom, then n is an integer from 1 to 6;

each $R^4$ is independently selected from hydrogen, halo, $C_1$-$C_4$ alkyl, —CH$_2$OH, —OH, —($C_0$-$C_4$ alkylene)-O—($C_1$-$C_4$ alkyl), —($C_0$-$C_4$ alkylene)-N($R^7$)$_2$, or —CN; or two $R^4$ are taken together with a common carbon atom to which they are both bound to form a carbocyclic, heterocyclic, or =O; or two $R^4$ bound to different carbon atoms are taken together with the different carbon atoms and any intervening atoms to form a carbocyclic, or heterocyclic;

$R^5$ is selected from hydrogen, $C_1$-$C_4$ alkyl, and $C_2$-$C_4$ haloalkyl; or $R^4$ and $R^5$ are taken together with the atoms to which they are bound and any intervening atoms to form a heterocyclic;

each $R^6$ is independently selected from halo, —CN, =O, —($C_1$-$C_4$ alkylene)-O—$R^8$, —($C_0$-$C_4$ alkylene)-O—($C_0$-$C_4$ alkylene)-$R^9$, —($C_0$-$C_4$ alkylene)-N($R^7$)$_2$, —($C_0$-$C_4$ alkylene)-$R^8$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^9$)$_2$, —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—N($R^9$)$_2$; or two $R^6$ bound to adjacent atoms in ring A are taken together with the atoms to which they are bound to form a monocyclic aryl, heteroaryl, heterocyclyl, or carbocyclyl;

each $R^7$ is independently selected from hydrogen, —($C_0$-$C_4$ alkylene)-$R^9$, —($C_2$-$C_4$ alkylene)-O—$R^8$, $C_2$-$C_4$ haloalkyl, —S(O)$_2$—$R^8$, —C(=O)—$R^8$, —C(=O)—N($R^9$)($R^9$), —($C_2$-$C_4$ alkylene)-O—C(=O)—$R^8$ and —($C_0$-$C_4$ alkylene)-C(=O)—O—$R^9$; or two $R^7$ are taken together with the nitrogen atom to which they are commonly bound to form an optionally substituted heterocyclyl or heteroaryl;

$R^8$ is selected from $C_1$-$C_4$ alkyl, aryl, heteroaryl, carbocyclyl and heterocyclyl;

each $R^9$ is independently selected from hydrogen or $R^8$;

═ represents a single or double bond;

n is 0 or an integer from 1 to 6;

wherein any portion of the compound designated as alkyl, alkylene, alkenyl, alkynyl, aryl, heteroaryl, heterocyclyl or carbocyclyl is optionally substituted; and each ring of any aryl, heteroaryl, heterocyclyl or carbocyclyl has not more than three substituents per ring; and wherein the compound is other than:

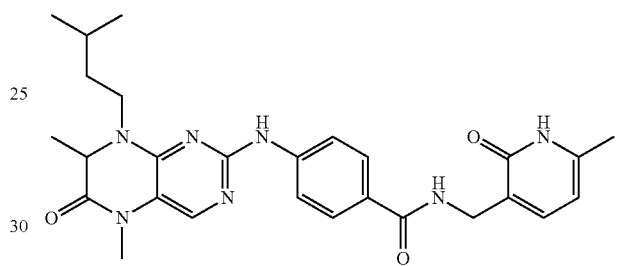

In certain embodiments, the present invention provides a compound of formula I:

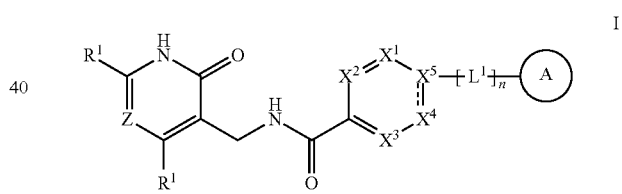

or a pharmaceutically acceptable salt thereof, wherein:

Z is =C($R^2$)— or =N—;

each of $X^1$, $X^2$ and $X^3$ is independently selected from =N— and =C($R^3$)—;

$X^4$ is selected from =N—, —C(=O)— and =C($R^3$)—;

$X^5$ is =C— or

no more than two of X, $X^2$, $X^3$, $X^4$, and $X^5$ are =N— or

ring A is phenyl, a monocyclic 5-6 membered heteroaryl comprising 1 to 3 hetero ring atoms independently selected from N, O and S, a carbocyclic comprising 4 or more ring atoms, or a heterocyclic, wherein ring A is optionally substituted with one or more $R^6$;

each $R^1$ and $R^2$ is independently selected from hydrogen, halo, —OH, —CN, $C_1$-$C_4$ alkyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, or —O—($C_0$-$C_4$ alkylene)-carbocyclyl; or
one $R^1$ and $R^2$ are taken together with atoms to which they are bound to form an aryl, heteroaryl, heterocyclyl, or carbocyclyl;

each $R^3$ is independently selected from hydrogen, halo, —OH, —CN, $C_1$-$C_4$ alkyl, $C_2$-$C_4$ alkenyl or alkynyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)$OR^9$, —C(O)$N(R^9)_2$, —S(O)$R^8$, —S(O)$_2R^8$ and —S(O)$_2N(R^9)_2$;

each $L^1$ is independently selected from —C($R^4$)$_2$—, —C($R^4$)=C($R^4$)—, —C≡C—, —O—, —S—, —S(O)—, —S(O)$_2$, or —N($R^5$)—; or
any $L^1$ is optionally taken together with $X^1$ or $X^4$ and any intervening atoms to form an aryl, heteroaryl, heterocyclyl or carbocyclyl fused to the ring comprising $X^1$, $X^2$, $X^3$, $X^4$ and $X^5$;

wherein when ring A is phenyl, a 5-6 membered heteroaryl, or a heterocyclyl bound to $L^1$ through a ring nitrogen atom, then n is an integer from 1 to 6;

each $R^4$ is independently selected from hydrogen, halo, $C_1$-$C_4$ alkyl, —$CH_2OH$, —OH, —($C_0$-$C_4$ alkylene)-O—($C_1$-$C_4$ alkyl), —($C_0$-$C_4$ alkylene)-$N(R^7)_2$, or —CN; or
two $R^4$ are taken together with a common carbon atom to which they are both bound to form a carbocyclic, heterocyclic, or =O; or
two $R^4$ bound to different carbon atoms are taken together with the different carbon atoms and any intervening atoms to form a carbocyclic, or heterocyclic;

$R^5$ is selected from hydrogen, $C_1$-$C_4$ alkyl, and $C_2$-$C_4$ haloalkyl; or
$R^4$ and $R^5$ are taken together with the atoms to which they are bound and any intervening atoms to form a heterocyclic;

each $R^6$ is independently selected from halo, —CN, =O, —($C_1$-$C_4$ alkylene)-O—$R^8$, —($C_0$-$C_4$ alkylene)-O—($C_0$-$C_4$ alkylene)-$R^9$, —($C_0$-$C_4$ alkylene)-$N(R^7)_2$, —($C_0$-$C_4$ alkylene)-$R^8$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—$N(R^9)_2$, —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—$N(R^9)_2$; or
two $R^6$ bound to adjacent atoms in ring A are taken together with the atoms to which they are bound to form a monocyclic aryl, heteroaryl, heterocyclyl, or carbocyclyl;

each $R^7$ is independently selected from hydrogen, —($C_0$-$C_4$ alkylene)-$R^9$, —($C_2$-$C_4$ alkylene)-O—$R^8$, $C_2$-$C_4$ haloalkyl, —S(O)$_2$—$R^8$, —C(=O)—$R^8$, —C(=O)—N($R^9$)($R^9$), —($C_2$-$C_4$ alkylene)-O—C(=O)—$R^8$ and —($C_0$-$C_4$ alkylene)-C(=O)—O—$R^9$; or
two $R^7$ are taken together with the nitrogen atom to which they are commonly bound to form an optionally substituted heterocyclyl or heteroaryl;

$R^8$ is selected from $C_1$-$C_4$ alkyl, aryl, heteroaryl, carbocyclyl and heterocyclyl;

each $R^9$ is independently selected from hydrogen or $R^5$;

═ represents a single or double bond;

n is 0 or an integer from 1 to 6;

wherein any portion of the compound designated as alkyl, alkylene, alkenyl, alkynyl, aryl, heteroaryl, heterocyclyl or carbocyclyl is optionally substituted; and each ring of any aryl, heteroaryl, heterocyclyl or carbocyclyl has not more than three substituents per ring; and wherein:
when each of $X^1$, $X^2$, $X^3$ and $X^4$ is =CH—, $X^5$ is =C—, and -[$L^1$]$_n$- is —S(O)$_2$—, then ring A is not an N-linked heterocyclyl;

when each of $X^1$, $X^2$, $X^3$ and $X^4$ is =CH—, $X^5$ is =C—, and -[$L^1$]$_n$- is —$CH_2$—, then ring A is other than piperidin-1-yl, 2,5-dioxo-1-imidazolidin-1-yl, or 2-oxo-1-pyrrolidin-1-yl;

when each of $X^1$, $X^2$, $X^3$ and $X^4$ is =CH—, $X^5$ is =C—, and -[$L^1$]$_n$- is —S(O)$_2$—NH-†, then ring A is other than pyridin-4-yl, 2,3-dimethylphenyl, or 4-chlorophenyl;

when each of $X^1$, $X^2$, $X^3$ and $X^4$ is =CH—, $X^5$ is =C—, and -[$L^1$]$_n$- is —S(O)$_2$—NH—$CH_2$-† or —NH—C(O)-†, then ring A is other than furan-2-yl or thiophen-2-yl;

when each of $X^1$, $X^2$, $X^3$ and $X^4$ is =CH—, $X^5$ is =C—, and -[$L^1$]$_n$- is —NH—S(O)$_2$-†, then ring A is other than benzodioxepin-7-yl, or benzodioxin-6-yl;

when each of $X^1$, $X^2$, $X^3$ and $X^4$ is =CH—, $X^5$ is =C—, and -[$L^1$]$_n$- is —O—$CH_2$-†, then ring A is other than 8-methylimidazo[1,2-a]pyridin-2-yl, 2-methylthiazol-4-yl, or 5-methyl-1,2,4-oxadiazol-3-yl;

when Z is =C($R^2$)—, $X^4$ is =N— or =C($R^3$)—, $X^1$ is =C($R^3$)—, and ring A is a heterocyclyl, then the portion of the compound represented by -[$L^1$]$_n$- is other than a bond, —O— or —C(=O)—O—;

when Z is =C($R^2$)—, $X^4$ is =C($R^3$)—, $X^1$ is =C($R^3$)—, n is 0, and ring A is a carbocyclyl or heterocyclyl, then the $R^3$ portion of each of $X^1$ and $X^4$ is independently selected from hydrogen, halo, —OH, —CN, $C_1$-$C_4$ alkyl, $C_2$-$C_4$ alkenyl or alkynyl, —O—($C_1$-$C_4$ alkyl), $N(R^7)_2$, —($C_1$-$C_4$ alkylene)-aryl, —($C_1$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)$OR^9$, —C(O)$N(R^9)_2$, —S(O)$R^8$, —S(O)$_2R^8$ and —S(O)$_2N(R^9)_2$;

† represents the portion of -[$L^1$]$_n$- bound to ring A; and the compound is other than:

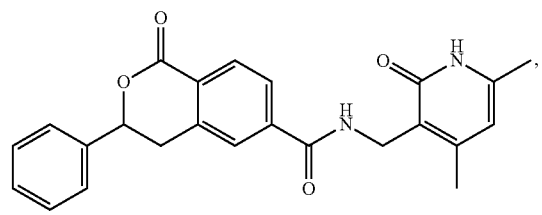

27
-continued
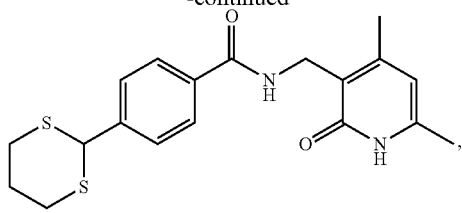
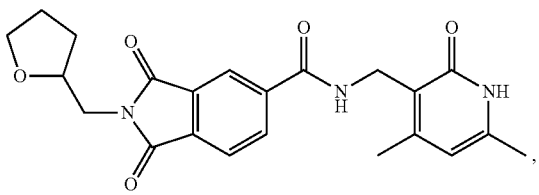
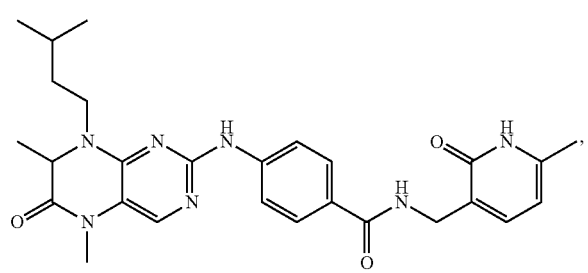
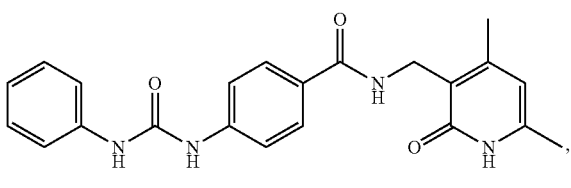
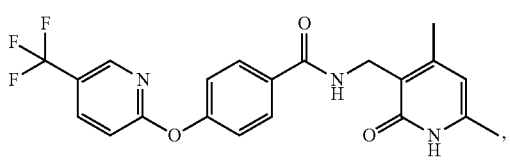
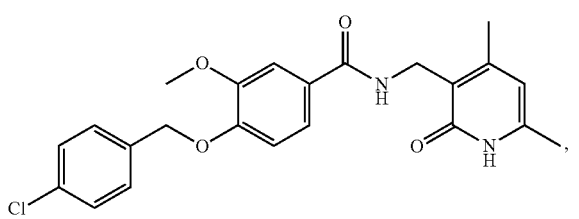
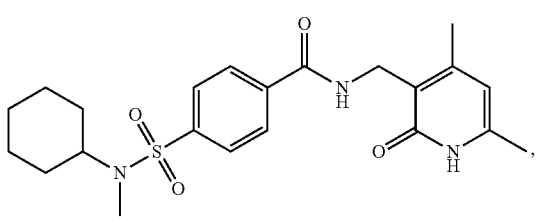
28
-continued
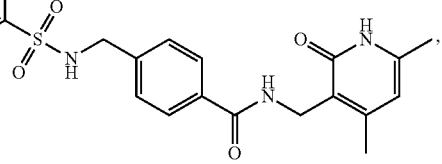
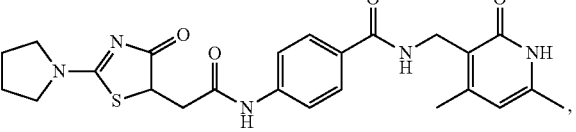
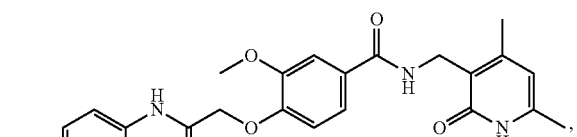
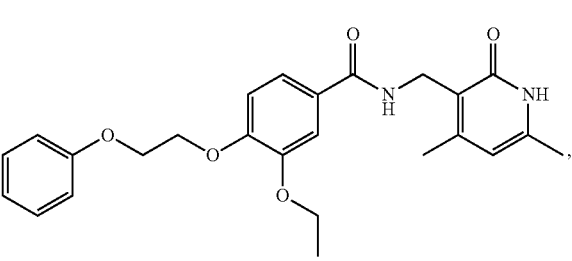
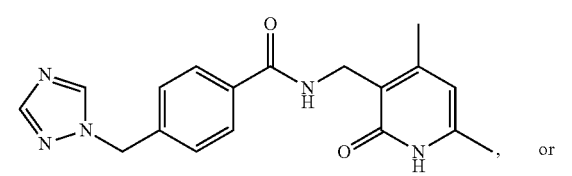
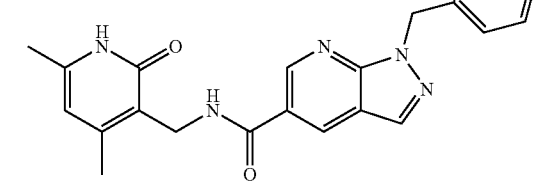
Exemplary compounds of formula I are set forth in Table 1, below.

TABLE 1
Exemplary Compounds of Formula I:
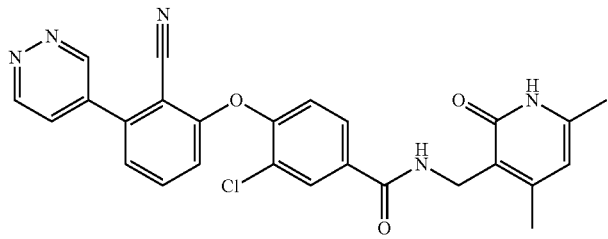 [SMILES: Cc1cc(C)c(CNC(=O)c2ccc(Oc3cccc(-c4ccnnc4)c3C#N)c(Cl)c2)c(=O)[nH]1]
I-1
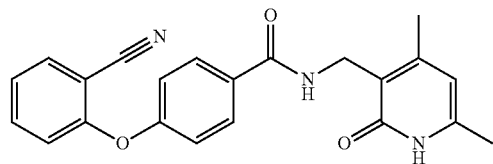 [SMILES: Cc1cc(C)c(CNC(=O)c2ccc(Oc3ccccc3C#N)cc2)c(=O)[nH]1]
I-2
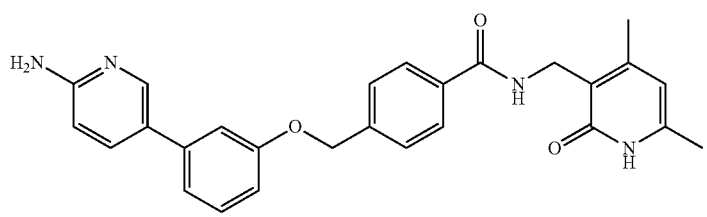 [SMILES: Cc1cc(C)c(CNC(=O)c2ccc(COc3cccc(-c4ccc(N)nc4)c3)cc2)c(=O)[nH]1]
I-3
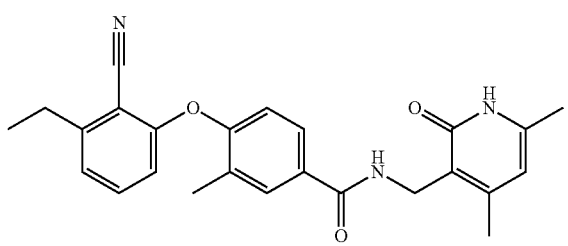 [SMILES: CCc1cccc(Oc2ccc(C(=O)NCc3c(C)cc(C)[nH]c3=O)cc2C)c1C#N]
I-4
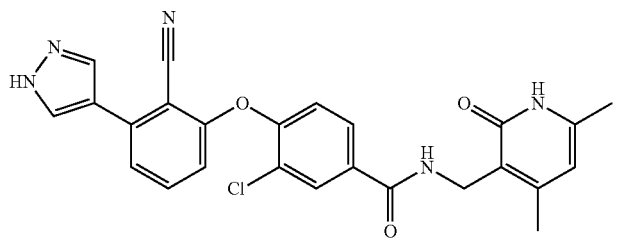 [SMILES: Cc1cc(C)c(CNC(=O)c2ccc(Oc3cccc(-c4cn[nH]c4)c3C#N)c(Cl)c2)c(=O)[nH]1]
I-5
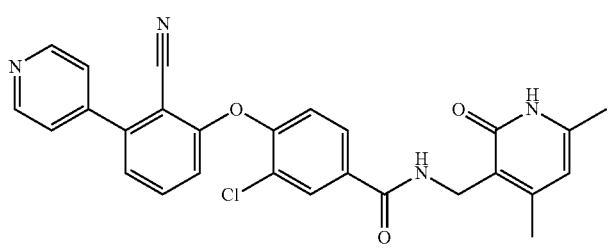 [SMILES: Cc1cc(C)c(CNC(=O)c2ccc(Oc3cccc(-c4ccncc4)c3C#N)c(Cl)c2)c(=O)[nH]1]
I-6

TABLE 1-continued
Exemplary Compounds of Formula I:
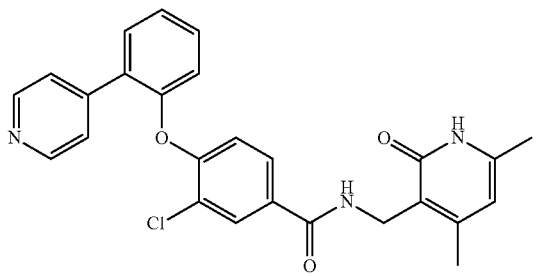 [SMILES: Cc1cc(C)c(CNC(=O)c2ccc(Oc3ccccc3-c3ccncc3)c(Cl)c2)c(=O)[nH]1]
I-7
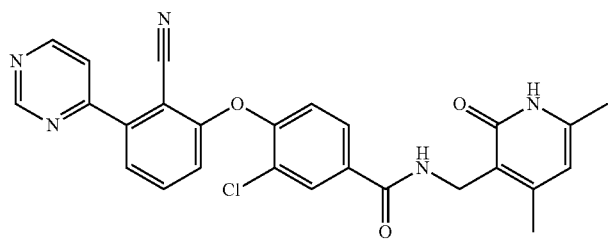 [SMILES: Cc1cc(C)c(CNC(=O)c2ccc(Oc3cccc(-c4ccncn4)c3C#N)c(Cl)c2)c(=O)[nH]1]
I-8
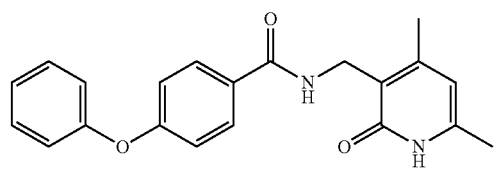 [SMILES: Cc1cc(C)c(CNC(=O)c2ccc(Oc3ccccc3)cc2)c(=O)[nH]1]
I-9
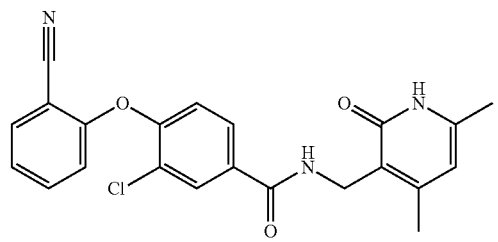 [SMILES: Cc1cc(C)c(CNC(=O)c2ccc(Oc3ccccc3C#N)c(Cl)c2)c(=O)[nH]1]
I-10
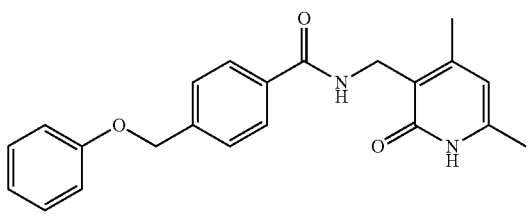 [SMILES: Cc1cc(C)c(CNC(=O)c2ccc(COc3ccccc3)cc2)c(=O)[nH]1]
I-11
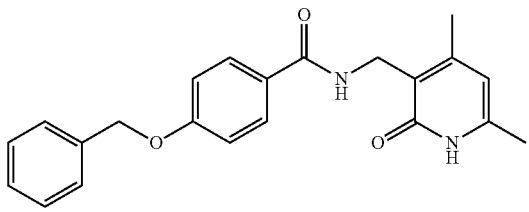
I-12

TABLE 1-continued

Exemplary Compounds of Formula I:

I-13

I-14

I-15

I-16

I-17

I-18

I-19

I-20

TABLE 1-continued

Exemplary Compounds of Formula I:

| | |
|---|---|
| (structure) | I-21 |
| (structure) | I-22 |
| (structure) | I-23 |
| (structure) | I-24 |
| (structure) | I-25 |
| (structure) | I-26 |
| (structure) | I-27 |

TABLE 1-continued

Exemplary Compounds of Formula I:

I-28

I-29

I-30

I-31

I-32

I-33

I-34

TABLE 1-continued
Exemplary Compounds of Formula I:
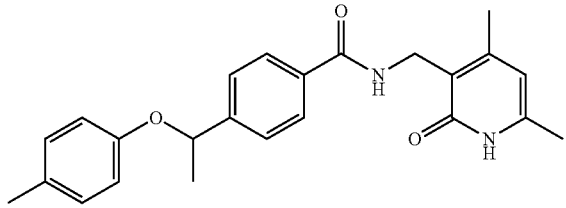
I-35
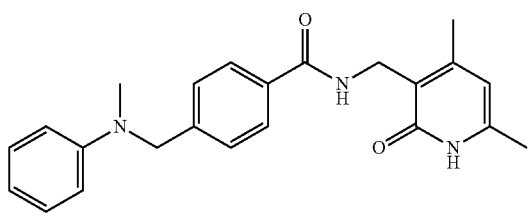 [SMILES: Cc1cc(C)c(CNC(=O)c2ccc(CN(C)c3ccccc3)cc2)c(=O)[nH]1]
I-36
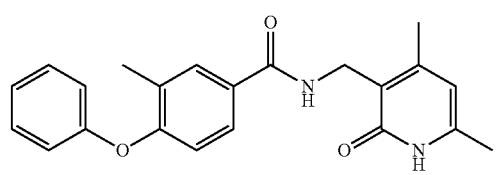 [SMILES: Cc1cc(C)c(CNC(=O)c2ccc(Oc3ccccc3)c(C)c2)c(=O)[nH]1]
I-37
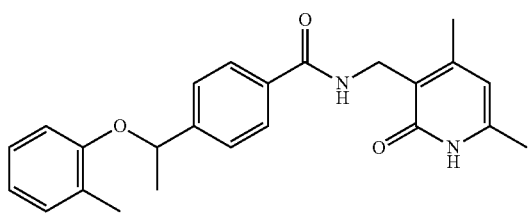 [SMILES: Cc1cc(C)c(CNC(=O)c2ccc(C(C)Oc3ccccc3C)cc2)c(=O)[nH]1]
I-38
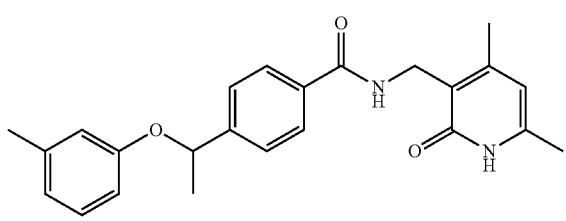
I-39
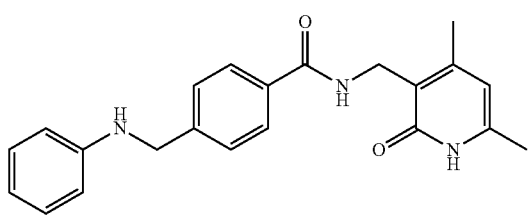 [SMILES: Cc1cc(C)c(CNC(=O)c2ccc(CNc3ccccc3)cc2)c(=O)[nH]1]
I-40
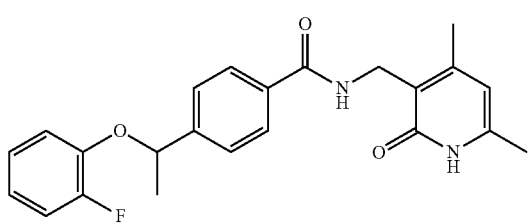 [SMILES: Cc1cc(C)c(CNC(=O)c2ccc(C(C)Oc3ccccc3F)cc2)c(=O)[nH]1]
I-41

TABLE 1-continued
Exemplary Compounds of Formula I:
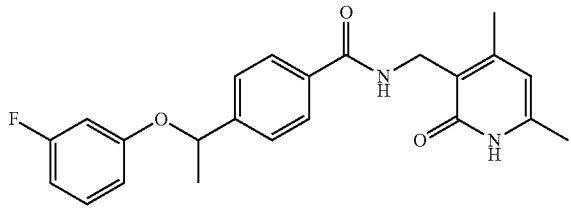 [SMILES: Cc1cc(C)c(CNC(=O)c2ccc(C(C)Oc3cccc(F)c3)cc2)c(=O)[nH]1]
I-42
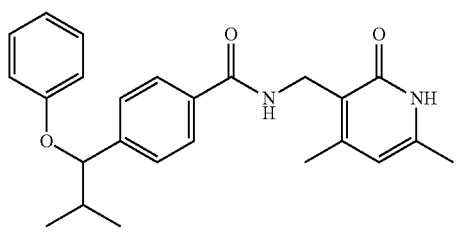 [SMILES: Cc1cc(C)c(CNC(=O)c2ccc(C(Oc3ccccc3)C(C)C)cc2)c(=O)[nH]1]
I-43
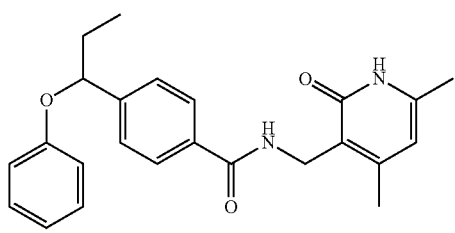 [SMILES: CCC(Oc1ccccc1)c1ccc(C(=O)NCc2c(C)cc(C)[nH]c2=O)cc1]
I-44
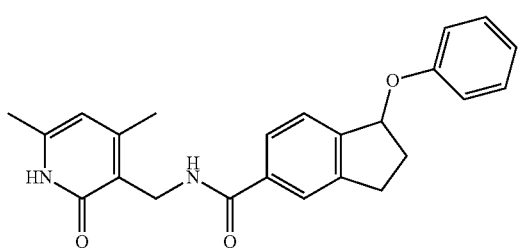 [SMILES: Cc1cc(C)c(CNC(=O)c2ccc3c(c2)CCC3Oc2ccccc2)c(=O)[nH]1]
I-45
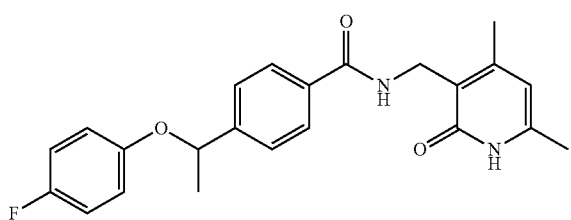 [SMILES: Cc1cc(C)c(CNC(=O)c2ccc(C(C)Oc3ccc(F)cc3)cc2)c(=O)[nH]1]
I-46
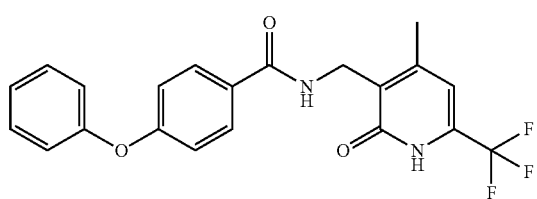 [SMILES: Cc1cc(C(F)(F)F)[nH]c(=O)c1CNC(=O)c1ccc(Oc2ccccc2)cc1]
I-47

TABLE 1-continued
Exemplary Compounds of Formula I:
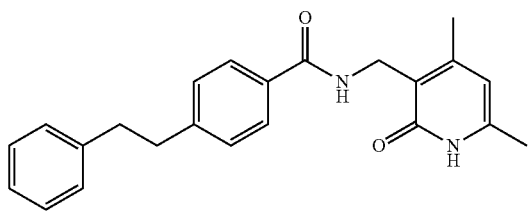 [SMILES: Cc1cc(C)c(CNC(=O)c2ccc(CCc3ccccc3)cc2)c(=O)[nH]1]
I-48
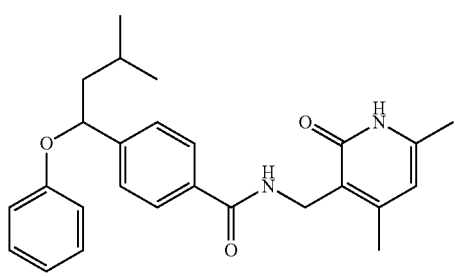 [SMILES: Cc1cc(C)c(CNC(=O)c2ccc(C(CC(C)C)Oc3ccccc3)cc2)c(=O)[nH]1]
I-49
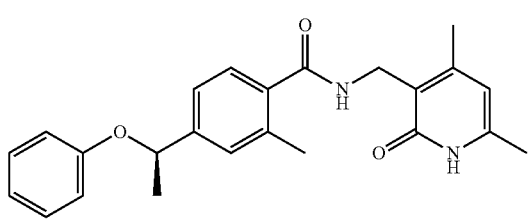 [SMILES: Cc1cc(C)c(CNC(=O)c2ccc([C@@H](C)Oc3ccccc3)cc2C)c(=O)[nH]1]
I-50
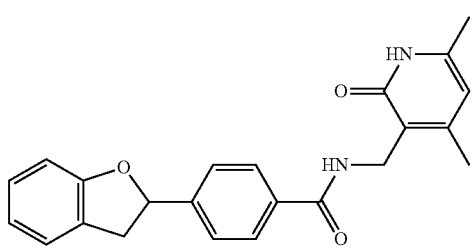 [SMILES: Cc1cc(C)c(CNC(=O)c2ccc(C3Cc4ccccc4O3)cc2)c(=O)[nH]1]
I-51
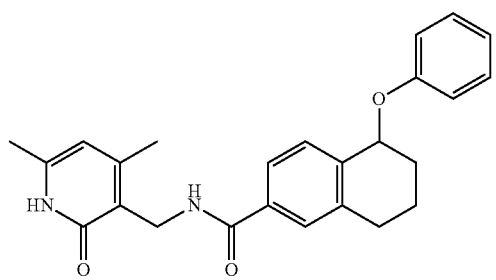 [SMILES: Cc1cc(C)c(CNC(=O)c2ccc3c(c2)CCCC3Oc2ccccc2)c(=O)[nH]1]
I-52
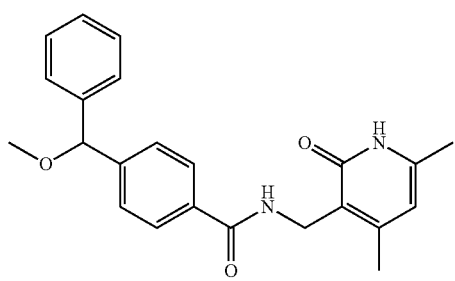
I-53

TABLE 1-continued
Exemplary Compounds of Formula I:
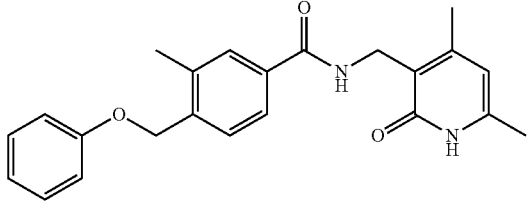 [SMILES: Cc1cc(C)c(CNC(=O)c2ccc(COc3ccccc3)c(C)c2)c(=O)[nH]1]
I-54
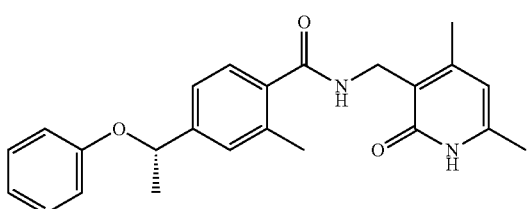
I-55
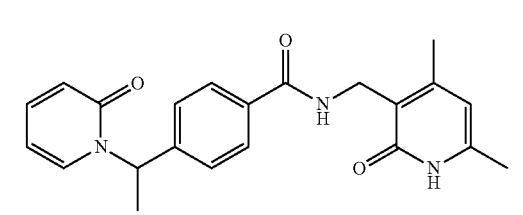 [SMILES: Cc1cc(C)c(CNC(=O)c2ccc(C(C)n3ccccc3=O)cc2)c(=O)[nH]1]
I-56
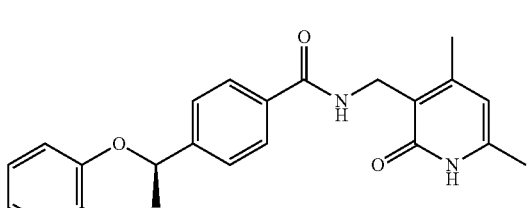
I-57
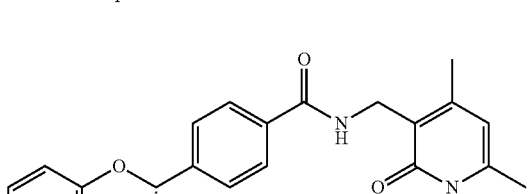
I-58
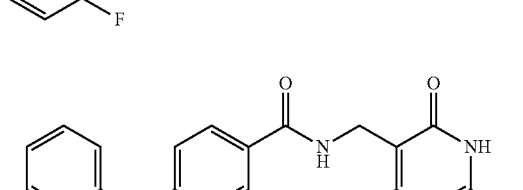
I-59
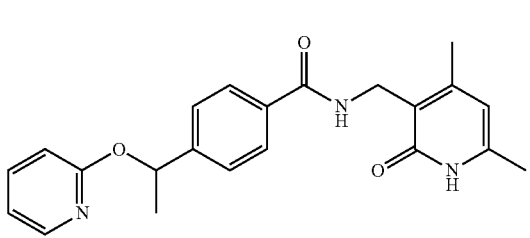 [SMILES: Cc1cc(C)c(CNC(=O)c2ccc(C(C)Oc3ccccn3)cc2)c(=O)[nH]1]
I-60

TABLE 1-continued
Exemplary Compounds of Formula I:
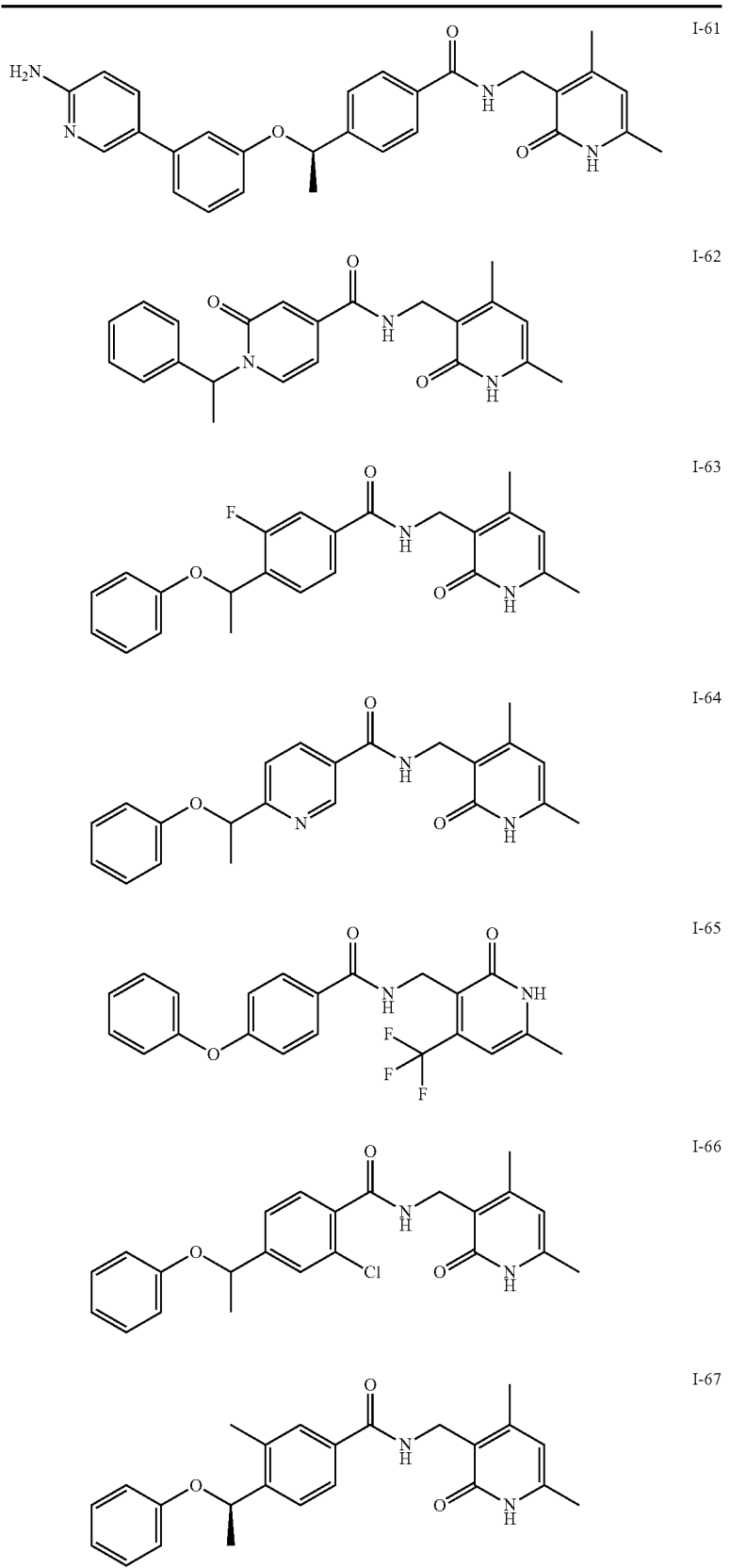
I-61
I-62
I-63
I-64
I-65
I-66
I-67

TABLE 1-continued
Exemplary Compounds of Formula I:
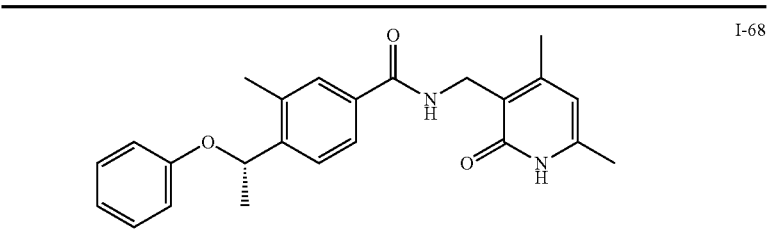
I-68
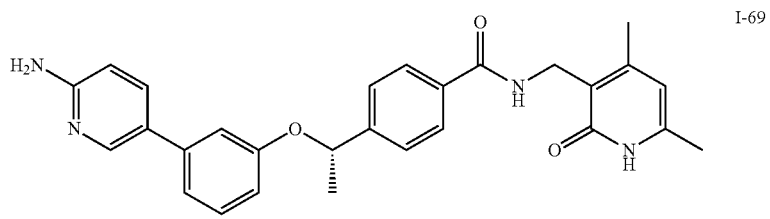
I-69
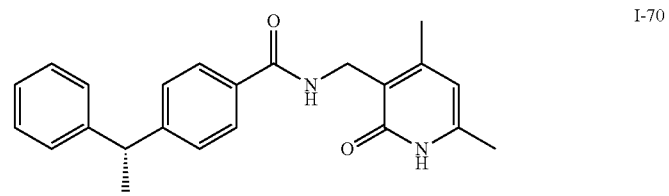
I-70
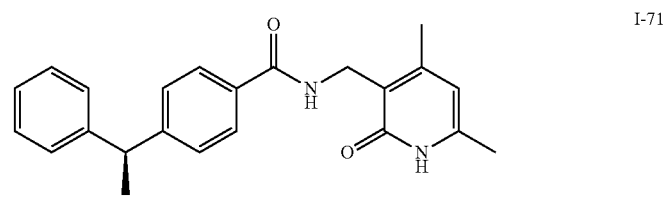
I-71
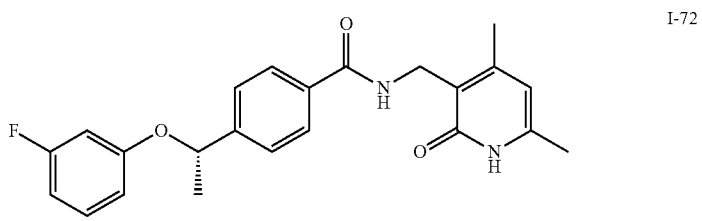
I-72
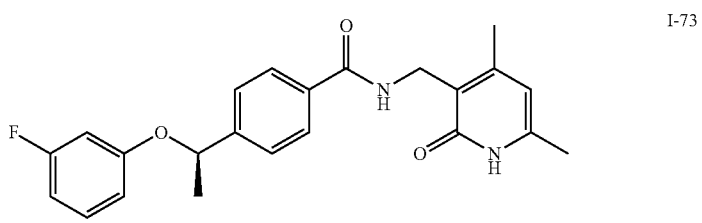
I-73
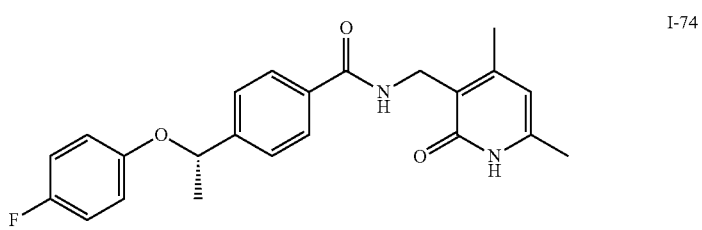
I-74

TABLE 1-continued
Exemplary Compounds of Formula I:
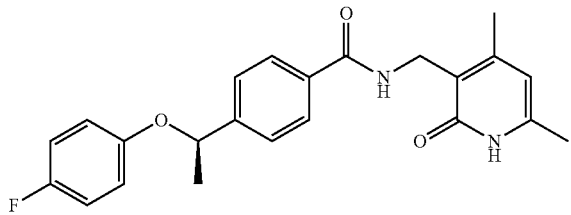 [SMILES: Cc1cc(C)c(CNC(=O)c2ccc([C@@H](C)Oc3ccc(F)cc3)cc2)c(=O)[nH]1]
I-75
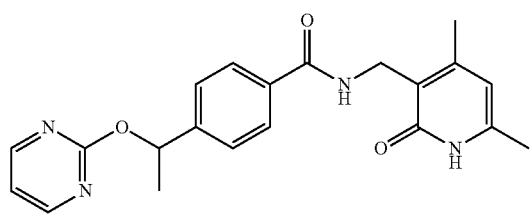 [SMILES: Cc1cc(C)c(CNC(=O)c2ccc(C(C)Oc3ncccn3)cc2)c(=O)[nH]1]
I-76
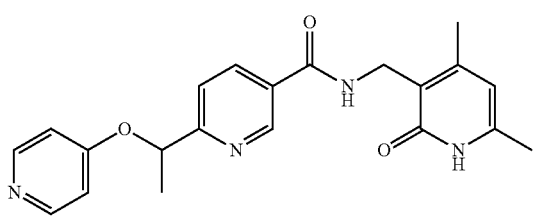 [SMILES: Cc1cc(C)c(CNC(=O)c2ccc(C(C)Oc3ccncc3)nc2)c(=O)[nH]1]
I-77
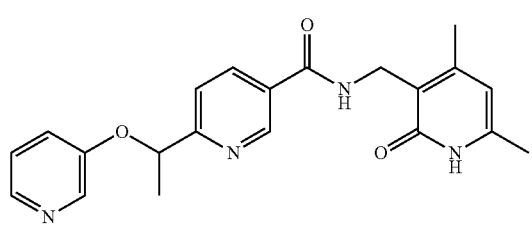 [SMILES: Cc1cc(C)c(CNC(=O)c2ccc(C(C)Oc3cccnc3)nc2)c(=O)[nH]1]
I-78
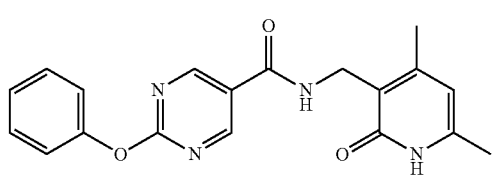 [SMILES: Cc1cc(C)c(CNC(=O)c2cnc(Oc3ccccc3)nc2)c(=O)[nH]1]
I-79
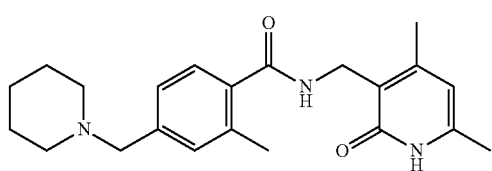 [SMILES: Cc1cc(C)c(CNC(=O)c2ccc(CN3CCCCC3)cc2C)c(=O)[nH]1]
I-80
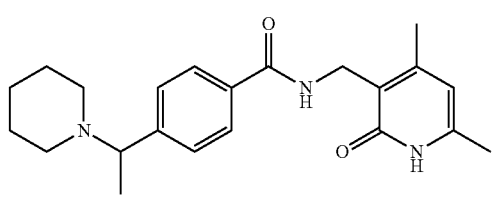 [SMILES: Cc1cc(C)c(CNC(=O)c2ccc(C(C)N3CCCCC3)cc2)c(=O)[nH]1]
I-81

TABLE 1-continued
Exemplary Compounds of Formula I:
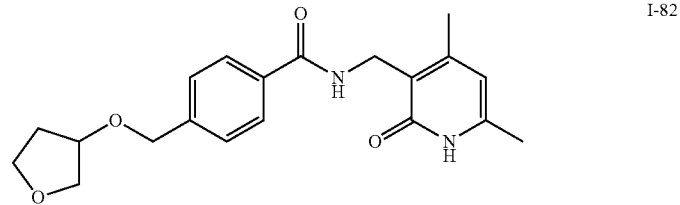
I-82
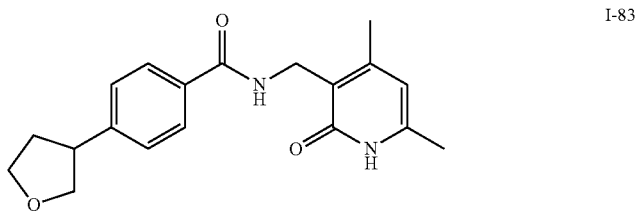
I-83
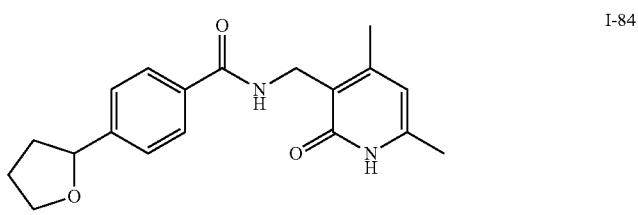
I-84
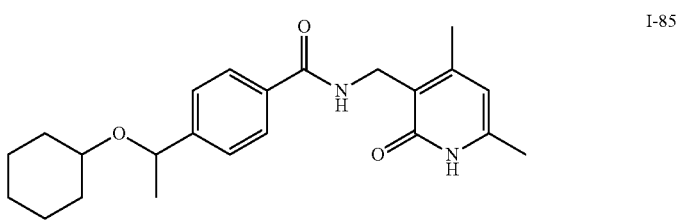
I-85
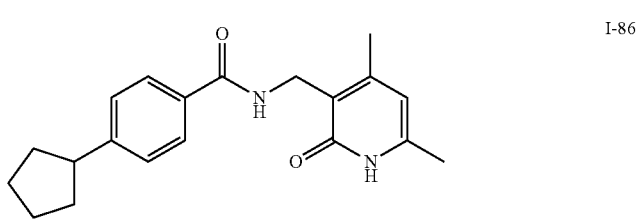
I-86
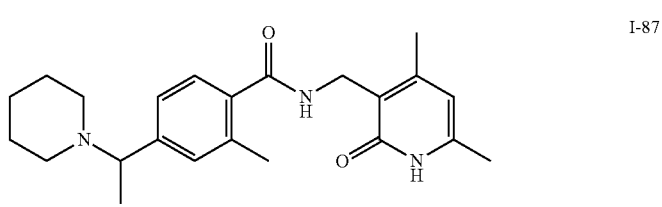
I-87
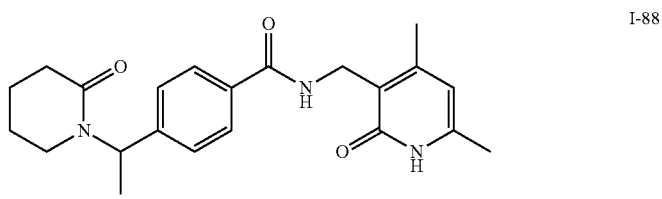
I-88

TABLE 1-continued
Exemplary Compounds of Formula I:
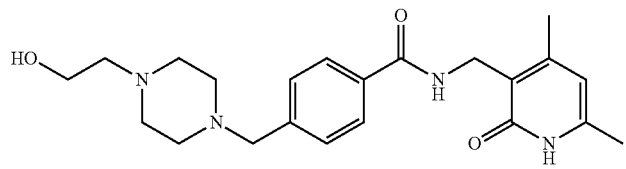 [SMILES: Cc1cc(C)c(CNC(=O)c2ccc(CN3CCN(CCO)CC3)cc2)c(=O)[nH]1]
I-89
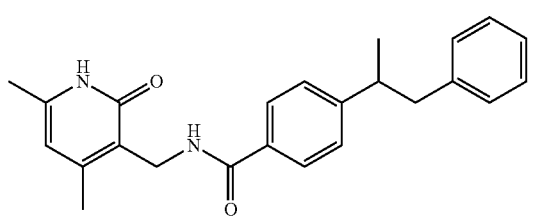 [SMILES: Cc1cc(C)c(CNC(=O)c2ccc(C(C)Cc3ccccc3)cc2)c(=O)[nH]1]
I-90
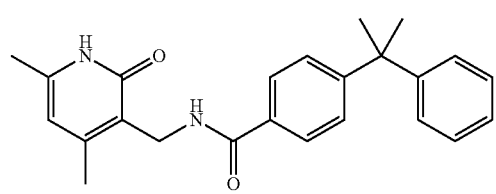 [SMILES: Cc1cc(C)c(CNC(=O)c2ccc(C(C)(C)c3ccccc3)cc2)c(=O)[nH]1]
I-91
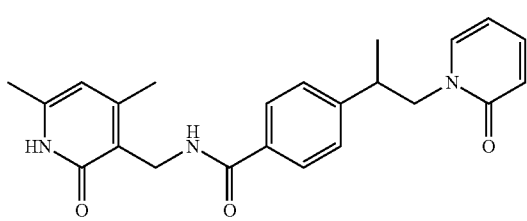 [SMILES: Cc1cc(C)c(CNC(=O)c2ccc(C(C)Cn3ccccc3=O)cc2)c(=O)[nH]1]
I-92
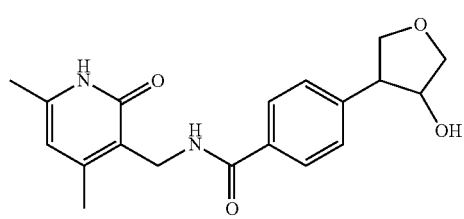 [SMILES: Cc1cc(C)c(CNC(=O)c2ccc(C3COCC3O)cc2)c(=O)[nH]1]
I-93
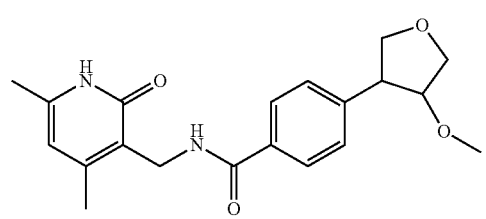
I-94
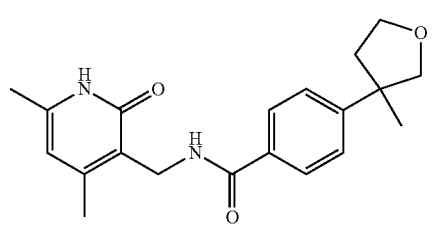 [SMILES: Cc1cc(C)c(CNC(=O)c2ccc(C3(C)CCOC3)cc2)c(=O)[nH]1]
I-95

TABLE 1-continued
Exemplary Compounds of Formula I:
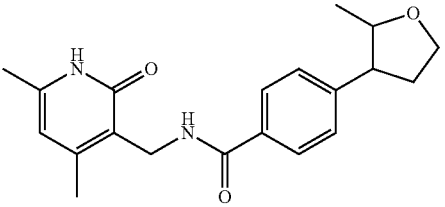 [SMILES: Cc1cc(C)c(CNC(=O)c2ccc(C3CCOC3C)cc2)c(=O)[nH]1]
I-96
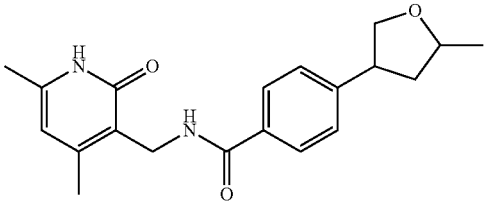
I-97
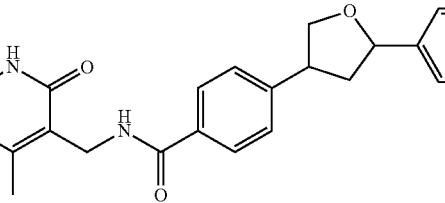
I-98
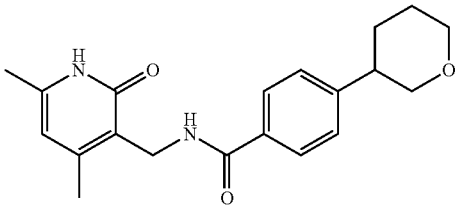 [SMILES: Cc1cc(C)c(CNC(=O)c2ccc(C3CCCOC3)cc2)c(=O)[nH]1]
I-99
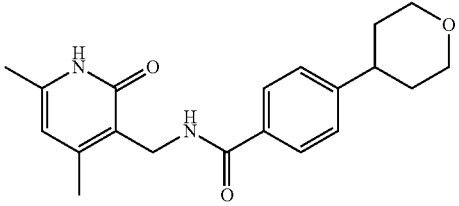 [SMILES: Cc1cc(C)c(CNC(=O)c2ccc(C3CCOCC3)cc2)c(=O)[nH]1]
I-100
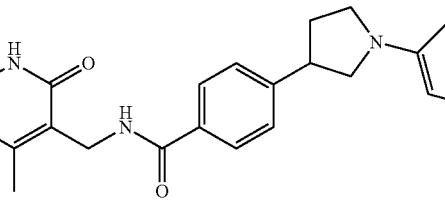
I-102
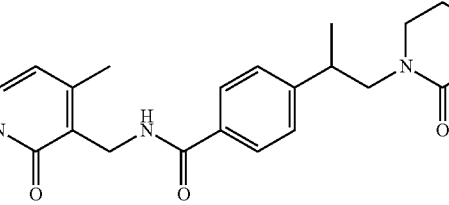
I-103

TABLE 1-continued
Exemplary Compounds of Formula I:
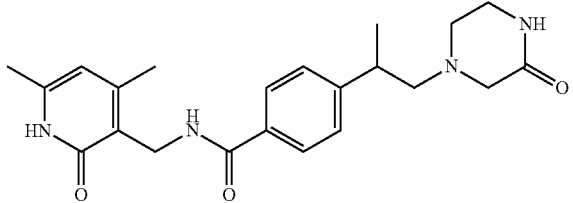 [SMILES: Cc1cc(C)c(CNC(=O)c2ccc(C(C)CN3CCNC(=O)C3)cc2)c(=O)[nH]1]
I-104
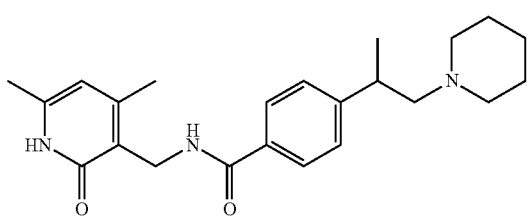 [SMILES: Cc1cc(C)c(CNC(=O)c2ccc(C(C)CN3CCCCC3)cc2)c(=O)[nH]1]
I-105
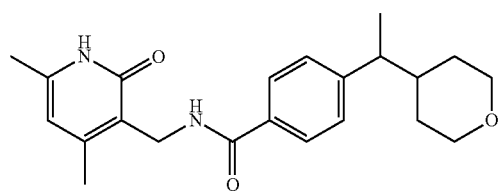 [SMILES: Cc1cc(C)c(CNC(=O)c2ccc(C(C)C3CCOCC3)cc2)c(=O)[nH]1]
I-106
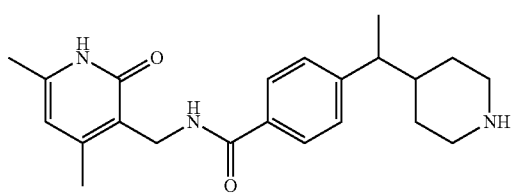 [SMILES: Cc1cc(C)c(CNC(=O)c2ccc(C(C)C3CCNCC3)cc2)c(=O)[nH]1]
I-107
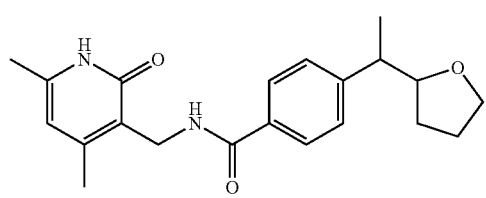 [SMILES: Cc1cc(C)c(CNC(=O)c2ccc(C(C)C3CCCO3)cc2)c(=O)[nH]1]
I-108
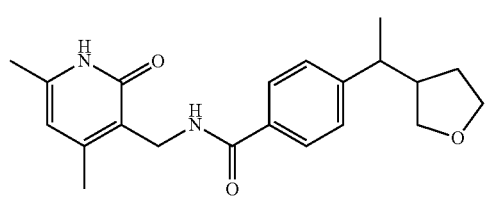 [SMILES: Cc1cc(C)c(CNC(=O)c2ccc(C(C)C3CCOC3)cc2)c(=O)[nH]1]
I-109
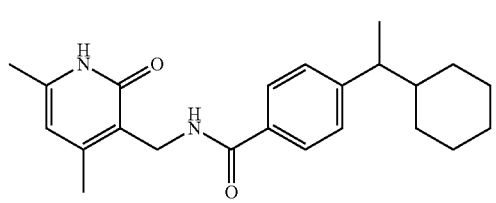 [SMILES: Cc1cc(C)c(CNC(=O)c2ccc(C(C)C3CCCCC3)cc2)c(=O)[nH]1]
I-110

US 9,206,128 B2
TABLE 1-continued
Exemplary Compounds of Formula I:
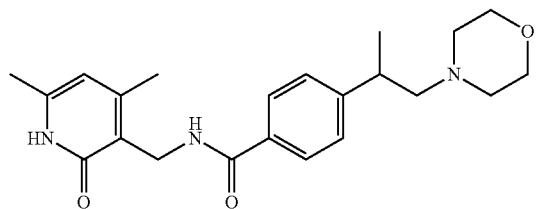 [SMILES: Cc1cc(C)c(CNC(=O)c2ccc(C(C)CN3CCOCC3)cc2)c(=O)[nH]1] I-111
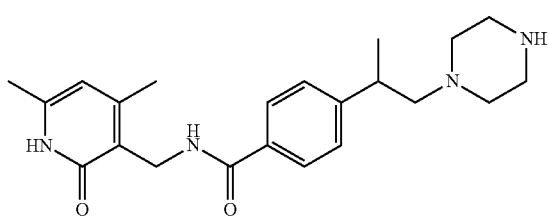 [SMILES: Cc1cc(C)c(CNC(=O)c2ccc(C(C)CN3CCNCC3)cc2)c(=O)[nH]1] I-112
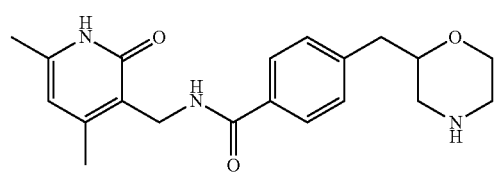 [SMILES: Cc1cc(C)c(CNC(=O)c2ccc(CC3CNCCO3)cc2)c(=O)[nH]1] I-113
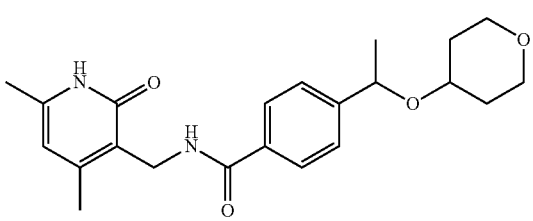 [SMILES: Cc1cc(C)c(CNC(=O)c2ccc(C(C)OC3CCOCC3)cc2)c(=O)[nH]1] I-114
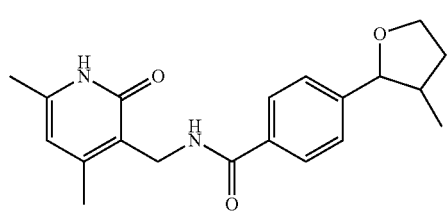 [SMILES: Cc1cc(C)c(CNC(=O)c2ccc(C3OCCC3C)cc2)c(=O)[nH]1] I-115
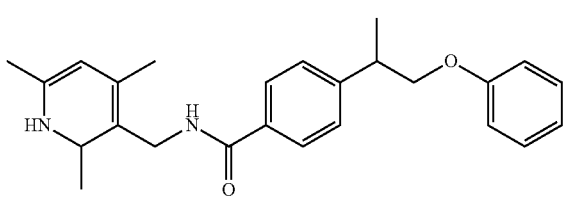 [SMILES: CC1=CC(C)=C(CNC(=O)c2ccc(C(C)COc3ccccc3)cc2)C(C)N1] I-116
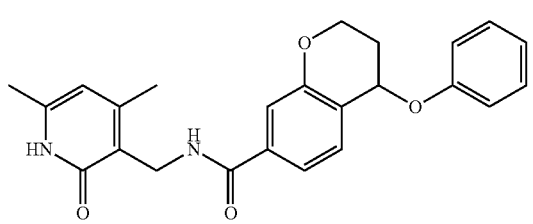 [SMILES: Cc1cc(C)c(CNC(=O)c2ccc3c(c2)OCCC3Oc2ccccc2)c(=O)[nH]1] I-117

TABLE 1-continued
Exemplary Compounds of Formula I:
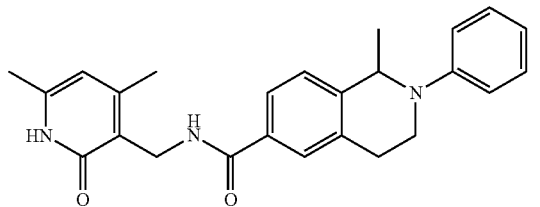 [SMILES: Cc1cc(C)c(CNC(=O)c2ccc3c(c2)CCN(c2ccccc2)C3C)c(=O)[nH]1]
I-118
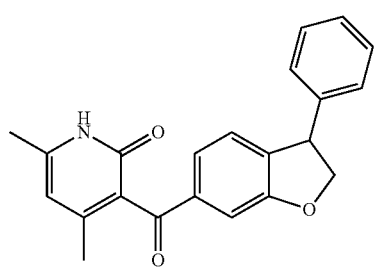 [SMILES: Cc1cc(C)c(C(=O)c2ccc3c(c2)OCC3c2ccccc2)c(=O)[nH]1]
I-119
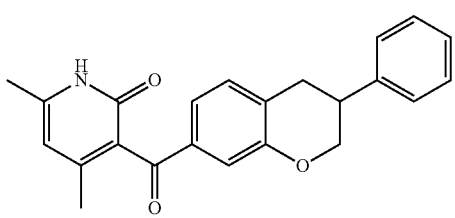 [SMILES: Cc1cc(C)c(C(=O)c2ccc3c(c2)OCC(c2ccccc2)C3)c(=O)[nH]1]
I-120
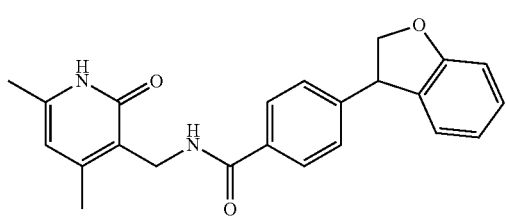 [SMILES: Cc1cc(C)c(CNC(=O)c2ccc(C3COc4ccccc43)cc2)c(=O)[nH]1]
I-121
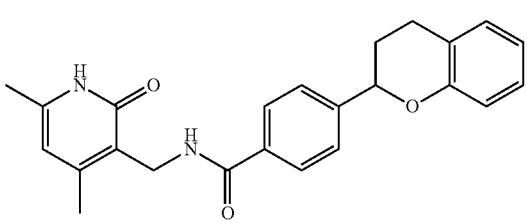 [SMILES: Cc1cc(C)c(CNC(=O)c2ccc(C3CCc4ccccc4O3)cc2)c(=O)[nH]1]
I-122
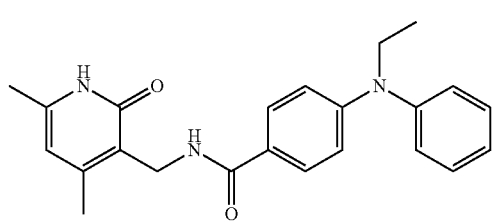 [SMILES: CCN(c1ccccc1)c1ccc(C(=O)NCc2c(C)cc(C)[nH]c2=O)cc1]
I-123

TABLE 1-continued
Exemplary Compounds of Formula I:
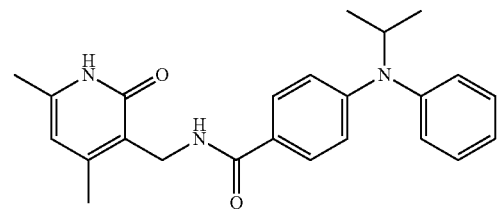 [SMILES: Cc1cc(C)c(CNC(=O)c2ccc(N(c3ccccc3)C(C)C)cc2)c(=O)[nH]1]
I-124
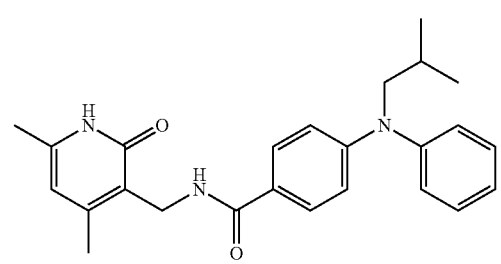 [SMILES: Cc1cc(C)c(CNC(=O)c2ccc(N(CC(C)C)c3ccccc3)cc2)c(=O)[nH]1]
I-125
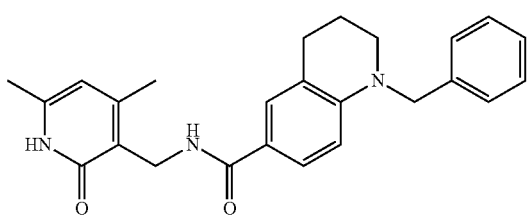 [SMILES: Cc1cc(C)c(CNC(=O)c2ccc3c(c2)CCCN3Cc2ccccc2)c(=O)[nH]1]
I-126
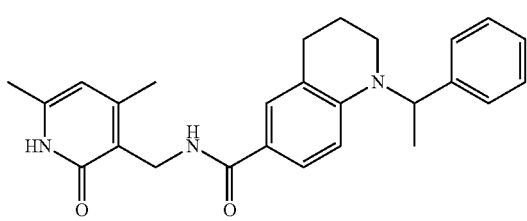 [SMILES: Cc1cc(C)c(CNC(=O)c2ccc3c(c2)CCCN3C(C)c2ccccc2)c(=O)[nH]1]
I-127
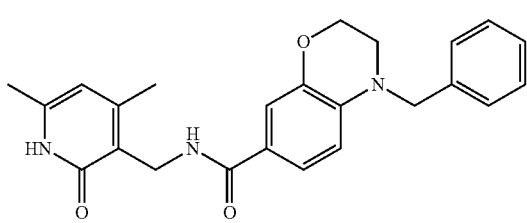 [SMILES: Cc1cc(C)c(CNC(=O)c2ccc3c(c2)OCCN3Cc2ccccc2)c(=O)[nH]1]
I-128
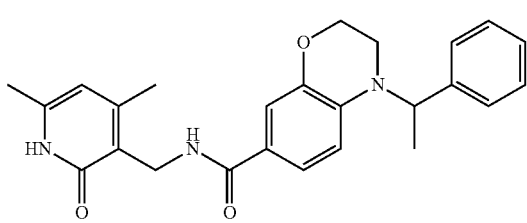 [SMILES: Cc1cc(C)c(CNC(=O)c2ccc3c(c2)OCCN3C(C)c2ccccc2)c(=O)[nH]1]
I-129

TABLE 1-continued
Exemplary Compounds of Formula I:
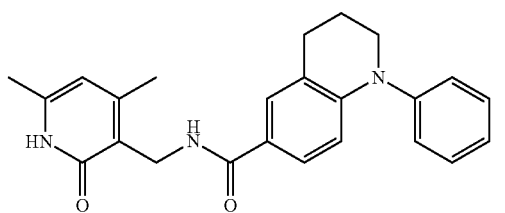 [SMILES: Cc1cc(C)c(CNC(=O)c2ccc3c(c2)CCCN3c2ccccc2)c(=O)[nH]1]
I-130
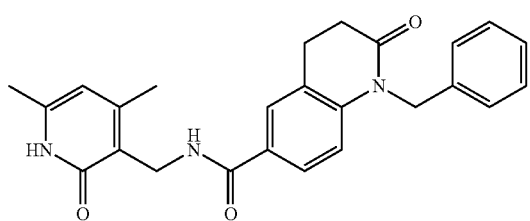 [SMILES: Cc1cc(C)c(CNC(=O)c2ccc3c(c2)CCC(=O)N3Cc2ccccc2)c(=O)[nH]1]
I-131
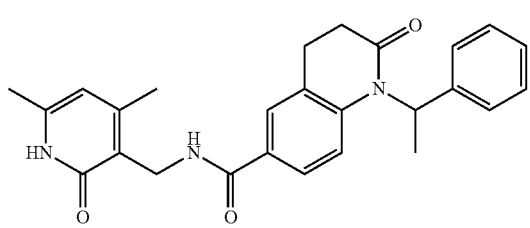 [SMILES: Cc1cc(C)c(CNC(=O)c2ccc3c(c2)CCC(=O)N3C(C)c2ccccc2)c(=O)[nH]1]
I-132
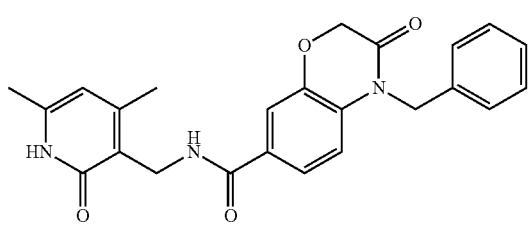 [SMILES: Cc1cc(C)c(CNC(=O)c2ccc3c(c2)OCC(=O)N3Cc2ccccc2)c(=O)[nH]1]
I-133
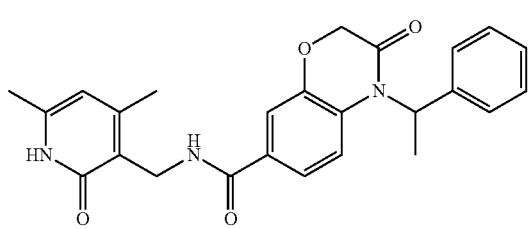 [SMILES: Cc1cc(C)c(CNC(=O)c2ccc3c(c2)OCC(=O)N3C(C)c2ccccc2)c(=O)[nH]1]
I-134
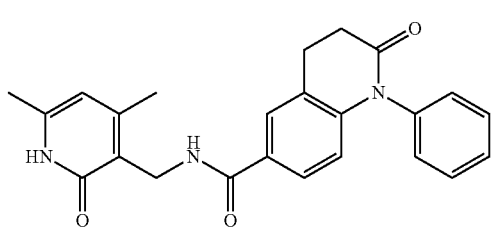 [SMILES: Cc1cc(C)c(CNC(=O)c2ccc3c(c2)CCC(=O)N3c2ccccc2)c(=O)[nH]1]
I-135

TABLE 1-continued
Exemplary Compounds of Formula I:
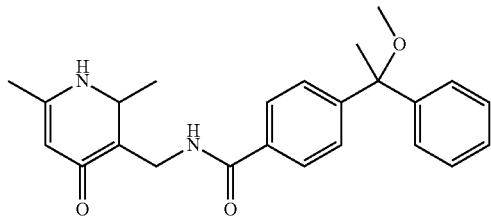
I-136
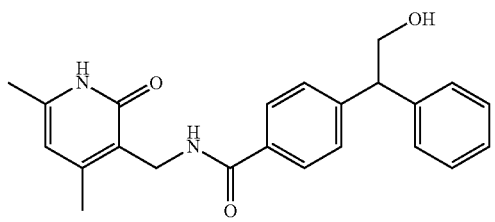 [SMILES: Cc1cc(C)c(CNC(=O)c2ccc(C(CO)c3ccccc3)cc2)c(=O)[nH]1]
I-137
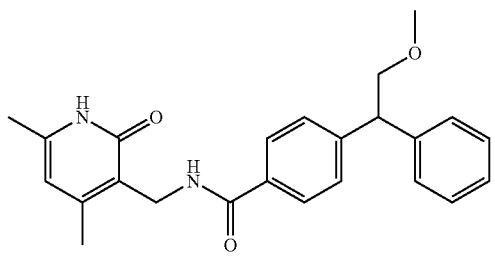 [SMILES: COCC(c1ccccc1)c1ccc(C(=O)NCc2c(C)cc(C)[nH]c2=O)cc1]
I-138
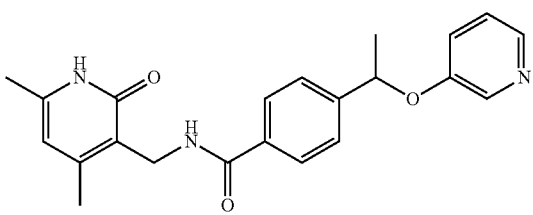 [SMILES: Cc1cc(C)c(CNC(=O)c2ccc(C(C)Oc3cccnc3)cc2)c(=O)[nH]1]
I-139
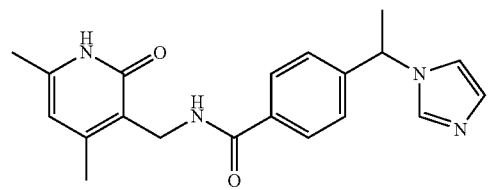 [SMILES: Cc1cc(C)c(CNC(=O)c2ccc(C(C)n3ccnc3)cc2)c(=O)[nH]1]
I-140
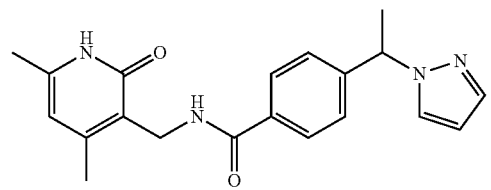 [SMILES: Cc1cc(C)c(CNC(=O)c2ccc(C(C)n3cccn3)cc2)c(=O)[nH]1]
I-141

TABLE 1-continued
Exemplary Compounds of Formula I:
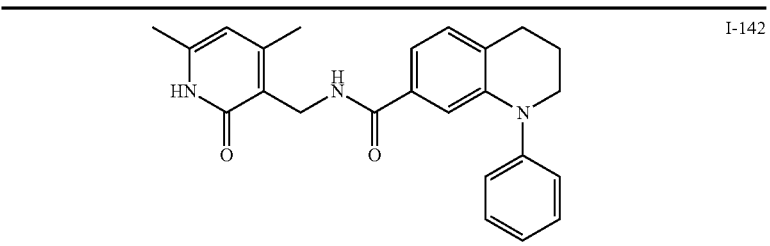
I-142
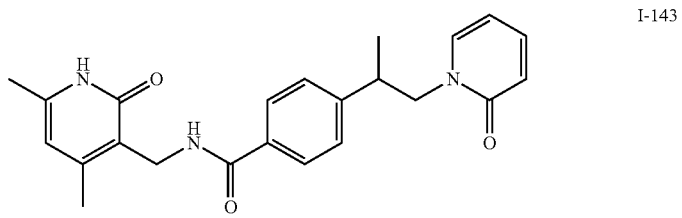
I-143
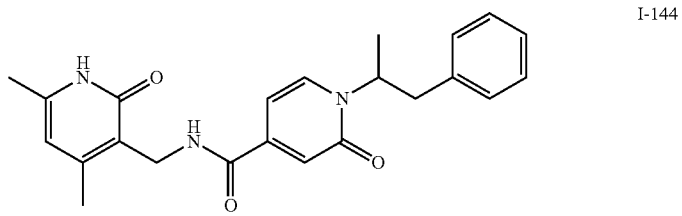
I-144
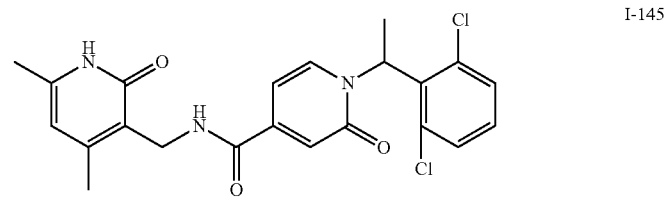
I-145
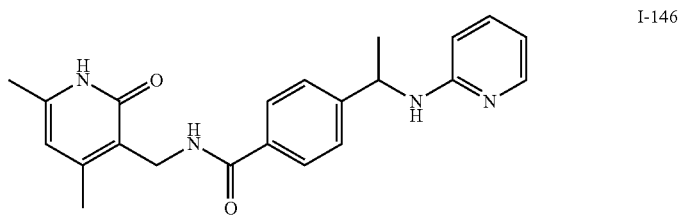
I-146
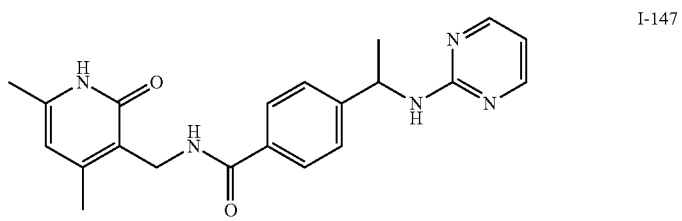
I-147
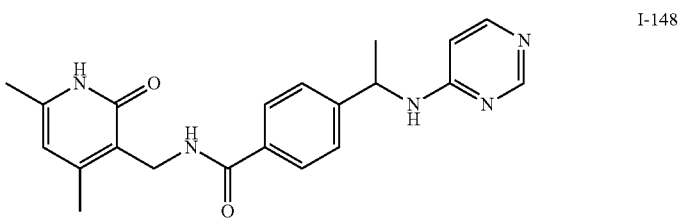
I-148

TABLE 1-continued
Exemplary Compounds of Formula I:
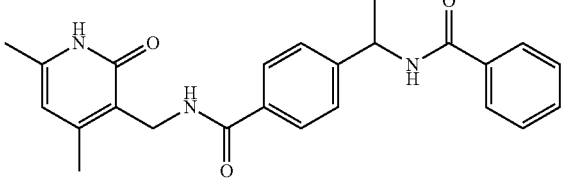 [SMILES: Cc1cc(C)c(CNC(=O)c2ccc(C(C)NS(=O)(=O)c3ccccc3)cc2)c(=O)[nH]1]
I-149
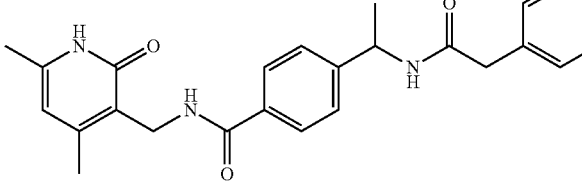
I-150
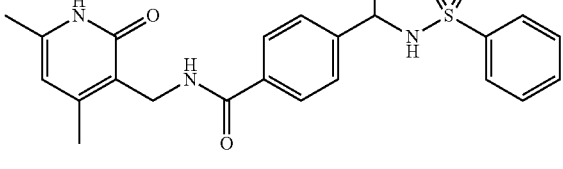
I-151
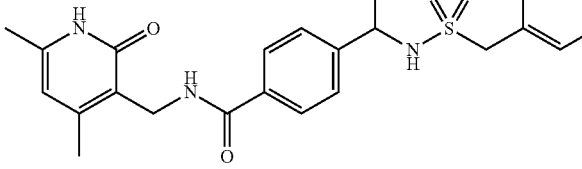
I-152
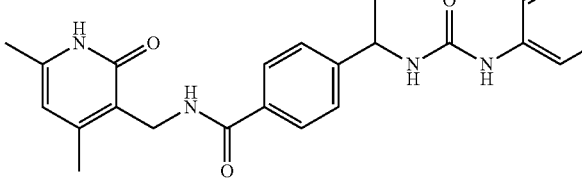
I-153
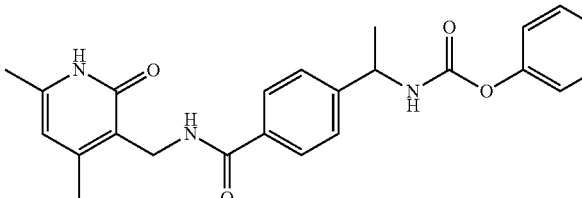
I-154
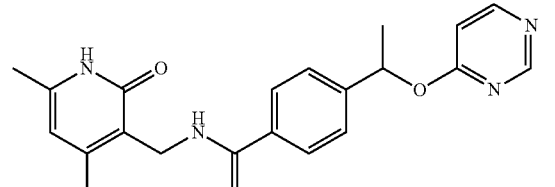
I-155

TABLE 1-continued
Exemplary Compounds of Formula I:
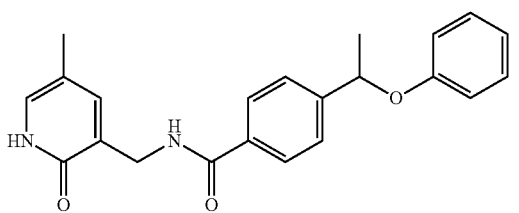 [SMILES: Cc1c[nH]c(=O)c(CNC(=O)c2ccc(C(C)Oc3ccccc3)cc2)c1]
I-156
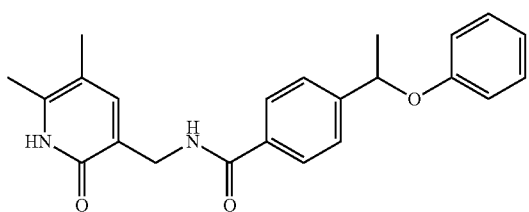 [SMILES: Cc1cc(CNC(=O)c2ccc(C(C)Oc3ccccc3)cc2)c(=O)[nH]c1C]
I-157
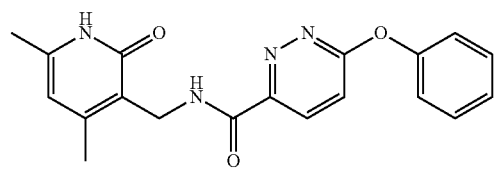 [SMILES: Cc1cc(C)c(CNC(=O)c2ccc(Oc3ccccc3)nn2)c(=O)[nH]1]
I-158
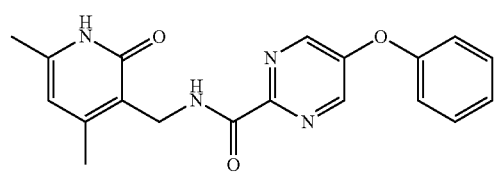 [SMILES: Cc1cc(C)c(CNC(=O)c2ncc(Oc3ccccc3)cn2)c(=O)[nH]1]
I-159
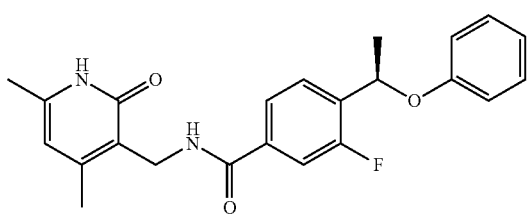 [SMILES: Cc1cc(C)c(CNC(=O)c2ccc([C@@H](C)Oc3ccccc3)c(F)c2)c(=O)[nH]1]
I-160
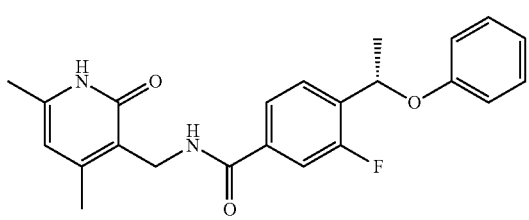 [SMILES: Cc1cc(C)c(CNC(=O)c2ccc([C@H](C)Oc3ccccc3)c(F)c2)c(=O)[nH]1]
I-161
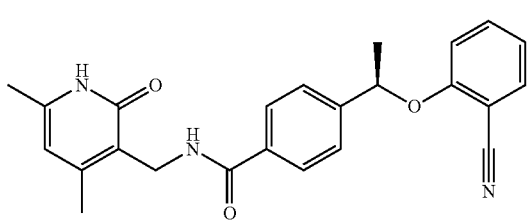 [SMILES: Cc1cc(C)c(CNC(=O)c2ccc([C@@H](C)Oc3ccccc3C#N)cc2)c(=O)[nH]1]
I-162

TABLE 1-continued
Exemplary Compounds of Formula I:
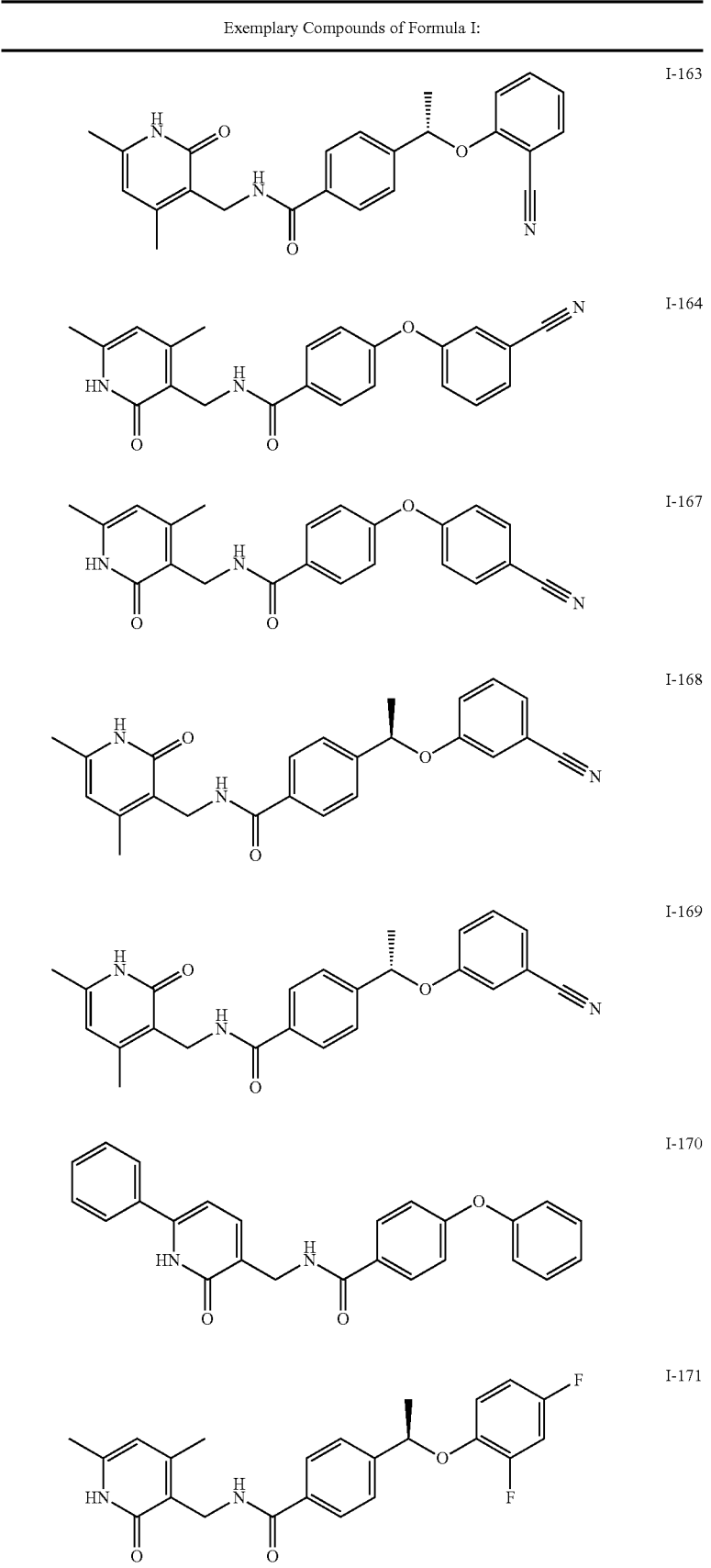
I-163
I-164
I-167
I-168
I-169
I-170
I-171

TABLE 1-continued
Exemplary Compounds of Formula I:
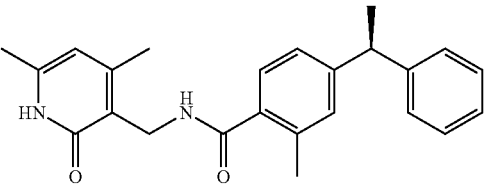 [SMILES: Cc1cc(C)c(CNC(=O)c2ccc([C@@H](C)c3ccccc3)cc2C)c(=O)[nH]1]  I-172
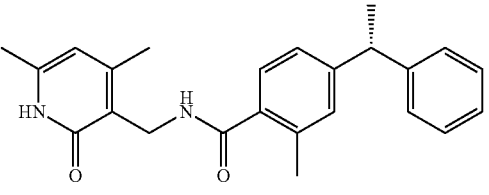 [SMILES: Cc1cc(C)c(CNC(=O)c2ccc([C@H](C)c3ccccc3)cc2C)c(=O)[nH]1]  I-173
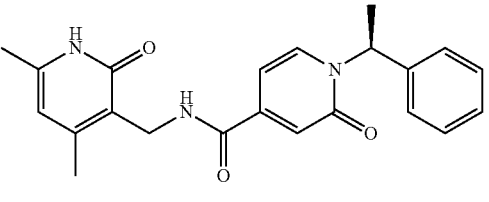 [SMILES: Cc1cc(C)c(CNC(=O)c2ccn([C@@H](C)c3ccccc3)c(=O)c2)c(=O)[nH]1]  I-174
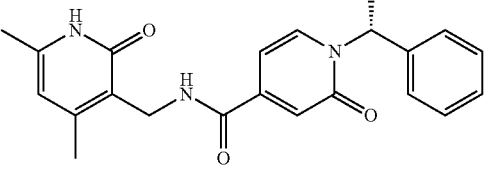  I-175
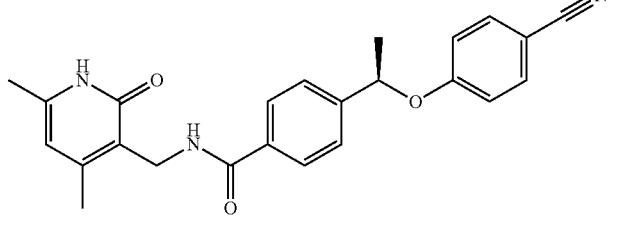  I-176
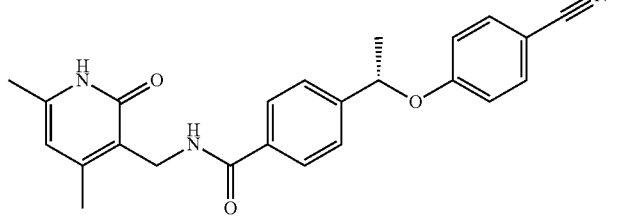  I-177
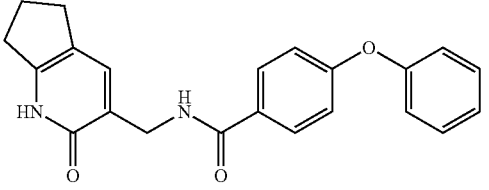 [SMILES: O=C(NCc1cc2c([nH]c1=O)CCC2)c1ccc(Oc2ccccc2)cc1]  I-178

TABLE 1-continued
Exemplary Compounds of Formula I:
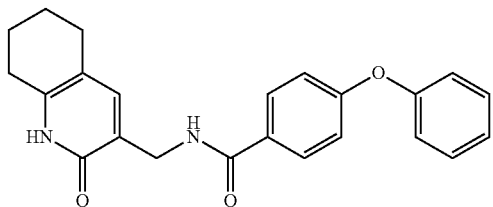 [SMILES: O=C(NCc1cc2c([nH]c1=O)CCCC2)c1ccc(Oc2ccccc2)cc1]
I-179
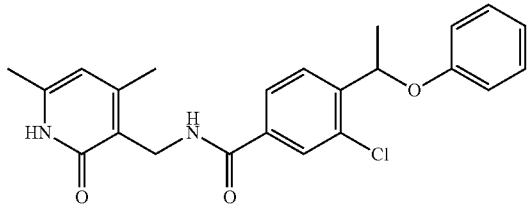 [SMILES: Cc1cc(C)c(CNC(=O)c2ccc(C(C)Oc3ccccc3)c(Cl)c2)c(=O)[nH]1]
I-180
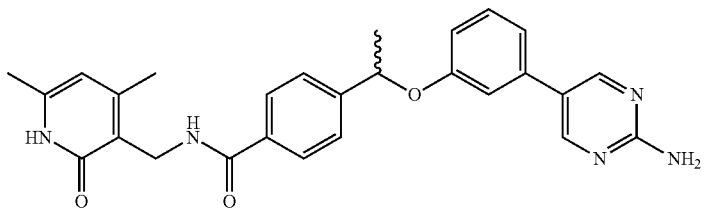 [SMILES: Cc1cc(C)c(CNC(=O)c2ccc(C(C)Oc3cccc(-c4cnc(N)nc4)c3)cc2)c(=O)[nH]1]
I-181
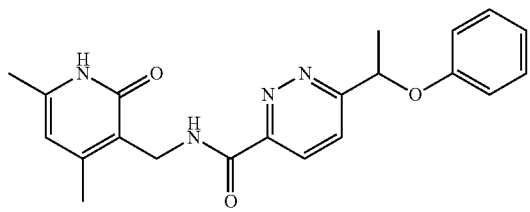 [SMILES: Cc1cc(C)c(CNC(=O)c2ccc(C(C)Oc3ccccc3)nn2)c(=O)[nH]1]
I-182
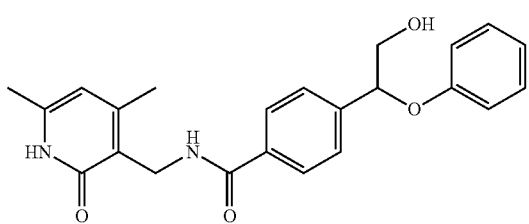 [SMILES: Cc1cc(C)c(CNC(=O)c2ccc(C(CO)Oc3ccccc3)cc2)c(=O)[nH]1]
I-183
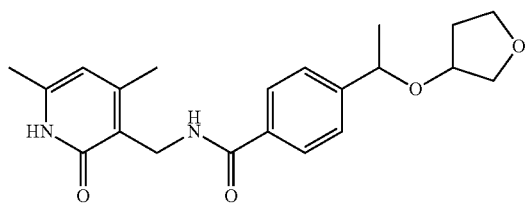 [SMILES: Cc1cc(C)c(CNC(=O)c2ccc(C(C)OC3CCOC3)cc2)c(=O)[nH]1]
I-184
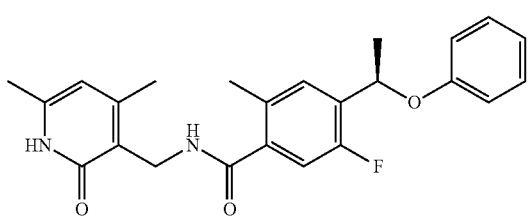 [SMILES: Cc1cc(C)c(CNC(=O)c2cc(F)c([C@@H](C)Oc3ccccc3)cc2C)c(=O)[nH]1]
I-185

TABLE 1-continued
Exemplary Compounds of Formula I:
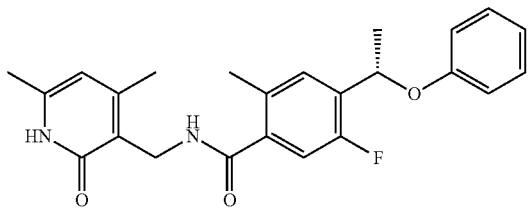 [SMILES: Cc1cc(C)c(CNC(=O)c2cc(F)c([C@H](C)Oc3ccccc3)cc2C)c(=O)[nH]1] I-186
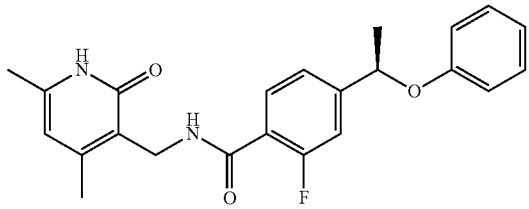 [SMILES: Cc1cc(C)c(CNC(=O)c2ccc([C@@H](C)Oc3ccccc3)cc2F)c(=O)[nH]1] I-187
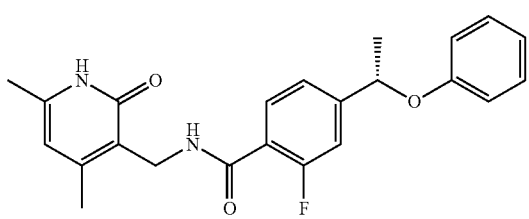 [SMILES: Cc1cc(C)c(CNC(=O)c2ccc([C@H](C)Oc3ccccc3)cc2F)c(=O)[nH]1] I-188
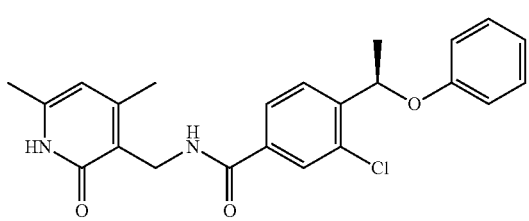 [SMILES: Cc1cc(C)c(CNC(=O)c2ccc([C@@H](C)Oc3ccccc3)c(Cl)c2)c(=O)[nH]1] I-189
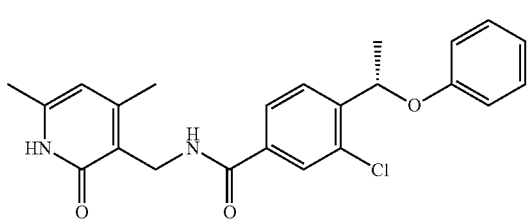 [SMILES: Cc1cc(C)c(CNC(=O)c2ccc([C@H](C)Oc3ccccc3)c(Cl)c2)c(=O)[nH]1] I-190
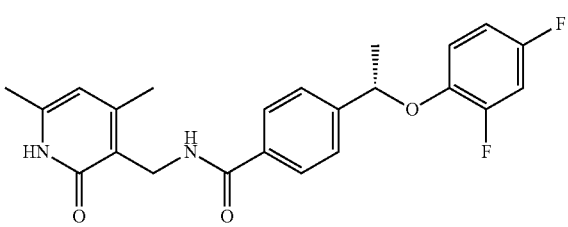 [SMILES: Cc1cc(C)c(CNC(=O)c2ccc([C@H](C)Oc3ccc(F)cc3F)cc2)c(=O)[nH]1] I-191
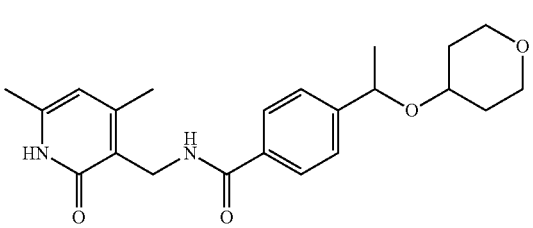 I-192

TABLE 1-continued
Exemplary Compounds of Formula I:
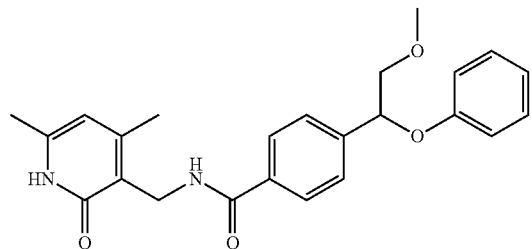 [SMILES: COCC(Oc1ccccc1)c1ccc(C(=O)NCc2c(C)cc(C)[nH]c2=O)cc1]
I-193
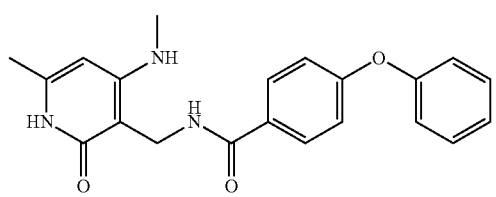 [SMILES: CNc1cc(C)[nH]c(=O)c1CNC(=O)c1ccc(Oc2ccccc2)cc1]
I-194
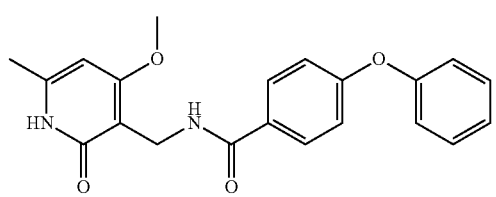 [SMILES: COc1cc(C)[nH]c(=O)c1CNC(=O)c1ccc(Oc2ccccc2)cc1]
I-195
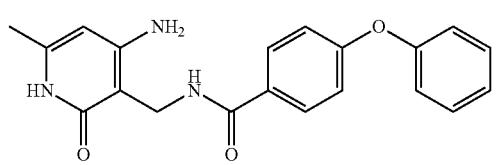 [SMILES: Cc1cc(N)c(CNC(=O)c2ccc(Oc3ccccc3)cc2)c(=O)[nH]1]
I-196
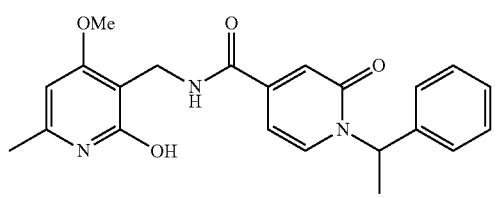 [SMILES: COc1cc(C)nc(O)c1CNC(=O)c1ccn(C(C)c2ccccc2)c(=O)c1]
I-197
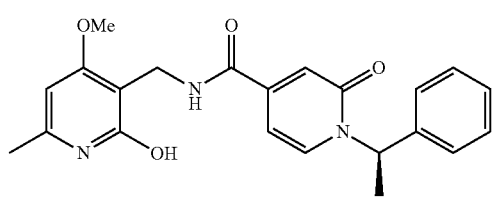 [SMILES: COc1cc(C)nc(O)c1CNC(=O)c1ccn([C@H](C)c2ccccc2)c(=O)c1]
I-198
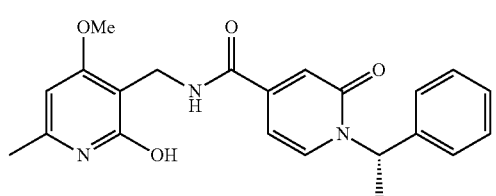
I-199

TABLE 1-continued

Exemplary Compounds of Formula I:

| | |
|---|---|
| (structure) | I-200 |
| (structure) | I-201 |
| (structure) | I-202 |
| (structure) | I-203 |
| (structure) | I-204 |
| (structure) | I-205 |
| (structure) | I-206 |

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate a histone methyl modifying enzyme, or a mutant thereof, in a biological sample or in a patient. In certain embodiments, the amount of compound in compositions of this invention is such that is effective to measurably modulate a histone methyl modifying enzyme, or a mutant thereof, in a biological sample or in a patient.

In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation.

Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulating of activity of one or more enzymes involved in epigenetic regulation.

Epigenetics is the study of heritable changes in gene expression caused by mechanisms other than changes in the underlying DNA sequence. Molecular mechanisms that play a role in epigenetic regulation include DNA methylation and chromatin/histone modifications. Histone methylation, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) *Curr. Opin. Genet. Dev.* 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) *Nature* 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation, sumoylation, ubiquitination, citrullination, deimination, and biotinylation. The core of histones H2A and H3 can also be modified. Histone modifications are integral to diverse biological processes such as gene regulation, DNA repair, and chromosome condensation.

The present disclosure provides compounds and compositions for modulating activity of histone methyl modifying enzymes. Histone methyl modifying enzymes are key regulators of cellular and developmental processes. Histone methyl modifying enzymes may be characterized as either histone methyl transferases or histone demethylases. Histone demethylase enzymes have modules that mediate binding to methylated residues. For example, multiple demethylases contain a Tudor domain (e.g., JMJD2C/GASC1) or a PHD domain (e.g., JARID1C/SMCX, PHF8).

The lysine specificities of many histone methyltransferases have been characterized. For example SET7/9, SMYD3, and MLL1-5 are specific for H3K4. SUV39H1, DIM-5, and G9a are specific for H3K9. SET8 is specific for H4K20.

DOT1 is an example of a non-SET domain containing histone methylase. DOT1 methylates H3 on lysine 79.

Just as histone methylases have been shown to regulate transcriptional activity, chromatin structure, and gene silencing, demethylases have also been discovered which impact gene expression. LSD1 was the first histone lysine demethylase to be characterized. This enzyme displays homology to FAD-dependent amine oxidases and acts as a transcriptional corepressor of neuronal genes (Shi et al., Cell 119:941-953, 2004). Additional demethylases defining separate demethylase families have been discovered, including JHDM1 (or KDM2), JHDM2 (or KDM3), JMJD2 (or KDM4), JARID (or KDM5), JMJD3 (or KDM6), and JMJD6 families (Lan et al., Curr. Opin. Cell Biol. 20(3):316-325, 2008).

Demethylases act on specific lysine residues within substrate sequences and discriminate between the degree of methylation present on a given residue. For example, LSD1 removes mono- or dimethyl-groups from H3K4. Members of the JARID1A-D family remove trimethyl groups from H3K4. UTX and JMJD3 demethylate H3K27, counteracting effects of EZH2 methylase activity. Substrate specificities of other demethylases have been characterized (see Shi, Nat. Rev. 8:829-833, 2007).

One class of histone methylases is characterized by the presence of a SET domain, named after proteins that share the domain, Su(var)$_{3-9}$, enhancer of zeste [E(Z)], and trithorax. A SET domain includes about 130 amino acids. SET domain-containing methylase families include SUV39H1, SET1, SET2, EZH2, RIZ1, SMYD3, SUV4-20H1, SET7/9, and PR-SET7/SET8 families (reviewed in Dillon et al., Genome Biol. 6:227, 2005). Members of a family typically include similar sequence motifs in the vicinity of and within the SET domain. The human genome encodes over 50 SET domain-containing histone protein methylases, any of which can be used in an assay described herein.

EZH2 is an example of a human SET-domain containing methylase. EZH2 associates with EED (Embryonic Ectoderm Development) and SUZ12 (suppressor of zeste 12 homolog) to form a complex known as PRC2 (Polycomb Group Repressive Complex 2) having the ability to tri-methylate histone H3 at lysine 27 (Cao and Zhang, Mol. Cell. 15:57-67, 2004). PRC2 complexes can also include RBAP46 and RBAP48 subunits.

The oncogenic activities of EZH2 have been shown by a number of studies. In cell line experiments, over-expression of EZH2 induces cell invasion, growth in soft agar, and motility while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor supressors, including E-cadherin, DAB21P and RUNX3 among others. In xenograft models, EZH2 knockdown inhibits tumor growth and metastasis. Recently, it has been shown that down modulation of EZH2 in murine models blocks prostate cancer metastasis (Min et al., "An oncogene-tumor suppressor cascade drives metastatic prostate cancer by coordinately activating Ras and nuclear factor-kappaB," Nat. Med. 2010 March; 16(3):286-94). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18; 17(5):443-454).

In some embodiments, compounds of the present invention modulate the activity of one or more enzymes involved in epigenetic regulation. In some embodiments, compounds of the present invention modulate the activity of a histone methyl modifying enzyme, or a mutant thereof. In some embodiments, compounds of the present invention modulate EZH2 activity. In some embodiments, compounds of the present invention down-regulate or suppress the activity of EZH2. In some embodiments, compounds of the present invention are antagonists of EZH2 activity.

In some embodiments, compounds and compositions of the present invention are useful in treating diseases and/or disorders associated with a histone methyl modifying enzyme. Accordingly, in some embodiments, the present invention provides a method of modulating a disease and/or disorder associated with a histone methyl modifying enzyme. In some embodiments, the present invention provides a method of treating a subject suffering from a disease and/or disorder associated with a histone methyl modifying enzyme comprising the step of administering a compound or composition of formula I.

In some embodiments, compounds and compositions of the present invention are useful in treating diseases and/or disorders associated with overexpression of EZH2. In some embodiments, the present invention provides a method of treating a subject suffering from a disease and/or disorder associated with overexpression of EZH2 comprising the step of administering a compound or composition of formula I. In some embodiments, the above method additionally comprises the preliminary step of determining if the subject is overexpressing EZH2.

In some embodiments, compounds and compositions of the present invention are useful in treating diseases and/or disorders associated with cellular proliferation. In some embodiments, compounds and compositions of the present invention are useful in treating diseases and/or disorders associated with misregulation of cell cycle or DNA repair. In some embodiments, compounds and compositions of the present invention are useful in treating cancer. Exemplary types of cancer include breast cancer, prostate cancer, colon cancer, renal cell carcinoma, glioblastoma multiforme cancer, bladder cancer, melanoma, bronchial cancer, lymphoma and liver cancer.

The study of EZH2 deletions, missense and frameshift mutations suggest that EZH2 functions as a tumor suppressor in blood disorders such as myelodysplastic syndromes (MDS) and myeloid malignancies (Ernst et al., Nat. Genet. 2010 August; 42(8):722-6; Nikoloski et al., Nat. Genet. 2010 August; 42(8):665-7). Accordingly, in some embodiments, compounds and compositions of the present invention are useful in treating diseases and/or disorders associated with the presence of a mutant form of EZH2. In some embodiments, compounds and compositions of the present invention are useful in treating diseases and/or disorders associated with the presence of Y641N EZH2. In some embodiment, the disease or disorder associated with the presence of a mutant form of EZH2 is a human B cell lymphoma. In some embodiments, the disease and/or disorder associated with the presence of Y641N EZH2 is follicular lymphoma or diffuse large-B-cell lymphoma. In some embodiments, compounds or compositions of the present invention are useful in treating blood disorders, such as myelodysplastic syndromes, leukemia, anemia and cytopenia. Sneeringer et al., "Coordinated activities of wild-type plus mutant EZH2 drive tumor-associated hypertrimethylation of lysine 27 on histone H3 (H3K27) in human B-cell lymphomas," Proceedings of the National Academy of Sciences, PNAS Early Edition published ahead of print on Nov. 15, 2010.

In some embodiments, the present invention provides a method of reducing the activity of a mutant form of EZH2, such as Y641N EZH2, in a subject in need thereof comprising the step of administering a compound or composition of formula I. In some embodiments, the present invention provides a method of treating a subject suffering from a disease and/or disorder associated with a mutant form of EZH2 comprising the step of administering a compound or composition of formula I. In some embodiments, the above method additionally comprises the preliminary step of determining if the subject is expressing a mutant form of EZH2, such as Y641N EZH2. In some embodiments, that determination is made by determining if the subject has increased levels of histone H3 Lys-27-specific trimethylation (H3K27 me3), as compared to a subject known not to express a mutant form of EZH2.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

It will be appreciated that for compound preparations described herein, when reverse phase HPLC is used to purify a compound, a compound may exist as an acid addition salt. In some embodiments, a compound may exist as a formic acid or mono-, di-, or tri-trifluoroacetic acid salt.

It will further be appreciated that the present invention contemplates individual compounds described herein. Where individual compounds exemplified are isolated and/or characterized as a salt, for example, as a trifluoroacetic acid salt, the present invention contemplates a free base of the salt, as well as other pharmaceutically acceptable salts of the free base.

The following examples contain important additional information, exemplification and guidance that can be adapted to the practice of this invention in its various embodiments and the equivalents thereof

EXAMPLES

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

Unless otherwise noted, all solvents, chemicals, and reagents were obtained commercially and used without purification. The $^1$H NMR spectra were obtained in $CDCl_3$, $d_6$-DMSO, $CD_3OD$, or $d_6$-acetone at 25° C. at 300 MHz on an OXFORD (Varian) with chemical shift (δ, ppm) reported relative to TMS as an internal standard. HPLC-MS chromatograms and spectra were obtained with Shimadzu LC-MS-2020 system. Chiral analysis and purification were obtained with Yilite P270.

Example 1

Synthesis of N-((2-hydroxy-4,6-dimethylpyridin-3-yl)methyl)-4-phenoxybenzamide (Compound I-9)

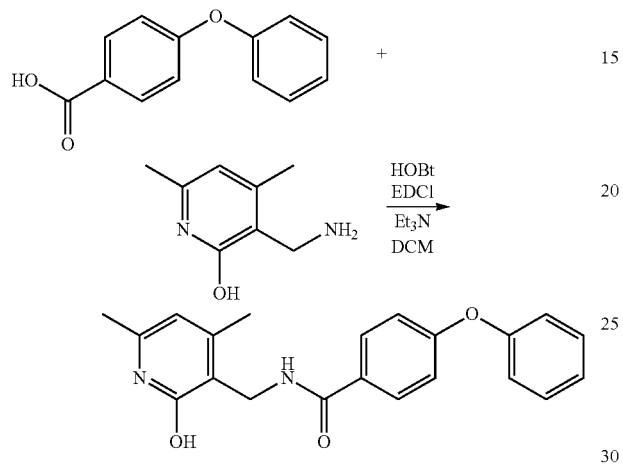

4-Phenoxybenzoic acid (214 mg, 1.0 mmol), 1-hydroxybenzotriazole (203 mg, 1.5 mmol), 1-(3-dimethylaminopropyl)-3-ethylcarbodiimide hydrochloride (290 mg, 1.5 mmol) and triethylamine (0.7 mL, 5 mmol) were dissolved in dichloromethane (15 mL). The mixture was stirred at room temperature for 0.5 hour. Then 3-(aminomethyl)-4,6-dimethylpyridin-2-ol (190 mg, 1.0 mmol) was added to the solution. The mixture was stirred at room temperature for 12 hours. After the reaction, the mixture was concentrated and the residue was purified by column chromatography (silica gel, dichloromethane/methane=40:1) to give the product as a white solid (120 mg, 34%). LRMS (M+H$^+$) m/z: calcd 348.15. found 348. $^1$H NMR (300 MHz, $d_6$-DMSO): δ 11.46 (s, 1H), 8.28 (m, 1H), 7.86 (s, 1H), 7.83 (s, 1H), 7.40 (t, J=7.2 Hz, 2H), 7.18 (t, J=7.5 Hz, 1H), 7.06 (s, 1H), 7.03 (s, 1H), 6.98 (s, 1H), 6.95 (s, 1H), 5.84 (s, 1H), 4.27 (d, J=7.5 Hz, J=3.6, 2H), 2.15 (s, 3H), 2.09 (s, 3H).

Example 2

Synthesis of N-((2-hydroxy-4,6-dimethylpyridin-3-yl)methyl)-4-(tetrahydrofuran-3-yl)benzamide (Compound I-83)

This synthesis involved four steps.

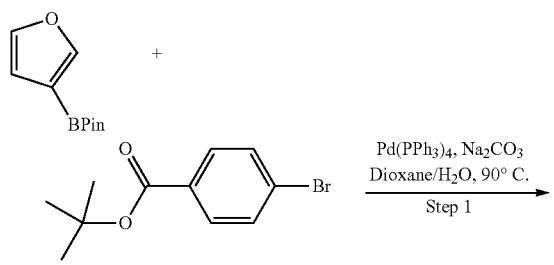

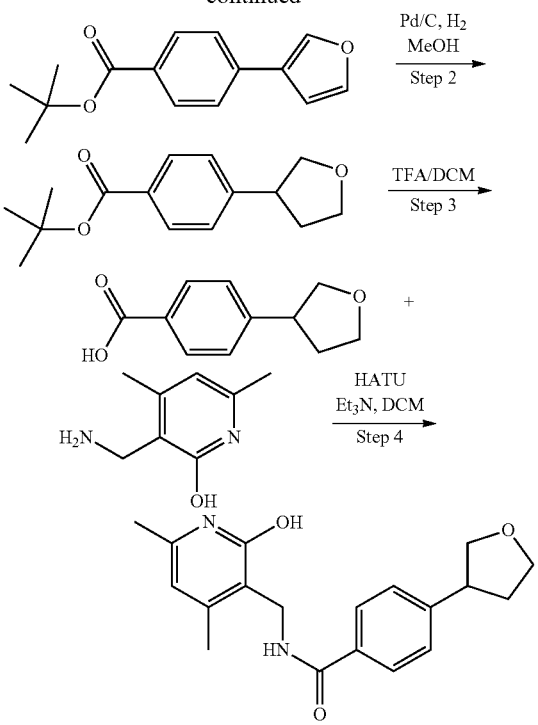

tert-butyl 4-(furan-3-yl)benzoate

A mixture of 2-(furan-3-yl)-4,4,5,5-tetramethyl-1,3-dioxolane (379 mg, 1.95 mmol), tert-butyl 4-bromobenzoate (500 mg, 1.95 mmol), sodium carbonate (621 mg, 5.86 mmol), tetrakis(triphenyl phosphine)palladium(0) (12 mg, 0.01 mmol) in a mixed solvent of 1,4-dioxane (16 ml) and water (4 ml) was stirred for 12 hours at 90° C. under nitrogen atmosphere. After cooling to room temperature, the mixture was concentrated. The residue was purified by preparative-HPLC to give 2-a as a yellow oil (400 mg, 84%). LRMS (M+H$^+$) m/z: calcd 244.11. found 244. $^1$H NMR (300 MHz, $CD_3OD$): δ 8.02 (s, 1H), 7.95 (d, J=8.1 Hz, 2H), 7.64 (d, J=8.4 Hz, 2H), 7.60 (s, 1H), 6.87 (s, 1H), 1.61 (s, 9H).

tert-butyl 4-(tetrahydrofuran-3-yl)benzoate

To a solution of tert-butyl 4-(furan-3-yl)benzoate (400 mg, 1.64 mmol) in methanol (20 mL) was added palladium on carbon (10%, 40 mg), and the mixture was stirred for 24 hours at room temperature under hydrogen atmosphere. Insoluble matters were removed using celite, and the filtrate was concentrated in vacuum to give title product as a white solid (350 mg, 86%). LRMS (M+H$^+$) m/z: calcd 248.14. found 248 $^1$H NMR (300 MHz, $CD_3OD$): δ 7.91 (m, 2H), 7.38 (d, J=8.4 Hz, 2H), 4.09 (m, 2H), 3.95 (m, 1H), 3.87 (m, 1H), 3.72 (m, 1H), 2.45 (m, 1H), 2.36 (m, 1H), 1.59 (s, 9H).

4-(tetrahydrofuran-3-yl)benzoic acid

To a solution of tert-butyl 4-(tetrahydrofuran-3-yl)benzoate (350 mg, 1.41 mmol) was added trifluoroacetic acid (2 mL) in dichloromethane (10 mL) and then stirred at room temperature for 0.5 hour. Solvent concentration gave final desired product 4-(tetrahydrofuran-3-yl)benzoic acid (200 mg, 74%) as a white solid. LRMS (M–H⁺) m/z: calcd 192.08. found 192.

N-((2-hydroxy-4,6-dimethylpyridin-3-yl)methyl)-4-(tetrahydrofuran-3-yl)benzamide (Compound I-83)

To a solution of 4-(tetrahydrofuran-3-yl)benzoic acid (100 mg, 0.52 mmol) in dichloromethane (20 mL) was added 2-(7-aza-1H-benzotriazole-1-yl)-1,1,3,3-tetramethyluronium hexafluorophosphate (35 mg, 0.5 mmol), triethylamine (32 mg, 0.7 mmol). The mixture was stirred for 0.5 hour. Then 3-(aminomethyl)-4,6-dimethylpyridin-2-ol (27 mg, 0.4 mmol) was added and the mixture was stirred at room temperature for 12 hours. The mixture was washed with water (50 mL), the organic layer was concentrated. The residue was purified by preparative-HPLC to give Compound I-83 as a white solid (35 mg, 21%). LRMS (M+H⁺) m/z: calcd 326.16. found 326. ¹H NMR (300 MHz, CD₃OD): δ 7.75 (d, J=6 Hz, 2H), 7.36 (d, J=6 Hz, 2H), 6.10 (s, 1H), 4.48 (s, 2H), 4.06 (m, 2H), 4.03 (m, 1H), 3.88 (m, 1H), 3.70 (m, 1H), 2.37 (s, 3H), 2.35 (s, 3H), 2.00 (m, 2H).

Example 3

Synthesis of compound (S)—N-((2-hydroxy-4,6-dimethylpyridin-3-yl)methyl)-2-methyl-4-(1-phenoxyethyl)benzamide (Compound I-55)

This synthesis involved 7 steps.

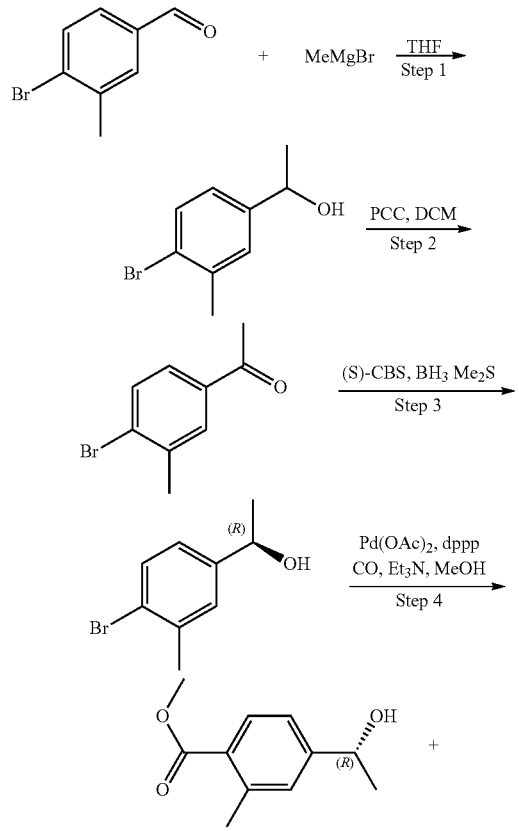

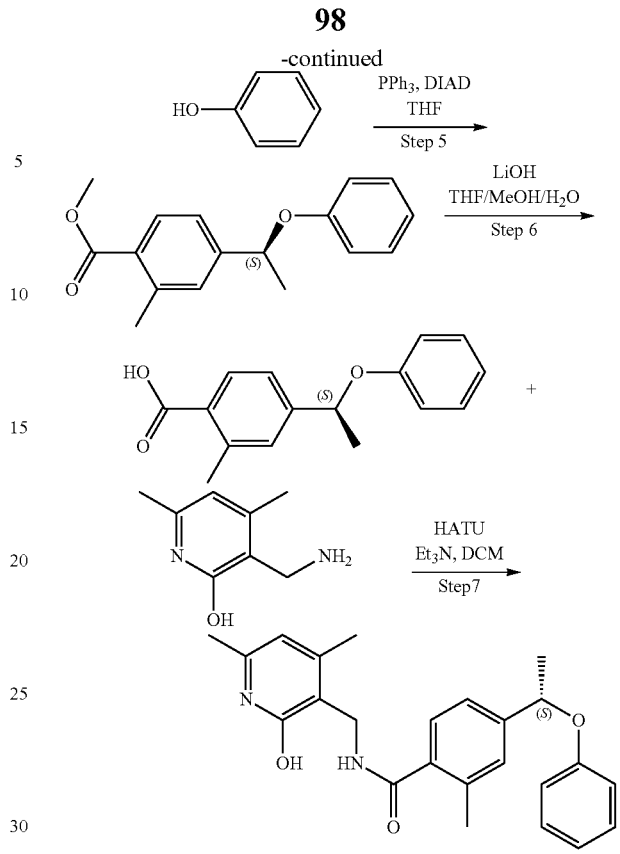

1-(4-bromo-3-methylphenyl)ethanol

A solution of 4-bromo-3-methylbenzaldehyde (4 g, 20 mmol) in dry tetrahydrofuran (40 mL) was cooled to 0° C. under nitrogen atmosphere, and then methyl magnesium bromide (20 mL, 1N in tetrahydrofuran) was added dropwise. The ice bath was removed, and the mixture was stirred for 2 hours. Ammonium chloride aqueous (40 mL) was added and the mixture was extracted with dichloromethane (20 mL*3). The organic phase was dried by sodium sulphate, filtered and concentrated to give a residue. The residue was purified by column chromatography (silica gel, petroleum ether/ethyl acetate=5:1) to give 1-(4-bromo-3-methylphenyl)ethanol as a colorless oil (4.0 g, 93%).

1-(4-bromo-3-methylphenyl)ethanone

Pyridinium chlorochromate (48 g, 223 mmol) was added to a solution of 1-(4-bromo-3-methylphenyl)ethanol (31.9 g, 148 mmol) in dichloromethane (800 mL). The mixture was stirred at room temperature for 2 hours. The mixture was concentrated to give a residue. The residue was purified by column chromatography (silica gel, petroleum ether/ethyl acetate=25:1) to give 1-(4-bromo-3-methylphenyl)ethanone (27.3 g, 87%).

(R)-1-(4-bromo-3-methylphenyl)ethanol

A mixture of 1-(4-bromo-3-methylphenyl)ethanone (27.3 g, 128 mmol) and (S)-2-Methyl-CBS-oxazaborolidine (3.6 g, 12.8 mmol) in dichloromethane (500 mL) was added dimethylsulfide-borane (64 mL, 2M in tetrahydrofuran) dropwise at −20° C. and maintained at the same temperature for 2 hours. Acetic acid (15 mL) was added to quench the reaction. The resultant mixture was concentrated to give a residue. Then the mixture was concentrated to give a residue. The residue was purified by column chromatography (silica gel, petroleum ether/ethyl acetate=3:1) to give (R)-1-(4-bromo-3-methylphenyl)ethanol (19.6 g, 71%)

(R)-methyl 4-(1-hydroxyethyl)-2-methylbenzoate

To a reversible vial was added (R)-1-(4-bromo-3-methylphenyl)ethanol (19.6 g, 91.6 mmol) in methanol (580 mL) was added triethylamine (80 mL, 578 mmol), palladium acetate (7.4 g, 33 mmol) and 1,3-bis(diphenylphosphino)propane (14 g, 34 mmol). Then the reaction mixture was charged with carbon monoxide. The mixture was stirred under carbon monoxide atmosphere (15 atm) at 110° C. for 12 hours. The suspension was concentrated in vacuo and the residue was purified by column chromatography (silica gel, petroleum ether/ethyl acetate=40:1) to give the product (R)-methyl 4-(1-hydroxyethyl)-2-methylbenzoate as colorless oil (15.4 g, 87%).

(S)-methyl 2-methyl-4-(1-phenoxyethyl)benzoate

To a solution of (R)-methyl 4-(1-hydroxyethyl)-2-methylbenzoate (15.4 g, 79.4 mmol) in tetrahydrofuran (500 mL) was added triphenylphosphine (31.2 g, 119 mmol) and phenol (8.4 g, 89.4 mmol). The mixture was stirred at room temperature for 30 minutes, and then diisopropyl azodicarboxylate (25.2 g, 125 mmol) was added. The mixture was concentrated to give a residue. The residue was purified by column chromatography (silica gel, petroleum ether/ethyl acetate=15:1) to give (S)-methyl 2-methyl-4-(1-phenoxyethyl)benzoate as colorless oil (18.4 g, 86%).

(S)-2-methyl-4-(1-phenoxyethyl)benzoic acid

To a solution of (S)-methyl 2-methyl-4-(1-phenoxyethyl)benzoate (13.0 g, 48.1 mmol) in a mixed solution of tetrahydrofuran (150 mL), methanol (50 mL) and water (50 mL) was added lithium hydroxide monohydrate (10.1 g, 241 mmol). The mixture was stirred at room temperature for 2 hours. The suspension was concentrated in vacuo and the residue was charged with concentrated hydrochloric acid (5 mL). Then the mixture was extracted with dichloromethane (20 mL*3). The combined organic phase was separated, dried by sodium sulphate, filtered and concentrated to give a residue. The residue was purified by column chromatography (silica gel, petroleum ether/ethyl acetate=5:1) to give (S)-2-methyl-4-(1-phenoxyethyl)benzoic acid as a pale solid (9.8 g, 80%).

(S)—N-((2-hydroxy-4,6-dimethylpyridin-3-yl)methyl)-2-methyl-4-(1-phenoxyethyl)benzamide To a solution of (S)-2-methyl-4-(1-phenoxyethyl)benzoic acid (5.3 g, 19.5 mmol) in dichloromethane (100 mL) was added 2-(7-aza-1H-benzotriazole-1-yl)-1,1,3,3-tetramethyluronium hexafluorophosphate (11.1 g, 29.3 mmol) and triethylamine (8.6 mL, 62.2 mmol). The mixture was stirred at room temperature for 30 minutes. Then 3-(aminomethyl)-4,6-dimethylpyridin-2-ol (3.15 g, 21 mmol) was added and the mixture was stirred at room temperature for 12 hours. The mixture was poured into water (100 mL) and extracted with dichloromethane (50 mL*2). The combined organic phase was separated, dried by sodium sulphate, filtered and concentrated to give a residue. The residue was purified by column chromatography (silica gel, methanol/dichloromethane=1:10) to give (S)—N-((2-hydroxy-4,6-dimethylpyridin-3-yl)methyl)-2-methyl-4-(1-phenoxyethyl)benzamide (Compound I-55) as a white solid (4.5 g, 59%). LRMS (M+H⁺) m/z: calcd 390.19. found 390. HPLC purity (214 nm): 100%.

¹H NMR (300 MHz, CD₃OD): δ 7.28-7.22 (m, 3H), 7.12-7.09 (m, 2H), 6.83-6.79 (m, 3H), 6.10 (s, 1H), 5.36-5.34 (m, 1H), 4.44 (s, 2H), 2.36 (s, 3H), 2.33 (s, 3H), 2.23 (s, 3H), 1.57 (d, J=6.6 Hz, 3H).

Example 4

Synthesis of N-((2-hydroxy-4,6-dimethylpyridin-3-yl)methyl)-2-oxo-1-(1-phenylethyl)-1,2-dihydropyridine-4-carboxamide (Compound I-63)

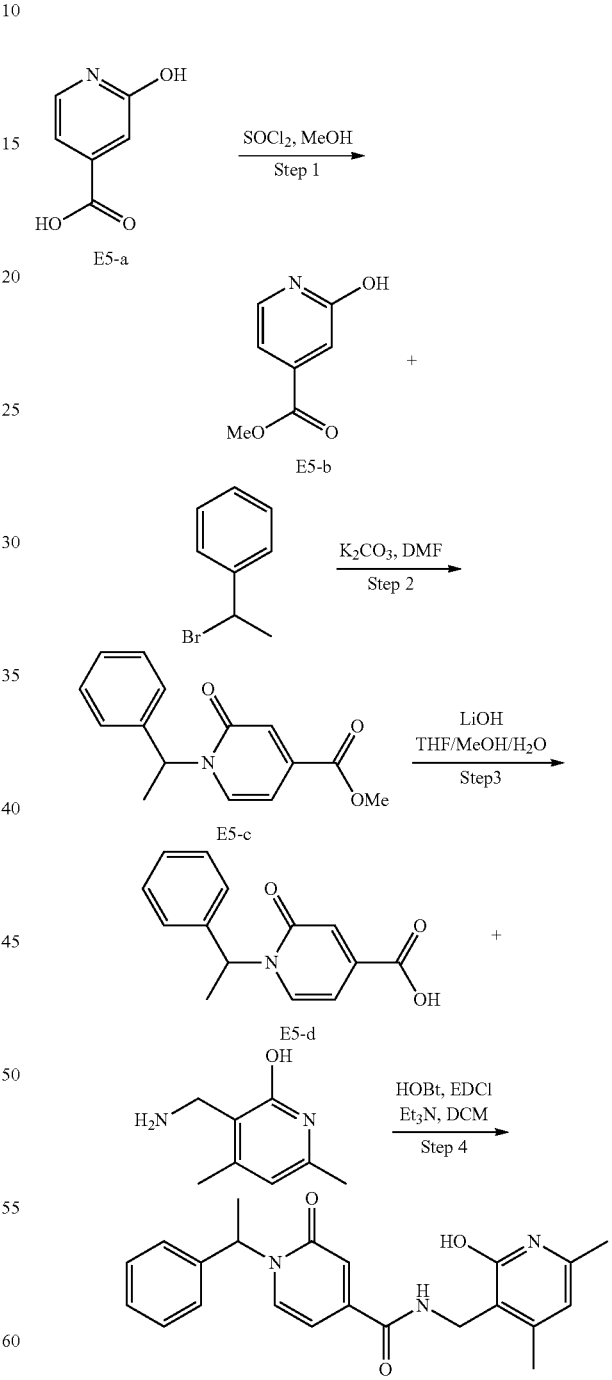

Methyl 2-hydroxyisonicotinate

To a solution of methyl 2-hydroxyisonicotinate (1.4 g, 10 mmol) in methanol (100 mL) was added thionyl chloride (5.73 g, 40 mmol) at 0° C. The mixture was stirred for 12 hours. The solvent was evaporated in vacuum. To the residue a saturated sodium bicarbonate aqueous solution was added and the mixture was extracted with acetic ether (100 mL×3). The organic phase was dried by sodium sulfate. The mixture was filtered and the filtrate was concentrated in vacuum to give methyl 2-hydroxyisonicotinate (1.2 g, 78%). 1H NMR (300 MHz, CD$_3$OD): δ 7.52 (d, J=6.9 Hz, 1H), 7.07 (s, 1H), 6.79 (dd, J=6.9 Hz, J=1.8 Hz, 1H), 3.91 (s, 3H).

Methyl 2-oxo-1-(1-phenylethyl)-1,2-dihydropyridine-4-carboxylate

To a solution of methyl 2-hydroxyisonicotinate (306 mg, 2 mmol) in N,N-dimethylformamide (30 mL) was added (1-bromoethyl)benzene (0.37 g, 2 mmol) and potassium carbonate (0.55 g, 4 mmol). The mixture was heated to 110° C. and stirred at the same temperature for 12 hours. The solvent was evaporated in vacuum and the residue was purified by preparative-HPLC to give methyl 2-oxo-1-(1-phenylethyl)-1,2-dihydropyridine-4-carboxylate (90 mg, 17%) The product was used directly in the next step.

2-oxo-1-(1-phenylethyl)-1,2-dihydropyridine-4-carboxylic acid

A mixture of methyl 2-oxo-1-(1-phenylethyl)-1,2-dihydropyridine-4-carboxylate (90 mg, 0.35 mmol), lithium hydroxide monohydrate (57.1 mg, 1.36 mmol), tetrahydrofuran (5 mL), methanol (1 mL) and water (1 mL) was stirred at 20° C. for 4 hours. The mixture was neutralized to pH=1 with concentrated hydrochloric acid and then extracted with acetic ether (15 mL×3). The combined organic phase was dried by sodium sulfate, then filtered. The filtrate was concentrated in vacuum to give 2-oxo-1-(1-phenylethyl)-1,2-dihydropyridine-4-carboxylic acid as a white solid (60 mg, 70%). LRMS (M+H)$^-$ m/z: cald. 243.09. found 243.

N-((2-hydroxy-4,6-dimethylpyridin-3-yl)methyl)-2-oxo-1-(1-phenylethyl)-1,2-dihydropyridine-4-carboxamide A mixture of 2-oxo-1-(1-phenylethyl)-1,2-dihydropyridine-4-carboxylic acid (60 mg, 0.25 mmol), 1-ethyl-3-(3-dimethylaminopropyl)carbodiimide (95 mg, 0.5 mmol), N-hydroxybenzotriazole (67 mg, 0.5 mmol), triethylamine (0.1 mL) and dichloromethane (5 mL) were stirred at 25° C. for half an hour before 3-(aminomethyl)-4,6-dimethylpyridin-2-ol (50 mg, 0.33 mmol) was added. The mixture was stirred at 25° C. for 12 hours. To the mixture, was added water (10 ml) and the mixture was extracted with dichloromethane (10 mL×3). The combined organic phase was dried by sodium sulfate and then filtered. The filtrate was concentrated in vacuum. The residue was purified by column chromatography (silica gel, dichloromethane/methanol=20:1) to give N-((2-hydroxy-4,6-dimethylpyridin-3-yl)methyl)-2-oxo-1-(1-phenylethyl)-1,2-dihydropyridine-4-carboxamide as a white solid (28 mg, 29%). LRMS (M+H$^+$) m/z: cald. 377.17. found 377. $^1$H NMR (300 MHz, d$^6$-DMSO): δ 11.47 (s, 1H), 8.55 (t, J=4.5 Hz, 1H), 7.67 (d, J=6.9 Hz, 1H), 7.38-7.27 (m, 5H), 6.79 (s, 1H), 6.54-6.51 (m, 1H), 6.14 (q, J=7.2 Hz, 1H), 5.85 (s, 1H), 4.23 (d, J=4.5 Hz, 2H), 2.12 (d, J=6.6 Hz, 6H), 1.68 (d, J=7.2 Hz, 3H).

Example 5

Synthesis of 3-(aminomethyl)-4-methoxy-6-methylpyridin-2-ol intermediate

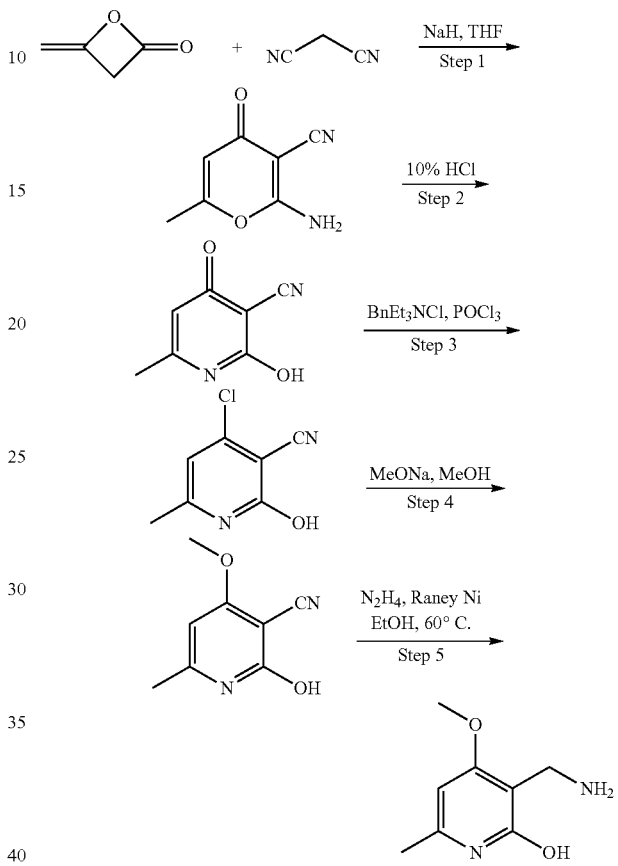

2-amino-6-methyl-4-oxo-4H-pyran-3-carbonitrile

To a solution of malononitrile (3.3 g, 50 mmol) in anhydrous tetrahydrofuran (100 mL) was added sodium hydride (60% w/w, 2.2 g, 55 mmol) at −10° C. The resultant mixture was stirred for 2 hours. Then diketene (4.2 g, 50 mmol) was added dropwise to the solution. The mixture was allowed to warm to room temperature and continued stirring for 30 minutes. The mixture was neutralized with hydrochloric acid and then concentrated in vacuo to give crude 2-amino-6-methyl-4-oxo-4H-pyran-3-carbonitrile (6.0 g, 80%) as a red solid, which was used in the next step without further purification.

2,4-dihydroxy-6-methylnicotinonitrile

A suspension of 2-amino-6-methyl-4-oxo-4H-pyran-3-carbonitrile (6.0 g, 40 mmol) in 10% hydrochloride acid (60 mL) was heated under reflux for 4 hours. The precipitate was collected by filtration and washed with water, and then recrystallized from methanol to give 2,4-dihydroxy-6-methylnicotinonitrile (5.0 g, 83%) as a brown solid. $^1$H NMR (300 MHz, CD$_3$OD): δ 12.46-12.44 (m, 1H), 11.69 (s, 1H), 5.85 (s, 1H), 2.15 (s, 3H).

4-chloro-2-hydroxy-6-methylnicotinonitrile

To a solution of 2,4-dihydroxy-6-methylnicotinonitrile (1.5 g, 10 mmol) in acetonitrile (50 mL) was added benzyltriethylammonium chloride (9.1 g, 40 mmol) and phosphorus oxychloride (6.13 g, 40 mmol). The resulting mixture was stirred for 4 hours at room temperature. The solvent was removed by rotary evaporation. To the residue was added dichloromethane (100 mL) and water (50 mL). The organic phase was separated, washed with brine (50 mL), dried over anhydrous magnesium sulfate, filtered and concentrated to give crude product which was purified by column chromatography (silica gel, petroleum ether/ethyl acetate=4:1) to afford 4-chloro-2-hydroxy-6-methylnicotinonitrile (800 mg, 48%) as a brown solid.

2-hydroxy-4-methoxy-6-methylnicotinonitrile

To a pressure vessel was added 4-chloro-2-hydroxy-6-methylnicotinonitrile (337 mg, 2.0 mmol), sodium methoxide (530 mg, 10.0 mmol), methanol (15 mL), and a magnetic stirrer. The pressure vessel was sealed, and was stirred at 100° C. for 16 hours before the solvent was removed by rotary evaporation. To the residue was added water (10 mL) and ethyl acetate (50 mL). The organic layer was separated and concentrated in vacuo to provide crude product which was purified by column chromatography (silica gel, dichloromethane/methanol=40:1) to afford 2-hydroxy-4-methoxy-6-methylnicotinonitrile (70 mg, 21%) as a brown solid.

3-(aminomethyl)-4-methoxy-6-methylpyridin-2-ol

2-Hydroxy-4-methoxy-6-methylnicotinonitrile (70 mg, 0.43 mmol) was dissolved in ethanol (10 mL) and warmed to 60° C. before it was treated with raney nickel (0.5 mL slurry in water) followed by addition of hydrazine monohydrate (2 mL). The resultant mixture was allowed to stir at 60° C. for 2 hours. The cooled reaction mixture was filtered through celite and rinsed with methanol. The filtrate was concentrated in vacuo to provide crude product which was purified by column chromatography (silica gel, dichloromethane/methanol=10:1) to afford 3-(aminomethyl)-4-methoxy-6-methylpyridin-2-ol (40 mg, 56%) as a white solid. LRMS (M+H$^+$) m/z: calcd 168.09. found 168. HPLC purity (214 nm): 73%. $^1$H NMR (300 MHz, d$^6$-DMSO): δ 6.04 (s, 1H), 3.77 (s, 3H), 3.42 (s, 2H), 2.15 (s, 3H).

Example 6

Synthesis of 3-chloro-4-(2-cyano-3-(pyridazin-4-yl)phenoxy)-N-((4,6-dimethyl-2-oxo-1,2-dihydro pyridin-3-yl)methyl)benzamide (Compound I-1)

This synthesis involved 2 steps.

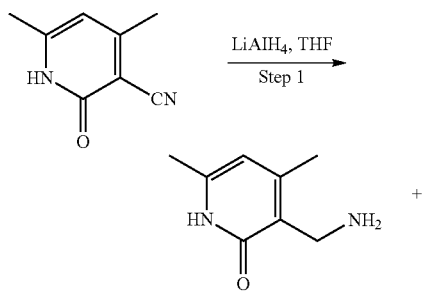

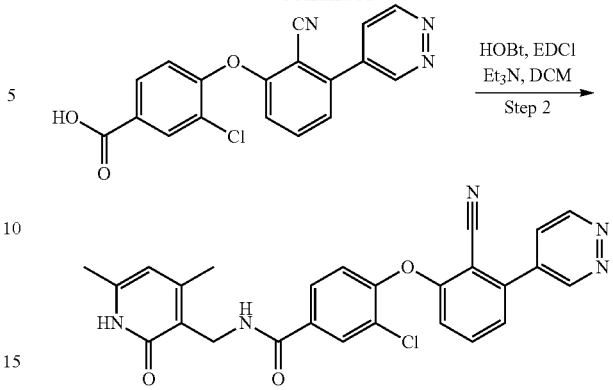

3-(aminomethyl)-4,6-dimethylpyridin-2(1H)-one

To a solution of 4,6-dimethyl-2-oxo-1,2-dihydropyridine-3-carbonitrile (500 mg, 3.4 mmol) in tetrahydrofuran (20 mL) was added lithium aluminum hydride (258 mg, 6.8 mmol) at 0° C. The mixture was stirred at 20° C. for 2 hours. Then water (1 mL) was added and the product 3-(aminomethyl)-4,6-dimethylpyridin-2(1H)-one was obtained as a white solid (300 mg, 60%). $^1$H NMR (300 MHz, d$^6$-DMSO): δ 11.84 (s, 1H), 7.95 (s, 2H), 5.97 (s, 1H), 3.77 (s, 2H), 2.19 (s, 3H), 2.15 (s, 3H).

3-chloro-4-(2-cyano-3-(pyridazin-4-yl)phenoxy)-N-((4,6-dimethyl-2-oxo-1,2-dihydropyridin-3-yl)methyl)benzamide (Compound I-1)

A mixture of 3-chloro-4-(2-cyano-3-(pyridazin-4-yl)phenoxy)benzoic acid (70 mg, 0.2 mmol), 1-ethyl-3-(3-dimethylaminopropyl)carbodiimide hydrochloride (60 mg, 0.3 mmol) and N-hydroxybenzotriazole (45 mg, 0.3 mmol), triethylamine (0.1 mL) and dichloromethane (5 mL) were stirred at 25° C. for half an hour and then 3-(aminomethyl)-4,6-dimethylpyridin-2(1H)-one (30 mg, 0.2 mmol) was added. The mixture was stirred at 25° C. for 12 hours. To the mixture, water (10 mL) was added and the mixture was extracted with dichloromethane (10 mL×3). The combined organic phase was dried by sodium sulfate and then filtered. The filtrate was concentrated in vacuo. The residue was purified by column chromatography (silica gel, dichloromethane/methanol=20:1) to give 3-chloro-4-(2-cyano-3-(pyridazin-4-yl)phenoxy)-N-((4,6-dimethyl-2-oxo-1,2-dihydropyridin-3-yl)methyl)benzamide as a white solid (70 mg, 70%).

LRMS (M+H$^+$) m/z: calcd 485.13. found 485. $^1$H NMR (300 MHz, d$^6$-DMSO): δ 11.54 (s, 1H), 9.60 (s, 1H), 9.50 (d, J=5.4 Hz, 1H), 8.61 (t, J=5.7 Hz, 1H), 8.22 (s, 1H), 8.08 (dd, J=5.1 Hz, J=2.4 Hz, 1H), 7.97 (dd, J=6.6 Hz, J=2.1 Hz, 1H), 7.85 (t, J=8.1 Hz, 1H), 7.60 (d, J=7.5 Hz, 1H), 7.43 (d, J=8.4 Hz, 1H), 7.11 (d, J=8.7 Hz, 1H), 5.91 (s, 1H), 4.34 (d, J=4.2 Hz, 2H), 2.21 (s, 3H), 2.15 (s, 3H).

Example 7

Synthesis of 4-(2-cyanophenoxy)-N-((2-hydroxy-4,6-dimethylpyridin-3-yl)methyl)benzamide (Compound I-2)

This synthesis involved 2 steps.

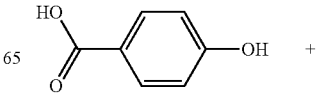

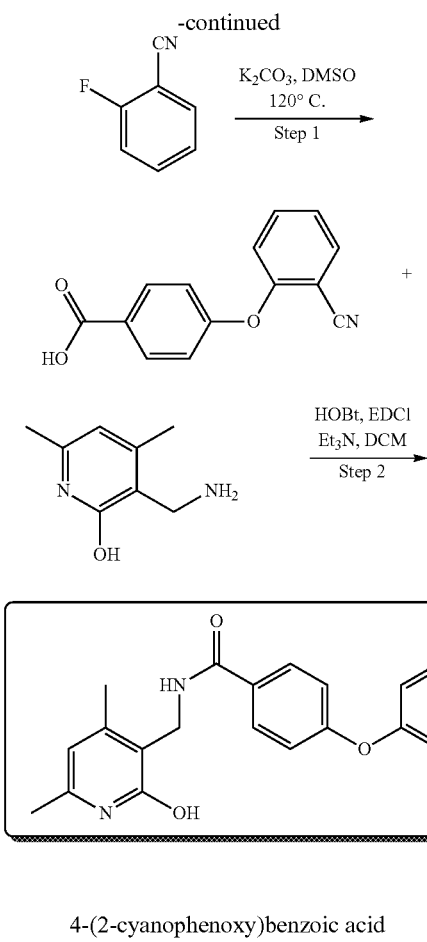

was purified by column chromatography (silica gel, dichloromethane/methanol=20:1) to give 4-(2-cyanophenoxy)-N-((2-hydroxy-4,6-dimethylpyridin-3-yl)methyl)benzamide as a white solid (400 mg, 51%). LRMS (M+H$^+$) m/z: calcd 373.14. found 373. $^1$H NMR (300 MHz, d$^6$-DMSO): δ 11.46 (s, 1H), 8.38 (s, 1H), 7.94-7.91 (m, 3H), 7.69 (t, J=8.1 Hz, 1H), 7.37-7.31 (m, 1H), 7.16-7.06 (m, 3H), 5.86 (s, 1H), 4.29 (d, J=4.2 Hz, 2H), 2.17 (s, 3H), 2.11 (s, 3H).

Example 8

Synthesis of 4-((3-(6-aminopyridin-3-yl)phenoxy)methyl)-N-((2-hydroxy-4,6-dimethylpyridin-3-yl)methyl)benzamide (Compound I-3)

This synthesis involved 4 steps.

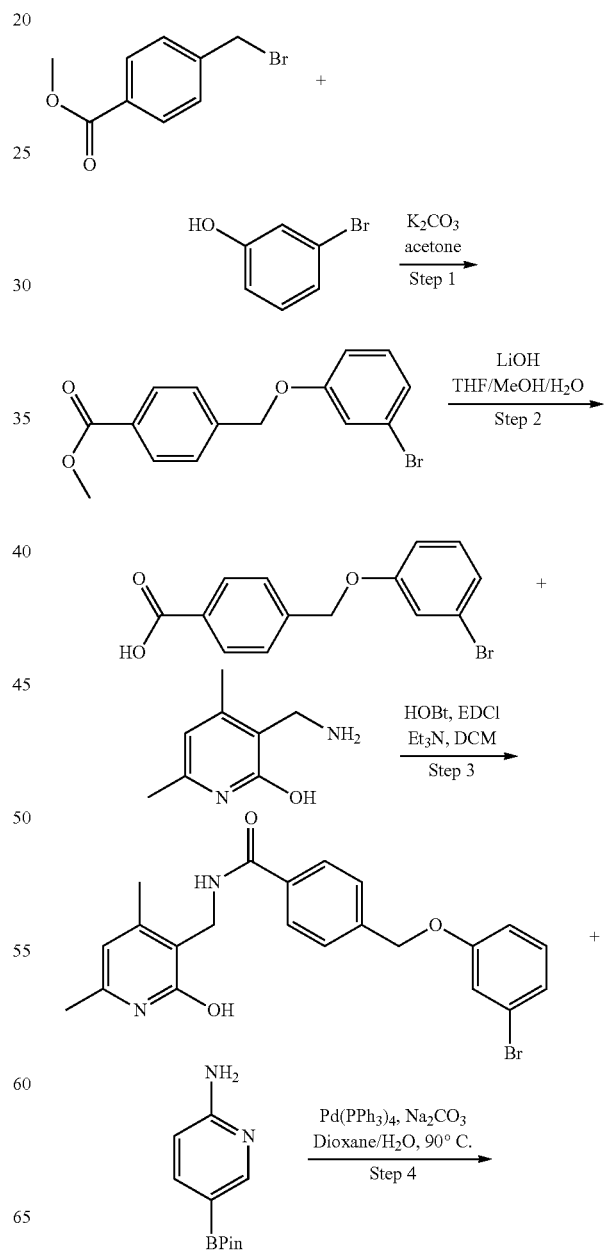

4-(2-cyanophenoxy)benzoic acid

To a solution of 4-hydroxybenzoic acid (7 g, 50 mmol) and 2-fluorobenzonitrile (7.36 g, 60 mmol) in dimethylsulfoxide (40 mL) was added potassium carbonate (20 g, 150 mmol). The reaction mixture was stirred at 120° C. for 4 hours. After the reaction, the temperature was allowed to cool to room temperature, then the mixture was poured into ice water (100 mL). The mixture was neutralized to pH=3 with concentrated hydrochloric acid and then extracted with ethyl acetate (15 mL×3). The combined organic phase was dried by sodium sulfate, and then filtered. The filtrate was concentrated in vacuo. The residue was purified by column chromatography (silica gel, petroleum ether/ethyl acetate=10:1) to give 4-(2-cyanophenoxy)benzoic acid as a white solid (5.80 g, 48.5%). LRMS (M+H)$^-$ m/z: calcd 239.06. found 239. $^1$H NMR (300 MHz, d$^6$-DMSO): δ 12.94 (s, 1H), 7.99-7.91 (m, 3H), 7.71 (t, J=8.4 Hz, 1H), 7.36 (t, J=7.8 Hz, 1H), 7.17-7.14 (m, 3H).

4-(2-cyanophenoxy)-N-((2-hydroxy-4,6-dimethylpyridin-3-yl)methyl)benzamide (Compound I-2)

A mixture of 4-(2-cyanophenoxy)benzoic acid (500 mg, 2.09 mmol), 1-ethyl-3-(3-dimethyl aminopropyl)carbodiimide hydrochloride (453 mg, 2.37 mmol), N-hydroxybenzotriazole (320 mg, 2.37 mmol), triethylamine (0.1 mL) and dichloromethane (5 mL) was stirred at 25° C. for half an hour. And then 3-(aminomethyl)-4,6-dimethylpyridin-2-ol (318 mg, 2.09 mmol) was added. The mixture was stirred at 25° C. for 12 hours. To the mixture, water (10 mL) was added and the mixture was extracted with dichloromethane (10 mL×3). The combined organic phase was dried by sodium sulfate and then filtered. The filtrate was concentrated in vacuo. The residue

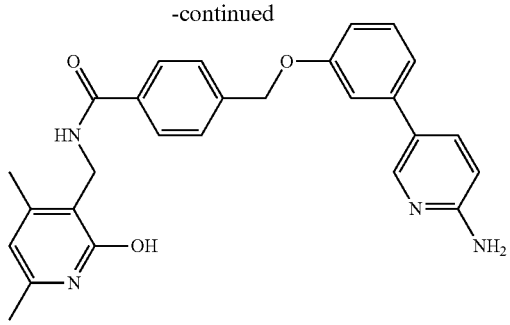

Methyl 4-((3-bromophenoxy)methyl)benzoate

To a solution of methyl 4-(bromomethyl)benzoate (1 g, 4.4 mmol) in acetone (60 mL) were added 3-bromophenol (1 g, 5.8 mol) and potassium carbonate (1.24 g, 9 mmol). After stirring at 40° C. for 12 hours, the reaction mixture was poured into water (50 mL) and extracted with ethyl acetate (50 mL). The organic layer was separated, washed with water (30 mL) and concentrated to give a residue. The residue was purified by column chromatography (silica gel, petroleum ether/ethyl acetate=10:1) to give methyl 4-((3-bromophenoxy)methyl)benzoate (1 g, 71.4%) as a white solid. LRMS (M+H$^+$) m/z: calcd 320.00. found 320. $^1$H NMR (300 MHz, d$^6$-DMSO): δ 7.98 (d, J=8.4 Hz, 2H), 7.57 (d, J=8.1 Hz, 2H), 7.28-7.22 (m, 2H), 7.15-7.12 (m, 1H), 7.05-7.01 (m, 1H), 5.23 (s, 2H), 3.84 (s, 3H).

4-((3-bromophenoxy)methyl)benzoic acid

To a solution of methyl 4-((3-bromophenoxy)methyl)benzoate (1 g, 3.1 mmol) in tetrahydrofuran (30 mL) and methanol (10 mL) was added lithium hydroxide monohydrate (1.3 g, 31 mmol) in water (10 mL). The mixture was stirred at room temperature for 2 hours. The suspension was concentrated in vacuo and acidified with concentrated hydrochloride acid (12 N, 15 mL). Then the mixture was extracted with ethyl acetate (20 mL). The organic phase was separated and concentrated to give the product 4-((3-bromophenoxy)methyl) benzoic acid as a white solid (0.6 g, 63%). LRMS (M+H$^+$) m/z: calcd 305.99. found 305. $^1$H NMR (300 MHz, d$^6$-DMSO): δ 12.95 (s, 1H), 7.96 (d, J=8.4 Hz, 2H), 7.55 (d, J=8.4 Hz, 2H), 7.27-7.22 (m, 2H), 7.15-7.12 (m, 1H), 7.05-7.01 (m, 1H), 5.21 (s, 2H).

4-((3-bromophenoxy)methyl)-N-((2-hydroxy-4,6-dimethylpyridin-3-yl)methyl)benzamide To a solution of 4-((3-bromophenoxy)methyl)benzoic acid (0.1 g, 0.32 mmol) in dichloromethane (20 mL) were added 1-ethyl-3-(3-dimethylaminopropyl)carbodiimide hydrochloride (147 mg, 0.76 mmol), 1H-benzo[d][1,2,3]triazol-1-ol (104 mg, 0.77 mmol) and triethylamine (77 mg, 0.7 mmol). The mixture was stirred for 0.5 hour. And then 3-(aminomethyl)-4,6-dimethylpyridin-2-ol (60 mg, 0.4 mmol) was added and the resultant mixture was stirred at room temperature for 4 hours. The reaction mixture was washed with water (20 mL). The organic phase was separated and concentrated to give a residue. The residue was purified through column chromatography (silica gel, dichloromethane/methanol=20: 1) to afford 4-((3-bromophenoxy)methyl)-N-((2-hydroxy-4, 6-dimethylpyridin-3-yl)methyl)benzamide as a white solid (80 mg, 57%). LRMS (M+H$^+$) m/z: calcd 440.07. found 440.

4-((3-(6-aminopyridin-3-yl)phenoxy)methyl)-N-((2-hydroxy-4,6-dimethylpyridin-3-yl)methyl)benzamide (Compound I-3)

A mixture of 4-((3-bromophenoxy)methyl)-N-((2-hydroxy-4,6-dimethylpyridin-3-yl)methyl)benzamide (80 mg, 0.18 mmol), 5-(4,4,5,5-tetramethyl-1,3,2-dioxaborolan-2-yl) pyridin-2-amine (40 mg, 0.43 mmol) and sodium carbonate (75 mg, 0.7 mmol), tetra(triphenylphosphine) palladium (23 mg, 0.02 mmol) in 1,4-dioxane (8 ml) and water (2 ml) was stirred for 15 hours at 90° C. under nitrogen atmosphere. After cooling to room temperature, the reaction mixture was concentrated to give a residue. The residue was purified by column chromatography (silica gel, dichloromethane/methanol=20:1) to give product 4-((3-(6-aminopyridin-3-yl) phenoxy)methyl)-N-((2-hydroxy-4,6-dimethylpyridin-3-yl) methyl)benzamide (30 mg, 37%) as a white solid. LRMS (M+H$^+$) m/z: calcd 454.20. found 454. HPLC purity (214 nm): 97%. $^1$H NMR (300 MHz, d$^6$-DMSO): δ 11.45 (s, 1H), 8.34 (t, J=4.5 Hz, 1H), 8.22 (s, 1H), 7.85-7.83 (m, 2H), 7.73-7.69 (m, 1H), 7.51-7.48 (m, 2H), 7.32-7.12 (m, 3H), 6.91-6.88 (m, 1H), 6.52 (d, J=8.7 Hz, 1H), 6.16 (s, 2H), 5.85 (s, 1H), 5.20 (s, 2H), 4.29 (d, J=4.5 Hz, 2H), 2.16 (s, 3H), 2.10 (s, 3H).

Example 9

Synthesis of compound 4-(2-cyano-3-ethylphenoxy)-N-((2-hydroxy-4,6-dimethylpyridin-3-yl)methyl)-3-methylbenzamide (Compound I-4)

This synthesis involved 4 steps.

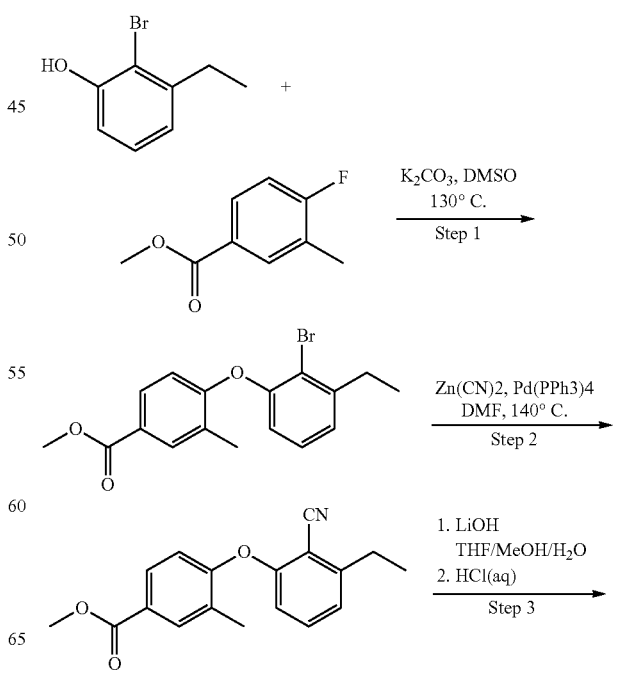

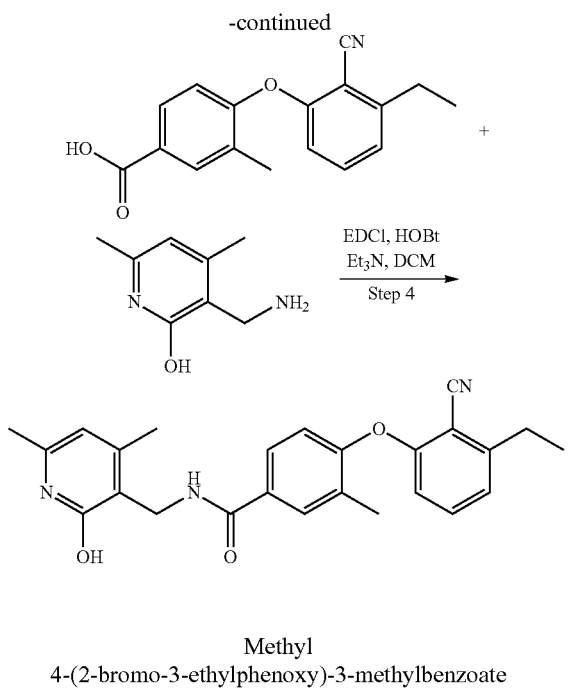

Methyl 4-(2-bromo-3-ethylphenoxy)-3-methylbenzoate

To a solution of methyl 4-fluoro-3-methylbenzoate (1.7 g, 10 mmol) and 2-bromo-3-ethylphenol (2.0 g, 10 mmol) in dimethyl sulfoxide (10 mL) was added potassium carbonate (2.8 g, 20 mmol). The reaction mixture was stirred at 130° C. for 3 hours. After the reaction, the mixture was poured into water (50 mL) and the solution was extracted with ethyl acetate (50 mL), washed with water (50 mL). The organic phase was dried over anhydrous sodium sulfate. The mixture was filtered and the solvent was removed under reduced pressure to give the pure product methyl 4-(2-bromo-3-ethylphenoxy)-3-methylbenzoate as colorless oil (2.10 g, 60%).

Methyl 4-(2-cyano-3-ethylphenoxy)-3-methylbenzoate

To a solution of methyl 4-(2-bromo-3-ethylphenoxy)-3-methylbenzoate (1.0 g, 2.9 mmol) in N,N-dimethylformamide was added tetrakis(triphenylphosphine) palladium(0) (0.35 g, 0.3 mmol) and zinc cyanide (1.2 g, 10 mmol). The reaction mixture was stirred at 140° C. for 12 hours. After the reaction, the mixture was poured into water (50 mL) and the solution was extracted with ethyl acetate (50 mL). The organic phase was dried over anhydrous sodium sulfate. The mixture was filtered and the filtrate was concentrated. The residue was purified by column chromatography (silica gel, petroleum ether/ethyl acetate=20:1) to give the pure product methyl 4-(2-cyano-3-ethylphenoxy)-3-methylbenzoate as a colorless oil (0.52 g, 61%). $^1$H NMR (300 MHz, CDCl$_3$): δ 7.99 (d, J=1.8 Hz, 1H), 7.89 (dd, J=8.4 Hz, J=2.1 Hz, 1H), 7.55 (d, J=8.7 Hz, 1H), 6.95 (d, J=8.4 Hz, 1H), 6.86 (d, J=2.4 Hz, 1H), 6.76 (dd, J=8.4 Hz, J=2.4 Hz, 1H), 3.92 (s, 3H), 2.83 (q, J=7.5 Hz, 2H), 2.26 (s, 3H), 1.27 (t, J=7.5 Hz, 3H).

4-(2-cyano-3-ethylphenoxy)-3-methylbenzoic acid

Lithium hydroxide hydrate (0.20 g, 5 mmol) was added to a solution of methyl 4-(2-bromo-3-ethylphenoxy)-3-methylbenzoate (0.40 g, 1.36 mmol) in mixed solution of tetrahydrofuran (6.0 mL), methanol (2 mL) and water (2 mL). The reaction mixture was stirred at room temperature for 3 hours. After the reaction, the solvent was removed in vacuo. Hydrochloric acid aqueous (3 mol/L) was added to adjust pH to 3-5, and the solution was extracted with dichloromethane (30 mL). The combined organic phase was washed with water (20 mL×3), dried over anhydrous sodium sulfate. And the solvent was evaporated to dryness to give pure product 4-(2-cyano-3-ethylphenoxy)-3-methylbenzoic acid (0.36 g, 94%). LRMS (M–H)$^-$ m/z: calcd for 281.1. found 281.

4-(2-cyano-3-ethylphenoxy)-N-((2-hydroxy-4,6-dimethylpyridin-3-yl)methyl)-3-methylbenzamide (Compound I-4)

To a solution of 4-(2-cyano-3-ethylphenoxy)-3-methylbenzoic acid (0.10 g, 0.36 mmol), 1-ethyl-3-(3-dimethylaminopropyl)carbodiimide hydrochloride (0.10 g, 0.5 mmol) and N-hydroxybenzotriazole (0.07 g, 0.5 mmol) in dichloromethane (20 mL) was added triethylamine (0.4 g, 4 mmol). The reaction mixture was stirred at room temperature for 15 minutes, then 3-(aminomethyl)-4,6-dimethylpyridin-2-ol (0.06 g, 0.4 mmol) was added. The reaction mixture was stirred at room temperature for 12 hours. After the reaction, the mixture was washed with water (30 mL). The organic phase was concentrated and purified by column chromatography (silica gel, dichloromethane/methanol=15:1) to give pure product 4-(2-cyano-3-ethylphenoxy)-N-((2-hydroxy-4,6-dimethylpyridin-3-yl)methyl)-3-methylbenzamide as a white solid (0.062 g, 41%). LRMS (M+H$^+$) m/z: calcd 415.19. found 415. $^1$H NMR (300 MHz, d$^6$-DMSO): δ 11.46 (s, 1H), 8.31 (d, J=4.5 Hz, 1H), 7.86 (s, 1H), 7.75 (s, 1H), 7.72 (s, 1H), 7.05-6.70 (m, 2H), 6.80 (dd, J=8.4 Hz, J=2.4 Hz, 1H), 5.85 (s, 1H), 4.29 (d, J=4.5 Hz, 2H), 2.74 (q, J=7.5 Hz, 2H), 2.16 (s, 3H), 2.14 (s, 3H), 2.10 (s, 3H), 1.17 (t, J=7.5 Hz, 3H).

Example 10

Synthesis of compound 3-chloro-4-(2-cyano-3-(1H-pyrazol-4-yl)phenoxy)-N-((2-hydroxy-4,6-dimethylpyridin-3-yl)methyl)benzamide (Compound I-5)

This synthesis involved 2 steps.

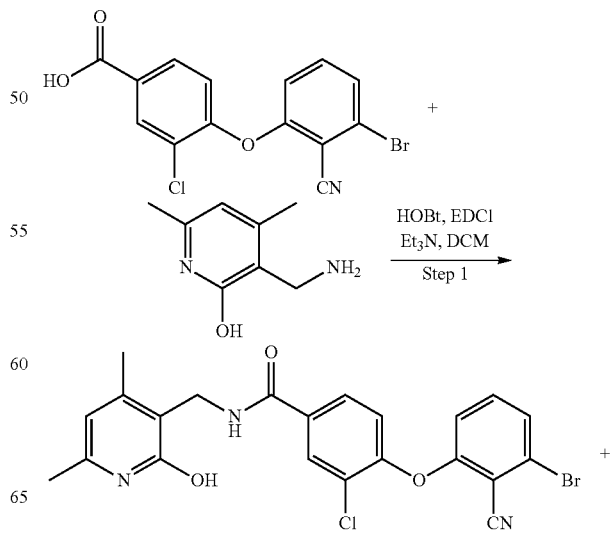

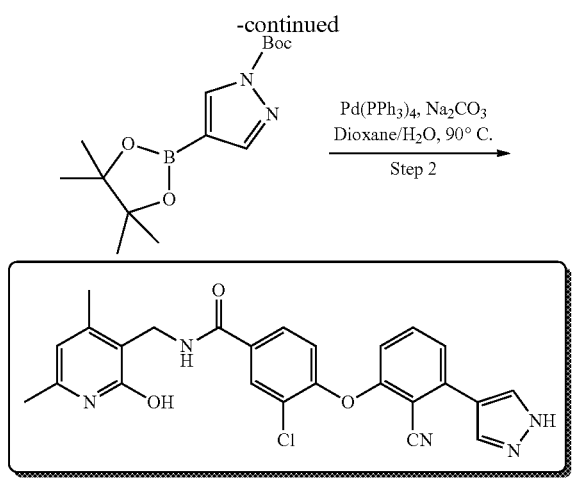

4-(3-bromo-2-cyanophenoxy)-3-chloro-N-((2-hydroxy-4,6-dimethylpyridin-3-yl)methyl)benzamide A mixture of 4-(3-bromo-2-cyanophenoxy)-3-chlorobenzoic acid (1 g, 2.8 mmol), 1-ethyl-3-(3-dimethylaminopropyl)carbodiimide hydrochloride (1.08 g, 5.7 mmol), N-hydroxybenzotriazole (769 mg, 5.7 mmol), triethylamine (0.1 mL) and dichloromethane (5 mL) was stirred at 25° C. for half an hour. And then 3-(aminomethyl)-4,6-dimethylpyridin-2-ol (430 mg, 2.8 mmol) was added. The mixture was stirred at 25° C. for 12 hours. To the mixture, water (10 mL) was added and the mixture was extracted with dichloromethane (10 mL×3). The combined organic phase was dried by sodium sulfate and then filtered. The filtrate was concentrated in vacuo. The residue was purified by column chromatography (silica gel, dichloromethane/methanol=20:1) to give 4-(3-bromo-2-cyanophenoxy)-3-chloro-N-((2-hydroxy-4,6-dimethylpyridin-3-yl)methyl)benzamide as a white solid (1.1 g, 83%). LRMS (M+H$^+$) m/z: calcd 485.01. found 485. $^1$H NMR (300 MHz, d$^6$-DMSO): δ 11.44 (s, 1H), 8.52 (s, 1H), 8.12 (s, 1H), 7.90-7.87 (m, 1H), 7.61-7.52 (m, 2H), 7.37 (d, J=6.0 Hz, 1H), 6.86 (d, J=6.3 Hz, 1H), 5.82 (s, 1H), 4.25 (s, 2H), 2.45 (s, 3H), 2.40 (s, 3H).

3-chloro-4-(2-cyano-3-(H-pyrazol-4-yl)phenoxy)-N-((2-hydroxy-4,6-dimethyl pyridin-3-yl)methyl)benzamide. (Compound I-5)

To a solution of 4-(3-bromo-2-cyanophenoxy)-3-chloro-N-((2-hydroxy-4,6-dimethylpyridin-3-yl)methyl)benzamide (500 mg, 1.03 mmol), tert-butyl-4-(4,4,5,5-tetramethyl-1,3,2-dioxaborolan-2-yl)-1H-pyrazole-1-carboxylate (323 mg, 1.1 mmol), sodium carbonate (425 mg, 3.07 mmol) in 1,4-dioxane (20 mL) and water (5 mL) was added tetrakis(triphenylphosphine)palladium(0) (118 mg, 0.1 mmol). The reaction mixture was stirred at 90° C. under nitrogen atmosphere for 12 hours. After the reaction, it was allowed to cool to room temperature, and concentrated in vacuo, then diluted with ethyl acetate, washed with water. The organic phase was dried over anhydrous sodium sulfate. The mixture was filtered and the filtrate was concentrated. The residue was purified by column chromatography (silica gel, dichloromethane/methanol=20:1) to give the pure product 3-chloro-4-(2-cyano-3-(1H-pyrazol-4-yl)phenoxy)-N-((2-hydroxy-4,6-dimethylpyridin-3-yl)methyl)benzamide (331 mg, 68%). LRMS (M+H$^+$) m/z: calcd 473.13. found 473. $^1$H NMR (300 MHz, d$^6$-DMSO): δ 13.33 (s, 1H), 11.48 (s, 1H), 8.53 (t, J=4.8 Hz, 1H), 8.35 (s, 1H), 8.15 (s, 1H), 8.07 (s, 1H), 7.90 (d, J=6.9 Hz, 1H), 7.61 (t, J=8.1 Hz, 1H), 7.51 (d, J=7.8 Hz, 1H), 7.32 (d, J=8.4 Hz, 1H), 6.74 (d, J=8.1 Hz, 1H), 5.86 (s, 1H), 4.29 (d, J=4.8 Hz, 2H), 2.16 (s, 3H), 2.11 (s, 3H).

Example 11

Synthesis of 3-chloro-4-(2-cyano-3-(pyridin-4-yl)phenoxy)-N-((2-hydroxy-4,6-dimethylpyridin-3-yl)methyl)benzamide (Compound I-6)

To a solution of 4-(3-bromo-2-cyanophenoxy)-3-chloro-N-((2-hydroxy-4,6-dimethylpyridin-3-yl)methyl)benzamide (500 mg, 1.03 mmol), pyridin-4-ylboronic acid (150 mg, 1.2 mmol), sodium carbonate (425 mg, 3.07 mmol) in 1,4-dioxane (20 mL) and water (5 mL) was added tetrakis(triphenylphosphine)palladium(0) (118 mg, 0.1 mmol). The reaction mixture was stirred at 90° C. under nitrogen atmosphere for 12 hours. After the reaction, it was allowed to cool to room temperature, and concentrated in vacuo, then diluted with ethyl acetate, washed with water. The organic phase was dried over anhydrous sodium sulfate. The mixture was filtered and the filtrate was concentrated. The residue was purified by column chromatography (silica gel, dichloromethane/methanol=20:1) to give the pure product 3-chloro-4-(2-cyano-3-(pyridin-4-yl)phenoxy)-N-((2-hydroxy-4,6-dimethylpyridin-3-yl)methyl)benzamide (348 mg, 70%). LRMS (M+H$^+$) m/z: calcd 484.13. found 484. $^1$H NMR (300 MHz, d$^6$-DMSO): δ 11.48 (s, 1H), 8.75 (d, J=6.0 Hz, 2H), 8.55 (t, J=4.5 Hz, 1H), 8.15 (s, 1H), 7.94-7.91 (m, 1H), 7.76 (t, J=7.8 Hz, 1H), 7.67-7.65 (m, 2H), 7.44 (d, J=7.5 Hz, 1H), 7.39 (d, J=8.4 Hz, 1H), 7.01 (d, J=8.4 Hz, 1H), 5.86 (s, 1H), 4.29 (d, J=4.8 Hz, 2H), 2.16 (s, 3H), 2.11 (s, 3H).

Example 12

Synthesis of compound 3-chloro-N-((2-hydroxy-4,6-dimethylpyridin-3-yl)methyl)-4-(2-(pyridin-4-yl)phenoxy)benzamide (Compound I-7)

This synthesis involved 2 steps.

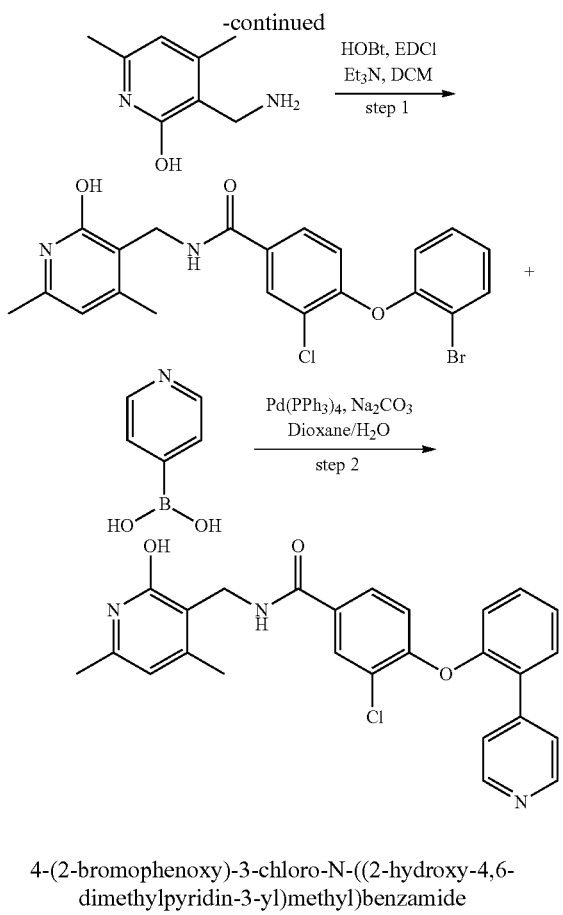

4-(2-bromophenoxy)-3-chloro-N-((2-hydroxy-4,6-dimethylpyridin-3-yl)methyl)benzamide 4-(2-Bromophenoxy)-3-chlorobenzoic acid (174 mg, 0.53 mmol), 1-hydroxybenzotriazole (108 mg, 0.8 mmol), 1-ethyl-3-(3-dimethylaminopropyl)carbodiimide hydrochloride (154 mg, 0.8 mmol), triethylamine (0.4 mL, 2.88 mmol) were dissolved in dichloromethane (20 mL). The mixture was stirred at room temperature for 0.5 hour. Then 3-(aminomethyl)-4,6-dimethylpyridin-2-ol (100 mg, 0.66 mmol) was added to the solution. The mixture was stirred at room temperature for 12 hours. To the mixture, water (20 mL) was added and the resultant mixture was extracted with dichloromethane (10 mL×3). The combined organic phase was separated, dried by sodium sulfate, filtered and concentrated to give a residue. The residue was purified by column chromatography (silica gel, dichloromethane/methanol=20:1) to give 4-(2-bromophenoxy)-3-chloro-N-((2-hydroxy-4,6-dimethylpyridin-3-yl)methyl)benzamide as a white solid (190 mg, 78%). LRMS (M+H) m/z: calcd 460.02. found 460. $^1$H NMR (300 MHz, d$^6$-DMSO): δ 11.46 (s, 1H), 8.44 (t, J=4.5 Hz, 1H), 8.09 (d, J=1.8 Hz, 1H), 7.81-7.75 (m, 2H), 7.46-7.40 (m, 1H), 7.23-7.17 (m, 1H), 7.10 (dd, J=6.9 Hz, J=1.2 Hz, 1H), 6.83 (d, J=8.4 Hz, 1H), 5.85 (s, 1H), 4.27 (d, J=4.5 Hz, 2H), 2.15 (s, 3H), 2.10 (s, 3H).

3-chloro-N-((2-hydroxy-4,6-dimethylpyridin-3-yl)methyl)-4-(2-(pyridin-4-yl)phenoxy)benzamide (Compound I-7)

4-(2-Bromophenoxy)-3-chloro-N-((2-hydroxy-4,6-dimethylpyridin-3-yl)methyl)benzamide (90 mg, 0.2 mmol), pyridin-4-ylboronic acid (48 mg, 0.4 mmol), tetrakis(triphenylphosphine)palladium (45 mg, 0.04 mmol), sodium carbonate (62 mg, 0.6 mmol), dioxane (8 mL) and water (2 mL) were added to a flask. The mixture was stirred at 90° C. for 12 hours under nitrogen atmosphere. The resultant mixture was concentrated to give a residue. The residue was purified by column chromatography (silica gel, dichloromethane/methanol=20:1) to give 3-chloro-N-((2-hydroxy-4,6-dimethylpyridin-3-yl)methyl)-4-(2-(pyridin-4-yl)phenoxy)benzamide as a light yellow solid (30 mg, 32%). LRMS (M+H$^+$) m/z: calcd 459.13. found 459. HPLC purity (214 nm): 98%. $^1$H NMR (300 MHz, d$^6$-DMSO): δ 11.46 (s, 1H), 8.57 (d, J=6.3 Hz, 2H), 8.40 (t, J=4.5 Hz, 1H), 8.02 (d, J=1.8 Hz, 1H), 7.73 (dd, J=8.7 Hz, J=2.1 Hz, 1H), 7.62-7.46 (m, 4H), 7.36 (t, J=6.3 Hz, 1H), 7.16 (d, J=2.1 Hz, 1H), 6.78 (d, J=6.3 Hz, 1H), 5.84 (s, 1H), 4.24 (d, J=4.5 Hz, 2H), 2.15 (s, 3H), 2.10 (s, 3H).

Example 13

Synthesis of 3-Chloro-4-(2-cyano-3-(pyrimidin-4-yl)phenoxy)-N-((2-hydroxy-4,6-dimethylpyridin-3-yl)methyl)benzamide (Compound I-8)

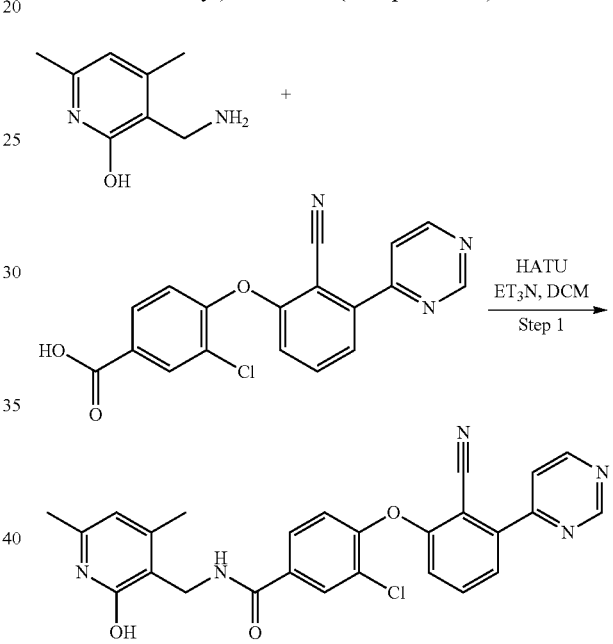

3-Chloro-4-(2-cyano-3-(pyrimidin-4-yl)phenoxy)-N-((2-hydroxy-4,6-dimethylpyridin-3-yl)methyl)benzamide A mixture of 3-chloro-4-(2-cyano-3-(pyrimidin-4-yl)phenoxy)benzoic acid (80 mg, 0.23 mmol), 2-(7-Aza-1H-benzotriazol-1-yl)-1,1,3,3-tetramethyluronium hexafluorophosphate (130 mg, 0.34 mmol) and triethylamine (70 mg, 0.69 mmol) in dichloromethane (20 mL) was stirred at room temperature for 2 hours. Then 3-(aminomethyl)-4,6-dimethylpyridin-2-ol (42 mmg, 0.28 mmol) was added. The resultant mixture was stirred at room temperature for additional 15 hours. To the reaction mixture, water (30 mL) was added. The mixture was extracted with dichloromethane (30 mL×3). The organic layers were combined and concentrated to give a residue in vacuo. The residue was purified by preparative-HPLC to give 3-Chloro-4-(2-cyano-3-(pyrimidin-4-yl)phenoxy)-N-((2-hydroxy-4,6-dimethylpyridin-3-yl)methyl)benzamide I-8 as a white solid (80 mg, 72%). LRMS (M+H$^+$) m/z: calcd 485.13. found 485. HPLC purity (214 nm): 96%. $^1$H NMR (300 MHz, d$^6$-DMSO): δ 11.49 (s, 1H), 9.39 (s, 1H), 9.04 (d, J=5.1 Hz, 1H), 8.57-8.56 (m, 1H), 8.17 (d, J=1.2 Hz, 1H), 8.05 (d, J=5.1 Hz, 1H), 7.93 (d, J=9 Hz, 1H), 7.83-7.73 (m, 2H), 7.39 (d, J=8.4 Hz, 1H), 7.11 (d, J=8.4 Hz, 1H), 5.87 (s, 1H), 4.30 (d, J=4.8 Hz, 2H), 2.18 (s, 3H), 2.12 (s, 3H).

Example 14

Synthesis of N-((2-hydroxy-4,6-dimethylpyridin-3-yl)methyl)-4-phenoxybenzamide (I-9)

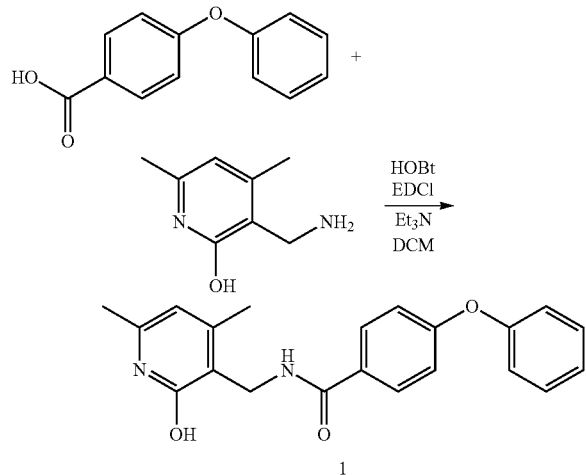

4-Phenoxybenzoic acid (214 mg, 1.0 mmol), 1-hydroxybenzotriazole (203 mg, 1.5 mmol), 1-(3-dimethylaminopropyl)-3-ethylcarbodiimide hydrochloride (290 mg, 1.5 mmol) and triethylamine (0.7 mL, 5 mmol) were dissolved in dichloromethane (15 mL). The mixture was stirred at room temperature for 0.5 hour. Then 3-(aminomethyl)-4,6-dimethylpyridin-2-ol (190 mg, 1.0 mmol) was added to the solution. The mixture was stirred at room temperature for 12 hours. After the reaction, the mixture was concentrated and the residue was purified by column chromatography (silica gel, dichloromethane/methane=40:1) to give 1 as a white solid (120 mg, 34%). LRMS (M+H) m/z: calcd 348.15. found 348. $^1$H NMR (300 MHz, d$_6$-DMSO): δ 11.46 (s, 1H), 8.28 (m, 1H), 7.86 (s, 1H), 7.83 (s, 1H), 7.40 (t, J=7.2 Hz, 2H), 7.18 (t, J=7.5 Hz, 1H), 7.06 (s, 1H), 7.03 (s, 1H), 6.98 (s, 1H), 6.95 (s, 1H), 5.84 (s, 1H), 4.27 (d, J=7.5 Hz, J=3.6, 2H), 2.15 (s, 3H), 2.09 (s, 3H).

Example 15

Synthesis of compound 3-chloro-4-(2-cyanophenoxy)-N-((2-hydroxy-4,6-dimethylpyridin-3-yl)methyl)benzamide (Compound I-10)

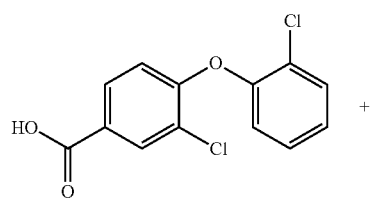

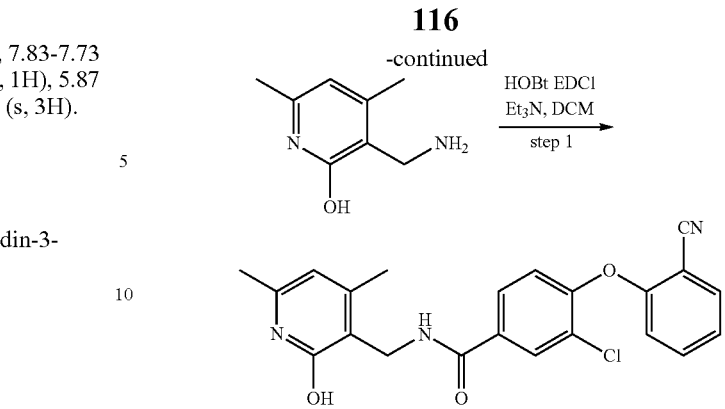

A solution of 3-chloro-4-(2-cyanophenoxy)benzoic acid (100 mg, 0.37 mmol) in dichloromethane (20 mL) was added 1-(3-dimethylaminopropyl)-3-ethylcarbodiimide hydrochloride (91 mg, 0.48 mmol), N-hydroxybenzotriazole (65 mg, 0.48 mmol) and triethylamine (104 mg, 0.7 mmol), stirred for 30 minutes. Then 3-(aminomethyl)-4,6-dimethylpyridin-2-ol (56 mg, 0.37 mmol) was added and the mixture was stirred at room temperature for 12 hours. The mixture was washed with water (50 mL). The residue was purified by column chromatography (silica gel, dichloromethane/methanol=20:1) to afford 3-chloro-4-(2-cyanophenoxy)-N-((2-hydroxy-4,6-dimethylpyridin-3-yl)methyl)benzamide (34 mg, 58%) as white solid. LRMS (M$^+$H$^+$) m/z: calcd 407.1. found 407; $^1$H-NMR (300 MHz, CD$_3$OD) δ 11.47 (s, 1H), 8.53 (m, 1H), 8.14 (d, J=2.1 Hz, 1H), 7.90 (m, 2H), 7.68 (m, 1H), 7.29 (m, 2H), 6.93 (d, J=0.9 Hz, 1H), 5.86 (s, 1H), 4.29 (d, 2H, J=4.8 Hz), 2.17 (s, 3H), 2.11 (s, 3H).

Example 16

Synthesis of N-((2-hydroxy-4,6-dimethylpyridin-3-yl)methyl)-4-(phenoxymethyl)benzamide (Compound I-11)

The synthesis involved 3 steps.

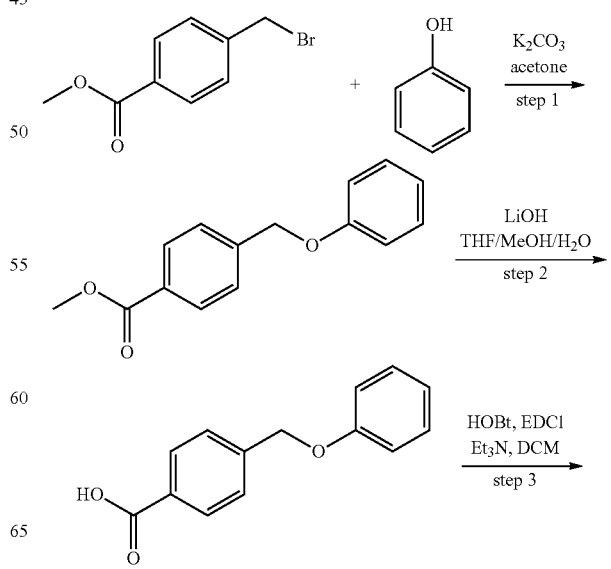

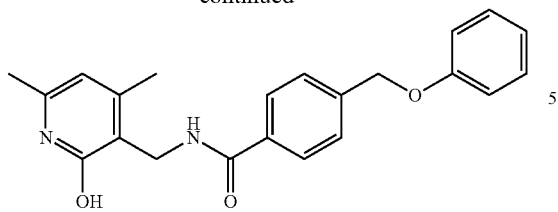

Methyl 4-(phenoxymethyl)benzoate

A mixture of methyl 4-(bromomethyl)benzoate (1000 mg, 4.37 mmol), phenol (493 mg, 5.24 mmol), potassium carbonate (1200 mg, 8.73 mmol) and acetone (20 mL) was stirred at 60° C. under nitrogen atmosphere for 4 hours. The resultant mixture was concentrated to give a residue. The residue was purified by column chromatography (silica gel, petroleum ether/ethyl acetate=4:1) to give methyl 4-(phenoxymethyl) benzoate as a white solid (1100 mg, 100%). $^1$H NMR (300 MHz, CDCl$_3$): δ 8.01 (d, J=8.1 Hz, 2H), 7.62 (d, J=8.1 Hz, 2H), 7.35-7.30 (m, 2H), 7.04 (d, J=7.8 Hz, 2H), 6.98 (t, J=7.2 Hz, 1H), 5.23 (s, 2H), 3.88 (s, 3H).

Methyl 4-(phenoxymethyl)benzoic acid

A mixture of methyl 4-(phenoxymethyl)benzoate (1.1 g, 4.55 mmol), lithium hydroxide monohydrate (955 mg, 22.8 mmol), tetrahydrofuran (20 mL), methanol (7 mL) and water (7 mL) were stirred at room temperature for 5 hours. The mixture was neutralized to pH to 1 with concentrated hydrochloric acid and then extracted with ethyl acetate (15 mL×3). The combined organic phase was separated, dried over sodium sulfate, and then filtered. The filtrate was concentrated in vacuo to give methyl 4-(phenoxymethyl)benzoic acid as a white solid (840 mg, 81%). LRMS (M+H)$^-$ m/z: calcd 228.08. found 228.

N-((2-hydroxy-4,6-dimethylpyridin-3-yl)methyl)-4-(phenoxymethyl)benzamide

A mixture of methyl 4-(phenoxymethyl)benzoic acid (420 mg, 1.84 mmol), 1-hydroxybenzotriazole (373 mg, 2.75 mmol), 1-ethyl-3-(3-dimethylaminopropyl)carbodiimide hydrochloride (530 mg, 2.75 mmol), triethylamine (0.8 mL, 5.7 mmol) were dissolved in dichloromethane (20 mL). The mixture was stirred at room temperature for 0.5 hour. Then 3-(aminomethyl)-4,6-dimethylpyridin-2-ol (280 mg, 1.84 mmol) was added to the solution. The mixture was stirred at room temperature for 12 hours. To the resultant mixture, water (10 mL) was added and then extracted with dichloromethane (10 mL×3). The combined organic phase was separated, dried over sodium sulfate, filtered. The filtrate was concentrated in vacuo to give a residue. The residue was purified by column chromatography (silica gel, petroleum ether/ethyl acetate=1:4) to give N-((2-hydroxy-4,6-dimethylpyridin-3-yl)methyl)-4-(phenoxymethyl)benzamide (Compound I-11) as a white solid (300 mg, 45%). LRMS (M+H$^+$) m/z: calcd 362.16. found 362. HPLC purity (214 nm): 98%. $^1$H NMR (300 MHz, d$^6$-DMSO): δ 11.49 (s, 1H), 8.37 (t, J=5.1 Hz, 1H), 7.87 (d, J=8.4 Hz, 2H), 7.51 (d, J=8.4 Hz, 2H), 7.31 (t, J=7.8 Hz, 2H), 7.04-6.96 (m, 3H), 5.88 (s, 1H), 5.17 (s, 2H), 4.32 (d, J=5.1 Hz, 2H), 2.20 (s, 3H), 2.14 (s, 3H).

Example 17

Synthesis of compound 4-(benzyloxy)-N-((2-hydroxy-4,6-dimethylpyridin-3-yl)methyl)benzamide (Compound I-12)

This synthesis involved 3 steps.

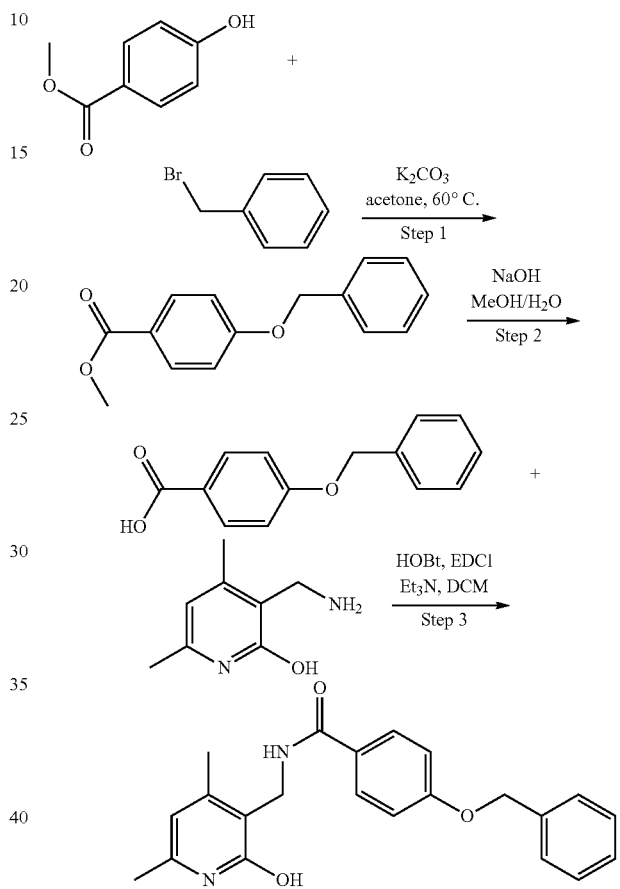

Methyl 4-(benzyloxy)benzoate

To a solution of methyl 4-hydroxybenzoate (1.37 g, 9 mmol) and (bromomethyl)benzene (1.71 g, 10 mmol) in acetonitrile (100 mL) was added potassium carbonate (2.76 g, 18.8 mmol). The reaction mixture was stirred at 60° C. for 2 hours. After the reaction, the solvent was removed under reduced pressure to give the crude product which was purified by column chromatography (silica gel, dichloromethane/methanol=100:1) to give the pure product (2.18 g, 99%). LRMS (M+H$^+$) m/z: calcd 243.09. found 243.

4-(benzyloxy)benzoic acid

Sodium hydroxide (1.80 g, 45 mmol) was added to a solution of methyl 4-(benzyloxy)benzoate (2.18 g, 9 mmol) in methanol (5 mL) and water (10 mL). The reaction mixture was stirred at 65° C. for 3 hours. After the reaction, the solvent was removed in vacuo. 3N hydrochloric acid was added to make pH 2, and the product was extracted with dichloromethane (100 mL×3). The combined organics phase was washed with brine (20 mL×3), dried over anhydrous sodium sulfate, and the solvent was evaporated to dryness to give 4-(benzyloxy)benzoic acid (1.95 g, 95%). LRMS (M+H⁺) m/z: calcd 227.08. found 227.

4-(benzyloxy)-N-((2-hydroxy-4,6-dimethylpyridin-3-yl)methyl)benzamide

To a solution of 4-(benzyloxy)benzoic acid (228 mg, 1 mmol), N-(3-dimethylaminopropyl)-N'-ethylcarbodiimide hydrochloride (210 mg, 1.1 mmol) and hydroxybenzotriazole (149 mg, 1.1 mmol) in dichloromethane (30 mL) was added triethylamine (202 mg, 2 mmol). The reaction mixture was stirred at room temperature for 1 hour, then 3-aminopropanenitrile (156 mg, 1 mmol) was added. The reaction mixture was stirred at room temperature overnight. After the reaction, the mixture was washed with saturated solution of sodium bicarbonate (10 mL×3), dried over anhydrous sodium sulfate to give crude product which was purified by column chromatography (silica gel, dichloromethane/methanol=50:1) to give 4-(benzyloxy)-N-((2-hydroxy-4,6-dimethylpyridin-3-yl)methyl)benzamide (Compound I-12) (110 mg, 30%). LRMS (M+H⁺) m/z: calcd 451.11. found 451. ¹H NMR (300 MHz, d⁶-DMSO) δ11.47 (s, 1H), 8.20 (s, 1H), 7.82 (d, J=8.7 Hz, 2H), 7.49-7.35 (m, 5H), 7.05 (d, J=8.7 Hz, 2H), 5.88 (s, 1H), 5.17 (s, 1H), 4.30 (d, J=4.8 Hz, 2H), 2.19 (s, 1H), 2.13 (s, 1H).

Example 18

Synthesis of 3-chloro-4-(2-cyano-3-(pyrimidin-4-yl)phenoxy)-N-((2-hydroxy-4,6-dimethylpyridin-3-yl)methyl)-N-methylbenzamide (Compound I-17)

This synthesis involved 3 steps.

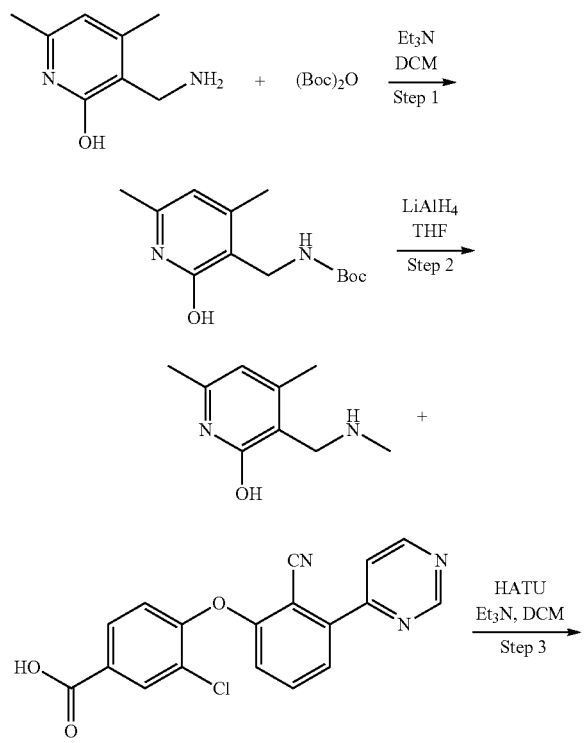

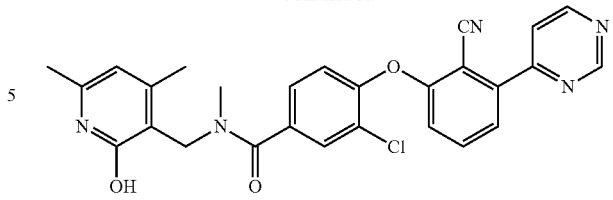

Tert-butyl (2-hydroxy-4,6-dimethylpyridin-3-yl)methylcarbamate

To a solution of 3-(Aminomethyl)-4,6-dimethylpyridin-2-ol (0.5 g, 3.29 mmol) and triethylamine (1 g, 9.87 mmol) in dichloromethane (30 mL) was added di-tert-butyl dicarbonate (0.86 g, 3.94 mmol). The reaction mixture was stirred at room temperature for 15 hours. To the reaction mixture, water (50 mL) was added. The reaction mixture was extracted with dichloromethane (20 mL×3). The organic layers were combined, dried over anhydrous sodium sulfate, filtered and concentrated in vacuo to give tert-butyl (2-hydroxy-4,6-dimethylpyridin-3-yl)methylcarbamate (0.7 g, 84%) as a pale solid. LRMS (M+H⁺) m/z: calcd 252.1. found 252.

4,6-dimethyl-3-((methylamino)methyl)pyridin-2-ol

To a solution of tert-butyl (2-hydroxy-4,6-dimethylpyridin-3-yl)methylcarbamate (700 mg, 2.78 mmol) in tetrahydrofuran (25 mL), lithium aluminum hydride (1 g, 26.3 mmol) was added in portions at room temperature. Then the mixture was heated at 70° C. for 15 hours with stirring. After cooling to room temperature, the reaction mixture was diluted with ethyl acetate (20 mL). And then water (20 mL) was added to the reaction mixture dropwise. The organic phase was separated and concentrated to provide 4,6-dimethyl-3-((methylamino)methyl)pyridin-2-ol as a pale yellow solid (0.4 g, 87%). LRMS (M+H⁺) m/z: calcd 166.1. found 166.

3-chloro-4-(2-cyano-3-(pyrimidin-4-yl)phenoxy)-N-((2-hydroxy-4,6-dimethylpyridin-3-yl)methyl)-N-methylbenzamide A mixture of 4,6-Dimethyl-3-((methylamino)methyl)pyridin-2-ol (28 mg, 0.17 mmol), 3-chloro-4-(2-cyano-3-(pyrimidin-4-yl)phenoxy)benzoic acid (50 mg, 0.14 mmol), triethylamine (42 mg, 0.42 mmol) and 2-(7-aza-1H-benzotriazole-1-yl)-1,1,3,3-tetramethyluronium hexafluorophosphate (65 mg, 0.17 mmol) in dichloromethane (20 mL) was stirred at room temperature for 15 hours. Water (20 mL) was added to the mixture. The organic phase was separated and concentrated in vacuo to give a residue. The residue was further purified by preparative-HPLC to provide 3-chloro-4-(2-cyano-3-(pyrimidin-4-yl)phenoxy)-N-((2-hydroxy-4,6-dimethylpyridin-3-yl)methyl)-N-methylbenzamide (Compound I-17) as a white solid (34 mg, 49%). LRMS (M+H⁺) m/z: calcd 499.1. found 499. HPLC purity (214 nm): 94%.

¹H NMR (300 MHz, d⁶-DMSO): δ 9.39 (s, 1H), 9.04 (d, J=5.1 Hz, 1H), 8.04 (d, J=5.1 Hz, 1H), 7.86-7.73 (m, 3H), 7.52 (d, J=9.6 Hz, 1H), 7.37 (d, J=8.4 Hz, 1H), 7.15 (d, J=8.4 Hz, 1H), 5.88 (s, 1H), 4.53 (s, 2H), 2.83 (s, 3H), 2.18 (s, 3H), 2.17 (s, 3H).

Example 19

Synthesis of N-((2-hydroxy-4,6-dimethylpyridin-3-yl)methyl)-N-methyl-4-phenoxybenzamide (Compound I-20)

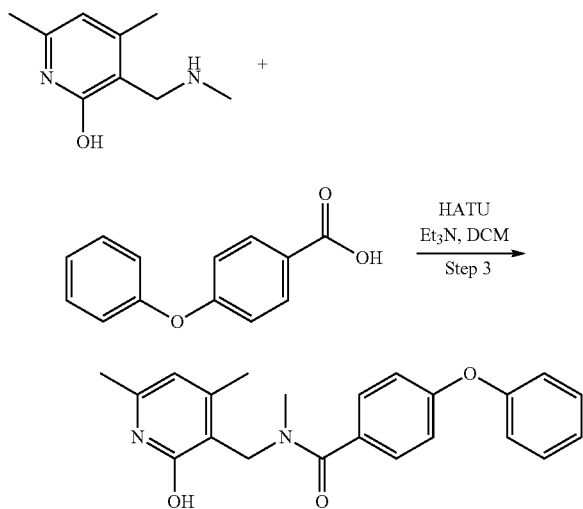

A mixture of 3-(Aminomethyl)-4,6-dimethylpyridin-2-ol (33 mg, 0.2 mmol), 4-benzoylbenzoic acid (42 mg, 0.2 mmol), triethylamine (40 mg, 0.4 mmol) and 2-(7-aza-1H-benzotriazole-1-yl)-1,1,3,3-tetramethyluronium hexafluorophosphate (77 mg, 0.2 mmol) in dichloromethane (20 mL) was stirred at room temperature for 15 hours. Then the mixture was washed with water (20 mL). The organic phase was separated and concentrated in vacuo to give a residue. The residue was purified by preparative-HPLC to obtain N-((2-hydroxy-4,6-dimethylpyridin-3-yl)methyl)-N-methyl-4-phenoxybenzamide as a white solid (36 mg, 50%). LRMS (M+H⁺) m/z: calcd 362.21. found 362. HPLC purity (214 nm): 99%. $^1$H NMR (300 MHz, CD$_3$OD): δ 7.51-7.48 (m, 2H), 7.44-7.39 (m, 2H), 7.22-7.17 (m, 1H), 7.09-7.04 (m, 4H), 6.11 (s, 1H), 4.71 (s, 2H), 2.93 (s, 3H), 2.27 (s, 6H).

Example 20

Synthesis of N-((2-hydroxy-4,6-dimethylpyridin-3-yl)methyl)-5-phenoxypicolinamide (Compound I-21)

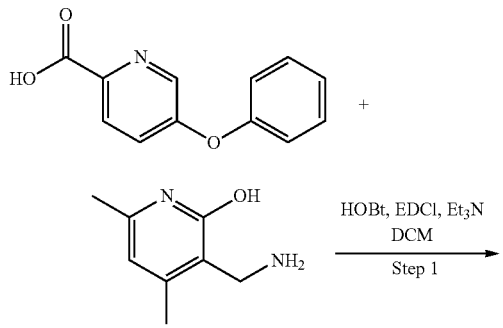

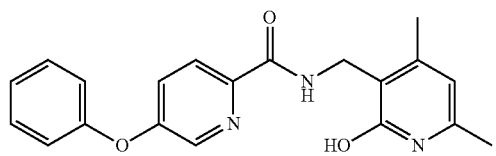

A mixture of 5-phenoxypicolinic acid (83 mg, 0.39 mmol), 1-ethyl-3-(3-dimethylaminopropyl)carbodiimide hydrochloride (191 mg, 1 mmol), N-hydroxybenzotriazole (135 mg, 1 mmol), triethylamine (0.2 mL) and dichloromethane (5 mL) was stirred at 25° C. for 0.5 hour. And then 3-(aminomethyl)-4,6-dimethylpyridin-2-ol (76 mg, 0.5 mmol) was added to the mixture. The resultant mixture was stirred at 25° C. for 12 hours. Then water (20 ml) was added to the mixture and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give N-((2-hydroxy-4,6-dimethylpyridin-3-yl)methyl)-5-phenoxypicolinamide (Compound I-21) as a white solid (50 mg, 37%). LRMS (M+H⁺) m/z: calcd 349.15. found 349. HPLC purity (214 nm): 99%. $^1$H NMR (300 MHz, d$^6$-DMSO): δ 11.53 (s, 1H), 8.56 (t, J=6.0 Hz, 1H), 8.37-8.36 (m, 1H), 8.01 (d, J=8.7 Hz, 1H), 7.48-7.42 (m, 3H), 7.26-7.16 (m, 3H), 5.86 (s, 1H), 4.32 (d, J=6.0 Hz, 2H), 2.22 (s, 3H), 2.10 (s, 3H).

Example 21

Synthesis of (S or R)—N-((2-hydroxy-4,6-dimethylpyridin-3-yl)methyl)-4-(1-phenoxyethyl)benzamide and (R or S)—N-((2-hydroxy-4,6-dimethylpyridin-3-yl)methyl)-4-(1-phenoxyethyl)benzamide (I-23)

This synthesis involved 5 steps.

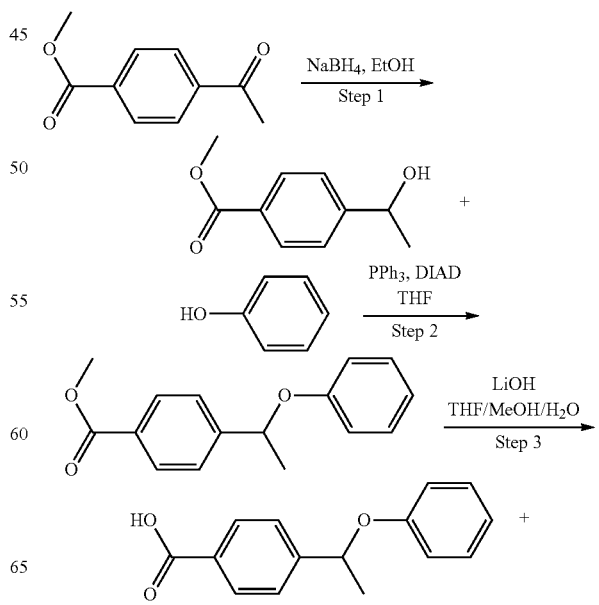

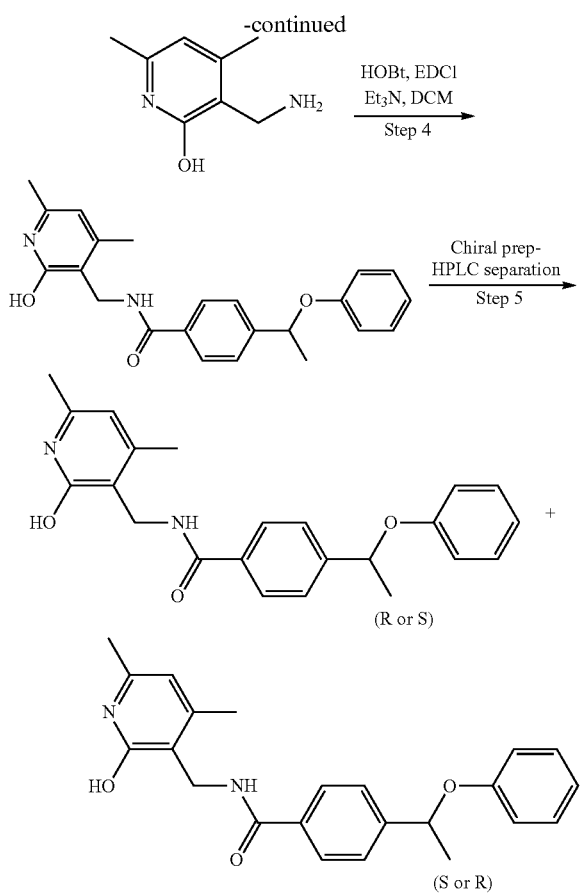

Methyl 4-(1-hydroxyethyl)benzoate

To a solution of methyl 4-acetylbenzoate (1.78 g, 10 mmol) in ethanol (100 mL) was added sodium borohydride (0.76 g, 20 mmol) in portions at 0° C. The mixture was stirred for 30 minutes and warmed to 20° C. Then the mixture was stirred at the same temperature for 12 hours. After that, the mixture was concentrated in vacuo to give methyl 4-(1-hydroxyethyl)benzoate (1.54 g, 85%).

Methyl 4-(1-phenoxyethyl)benzoate

To a solution of methyl 4-(1-hydroxyethyl)benzoate (0.9 g, 5 mmol), phenol (525 mg, 5.6 mmol), triphenylphosphine (2198 mg, 8.4 mmol) in tetrahydrofuran (30 mL) was added diisopropyl azodicarboxylate (1695 mg, 8.4 mmol) at 0° C. The mixture was stirred at 20° C. for 12 hours. Water (15 mL) was added to the mixture and then the mixture was extracted with ethyl acetate (35 mL×3). The combined organic phase was dried by sodium sulfate, and then filtered. The filtrate was concentrated in vacuo and purified by column chromatography (silica gel, petroleum ether/ethyl acetate=5:1) to give methyl 4-(1-phenoxyethyl)benzoate (700 mg, 54%). $^1$H NMR (300 MHz, d$^6$-DMSO): δ 8.02-7.98 (m, 2H), 7.46-7.43 (m, 2H), 7.23-7.16 (m, 2H), 6.91-6.80 (m, 3H), 5.36 (q, J=6.0 Hz, 1H), 3.90 (s, 3H), 1.64 (d, J=6.6 Hz, 3H).

4-(1-phenoxyethyl)benzoic acid

A mixture of methyl 4-(1-phenoxyethyl)benzoate (0.7 g, 2.7 mmol), lithium hydroxide monohydrate (571 mg, 13.6 mmol), tetrahydrofuran (15 mL), methanol (5 mL) and water (5 mL) was stirred at 20° C. for 4 hours. The mixture was adjusted to pH=1 with concentrated hydrochloric acid and then extracted with ethyl acetate (15 mL×3). The combined organic phase was dried by sodium sulfate, and then filtered. The filtrate was concentrated in vacuo to give 4-(1-phenoxyethyl)benzoic acid (0.5 g, 76%).

N-((2-hydroxy-4,6-dimethylpyridin-3-yl)methyl)-4-(1-phenoxyethyl)benzamide (Compound I-23)

A mixture of 4-(1-phenoxyethyl)benzoic acid (121 mg, 0.5 mmol), 1-ethyl-3-(3-dimethylaminopropyl)carbodiimide hydrochloride (191 mg, 1 mmol), N-hydroxybenzotriazole (135 mg, 1 mmol) and triethylamine (0.2 mL) in dichloromethane (5 mL) was stirred at 25° C. for 0.5 hour. And then 3-(aminomethyl)-4,6-dimethylpyridin-2-ol (76 mg, 0.5 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give N-((2-hydroxy-4,6-dimethylpyridin-3-yl)methyl)-4-(1-phenoxyethyl)benzamide as a white solid (100 mg, 53%).

LRMS (M+H$^+$) m/z: calcd. 376.18. found 376. $^1$H NMR (300 MHz, d$^6$-DMSO): δ 11.44 (s, 1H), 8.29-8.27 (m, 1H), 7.77 (d, J=8.1 Hz, 2H), 7.42 (d, J=8.1 Hz, 2H), 7.20-7.15 (m, 2H), 6.87-6.83 (m, 3H), 5.83 (s, 1H), 5.53-5.51 (m, 1H), 4.26 (d, J=5.1 Hz, 2H), 2.14 (s, 3H), 2.10 (s, 3H), 1.53 (d, J=6.6 Hz, 3H).

Example 22

Synthesis of N-((2-hydroxy-4,6-dimethylpyridin-3-yl)methyl)-4-(phenylsulfonyl)benzamide (Compound I-26)

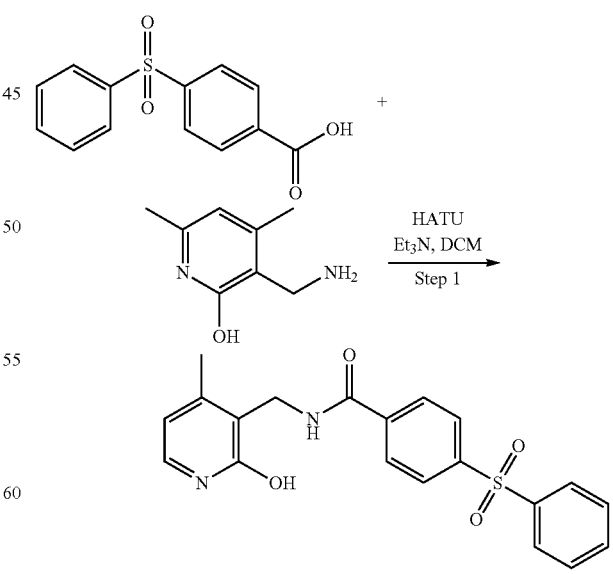

A solution of 4-(phenylsulfonyl)benzoic acid (80 mg, 0.3 mmol) in dichloromethane (15 mL) was added 2-(7-aza-1H-benzotriazole-1-yl)-1,1,3,3-tetramethyluronium hexafluorophosphate (171 mg, 0.45 mmol) and triethylamine (61 mg, 0.6 mmol), stirred for 30 minutes. Then 3-(aminomethyl)-4,6-dimethylpyridin-2-ol (50 mg, 0.3 mmol) was added and the mixture was stirred at room temperature for 12 hours. The mixture was washed with water (10 mL), dried over sodium sulfate, filtered and concentrated to give a residue. The residue was purified by prep-TLC (silica gel, dichloromethane/methanol=20:1) to give N-((2-hydroxy-4,6-dimethylpyridin-3-yl)methyl)-4-(phenylsulfonyl)benzamide as a light yellow solid (108 mg, 90.7%). LRMS (M+H$^+$) m/z: calcd 396.11. found 396. HPLC purity (214 nm): 99%. $^1$H NMR (300 MHz, d$^6$-DMSO): δ 11.50 (s, 1H), 8.63 (t, J=4.8 Hz, 1H), 8.03-7.98 (m, 6H), 7.76-7.63 (m, 3H), 5.88 (s, 1H), 4.31 (d, J=4.8 Hz, 2H), 2.17 (s, 3H), 2.13 (s, 3H).

Example 23

Synthesis of compound N-((2-hydroxy-4,6-dimethylpyridin-3-yl)methyl)-2-methyl-4-(phenoxymethyl)benzamide (Compound I-27)

This synthesis involved 4 steps.

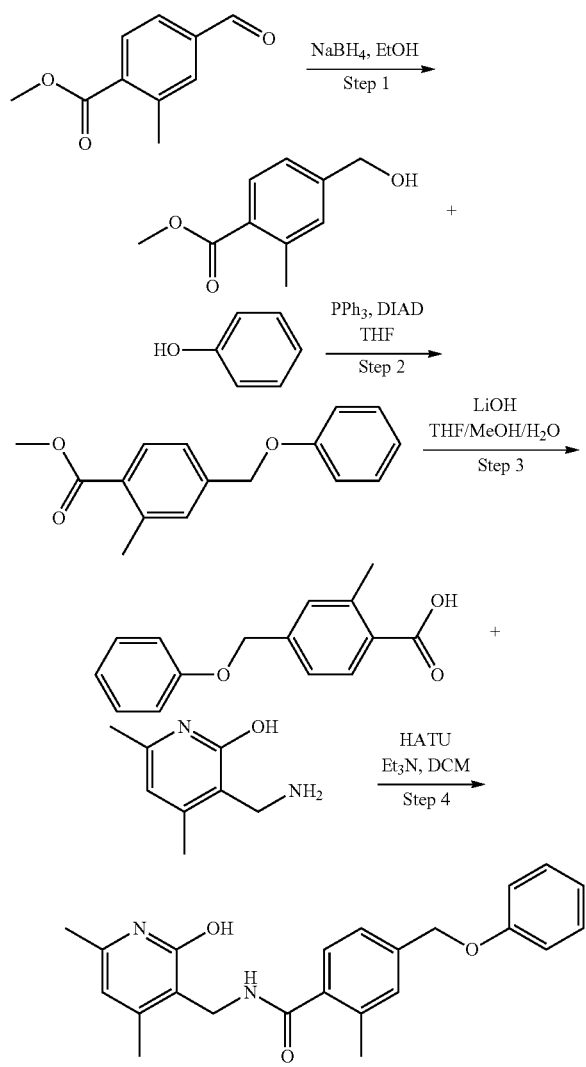

Methyl 4-(hydroxymethyl)-2-methylbenzoate

A mixture of methyl 4-formyl-2-methylbenzoate (200 mg, 1.1 mmol), sodium borohydride (210 mg, 5.5 mmol) and ethanol (10 mL) was stirred at room temperature for 4 hours. To the resultant mixture, water (0.4 mL) was added. The organic phase was separated, concentrated to give a residue. The residue was purified by column chromatography (silica gel, petroleum ether/ethyl acetate=2:1) to give methyl 4-(hydroxymethyl)-2-methylbenzoate (126 mg, 64%). $^1$H NMR (300 MHz, d$^6$-DMSO): δ 7.78 (d, J=7.8 Hz, 1H), 7.15 (dd, J=7.8 Hz, J=1.8 Hz, 1H), 7.06 (d, J=1.8 Hz, 1H), 5.39 (t, J=5.7 Hz, 1H), 4.79 (d, J=5.7 Hz, 2H), 3.88 (s, 3H), 2.35 (s, 3H).

Methyl 2-methyl-4-(phenoxymethyl)benzoate

A mixture of methyl 4-(hydroxymethyl)-2-methylbenzoate (126 mg, 0.7 mmol), phenol (66 mg, 0.7 mmol), triphenylphosphine (275 mg, 1.0 mmol) and tetrahydrofuran (15 mL) was stirred at room temperature for half hour. And then azodicarboxylic acid diisopropyl ester (212 mg, 1.0 mmol) was added. The mixture was stirred at room temperature for 12 hours. The resultant mixture was washed with water (20 mL×2). The organic phase was separated, dried over sodium sulfate, filtered and concentrated to give a residue. The residue was purified by column chromatography (silica gel, petroleum ether/ethyl acetate=5:1) to give methyl 2-methyl-4-(phenoxymethyl)benzoate as a colorless oil (66 mg, 37%). $^1$H NMR (300 MHz, CDCl$_3$): δ 7.92 (d, J=8.4 Hz, 1H), 7.30-7.24 (m, 4H), 6.97-6.94 (m, 3H), 5.06 (s, 2H), 3.88 (s, 3H), 2.61 (s, 3H).

2-methyl-4-(phenoxymethyl)benzoic acid

A mixture of methyl 2-methyl-4-(phenoxymethyl)benzoate (66 mg, 0.26 mmol), lithium hydroxide (54 mg, 1.29 mmol), tetrahydrofuran (6 mL), methanol (2 mL), and water (2 mL) were stirred at room temperature for 12 hours. The mixture was neutralized to pH to 1 with concentrated hydrochloric acid and then extracted with ethyl acetate (20 mL×3). The combined organic phase was separated, dried over sodium sulfate, and then filtered. The filtrate was concentrated in vacuo to give 2-methyl-4-(phenoxymethyl)benzoic acid used in next step without further purification (42 mg, 67%). LRMS (M+H)$^-$ m/z: calcd 242.09. found 242.

N-((2-hydroxy-4,6-dimethylpyridin-3-yl)methyl)-2-methyl-4-(phenoxymethyl)benzamide (Compound I-27)

2-Methyl-4-(phenoxymethyl)benzoic acid (42 mg, 0.17 mmol), o-(7-azabenzotriazol-1-yl)-N,N,N',N'-tetramethylfluoroniumhexafluorophosphate (99 mg, 0.26 mmol), triethylamine (0.1 mL) and dichloromethane (15 mL) were stirred at 25° C. for half hour. Then 3-(aminomethyl)-4,6-dimethylpyridin-2-ol (27 mg, 0.17 mmol) was added to the mixture. The mixture was stirred at 25° C. for 12 hours. The resultant mixture was washed with water (20 mL), dried over sodium, filtered, and concentrated to give a residue. The residue was purified by column chromatography (silica gel, dichloromethane/methanol=10:1) to give N-((2-hydroxy-4,6-dimethylpyridin-3-yl)methyl)-2-methyl-4-(phenoxymethyl) benzamide as a white solid (50 mg, 78%). LRMS (M+H$^+$) m/z: calcd 376.18. found 376. HPLC purity (214 nm): 98%. $^1$H NMR (300 MHz, d$^6$-DMSO): δ 11.46 (s, 1H), 8.11 (t, J=4.8 Hz, 1H), 7.28-7.20 (m, 5H), 7.00-6.84 (m, 3H), 5.86 (s, 1H), 5.07 (s, 2H), 4.27 (d, J=4.8 Hz, 2H), 2.31 (s, 3H), 2.19 (s, 3H), 2.11 (s, 3H).

Example 24

Synthesis of N-((2-hydroxy-4,6-dimethylpyridin-3-yl)methyl)-2-methyl-4-phenoxybenzamide (Compound I-28)

This synthesis involved 4 steps.

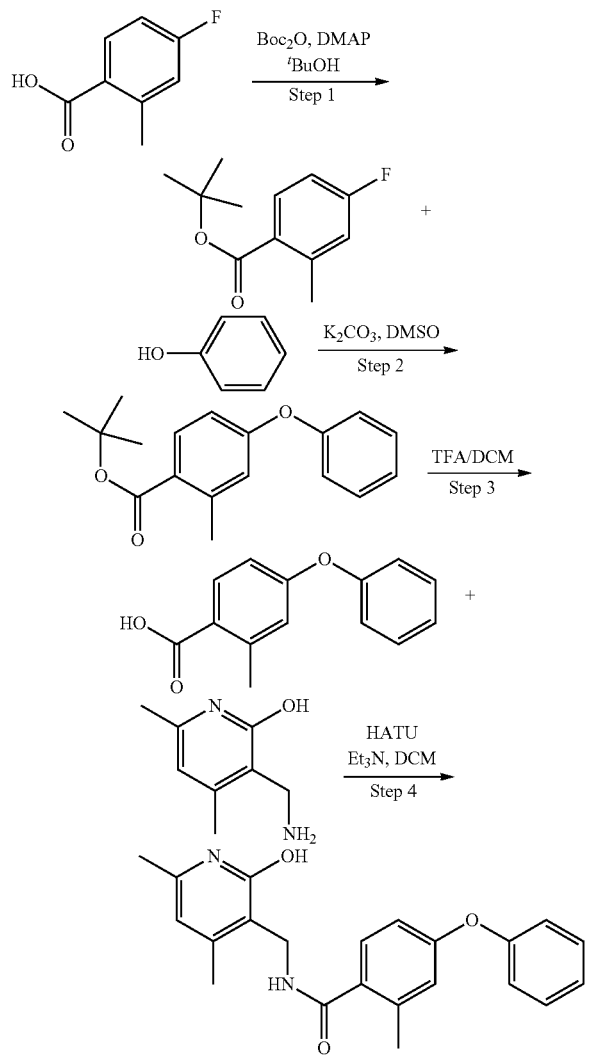

Tert-butyl 4-fluoro-2-methylbenzoate

To a solution of 4-fluoro-2-methylbenzoic acid (5 g, 32.5 mmol) in 2-methylpropan-2-ol (100 mL) were added di-tert-butyl dicarbonate (13 g, 60 mmol) and N,N-dimethylpyridin-4-amine (1.5 g, 12.3 mmol). Then the mixture was stirred at room temperature for 15 hours. The mixture was concentrated to give a residue and the residue was purified by column chromatography (silica gel, petroleum ether/ethyl acetate=10:1) to give tert-butyl 4-fluoro-2-methylbenzoate (1.8 g, 26%) as a yellow oil. LRMS (M+H$^+$) m/z: calcd 210.11. found 210.

Tert-butyl 2-methyl-4-phenoxybenzoate

To a solution of tert-butyl 4-fluoro-2-methylbenzoate (1 g, 4.8 mmol) in methylsulfinylmethane (45 mL) were added phenol (0.43 g, 4.6 mmol) and potassium carbonate (1.24 g, 9 mmol). Then the mixture was stirred at 130° C. for 12 hours. The reaction mixture was poured into water (50 mL) and extracted with ethyl acetate (50 mL). The organic phase was separated, washed with water (20 mL). The organic phase was separated and concentrated to give a residue. The residue was purified by column chromatography (petroleum ether/ethyl acetate=10:1) to give tert-butyl 2-methyl-4-phenoxybenzoate (1.1 g, 86%) as a yellow solid. LRMS (M+H$^+$) m/z: calcd 284.14. found 284.

2-methyl-4-phenoxybenzoic acid

To a solution of tert-butyl 2-methyl-4-phenoxybenzoate (150 mg, 0.53 mmol) in dichloromethane (10 mL) was added 2,2,2-trifluoroacetic acid (2 mL). The mixture was stirred at room temperature for 0.5 hour, and then concentrated to give 2-methyl-4-phenoxybenzoic acid (100 mg, 84% yield) as a white solid.
LRMS (M+H)$^-$ m/z: calcd 228.08. found 228.

N-((2-hydroxy-4,6-dimethylpyridin-3-yl)methyl)-2-methyl-4-phenoxybenzamide (Compound I-28)

To a solution of 2-methyl-4-phenoxybenzoic acid (100 mg, 0.44 mmol) in dichloromethane (20 mL) were added o-(7-azabenzotriazol-1-yl)-N,N,N',N'-tetramethyluronium hexafluorophosphate (190 mg, 0.5 mmol), and triethylamine (77 mg, 0.7 mmol). The mixture was stirred for 0.5 hour. Then 3-(aminomethyl)-4,6-dimethylpyridin-2-ol (60 mg, 0.4 mmol) was added and the mixture was stirred at room temperature for 4 hours. The mixture was washed with water (50 mL) and the organic phase was separated, concentrated to give a residue. The residue was purified by column chromatography (silica gel, dichloromethane/methanol=20:1) to afford N-((2-hydroxy-4,6-dimethylpyridin-3-yl)methyl)-2-methyl-4-phenoxybenzamide (40 mg, 25%) as a white solid. LRMS (M+H$^+$) m/z: calcd 362.16. found 362. HPLC purity (214 nm): 100%. $^1$H NMR (300 MHz, d$^6$-DMSO): δ 7.40-7.31 (m, 3H), 7.18-7.13 (m, 1H), 7.02-6.99 (m, 2H), 6.83-6.76 (m, 2H), 6.12 (s, 2H), 4.47 (s, 2H), 2.43 (s, 3H), 2.41 (s, 3H), 2.20 (s, 3H).

Example 25

Synthesis of compound N-((2-hydroxy-4,6-dimethylpyridin-3-yl)methyl)-4-(phenylsulfinyl)benzamide (Compound I-29)

This synthesis involved 4 steps.

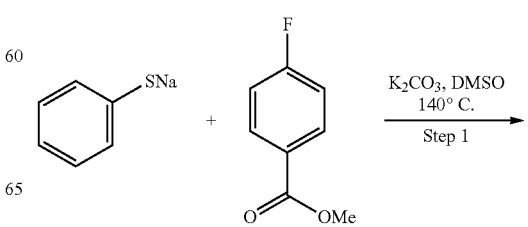

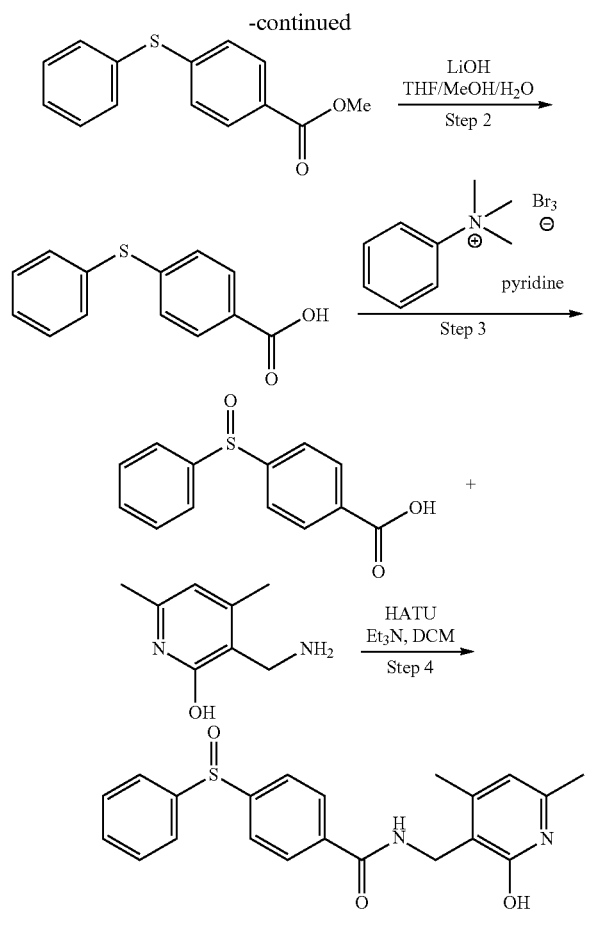

Methyl 4-(phenylthio)benzoate

To a solution of sodium benzenethiolate (5 g, 38 mmol) and methyl 4-fluorobenzoate (5.85 g, 38 mmol) in dimethyl sulfoxide (20 mL) was added potassium carbonate (14.6 g, 106 mmol). The reaction mixture was stirred at 140° C. for 12 hours. After the reaction, the temperature was allowed to cool to room temperature, and then the mixture was poured into ice water (50 mL) and extracted with acetic ether (50 mL×3). The combined organic phase was dried by sodium sulfate, and then filtered. The filtrate was concentrated in vacuo. The residue was purified by column chromatography (silica gel, petroleum ether/ethyl acetate=10:1) to give methyl 4-(phenylthio) benzoate as a white solid (5.0 g, 54%). LRMS (M+H$^+$) m/z: calcd 244.06. found 244.

4-(phenylthio)benzoic acid

A mixture of methyl 4-(phenylthio)benzoate (5 g, 20.4 mmol), lithium hydroxide monohydrate (1.1 g, 26 mmol), tetrahydrofuran (5 mL), methanol (1 mL) and water (1 mL) was stirred at 20° C. for 4 hours. The mixture was neutralized to pH=1 with concentrated hydrochloric acid and then extracted with ethyl acetate (15 mL×3). The combined organic phase was dried by sodium sulfate, and then filtered. The filtrate was concentrated in vacuo to give 4-(phenylthio) benzoic acid as a white solid (4.5 g, 96%). LRMS (M+H$^+$) m/z: calcd 230.04. found 230.

4-(phenylsulfinyl)benzoic acid

To a suspension of 4-(phenylthio)benzoic acid (800 mg, 3.5 mmol) in pyridine (5 mL) and water (5 mL) was added N-phenyl-N,N,N-trimethylammonium tribromide (1.4 g, 3.7 mmol). The mixture was stirred at 20° C. for 12 hours. Then the solvent was evaporated in vacuo to give 4-(phenylsulfinyl)benzoic acid which was used directly without further purification. LRMS (M+H)$^-$ m/z: calcd 246.04. found 246.

N-((2-hydroxy-4,6-dimethylpyridin-3-yl)methyl)-4-(phenylsulfinyl)benzamide (Compound I-29)

A mixture of 4-(phenylsulfinyl)benzoic acid (130 mg, 0.53 mmol), 3-(aminomethyl)-4,6-dimethylpyridin-2-ol (100 mg, 0.6 mmol), o-(7-Azabenzotriazol-1-yl)-N,N,N',N'-tetramethyluronium hexafluorophosphate (380 mg, 1.0 mmol) and triethylamine (0.1 mL) in dichloromethane (6 mL) was stirred at 25° C. for 12 hours. After the reaction, water (10 mL) was added and the mixture was extracted with dichloromethane (10 mL×3). The combined organic phase was dried by sodium sulfate and then filtered. The filtrate was concentrated in vacuo. The residue was purified by column chromatography (silica gel, dichloromethane/methanol=15:1) to give N-((2-hydroxy-4,6-dimethylpyridin-3-yl)methyl)-4-(phenylsulfinyl)benzamide as a white solid (90 mg, 44%). LRMS (M+H$^+$) m/z: calcd 380.12. found 380. $^1$H NMR (300 MHz, d$^6$-DMSO): δ 11.46 (s, 1H), 8.47 (t, J=4.8 Hz, 1H), 7.94 (d, J=8.7 Hz, 2H), 7.78-7.71 (m, 4H), 7.54-7.50 (m, 3H), 5.84 (s, 1H), 4.28 (d, J=4.8 Hz, 2H), 2.14 (s, 3H), 2.10 (s, 3H).

Example 26

Synthesis of compound (S)—N-((2-hydroxy-4,6-dimethylpyridin-3-yl)methyl)-4-(1-phenoxyethyl)benzamide This synthesis involved 3 steps.

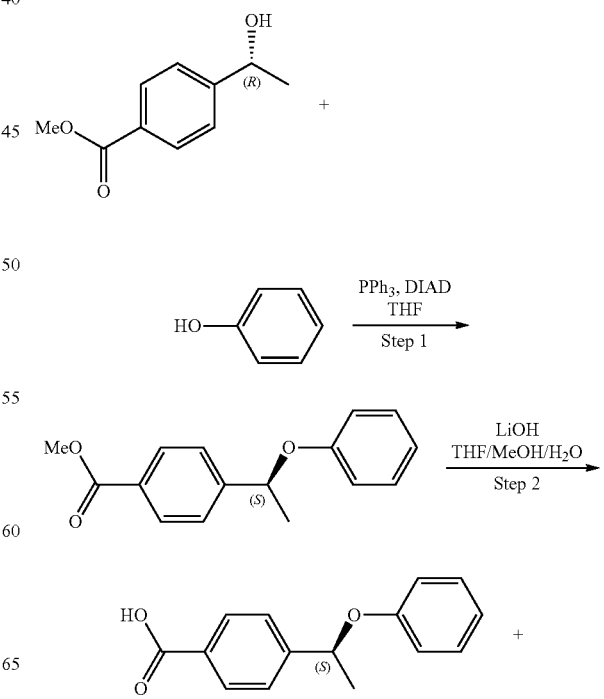

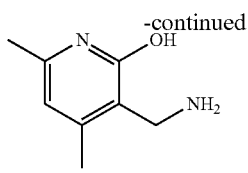

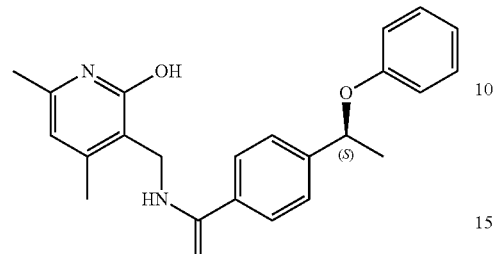

(S)-methyl 4-(1-phenoxyethyl)benzoate

To a solution of (R)-methyl 4-(1-hydroxyethyl)benzoate (360 mg, 2 mmol) in anhydrous tetrahydrofuran (20 mL) was added phenol (188 mg, 2 mmol) and triphenylphosphine (524 mg, 2 mmol) at 0° C., then stirred for 1 hour, (E)-diisopropyl diazene-1,2-dicarboxylate (404 mg, 2 mmol) was added, then stirred at room temperature for 12 hours. The reaction mixture was concentrated in vacuo. The residue was purified by column chromatography (silica gel, dichloromethane/methanol=4:1) to give (S)-methyl 4-(1-phenoxyethyl)benzoate (410 mg, 80%). LRMS (M+H$^+$) m/z: calcd 256.11. found 256.

(S)-4-(1-phenoxyethyl)benzoic acid

To a solution of(S)-methyl 4-(1-phenoxyethyl)benzoate (410 mg, 1.6 mmol) in tetrahydrofuran (20 mL) and methanol (7 mL) were added lithium hydroxide (120 mg, 5 mmol) in water (7 mL), then stirred at room temperature for 4 hours. The reaction mixture was concentrated, to the residue was added water (10 mL), acidified with hydrochloric acid to PH=4, collected and dried the solid to give (S)-4-(1-phenoxyethyl)benzoic acid (242 mg, 62%). LRMS (M+H$^+$) m/z: calcd 242.09. found 242.

(S)—N-((2-hydroxy-4,6-dimethylpyridin-3-yl)methyl)-4-(1-phenoxyethyl)benzamide

To a solution of (S)-4-(1-phenoxyethyl)benzoic acid (121 mg, 0.5 mmol) in dichloromethane (20 mL) was added 1H-benzo[d][1,2,3]triazol-1-ol (135 mg, 1 mmol), 1-(3-Dimethylaminopropyl)-3-ethylcarbodiimide hydrochloride (190 mg, 1 mmol) and triethylamine (252 mg, 2.5 mmol), and stirred at room temperature for 0.5 hour, 3-(aminomethyl)-4,6-dimethylpyridin-2-ol (152 mg, 1 mmol) was added and stirred for 4 hours. To the reaction mixture was added water (20 mL), extracted with dichloromethane (20 mL) two times, combined and concentrated the organic layers, the residue was purified by chromatography with dichloromethane/methanol=20:1 to afford (S)—N-((2-hydroxy-4,6-dimethylpyridin-3-yl)methyl)-4-(1-phenoxyethyl)benzamide (150 mg, 80%). LRMS (M+H+) m/z: calcd for 376.18. found 376. HPLC Purity (214 nm): 96%. $^1$H NMR (300 MHz, DMSO-d$^6$): δ 11.45 (s, 1H), 8.30 (t, J=5.1 Hz, 1H), 7.79 (d, J=8.1 Hz, 2H), 7.44 (d, J=8.1 Hz, 2H), 7.18 (t, J=7.2 Hz, 2H), 6.88-6.81 (m, 3H), 5.84 (s, 1H), 5.52 (q, J=6.3 Hz, 1H), 4.27 (d, J=4.8 Hz, 2H), 2.15 (s, 3H), 2.10 (s, 3H), 1.54 (d, J=6.6 Hz, 3H).

Example 27

Synthesis of compound (S)—N-((2-hydroxy-4,6-dimethylpyridin-3-yl)methyl)-4-(1-phenoxyethyl)benzamide (Compound I-30)

This synthesis involved 5 steps.

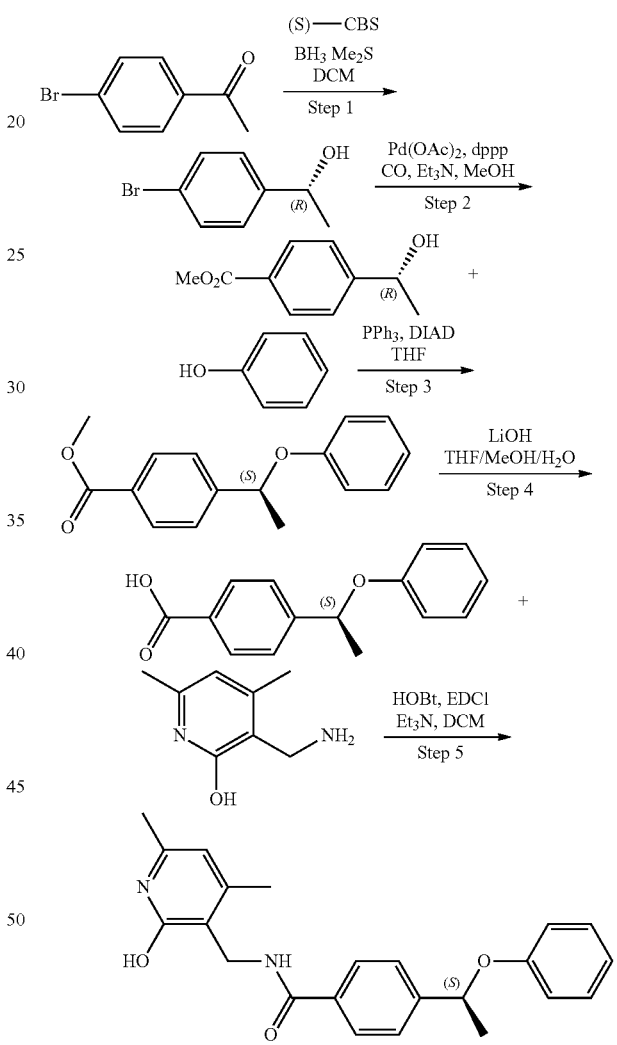

(R)-1-(4-bromophenyl)ethanol

To a solution of 4-bromoacetophenone (5.0 g, 25 mmol) and (S)-2-Methyl-CBS-oxazaborolidine (1.25 mL, 1 M) in anhydrous dichloromethane (80 mL) was added borane-methyl sulfide complex (2.1 g, 27 mmol) over 1 hour at −20° C. After addition completed, the mixture was stirred at −20° C. for 2 hours, then stirred at room temperature for 12 hours. After the reaction, methanol (20 mL) was added, and stirred for 0.5 hour. Then the mixture was diluted with water (100 mL) and the organic phase was dried over anhydrous sodium sulfate. The mixture was filtered and the filtrate was concentrated. The residue was purified by column chromatography (silica gel, ethyl acetate/petroleum ether=1:8) to give pure product (R)-1-(4-bromophenyl)ethanol as a white solid (4.6 g, 92%).

(R)-methyl 4-(1-hydroxyethyl)benzoate

To a solution of (R)-1-(4-bromophenyl)ethanol (3.0 g, 15 mmol) in methanol (20 mL) was added palladium acetate (2.0 g, 8.9 mmol), 1,3-bis(diphenylphosphino) propane (1.2 g, 3 mmol) and triethyl amine (3.0 g, 30 mmol). The reaction mixture was stirred at 90° C. under carbon monoxide atmosphere (20 atm) for 12 hours. After the reaction, the mixture was diluted with water (100 mL), extracted with dichloromethane (100 mL). The organic phase was dried over anhydrous sodium sulfate and then filtered. The filtrate was concentrated and the residue purified by column chromatography (silica gel, petroleum ether/ethyl acetate=8:1) to give pure product (R)-methyl 4-(1-hydroxyethyl)benzoate as a white solid (2.4 g, 89%).

(S)-methyl 4-(1-phenoxyethyl)benzoate

To a solution of (R)-methyl 4-(1-hydroxyethyl)benzoate (0.9 g, 5 mmol), phenol (525 mg, 5.6 mmol), triphenylphosphine (2198 mg, 8.4 mmol) in tetrahydrofuran (30 mL) was added diisopropyl azodicarboxylate (1695 mg, 8.4 mmol) at 0° C. The mixture was stirred at 20° C. for 12 hours. Water (15 mL) was added to the mixture and then extracted with ethyl acetate (35 mL×3). The combined organic phase was dried by sodium sulfate, and then filtered. The filtrate was concentrated in vacuo and purified by column chromatography (silica gel, petroleum ether/ethyl acetate=5:1) to give (S)-methyl 4-(1-phenoxyethyl)benzoate (700 mg, 54%). $^1$H NMR (300 MHz, d$^6$-DMSO): δ 8.02-7.98 (m, 2H), 7.46-7.43 (m, 2H), 7.23-7.16 (m, 2H), 6.91-6.80 (m, 3H), 5.36 (q, J=6.0 Hz, 1H), 3.90 (s, 3H), 1.64 (d, J=6.6 Hz, 3H).

(S)-4-(1-phenoxyethyl)benzoic acid

A mixture of (S)-methyl 4-(1-phenoxyethyl)benzoate (0.7 g, 2.7 mmol), lithium hydroxide monohydrate (571 mg, 13.6 mmol), tetrahydrofuran (15 mL), methanol (5 mL) and water (5 mL) was stirred at 20° C. for 4 hours. The mixture was neutralized to pH=1 with concentrated hydrochloric acid and then extracted with ethyl acetate (15 mL×3). The combined organic phase was dried by sodium sulfate, and then filtered. The filtrate was concentrated in vacuo to give (S)-4-(1-phenoxyethyl)benzoic acid (0.5 g, 76%).

(S)—N-((2-hydroxy-4,6-dimethylpyridin-3-yl)methyl)-4-(1-phenoxyethyl)benzamide (Compound I-30)

A mixture of (S)-4-(1-phenoxyethyl)benzoic acid (121 mg, 0.5 mmol), 1-ethyl-3-(3-dimethylaminopropyl)carbodiimide hydrochloride (191 mg, 1 mmol), N-hydroxybenzotriazole (135 mg, 1 mmol), triethylamine (0.2 mL) and dichloromethane (5 mL) were stirred at 25° C. for half an hour. And then 3-(aminomethyl)-4,6-dimethylpyridin-2-ol (76 mg, 0.5 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give (S)—N-((2-hydroxy-4,6-dimethylpyridin-3-yl)methyl)-4-(1-phenoxyethyl)benzamide as a white solid (100 mg, 53%). LRMS (M+H$^+$) m/z: calcd. 376.18. found 376. HPLC purity (214 nm): 100%. $^1$H NMR (300 MHz, d$^6$-DMSO): δ 11.44 (s, 1H), 8.29-8.27 (m, 1H), 7.77 (d, J=8.1 Hz, 2H), 7.42 (d, J=8.1 Hz, 2H), 7.20-7.15 (m, 2H), 6.87-6.83 (m, 3H), 5.83 (s, 1H), 5.53-5.51 (m, 1H), 4.26 (d, J=5.1 Hz, 2H), 2.14 (s, 3H), 2.10 (s, 3H), 1.53 (d, J=6.6 Hz, 3H).

(R)—N-((2-hydroxy-4,6-dimethylpyridin-3-yl)methyl)-4-(1-phenoxyethyl)benzamide (Compound I-30) was similarly prepared using the appropriate chiral reagents.

Example 28

Synthesis of compound (S)—N-((2-hydroxy-4,6-dimethylpyridin-3-yl)methyl)-4-(1-phenoxyethyl) benzamide (Compound I-31)

This synthesis involved 3 steps.

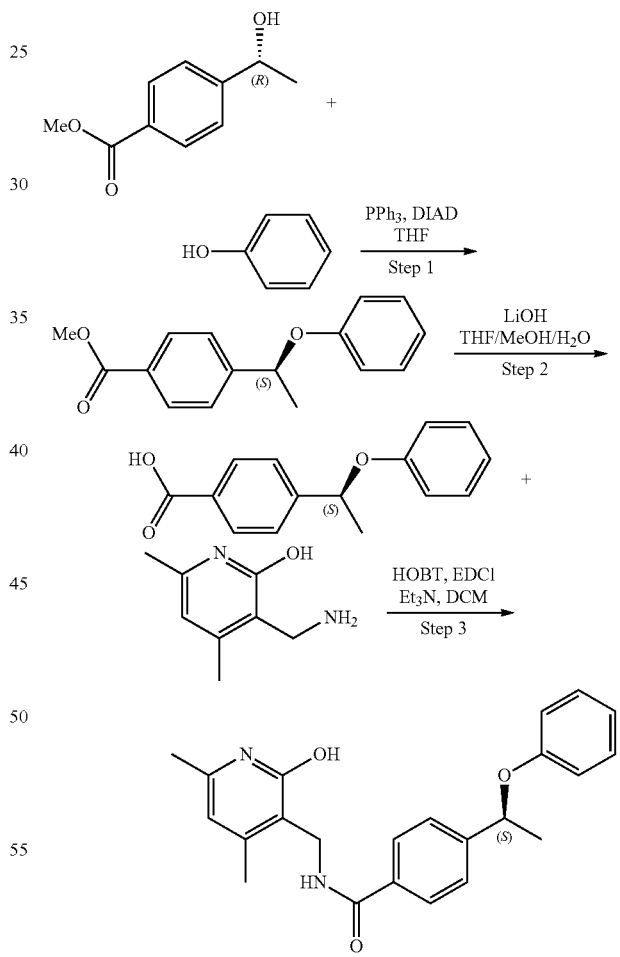

(S)-methyl 4-(1-phenoxyethyl)benzoate

To a solution of (R)-methyl 4-(1-hydroxyethyl)benzoate (360 mg, 2 mmol) in anhydrous tetrahydrofuran (20 mL) was added phenol (188 mg, 2 mmol) and triphenylphosphine (524 mg, 2 mmol) at 0° C., then stirred for 1 hour, (E)-diisopropyl diazene-1,2-dicarboxylate (404 mg, 2 mmol) was added, then stirred at room temperature for 12 hours. The reaction mixture was concentrated in vacuo. The residue was purified by column chromatography (silica gel, dichloromethane/methanol=4:1) to give (S)-methyl 4-(1-phenoxyethyl)benzoate (410 mg, 80%). LRMS (M+H$^+$) m/z: calcd 256.11. found 256.

(S)-4-(1-phenoxyethyl)benzoic acid

To a solution of(S)-methyl 4-(1-phenoxyethyl)benzoate (410 mg, 1.6 mmol) in tetrahydrofuran (20 mL) and methanol (7 mL) were added lithium hydroxide (120 mg, 5 mmol) in water (7 mL), then stirred at room temperature for 4 hours. The reaction mixture was concentrated, to the residue was added water (10 mL), acidified with hydrochloric acid to PH=4, collected and dried the solid to give (S)-4-(1-phenoxyethyl)benzoic acid (242 mg, 62%). LRMS (M+H$^+$) m/z: calcd 242.09. found 242.

(S)—N-((2-hydroxy-4,6-dimethylpyridin-3-yl)methyl)-4-(1-phenoxyethyl)benzamide

To a solution of (S)-4-(1-phenoxyethyl)benzoic acid (121 mg, 0.5 mmol) in dichloromethane (20 mL) was added 1H-benzo[d][1,2,3]triazol-1-ol (135 mg, 1 mmol), 1-(3-Dimethylaminopropyl)-3-ethylcarbodiimide hydrochloride (190 mg, 1 mmol) and triethylamine (252 mg, 2.5 mmol), and stirred at room temperature for 0.5 hour, 3-(aminomethyl)-4,6-dimethylpyridin-2-ol (152 mg, 1 mmol) was added and stirred for 4 hours. To the reaction mixture was added water (20 mL), extracted with dichloromethane (20 mL) two times, combined and concentrated the organic layers, the residue was purified by chromatography with dichloromethane/methanol=20:1 to afford (S)—N-((2-hydroxy-4,6-dimethylpyridin-3-yl)methyl)-4-(1-phenoxyethyl)benzamide (Compound I-31) (150 mg, 80%). LRMS (M+H$^+$) m/z: calcd for 376.18. found 376. HPLC Purity (214 nm): 96%. $^1$H NMR (300 MHz, DMSO-d$^6$): δ 11.45 (s, 1H), 8.30 (t, J=5.1 Hz, 1H), 7.79 (d, J=8.1 Hz, 2H), 7.44 (d, J=8.1 Hz, 2H), 7.18 (t, J=7.2 Hz, 2H), 6.88-6.81 (m, 3H), 5.84 (s, 1H), 5.52 (q, J=6.3 Hz, 1H), 4.27 (d, J=4.8 Hz, 2H), 2.15 (s, 3H), 2.10 (s, 3H), 1.54 (d, J=6.6 Hz, 3H).

Example 29

Synthesis of compound N-((2-hydroxy-4,6-dimethylpyridin-3-yl)methyl)-2-methoxy-4-phenoxybenzamide (Compound I-32)

This synthesis involved 4 steps.

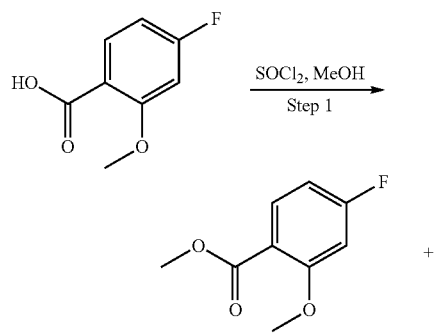

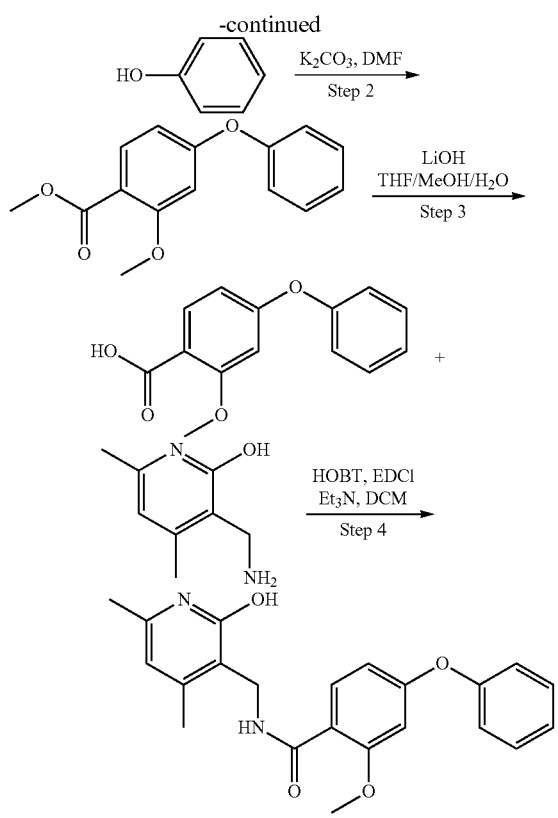

Methyl 4-fluoro-2-methoxybenzoate

To a solution of 4-fluoro-2-methoxybenzoic acid (1.7 g, 10 mmol) in methanol (100 mL) was added thionyl chloride (5.73 g, 48 mmol) at 0° C. The resultant mixture was stirred for 12 hours and then solvent was evaporated in vacuo. To the residue, saturated sodium bicarbonate aqueous solution (50 mL) was added and the mixture was extracted with ethyl acetate (100 mL×3). The organic phase was dried by sodium sulfate. The mixture was filtered and the filtrate was concentrated in vacuo to give methyl 4-fluoro-2-methoxybenzoate (1.3 g, 70%).

Methyl 2-methoxy-4-phenoxybenzoate

To a solution of methyl 4-fluoro-2-methoxybenzoate (1.84 g, 10 mmol) in N,N-dimethylformamide (100 mL) were added phenol (0.94 g, 10 mmol) and potassium carbonate (2.67 g, 20 mmol). The mixture was heated to 80° C. and stirred for 12 hours. The solvent was evaporated in vacuo and the residue was purified by column chromatography (silica gel, petroleum ether/ethyl acetate=7:1) to give methyl 2-methoxy-4-phenoxybenzoate (2.1 g, 81%).

2-methoxy-4-phenoxybenzoic acid

A mixture of methyl 2-methoxy-4-phenoxybenzoate (1.3 g, 5 mmol), lithium hydroxide monohydrate (571 mg, 13.6 mmol), tetrahydrofuran (150 mL), methanol (50 mL) and water (50 mL) was stirred at 20° C. for 4 hours. The mixture was adjusted to pH=1 with concentrated hydrochloric acid and then extracted with ethyl acetate (15 mL×3). The combined organic phase was dried by sodium sulfate, and then filtered. The filtrate was concentrated in vacuo to give 2-methoxy-4-phenoxybenzoic acid (1 g, 82%).

N-((2-hydroxy-4,6-dimethylpyridin-3-yl)methyl)-2-methoxy-4-phenoxybenzamide (Compound I-32)

A mixture of 4-(1-phenoxyethyl)benzoic acid (122 mg, 0.5 mmol), 1-ethyl-3-(3-dimethylaminopropyl)carbodiimide hydrochloride (191 mg, 1 mmol), N-hydroxybenzotriazole (135 mg, 1 mmol) and triethylamine (0.2 mL) in dichloromethane (5 mL) was stirred at 25° C. for 0.5 hour. And then 3-(aminomethyl)-4,6-dimethylpyridin-2-ol (76 mg, 0.5 mmol) was added. The mixture was stirred at 25° C. for 12 hours. To the mixture, water (20 ml) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give N-((2-hydroxy-4,6-dimethylpyridin-3-yl)methyl)-2-methoxy-4-phenoxybenzamide as a white solid (80 mg, 42%). LRMS (M+H$^+$) m/z: calcd. 378.16. found 378. HPLC purity (214 nm): 99%. $^1$H NMR (300 MHz, d$^6$-DMSO): δ 11.56 (s, 1H), 8.72-8.68 (m, 1H), 7.88 (d, J=8.7 Hz, 1H), 7.45-7.39 (m, 2H), 7.22-7.17 (m, 1H), 7.09-7.06 (m, 2H), 6.79 (s, 1H), 6.52-6.49 (m, 1H), 5.86 (s, 1H), 4.30 (d, J=5.7 Hz, 2H), 3.85 (s, 3H), 2.11 (s, 3H), 1.98 (s, 3H)
I-33

Example 30

Synthesis of N-((2-hydroxy-4,6-dimethylpyridin-3-yl)methyl)-4-(1-phenylethyl)benzamide (Compound I-33)

This synthesis involved 6 steps.

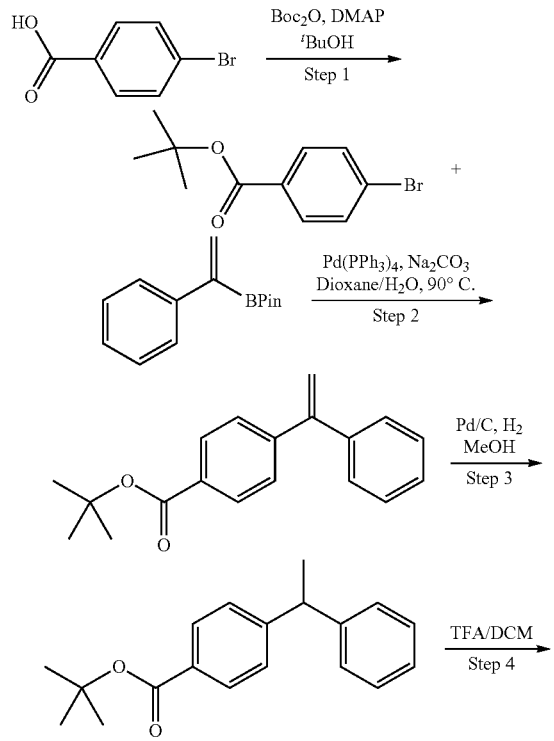

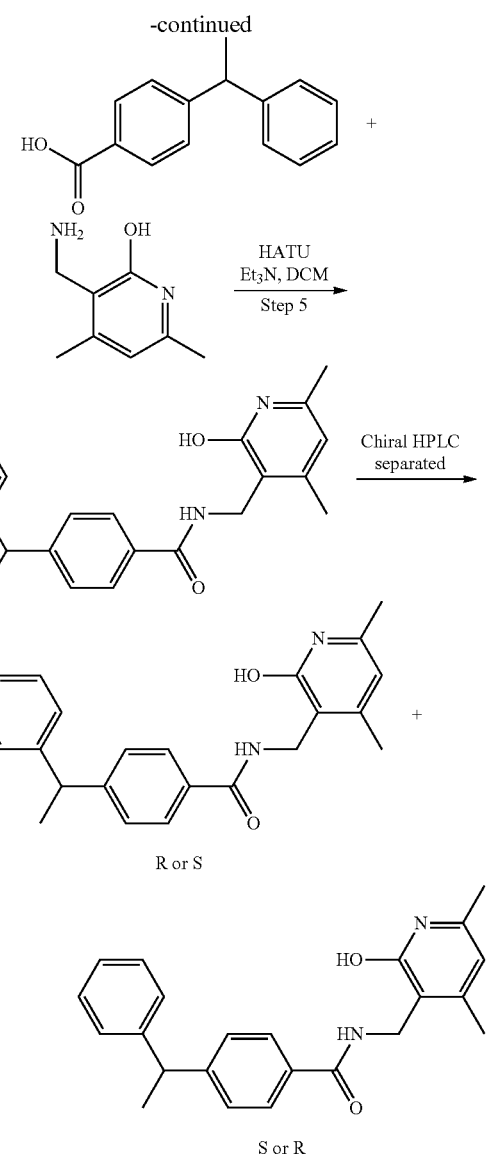

Tert-butyl 4-bromobenzoate

To a solution of 4-dimethylamiopryidine (1.5 g, 12.5 mmol) in tert-butanol (20 mL) were added 4-bromobenzoic acid (5 g, 25 mmol) and di-tert-butyl dicarbonate (10.95 g, 0.05 mol). The mixture was stirred at 20° C. for 12 hours. The resultant mixture was concentrated in vacuo to give a residue and the residue was purified by column chromatography (silica gel, petroleum ether/ethyl acetate=30:1) to give tert-butyl 4-bromobenzoate (4 g, 62%).

Tert-butyl 4-(1-phenylvinyl)benzoate

To a solution of tert-butyl 4-bromobenzoate (616 mg, 2.4 mmol) in 1,4-dioxane and water (4:1, 10 mL) were added (E)-4,4,5,5-tetramethyl-2-styryl-1,3,2-dioxaborolane (553 mg, 2.4 mmol), tetrakis(triphenylphosphine)palladium (58.9 mg, 0.05 mmol) and sodium carbonate (164 mg, 1.55 mmol). The mixture was stirred at 90° C. under nitrogen atmosphere for 18 hours. Once the start material was consumed, the resultant mixture was concentrated to give a residue and the residue was purified by column chromatography (silica gel, petroleum ether/ethyl acetate=30:1) to give tert-butyl 4-(1-phenylvinyl)benzoate (0.59 g, 87.5%). $^1$H NMR (300 MHz, CDCl$_3$): δ 7.96 (d, J=4.8 Hz, 2H), 7.41-7.26 (m, 7H), 5.55-5.53 (m, 2H), 1.61 (s, 9H).

Tert-butyl 4-(1-phenylethyl)benzoate

A mixture of tert-butyl 4-(1-phenylvinyl)benzoate (0.59 g, 2.1 mmol) and palladium on carbon (10%, 100 mg) in methanol (20 mL) was stirred at 20° C. under hydrogen atmosphere (4 atm) for 24 hours. Once the start material has been consumed, the resultant mixture was filtered and concentrated in vacuo to give a residue. The residue was purified by column chromatography (silica gel, petroleum ether/ethyl acetate=20:1) to give tert-butyl 4-(1-phenylethyl)benzoate (500 mg, 84%). $^1$H NMR (300 MHz, CD$_3$OD): δ 7.85 (d, J=4.8 Hz, 2H), 7.30-7.15 (m, 7H), 4.19-4.16 (m, 1H), 1.61 (d, J=7.2 Hz, 3H), 1.50 (s, 9H).

4-(1-phenylethyl)benzoic acid

To a solution of tert-butyl 4-(1-phenylethyl)benzoate (500 mg, 1.77 mmol) in dichloromethane (8 mL), trifluoroacetic acid (2 mL) was added. The mixture was stirred for 0.5 hour. Once the start material was consumed, the resultant mixture was concentrated to give 4-(1-phenylethyl)benzoic acid (360 mg, 90%).

N-((2-hydroxy-4,6-dimethylpyridin-3-yl)methyl)-4-(1-phenylethyl)benzamide (Compound I-33)

A mixture of 4-(1-phenylethyl)benzoic acid (150 mg, 0.66 mol), 2-(7-aza-1H-benzotriazole-1-yl)-1,1,3,3-tetramethyluronium hexafluorophosphate (303 mg, 0.797 mmol), triethylamine (2 mL) in dichloromethane (25 mL) was stirred at 25° C. for 0.5 hour. And then 3-(aminomethyl)-4,6-dimethylpyridin-2-ol (101 mg, 0.66 mmol) was added. After stirring at 25° C. for 12 hours, water (15 mL) was added to the reaction mixture. And the mixture was extracted with dichloromethane (10 mL×3). The combined organic phase was separated, dried by sodium sulfate and then filtered. The filtrate was concentrated to give a residue in vacuo. The residue was purified by column chromatography (silica gel, dichloromethane/methanol=10:1) to give N-((2-hydroxy-4,6-dimethylpyridin-3-yl)methyl)-4-(1-phenylethyl)benzamide (100 mg, 42%).

LRMS (M+H$^+$) m/z: calcd 360.02. found 360. HPLC purity (214 nm): 99%. $^1$H NMR (300 MHz, d$^6$-DMSO): δ 11.46 (s, 1H), 8.25 (t, J=4.5 Hz, 1H), 7.83 (d, J=7.2 Hz, 2H), 7.32-7.26 (m, 7H), 5.85 (s, 1H), 4.29 (d, J=4.8 Hz, 2H), 4.28-4.26 (m, 1H), 2.15 (s, 3H), 2.10 (s, 3H), 1.57 (d, J=7.2 Hz, 3H).

Example 31

Synthesis of 4-benzyl-N-((2-hydroxy-4,6-dimethylpyridin-3-yl)methyl)benzamide (Compound I-34)

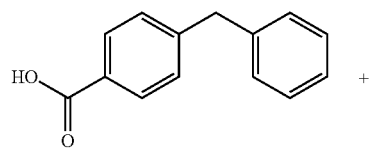

+

-continued

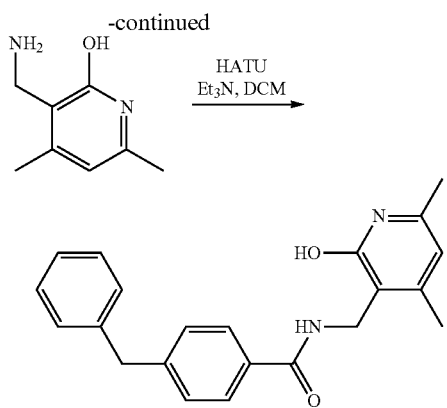

A mixture of 4-benzoylbenzoic acid (106 mg, 0.5 mmol), o-(7-azabenzotriazol-1-yl)-N,N,N',N'-tetramethyluronium-hexafluorophosphate (285 mg, 0.75 mmol), triethylamine (152 mg, 1.5 mmol) and dichloromethane (15 mL) were stirred at 25° C. for half an hour. Then 3-(aminomethyl)-4,6-dimethylpyridin-2-ol (76 mg, 0.5 mmol) was added. The mixture was stirred at 25° C. for 12 hours. The resultant mixture was washed with water (20 mL). The organic phase was separated, dried over sodium, filtered and concentrated to give a residue. The residue was purified by column chromatography (silica gel, dichloromethane/methanol=10:1) to give 4-benzyl-N-((2-hydroxy-4,6-dimethylpyridin-3-yl)methyl)benzamide as a white solid (50 mg, 29%). LRMS (M+H$^+$) m/z: 346.17. found 346. HPLC purity (214 nm): 97%. $^1$H NMR (300 MHz, d$^6$-DMSO): δ 11.50 (s, 1H), 8.29 (t, J=4.8 Hz, 1H), 7.76 (d, J=8.4 Hz, 2H), 7.28-7.13 (m, 7H), 5.85 (s, 1H), 4.30 (d, J=4.8 Hz, 2H), 3.96 (s, 2H), 2.16 (s, 3H), 2.11 (s, 3H).

Example 32

Synthesis of N-((2-hydroxy-4,6-dimethylpyridin-3-yl)methyl)-4-(1-(p-tolyloxy)ethyl)benzamide (Compound I-35)

This synthesis involved 3 steps.

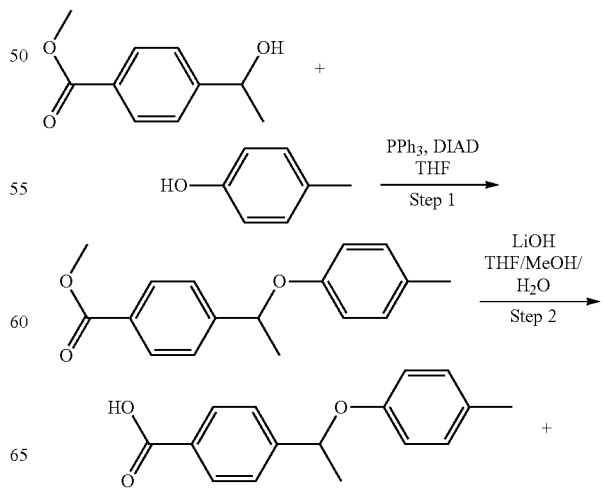

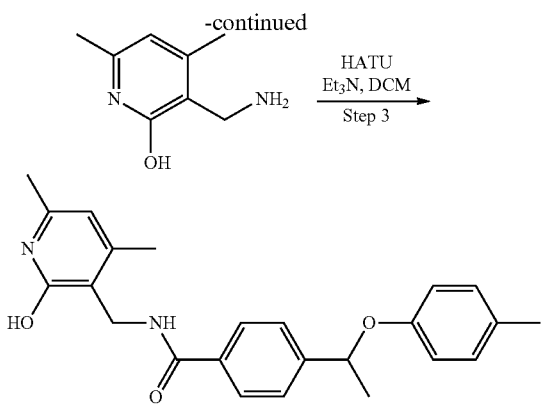

Methyl 4-(1-(p-tolyloxy)ethyl)benzoate

A mixture of methyl 4-(1-hydroxyethyl)benzoate (180 mg, 1.0 mmol), p-cresol (130 mg, 1.2 mmol), triphenylphosphine (393 mg, 1.5 mmol) and tetrahydrofuran (15 mL) were stirred at 20° C. for half an hour. Then azodicarboxylic acid diisopropyl ester (303 mg, 1.5 mmol) was added. The mixture was stirred at 20° C. for 12 hours. The resultant mixture was washed with water (20 mL×3). The organic phase was separated, dried over sodium sulfate, filtered, and concentrated to give a residue. The residue was purified by column chromatography (silica gel, petroleum ether/ethyl acetate=5:1) to furnish methyl 4-(1-(p-tolyloxy)ethyl)benzoate as a colorless oil (100 mg, 37%).

$^1$H NMR (300 MHz, CDCl$_3$): δ 8.01 (dd, J=6.3 Hz, J=1.8 Hz, 2H), 7.44 (d, J=7.8 Hz, 2H), 7.05-6.98 (m, 2H), 6.76-6.72 (m, 2H), 5.31 (q, J=6.3 Hz, 1H), 3.90 (s, 3H), 2.23 (s, 3H), 1.62 (d, J=6.3 Hz, 3H).

4-(1-(p-tolyloxy)ethyl)benzoic acid

A mixture of methyl 4-(1-(p-tolyloxy)ethyl)benzoate (50 mg, 0.19 mmol), lithium hydroxide monohydrate (39 mg, 0.92 mmol), tetrahydrofuran (6 mL), methanol (2 mL), and water (2 mL) were stirred at 20° C. for 12 hours. The reaction mixture was concentrated, acidified with concentrated hydrochloric acid to pH=1, extracted with ethyl acetate (20 mL×3). The organic phase was separated, dried over sodium sulfate, filtered and concentrated to give 4-(1-(p-tolyloxy)ethyl)benzoic acid used in next step without further purification (42 mg, 86%). LRMS (M+H)$^-$ m/z: calcd 256.11. found 256.

N-((2-hydroxy-4,6-dimethylpyridin-3-yl)methyl)-4-(1-(p-tolyloxy)ethyl)benzamide (Compound I-35)

A mixture of 4-(1-(p-tolyloxy)ethyl)benzoic acid (30 mg, 0.12 mmol), o-(7-azabenzotriazol-1-yl)-N,N,N',N'-tetramethyluroniumhexafluorophosphate (67 mg, 0.18 mmol), triethylamine (0.1 mL) and dichloromethane (15 mL) were stirred at 25° C. for half an hour. Then 3-(aminomethyl)-4,6-dimethylpyridin-2-ol (22 mg, 0.14 mmol) was added. The mixture was stirred at 25° C. for 12 hours. The resultant mixture was washed with water (30 mL), dried over sodium, filtered, and concentrated to give a residue. The residue was purified by column chromatography (silica gel, dichloromethane/methanol=10:1) to give N-((2-hydroxy-4,6-dimethylpyridin-3-yl)methyl)-4-(1-(p-tolyloxy)ethyl)benzamide as a white solid (26 mg, 56%).

LRMS (M+H$^+$) m/z: calcd 390.19. found 390. HPLC purity (214 nm): 99%. $^1$H NMR (300 MHz, d$^6$-DMSO): δ 11.45 (s, 1H), 8.33 (t, J=4.5 Hz, 1H), 8.07-7.98 (m, 2H), 7.56-7.48 (m, 2H), 7.32-7.28 (m, 2H), 6.84-6.77 (m, 2H), 5.84 (s, 1H), 5.54 (q, J=6.6 Hz, 1H), 4.25 (d, J=4.5 Hz, 2H), 2.17 (s, 3H), 2.13 (s, 3H), 2.08 (s, 3H), 1.20 (d, J=6.6 Hz, 3H).

Example 33

Synthesis of N-((2-hydroxy-4,6-dimethylpyridin-3-yl)methyl)-4-((methyl(phenyl)amino)methyl)benzamide (Compound I-36)

This synthesis involved 3 steps.

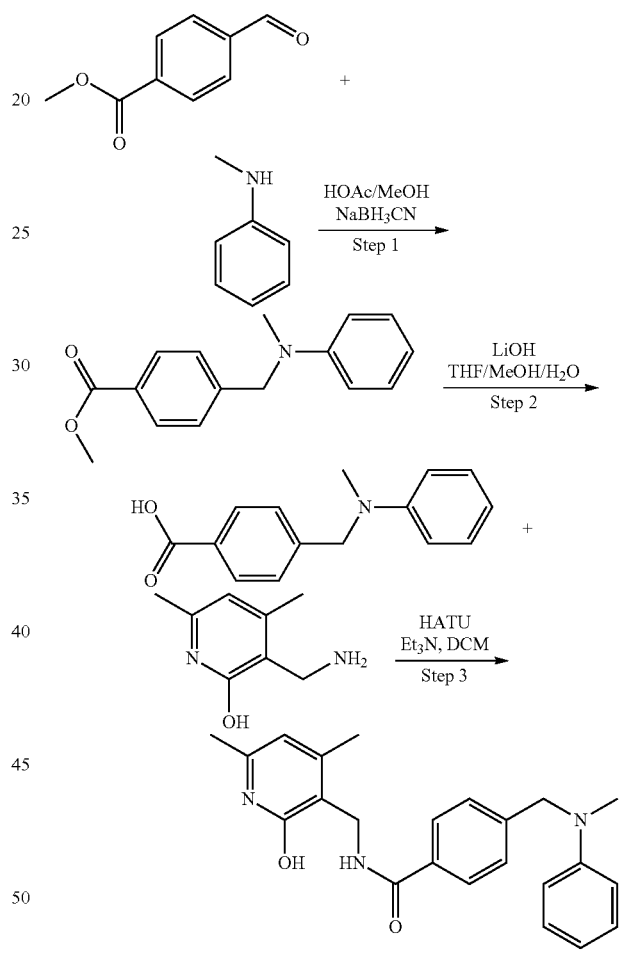

Methyl 4-((methyl(phenyl)amino)methyl)benzoate

To a solution of methyl 4-formylbenzoate (1 g, 6.1 mmol) and N-methylbenzenamine (650 mg, 6.1 mmol) in methanol (50 mL) was added acetic acid (2 drops) and the mixture was stirred for 0.5 hour. Then sodium cyanoborohydride (660 mg, 10 mmol) was added in portions. The mixture was stirred at room temperature for 24 hours. The mixture was washed with water (50 mL) and extracted with dichloromethane (50 mL). The organic phase was separated and concentrated to give a residue. The residue was purified by column chromatography (petroleum ether/ethyl acetate=1:1) to give methyl 4-((methyl(phenyl)amino)methyl)benzoate (400 mg, 26%) as a yellow oil. LRMS (M+H⁺) m/z: calcd 255.13. found 255. ¹H NMR (300 MHz, CD₃OD): δ 7.96-7.32 (m, 2H), 7.33 (d, J=8.4 Hz, 2H), 7.18-7.12 (m, 2H), 6.74-6.60 (m, 3H), 4.60 (s, 2H), 3.88 (s, 3H), 3.02 (s, 3H).

4-((methyl(phenyl)amino)methyl)benzoic acid

To a solution of methyl 4-((methyl(phenyl)amino)methyl) benzoate (400 mg, 1.57 mmol) in tetrahydrofuran (30 mL) and methanol (10 mL) was added lithium hydroxide (210 mg, 5 mmol) in water (10 mL). The mixture was stirred at room temperature for 2 hours. The suspension was concentrated in vacuo and acidified with concentrated hydrochloric acid (12 N, 5 mL). The mixture was re-dissolved by water (50 mL) and dichloromethane (50 mL). Organic phase was separated and concentrated to give the product 4-((methyl(phenyl)amino) methyl)benzoic acid (200 mg, 53%) as a white solid.

LRMS (M+H⁺)⁻ m/z: calcd 241.11. found 241.

N-((2-hydroxy-4,6-dimethylpyridin-3-yl)methyl)-4-((methyl(phenyl)amino)methyl)benzamide (Compound I-36)

To a solution of 4-((methyl(phenyl)amino)methyl)benzoic acid (200 mg, 0.83 mmol) in dichloromethane (50 mL) were added o-(7-azabenzotriazol-1-yl)-N,N,N',N'-tetramethyluronium hexafluorophosphate (380 mg, 1 mmol) and triethylamine (202 mg, 2 mmol). The mixture was stirred for 0.5 hour. Then 3-(aminomethyl)-4,6-dimethylpyridin-2-ol (120 mg, 0.8 mmol) was added and the mixture was stirred at room temperature for 4 hours. The mixture was washed with water (50 mL) and the organic phase was separated, concentrated to give a residue. The residue was purified by column chromatography (silica gel, dichloromethane/methanol=20:1) and to afford N-((2-hydroxy-4,6-dimethylpyridin-3-yl)methyl)-4-((methyl(phenyl)amino)methyl)benzamide (50 mg, 16%) as white solid. LRMS (M+H⁺) m/z: calcd 375.19. found 375. HPLC purity (214 nm): 96%. ¹H NMR (300 MHz, CD₃OD): δ 7.73 (d, J=8.4 Hz, 2H), 7.29 (d, J=8.1 Hz, 2H), 7.15-7.13 (m, 2H), 6.74-6.70 (m, 3H), 6.10 (s, 1H), 4.57 (s, 2H), 4.47 (s, 2H), 3.01 (s. 3H), 2.35 (s, 3H), 2.23 (s, 3H).

Example 34

Synthesis of compound N-((2-hydroxy-4,6-dimethylpyridin-3-yl)methyl)-3-methyl-4-phenoxybenzamide (Compound I-37)

This synthesis involved 4 steps.

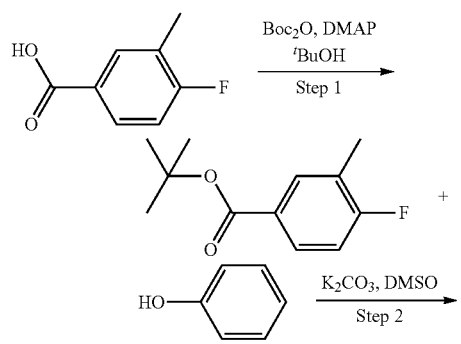

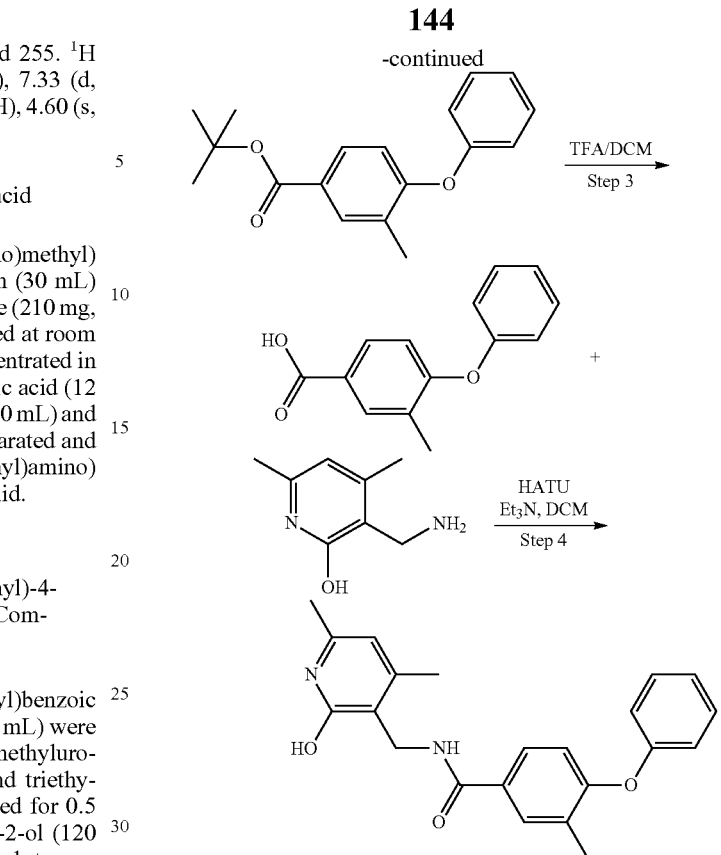

Tert-butyl 4-fluoro-3-methylbenzoate

N,N-dimethylpyridin-4-amine (246 mg, 2 mmol) was added to the mixture of 4-fluoro-3-methylbenzoic acid (616 mg, 4 mmol), di-tert-butyl dicarbonate (1.75 g, 8 mmol) and 2-methylpropan-2-ol (100 mL). The mixture was stirred at 25° C. for 12 hours. And then the mixture was concentrated to give a residue. The residue was purified by column chromatography (silica gel, petroleum ether/ethyl acetate=100:1) to give tert-butyl 4-fluoro-3-methylbenzoate (740 mg, 88%). ¹H NMR (300 MHz, CDCl₃): δ 7.85-7.79 (m, 2H), 7.01 (d, J=8.7 Hz, 1H), 2.30 (s, 3H), 1.59 (s, 9H).

Tert-butyl 3-methyl-4-phenoxybenzoate

A mixture of tert-butyl 4-fluoro-3-methylbenzoate (740 mg, 3.5 mmol), phenol (700 mg, 7.4 mmol), potassium carbonate (993 mg, 7.2 mmol) and methylsulfinylmethane (10 mL) was stirred at 120° C. for 12 hours. The mixture was concentrated to give a residue. The residue was purified by column chromatography (silica gel, petroleum ether/ethyl acetate=80:1) to give tert-butyl 3-methyl-4-phenoxybenzoate as a colorless oil (654 mg, 66%). ¹H NMR (300 MHz, CDCl₃): δ 8.08 (s, 1H), 7.68 (s, 1H), 7.38 (s, 1H), 7.32-7.28 (m, 2H), 6.84-6.77 (m, 3H), 2.26 (s, 3H), 1.56 (s, 9H).

3-methyl-4-phenoxybenzoic acid

A mixture of tert-butyl 3-methyl-4-phenoxybenzoate (654 mg, 2.3 mmol), 2,2,2-trifluoroacetic acid (1 mL) and dichloromethane (4 mL) were stirred at 20° C. for 4 hours. The mixture was washed with water (10 mL×2). The organic phase was separated, dried over sodium sulfate, filtered and concentrated to give a residue. The residue was purified by column chromatography (silica gel, petroleum ether/ethyl acetate=2:1) to give 3-methyl-4-phenoxybenzoic acid as a white solid (200 mg, 38%). LRMS (M+H)⁻ m/z: calcd 228.08. found 228.

N-((2-hydroxy-4,6-dimethylpyridin-3-yl)methyl)-3-methyl-4-phenoxybenzamide (Compound I-37)

A mixture of 3-methyl-4-phenoxybenzoic acid (114 mg, 0.5 mmol), o-(7-azabenzotriazol-1-yl)-N,N,N',N'-tetramethyluroniumhexafluorophosphate (285 mg, 0.75 mmol), triethylamine (0.2 mL) and dichloromethane (15 mL) were stirred at 25° C. for half an hour. Then 3-(aminomethyl)-4,6-dimethylpyridin-2-ol (76 mg, 0.5 mmol) was added. The mixture was stirred at 25° C. for 12 hours. The mixture was washed with water (30 mL). The organic phase was separated, dried over sodium, filtered, concentrated to give a residue. The residue was purified by column chromatography (silica gel, dichloromethane/methanol=10:1) to give N-((2-hydroxy-4,6-dimethylpyridin-3-yl)methyl)-3-methyl-4-phenoxybenzamide as a white solid (50 mg, 28%). LRMS (M+H⁺) m/z: calcd 362.16. found 362. HPLC purity (214 nm): 95%. ¹H NMR (300 MHz, d⁶-DMSO): δ 11.47 (s, 1H), 8.24 (t, J=4.8 Hz, 1H), 8.83 (s, 1H), 7.68 (dd, J=9.6 Hz, J=2.1 Hz, 1H), 7.41-7.35 (m, 2H), 7.13 (t, J=7.5 Hz, 1H), 6.96-6.93 (m, 2H), 6.82 (d, J=8.4 Hz, 1H), 5.80 (s, 1H), 4.29 (d, J=4.8 Hz, 2H), 2.21 (s, 3H), 2.16 (s, 3H), 2.11 (s, 3H).

Example 35

Synthesis of N-((2-hydroxy-4,6-dimethylpyridin-3-yl)methyl)-4-(1-(o-tolyloxy)ethyl)benzamide (Compound I-38)

This synthesis involved 3 steps.

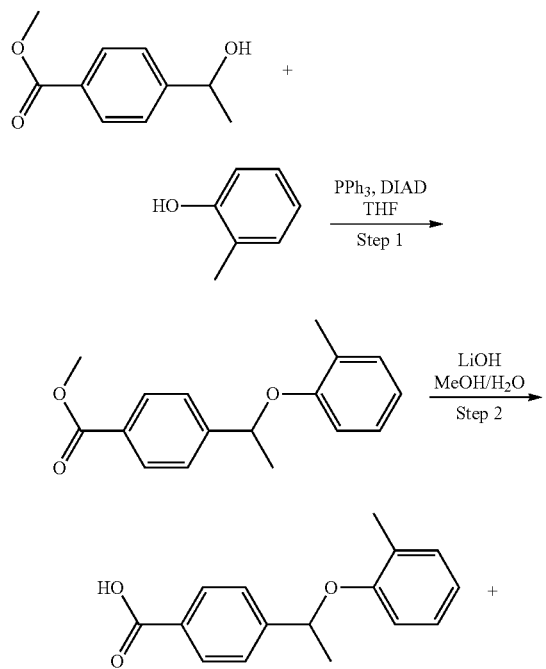

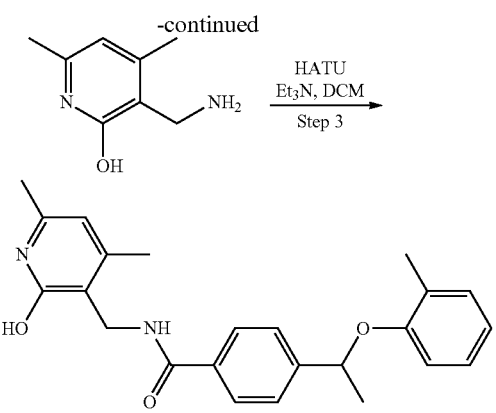

Methyl 4-(1-(o-tolyloxy)ethyl)benzoate

To the solution of 4-(1-hydroxyethyl)benzoate (300 mg. 1.67 mmol) in tetrahydrofuran (50 mL) was added triphenylphosphine (570 mg, 2.2 mmol) and o-cresol (180 mg, 1.67 mmol), the mixture was stirred for 30 minutes at room temperature, then diisopropylazodicarboxylate (568.3 mg, 2.2 mmol) was added dropwise to the solution at 0° C., the mixture was stirred at room temperature for 12 hours. Then the mixture was concentrated and purified by column chromatography (silica gel, Petroleum ether/ethyl acetate=20:1) to give methyl 4-(1-(o-tolyloxy)ethyl)benzoate (151 mg, 33%) as oil.

4-(1-(o-tolyloxy)ethyl)benzoic acid

Lithium hydroxide (54 mg, 2.24 mmol) was added to a solution of methyl 4-(1-(o-tolyloxy)ethyl)benzoate (151 mg, 0.56 mmol) in methanol (100 mL) and water (10 mL). The reaction mixture was stirred at room temperature for 3 hours. After the reaction, the solvent was removed in vacuo. 3 mol/L aqueous hydrogen chloride was added to make pH 2~3, and the product was extracted with dichloromethane (100 mL*3) The combined organic phase was washed with Sodium Chloride (20 mL*3), dried over anhydrous sodium sulfate, and the solvent was evaporated to dryness to give 4-(1-(o-tolyloxy)ethyl)benzoic acid (127 mg, 88%).

N-((2-hydroxy-4,6-dimethylpyridin-3-yl)methyl)-4-(1-(o-tolyloxy)ethyl)benzamide (Compound I-38)

To the solution of 4-(1-(o-tolyloxy)ethyl)benzoic acid (127 mg, 0.5 mmol) in dichloromethane (80 mL) was added o-(7-Azabenzotriazol-1-yl)-N,N,N',N'-tetramethyluronium hexafluorophosphate (285 mg, 0.75 mmol) and triethylamine (151 mg, 1.5 mmol). then the 3-(aminomethyl)-4,6-dimethylpyridin-2-ol (76 mg, 0.5 mmol) was added, the solution was stirred at room temperature for 12 hours, then washed with water (50 mL*3), the organic layer was evaporated and purified by column chromatography (silica gel, dichloromethane/methanol=20:1) to give N-((2-hydroxy-4,6-dimethylpyridin-3-yl)methyl)-4-(1-(o-tolyloxy)ethyl)benzamide (57 mg, 30%). LRMS (M+H⁺) m/z: calcd: 390.19. found 390; ¹H-NMR (300 MHz, CD₃OD) δ 7.75 (d, J=8.4 Hz, 2H), 7.45 (d, J=8.4 Hz, 2H), 7.71-7.08 (m, 1H), 6.97-6.92 (m, 1H), 6.77-6.66 (m, 2H), 6.10 (s, 1H), 5.46-5.44 (m, 1H), 4.48 (s, 2H), 2.36 (s, 3H), 2.28 (s, 3H), 2.24 (s, 3H), 1.62 (d, 3H).

Example 36

Synthesis of compound N-((2-hydroxy-4,6-dimethylpyridin-3-yl)methyl)-4-(1-(m-tolyloxy)ethyl)benzamide (Compound I-39)

This synthesis involved 3 steps.

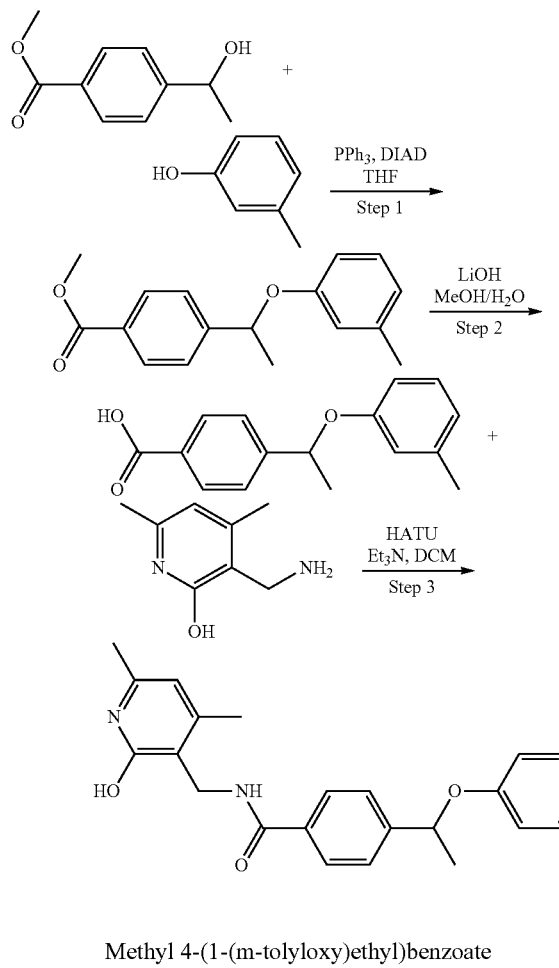

Methyl 4-(1-(m-tolyloxy)ethyl)benzoate

To the solution of 4-(1-hydroxyethyl)benzoate (300 mg, 1.67 mmol) in tetrahydrofuran (50 mL) was added triphenylphosphine (569 mg, 2.17 mmol) and m-cresol (180 mg, 1.67 mmol), the solution was stirred for 30 minutes at room temperature, then diisopropylazodicarboxylate (438 mg, 2.17 mmol) was added dropwise to the solution at 0° C., the mixture was stirred at room temperature for 12 hours. Then the mixture was concentrated and purified by column chromatography (silica gel, Petroleum ether/ethyl acetate=20:1) to give methyl 4-(1-(m-tolyloxy)ethyl)benzoate (148 mg 33%) as oil.

4-(1-(m-tolyloxy)ethyl)benzoic acid

Lithium hydroxide (54 mg, 2.2 mmol) was added to a solution of methyl 4-(1-(m-tolyloxy)ethyl)benzoate (148 mg, 0.55 mmol) in methanol (100 mL) and water (10 mL). The reaction mixture was stirred at room temperature for 3 hours. After the reaction, the solvent was removed in vacuo. 3 mol/L aqueous hydrogen chloride was added to make pH 2-3, and the product was extracted with dichloromethane (100 mL*3) The combined organic phase was washed with sodium Chloride (20 mL*3), dried over anhydrous sodium sulfate, and the solvent was evaporated to dryness to give 4-(1-(m-tolyloxy)ethyl)benzoic acid (124 mg, 88%).

N-((2-hydroxy-4,6-dimethylpyridin-3-yl)methyl)-4-(1-(m-tolyloxy)ethyl)benzamide (Compound I-39)

To the solution of 4-(1-(o-tolyloxy)ethyl)benzoic acid (124 mg, 0.48 mmol) in dichloromethane (80 mL) was added o-(7-Azabenzotriazol-1-yl)-N,N,N',N'-tetramethyluronium hexafluorophosphate (274 mg, 0.72 mmol) and triethylamine (145 mg, 1.44 mmol). then the 3-(aminomethyl)-4,6-dimethylpyridin-2-ol (73 mg, 0.48 mmol) was added, the solution was stirred at room temperature for 12 hours, then washed with water (50 mL*3), the organic layer was evaporated and purified by column chromatography (silica gel, dichloromethane/methanol=20:1) to give N-((2-hydroxy-4,6-dimethylpyridin-3-yl)methyl)-4-(1-(m-tolyloxy)ethyl)benzamide (57 mg, 30%). LRMS (M+H$^+$) m/z: calcd: 390.19. found 390; $^1$H-NMR (300 MHz, CD$_3$OD) δ 7.75 (d, J=8.4 Hz, 2H), 7.45 (d, J=8.4 Hz, 2H), 7.71-7.08 (m, 1H), 6.97-6.92 (m, 1H), 6.77-6.66 (m, 2H), 6.10 (s, 1H), 5.46-5.44 (m, 1H), 4.48 (s, 2H), 2.36 (s, 3H), 2.28 (s, 3H), 2.24 (s, 3H), 1.62 (d, J=6.3 Hz, 3H).

Example 37

Synthesis of N-((2-hydroxy-4,6-dimethylpyridin-3-yl)methyl)-4-((phenylamino)methyl)benzamide (Compound I-40)

This synthesis involved 3 steps.

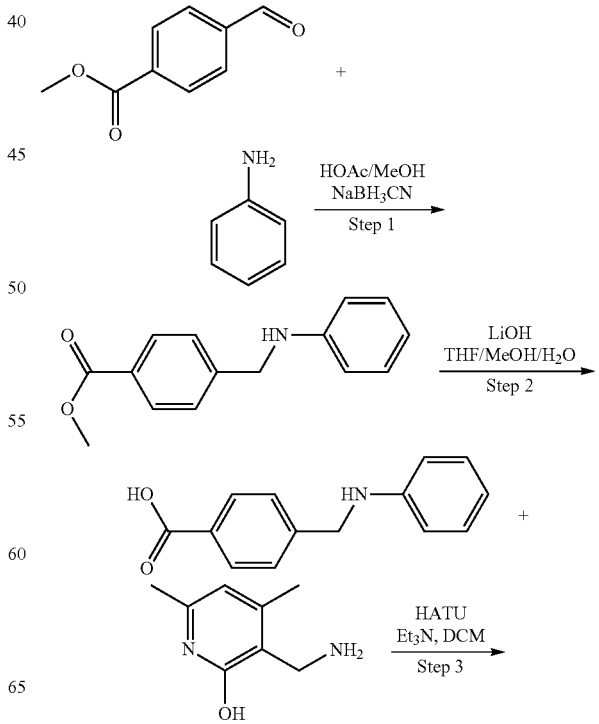

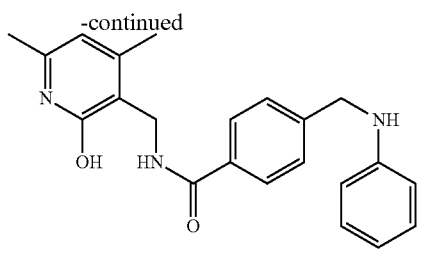

CD$_3$OD): δ 7.75 (d, J=8.1 Hz, 2H), 7.44 (d, J=8.1 Hz, 2H), 7.06-7.04 (m, 2H), 6.60-6.58 (m, 3H), 6.11 (s, 1H), 4.49 (s, 2H), 4.37 (s, 2H), 2.36 (s, 3H), 2.24 (s, 3H).

Example 38

Synthesis of 4-(1-(2-fluorophenoxy)ethyl)-N-((2-hydroxy-4,6-dimethylpyridin-3-yl)methyl)benzamide (Compound I-41)

This synthesis involved 3 steps.

Methyl 4-((phenylamino)methyl)benzoate

Methyl 4-formylbenzoate (1 g, 6 mmol) and aniline (837 mg, 9 mmol) were dissolved in methanol (30 mL). The mixture was heated to 50° C., and acetic acid (two or three drop) was added to the reaction mixture. The resultant mixture was stirred at 50° C. for 1 hour. After the mixture was cooled to room temperature, sodium cyanoborohydride (1.13 g, 18 mmol) was added. The mixture was stirred at room temperature for 18 hours. The reaction was quenched with water (10 mL) and the mixture was extracted with dichloromethane (10 mL×3). The combined organic phase was separated, dried by sodium sulfate and then filtered. The filtrate was concentrated in vacuo. The residue was purified by column chromatography (silica gel, petroleum ether/ethyl acetate=8:1) to give methyl 4-((phenylamino)methyl)benzoate (0.8 g, 55%). LRMS (M+H$^+$) m/z: cald. 241.08. found 241. LRMS (M+H$^+$) m/z: calcd 241.08. found 241. $^1$H NMR (300 MHz, CD$_3$OD): δ 7.95 (dd, J=7.2 Hz, J=2.1 Hz, 2H), 7.44 (d, J=7.8 Hz, 2H), 7.05 (t, J=6.0 Hz, 2H), 6.60-6.56 (m, 3H), 4.37 (s, 2H), 3.86 (s, 3H).

4-((phenylamino)methyl)benzoic acid

A mixture of methyl 4-((phenylamino)methyl)benzoate (800 mg, 3.2 mmol), lithium hydroxide monohydrate (72 mg, 3 mmol), tetrahydrofuran (6 mL), methanol (2 mL) and water (2 mL) was stirred at 20° C. for 2 hours. The mixture was acidified to pH=1 with concentrated hydrochloric acid and then extracted with ethyl acetate (15 mL×3). The combined organic phase was separated, dried by sodium sulfate and then filtered. The filtrate was concentrated in vacuo to give 4-((phenylamino)methyl)benzoic acid (600 mg, 80%). The product was used for the next step directly without further purification. LRMS (M+H$^+$) m/z: calcd 227.09. found 227.

N-((2-hydroxy-4,6-dimethylpyridin-3-yl)methyl)-4-((phenylamino)methyl)benzamide (Compound I-40)

4-((Phenylamino)methyl)benzoic acid (150 mg, 0.66 mmol), 2-(7-aza-1H-benzotriazole-1-yl)-1,1,3,3-tetramethyluronium hexafluorophosphate (301 mg, 0.79 mmol) and triethylamine (2 mL) were dissolved in dichloromethane (20 mL). The mixture was stirred for 0.5 hour. And then 3-(aminomethyl)-4,6-dimethylpyridin-2-ol (100 mg, 0.66 mmol) was added to the mixture. The mixture was stirred at 25° C. for 12 hours. To the mixture, water (10 mL) was added and the mixture was extracted with dichloromethane (10 mL×3). The combined organic phase was dried by sodium sulfate and then filtered. The filtrate was concentrated in vacuo. The residue was purified by column chromatography (silica gel, dichloromethane/methanol=20:1) to give N-((2-hydroxy-4,6-dimethylpyridin-3-yl)methyl)-4-((phenylamino)methyl)benzamide (100 mg, 42%). LRMS (M+H$^+$) m/z: calcd 361.18. found 361. HPLC purity (214 nm): 99%. $^1$H NMR (300 MHz,

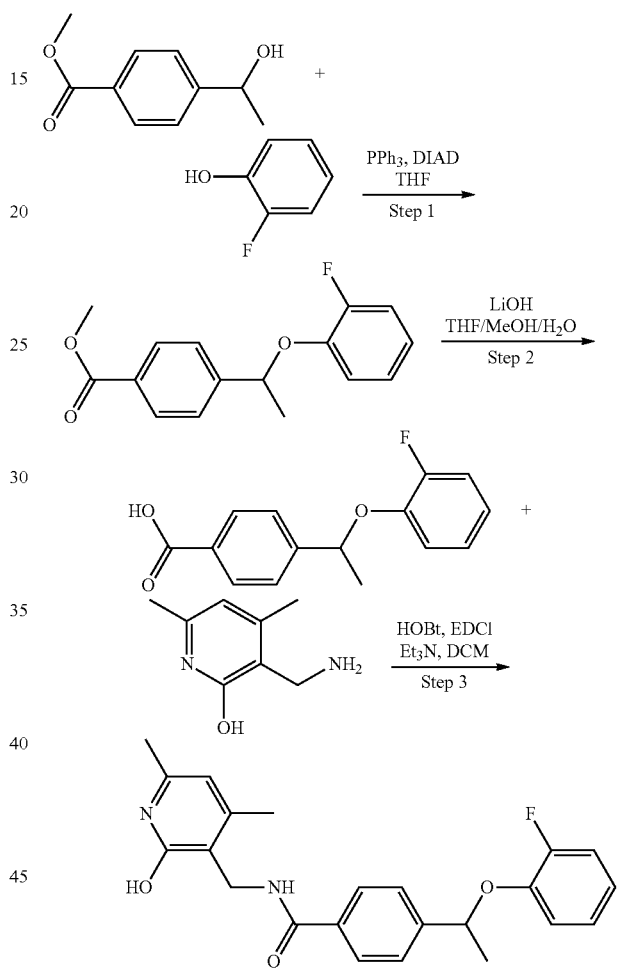

Methyl 4-(1-(2-fluorophenoxy)ethyl)benzoate

To a solution of methyl 4-(1-hydroxyethyl)benzoate (0.9 g, 5 mmol), 2-fluorophenol (627 mg, 5.6 mmol), triphenylphosphine (2.2 g, 8.4 mmol) in tetrahydrofuran (30 mL) was added diisopropyl azodicarboxylate (1.7 g, 8.4 mmol) at 0° C. The mixture was stirred at 20° C. for 12 hours. Water (15 mL) was added to the mixture and then extracted with ethyl acetate (35 mL×3). The combined organic phase was dried by sodium sulfate, and then filtered. The filtrate was concentrated in vacuo and purified by column chromatography (silica gel, petroleum ether/ethyl acetate=5:1) to give methyl 4-(1-(2-fluorophenoxy)ethyl)benzoate (450 mg, 33%).

4-(1-(2-fluorophenoxy)ethyl)benzoic acid

A mixture of methyl 4-(1-(2-fluorophenoxy)ethyl)benzoate (0.45 g, 1.6 mmol), lithium hydroxide monohydrate (0.57 g, 13.6 mmol), tetrahydrofuran (15 mL), methanol (5 mL) and water (5 mL) was stirred at 20° C. for 4 hours. The mixture was turned to pH=1 with concentrated hydrochloric acid and then extracted with ethyl acetate (15 mL×3). The combined organic phase was dried by sodium sulfate, and then filtered. The filtrate was concentrated in vacuo to give 4-(1-(2-fluorophenoxy)ethyl)benzoic acid (0.31 g, 74%).

4-(1-(2-fluorophenoxy)ethyl)-N-((2-hydroxy-4,6-dimethylpyridin-3-yl)methyl)benzamide A mixture of 4-(1-(2-fluorophenoxy)ethyl)benzoic acid (260 mg, 1 mmol), 1-ethyl-3-(3-dimethylaminopropyl)carbodiimide hydrochloride (382 mg, 2 mmol), N-hydroxybenzotriazole (270 mg, 2 mmol), triethylamine (0.3 mL) and dichloromethane (15 mL) were stirred at 25° C. for half an hour. And then 3-(aminomethyl)-4,6-dimethylpyridin-2-ol (152 mg, 1 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give 4-(1-(2-fluorophenoxy)ethyl)-N-((2-hydroxy-4,6-dimethylpyridin-3-yl)methyl)benzamide (Compound I-41) (75 mg, 38%). LRMS (M+H$^+$) m/z: calcd. 394.17. found 394. HPLC purity (214 nm): 99%. $^1$H NMR (300 MHz, d$^6$-DMSO): δ 11.44 (s, 1H), 8.30 (t, J=4.8 Hz, 1H), 7.78 (d, J=8.4 Hz, 2H), 7.43 (d, J=8.1 Hz, 2H), 7.19-6.83 (m, 4H), 5.83 (s, 1H), 5.58 (q, J=6.3 Hz, 1H), 4.27 (d, J=4.8 Hz, 2H), 2.15 (s, 3H), 2.10 (s, 3H), 1.56 (d, J=6.3 Hz, 3H).

Example 39

Synthesis of compound 4-(1-(3-fluorophenoxy)ethyl)-N-((2-hydroxy-4,6-dimethylpyridin-3-yl)methyl)benzamide This synthesis involved 3 steps.

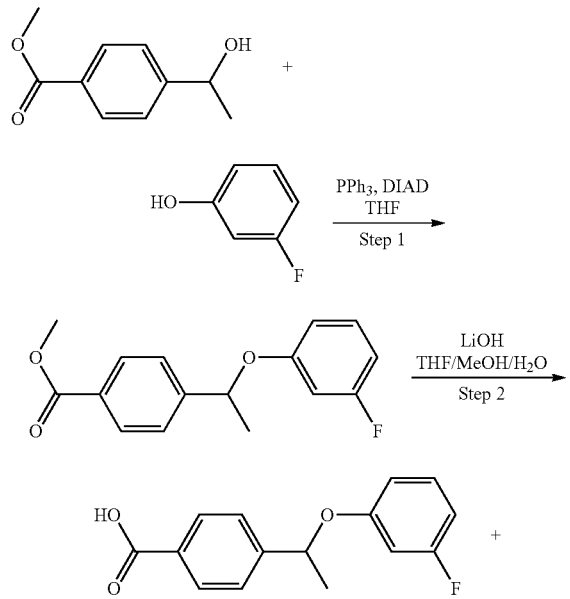

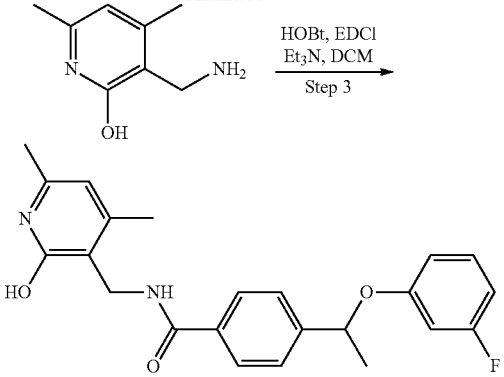

Methyl 4-(1-(3-fluorophenoxy)ethyl)benzoate

To a solution of methyl 4-(1-hydroxyethyl)benzoate (0.9 g, 5 mmol), 3-fluorophenol (627 mg, 5.6 mmol), triphenylphosphine (2.2 g, 8.4 mmol) in tetrahydrofuran (30 mL) was added diisopropyl azodicarboxylate (1.7 g, 8.4 mmol) at 0° C. The mixture was stirred at 20° C. for 12 hours. Water (15 mL) was added to the mixture and then extracted with ethyl acetate (35 mL×3). The combined organic phase was dried by sodium sulfate, and then filtered. The filtrate was concentrated in vacuo and the residue was purified by column chromatography (silica gel, petroleum ether/ethyl acetate=5:1) to give methyl 4-(1-(3-fluorophenoxy)ethyl)benzoate (400 mg, 29%).

4-(1-(3-fluorophenoxy)ethyl)benzoic acid

A mixture of methyl 4-(1-(2-fluorophenoxy)ethyl)benzoate (0.40 g, 1.4 mmol), lithium hydroxide monohydrate (571 mg, 13.6 mmol), tetrahydrofuran (15 mL), methanol (5 mL) and water (5 mL) was stirred at 20° C. for 4 hours. The mixture was turned to pH=1 with concentrated hydrochloric acid and then extracted with ethyl acetate (15 mL×3). The combined organic phase was dried by sodium sulfate, and then filtered. The filtrate was concentrated in vacuo to give 4-(1-(3-fluorophenoxy)ethyl)benzoic acid (0.34 g, 93%).

4-(1-(3-fluorophenoxy)ethyl)-N-((2-hydroxy-4,6-dimethylpyridin-3-yl)methyl)benzamide A mixture of 4-(1-(3-fluorophenoxy)ethyl)benzoic acid (260 mg, 1 mmol), 1-ethyl-3-(3-dimethylaminopropyl)carbodiimide hydrochloride (382 mg, 2 mmol), N-hydroxybenzotriazole (270 mg, 2 mmol), triethylamine (0.3 mL) and dichloromethane (15 mL) were stirred at 25° C. for half an hour. And then 3-(aminomethyl)-4,6-dimethylpyridin-2-ol (152 mg, 1 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give 4-(1-(3-fluorophenoxy)ethyl)-N-((2-hydroxy-4,6-dimethylpyridin-3-yl)methyl)benzamide (Compound I-42) (135 mg, 34%). LRMS (M+H$^+$) m/z: calcd. 394.17. found 394. HPLC purity (214 nm): 91%. $^1$H NMR (300 MHz, d$^6$-DMSO): δ 11.44 (s, 1H), 8.30 (t, J=4.8 Hz, 1H), 7.78 (d, J=8.4 Hz, 2H), 7.43 (d, J=8.1 Hz, 2H), 7.20 (q, J=8.1 Hz, 1H), 6.77-6.64 (m, 3H), 5.83 (s, 1H), 5.57 (q, J=6.3 Hz, 1H), 4.27 (d, J=4.8 Hz, 2H), 2.15 (s, 3H), 2.10 (s, 3H), 1.53 (d, J=6.0 Hz, 3H).

Example 40

Synthesis of compound N-((2-hydroxy-4,6-dimethylpyridin-3-yl)methyl)-4-(2-methyl 1-phenoxypropylbenzamide (Compound I-43)

This synthesis involved 5 steps.

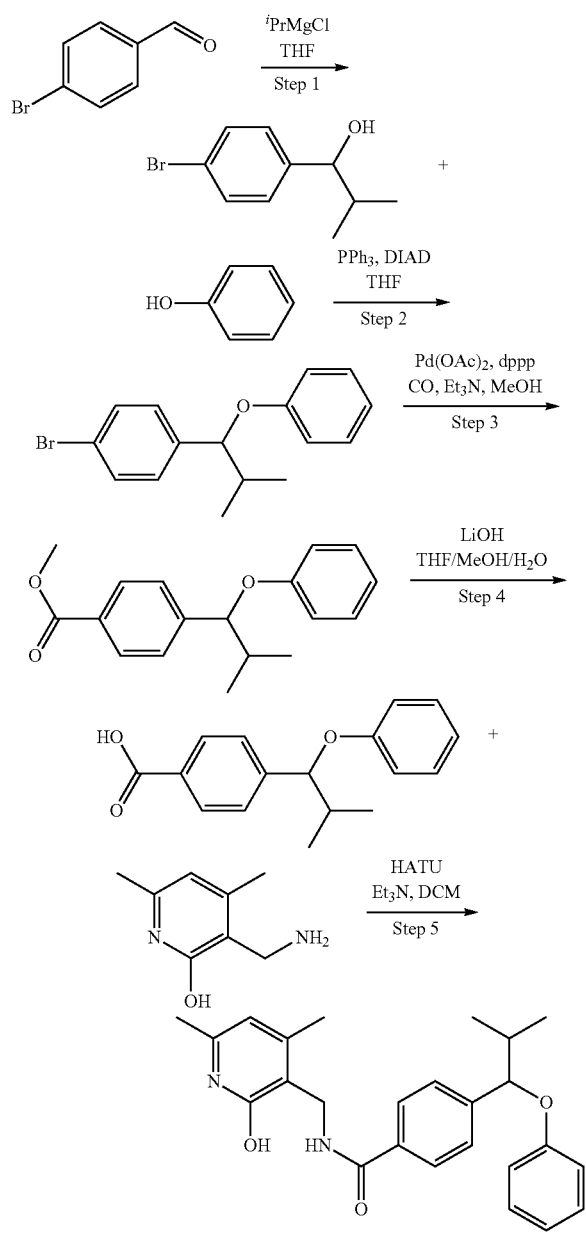

1-(4-bromophenyl)-2-methylpropan-1-ol

A solution of isopropylmagnesium chloride (17.0 L, 1M in tetrahydrofuran) was added dropwise to the solution of 4-bromobenzaldehyde (2.1 g, 11.4 mol) in tetrahydrofuran (30 mL) at −10° C. Then the mixture was stirred at 25° C. for 4 hours. The resultant reaction was quenched with saturated ammonium chloride aqueous (20 mL). The organic phase was separated, dried over sodium sulfate, filtered and concentrated to give a residue. The residue was purified by column chromatography (silica gel, petroleum ether/ethyl acetate=2:1) to give 1-(4-bromophenyl)-2-methylpropan-1-ol (620 mg, 24%). $^1$H NMR (300 MHz, CDCl$_3$): δ 7.98-7.85 (m, 2H), 7.48-7.35 (m, 2H), 5.17 (s, 1H), 4.49 (d, J=6.6 Hz, 1H), 2.35-2.30 (m, 1H), 1.01 (d, J=6.6 Hz, 6H).

1-bromo-4-(2-methyl-1-phenoxypropyl)benzene

Azodicarboxylic acid diisopropyl ester (824 mg, 4.1 mmol) was added to the mixture of 1-(4-bromophenyl)-2-methylpropan-1-ol (620 mg, 2.7 mmol), phenol (307 mg, 3.2 mmol), triphenylphosphine (1.07 g, 4.1 mmol) and tetrahydrofuran (15 mL) at 20° C. Then the mixture was stirred at 20° C. for 12 hours. The resultant mixture was washed with water (20 mL×2). The organic phase was separated, dried over sodium sulfate, filtered and concentrated to give a residue. The residue was purified by column chromatography (silica gel, petroleum ether/ethyl acetate=10:1) to gave 1-bromo-4-(2-methyl-1-phenoxypropyl)benzene as a colorless oil (353 g, 44%). $^1$H NMR (300 MHz, CDCl$_3$): δ 8.07-7.98 (m, 2H), 7.56-7.48 (m, 2H), 7.32-7.28 (m, 2H), 6.84-6.77 (m, 3H), 4.49 (d, J=6.6 Hz, 1H), 2.35-2.30 (m, 1H), 1.01 (d, J=6.6 Hz, 6H).

Methyl 4-(2-methyl-1-phenoxypropyl)benzoate

A mixture of 1-bromo-4-(2-methyl-1-phenoxypropyl)benzene (353 mg, 1.2 mmol), palladium acetate (52 mg, 0.23 mmol), 1,3-bis(diphenylphosphino) propane (144 mg, 0.35 mmol), triethylamine (0.8 mL), methanol (30 mL) were stirred at 100° C. under carbon monoxide atmosphere (2.0 MPa). The resultant mixture was concentrated to give a residue. The residue was purified by column chromatography (silica gel, petroleum ether/ethyl acetate=40:1) to give methyl 4-(2-methyl-1-phenoxypropyl)benzoate as a colorless oil (240 mg, 73%). $^1$H NMR (300 MHz, CDCl$_3$): δ 8.07-7.98 (m, 2H), 7.56-7.48 (m, 2H), 7.32-7.28 (m, 2H), 6.84-6.77 (m, 3H), 4.49 (d, J=6.6 Hz, 1H), 3.88 (s, 3H), 2.35-2.30 (m, 1H), 1.01 (d, J=6.6 Hz, 6H).

4-(2-methyl-1-phenoxypropyl)benzoic acid

A mixture of methyl 4-(2-methyl-1-phenoxypropyl)benzoate (240 mg, 0.84 mmol), lithium hydroxide monohydrate (178 mg, 4.2 mmol), tetrahydrofuran (12 mL), methanol (4 mL) and water (4 mL) was stirred at 20° C. for 4 hours. The reaction mixture was concentrated, acidified with concentrated hydrochloric acid to pH=1, extracted with ethyl acetate (20 mL×3). The organic phase was separated, dried over sodium sulfate, filtered and concentrated to give a residue. The residue was purified by column chromatography (silica gel, petroleum ether/ethyl acetate=2:1) to give 4-(2-methyl-1-phenoxypropyl)benzoic acid as a white solid (227 mg, 100%). LRMS (M+H)⁻ m/z: calcd 268.15. found 268.

N-((2-hydroxy-4,6-dimethylpyridin-3-yl)methyl)-4-(2-methyl-1-phenoxypropyl) enzamide A mixture of 4-(2-methyl-1-phenoxypropyl)benzoic acid (208 mg, 0.77 mmol), o-(7-azabenzotriazol-1-yl)-N,N,N',N'-te-tramethyluroniumhexafluorophosphate (439 mg, 1.2 mmol), triethylamine (0.32 mL) and dichloromethane (15 mL) were stirred at 25° C. for half an hour. Then 3-(aminomethyl)-4,6-dimethylpyridin-2-ol (152 mg, 1.0 mmol) was added. The mixture was stirred at 25° C. for 12 hours. The resultant mixture was washed with water (30 mL). The organic phase was separated, dried over sodium, filtered, concentrated to give a residue. The residue was purified by column chromatography (silica gel, dichloromethane/methanol=10:1) to give N-((2-hydroxy-4,6-dimethylpyridin-3-yl)methyl)-4-(2-methyl-1-phenoxypropyl)benzamide (Compound I-43) as a white solid (100 mg, 32%). LRMS (M+H$^+$) m/z: calcd 404.21. found 404. HPLC purity (214 nm): 100%. $^1$H NMR (300 MHz, d$^6$-DMSO): δ 11.46 (s, 1H), 8.33 (t, J=5.1 Hz, 1H), 7.47 (s, 1H), 7.34 (m, 3H), 7.20 (m, 3H), 6.88 (m, 2H), 5.84 (s, 1H), 5.54 (d, J=6.6 Hz, 1H), 4.25 (d, J=4.5 Hz, 2H), 2.35-2.30 (m, 1H), 2.17 (s, 3H), 2.13 (s, 3H), 1.01 (d, J=6.6 Hz, 6H).

Example 41

Synthesis of N-((2-hydroxy-4,6-dimethylpyridin-3-yl)methyl)-4-(1-phenoxypropyl)benzamide (Compound I-44)

This synthesis involved 5 steps.

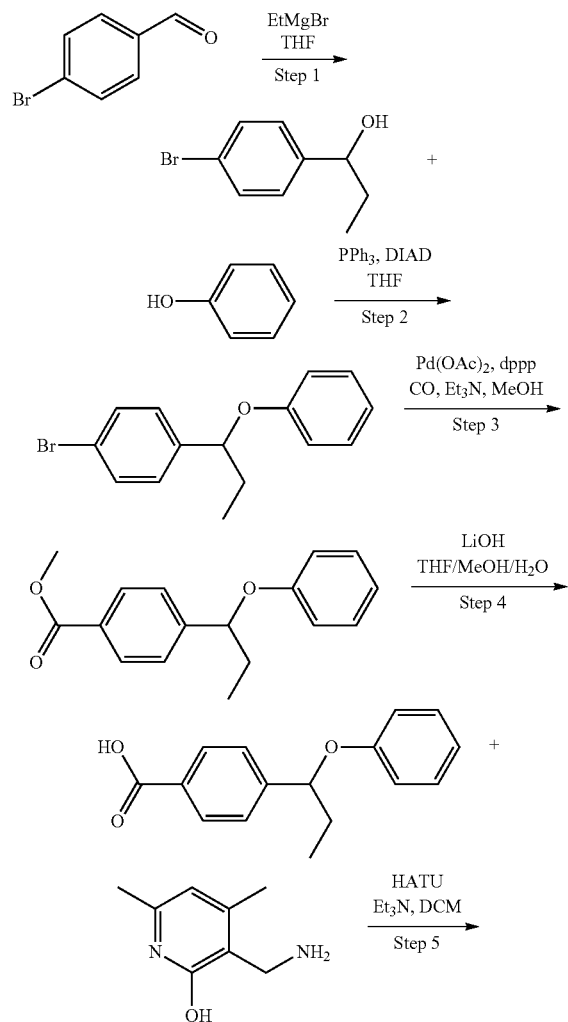

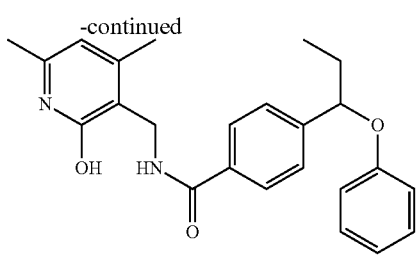

1-(4-bromophenyl)propan-1-ol

Ethylmagnesium bromide (5.4 mL, 3 M solution in tetrahydrofuran) was added dropwise to the solution of 4-bromobenzaldehyde (2.0 g, 10.8 mmol) in tetrahydrofuran (30 mL) at −30° C. Then the resultant mixture stirred at room temperature for 4 hours. The reaction was quenched with saturated ammonium chloride aqueous. The organic phase was separated, dried over sodium sulfate, filtered and concentrated to give a residue. The residue was purified by column chromatography (silica gel, petroleum ether/ethyl acetate=2:1) to give 1-(4-bromophenyl)propan-1-ol (2.0 g, 88%). $^1$H NMR (300 MHz, d$^6$-DMSO): δ 7.49 (d, J=8.4 Hz, 2H), 7.27 (d, J=8.4 Hz, 2H), 5.20 (d, J=4.5 Hz, 1H), 4.45-4.41 (m, 1H), 1.63-1.53 (m, 2H), 0.80 (t, J=7.5 Hz, 3H).

1-bromo-4-(1-phenoxypropyl)benzene

Azodicarboxylic acid diisopropyl ester (2.8 g, 14.0 mmol) was added to the mixture of 1-(4-bromophenyl)propan-1-ol (2.0 g, 9.3 mmol), phenol (1.05 g, 11.2 mmol), triphenylphosphine (3.7 g, 14.0 mmol) and tetrahydrofuran (40 mL) at room temperature. Then the mixture was stirred at room temperature for 12 hours. The resultant mixture was concentrated to give a residue. The residue was purified by column chromatography (silica gel, petroleum ether/ethyl acetate=10:1) to give 1-bromo-4-(1-phenoxypropyl)benzene as a colorless oil (2.0 g, 4%). $^1$H NMR (300 MHz, CDCl$_3$): δ 7.44 (d, J=8.4 Hz, 2H), 7.25-7.15 (m, 4H), 6.89-6.80 (m, 3H), 4.98 (t, J=6.5 Hz, 1H), 2.00-1.72 (m, 2H), 0.99 (t, J=7.5 Hz, 3H).

Methyl 4-(1-phenoxypropyl)benzoate

A mixture of 1-bromo-4-(1-phenoxypropyl)benzene (1.0 g, 3.4 mmol), palladium acetate (154 mg, 0.7 mmol), 1,3-bis(diphenylphosphino) propane (425 mg, 1.0 mmol), triethylamine (2.5 mL), methanol (30 mL) were stirred at 100° C. under carbon monoxide atmosphere (2.0 MPa). The resultant mixture was concentrated to give a residue. The residue was purified by column chromatography (silica gel, petroleum ether/ethyl acetate=15:1) to give methyl 4-(1-phenoxypropyl)benzoate as a colorless oil (683 mg, 74%). $^1$H NMR (300 MHz, CDCl$_3$): δ 8.01 (d, J=8.4 Hz, 2H), 7.42 (d, J=8.4 Hz, 2H), 7.18 (t, J=7.8 Hz, 2H), 6.90-6.81 (m, 3H), 5.08 (t, J=5.7 Hz, 1H), 3.90 (s, 3H), 2.04-1.89 (m, 2H), 1.02 (t, J=7.5 Hz, 3H).

4-(1-phenoxypropyl)benzoic acid

A mixture of methyl 4-(1-phenoxypropyl)benzoate (683 mg, 2.5 mmol) lithium hydroxide monohydrate (531 mg, 12.6 mmol), tetrahydrofuran (12 mL), methanol (4 mL) and water (4 mL) was stirred at 20° C. for 4 hours. The mixture was neutralized to pH to 1 with concentrated hydrochloric acid and then extracted with ethyl acetate (20 mL×3). The combined organic phase was separated, dried over sodium sulfate, and then filtered. The filtrate was concentrated in vacuo to give a residue. The residue was purified by column chromatography (silica gel, petroleum ether/ethyl acetate=2:1) to give 4-(1-phenoxypropyl)benzoic acid as a white solid (640 mg, 100%). LRMS (M+H)⁻ m/z: calcd 256.11. found 256.

N-((2-hydroxy-4,6-dimethylpyridin-3-yl)methyl)-4-(1-phenoxypropyl)benzamide

A mixture of 4-(1-phenoxypropyl)benzoic acid (256 mg, 1.0 mmol), o-(7-azabenzotriazol-1-yl)-N,N,N',N'-tetramethyluroniumhexafluorophosphate (570 mg, 1.5 mmol), triethylamine (0.45 mL) and dichloromethane (15 mL) were stirred at 25° C. for half an hour. Then 3-(aminomethyl)-4,6-dimethylpyridin-2-ol (152 mg, 1.0 mmol) was added. The mixture was stirred at 25° C. for 12 hours. The mixture was washed with water (20 mL), dried over sodium, filtered and concentrated to give a residue. The residue was purified by column chromatography (silica gel, dichloromethane/methanol=10:1) to give N-((2-hydroxy-4,6-dimethylpyridin-3-yl)ethyl)-4-(1-phenoxypropyl)benzamide (Compound I-44) as a white solid (125 mg, 32%). LRMS (M+H⁺) m/z: calcd 390.19. found 390. HPLC purity (214 nm): 95%. ¹H NMR (300 MHz, d⁶-DMSO): δ 11.44 (s, 1H), 8.28 (t, J=5.1 Hz, 1H), 7.78 (d, J=8.4 Hz, 2H), 7.42 (d, J=8.4 Hz, 2H), 7.17 (t, J=8.0 Hz, 2H), 6.87-6.83 (m, 3H), 5.84 (s, 1H), 5.27 (t, J=6.0 Hz, 1H), 4.27 (d, J=5.1 Hz, 2H), 2.68 (s, 3H), 2.51 (s, 3H), 1.89-1.80 (m, 2H), 0.92 (t, J=6.6 Hz, 3H).

Example 42

Synthesis of N-((2-hydroxy-4,6-dimethylpyridin-3-yl)methyl)-1-phenoxy-2,3-dihydro-1H-indene-5-carboxamide (Compound I-45)

This synthesis involved 5 steps.

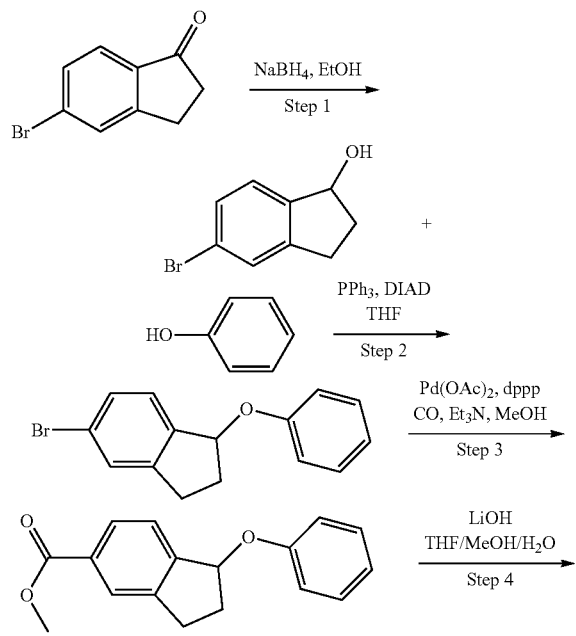

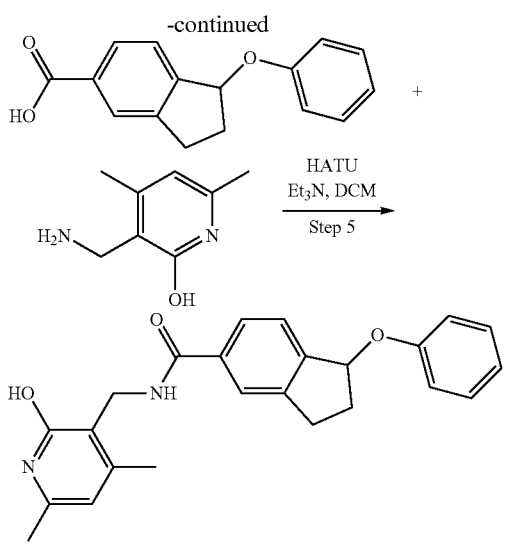

5-bromo-2,3-dihydro-1H-inden-1-ol

To a solution of 5-bromo-2,3-dihydroinden-1-one (1.1 g, 5.2 mmol) in ethanol (100 mL) was added sodium borohydride (218 mg, 5.7 mmol). The mixture was stirred at room temperature for 24 hours. Then the resultant mixture was filtered. The filtrate was acidified with hydrochloric acid aqueous solution (1N) and the solvent was removed in vacuo. The residue was taken up with water (50 mL) and extracted with dichloromethane (50 mL). The combined organic phase was dried over sodium sulfate, filtered and concentrated to give a residue. The residue was purified by column chromatography (silica gel, petroleum ether/ethyl acetate=4:1) to give 5-bromo-2,3-dihydro-1H-inden-1-ol (1 g, 90%) as a yellow oil. LRMS (M+H⁺) m/z: calcd 211.98. found 211. ¹H NMR (300 MHz, CDCl₃): δ 7.40 (s, 1H), 7.37 (d, J=7.8 Hz, 1H), 7.27 (d, J=7.8 Hz, 1H), 5.22-5.18 (m, 1H), 3.09-2.99 (m, 1H), 2.86-2.76 (m, 1H), 2.55-2.46 (m, 1H), 2.01-1.76 (m, 1H), 1.75 (s, 1H).

5-bromo-1-phenoxy-2,3-dihydro-1H-indene

A solution of 5-bromo-2,3-dihydro-1H-inden-1-ol (1 g, 4.7 mmol), phenol (835 mg, 8.9 mmol) and triphenylphosphine (1.8 g, 6.9 mmol) in anhydrous tetrahydrofuran (70 mL) was stirred at 0° C. under nitrogen atmosphere. To this mixture was added dropwise diisopropyl azodicarboxylate (1.4 g, 6.9 mmol) over 5 minutes. Until TLC indicated that starting material was consumed, the solvent was evaporated in vacuo and the resulting oil was purified by column chromatography (silica gel, hexane/ethyl acetate=1/1) to give the product 5-bromo-1-phenoxy-2,3-dihydro-1H-indene (1.1 g, 85%) as a white solid. LRMS (M+H⁺) m/z: calcd 288.01. found 288. ¹H NMR (300 MHz, CDCl₃): δ 7.46-7.27 (m, 6H), 7.02 (s, 1H), 6.99-6.98 (m, 1H), 5.73-5.70 (m, 1H), 3.14-3.09 (m, 1H), 2.96-2.95 (m, 1H), 2.59-2.54 (m, 1H), 2.27-2.23 (m, 1H).

Methyl 1-phenoxy-2,3-dihydro-1H-indene-5-carboxylate

A mixture of 5-bromo-1-phenoxy-2,3-dihydro-1H-indene (1 g, 3.5 mmol), triethylamine (2.4 g, 23.7 mmol) and 1,3-bis(diphenylphosphino) propane (400 mg, 0.97 mmol), palladium(II) acetate (200 mg, 0.89 mmol) in methanol (50 mL) the mixture was stirred at 100° C. overnight under carbon monoxide atmosphere (15 atm). After cooling to room temperature, the reaction was concentrated to give a residue. The residue was purified by column chromatography (silica gel, petroleum ether/ethyl acetate=2:1) to give methyl 1-phenoxy-2,3-dihydro-1H-indene-5-carboxylate (400 mg, 42%) as a white solid. LRMS (M+H⁺) m/z: calcd 268.11. found 268. ¹H NMR (300 MHz, CDCl₃): δ 7.97-7.92 (m, 1H), 7.49-7.45 (m, 1H), 7.35-7.28 (m, 3H), 7.03-6.97 (m, 3H), 5.80-5.77 (m, 1H), 3.92 (s, 3H), 3.22-3.11 (m, 1H), 3.01-2.91 (m, 1H), 2.69-2.56 (m, 1H), 2.30-2.19 (m, 1H).

1-phenoxy-2,3-dihydro-1H-indene-5-carboxylic acid

To a solution of methyl 1-phenoxy-2,3-dihydro-1H-indene-5-carboxylate (400 mg, 1.49 mmol) in tetrahydrofuran, methanol and water (3:1:1, 20 mL) was added lithium hydroxide monohydrate (377 mg, 8.98 mmol). The mixture was stirred at room temperature for 2 hours. The mixture was concentrated in vacuo and quenched with hydrochloric acid aqueous (1N, 15 mL). Then the mixture was concentrated to give 1-phenoxy-2,3-dihydro-1H-indene-5-carboxylic acid (350 mg, 92%) as white solid. LRMS (M+H)⁻ m/z: calcd 254.09. found 254.

N-((2-hydroxy-4,6-dimethylpyridin-3-yl)methyl)-1-phenoxy-2,3-dihydro-1H-indene-5-carboxamide To a solution of 1-phenoxy-2,3-dihydro-1H-indene-5-carboxylic acid (100 mg, 0.39 mmol) in dichloromethane (50 mL) were added 2-(7-aza-1H-benzotriazole-1-yl)-1,1,3,3-tetramethyluronium hexafluorophosphate (190 mg, 0.5 mmol) and triethylamine (71 mg, 0.7 mmol). And then the mixture was stirred for 30 minutes. Then 3-(aminomethyl)-4,6-dimethylpyridin-2-ol (61 mg, 0.4 mmol) was added. The mixture was stirred at room temperature for 12 hours. The resultant mixture was washed with water (50 mL), dried over anhydrous sodium sulfate, filtered and concentrated to give a residue. The residue was purified by prep-TLC (silica gel, dichloromethane/methanol=20:1) to give N-((2-hydroxy-4,6-dimethylpyridin-3-yl)methyl)-1-phenoxy-2,3-dihydro-1H-indene-5-carboxamide (Compound I-45) (35 mg, 23%) as white solid. LRMS (M+H⁺) m/z: calcd 388.18. found 388. HPLC purity (214 nm): 99%. ¹H NMR (300 MHz, d⁶-DMSO): δ 11.47 (s, 1H), 8.33 (s, 1H), 8.30 (s, 1H), 7.70 (d, J=7.8 Hz, 1H), 7.41-7.29 (m, 3H), 7.05-6.93 (m, 3H), 5.89-5.86 (m, 2H), 4.30 (d, J=4.8 Hz, 2H), 3.10-2.84 (m, 2H), 2.64-2.56 (m, 1H), 2.16 (s, 3H), 2.11 (s, 3H), 2.09-1.98 (m, 1H).

Example 43

Synthesis of compound 4-(1-(4-fluorophenoxy)ethyl)-N-((2-hydroxy-4,6-dimethylpyridin-3-yl)methyl)benzamide (Compound I-46)

This synthesis involved 4 steps.

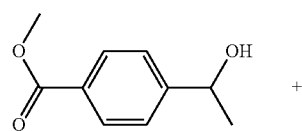

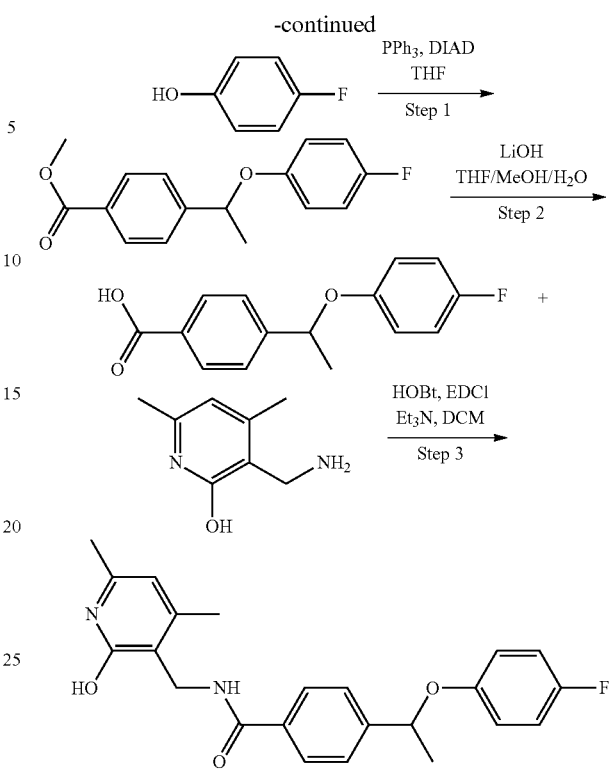

Methyl 4-(1-(4-fluorophenoxy)ethyl)benzoate

To a solution of methyl 4-(1-hydroxyethyl)benzoate (0.9 g, 5 mmol), 4-fluorophenol (627 mg, 5.6 mmol), triphenylphosphine (2.2 g, 8.4 mmol) in tetrahydrofuran (30 mL) was added diisopropyl azodicarboxylate (1.7 g, 8.4 mmol) at 0° C. The mixture was stirred at 20° C. for 12 hours. Water (15 mL) was added to the mixture and then extracted with ethyl acetate (35 mL×3). The combined organic phase was dried by sodium sulfate, and then filtered. The filtrate was concentrated in vacuo and the residue was purified by column chromatography (silica gel, petroleum ether/ethyl acetate=5:1) to give methyl 4-(1-(4-fluorophenoxy)ethyl)benzoate (490 mg, 35%).

4-(1-(4-fluorophenoxy)ethyl)benzoic acid

A mixture of methyl 4-(1-(4-fluorophenoxy)ethyl)benzoate (0.49 g, 1.8 mmol), lithium hydroxide monohydrate (571 mg, 13.6 mmol), tetrahydrofuran (15 mL), methanol (5 mL) and water (5 mL) was stirred at 20° C. for 4 hours. The mixture was neutralized to pH=1 with concentrated hydrochloric acid and then extracted with ethyl acetate (15 mL×3). The combined organic phase was dried by sodium sulfate, and then filtered. The filtrate was concentrated in vacuo to give 4-(1-(4-fluorophenoxy)ethyl)benzoic acid (0.39 g, 83%).

4-(1-(4-fluorophenoxy)ethyl)-N-((2-hydroxy-4,6-dimethylpyridin-3-yl)methyl)benzamide A mixture of 4-(1-(4-fluorophenoxy)ethyl)benzoic acid (260 mg, 1 mmol), 1-ethyl-3-(3-dimethylaminopropyl)carbodiimide hydrochloride (382 mg, 2 mmol), N-hydroxybenzotriazole (270 mg, 2 mmol), triethylamine (0.3 mL) and dichloromethane (15 mL) were stirred at 25° C. for half an hour. Then 3-(aminomethyl)-4,6-dimethylpyridin-2-ol (152 mg, 1 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give 4-(1-(4-fluorophenoxy)ethyl)-N-((2-hydroxy-4,6-dimethylpyridin-3-yl)methyl)benzamide (Compound I-46) (115 mg, 29%). LRMS (M+H$^+$) m/z: calcd 394.17. found 394. HPLC purity (214 nm): 94%. $^1$H NMR (300 MHz, d$^6$-DMSO): δ 11.44 (s, 1H), 8.30 (t, J=5.1 Hz, 1H), 7.77 (d, J=8.4 Hz, 2H), 7.41 (d, J=8.4 Hz, 2H), 7.04-6.85 (m, 4H), 5.83 (s, 1H), 5.47 (q, J=6.6 Hz, 1H), 4.26 (d, J=5.1 Hz, 2H), 2.16 (s, 3H), 2.10 (s, 3H), 1.52 (d, J=6.6 Hz, 3H).

Example 44

Synthesis of N-((2-hydroxy-4-methyl-6-(trifluoromethyl)pyridin-3-yl)methyl)-4-phenoxybenzamide (Compound I-47)

This synthesis involved 2 steps.

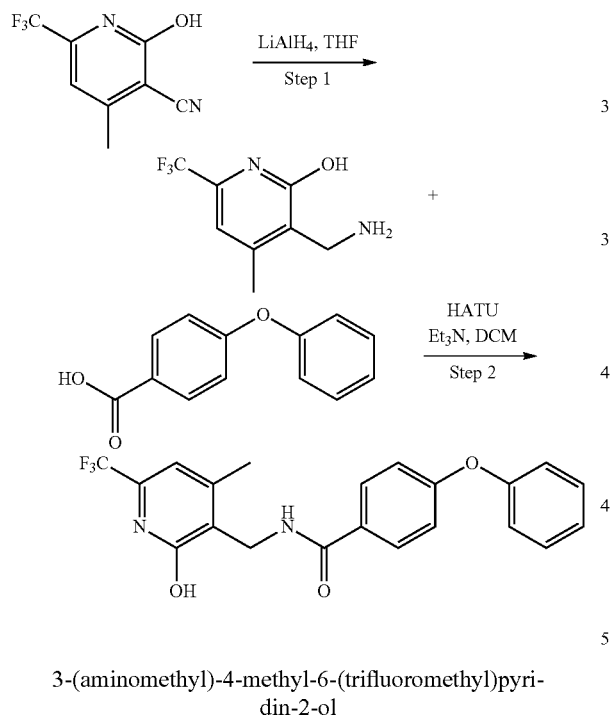

3-(aminomethyl)-4-methyl-6-(trifluoromethyl)pyridin-2-ol

To a solution of 2-hydroxy-4-methyl-6-(trifluoromethyl)nicotinonitrile (1 g, 5 mmol) in tetrahydrofuran (100 mL) was added lithium aluminum hydride (0.3 g, 7.9 mmol). The mixture was stirred at room temperature for 24 hours. The mixture was filtered, acidified and concentrated. To the residue, water (50 mL) was added and then extracted with dichloromethane (2*50 mL). The combined organic phase was separated, dried over sodium sulfate, filtered and concentrated. The residue was purified by column chromatography (silica gel, methanol/dichloromethane=1:5, 1% NH$_3$) to give 3-(aminomethyl)-4-methyl-6-(trifluoromethyl)pyridin-2-ol as a yellow oil (0.8 g, 78%).

LRMS (M+H$^+$) m/z: calcd 206.07. found 206.

N-((2-hydroxy-4-methyl-6-(trifluoromethyl)pyridin-3-yl)methyl)-4-phenoxybenzamide The solution of 3-(aminomethyl)-4-methyl-6-(trifluoromethyl)pyridin-2-ol (100 mg, 0.49 mmol) in dichloromethane (50 mL) was added 2-(7-aza-1H-benzotriazole-1-yl)-1,1,3,3-tetramethyl uronium hexafluorophosphate (350 mg, 1 mmol), triethylamine (101 mg, 1 mmol). The mixture was stirred for 30 minutes. Then 3-(aminomethyl)-4-methyl-6-(trifluoromethyl)pyridin-2-ol (103 mg, 0.5 mmol) was added and the mixture was stirred at room temperature for 12 hours. The mixture was washed with water (50 mL), extracted with dichloromethane (2*50 mL). The combined organic phase was separated, dried over sodium sulfate, filtered and concentrated to give a residue. The residue was purified by preparative-TLC (silica gel, methanol/dichloromethane=1:15, 1% NH$_3$) to give N-((2-hydroxy-4-methyl-6-(trifluoromethyl)pyridin-3-yl)methyl)-4-phenoxybenzamide (Compound I-47) as white solid (35 mg, 18%). LRMS (M+H$^+$) m/z: calcd 402.12. found 402. HPLC purity (214 nm): 98%. $^1$H NMR (300 MHz, CD$_3$OD): δ 7.81 (d, J=9 Hz, 2H), 7.43-7.37 (m, 2H), 7.21-7.16 (m, 1H), 7.06-6.94 (m, 5H), 4.57 (s, 2H), 2.49 (s, 3H).

Example 45

Synthesis of N-((2-hydroxy-4,6-dimethylpyridin-3-yl)methyl)-4-phenethylbenzamide (Compound I-48)

This synthesis involved 4 steps.

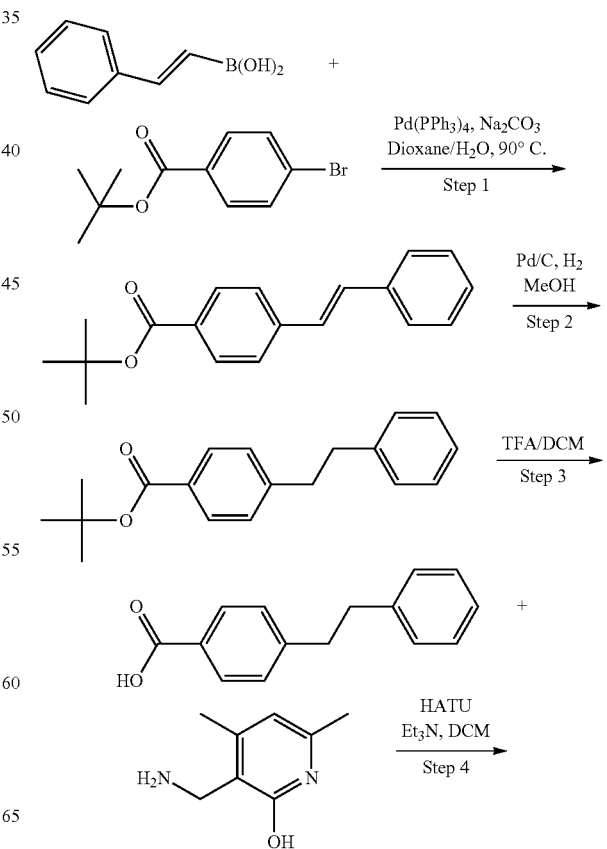

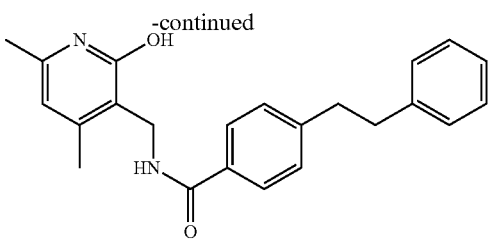

(E)-tert-butyl 4-styrylbenzoate

To a solution of (E)-styrylboronic acid (289 mg, 1.95 mmol) in mixed solution of dioxane and water (4:1, 15 mL) were added tert-butyl 4-bromobenzoate (500 mg, 1.95 mmol), tetrakis(triphenylphosphine)palladium (225 mg, 0.2 mmol) and sodium carbonate (622 mg, 5.9 mmol). The mixture was stirred at 90° C. under nitrogen atmosphere for 18 hours. Once start material has been consumed, the mixture was concentrated to give a residue and the residue was purified by column chromatography (silica gel, petroleum ether/ethyl acetate=25:1) to give (E)-tert-butyl 4-styrylbenzoate (0.1 g, 18%). The product was used for the next step directly without further purification.

Tert-butyl 4-phenethylbenzoate

A suspension of (E)-tert-butyl 4-styrylbenzoate (0.1 g, 0.36 mmol), palladium on carbon (10%, 100 mg) in methanol (20 mL) was stirred at 20° C. under hydrogen atmosphere (4 atm) for 24 hours. Once the start material has been consumed, the mixture was filtered. The filtrate was concentrated in vacuo. The residue was purified by column chromatography (silica gel, petroleum ether/ethyl acetate=20:1) to give tert-butyl 4-phenethylbenzoate (90 mg, 89%). $^1$H NMR (300 MHz, CDCl$_3$): δ 7.90-7.89 (m, 2H), 7.27-7.18 (m, 7H), 2.95-2.94 (m, 4H), 1.59 (s, 9H).

4-phenethylbenzoic acid

To a solution of tert-butyl 4-phenethylbenzoate (50 mg, 0.18 mmol) in dichloromethane (8 mL), trifluoroacetic acid (2 mL) was added. The mixture was stirred 0.5 hour. Once the start material has been consumed, the resultant mixture was concentrated to give 4-phenethylbenzoic acid (36 mg, 90%).

N-((2-hydroxy-4,6-dimethylpyridin-3-yl)methyl)-4-phenethylbenzamide (Compound I-48)

4-Phenethylbenzoic acid (30 mg, 0.13 mmol), 2-(7-aza-1H-benzotriazol-1-yl)-1,1,3,3-tetramethyluronium hexafluorophosphate (103 mg, 0.27 mmol) was dissolved in dichloromethane (20 mL), and then added triethylamine (2 mL) was added. After the mixture were stirred at 25° C. for 0.5 hour, 3-(aminomethyl)-4,6-dimethylpyridin-2-ol (20 mg, 0.13 mmol) was added. The mixture was stirred at 25° C. for 12 hours. To the mixture, water (15 ml) was added. And the mixture was extracted with dichloromethane (10 mL×3). The combined organic phase was separated, dried by sodium sulfate and then filtered. The filtrate was concentrated in vacuo. The residue was purified by column chromatography (silica gel, dichloromethane/methanol=10:1) to give N-((2-hydroxy-4,6-dimethylpyridin-3-yl)methyl)-4-phenethylbenzamide (10 mg, 21%). LRMS (M+H$^+$) m/z: calcd 360.18. found 360. HPLC purity (214 nm): 94%. $^1$H NMR (300 MHz, CD$_3$OD): δ 7.67 (d, J=8.7 Hz, 2H), 7.24-7.12 (m, 7H), 6.10 (s, 1H), 4.48 (s, 2H), 2.95-2.91 (m, 4H), 2.36 (s, 3H), 2.24 (s, 3H).

Example 46

Synthesis of N-((2-hydroxy-4,6-dimethylpyridin-3-yl)methyl)-4-(3-methyl-1-phenoxybutyl)benzamide (Compound I-49)

This synthesis involved 5 steps.

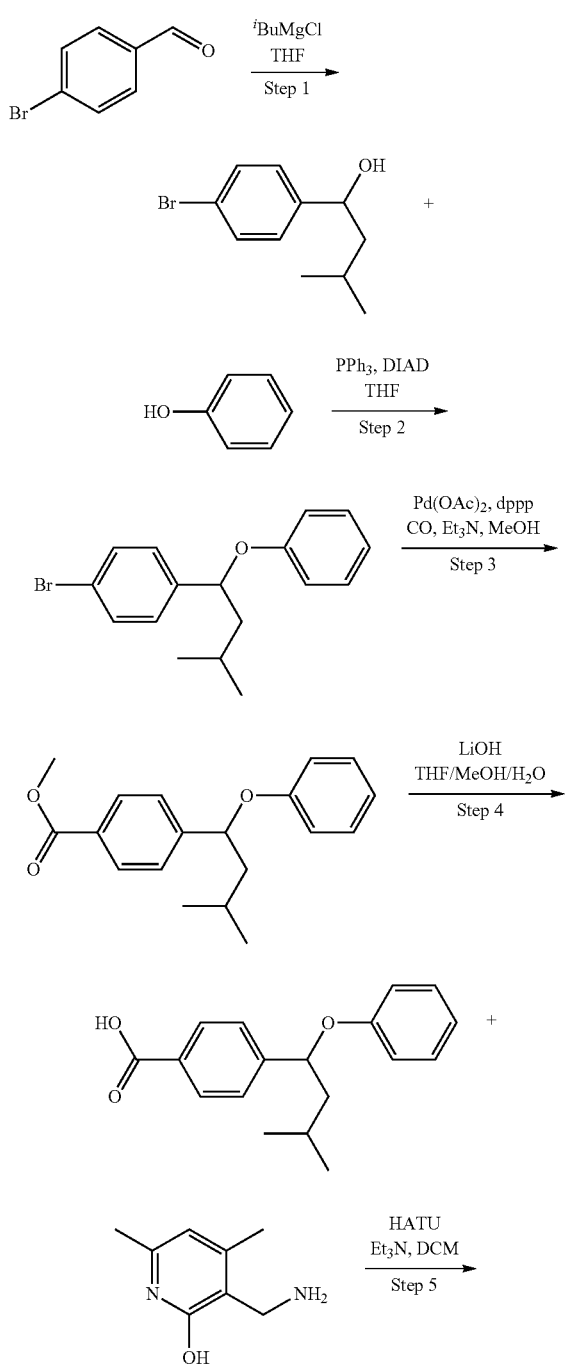

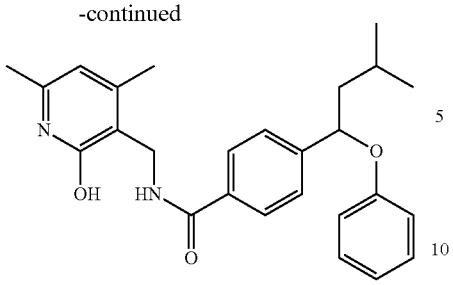

1-(4-bromophenyl)-3-methylbutan-1-ol

A solution of 4-bromobenzaldehyde (2 g, 10.8 mmol) in tetrahydrofuran (30 mL) in a two-necked round flask was cooled to −5° C. under nitrogen atmosphere. After 0.5 hour, isobutylmagnesium bromide (8 mL) was added dropwise. And then the mixture was warmed to room temperature. The resultant reaction mixture was quenched with saturated ammonium chloride aqueous solution (10 mL) and extracted with ethyl acetate (10 mL×3). The organic layers were combined, dried over sodium sulfate and concentrated to give a residue. The crude product was purified by silica gel column chromatography (silica gel, petroleum ether/ethyl acetate=8:1) to give 1-(4-bromophenyl)-3-methylbutan-1-ol (0.35 g, 13%). $^1$H NMR (300 MHz, CDCl$_3$): δ 7.48-7.45 (m, 2H), 7.25-7.21 (m, 2H), 4.74-4.72 (m, 1H), 1.72-1.68 (m, 2H), 1.47-1.46 (m, 1H), 0.95 (d, J=6.0 Hz, 6H).

1-bromo-4-(3-methyl-1-phenoxybutyl)benzene

A solution of 1-(4-bromophenyl)-3-methylbutan-1-ol (500 mg, 2.06 mmol), phenol (252 mg, 2.69 mmol) and triphenyl phosphine (1.06 g, 4.04 mmol) in anhydrous tetrahydrofuran (20 mL) was stirred at room temperature under nitrogen atmosphere. After 1 hour, the mixture was cooled to 0° C. Diisopropyl azodicarboxylate (500 mg, 2.48 mmol) was added dropwise and the reaction was stirred at room temperature for 18 hours. The mixture was concentrated to give a residue and the residue was purified by column chromatography (silica gel, pure ether) to 1-bromo-4-(3-methyl-1-phenoxybutyl)benzene (300 mg, 46%).

Methyl 4-(3-methyl-1-phenoxybutyl)benzoate

To a mixture of 1-bromo-4-(3-methyl-1-phenoxybutyl)benzene (300 mg, 0.94 mmol) in methanol (20 mL) were added palladium acetate (41 mg, 0.18 mmol), 1,3-bis(diphenylphosphino) propane (75 mg, 0.18 mmol) and triethylamine (460 mg, 4.55 mmol). And the resultant mixture was stirred and heated to 100° C. under carbon monoxide atmosphere (20 atm) for 24 hours. The mixture was cooled to room temperature and filtered. The organic phase was separated and concentrated to dryness. And then the residue was purified by column chromatography (silica gel, petroleum ether/ethyl acetate=8/1) to give methyl-4-(3-methyl-1-phenoxybutyl)benzoate (25 mg, 8.9%). $^1$H NMR (300 MHz, CDCl$_3$): δ 8.00 (d, J=8.7 Hz, 2H), 7.51 (d, J=8.4 Hz, 2H), 7.21-7.16 (m, 2H), 6.89-6.85 (m, 3H), 5.36-5.33 (m, 1H), 3.91 (s, 3H), 1.97-1.91 (m, 2H), 1.60-1.59 (m, 1H), 1.02 (d, J=3.2 Hz, 6H).

4-(3-methyl-1-phenoxybutyl)benzoic acid

A mixture of methyl 4-(3-methyl-1-phenoxybutyl)benzoate (25 mg, 0.084 mmol), lithium hydroxide monohydrate (42 mg, 1 mmol), tetrahydrofuran (6 mL), methanol (2 mL) and water (2 mL) was stirred at 20° C. for 4 hours. The mixture was acidified to pH=1 with concentrated hydrochloric acid and then extracted with dichloromethane (10 mL×3). The combined organic phase was dried by sodium sulfate and filtered. The filtrate was concentrated in vacuo to give 4-(3-methyl-1-phenoxybutyl)benzoic acid (24 mg, 99%).

N-((2-hydroxy-4,6-dimethylpyridin-3-yl)methyl)-4-(3-methyl-1-phenoxybutyl)benzamide A mixture of 4-(3-Methyl-1-phenoxybutyl)benzoic acid (20 mg, 0.07 mmol), 2-(7-aza-1H-benzotriazole-1-yl)-1,1,3,3-tetramethyluronium hexafluorophosphate (59 mg, 0.15 mmol) and triethylamine (2 mL) was dissolved in dichloromethane (20 mL). The mixture was stirred for 0.5 hour. And then added 3-(aminomethyl)-4,6-dimethylpyridin-2-ol (100 mg, 0.66 mmol) was added to the mixture and the resultant mixture was stirred at 25° C. for 12 hours. To the mixture, water (10 mL) was added and the reaction mixture was extracted with dichloromethane (10 mL×3). The combined organic phase was dried by sodium sulfate and then filtered. The filtrate was concentrated in vacuo. The residue was purified by column chromatography (silica gel, dichloromethane/methanol=10:1) to give N-((2-hydroxy-4,6-dimethylpyridin-3-yl)methyl)-4-(3-methyl-1-phenoxybutyl)benzamide (Compound I-49) (15 mg, 52%). LRMS (M+H$^+$) m/z: calcd 418.23. found 418. HPLC purity (214 nm): 95%. $^1$H NMR (300 MHz, CD$_3$OD): δ 7.73 (d, J=8.4 Hz, 2H), 7.42 (d, J=8.1 Hz, 2H), 7.13 (t, J=7.5 Hz, 2H), 6.83-6.79 (m, 3H), 6.09 (s, 1H), 5.26-5.21 (m, 1H), 4.47 (s, 2H) 2.34 (s, 3H), 2.23 (s, 3H), 1.95-1.82 (m, 2H), 1.61-1.56 (m, 1H), 1.02-0.95 (m, 6H).

Example 47

Synthesis of 4-(2,3-dihydrobenzofuran-2-yl)-N-((2-hydroxy-4,6-dimethylpyridin-3-yl)methyl)benzamide (Compound I-51)

This synthesis involved 8 steps.

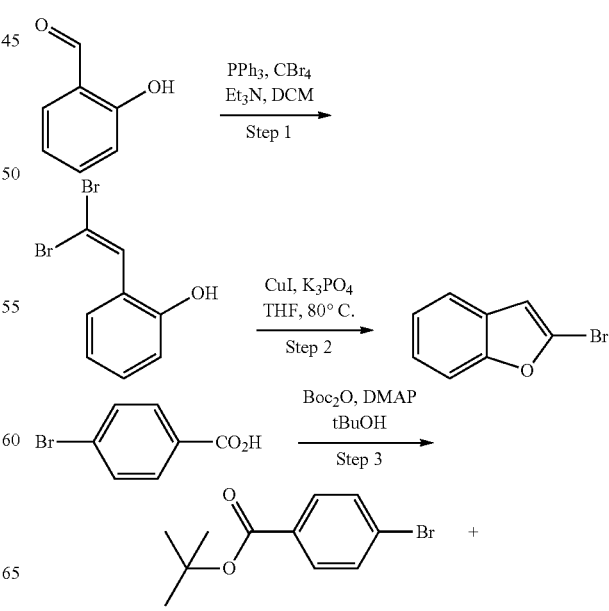

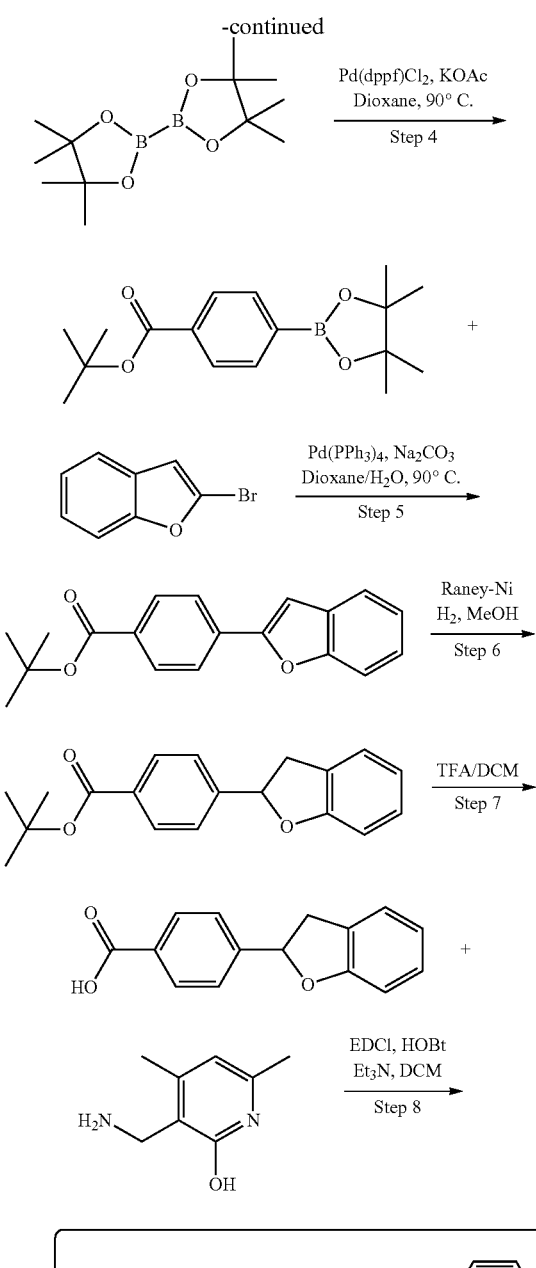

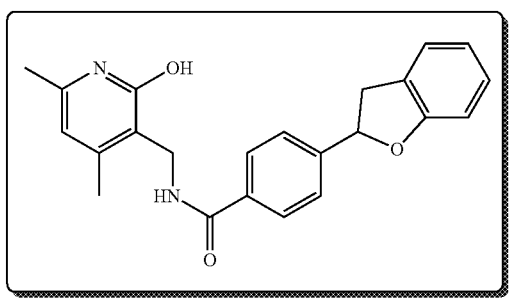

2-(2,2-dibromovinyl)phenol

To a solution of triphenylphosphine (10.5 g, 40 mmol), carbon tetrabromide (6.6 g, 20 mmol) and triethylamine (3.0 g, 30 mmol) in dichloromethane (10 mL) was added 2-hydroxy-benzaldehyde (1.62 g, 13 mmol), and the mixture temperature was maintained at around 0° C. during the addition. After the addition was completed, the reaction mixture was stirred at room temperature for 1 hour. After the reaction, the mixture was poured into water (200 mL). And then the mixture was extracted with ethyl acetate (200 mL), washed with water (200 mL). The organic phase was dried over anhydrous sodium sulfate, and then filtered. The filtrate was concentrated and the residue was purified by column chromatography (silica gel, ethyl acetate/petroleum ether=1:5) to give the pure product 2-(2,2-dibromovinyl)phenol as a pink solid (2.8 g, 76%). LRMS (M–H)⁻: calcd 275.9. found 275.

2-bromobenzofuran

To a solution of 2-(2,2-dibromovinyl)phenol (2.8 g, 10 mmol) in tetrahydrofuran (30 mL) was added copper (I) iodide (0.1 g, 0.5 mmol) and potassium phosphate (4.2 g, 20 mmol). The reaction mixture was stirred at 80° C. under nitrogen atmosphere for 12 hours. After the reaction, the mixture was poured into water (200 mL) and the mixture was extracted with ethyl acetate (200 mL). The organic phase was dried over anhydrous sodium sulfate and then filtered. The filtrate was concentrated and the residue was purified by column chromatography (silica gel, ethyl acetate/petroleum ether=1:20) to give the pure product 2-bromobenzofuran (1.8 g, 92%).

Tert-butyl 4-bromobenzoate

To a solution of 4-bromobenzoic acid (10.0 g, 50 mmol) in tert-butyl alcohol (50 mL) was added di-tert-butyl dicarbonate (13.0 g, 60 mmol) and N,N-dimethylpyridin-4-amine (0.6 g, 5 mmol). The reaction mixture was stirred at room temperature for 24 hours. After the reaction, it was concentrated in vacuo, then diluted with ethyl acetate (100 mL), washed with water (100 mL). The organic phase was dried over anhydrous sodium sulfate and filtered. The filtrate was concentrated and the residue was purified by column chromatography (silica gel, ethyl acetate/petroleum ether=1:30) to give the pure product tert-butyl 4-bromobenzoate as a colorless oil (4.8 g, 38%).

Tert-butyl 4-(4,4,5,5-tetramethyl-1,3,2-dioxaborolan-2-yl)benzoate

To a solution of tert-butyl 4-bromobenzoate (2 g, 7.8 mmol) and 4,4,4',4',5,5,5',5'-octamethyl-2,2'-bi(1,3,2-dioxaborolane) (4 g, 16 mmol) in 1,4-dioxane (30 mL) was added 1,1'-bis(diphenylphosphino)ferrocene-palladium(II) dichloride dichloromethane (0.64 g, 0.8 mmol) and potassium acetate (3.0 g, 31 mmol). The reaction mixture was stirred at 90° C. under nitrogen for 12 hours. After the reaction, it was allowed to cool to room temperature and concentrated in vacuo, then diluted with ethyl acetate (100 mL), washed with water (100 mL). The organic phase was dried over anhydrous sodium sulfate and filtered. The filtrate was concentrated and the residue was purified by column chromatography (silica gel, ethyl acetate/petroleum ether=1:20) to give the pure product tert-butyl 4-(4,4,5,5-tetramethyl-1,3,2-dioxaborolan-2-yl)benzoate (1.8 g, 75%). $^1$H NMR (300 MHz, CDCl$_3$): δ 7.95 (d, J=8.1 Hz, 2H), 7.83 (d, J=8.4 Hz, 2H), 1.59 (s, 9H), 1.35 (s, 12H).

Tert-butyl 4-(benzofuran-2-yl)benzoate

To a solution of tert-butyl 4-(4,4,5,5-tetramethyl-1,3,2-dioxaborolan-2-yl)benzoate (1.0 g, 3.3 mmol), 2-bromobenzofuran (0.64 g, 3.3 mmol) and tetrakis(triphenylphosphine)palladium(0) (0.5 g, 0.4 mmol) in a mixed solution of 1,4-dioxane (20 mL) and water (2.0 mL) was added sodium carbonate (1.0 g, 7.2 mmol). The reaction mixture was stirred at 90° C. under nitrogen for 12 hours. After the reaction, it was allowed to cool to room temperature, and concentrated in vacuo, then diluted with ethyl acetate (100 mL), washed with water (100 mL). The organic phase was dried over anhydrous sodium sulfate and filtered. The filtrate was concentrated and the residue was purified by column chromatography (silica gel, ethyl acetate/petroleum ether=1:20) to give the pure product tert-butyl 4-(benzofuran-2-yl)benzoate as a white solid (0.65 g, 67%). $^1$H NMR (300 MHz, CDCl$_3$): δ 8.06 (d, J=8.7 Hz, 2H), 7.90 (d, J=8.4 Hz, 2H), 7.62-7.53 (m, 2H), 7.32-7.25 (m, 2H), 7.14 (s, 1H), 1.62 (s, 9H).

Tert-butyl 4-(2,3-dihydrobenzofuran-2-yl)benzoate

To a solution of tert-butyl 4-(benzofuran-2-yl)benzoate (0.3 g, 1.0 mmol) in methanol (20 mL) was added raney nickel (0.20 g). The reaction mixture was stirred at room temperature for 2 hours under hydrogen (4 atm). After the reaction, the mixture was filtered and the filtrate was concentrated. The residue was purified by column chromatography (silica gel, ethyl acetate/petroleum ether=1:20) to give pure product tert-butyl 4-(2,3-dihydrobenzofuran-2-yl)benzoate as a white solid (0.03 g, 10%).

4-(2,3-dihydrobenzofuran-2-yl)benzoic acid

To a solution of tert-butyl 4-(2,3-dihydrobenzofuran-2-yl)benzoate (0.03 g, 0.1 mmol) in dichloromethane (3.0 mL) was added trifluoroacetic acid (1.0 mL). The reaction mixture was stirred at room temperature for 1 hour. After the reaction, the solvent was removed in vacuo, and the mixture was dissolved in dichloromethane (50 mL), washed with water (50 mL). The organic phase was dried over anhydrous sodium sulfate and filtered. The solvent was removed in vacuo to give pure product 4-(2,3-dihydrobenzofuran-2-yl)benzoic acid as a white solid (0.02 g, 80%).

LRMS (M+H)$^-$ m/z: calcd 240.08. found 240.

4-(2,3-dihydrobenzofuran-2-yl)-N-((2-hydroxy-4,6-dimethylpyridin-3-yl)methyl)benzamide To a solution of 4-(2,3-dihydrobenzofuran-2-yl)benzoic acid (0.02 g, 0.08 mmol), 1-ethyl-3-(3-dimethylaminopropyl)carbodiimide hydrochloride (0.04 g, 0.2 mmol) and N-hydroxybenzotriazole (0.02 g, 0.15 mmol) in dichloromethane (10 mL) was added triethylamine (0.10 g, 1.0 mmol). The reaction mixture was stirred for 15 minutes at room temperature, 3-(aminomethyl)-4,6-dimethylpyridin-2-ol (0.03 g, 0.2 mmol) was added. The reaction mixture was stirred at room temperature for 12 hours. After the reaction, the mixture was washed with water. The organic phase was concentrated and the residue was purified by column chromatography (silica gel, dichloromethane/methanol=15:1) to give pure product as a white solid 4-(2,3-dihydrobenzofuran-2-yl)-N-((2-hydroxy-4,6-dimethylpyridin-3-yl)methyl)benzamide (Compound I-51) (0.02 g, 66%). LRMS (M+H$^+$) m/z: calcd 374.16. found 374. $^1$H NMR (300 MHz, CD$_3$OD): δ 7.80-7.77 (m, 2H), 7.45 (d, J=8.1 Hz, 2H), 7.18-7.12 (m, 2H), 6.87-7.80 (m, 2H), 6.09 (s, 1H), 5.79 (t, J=9.0 Hz, 1H), 4.49 (s, 2H), 3.73-3.64 (m, 1H), 3.14-3.06 (m, 1H), 2.36 (s, 3H), 2.24 (s, 3H).

Example 48

Synthesis of compound N-((2-hydroxy-4,6-dimethylpyridin-3-yl)methyl)-5-phenoxy-5,6,7,8-tetrahydronaphthalene-2-carboxamide (Compound I-52)

This synthesis involved 6 steps.

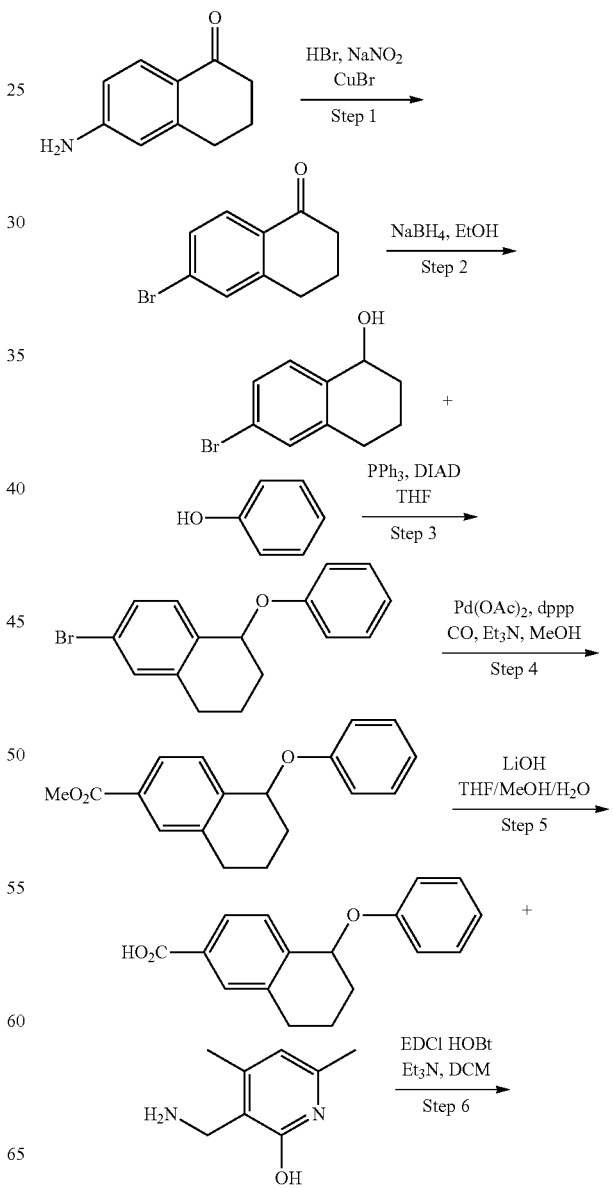

-continued

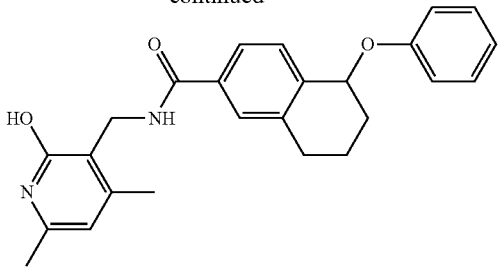

6-bromo-3,4-dihydronaphthalen-1(2H)-one

To a solution of 6-amino-3,4-dihydronaphthalen-1(2H)-one (2.0 g, 12 mmol) in bromic acid (aqueous, 10 mL, 25%) was added sodium nitrite (0.92 g, 13.3 mmol) at 0° C. The mixture was stirred at 0° C. for 15 minutes, and then copper (I) bromide (2.0 g, 13.8 mmol) and bromic acid (aqueous, 20 mL, 25%) was added at 0° C. After addition completed, the reaction mixture was stirred at room temperature for 1 hour. After the reaction, it was diluted with water (200 mL) and the product was extracted with ethyl acetate (200 mL), dried over anhydrous sodium sulfate, concentrated and purified by column chromatography (silica gel, ethyl acetate/petroleum ether=1:20) to give the pure product 6-bromo-3,4-dihydronaphthalen-1(2H)-one (1.2 g, 45%). $^1$H NMR (300 MHz, CDCl$_3$): δ 7.87 (d, J=8.7 Hz, 1H), 7.44-7.42 (m, 2H), 2.93 (t, J=6.0 Hz, 2H), 2.64 (t, J=6.0 Hz, 2H), 2.15-2.11 (m, 2H).

6-bromo-1,2,3,4-tetrahydronaphthalen-1-ol

To a solution of 6-bromo-3,4-dihydronaphthalen-1(2H)-one (1.0 g, 4.4 mmol) in ethanol (10 mL) was added sodium borohydride (0.8 g, 21 mmol). The reaction mixture was stirred at room temperature for 0.5 hour. After the reaction, the mixture was poured into water (100 mL) and the mixture was extracted with dichloromethane (100 mL). The organic phase was dried over anhydrous sodium sulfate and filtered. The filtrate was concentrated in vacuo to give the pure product 6-bromo-1,2,3,4-tetrahydronaphthalen-1-ol (1.0 g, 100%).

6-bromo-1-phenoxy-1,2,3,4-tetrahydronaphthalene

To a solution of 6-bromo-1,2,3,4-tetrahydronaphthalen-1-ol (0.68 g, 3.0 mmol) and phenol (0.38 g, 4.0 mmol) in anhydrous tetrahydrofuran (10 mL) was added triphenylphosphine (1.04 g, 4 mmol). The reaction mixture was stirred at room temperature for 0.5 hour under nitrogen atmosphere. Then diisopropyl azodicarboxylate (0.8 g, 4 mmol) was added dropwise at 0° C., and then the reaction mixture was stirred at room temperature for 12 hours. After the reaction, it was quenched with water (100 mL), and the product was extracted with ethyl acetate (100 mL), dried over anhydrous sodium sulfate. The mixture was filtered and the filtrate was concentrated. The residue was purified by column chromatography (silica gel, ethyl acetate/petroleum ether=1:20) to give the pure product 6-bromo-1-phenoxy-1,2,3,4-tetrahydro naphthalene (0.73 g, 80%). $^1$H NMR (300 MHz, CDCl$_3$): δ 7.32-7.20 (m, 5H), 7.00-6.97 (m, 3H), 5.27 (t, J=4.5 Hz, 1H), 2.86-2.67 (m, 2H), 2.11-1.74 (m, 4H).

Methyl 5-phenoxy-5,6,7,8-tetrahydronaphthalene-2-carboxylate

To a solution of 6-bromo-1-phenoxy-1,2,3,4-tetrahydronaphthalene (0.6 g, 2.0 mmol) in ethanol (20 mL) was added palladium acetate (0.27 g, 1.2 mmol), 1,3-bis(diphenylphosphino) propane (0.17 g, 0.4 mmol) and triethylamine (0.4 g, 4.0 mol). The reaction mixture was stirred at 90° C. under carbon monoxide atmosphere (20 atm) for 12 hours. After the reaction, the mixture was diluted with water (100 mL), and the mixture was extracted with dichloromethane (100 mL). The organic phase was dried over anhydrous sodium sulfate and filtered. The filtrate was concentrated and the residue was purified by column chromatography (silica gel, ethyl acetate/petroleum ether=1:20) to give pure product methyl 5-phenoxy-5,6,7,8-tetrahydronaphthalene-2-carboxylate as a white solid (0.04 g, 7%). $^1$H NMR (300 MHz, CDCl$_3$): δ 7.85 (d, J=6.0 Hz, 2H), 7.47 (d, J=8.4 Hz, 1H), 7.36-7.31 (m, 2H), 7.05-7.01 (m, 3H), 5.39 (t, J=4.8 Hz, 1H), 3.92 (s, 3H), 2.95-2.85 (m, 2H), 2.14-2.04 (m, 4H).

5-phenoxy-5,6,7,8-tetrahydronaphthalene-2-carboxylic acid

Lithium hydroxide hydrate (0.04 g, 1.0 mmol) was added to a solution of methyl 5-phenoxy-5,6,7,8-tetrahydronaphthalene-2-carboxylate (0.04 g, 0.14 mmol) in a mixed solution of tetrahydrofuran (6.0 mL), methanol (2 mL) and water (2 mL). The reaction mixture was stirred at room temperature for 1 hour. After the reaction, the solvent was removed in vacuo. Hydrochloric acid aqueous (3 mol/L) was added to make pH 3-5, and the mixture was extracted with dichloromethane. The combined organic phase was washed with water (20 mL×3), dried over anhydrous sodium sulfate. The mixture was filtered and the filtrate was concentrated to dryness to give pure product 5-phenoxy-5,6,7,8-tetrahydronaphthalene-2-carboxylic acid as a white solid (0.032 g, 86%).

N-((2-hydroxy-4,6-dimethylpyridin-3-yl)methyl)-5-phenoxy-5,6,7,8-tetrahydronaphthalene-2-carboxamide To a solution of 5-phenoxy-5,6,7,8-tetrahydronaphthalene-2-carboxylic acid (0.032 g, 0.12 mmol), 1-ethyl-3-(3-dimethylaminopropyl)carbodiimide hydrochloride (0.06 g, 0.3 mmol) and N-hydroxybenzotriazole (0.03 g, 0.22 mmol) in dichloromethane (10 mL) was added triethylamine (0.03 g, 0.3 mmol). The reaction mixture was stirred for 15 minutes at room temperature, then 3-(aminomethyl)-4,6-dimethylpyridin-2-ol (0.03 g, 0.2 mmol) was added. The reaction mixture was stirred at room temperature for 12 hours. After the reaction, the mixture was washed with water (10 mL×3). The organic phase was concentrated and the residue was purified by column chromatography (silica gel, dichloromethane/methanol=15:1) to give pure product N-((2-hydroxy-4,6-dimethylpyridin-3-yl)methyl)-5-phenoxy-5,6,7,8-tetrahydronaphthalene-2-carboxamide (Compound I-52) as a white solid (0.031 g, 63%). LRMS (M+H$^+$) m/z: calcd 402.19. found 402. $^1$H NMR (300 MHz, CD$_3$OD): δ 7.59 (s, 1H), 7.57 (d, J=7.5 Hz, 1H), 7.37 (d, J=7.8 Hz, 1H), 7.28 (t, J=7.2 Hz, 2H), 7.02-6.92 (m, 3H), 6.10 (s, 1H), 5.43 (t, J=4.5 Hz, 1H), 4.48 (s, 2H), 2.90-2.82 (m, 2H), 2.37 (s, 3H), 2.24 (s, 3H), 2.08-1.83 (m, 4H).

Example 49

Synthesis of compound N-((2-hydroxy-4,6-dimethylpyridin-3-yl)methyl)-4-(methoxy(phenyl)methyl)benzamide (Compound I-53)

This synthesis involved 5 steps.

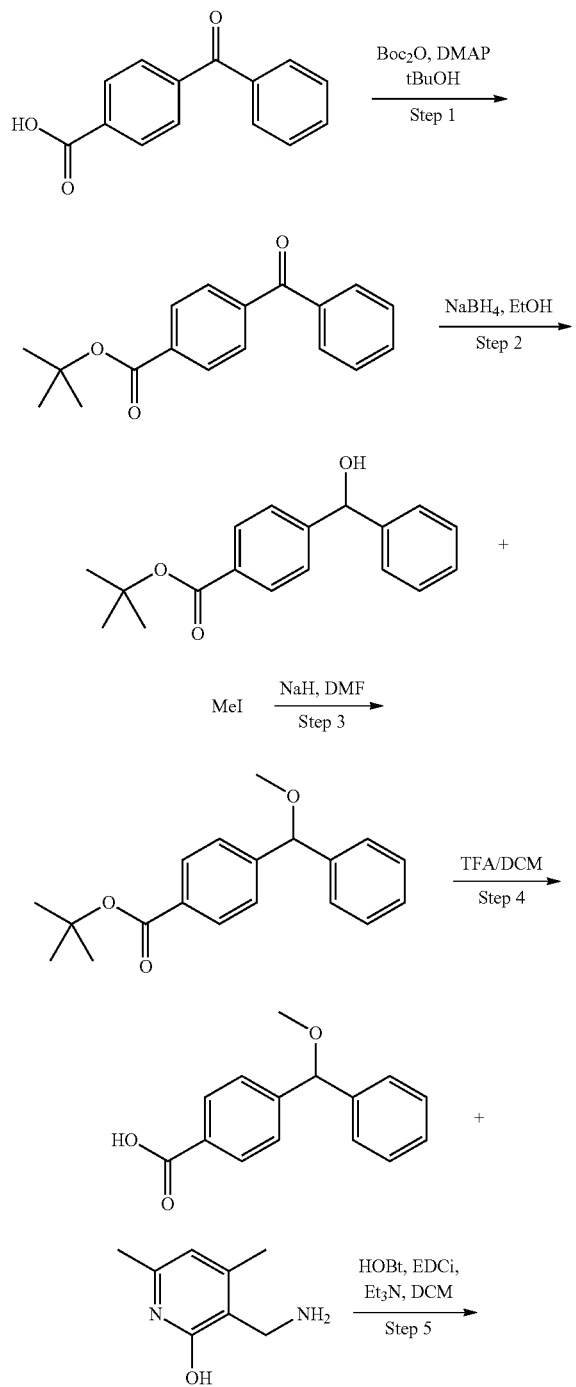

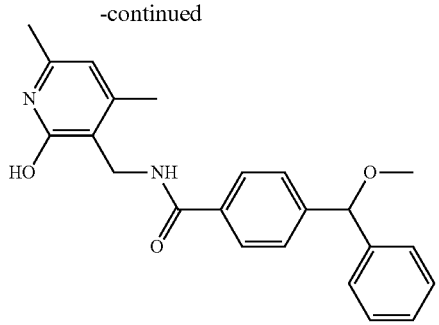

Tert-butyl 4-benzoylbenzoate

N,N-dimethylpyridin-4-amine (544 mg, 4.4 mmol) was added to the mixture of 4-benzoylbenzoic acid (2.0 g, 8.8 mol), di-tert-butyl dicarbonate (3.86 g, 17.7 mmol) and 2-methylpropan-2-ol (100 mL). Then the mixture was stirred at 25° C. for 12 hours. The resultant mixture was concentrated to give a residue. The residue was purified by column chromatography (silica gel, petroleum ether/ethyl acetate=3:1) to give tert-butyl 4-benzoylbenzoate (1.54 g, 62%). $^1$H NMR (300 MHz, CDCl$_3$): δ 8.10-8.08 (m, 2H), 7.83-7.78 (m, 4H), 7.64-7.58 (m, 1H), 7.51-7.46 (m, 2H), 1.62 (s, 9H).

Tert-butyl 4-(hydroxy(phenyl)methyl)benzoate

Sodium borohydride (1.04 g, 27.4 mmol) was added to the solution of tert-butyl 4-benzoylbenzoate (1.54 g, 5.46 mmol) in ethanol (50 mL). Then the mixture was stirred at room temperature for 2 hours. The resultant mixture was concentrated to give a residue. The residue was purified by column chromatography (silica gel, petroleum ether/ethyl acetate=3:1) to give tert-butyl 4-(hydroxy(phenyl)methyl)benzoate (1.55 g, 100%). $^1$H NMR (300 MHz, d$^6$-DMSO): δ 7.82 (d, J=8.1 Hz, 2H), 7.48 (d, J=8.1 Hz, 2H), 7.36-7.26 (m, 4H), 7.22-7.17 (m, 1H), 6.04 (d, J=3.9 Hz, 1H), 5.76 (d, J=3.9 Hz, 1H), 1.52 (s, 9H).

Tert-butyl 4-(methoxy(phenyl)methyl)benzoate

A solution of tert-butyl 4-(hydroxy(phenyl)methyl)benzoate (1.4 g, 4.9 mmol) was dropped to the suspension of sodium hydride (237 mg, 5.9 mmol) in N,N-dimethylformamide (20 mL) and then the mixture was stirred 0.5 hour. Then iodomethane (3.0 mL) was added to the mixture and stirred at room temperature for 2 hours. The resultant mixture was concentrated to give a residue. The residue was purified by column chromatography (silica gel, petroleum ether/ethyl acetate=6:1) to give tert-butyl 4-(methoxy(phenyl)methyl)benzoate as a colorless oil (1.25 g, 86%). $^1$H NMR (300 MHz, CDCl$_3$): δ 7.95 (d, J=8.1 Hz, 2H), 7.42-7.31 (m, 7H), 5.28 (s, 1H), 3.39 (s, 3H), 1.58 (s, 9H).

4-(methoxy(phenyl)methyl)benzoic acid

A mixture of tert-butyl 4-(methoxy(phenyl)methyl)benzoate (200 mg, 0.67 mmol), 2,2,2-trifluoroacetic acid (1 mL) and dichloromethane (4 mL) were stirred at 20° C. for 4 hours. The mixture was concentrated to give a residue. The residue was purified by column chromatography (silica gel, petroleum ether/ethyl acetate=2:1) to give 4-(methoxy(phenyl)methyl)benzoic acid as a white solid (162 mg, 100%).
LRMS (M+H)$^-$ m/z: calcd 242.09. found 242.

N-((2-hydroxy-4,6-dimethylpyridin-3-yl)methyl)-4-(methoxy(phenyl)methyl)benzamide A mixture of 4-(methoxy(phenyl)methyl)benzoic acid (0.26 g, 1.07 mmol), 1-ethyl-3-(3-dimethyl aminopropyl)carbodiimide hydrochloride (309 mg, 1.61 mmol), 1-hydroxybenzotriazole (218 mg, 1.61 mmol), triethylamine (0.45 mL) and dichloromethane (15 mL) was stirred at 25° C. for half an hour. Then 3-(aminomethyl)-4,6-dimethylpyridin-2-ol (163 mg, 1.07 mmol) was added. The mixture was stirred at 25° C. for 12 hours. The resultant mixture was concentrated to give a residue. The residue was purified by column chromatography (silica gel, dichloromethane/methanol=10:1) to give N-((2-hydroxy-4,6-dimethylpyridin-3-yl)methyl)-4-(methoxy(phenyl)methyl)benzamide (Compound I-53) as a white solid (80 mg, 20%). LRMS (M+H$^+$) m/z: calcd 376.18. found 376. HPLC purity (214 nm): 96%. $^1$H NMR (300 MHz, d$^6$-DMSO): δ 11.43 (s, 1H), 8.25 (t, J=3.6 Hz, 1H), 7.30 (d, J=6.9 Hz, 2H), 7.41-7.18 (m, 7H), 5.95 (s, 1H), 5.83 (s, 1H), 4.27 (d, J=3.6 Hz, 2H), 3.31 (s, 3H), 2.14 (s, 3H), 2.10 (s, 3H).

Example 50

Synthesis of N-((2-hydroxy-4,6-dimethylpyridin-3-yl)methyl)-3-methyl-4-(phenoxymethyl)benzamide (Compound I-54)

This synthesis involved 5 steps.

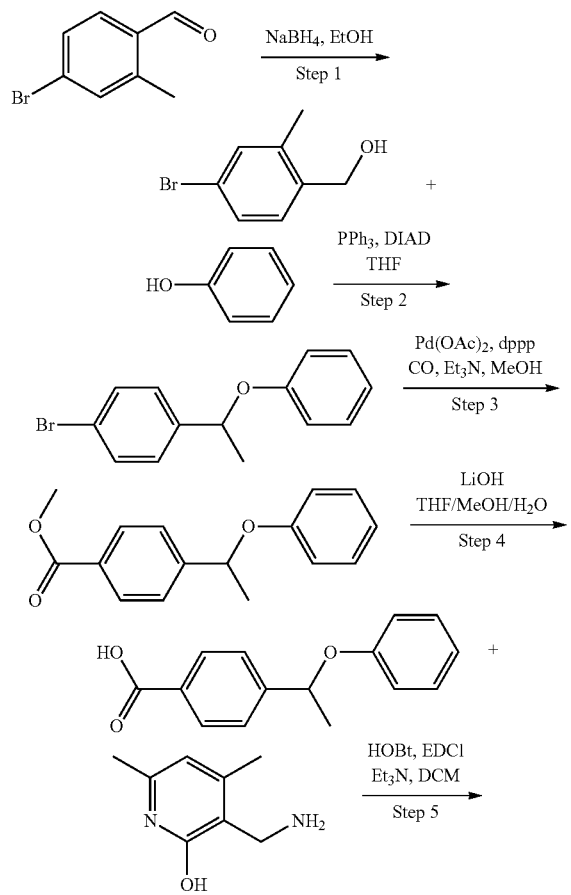

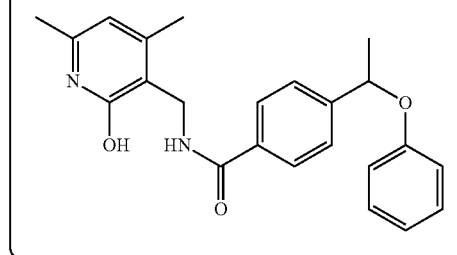

4-bromo-2-methylphenyl methanol

To a solution of 4-bromo-2-methylbenzaldehyde (1.99 g, 10 mmol) in ethanol (100 mL) was added sodium borohydride (0.76 g, 20 mmol) in portions at 0° C. The mixture was stirred for 30 minutes and warmed to 20° C. and stirred at the same temperature for 12 hours. The mixture was concentrated in vacuo to give (4-bromo-2-methylphenyl)methanol (1.3 g, 65%).

4-bromo-2-methyl-1-(phenoxymethyl)benzene

To a solution of (4-bromo-2-methylphenyl)methanol (1 g, 5 mmol), phenol (525 mg, 5.6 mmol) and triphenylphosphine (2.2 g, 8.4 mmol) in tetrahydrofuran (30 mL) was added diisopropyl azodicarboxylate (1.7 g, 8.4 mmol) at 0° C. The mixture was stirred at 20° C. for 12 hours. Water (15 mL) was added to the mixture and then extracted with ethyl acetate (35 mL×3). The combined organic phase was dried by sodium sulfate, and then filtered. The filtrate was concentrated in vacuo and the residue was purified by column chromatography (silica gel, petroleum ether/ethyl acetate=5:1) to give 4-bromo-2-methyl-1-(phenoxymethyl)benzene (640 mg, 46%).

Methyl 3-methyl-4-(phenoxymethyl)benzoate

A mixture of 4-bromo-2-methyl-1-(phenoxymethyl)benzene (545 mg, 2 mmol), palladium acetate (137 mg, 0.6 mmol), 1,3-bis(diphenylphosphino) propane (376 mg, 0.9 mmol), triethylamine (4 mL) and methanol (100 mL) were stirred at 100° C. under carbon monoxide (20 atm). The mixture was concentrated in vacuo and the residue was purified by column chromatography (silica gel, petroleum ether/ethyl acetate=5:1) to give methyl 3-methyl-4-(phenoxymethyl)benzoate (320 mg, 63%).

3-methyl-4-(phenoxymethyl)benzoic acid

A mixture of methyl 4-(1-phenoxyethyl)benzoate (0.32 g, 1.2 mmol), lithium hydroxide monohydrate (571 mg, 13.6 mmol), tetrahydrofuran (15 mL), methanol (5 mL) and water (5 mL) was stirred at 20° C. for 4 hours. The mixture was neutralized to pH=1 with concentrated hydrochloric acid and then extracted with ethyl acetate (15 mL×3). The combined organic phase was dried by sodium sulfate, and then filtered. The filtrate was concentrated in vacuo to give 3-methyl-4-(phenoxymethyl)benzoic acid (0.21 g, 72%).

N-((2-hydroxy-4,6-dimethylpyridin-3-yl)methyl)-3-methyl-4-(phenoxymethyl)benzamide A mixture of 3-methyl-4-(phenoxymethyl)benzoic acid (121 mg, 0.5 mmol), 1-ethyl-3-(3-dimethylaminopropyl)carbodiimide hydrochloride (191 mg, 1 mmol), N-hydroxybenzotriazole (135 mg, 1 mmol), triethylamine (0.2 mL) and dichloromethane (5 mL) were stirred at 25° C. for half an hour. And then 3-(aminomethyl)-4,6-dimethylpyridin-2-ol (76 mg, 0.5 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give N-((2-hydroxy-4,6-dimethylpyridin-3-yl)methyl)-3-methyl-4-(phenoxymethyl)benzamide (Compound I-54) as a white solid (51 mg, 26%). LRMS (M+H$^+$) m/z: calcd 376.45. found 376. HPLC purity (214 nm): 99%. $^1$H NMR (300 MHz, d$^6$-DMSO): δ 11.43 (s, 1H), 8.29 (t, J=4.2 Hz, 1H), 7.69-7.63 (m, 2H), 7.43 (d, J=8.1 Hz, 1H), 7.29 (t, J=7.5 Hz, 2H), 7.03-6.91 (m, 3H), 5.85 (s, 1H), 5.11 (s, 2H), 4.29 (d, J=4.8 Hz, 2H), 2.34 (s, 3H), 2.17 (s, 3H), 2.11 (s, 3H).

Example 51

Synthesis of N-((2-hydroxy-4,6-dimethylpyridin-3-yl)methyl)-4-(1-(2-oxopyridin-1(2H)-yl)ethyl)benzamide (Compound I-56)

The synthesis involved 5 steps.

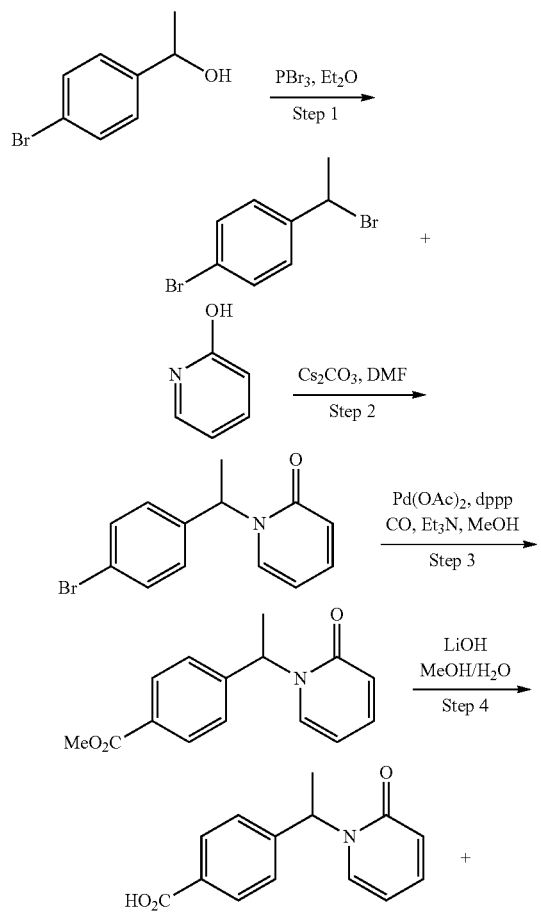

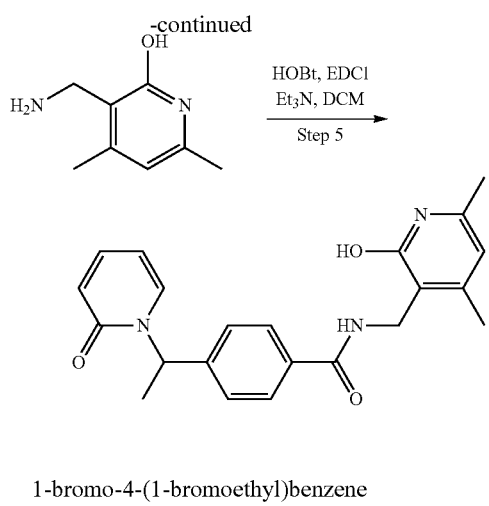

1-bromo-4-(1-bromoethyl)benzene

To a solution of 1-(4-bromophenyl)ethanol (1 g, 5 mmol) in tetrahydrofuran (80 mL) was added dropwise tribromophosphine (669 mg, 2.5 mmol) at 0° C. The solution was stirred at room temperature for 2 hours, and then water was added to quench the reaction at 0° C. The mixture was extracted with ethyl acetate (20 mL×3). The organic layers were combined and concentrated to give a residue. And the residue was purified by column chromatography (silica gel, ethyl acetate/petroleum ether=1:50) to give 1-bromo-4-(1-bromoethyl)benzene as an oil (780 mg, 59%). $^1$H NMR (300 MHz, CD$_3$OD): δ 7.46 (d, J=8.1 Hz, 2H), 7.36 (d, J=8.1 Hz, 2H), 5.25 (q, J=6.9 Hz, 1H), 1.98 (d, J=6.9 Hz, 3H).

1-(1-(4-bromophenyl)ethyl)pyridin-2 (H)-one

To a solution of 1-bromo-4-(1-bromoethyl)benzene (200 mg, 0.76 mmol) and pyridin-2-ol (87 mg, 0.91 mmol) in N,N-dimethylformamide (30 mL) was added cesium carbonate (496 mg, 1.52 mmol). The mixture was stirred at room temperature for 12 hours. And then solvent was removed to give a residue. The residue was purified by column chromatography (silica gel, ethyl acetate/petroleum ether=1:10) to give 1-(1-(4-bromophenyl)ethyl)pyridin-2(1H)-one (161 mg, 76%) LRMS (M+H$^+$) m/z: calcd 277.0. found 277.

Methyl 4-(1-(2-oxopyridin-1(2H)-yl)ethyl)benzoate

To a solution of 1-(1-(4-bromophenyl)ethyl)pyridin-2 (1H)-one (161 mg, 0.58 mmol) in methanol (30 mL) were added diacetoxypalladium (28 mg, 0.12 mmol), 1,3-bis(diphenylphosphino)propane (54 mg, 0.13 mmol) and triethylamine (131 mg, 1.3 mmol). The mixture was stirred at 90° C. for 12 hours under carbon monoxide atmosphere (15 atm). Then the mixture was concentrated to give a residue and the residue was purified by column chromatography (silica gel, ethyl acetate/petroleum ether=1:10) to give methyl 4-(1-(2-oxopyridin-1(2H)-yl)ethyl)benzoate (145 mg, 97%) LRMS (M+H$^+$) m/z: calcd 257.1. found 257.

4-(1-(2-oxopyridin-1(2H)-yl)ethyl)benzoic acid

To a mixed solution of methanol (10 mL) and water (2 mL), methyl 4-(1-(2-oxopyridin-1(2H)-yl)ethyl)benzoate (145 mg, 0.56 mmol) and lithium hydroxide hydrate (40 mg, 0.95 mmol) were added. The reaction mixture was stirred at room temperature for 12 hours. Then the mixture was acidified by hydrogen chloride aqueous solution (1N) to pH=6 and extracted with dichloromethane (20 mL×3). The organic phase was concentrated to give 4-(1-(2-oxopyridin-1(2H)-yl)ethyl)benzoic acid (111 mg, 81%).

N-((2-hydroxy-4,6-dimethylpyridin-3-yl)methyl)-4-(1-(2-oxopyridin-1(2H)-yl)ethyl)benzamide (Compound I-56)

To a solution of 4-(1-(2-oxopyridin-1(2H)-yl)ethyl)benzoic acid (111 mg, 0.46 mmol) in dichloromethane (20 mL) were added o-(7-azabenzotriazol-1-yl)-N,N,N',N'-tetramethyluronium hexafluorophosphate (285 mg, 0.75 mmol) and triethylamine (151 mg, 1.5 mmol). Then 3-(aminomethyl)-4,6-dimethylpyridin-2-ol (76 mg, 0.5 mmol) was added. The mixture was stirred at room temperature for 12 hours. The resultant mixture was washed with water (20 mL×3) and the organic layer was concentrated to give a residue. The residue was purified by column chromatography (silica gel, dichloromethane/methanol=20:1) to give N-((2-hydroxy-4,6-dimethylpyridin-3-yl)methyl)-4-(1-(2-oxopyridin-1(2H)-yl)ethyl)benzamide (57 mg, 33%). LRMS (M+H$^+$) m/z: calcd 377.17. found 377. HPLC purity (214 nm): 98%. $^1$H NMR (300 MHz, d$^6$-DMSO): δ 11.46 (s, 1H), 8.35-8.33 (m, 1H), 7.80 (d, J=8.1 Hz, 2H), 7.60-7.57 (m, 1H), 7.33-7.30 (m, 3H), 6.39 (d, J=9.3 Hz, 1H), 6.22-6.18 (m, 2H), 5.84 (s, 1H), 4.27 (s, 2H), 2.15 (s, 3H), 2.10 (s, 3H), 1.68 (d, J=7.2 Hz, 3H).

Example 52

Synthesis of (R or S)-4-(1-(2-fluorophenoxy)ethyl)-N-((2-hydroxy-4,6-dimethylpyridin-3-yl)methyl)benzamide (Compound I-57) and (S or R)-4-(1-(2-fluorophenoxy)ethyl)-N-((2-hydroxy-4,6-dimethylpyridin-3-yl)methyl)benzamide (Compound I-58)

This synthesis involved 4 steps.

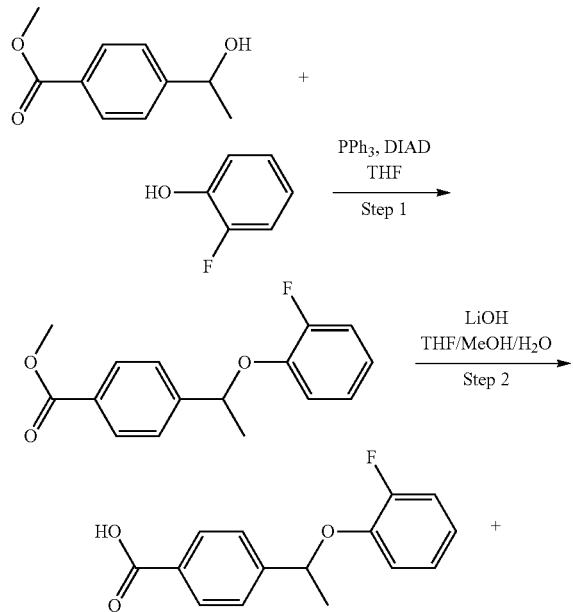

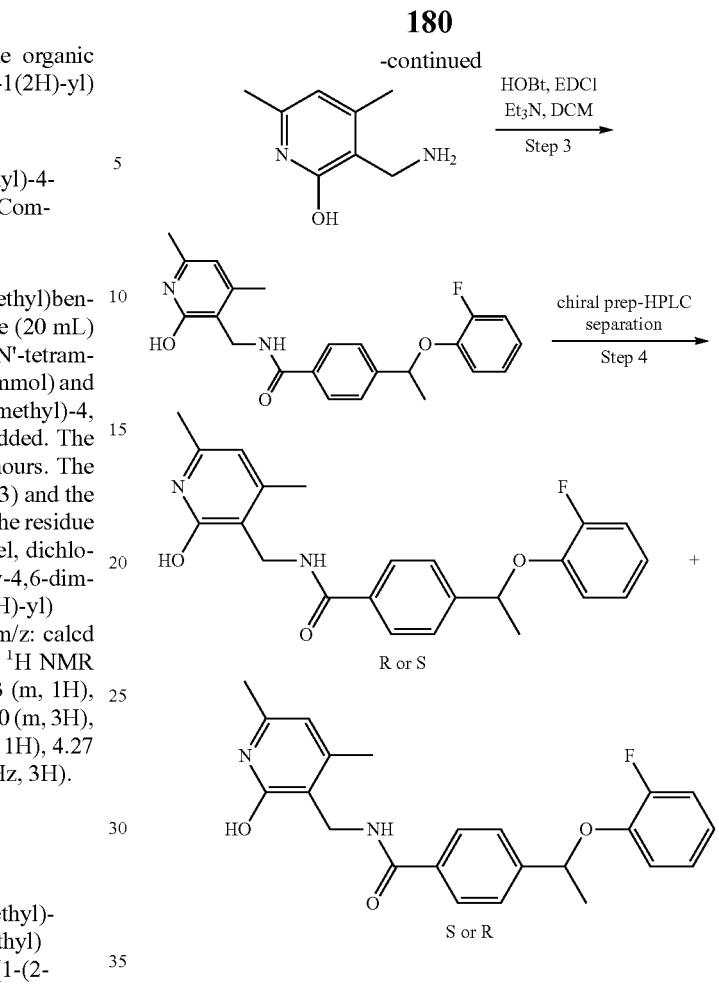

Methyl 4-(1-(2-fluorophenoxy)ethyl)benzoate

To a solution of methyl 4-(1-hydroxyethyl)benzoate (0.9 g, 5 mmol), 2-fluorophenol (627 mg, 5.6 mmol), triphenylphosphine (2.2 g, 8.4 mmol) in tetrahydrofuran (30 mL) was added diisopropyl azodicarboxylate (1.7 g, 8.4 mmol) at 0° C. The mixture was stirred at 20° C. for 12 hours. Water (15 mL) was added to the mixture and then extracted with ethyl acetate (35 mL×3). The combined organic phase was dried by sodium sulfate, and then filtered. The filtrate was concentrated in vacuo and purified by column chromatography (silica gel, petroleum ether/ethyl acetate=5:1) to give methyl 4-(1-(2-fluorophenoxy)ethyl)benzoate (450 mg, 33%).

4-(1-(2-fluorophenoxy)ethyl)benzoic acid

A mixture of methyl 4-(1-(2-fluorophenoxy)ethyl)benzoate (0.45 g, 1.6 mmol), lithium hydroxide monohydrate (0.57 g, 13.6 mmol), tetrahydrofuran (15 mL), methanol (5 mL) and water (5 mL) was stirred at 20° C. for 4 hours. The mixture was turned to pH=1 with concentrated hydrochloric acid and then extracted with ethyl acetate (15 mL×3). The combined organic phase was dried by sodium sulfate, and then filtered. The filtrate was concentrated in vacuo to give 4-(1-(2-fluorophenoxy)ethyl)benzoic acid (0.31 g, 74%).

4-(1-(2-fluorophenoxy)ethyl)-N-((2-hydroxy-4,6-dimethylpyridin-3-yl)methyl)benzamide A mixture of 4-(1-(2-fluorophenoxy)ethyl)benzoic acid (260 mg, 1 mmol), 1-ethyl-3-(3-dimethylaminopropyl)carbodiimide hydrochloride (382 mg, 2 mmol), N-hydroxybenzotriazole (270 mg, 2 mmol), triethylamine (0.3 mL) and dichloromethane (15 mL) were stirred at 25° C. for half an hour. And then 3-(aminomethyl)-4,6-dimethylpyridin-2-ol (152 mg, 1 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give 4-(1-(2-fluorophenoxy)ethyl)-N-((2-hydroxy-4,6-dimethylpyridin-3-yl)methyl)benzamide (75 mg, 38%). LRMS (M+H$^+$) m/z: calcd. 394.17. found 394. HPLC purity (214 nm): 99%. $^1$H NMR (300 MHz, d$^6$-DMSO): δ 11.44 (s, 1H), 8.30 (t, J=4.8 Hz, 1H), 7.78 (d, J=8.4 Hz, 2H), 7.43 (d, J=8.1 Hz, 2H), 7.19-6.83 (m, 4H), 5.83 (s, 1H), 5.58 (q, J=6.3 Hz, 1H), 4.27 (d, J=4.8 Hz, 2H), 2.15 (s, 3H), 2.10 (s, 3H), 1.56 (d, J=6.3 Hz, 3H).

(R or S)-4-(1-(2-fluorophenoxy)ethyl)-N-((2-hydroxy-4,6-dimethylpyridin-3-yl)methyl)benzamide (Compound I-57) and (S or R)-4-(1-(2-fluorophenoxy)ethyl)-N-((2-hydroxy-4,6-dimethylpyridin-3-yl)methyl)benzamide (Compound I-58)

4-(1-(2-Fluorophenoxy)ethyl)-N-((2-hydroxy-4,6-dimethylpyridin-3-yl)methyl)benzamide (75 mg, 0.19 mmol) was separated by chiral prep-HPLC (Daicel AD-H (250 mm×20 mm×5 um), hexane:ethanol (0.2% diethylamine)=50:50, flow rate: 13 mL/min), then (R or S)-4-(1-(2-fluorophenoxy)ethyl)-N-((2-hydroxy-4,6-dimethylpyridin-3-yl)methyl)benzamide (Compound I-57) (10 mg, 27%) and (S or R)-4-(1-(2-fluorophenoxy)ethyl)-N-((2-hydroxy-4,6-dimethylpyridin-3-yl)methyl)benzamide (Compound I-58) (13 mg, 35%) was obtained. The retention times for the two enantiomers were 8.912 minute and 9.855 minutes in chiral HPLC chromatography. LRMS (M+H$^+$) m/z: calcd. 394.17. found 394. HPLC purity (214 nm): 99%. $^1$H NMR (300 MHz, d$^6$-DMSO): δ 11.44 (s, 1H), 8.30 (t, J=4.8 Hz, 1H), 7.78 (d, J=8.4 Hz, 2H), 7.43 (d, J=8.1 Hz, 2H), 7.19-6.83 (m, 4H), 5.83 (s, 1H), 5.58 (q, J=6.3 Hz, 1H), 4.27 (d, J=4.8 Hz, 2H), 2.15 (s, 3H), 2.10 (s, 3H), 1.56 (d, J=6.3 Hz, 3H). Although the separated enantiomers were not optically characterized, for convenience sake, the (R)-enantiomer was designated as Compound I-57 and the (S)-enantiomer as Compound I-58.

Example 53

Synthesis of N-((4-hydroxy-2,6-dimethylpyrimidin-5-yl)methyl)-4-phenoxybenzamide (Compound I-59)

This synthesis involved 5 steps.

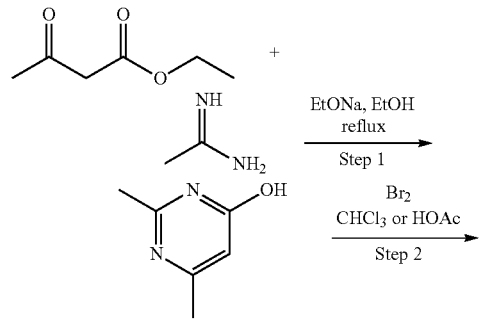

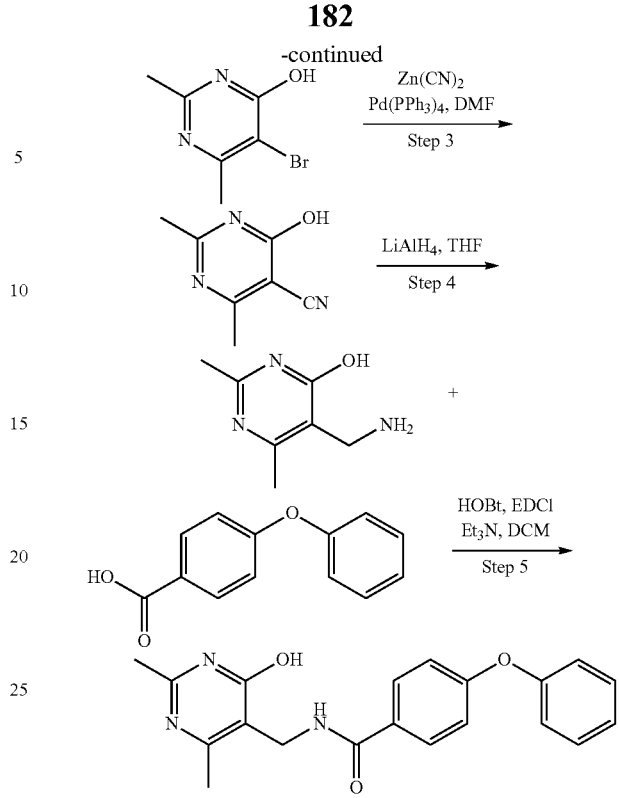

2,6-dimethylpyrimidin-4-ol

Ethyl 3-oxobutanoate (10.0 g, 77 mmol) and acetimidamide hydrochloride (7.23 g, 77 mmol) were added to the solution of sodium ethanolate (10.5 g, 154 mmol) in ethanol (200 mL). And the mixture was refluxed for 20 hours. Water (10 mL) was added to the mixture. The resultant mixture was concentrated to give a residue. The residue was purified by column chromatography (silica gel, dichloromethane/methanol=15:1) to give 2,6-dimethylpyrimidin-4-ol as a yellow solid (3.43 g, 36%). LRMS (M+H) m/z: calcd 124.06. found 124.

5-bromo-2,6-dimethylpyrimidin-4-ol

The solution of bromine (5.1 g, 31.9 mmol) in chloroform (30 mL) was added dropwise to the solution of 2,6-dimethylpyrimidin-4-ol (3.43 g, 27.6 mmol) in chloroform (50 mL) at 0° C. Then the mixture was stirred at 25° C. for 12 hours. Saturated sodium sulfite solution was added to the mixture until the colour of the mixture changed to colourless. The organic phase was separated, dried over sodium sulphate, filtered, and then concentrated to give a residue. The residue was purified by column chromatography (silica gel, dichloromethane/methanol=15:1) to give 5-bromo-2,6-dimethylpyrimidin-4-ol as a white solid (3.7 g, 66%). $^1$H NMR (300 MHz, d$^6$-DMSO): δ 2.33 (s, 3H), 2.24 (s, 3H).

4-hydroxy-2,6-dimethylpyrimidine-5-carbonitrile

A mixture of 5-bromo-2,6-dimethylpyrimidin-4-ol (3.7 g, 18.3 mmol), dicyano zinc (10.7 g, 91.5 mmol) and tetrakis (triphenylphosphine)palladium (6.3 g, 5.1 mmol) and N,N-dimethylformamide (60 mL) was stirred at 140° C. for 12 hours. The mixture was concentrated to give a residue. The residue was purified by column chromatography (silica gel, dichloromethane/methanol=15:1) to give 4-hydroxy-2,6-dimethylpyrimidine-5-carbonitrile as a white solid (2.7 g, 99%). LRMS (M+H) m/z: calcd 149.06. found 149.

5-(aminomethyl)-2,6-dimethylpyrimidin-4l

A mixture of 4-hydroxy-2,6-dimethylpyrimidine-5-carbonitrile (2.7 g, 18.1 mmol), lithium aluminium hydride (2.1 g, 54.3 mmol), and tetrahydrofuran (80 mL) was stirred at 25° C. for 4 hours. Water (5 mL) was added to the mixture. The mixture was concentrated to give a residue. The residue was purified by column chromatography (silica gel, dichloromethane/methanol=10:1) to give 5-(aminomethyl)-2,6-dimethylpyrimidin-4-ol as a white solid (525 mg, 19%). LRMS (M+H$^+$) m/z: calcd 153.09. found 153.

N-((4-hydroxy-2,6-dimethylpyrimidin-5-yl)methyl)-4-phenoxybenzamide (Compound I-5)9

A mixture of 4-phenoxybenzoic acid (92 mg, 0.43 mmol), 1-hydroxybenzotriazole (80 mg, 0.6 mmol), 1-ethyl-3-(3-dimethylaminopropyl)carbodiimide hydrochloride (113 mg, 0.6 mmol), triethylamine (0.16 mL) and dichloromethane (15 mL) was stirred at 25° C. for half an hour. Then 5-(aminomethyl)-2,6-dimethylpyrimidin-4-ol (60 mg, 0.4 mmol) was added. The mixture was stirred at 25° C. for 12 hours and then concentrated to give a residue. The residue was purified by column chromatography (silica gel, dichloromethane/methanol=10:1) to give N-((4-hydroxy-2,6-dimethylpyrimidin-5-yl)methyl)-4-phenoxybenzamide as a white solid (30 mg, 21%). LRMS (M+H$^+$) m/z: calcd 349.14. found 349. HPLC purity (214 nm): 98%. $^1$H NMR (300 MHz, d$^6$-DMSO): δ 12.36 (s, 1H), 8.35 (t, J=4.5 Hz, 1H), 7.86 (d, J=8.4 Hz, 2H), 7.42 (t, J=8.4 Hz, 2H), 7.24-6.97 (m, 5H), 4.25 (d, J=4.5 Hz, 2H), 2.29 (s, 3H), 2.20 (s, 3H).

Example 54

Synthesis of N-((2-hydroxy-4,6-dimethylpyridin-3-yl)methyl)-4-(1-(pyridin-2-yloxy)ethyl)benzamide (Compound I-60)

This synthesis involved 4 steps.

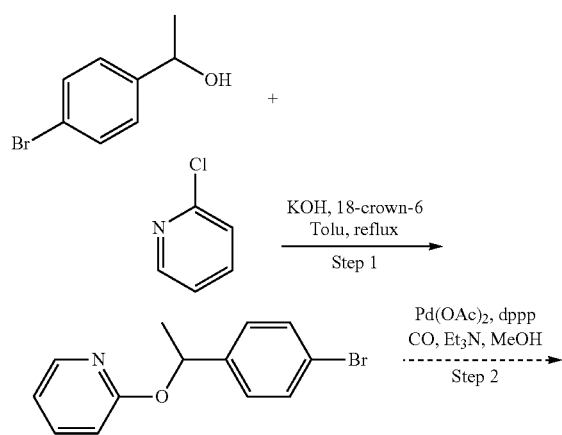

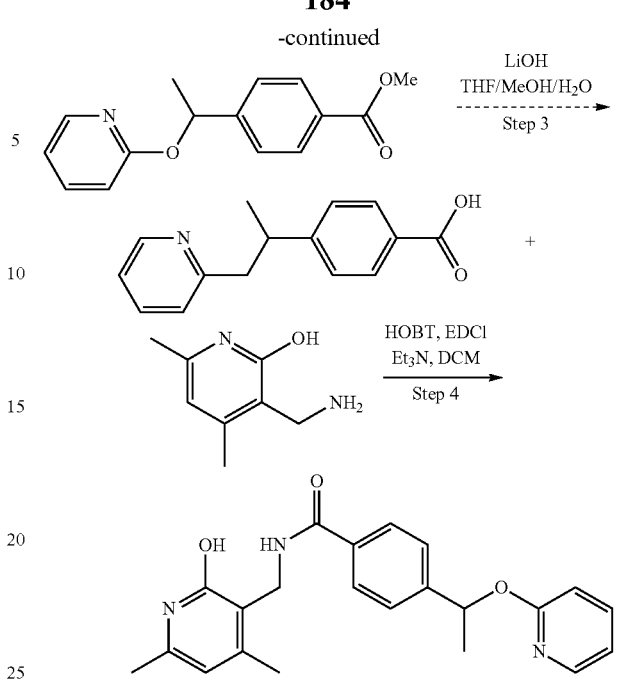

2-(1-(4-bromophenyl)ethoxy)pyridine

A solution of 1-(4-bromophenyl)ethanol (2.0 g, 10.0 mmol), 2-chloropyridine (1237 mg, 11.0 mmol), potassium hydroxide (1839 mg, 32.8 mmol) and 18-crown-6 (132 mg, 0.5 mmol) in toluene (40 mL) was stirred at reflux for 3 hrs. The mixture was concentrated to give a residue. The residue was purified by column chromatography (silica gel, petroleum ethe/ethyl acetate=20:1) to give 2-(1-(4-bromophenyl)ethoxy)pyridine as a white solid (2.6 g, 94%). LRMS (M+H$^+$) m/z: calcd 277.01. found 277.

Methyl 4-(1-(pyridin-2-yloxy)ethyl)benzoate

A mixture of 2-(1-(4-bromophenyl)ethoxy)pyridine (1.0 g, 3.6 mmol), palladium acetate (162 mg, 0.7 mmol), 1,3-bis(diphenylphosphino)propane (445 mg, 1.1 mmol), triethylamine (2.5 mL) in methanol (30 mL) was stirred at 100° C. under carbon monoxide (20 atms) for 12 hours. The mixture was concentrated to give a residue. The residue was purified by column chromatography (silica gel, petroleum ether/ethyl acetate=15:1) to give methyl 4-(1-(pyridin-2-yloxy)ethyl)benzoate (590 mg, 64%). $^1$H NMR (300 MHz, CDCl$_3$): 8.07-7.98 (m, 3H), δ 7.56-7.48 (m, 3H), 6.84-6.77 (m, 2H), δ 6.24 (q, J=6.6, 1H), 3.89 (s, 3H), 1.57 (d, J=6.6, 3H).

4-(1-(pyridin-2-yloxy)ethyl)benzoic acid

A mixture of methyl 4-(1-(pyridin-2-yloxy)ethyl)benzoate (590 mg, 2.3 mmol), lithium hydroxide monohydrate (482 mg, 11.5 mmol), water (4 mL) and methanol (4 mL) in tetrahydrofuran (12 mL) was stirred at 20° C. for 5 hours. The reaction mixture was concentrated. The residue was acidified to pH=2 with concentrated hydrochloride solution. The mixture was extracted with ethyl acetate (20 mL×2). The organic phase was dried over sodium sulfate and filtered. The filtrate was concentrated. The residue was purified by column chromatography (silica gel, petroleum ether/ethyl acetate=2:1) to give 4-(1-(pyridin-2-yloxy)ethyl)benzoic acid as a white solid (520 mg, 93%). LRMS (M+H$^+$) m/z: calcd 243.09. found 243.

N-((2-hydroxy-4,6-dimethylpyridin-3-yl)methyl)-4-(1-(pyridin-2-yloxy)ethyl)benzamide (Compound I-60)

To a solution of 4-(1-(pyridin-2-yloxy)ethyl)benzoic acid (160 mg, 0.66 mmol), 1-hydroxybenzotriazole (135 mg, 1.0 mmol), 1-(3-Dimethylaminopropyl)-3-ethylcarbodiimide hydrochloride (192 mg, 1.0 mmol), triethylamine (0.3 mL) in dichloromethane (15 mL) was added 3-(aminomethyl)-4,6-dimethylpyridin-2-ol (100 mg, 0.66 mmol). The reaction mixture was stirred at 20° C. for 13 hours. The mixture was washed with water (20 mL×2). The organic phase was dried over sodium sulfate and filtered. The filtrate was concentrated. The residue was purified by column chromatography (silica gel, dichloromethane/methanol=10:1) to give N-((2-hydroxy-4,6-dimethylpyridin-3-yl)methyl)-4-(1-(pyridin-2-yloxy)ethyl)benzamide as a white solid (50 mg, 40%). LRMS (M+H$^+$) m/z: 377.17. found 377. HPLC Purity (214 nm): 98%. $^1$H NMR (300 MHz, d$^6$-DMSO): δ 11.46 (s, 1H), 8.30 (d, J=4.8 Hz, 1H), 8.06-8.04 (m, 1H), 7.80-7.68 (m, 3H), 7.44-7.42 (m, 2H), 6.93-6.84 (m, 2H), 6.17 (q, J=6.6 Hz, 1H), 5.84 (s, 1H), 4.27 (d, J=4.8 Hz, 2H), 2.15 (s, 3H), 2.11 (s, 3H), 1.55 (d, J=6.6 Hz, 3H).

Example 55

Synthesis of N-((2-hydroxy-4,6-dimethylpyridin-3-yl)methyl)-6-(1-phenoxyethyl)nicotinamide (Compound I-61)

This synthesis involved 5 steps.

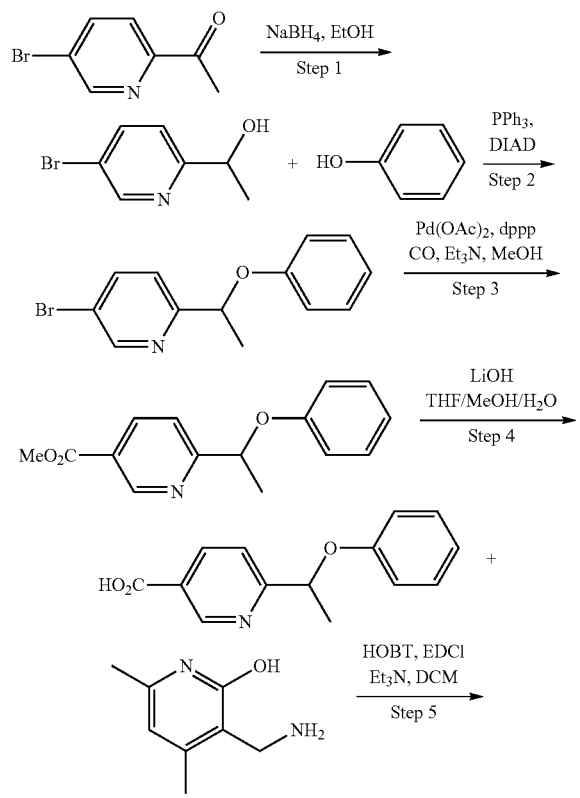

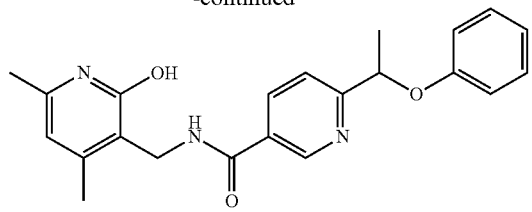

1(5-bromopyridin-2-yl)ethanol

To a solution of 1-(5-bromopyridin-2-yl)ethanone (1.1 g, 5.5 mmol) in ethanol (100 mL) was added sodium borohydride (2.5 g, 66.1 mmol). The reaction mixture was stirred at room temperature for 24 hours. The mixture was filtered, the filtrate was acidified and the solvent removed on a rotary evaporator. The residue was taken up with water (50 mL) and extracted with dichloromethane (50 mL). The combined extract was dried over sodium sulfate, filtered, concentrated and purified by column chromatography to give 1-(5-bromopyridin-2-yl)ethanol (1.0 g, 90.0%) as a yellow oil. LRMS (M+H$^+$) m/z: calcd 201.98. found 202. $^1$H NMR (300 MHz, CD$_3$OD) δ 8.54 (d, J=2.4 Hz, 1H), 7.98 (dd, J$_1$=8.4 Hz, J$_2$=2.4 Hz, 1H), 7.50 (d, J=8.4 Hz, 1H), 4.85 (m, 1H), 1.45 (d, J=6.6 Hz, 3H).

5-bromo-2-(1-phenoxyethyl)pyridine

A solution of 1-(5-bromopyridin-2-yl)ethanol (1.0 g, 4.95 mmol), phenol (835 mg, 8.87 mmol), and triphenylphosphine (1.8 g, 6.86 mmol) was stirred in dry tetrahydrofuran (70 mL) at 0° C. under nitrogen atmosphere. To this mixture was added dropwise diisopropyl diazene-1,2-dicarboxylate (1.4 g, 6.92 mmol) over 5 minutes, and the reaction was monitored by thin layer chromatography. After complete disappearance of starting material, the solvent was removed under reduced pressure and the resultant oil was purified by flash column chromatography (hexane/ethyl acetate, 1/1) to give 5-bromo-2-(1-phenoxyethyl)pyridine (1.3 g, 94.4%) as a white solid. LRMS (M+H$^+$) m/z: calcd 278.01. found 278 $^1$H NMR (300 MHz, DMSO) δ 8.60 (d, J=2.1 Hz, 1H), 7.93 (dd, J$_1$=8.4 Hz, J$_2$=2.1 Hz, 1H), 7.41 (d, J=8.4 Hz, 1H), 7.18 (m, 2H), 6.86 (m, 3H), 5.39 (m, 1H), 1.63 (d, J=6.3 Hz, 3H).

Methyl 6-(1-phenoxyethyl)nicotinate

To a solution of 5-bromo-2-(1-phenoxyethyl)pyridine (1.0 g, 3.60 mmol) in methanol (50 ml) were added triethylamine (2.4 g, 23.72 mmol), 1,3-bis(diphenylphosphino)propane (400 mg, 0.97 mmol) and palladium acetate (200 mg, 0.89 mmol). The resultant reaction mixture was stirred overnight at 100° C. under carbon monoxide atmosphere. After being cooled to room temperature, the reaction mixture was concentrated. The residue was purified by pre-HPLC to get methyl 6-(1-phenoxyethyl)nicotinate (400 mg, 43.2%) as a white solid. LRMS (M+H$^+$) m/z: calcd 258.11. found 258. $^1$H NMR (300 MHz, DMSO) δ 9.08 (d, J=2.1 Hz, 1H), 8.32 (dd, J$_1$=8.1 Hz, J$_2$=2.1 Hz, 1H), 7.61 (d, J=8.1 Hz, 1H), 7.18 (m, 2H), 6.86 (m, 3H), 5.49 (m, 1H), 3.93 (s, 3H), 1.66 (d, J=6.6 Hz, 3H).

6-(1-phenoxyethyl)nicotinic acid

To a solution of methyl 6-(1-phenoxyethyl)nicotinate (400 mg, 1.55 mmol) in tetrahydrofuran (12 mL), methanol (4 mL)

and water (4 mL) was added lithium hydroxide (377 mg, 15.7 mmol). The resultant reaction mixture was stirred at room temperature for 2 hours. The solution was concentrated under reduced pressure and was treated with aqueous 1N hydrochloric acid (5 mL). Then the mixture was concentrated and the residue was purified by prep-thin layer chromatography to give 6-(1-phenoxyethyl)nicotinic acid (350 mg, 92.5%) as a white solid. LRMS (M+H$^+$) m/z: calcd 244.09. found 244 $^1$H NMR (300 MHz, DMSO) δ 9.08 (d, J=2.1 Hz, 1H), 8.32 (dd, J=8.1 Hz, J$_2$=2.1 Hz, 1H), 7.60 (d, J=8.1 Hz, 1H), 7.19 (m, 2H), 6.87 (m, 3H), 5.49 (s, 1H), 1.66 (d, J=6.6 Hz, 3H).

N-((2-hydroxy-4,6-dimethylpyridin-3-yl)methyl)-6-(1-phenoxyethyl)nicotinamide (Compound I-61)

To a solution of 6-(1-phenoxyethyl)nicotinic acid (100 mg, 0.41 mmol) in dichloromethane (20 mL) were added N-ethyl-N'-(3-dimethylaminopropyl)carbodiimide hydrochloride (115 mg, 0.60 mmol), N-hydroxybenzotriazole (81 mg, 0.60 mmol) and triethylamine (122 mg, 1.20 mmol). The resultant reaction mixture was stirred for 30 minutes at room temperature. Then 3-(aminomethyl)-4,6-dimethylpyridin-2-ol (76 mg, 0.50 mmol) was added and the mixture was stirred at ambient temperature overnight. The mixture was washed with brine (20 mL), dried over sodium sulfate, filtered, and concentrated. The residue was purified through pre-HPLC and the obtained solution was freeze-dried to afford N-((2-hydroxy-4,6-dimethylpyridin-3-yl)methyl)-6-(1-phenoxyethyl)nicotinamide (50 mg, 32.2%) as a white solid. LRMS (M+H$^+$) m/z: calcd 378.17. found 378. $^1$H NMR (300 MHz, DMSO) δ 8.91 (d, J=2.1 Hz, 1H), 8.14 (dd, J1=8.1 Hz, J2=2.1 Hz, 1H), 7.55 (d, J=8.1 Hz, 1H), 7.17 (m, 2H), 6.85 (m, 3H), 6.10 (s, 1H), 5.45 (m, 1H), 4.48 (s, 2H), 2.35 (s, 3H), 2.24 (s, 3H), 1.64 (d, J=6.6 Hz, 3H).

3-fluoro-N-((2-hydroxy-4,6-dimethylpyridin-3-yl)methyl)-4-(1-phenoxyethyl)benzamide (Compound I-63)

This synthesis involved 6 steps

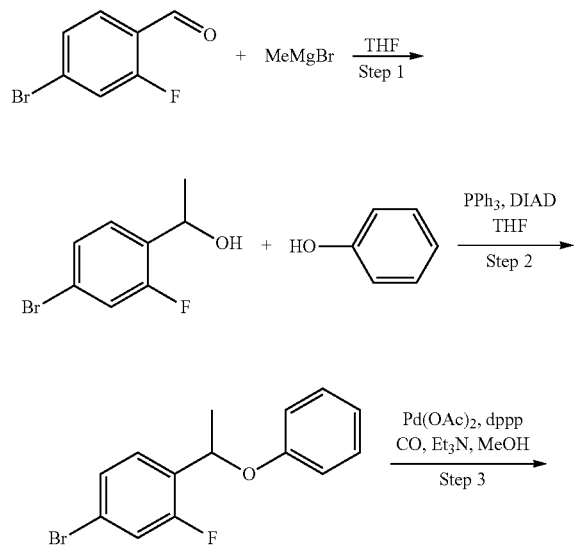

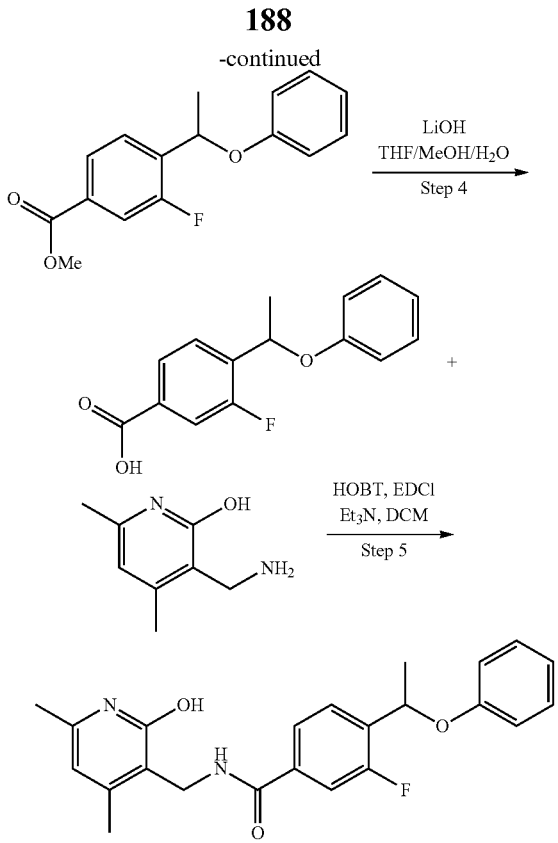

1-(4-bromo-2-fluorophenyl)ethanol

To a solution of 4-bromo-2-fluorobenzaldehyde (2.01 g, 9.9 mmol) in tetrahydrofuran (20 mL) was dropped methylmagnesium bromide (10 mmol, 1N in tetrahydrofuran) and the mixture was stirred at room temperature for 30 minutes. TLC showed all starting material was consumed, then mixture was quenched with aqueous ammonium chloride (1N, 5 mL). To the mixture, water (50 mL) was added and extracted with dichloromethane (2*50 mL). The combined organic phase was separated, dried over sodium sulfate, filtered and concentrated. The residue was purified by column chromatography (silica gel, petroleum ether/ethyl acetate=20:1) to give the product 1-(4-bromo-2-fluorophenyl)ethanol as colorless oil (2.0 g, 92%). $^1$H NMR (300 MHz, CDCl$_3$): δ 7.40-7.19 (m, 3H), 5.16 (q, J=6.3 Hz, 1H), 1.76 (s, 1H), 1.49 (d, J=6.3 Hz, 3H).

4-bromo-2-fluoro-1-(1-phenoxyethyl)benzene

To a solution of 1-(4-bromo-2-fluorophenyl)ethanol (0.5 g, 2.3 mmol) in tetrahydrofuran (20 mL) was added triphenylphosphine (0.78 g, 3 mmol) and phenol (284 mg, 3 mmol). The mixture was stirred at room temperature for 30 minutes then diisopropyl azodicarboxylate (0.6 g, 3 mmol) was added and the mixture was stirred at room temperature for 12 hours. The mixture was concentrated in vacuo. To the residue, water (50 mL) was added, extracted with dichloromethane (2*50 mL). The combined organic phase was separated, dried over sodium sulfate, filtered and concentrated to give a residue. The residue was purified by column chromatography (silica gel, petroleum ether/ethyl acetate=100:1) to give 4-bromo-2-fluoro-1-(1-phenoxyethyl)benzene (600 mg, 88%) as colorless oil. $^1$H NMR (300

MHz, CDCl$_3$): δ 7.34-7.18 (m, 5H), 6.93-6.81 (m, 3H), 5.57 (q, J=6.3 Hz, 1H), 1.63 (d, J=6.3 Hz, 3H).

Methyl 3-fluoro-4-(1-phenoxyethyl)benzoate

To a reversible vial was added 4-bromo-2-fluoro-1-(1-phenoxyethyl)benzene (600 mg, 2 mmol) in methanol (16 mL) was added triethylamine (909 mg, 9 mmol), palladium diacetate (116 mg, 0.5 mmol) and 1,3-bis(diphenylphosphino) propane (480 mg, 1.16 mmol). Then the reaction mixture was charged with carbon monoxide. The mixture was reacted under carbon oxide atmosphere (15 atm) at 110° C. for 12 hours. The suspension was concentrated in vacuo. To the residue, water was added (50 mL), extracted with dichloromethane (2*50 mL). The combined organic phase was separated, dried over sodium sulfate, filtered and concentrated to give a residue. The residue was purified by column chromatography (silica gel, petroleum ether/ethyl acetate=40:1) to give methyl 3-fluoro-4-(1-phenoxyethyl) benzoate as colorless oil (0.40 g, 72%). $^1$H NMR (300 MHz, CDCl$_3$): δ 7.77-7.68 (m, 2H), 7.50 (t, J=7.8 Hz, 1H), 7.23-7.16 (m, 2H), 6.91-6.80 (m, 3H), 5.64 (q, J=6.3 Hz, 1H), 3.90 (s, 3H), 1.64 (d, J=6.3 Hz, 3H).

3-fluoro-4-(1-phenoxyethyl)benzoic acid

To a solution of methyl 3-fluoro-4-(1-phenoxyethyl)benzoate (400 mg, 1.5 mmol) in mixed solution of tetrahydrofuran/methanol/water=3:1:1 (4 mL) was added lithium hydroxide (200 mg, 8.4 mmol). The mixture was stirred at room temperature for 2 hours. The suspension was concentrated in vacuo and quenched with hydrochloride acid aqueous (1N, 5 mL). To the residue, water (50 mL) was added and extracted with dichloromethane (2*50 mL). The combined organic phase was separated, dried over sodium sulfate, filtered and concentrated to give a residue. The residue was purified by column chromatography (silica gel, petroleum ether/ethyl acetate=5:1) to give 3-fluoro-4-(1-phenoxyethyl)benzoic acid as pale solid (300 mg, 82%).

3-fluoro-N-((2-hydroxy-4,6-dimethylpyridin-3-yl) methyl)-4-(1-phenoxyethyl)benzamide (Compound I-63)

A solution of 3-fluoro-4-(1-phenoxyethyl)benzoic acid (300 mg, 1.2 mmol) in dichloromethane (15.0 mL) was added N-hydroxybenzotriazole (270 mg, 2 mmol), 1-(3-dimethylaminopropyl)-3-ethylcarbodiimide hydrochloride (384 mg, 2 mmol), triethylamine (202 mg, 2 mmol). The mixture was stirred for 30 minutes. Then 3-(aminomethyl)-4,6-dimethylpyridin-2-ol (270 mg, 1.8 mmol) was added and the mixture was stirred at room temperature for 12 hours. To the mixture, water (50 mL) was added. The mixture was extracted with dichloromethane (2*50 mL). The combined organic phase was separated, dried over sodium sulfate, filtered and concentrated to give a residue. The residue was purified by preparative-TLC (silica gel, methanol/dichloromethane=1:20, 1% NH$_3$) to give 3-fluoro-N-((2-hydroxy-4,6-dimethylpyridin-3-yl)methyl)-4-(1-phenoxyethyl)benzamide as white solid (217 mg, 46%). LRMS (M+H$^+$) m/z: calcd 394.17. found 394. HPLC purity (214 nm): 96%. $^1$H NMR (300 MHz, CD$_3$OD): δ 7.57-7.49 (m, 3H), 7.16 (t, J=8.4 Hz, 2H), 6.85-6.82 (m, 3H), 6.09 (s, 1H), 5.68 (q, J=6.6 Hz, 1H), 4.45 (s, 2H), 2.34 (s, 3H), 2.23 (s, 3H), 1.62 (d, J=8.4 Hz, 3H).

Example 56

Synthesis of N-((2-hydroxy-4,6-dimethylpyridin-3-yl)methyl)-6-(1-phenoxyethyl)nicotinamide (Compound I-64)

This synthesis involved 5 steps.

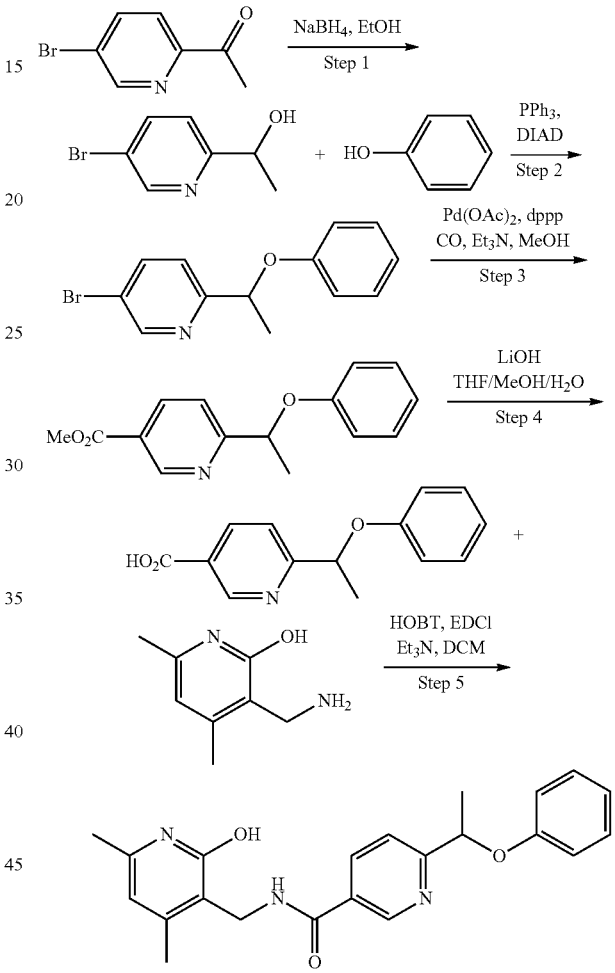

1-(5-bromopyridin-2-yl)ethanol

To a solution of 1-(5-bromopyridin-2-yl)ethanone (1.1 g, 5.5 mmol) in ethanol (100 mL) was added sodium borohydride (2.5 g, 66.1 mmol). The reaction mixture was stirred at room temperature for 24 hours. The mixture was filtered, the filtrate was acidified and the solvent removed on a rotary evaporator. The residue was taken up with water (50 mL) and extracted with dichloromethane (50 mL). The combined extract was dried over sodium sulfate, filtered, concentrated and purified by column chromatography to give 1-(5-bromopyridin-2-yl)ethanol (1.0 g, 90.0%) as a yellow oil. LRMS (M+H$^+$) m/z: calcd 201.98. found 202. $^1$H NMR (300 MHz, CD$_3$OD) δ 8.54 (d, J=2.4 Hz, 1H), 7.98 (dd, J=8.4 Hz, J$_2$=2.4 Hz, 1H), 7.50 (d, J=8.4 Hz, 1H), 4.85 (m, 1H), 1.45 (d, J=6.6 Hz, 3H).

5-bromo-2-(1-phenoxyethyl)pyridine

A solution of 1-(5-bromopyridin-2-yl)ethanol (1.0 g, 4.95 mmol), phenol (835 mg, 8.87 mmol), and triphenylphosphine (1.8 g, 6.86 mmol) was stirred in dry tetrahydrofuran (70 mL) at 0° C. under nitrogen atmosphere. To this mixture was added dropwise diisopropyl diazene-1,2-dicarboxylate (1.4 g, 6.92 mmol) over 5 minutes, and the reaction was monitored by thin layer chromatography. After complete disappearance of starting material, the solvent was removed under reduced pressure and the resultant oil was purified by flash column chromatography (hexane/ethyl acetate, 1/1) to give 5-bromo-2-(1-phenoxyethyl)pyridine (1.3 g, 94.4%) as a white solid. LRMS (M+H$^+$) m/z: calcd 278.01. found 278 $^1$H NMR (300 MHz, DMSO) δ 8.60 (d, J=2.1 Hz, 1H), 7.93 (dd, J$_1$=8.4 Hz, J$_2$=2.1 Hz, 1H), 7.41 (d, J=8.4 Hz, 1H), 7.18 (m, 2H), 6.86 (m, 3H), 5.39 (m, 1H), 1.63 (d, J=6.3 Hz, 3H).

Methyl 6-(1-phenoxyethyl)nicotinate

To a solution of 5-bromo-2-(1-phenoxyethyl)pyridine (1.0 g, 3.60 mmol) in methanol (50 ml) were added triethylamine (2.4 g, 23.72 mmol), 1,3-bis(diphenylphosphino)propane (400 mg, 0.97 mmol) and palladium acetate (200 mg, 0.89 mmol). The resultant reaction mixture was stirred overnight at 100° C. under carbon monoxide atmosphere. After being cooled to room temperature, the reaction mixture was concentrated. The residue was purified by pre-HPLC to get methyl 6-(1-phenoxyethyl)nicotinate (400 mg, 43.2%) as a white solid. LRMS (M+H$^+$) m/z: calcd 258.11. found 258. $^1$H NMR (300 MHz, DMSO) δ 9.08 (d, J=2.1 Hz, 1H), 8.32 (dd, J$_1$=8.1 Hz, J$_2$=2.1 Hz, 1H), 7.61 (d, J=8.1 Hz, 1H), 7.18 (m, 2H), 6.86 (m, 3H), 5.49 (m, 1H), 3.93 (s, 3H), 1.66 (d, J=6.6 Hz, 3H).

6-(1-phenoxyethyl)nicotinic acid

To a solution of methyl 6-(1-phenoxyethyl)nicotinate (400 mg, 1.55 mmol) in tetrahydrofuran (12 mL), methanol (4 mL) and water (4 mL) was added lithium hydroxide (377 mg, 15.7 mmol). The resultant reaction mixture was stirred at room temperature for 2 hours. The solution was concentrated under reduced pressure and was treated with aqueous 1N hydrochloric acid (5 mL). Then the mixture was concentrated and the residue was purified by prep-thin layer chromatography to give 6-(1-phenoxyethyl)nicotinic acid (350 mg, 92.5%) as a white solid. LRMS (M+H$^+$) m/z: calcd 244.09. found 244 $^1$H NMR (300 MHz, DMSO) δ 9.08 (d, J=2.1 Hz, 1H), 8.32 (dd, J=8.1 Hz, J$_2$=2.1 Hz, 1H), 7.60 (d, J=8.1 Hz, 1H), 7.19 (m, 2H), 6.87 (m, 3H), 5.49 (s, 1H), 1.66 (d, J=6.6 Hz, 3H).

N-((2-hydroxy-4,6-dimethylpyridin-3-yl)methyl)-6-(1-phenoxyethyl)nicotinamide (Compound I-64)

To a solution of 6-(1-phenoxyethyl)nicotinic acid (100 mg, 0.41 mmol) in dichloromethane (20 mL) were added N-ethyl-N'-(3-dimethylaminopropyl)carbodiimide hydrochloride (115 mg, 0.60 mmol), N-hydroxybenzotriazole (81 mg, 0.60 mmol) and triethylamine (122 mg, 1.20 mmol). The resultant reaction mixture was stirred for 30 minutes at room temperature. Then 3-(aminomethyl)-4,6-dimethylpyridin-2-ol (76 mg, 0.50 mmol) was added and the mixture was stirred at ambient temperature overnight. The mixture was washed with brine (20 mL), dried over sodium sulfate, filtered, concentrated. The residue was purified through pre-HPLC and the obtained solution was freeze-dried to afford N-((2-hydroxy-4,6-dimethylpyridin-3-yl)methyl)-6-(1-phenoxyethyl)nicotinamide (50 mg, 32.2%) as a white solid.

LRMS (M+H$^+$) m/z: calcd 378.17. found 378. $^1$H NMR (300 MHz, DMSO) δ 8.91 (d, J=2.1 Hz, 1H), 8.14 (dd, J1=8.1 Hz, J2=2.1 Hz, 1H), 7.55 (d, J=8.1 Hz, 1H), 7.17 (m, 2H), 6.85 (m, 3H), 6.10 (s, 1H), 5.45 (m, 1H), 4.48 (s, 2H), 2.35 (s, 3H), 2.24 (s, 3H), 1.64 (d, J=6.6 Hz, 3H).

Example 57

Synthesis of N-((2-hydroxy-6-methyl-4-(trifluoromethyl)pyridin-3-yl)methyl)-4-phenoxybenzamide (Compound I-65)

This synthesis involved 6 steps.

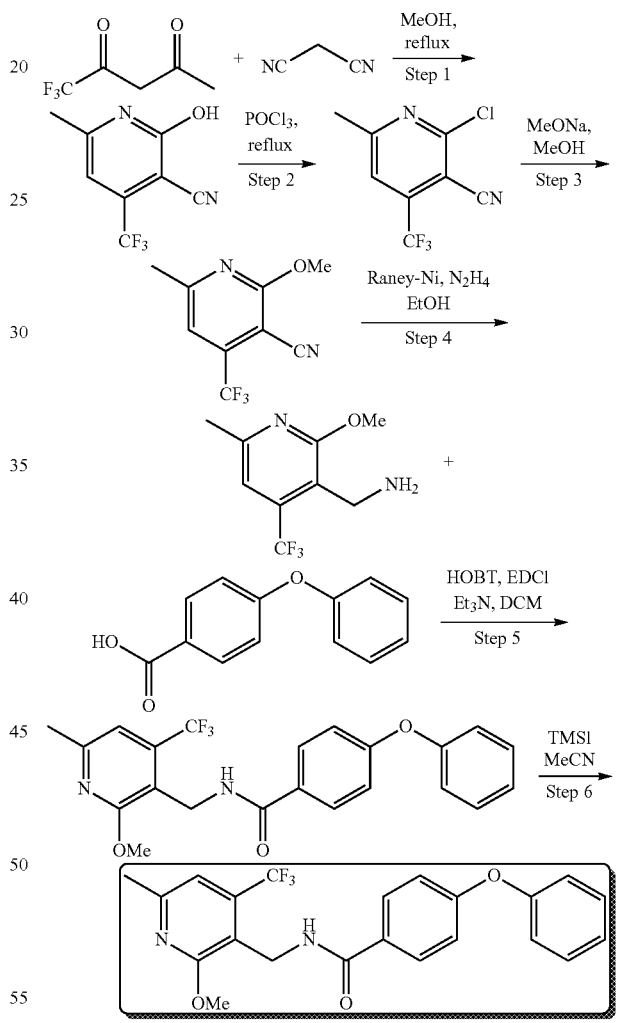

2-hydroxy-6-methyl-4-(trifluoromethyl)nicotinonitrile

To a solution of 1,1,1-trifluoropentane-2,4-dione (5.8 g, 37.7 mmol) in methanol (20 mL) was added malononitrile (5 g, 75 mmol) and then the mixture was heated to reflux. The mixture was maintained at the same temperature for 12 hours. The resultant mixture was cooled to room temperature, and then filtered. The solid was washed with methanol to give pure 2-hydroxy-6-methyl-4-(trifluoromethyl)nicotinonitrile (3 g, 40%). $^1$H NMR (300 MHz, d$^6$-DMSO): δ 13.36 (s, 1H), 6.65 (s, 1H), 2.38 (s, 3H).

2-chloro-6-methyl-4-(trifluoromethyl)nicotinonitrile

To 2-hydroxy-6-methyl-4-(trifluoromethyl)nicotinonitrile (1 g, 5 mmol) was added phosphoryl trichloride (15 mL). Then the mixture was heated to reflux and maintained at the same temperature with stirring for 2 hours. The resultant mixture was concentrated to give a residue and the residue was purified by chromatography (petroleum ether/ethyl acetate=1:1) to give 2-chloro-6-methyl-4-(trifluoromethyl)nicotinonitrile (1 g, 90%). $^1$H NMR (300 MHz, CD$_3$OD): δ 7.81 (s, 1H), 2.70 (s, 3H).

2-methoxy-6-methyl-4-(trifluoromethyl)nicotinonitrile

To a solution of 2-chloro-6-methyl-4-(trifluoromethyl)nicotinonitrile (1 g, 4.5 mmol) in anhydrous methanol (20 mL) was added sodium methoxide (540 mg, 10 mmol). After stirring at room temperature for 2 hours, the resultant mixture was concentrated to give a residue. And the residue was purified by column chromatography (silica gel, petroleum ether/ethyl acetate=1:1) to give 2-methoxy-6-methyl-4-(trifluoromethyl)nicotinonitrile (0.9 g, 92%). LRMS (M+H) m/z: calcd 216.05. found 216.

(2-methoxy-6-methyl-4-(trifluoromethyl)pyridin-3-yl)methanamine

To a solution of 2-methoxy-6-methyl-4-(trifluoromethyl)nicotinonitrile (0.6 g, 2.7 mmol) in ethanol (50 mL) was added the suspension of raney-Ni in water (1 mL) and hydrazine (5 mL). After stirring at 60° C. for 3 hours, the mixture was filtered and concentrated to give a residue. The residue was purified by chromatography (dichloromethane/methanol=10:1) to give (2-methoxy-6-methyl-4-(trifluoromethyl)pyridin-3-yl)methanamine (0.47 g, 77%) and used directly in next step without further purification. LRMS (M+H) m/z: calcd 220.08. found 220.

N-((2-methoxy-6-methyl-4-(trifluoromethyl)pyridin-3-yl)methyl)-4-phenoxybenzamide To a solution of 4-phenoxybenzoic acid (640 mg, 3 mmol) in anhydrous dichloromethane (30 mL) were added 1H-benzo[d][1,2,3]triazol-1-ol (600 mg, 4.5 mmol), 1-ethyl-3-(3-dimethylaminopropyl)carbodiimide hydrochloride (864 mg, 4.5 mmol) and triethylamine (1.1 g, 10 mmol). After stirring at room temperature for 0.5 hour, (2-methoxy-6-methyl-4-(trifluoromethyl)pyridin-3-yl)methanamine (0.47 g, 2.1 mmol) was added. After stirring at room temperature for 4 hours, to the mixture was added water (20 mL). The resultant mixture was extracted with dichloromethane (20 mL×2). Organic layers were combined and concentrated to give a residue. The residue was purified by chromatography (petroleum ether/ethyl acetate=1:1) to give N-((2-methoxy-6-methyl-4-(trifluoromethyl)pyridin-3-yl)methyl)-4-phenoxybenzamide (600 mg, 67.5%). LRMS (M+H) m/z: calcd 416.13. found 416. $^1$H NMR (300 MHz, CD$_3$OD): δ 7.78 (d, J=8.7 Hz, 2H), 7.40 (t, J=7.8 Hz, 2H), 7.18 (t, J=7.2 Hz, 1H), 7.12 (s, 1H), 7.05 (d, J=8.1 Hz, 2H), 6.97 (d, J=8.7 Hz, 2H), 4.63 (s, 2H), 4.01 (s, 3H), 2.53 (s, 3H).

N-((2-hydroxy-6-methyl-4-(trifluoromethyl)pyridin-3-yl)methyl)-4-phenoxybenzamide (Compound I-65)

To a solution of N-((2-methoxy-6-methyl-4-(trifluoromethyl)pyridin-3-yl)methyl)-4-phenoxybenzamide (0.12 g, 0.3 mmol) in anhydrous acetonitrile (20 mL) was added iodotrimethylsilane (200 mg, 1 mmol). Then the mixture was stirred at room temperature for 2 hours. Then the reaction mixture was concentrated to give a residue and the residue was purified by column chromatography (silica gel, dichloromethane/methanol=15:1) to give the pure product N-((2-hydroxy-6-methyl-4-(trifluoromethyl)pyridin-3-yl)methyl)-4-phenoxybenzamide (90 mg, 75%). LRMS (M+H) m/z: calcd 402.12. found 402. HPLC purity (214 nm): 98%. $^1$H NMR (300 MHz, CD$_3$OD): δ 7.79-7.77 (m, 2H), 7.42-7.37 (m, 2H), 7.18 (t, J=6.3 Hz, 1H), 7.04 (d, J=7.5 Hz, 2H), 6.97 (d, J=7.8 Hz, 2H), 6.40 (s, 1H), 4.57 (s, 2H), 2.36 (s, 3H).

Example 58

Synthesis of 2-chloro-N-((2-hydroxy-4,6-dimethylpyridin-3-yl)methyl)-4-(1-phenoxyethyl)benzamide (Compound I-66)

This synthesis involved 7 steps.

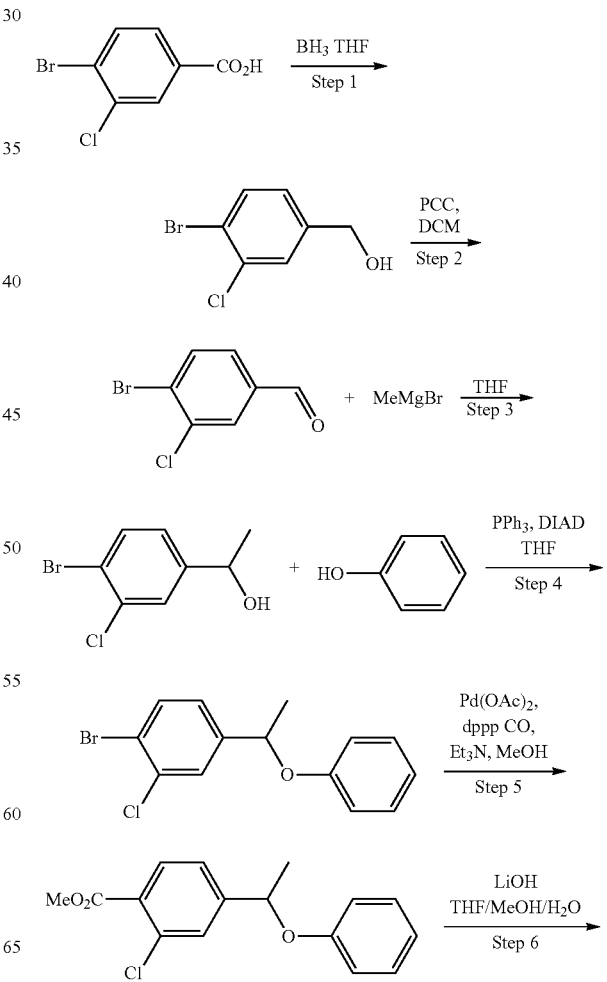

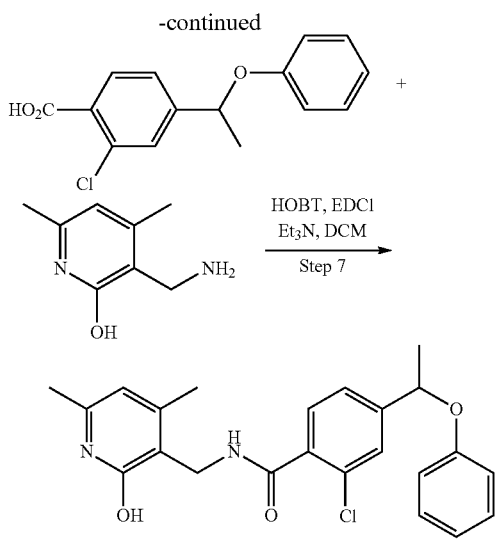

(4-bromo-3-chlorophenyl)methanol

A solution of BH3 (34 mL, IM in tetrahydrofuran) was added dropwise to the solution of 4-bromo-3-chlorobenzoic acid (2.5 g, 11.4 mmol) in tetrahydrofuran at 0° C. The mixture was stirred at 40° C. overnight. Acetic acid (5 mL) was added dropwise to the reaction mixture. The mixture was concentrated to give a residue. The residue was purified by column chromatography (silica gel, petroleum ethe/ethyl acetate=1:1) to give (4-bromo-3-chlorophenyl)methanol as a white solid (4.47 g, 91%). $^1$H NMR (300 MHz, d$^6$-DMSO): 7.69 (d, J=8.1, 1H), δ 7.53 (d, J=0.9, 1H), 7.19 (dd, J$_1$=8.1, 1H J$_2$=0.9, 1H), 5.38 (s, 1H), δ 4.48 (s, 2H).

4-bromo-3-chlorobenzaldehyde

A mixture of (4-bromo-3-chlorophenyl)methanol (2.0 g, 9.0 mmol), pyridinium chlorochromate (2912 mg, 13.5 mmol) in dichloromethane (50 mL0 was stirred at 25° C. for 3 hours. The mixture was concentrated to give a residue. The residue was purified by column chromatography (silica gel, petroleum ethe/ethyl acetate=1:1) to give 4-bromo-3-chlorobenzaldehyde as a white solid (1.6 g g, 81%). $^1$H NMR (300 MHz, d$^6$-DMSO): δ 9.96 (s, 1H), 7.69 (d, J=8.1, 1H), δ 7.53 (d, J=0.9, 1H), 7.19 (dd, J=8.1, 1H J$_2$=0.9, 1H)

1-(4-bromo-3-chlorophenyl)ethanol

A solution of methylmagnesium bromide (4.8 mL, 3M, 14.4 mmol) was added dropwise to the solution of 4-bromo-3-chlorobenzaldehyde (1.52 g, 7.0 mmol) in tetrahydrofuran at −40° C. Then the mixture was stirred at 25° C. for 3 hrs. Saturated ammonium chloride solution (10 mL) was added to the mixture. The mixture was concentrated to give a residue. The residue was purified by column chromatography (silica gel, petroleum ethe/ethyl acetate=1:1) to give 1-(4-bromo-3-chlorophenyl)ethanol as a white solid (1.32 g, 81%). $^1$H NMR (300 MHz, d$^6$-DMSO): 7.69 (d, J=8.1, 1H), δ 7.53 (d, J=0.9, 1H), 7.19 (dd, J$_1$=8.1, 1H J$_2$=0.9, 1H), 5.38 (d, J=3.6, 1H), δ 4.70 (m, 1H), 1.30 (d, J=6.6, 3H).

1-bromo-2-chloro-4-(1-phenoxyethyl)benzene

A solution of 1-(4-bromo-3-chlorophenyl)ethanol (1.32 g, 5.6 mmol), phenol (525 mg, 5.6 mmol) and triphenylphosphine (2198 mg, 8.4 mmol) in tetrahydrofuran (30 mL) was stirred at room temperature for 0.5 hour. Diisopropyl azodicarboxylate (1695 mg, 8.4 mmol) was dropwise to the reaction mixture and was stirred at room temperature for 12 hours. The mixture was concentrated to give a residue. The residue was purified by column chromatography (silica gel, petroleum ethe/ethyl acetate=5:1) to give 1-bromo-2-chloro-4-(1-phenoxyethyl)benzene as a colorless oil (882 mg 54%). $^1$H NMR (300 MHz, CDCl$_3$): 7.37 (d, J=8.1, 1H), 7.27-7.20 (m, 4H), 6.92-6.82 (m, 3H), 5.30 (q, J=6.6, 1H), 1.62 (d, J=6.6, 3H).

Methyl 2-chloro-4-(1-phenoxyethyl)benzoate

A mixture of 1-bromo-2-chloro-4-(1-phenoxyethyl)benzene (882 mg, 3.0 mmol), palladium acetate (137 mg, 0.6 mmol), 1,3-bis(diphenylphosphino)propane (376 mg, 0.9 mmol), triethylamine (2.1 mL) in methanol (30 mL) was stirred at 100° C. under carbon monoxide (20 atms) for 12 hours. The mixture was concentrated to give a residue. The residue was purified by column chromatography (silica gel, petroleum ether/ethyl acetate=5:1) to give methyl 2-chloro-4-(1-phenoxyethyl)benzoate (750 mg, 90%). $^1$H NMR (300 MHz, CDCl$_3$): 7.37 (d, J=8.1, 1H), δ 7.27-7.20 (m, 4H), 6.92-6.82 (m, 3H), 5.30 (q, J=6.6, 1H), 3.92 (s, 3H), 1.62 (d, J=6.6, 3H).

2-chloro-4-(1-phenoxyethyl)benzoic acid

A mixture of methyl 2-chloro-4-(1-phenoxyethyl)benzoate (750 mg, 2.7 mmol), lithium hydroxide monohydrate (571 mg, 13.6 mmol), water (5 mL) and methanol (5 mL) in tetrahydrofuran (15 mL) was stirred at 20° C. for 5 hours. The reaction mixture was concentrated. The residue was acidified to pH=2 with concentrated hydrochloride solution. The mixture was extracted with ethyl acetate (20 mL×2). The organic phase was dried over sodium sulfate and filtered. The filtrate was concentrated. The residue was purified by column chromatography (silica gel, petroleum ether/ethyl acetate=2:1) to give 2-chloro-4-(1-phenoxyethyl)benzoic acid as a white solid (500 mg, 71%). LRMS (M+H$^+$) m/z: 276.06. found 276.

2-chloro-N-((2-hydroxy-4,6-dimethylpyridin-3-yl)methyl)-4-(1-phenoxyethyl)benzamide (Compound I-66)

To a solution of 2-chloro-4-(1-phenoxyethyl)benzoic acid (262 mg, 1.0 mmol), 1-hydroxybenzotriozole (202 mg, 1.5 mmol), 1-(3-Dimethylaminopropyl)-3-ethylcarbodiimide hydrochloride (288 mg, 1.5 mmol) triethylamine (0.4 mL) in dichloromethane (15 mL) was added 3-(aminomethyl)-4,6-dimethylpyridin-2-ol (152 mg, 1.0 mmol). The reaction mixture was stirred at 20° C. for 13 hours. The mixture was washed with water (20 mL×2). The organic phase was dried over sodium sulfate and filtered. The filtrate was concentrated. The residue was purified by column chromatography (silica gel, dichloromethane/methanol=10:1) to give 2-chloro-N-((2-hydroxy-4,6-dimethylpyridin-3-yl)methyl)-4-(1-phenoxyethyl)benzamide as a white solid (360 mg, 88%).

LRMS (M+H$^+$) m/z: 410.14. found 410. $^1$H NMR (300 MHz, d$^6$-DMSO): 11.46 (s, 1H), δ 8.33 (d, J=4.5, 1H), 7.47 (s, 1H), 7.34 (m, 2H), δ7.20 (m, 2H), 6.88 (m, 3H), 5.84 (s, 1H), δ 5.54 (q, J=6, 1H), 4.25 (d, J=4.5, 2H), 2.17 (s, 3H), δ2.13 (s, 3H), 1.62 (d, J=6, 3H).

Example 59

Synthesis of (R or S)—N-((2-hydroxy-4,6-dimethylpyridin-3-yl)methyl)-3-methyl-4-(1-phenoxyethyl)benzamide (Compound I-67) and (S or R)—N-((2-hydroxy-4,6-dimethylpyridin-3-yl)methyl)-3-methyl-4-(1-phenoxyethyl)benzamide (Compound I-68)

This synthesis involved 6 steps.

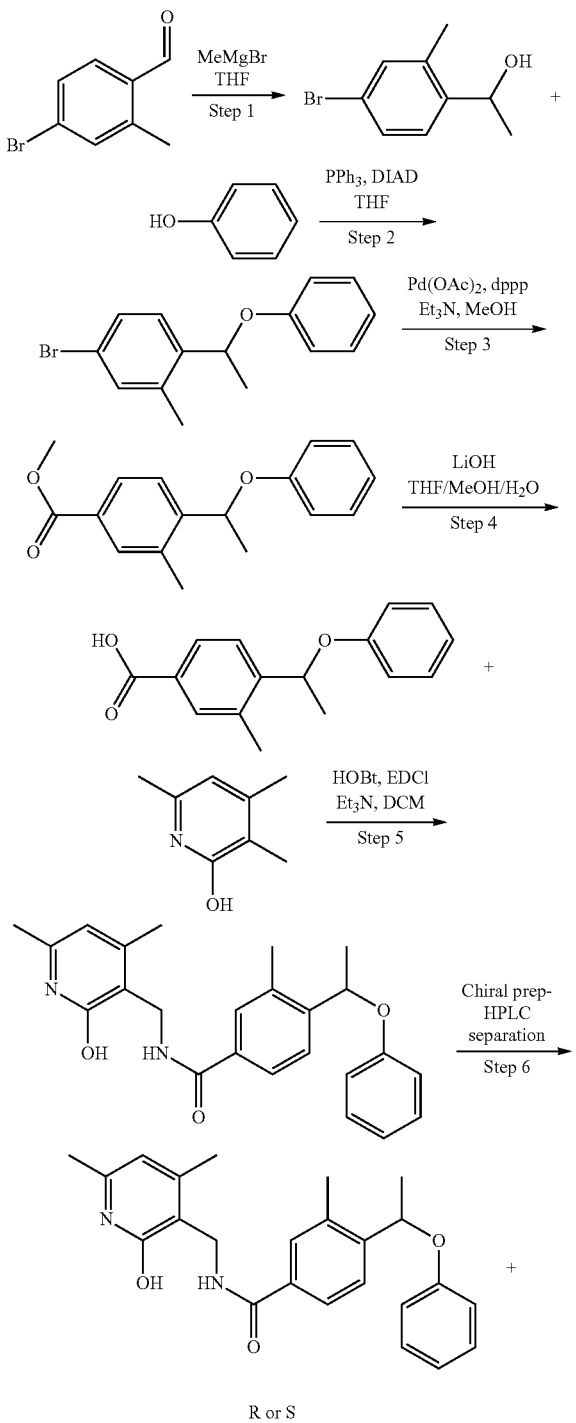

R or S

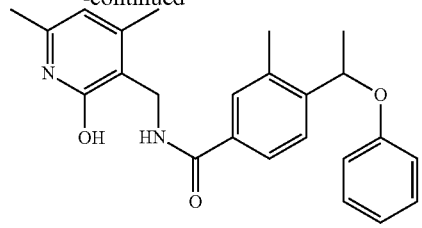

S or R

1-(4-bromo-2-methylphenyl)ethanol

To a solution of 4-bromo-2-methylbenzaldehyde (1 g, 5 mmol) in tetrahydrofuran (30 mL) was added methylmagnesium bromide (3N in tetrahydrofuran, 2 mL) at −40° C. Then the mixture was stirred at 25° C. for 3 hours. Water (15 mL) was added to the mixture and then extracted with ethyl acetate (35 mL×3). The combined organic phase was dried by sodium sulfate, and then filtered. The filtrate was concentrated in vacuo and purified by column chromatography (silica gel, petroleum ether/ethyl acetate=5:1) to give 1-(4-bromo-2-methylphenyl)ethanol (600 mg, 56%).

4-bromo-2-methyl-1-(1-phenoxyethyl)benzene

To a solution of 1-(4-bromo-2-methylphenyl)ethanol (430 mg, 2 mmol), phenol (184 mg, 2 mmol), triphenylphosphine (655 mg, 2.5 mmol) in tetrahydrofuran (30 mL) was added diisopropyl azodicarboxylate (505 mg, 2.5 mmol) at 0° C. The mixture was stirred at 20° C. for 12 hours. Water (15 mL) was added to the mixture and then extracted with ethyl acetate (35 mL×3). The combined organic phase was dried by sodium sulfate, and then filtered. The filtrate was concentrated in vacuo and the residue was purified by column chromatography (silica gel, petroleum ether/ethyl acetate=5:1) to give 4-bromo-2-methyl-1-(1-phenoxyethyl)benzene (210 mg, 36%).

Methyl 3-methyl-4-(1-phenoxyethyl)benzoate

A mixture of 4-bromo-2-methyl-1-(1-phenoxyethyl)benzene (210 mg, 0.7 mmol), palladium acetate (67 mg, 0.3 mmol), 1,3-bis(diphenylphosphino) propane (188 mg, 0.45 mmol), triethylamine (3 mL) and methanol (100 mL) were stirred at 100° C. under carbon monoxide (20 atm) atmosphere. The mixture was concentrated in vacuo and the residue was purified by column chromatography (silica gel, petroleum ether/ethyl acetate=5:1) to give methyl 3-methyl-4-(1-phenoxyethyl)benzoate (120 mg, 63%).

3-methyl-4-(1-phenoxyethyl)benzoic acid

A mixture of methyl 3-methyl-4-(1-phenoxyethyl)benzoate (0.12 g, 0.44 mmol), lithium hydroxide monohydrate (285 mg, 6.8 mmol), tetrahydrofuran (15 mL), methanol (5 mL) and water (5 mL) was stirred at 20° C. for 4 hours. The mixture was neutralized to pH=1 with concentrated hydrochloric acid and then extracted with ethyl acetate (15 mL×3). The combined organic phase was dried by sodium sulfate, and then filtered. The filtrate was concentrated in vacuo to give 3-methyl-4-(1-phenoxyethyl)benzoic acid (95 mg, 84%).

N-((2-hydroxy-4,6-dimethylpyridin-3-yl)methyl)-3-methyl-4-(1-phenoxyethyl)benzamide A mixture of 3-methyl-4-(1-phenoxyethyl)benzoic acid (95 mg, 0.4 mmol), 1-ethyl-3-(3-dimethylaminopropyl)carbodiimide hydrochloride (191 mg, 1 mmol), N-hydroxybenzotriazole (135 mg, 1 mmol), triethylamine (0.2 mL) and dichloromethane (5 mL) were stirred at 25° C. for half an hour. And then 3-(aminomethyl)-4,6-dimethylpyridin-2-ol (76 mg, 0.5 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give N-((2-hydroxy-4,6-dimethylpyridin-3-yl)methyl)-3-methyl-4-(1-phenoxyethyl)benzamide as a white solid (100 mg, 51%). LRMS (M+H$^+$) m/z: calcd. 390.19. found 390. $^1$H NMR (300 MHz, d$^6$-DMSO): δ 11.47 (s, 1H), 8.23 (t, J=4.8 Hz, 1H), 7.65-7.58 (m, 2H), 7.35 (d, J=8.1 Hz, 1H), 7.18 (t, J=8.1 Hz, 2H), 6.86-6.73 (m, 3H), 5.84 (s, 1H), 5.60 (q, J=6.3 Hz, 1H), 4.27 (d, J=4.8 Hz, 2H), 2.41 (s, 3H), 2.14 (s, 3H), 2.10 (s, 3H), 1.51 (d, J=6.3 Hz, 3H).

(S)— or (R)—N-((2-hydroxy-4,6-dimethylpyridin-3-yl)methyl)-3-methyl-4-(1-phenoxyethyl)benzamide (Compound I-67) and (R)— or (S)—N-((2-hydroxy-4,6-dimethylpyridin-3-yl)methyl)-3-methyl-4-(1-phenoxyethyl)benzamide (Compound I-68)

N-((2-hydroxy-4,6-dimethylpyridin-3-yl)methyl)-3-methyl-4-(1-phenoxyethyl)benzamide (150 mg, 0.36 mmol) was separated by chiral prep-HPLC (Daicel AD-H (250 mm×20 mm×5 um), hexane: ethanol (0.2% diethylamine)= 50:50, flow rate: 13 mL/min), then (R or S)—N-((2-hydroxy-4,6-dimethylpyridin-3-yl)methyl)-3-methyl-4-(1-phenoxyethyl)benzamide (50 mg, 66%) and (S or R)—N-((2-hydroxy-4,6-dimethylpyridin-3-yl)methyl)-3-methyl-4-(1-phenoxyethyl)benzamide and (55 mg, 73%) was obtained. The retention times were 7.253 minute and 11.496 minute respectively in chiral HPLC chromatography. LRMS (M+H$^+$) m/z: calcd. 390.19. found 390.

HPLC purity (214 nm): 100%. $^1$H NMR (300 MHz, d$^6$-DMSO): δ 11.47 (s, 1H), 8.23 (t, J=4.8 Hz, 1H), 7.65-7.58 (m, 2H), 7.35 (d, J=8.1 Hz, 1H), 7.18 (t, J=8.1 Hz, 2H), 6.86-6.73 (m, 3H), 5.84 (s, 1H), 5.60 (q, J=6.3 Hz, 1H), 4.27 (d, J=4.8 Hz, 2H), 2.41 (s, 3H), 2.14 (s, 3H), 2.10 (s, 3H), 1.51 (d, J=6.3 Hz, 3H). Although the separated enantiomers were not optically characterized, for convenience sake, the (R)-enantiomer was designated Compound I-67 and the (S)-enantiomer was designated Compound I-68.

Example 60

Synthesis of compound (S)-4-(1-(3-(6-aminopyridin-3-yl)phenoxy)ethyl)-N-((2-hydroxy-4,6-dimethylpyridin-3-yl)methyl)benzamide (Compound I-69)

This synthesis involved 6 steps.

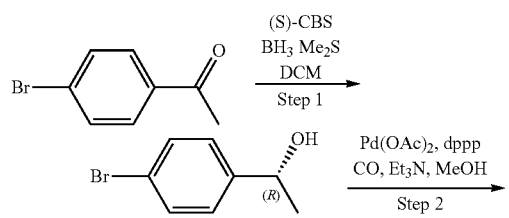

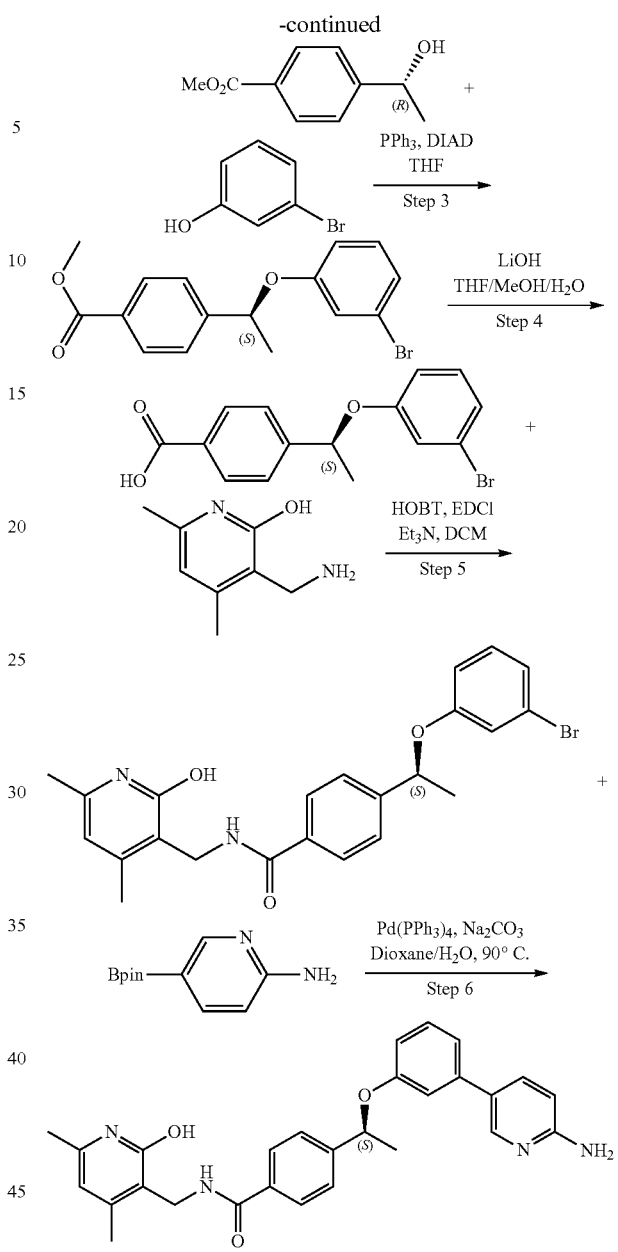

(R)-1-(4-bromophenyl)ethanol

To a solution of 1-(4-bromophenyl)ethanone (5.0 g, 25 mmol) and (S)-1-methyl-3,3-diphenyl-hexahydropyrrolo[1,2-c][1,3,2]oxazaborole (1.25 mL, 1 M) in 80 mL of anhydrous dichloromethane was added Borane-methyl sulfide complex (2.1 g, 27 mmol) over 1 hour at −200C. After addition completed, the mixture was stirred at −20° C. for 2 hours, then stirred at room temperature for 12 hours. After the reaction, 20 mL of methanol was added, and stirred for 0.5 hour. Then the mixture was diluted with 100 mL of water and the organic phase was collected, dried over anhydrous sodium sulfate, concentrated and purified by column chromatography (silica gel, Petroleum ether/ethyl acetate=20:1) to give (R)-1-(4-bromophenyl)ethanol (4.6 g, 92%) as the white solid.

(R)-methyl 4-(1-hydroxyethyl)benzoate

To a solution of (R)-1-(4-bromophenyl)ethanol (3.0 g, 15 mmol) in 20 mL of methanol was added Palladium acetate (2.0 g, 6 mmol), 1,3-bis(diphenylphosphino) propane (1.2 g, 3 mmol) and triethylamine (3 g, 30 mol). The reaction mixture was stirred at 90° C. under atmosphere of carbon monoxide for 12 hours. After the reaction, the mixture was diluted with 100 mL of water, and the product was extracted with dichloromethane, dried over anhydrous sodium sulfate, concentrated and purified by column chromatography (silica gel, Petroleum ether/ethyl acetate=20:1) to give (R)-methyl 4-(1-hydroxyethyl)benzoate as the white solid (2.4 g, 89%)

(S)-methyl 4-(1-(3-bromophenoxy)ethyl)benzoate

To a solution of (R)-methyl 4-(1-hydroxyethyl)benzoate (1.8 g, 10 mmol), 3-bromophenol (1.9 g, 11 mmol) in 30 mL of anhydrous tetrahydrofuran was added Triphenyl phosphine (2.9 g, 11 mmol). The reaction mixture was stirred at room temperature for 0.5 hour under nitrogen atmosphere. Then diisopropylazodicarboxylate (2.4 g, 12 mmol) was added dropwise at 0° C., and the reaction mixture was stirred at room temperature for 12 hours. After the reaction, it was quenched with water, and the product was extracted with ethyl acetate, dried over anhydrous sodium sulfate, concentrated and purified by column chromatography (silica gel, Petroleum ether/ethyl acetate=20:1) to give (S)-methyl 4-(1-(3-bromophenoxy)ethyl)benzoate (2.2 g, 66%)

(S)-4-(1-(3-bromophenoxy)ethyl)benzoic acid

Lithium hydroxide (2 g, 83.3 mmol) was added to a solution of (S)-methyl 4-(1-(3-bromophenoxy)ethyl)benzoate (1.8 g, 5.4 mmol) in methanol (100 mL) and water (10 mL). The reaction mixture was stirred at room temperature for 3 hours. After the reaction, the solvent was removed in vacuo. 3 mol/L hydrogen chloride (aq) was added to make pH 2-3, and the product was extracted with dichloromethane. The combined organic phase was washed with Sodium Chloride (aq) (20 mL×3), dried over anhydrous sodium sulfate, and the solvent was evaporated to dryness to give (S)-4-(1-(3-bromophenoxy)ethyl)benzoic acid (1.7 g, 98%).

(S)-4-(1-(3-(6-aminopyridin-3-yl)phenoxy)ethyl)-N-((2-hydroxy-4,6-dimethylpyridin-3-yl)methyl)benzamide To a solution of (S)-4-(1-(3-bromophenoxy)ethyl)benzoic acid (0.5 g, 1.56 mmol), 1-ethyl-3-(3-dimethylaminopropyl)carbodiimide hydrochloride (0.36 g, 1.87 mmol) and N-hydroxybenzotriazole (0.25 g, 1.87 mmol) in 20 mL of dichloromethane was added 0.4 g of triethylamine. The reaction mixture was stirred for 15 minutes at room temperature, then 3-(aminomethyl)-4,6-dimethylpyridin-2-ol (0.26 g, 1.71 mmol) was added. The reaction mixture was stirred at room temperature for 12 hours. After the reaction, the mixture was washed with Sodium Bicarbonate (aq), concentrated and purified by column chromatography (silica gel, dichloromethane/meth anol=20:1) to give (S)-4-(1-(3-(6-aminopyridin-3-yl)phenoxy)ethyl)-N-((2-hydroxy-4,6-dimethylpyridin-3-yl)methyl)benzamide as the white solid (0.61 g, 86%)

(S)-4-(1-(3-(6-aminopyridin-3-yl)phenoxy)ethyl)-N-((2-hydroxy-4,6-dimethylpyridin-3-yl)methyl)benzamide (Compound I-69)

To a solution of (S)-4-(1-(3-(6-aminopyridin-3-yl)phenoxy)ethyl)-N-((2-hydroxy-4,6-dimethylpyridin-3-yl)methyl)benzamide (0.23 g, 0.5 mmol), 5-(4,4,5,5-tetramethyl-1,3,2-dioxaborolan-2-yl)pyridine-2-amine (0.13 g, 0.6 mmol), (beta-4)-platinum (0.06 g, 0.05 mmol) in 10 mL of 1,4-dioxane and 1.0 mL of water was added 0.11 g of sodium carbonate. The reaction mixture was stirred at 90° C. for 12 hours. After the reaction, the reaction mixture was poured to the water and the product was extracted by dichloromethane, concentrated and purified by column chromatography (silica gel, dichloromethane/meth anol=10:1) to give pure product as the white solid (0.16 g, 60%). LRMS ([M+H]$^+$): calcd for 469. found 469. $^1$H NMR (300 MHz, d$_6$-DMSO) δ: 11.46 (s, 1H), 8.03 (t, 1H, J=2.4 Hz), 8.13 (d, J=2.4 Hz, 1H), 7.79 (d, J=8.4 Hz, 2H), 7.60 (dd, J=2.4, 8.7 Hz, 1H), 7.47 (d, J=7.8 Hz, 2H), 7.19 (t, J=7.8 Hz, 1H), 7.06-7.02 (m, 2H), 6.76 (dd, J=2.1, 8.4 Hz, 1H), 6.47 (d, J=8.4 Hz, 1H), 6.06 (s, 2H), 5.84 (s, 1H), 5.64 (q, J=6.3 Hz, 1H), 4.27 (d, J=4.8 Hz, 1H), 2.15 (s, 3H), 2.10 (s, 3H), 1.56 (d, J=6.3 Hz, 3H).

(R)— or (S)—N-((2-hydroxy-4,6-dimethylpyridin-3-yl)methyl)-4-(1-phenylethyl)benzamide (Compound I-70) and (S)— or (R)—N-((2-hydroxy-4,6-dimethylpyridin-3-yl)methyl)-4-(1-phenylethyl)benzamide (Compound I-71)

This synthesis involved 6 steps.

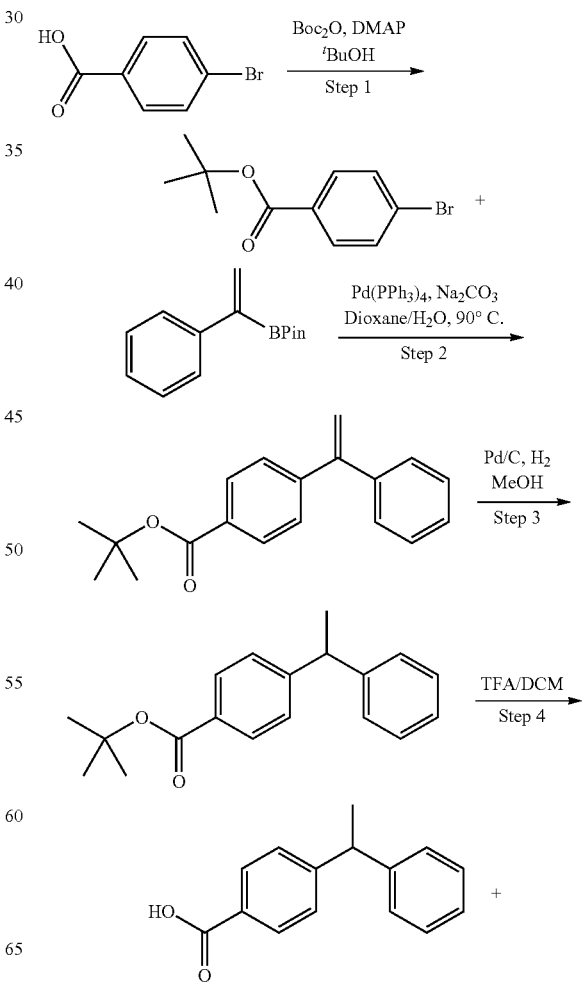

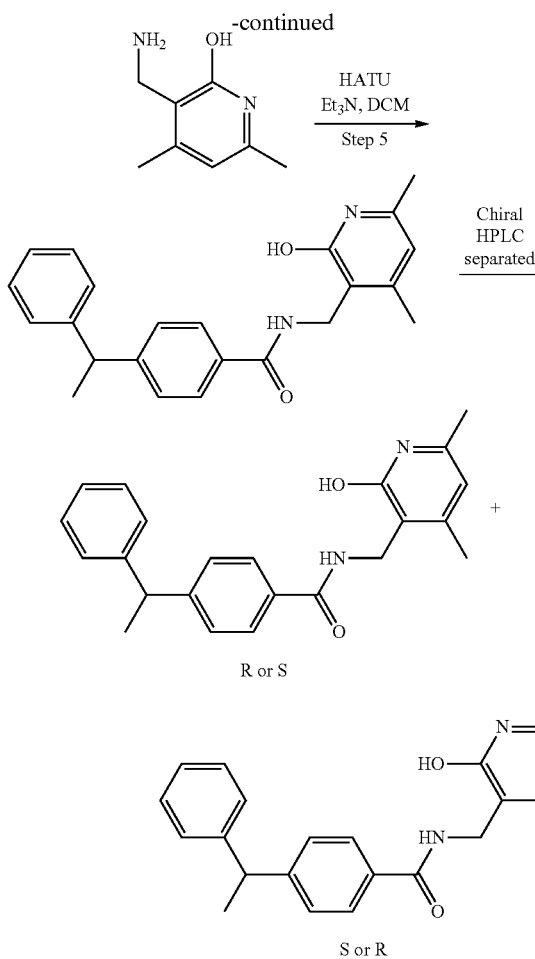

Tert-butyl 4-bromobenzoate

To a solution of 4-dimethylamiopryidine (1.5 g, 12.5 mmol) in tert-butanol (20 mL) were added 4-bromobenzoic acid (5 g, 25 mmol) and di-tert-butyl dicarbonate (10.95 g, 0.05 mol). The mixture was stirred at 20° C. for 12 hours. The resultant mixture was concentrated in vacuo to give a residue and the residue was purified by column chromatography (silica gel, petroleum ether/ethyl acetate=30:1) to give tert-butyl 4-bromobenzoate (4 g, 62%).

Tert-butyl 4-(1-phenylvinyl)benzoate

To a solution of tert-butyl 4-bromobenzoate (616 mg, 2.4 mmol) in 1,4-dioxane and water (4:1, 10 mL) were added (E)-4,4,5,5-tetramethyl-2-styryl-1,3,2-dioxaborolane (553 mg, 2.4 mmol), tetrakis(triphenylphosphine)palladium (58.9 mg, 0.05 mmol) and sodium carbonate (164 mg, 1.55 mmol). The mixture was stirred at 90° C. under nitrogen atmosphere for 18 hours. Once the start material was consumed, the resultant mixture was concentrated to give a residue and the residue was purified by column chromatography (silica gel, petroleum ether/ethyl acetate=30:1) to give tert-butyl 4-(1-phenylvinyl)benzoate (0.59 g, 87.5%). $^1$H NMR (300 MHz, CDCl$_3$): δ 7.96 (d, J=4.8 Hz, 2H), 7.41-7.26 (m, 7H), 5.55-5.53 (m, 2H), 1.61 (s, 9H).

tert-butyl 4-(1-phenylethyl)benzoate

A mixture of tert-butyl 4-(1-phenylvinyl)benzoate (0.59 g, 2.1 mmol) and palladium on carbon (10%, 100 mg) in methanol (20 mL) was stirred at 20° C. under hydrogen atmosphere (4 atm) for 24 hours. Once the start material has been consumed, the resultant mixture was filtered and concentrated in vacuo to give a residue. The residue was purified by column chromatography (silica gel, petroleum ether/ethyl acetate=20:1) to give tert-butyl 4-(1-phenylethyl)benzoate (500 mg, 84%). $^1$H NMR (300 MHz, CD$_3$OD): δ 7.85 (d, J=4.8 Hz, 2H), 7.30-7.15 (m, 7H), 4.19-4.16 (m, 1H), 1.61 (d, J=7.2 Hz, 3H), 1.50 (s, 9H).

4-(1-phenylethyl)benzoic acid

To a solution of tert-butyl 4-(1-phenylethyl)benzoate (500 mg, 1.77 mmol) in dichloromethane (8 mL), trifluoroacetic acid (2 mL) was added. The mixture was stirred for 0.5 hour. Once the start material was consumed, the resultant mixture was concentrated to give 4-(1-phenylethyl)benzoic acid (360 mg, 90%).

N-((2-hydroxy-4,6-dimethylpyridin-3-yl)methyl)-4-(1-phenylethyl)benzamide

A mixture of 4-(1-phenylethyl)benzoic acid (150 mg, 0.66 mol), 2-(7-aza-1H-benzotriazole-1-yl)-1,1,3,3-tetramethyluronium hexafluorophosphate (303 mg, 0.797 mmol), triethylamine (2 mL) in dichloromethane (25 mL) was stirred at 25° C. for 0.5 hour. And then 3-(aminomethyl)-4,6-dimethylpyridin-2-ol (101 mg, 0.66 mmol) was added. After stirring at 25° C. for 12 hours, water (15 mL) was added to the reaction mixture. And the mixture was extracted with dichloromethane (10 mL×3). The combined organic phase was separated, dried by sodium sulfate and then filtered. The filtrate was concentrated to give a residue in vacuo. The residue was purified by column chromatography (silica gel, dichloromethane/methanol=10:1) to give N-((2-hydroxy-4,6-dimethylpyridin-3-yl)methyl)-4-(1-phenylethyl)benzamide (100 mg, 42%). LRMS (M+H$^+$) m/z: calcd 360.02. found 360. HPLC purity (214 nm): 99%. $^1$H NMR (300 MHz, d$^6$-DMSO): δ 11.46 (s, 1H), 8.25 (t, J=4.5 Hz, 1H), 7.83 (d, J=7.2 Hz, 2H), 7.32-7.26 (m, 7H), 5.85 (s, 1H), 4.29 (d, J=4.8 Hz, 2H), 4.28-4.26 (m, 1H), 2.15 (s, 3H), 2.10 (s, 3H), 1.57 (d, J=7.2 Hz, 3H).

(R)— or (S)—N-((2-hydroxy-4,6-dimethylpyridin-3-yl)methyl)-4-(1-phenylethyl)benzamide (Compound I-70) and (S)— or (R)—N-((2-hydroxy-4,6-dimethylpyridin-3-yl)methyl)-4-(1-phenylethyl)benzamide (Compound I-71)

N-((2-hydroxy-4,6-dimethylpyridin-3-yl)methyl)-4-(1-phenylethyl)benzamide (100 mg, 0.27 mmol) was separated by chiral prep-HPLC (Daicel AD-H (250 mm×20 mm×5 um), hexane: ethanol (0.2% diethylamine)=50:50, flow rate: 13 mL/min), then (R or S)—N-((2-hydroxy-4,6-dimethylpyridin-3-yl)methyl)-4-(1-phenylethyl)benzamide (25 mg, 50%) and (S or R)—N-((2-hydroxy-4,6-dimethylpyridin-3-yl)methyl)-4-(1-phenylethyl)benzamide (25 mg, 50%) was obtained. The retention times were 8.030 minutes and 10.116 minutes respectively in chiral HPLC chromatography. Although the separated enantiomers were not optically characterized, for convenience sake, the (R)-enantiomer was designated as Compound I-70 and the (S)-enantiomer as Compound I-71.

Example 61

Synthesis of compound (S)— or (R)-4-(1-(3-fluorophenoxy)ethyl)-N-((2-hydroxy-4,6-dimethylpyridin-3-yl)methyl)benzamide (Compound I-72) and (R)— or (S)-4-(1-(3-fluorophenoxy)ethyl)-N-((2-hydroxy-4,6-dimethylpyridin-3-yl)methyl)benzamide (Compound I-73)

This synthesis involved 4 steps.

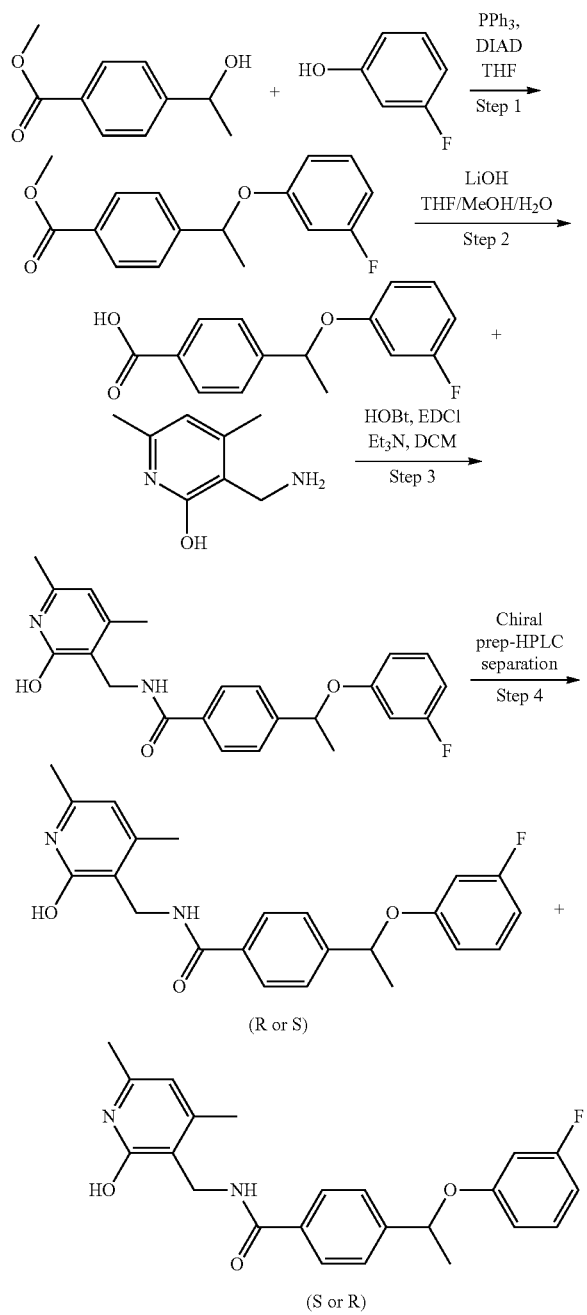

Methyl 4-(1-(3-fluorophenoxy)ethyl)benzoate

To a solution of methyl 4-(1-hydroxyethyl)benzoate (0.9 g, 5 mmol), 3-fluorophenol (627 mg, 5.6 mmol), triphenylphosphine (2.2 g, 8.4 mmol) in tetrahydrofuran (30 mL) was added diisopropyl azodicarboxylate (1.7 g, 8.4 mmol) at 0° C. The mixture was stirred at 20° C. for 12 hours. Water (15 mL) was added to the mixture and then extracted with ethyl acetate (35 mL×3). The combined organic phase was dried by sodium sulfate, and then filtered. The filtrate was concentrated in vacuo and the residue was purified by column chromatography (silica gel, petroleum ether/ethyl acetate=5:1) to give methyl 4-(1-(3-fluorophenoxy)ethyl)benzoate (400 mg, 29%).

4-(1-(3-fluorophenoxy)ethyl)benzoic acid

A mixture of methyl 4-(1-(2-fluorophenoxy)ethyl)benzoate (0.40 g, 1.4 mmol), lithium hydroxide monohydrate (571 mg, 13.6 mmol), tetrahydrofuran (15 mL), methanol (5 mL) and water (5 mL) was stirred at 20° C. for 4 hours. The mixture was turned to pH=1 with concentrated hydrochloric acid and then extracted with ethyl acetate (15 mL×3). The combined organic phase was dried by sodium sulfate, and then filtered. The filtrate was concentrated in vacuo to give 4-(1-(3-fluorophenoxy)ethyl)benzoic acid (0.34 g, 93%).

4-(1-(3-fluorophenoxy)ethyl)-N-((2-hydroxy-4,6-dimethylpyridin-3-yl)methyl)benzamide A mixture of 4-(1-(3-fluorophenoxy)ethyl)benzoic acid (260 mg, 1 mmol), 1-ethyl-3-(3-dimethylaminopropyl)carbodiimide hydrochloride (382 mg, 2 mmol), N-hydroxybenzotriazole (270 mg, 2 mmol), triethylamine (0.3 mL) and dichloromethane (15 mL) were stirred at 25° C. for half an hour. And then 3-(aminomethyl)-4,6-dimethylpyridin-2-ol (152 mg, 1 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give 4-(1-(3-fluorophenoxy)ethyl)-N-((2-hydroxy-4,6-dimethylpyridin-3-yl)methyl)benzamide (135 mg, 34%). LRMS (M+H$^+$) m/z: calcd. 394.17. found 394. HPLC purity (214 nm): 91%. $^1$H NMR (300 MHz, d$^6$-DMSO): δ 11.44 (s, 1H), 8.30 (t, J=4.8 Hz, 1H), 7.78 (d, J=8.4 Hz, 2H), 7.43 (d, J=8.1 Hz, 2H), 7.20 (q, J=8.1 Hz, 1H), 6.77-6.64 (m, 3H), 5.83 (s, 1H), 5.57 (q, J=6.3 Hz, 1H), 4.27 (d, J=4.8 Hz, 2H), 2.15 (s, 3H), 2.10 (s, 3H), 1.53 (d, J=6.0 Hz, 3H).

Synthesis of(S)— or (R)-4-(1-(3-fluorophenoxy)ethyl)-N-((2-hydroxy-4,6-dimethylpyridin-3-yl)methyl)benzamide (Compound I-72) and (R)— or (S)-4-(1-(3-fluorophenoxy)ethyl)-N-((2-hydroxy-4,6-dimethylpyridin-3-yl)methyl)benzamide (Compound-73)

4-(1-(3-fluorophenoxy)ethyl)-N-((2-hydroxy-4,6-dimethylpyridin-3-yl)methyl)benzamide (135 mg, 0.34 mmol) was separated by chiral prep-HPLC (Daicel AD-H (250 mm×20 mm×5 um), hexane: ethanol (0.2% diethylamine)=50:50, flow rate: 13 mL/min), then we obtained (R or S)-4-(1-(3-fluorophenoxy)ethyl)-N-((2-hydroxy-4,6-dimethylpyridin-3-yl)methyl)benzamide (25 mg, 37%) and (S or R)-4-(1-(3-fluorophenoxy)ethyl)-N-((2-hydroxy-4,6-dimethylpyridin-3-yl)methyl)benzamide (30 mg, 80%). The retention time were 8.515 minute and 11.982 minute respectively in chiral HPLC chromatography. LRMS (M+H$^+$) m/z: calcd. 394.17. found 394. HPLC purity (214 nm): 96%.

$^1$H NMR (300 MHz, d$^6$-DMSO): δ 11.44 (s, 1H), 8.30 (t, J=4.8 Hz, 1H), 7.78 (d, J=8.4 Hz, 2H), 7.43 (d, J=8.1 Hz, 2H), 7.20 (q, J=8.1 Hz, 1H), 6.77-6.64 (m, 3H), 5.83 (s, 1H), 5.57 (q, J=6.3 Hz, 1H), 4.27 (d, J=4.8 Hz, 2H), 2.15 (s, 3H), 2.10 (s, 3H), 1.53 (d, J=6.0 Hz, 3H). Although the separated enantiomers were not optically characterized, for convenience sake, the (S)-enantiomer was designated as Compound I-72 and the (R)-enantiomer as Compound I-73.

Example 62

Synthesis of compound (R or S)-4-(1-(4-fluorophenoxy)ethyl)-N-((2-hydroxy-4,6-dimethylpyridin-3-yl)methyl)benzamide (Compound I-74) and (S or R)-4-(1-(4-fluorophenoxy)ethyl)-N-((2-hydroxy-4,6-dimethylpyridin-3-yl)methyl)benzamide (Compound I-75)

This synthesis involved 4 steps.

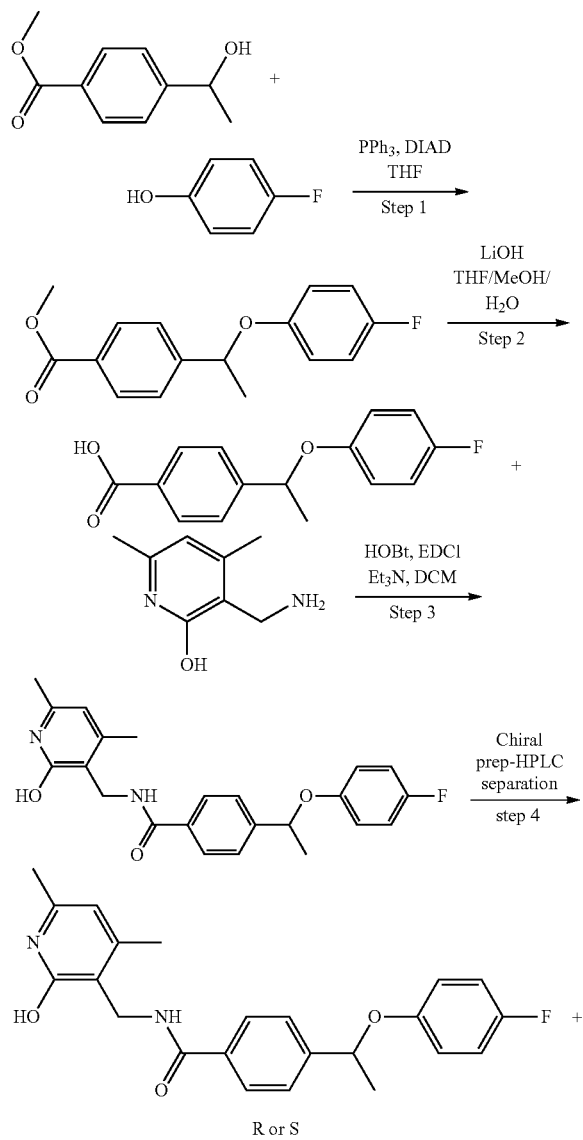

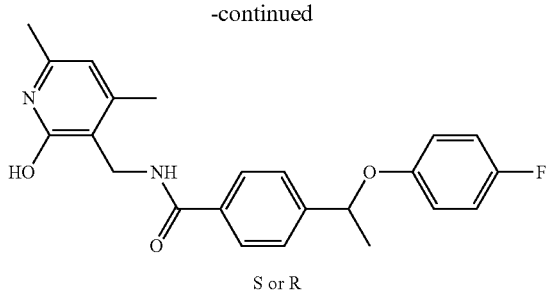

Methyl 4-(1-(4-fluorophenoxy)ethyl)benzoate

To a solution of methyl 4-(1-hydroxyethyl)benzoate (0.9 g, 5 mmol), 4-fluorophenol (627 mg, 5.6 mmol), triphenylphosphine (2.2 g, 8.4 mmol) in tetrahydrofuran (30 mL) was added diisopropyl azodicarboxylate (1.7 g, 8.4 mmol) at 0° C. The mixture was stirred at 20° C. for 12 hours. Water (15 mL) was added to the mixture and then extracted with ethyl acetate (35 mL×3). The combined organic phase was dried by sodium sulfate, and then filtered. The filtrate was concentrated in vacuo and the residue was purified by column chromatography (silica gel, petroleum ether/ethyl acetate=5:1) to give methyl 4-(1-(4-fluorophenoxy)ethyl)benzoate (490 mg, 35%).

4-(1-(4-fluorophenoxy)ethyl)benzoic acid

A mixture of methyl 4-(1-(4-fluorophenoxy)ethyl)benzoate (0.49 g, 1.8 mmol), lithium hydroxide monohydrate (571 mg, 13.6 mmol), tetrahydrofuran (15 mL), methanol (5 mL) and water (5 mL) was stirred at 20° C. for 4 hours. The mixture was neutralized to pH=1 with concentrated hydrochloric acid and then extracted with ethyl acetate (15 mL×3). The combined organic phase was dried by sodium sulfate, and then filtered. The filtrate was concentrated in vacuo to give 4-(1-(4-fluorophenoxy)ethyl)benzoic acid (0.39 g, 83%).

4-(1-(4-fluorophenoxy)ethyl)-N-((2-hydroxy-4,6-dimethylpyridin-3-yl)methyl)benzamide A mixture of 4-(1-(4-fluorophenoxy)ethyl)benzoic acid (260 mg, 1 mmol), 1-ethyl-3-(3-dimethylaminopropyl)carbodiimide hydrochloride (382 mg, 2 mmol), N-hydroxybenzotriazole (270 mg, 2 mmol), triethylamine (0.3 mL) and dichloromethane (15 mL) were stirred at 25° C. for half an hour. And then 3-(aminomethyl)-4,6-dimethylpyridin-2-ol (152 mg, 1 mmol) was added. The mixture was stirred at 25° C. for 12 hours. To the mixture, water (20 mL) was added and the mixture was extracted with dichloromethane (30 mL×3). The combined organic phase was dried by sodium sulfate and then filtered. The filtrate was concentrated in vacuo. The residue was purified by column chromatography (silica gel, dichloromethane/methanol=20:1) to give 4-(1-(4-fluorophenoxy)ethyl)-N-((2-hydroxy-4,6-dimethylpyridin-3-yl)methyl)benzamide (115 mg, 29%). LRMS (M+H$^+$) m/z: calcd 394.17. found 394. HPLC purity (214 nm): 94%. $^1$H NMR (300 MHz, d$^6$-DMSO): δ 11.44 (s, 1H), 8.30 (t, J=5.1 Hz, 1H), 7.77 (d, J=8.4 Hz, 2H), 7.41 (d, J=8.4 Hz, 2H), 7.04-6.85 (m, 4H), 5.83 (s, 1H), 5.47 (q, J=6.6 Hz, 1H), 4.26 (d, J=5.1 Hz, 2H), 2.16 (s, 3H), 2.10 (s, 3H), 1.52 (d, J=6.6 Hz, 3H).

(R)— or (S)-4-(1-(4-fluorophenoxy)ethyl)-N-((2-hydroxy-4,6-dimethylpyridin-3-yl)methyl)benzamide (Compound I-74) and (S)— or (R)-4-(1-(4-fluorophenoxy)ethyl)-N-((2-hydroxy-4,6-dimethylpyridin-3-yl)methyl)benzamide (Compound I-75)

4-(1-(4-Fluorophenoxy)ethyl)-N-((2-hydroxy-4,6-dimethylpyridin-3-yl)methyl)benzamide (115 mg, 0.29 mmol) was separated by chiral prep-HPLC (Daicel AD-H (250 mm×20 mm×5 um), hexane: ethanol (0.2% diethylamine)= 50:50, flow rate: 13 mL/min), then (R or S)-4-(1-(4-fluorophenoxy)ethyl)-N-((2-hydroxy-4,6-dimethylpyridin-3-yl) methyl)benzamide (30 mg, 52%) and (S or R)-4-(1-(4-fluorophenoxy)ethyl)-N-((2-hydroxy-4,6-dimethylpyridin-3-yl) methyl)benzamide (25 mg, 43%) was obtained. The retention time were 8.573 minute and 13.508 minute respectively in chiral HPLC chromatography. LRMS (M+H$^+$) m/z: calcd 394.17. found 394. HPLC purity (214 nm): 100%. $^1$H NMR (300 MHz, d$^6$-DMSO): δ 11.44 (s, 1H), 8.30 (t, J=5.1 Hz, 1H), 7.77 (d, J=8.4 Hz, 2H), 7.41 (d, J=8.4 Hz, 2H), 7.04-6.85 (m, 4H), 5.83 (s, 1H), 5.47 (q, J=6.6 Hz, 1H), 4.26 (d, J=5.1 Hz, 2H), 2.16 (s, 3H), 2.10 (s, 3H), 1.52 (d, J=6.6 Hz, 3H). Although the separated enantiomers were not optically characterized, for convenience sake, the (S)-enantiomer was designated as Compound I-72 and the (R)-enantiomer as Compound I-74.

Example 63

Synthesis of N-((2-hydroxy-4,6-dimethylpyridin-3-yl)methyl)-4-(1-(pyrimidin-2-yloxy)ethyl)benzamide (Compound I-76)

This synthesis involved 4 steps.

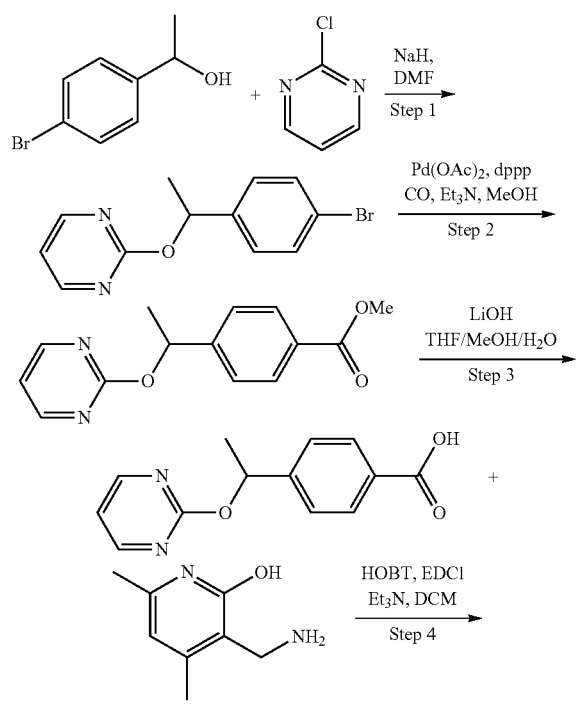

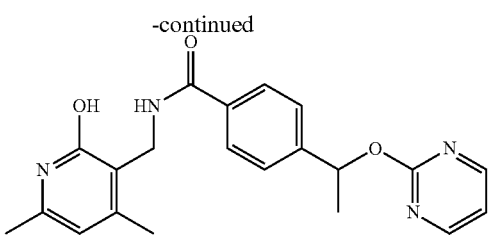

2-(1-(4-bromophenyl)ethoxy)pyrimidine

NaH (300 mg, 60%, 7.5 mmol) was suspended in N,N-dimethylformamide. 1-(4-bromophenyl)ethanol was added to the above mixture and stirred at 40° C. for 0.5 hour. Then 2-chloropyrimidine was added to the above mixture and stirred at 100° C. for 12 hours. The mixture was concentrated to give a residue. The residue was purified by column chromatography (silica gel, petroleum ethe/ethyl acetate=3:1) to give 2-(1-(4-bromophenyl)ethoxy)pyrimidine as a white solid (2.6 g, 94%). LRMS (M+H$^+$) m/z: calcd 278.01. found 278.

Methyl 4-(1-(pyrimidin-2-yloxy)ethyl)benzoate

A mixture of 2-(1-(4-bromophenyl)ethoxy)pyrimidine (1.226 g, 4.4 mmol), palladium acetate (198 mg, 0.88 mmol), 1,3-bis(diphenylphosphino)propane (545 mg, 1.3 mmol), triethylamine (3 mL) in methanol (30 mL) was stirred at 100° C. under carbon monoxide (20 atms) for 12 hours. The mixture was concentrated to give a residue. The residue was purified by column chromatography (silica gel, petroleum ether/ethyl acetate=4:1) to give methyl 4-(1-(pyrimidin-2-yloxy)ethyl) benzoate as a colorless oil (770 mg, 68%). $^1$H NMR (300 MHz, CDCl$_3$): δ 8.07-7.98 (m, 2H), 7.56-7.48 (m, 2H), 7.32-7.28 (m, 2H), 6.84-6.77 (m, 1H), 6.24 (q, J=6.6, 1H), 3.89 (s, 3H), 1.67 (d, J=6.6, 3H).

4-(1-(pyrimidin-2-yloxy)ethyl)benzoic acid

A mixture of methyl 4-(1-(pyrimidin-2-yloxy)ethyl)benzoate (400 mg, 1.6 mmol), lithium hydroxide monohydrate (326 mg, 7.8 mmol), water (4 mL) and methanol (4 mL) in tetrahydrofuran (12 mL) was stirred at 20° C. for 5 hours. The reaction mixture was concentrated. The residue was acidified to pH=2 with concentrated hydrochloride solution. The mixture was extracted with ethyl acetate (20 mL×2). The organic phase was dried over sodium sulfate and filtered. The filtrate was concentrated. The residue was purified by column chromatography (silica gel, petroleum ether/ethyl acetate=2:1) to give 4-(1-(pyrimidin-2-yloxy)ethyl)benzoic acid as a white solid (300 mg, 88%). LRMS (M+H$^+$) m/z: 244.08. found 244.

N-((2-hydroxy-4,6-dimethylpyridin-3-yl)methyl)-4-(1-(pyrimidin-2-yloxy)ethyl)benzamide (Compound I-76)

To a solution of 4-(1-(pyrimidin-2-yloxy)ethyl)benzoic acid (100 mg, 0.41 mmol), 1-hydroxybenzotriozole (83 mg, 0.61 mmol), 1-(3-Dimethylaminopropyl)-3-ethylcarbodiimide hydrochloride (118 mg, 0.61 mmol), triethylamine (0.2 mL) in dichloromethane (15 mL) was added 3-(aminomethyl)-4,6-dimethylpyridin-2-ol (62 mg, 0.41 mmol). The reaction mixture was stirred at 20° C. for 13 hours. The mixture was washed with water (20 mL×2). The organic phase was dried over sodium sulfate and filtered. The filtrate was concentrated. The residue was purified by column chromatography (silica gel, dichloromethane/methanol=10:1) to give N-((2-hydroxy-4,6-dimethylpyridin-3-yl)methyl)-4-(1-(pyrimidin-2-yloxy)ethyl)benzamide as a white solid (50 mg, 32%). LRMS (M+H$^+$) m/z: 378.17. found 378. HPLC Purity (214 nm): 100%. $^1$H NMR (300 MHz, d$^6$-DMSO): δ 11.46 (s, 1H), 8.30 (d, J=4.8 Hz, 1H), 8.06-8.04 (m, 1H), 7.80-7.68 (m, 2H), 7.44-7.42 (m, 2H), 6.93-6.84 (m, 2H), 6.17 (q, J=6.6 Hz, 1H), 5.84 (s, 1H), 4.27 (d, J=4.8, 2H), 2.15 (s, 3H), 2.11 (s, 3H), 1.55 (d, J=6.6 Hz, 3H).

Example 64

Synthesis of N-((2-hydroxy-4,6-dimethylpyridin-3-yl)methyl)-4-(1-(pyridin-4-yloxy)ethyl)benzamide (Compound I-77)

This synthesis involved 3 steps.

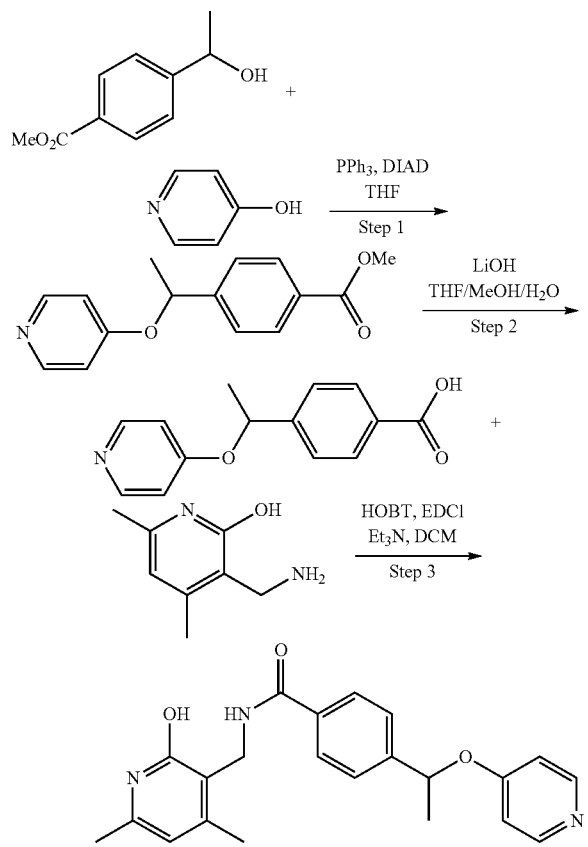

Methyl 4-(1-(pyridin-4-yloxy)ethyl)benzoate

To a solution of 4-(1-hydroxyethyl)benzoate (300 mg. 1.67 mmol) in tetrahydrofuran (80 mL) were added triphenylphosphine (570 mg, 2.2 mmol) and pyridin-4-ol (159 mg, 1.67 mmol). The mixture was stirred for 30 minutes at room temperature, and then cooled to 0° C. And diisopropylazodicarboxylate (568.3 mg, 2.8 mmol) was added dropwise to the solution at 0° C. The resultant mixture was stirred at room temperature for 12 hours. Then the mixture was concentrated to give a residue and the residue was purified by column chromatography (silica gel, ethyl acetate/petroleum ether=1: 10) to give methyl 4-(1-(pyridin-4-yloxy)ethyl)benzoate as an oil (151 mg, 35%). LRMS (M+H) m/z: calcd 257.1. found 257.

4-(1-(pyridin-4-yloxy)ethyl)benzoic acid

To a mixed solution of methanol (10 mL) and water (2 mL), methyl 4-(1-(pyridin-4-yloxy)ethyl)benzoate (151 mg, 0.59 mmol) and lithium hydroxide were added. The mixture was stirred at room temperature for 12 hours. Then the reaction mixture was acidified by hydrogen chloride aqueous solution (1N) to adjust pH=6, and then extracted with dichloromethane (20 mL×3). And the mixture was concentrated to give 4-(1-(pyridin-4-yloxy)ethyl)benzoic acid (127 mg, 88%).

N-((2-hydroxy-4,6-dimethylpyridin-3-yl)methyl)-4-(1-(pyridin-4-yloxy)ethyl)benzamide (Compound I-77)

A mixture of 4-(1-(pyridin-4-yloxy)ethyl)benzoic acid (127 mg, 0.5 mmol), N-hydroxybenzotriazole (101.25 mg, 0.75 mmol), 1-ethyl-3-(3-dimethylaminopropyl)carbodiimide hydrochloride (144 mg, 0.75 mmol) and triethylamine (151 mg, 1.5 mmol) in dichloromethane (50 mL) was stirred for 30 minutes at room temperature. Then 3-(aminomethyl)-4,6-dimethylpyridin-2-ol (76 mg, 0.5 mmol) was added. The resultant mixture was stirred at room temperature for 12 hours. The mixture was washed with water (10 mL×3). The organic layer was concentrated to give a residue and the residue was purified by column chromatography (silica gel, dichloromethane/methanol=20:1) to give N-((2-hydroxy-4,6-dimethylpyridin-3-yl)methyl)-4-(1-(pyridin-4-yloxy)ethyl)benzamide (57 mg, 30%). LRMS (M+H$^+$) m/z: calcd 377.17. found 377. HPLC purity (214 nm): 99%. $^1$H NMR (300 MHz, CD$_3$OD): δ 8.23 (d, J=5.1 Hz, 2H), 7.78 (d, J=8.1 Hz, 2H), 7.46 (d, J=8.1 Hz, 2H), 6.93-6.91 (m, 2H), 6.08 (s, 1H), 5.62 (q, J=6.3 Hz, 1H), 4.47 (s, 2H), 2.34 (s, 3H), 2.23 (s, 3H), 1.64 (d, J=6.3 Hz, 3H).

Example 65

Synthesis of N-((2-hydroxy-4,6-dimethylpyridin-3-yl)methyl)-6-(1-(pyridin-3-yloxy)ethyl)nicotinamide (Compound I-78)

This synthesis involved 5 steps.

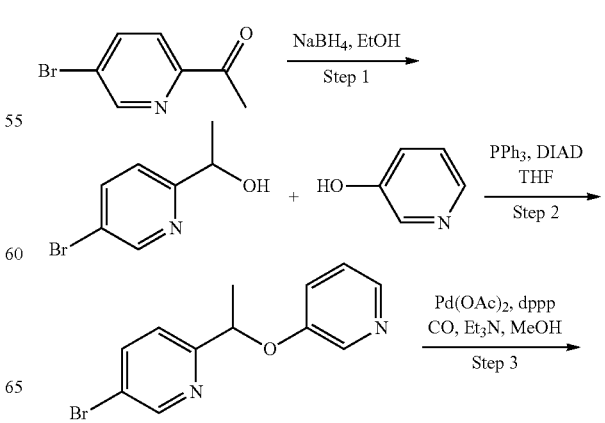

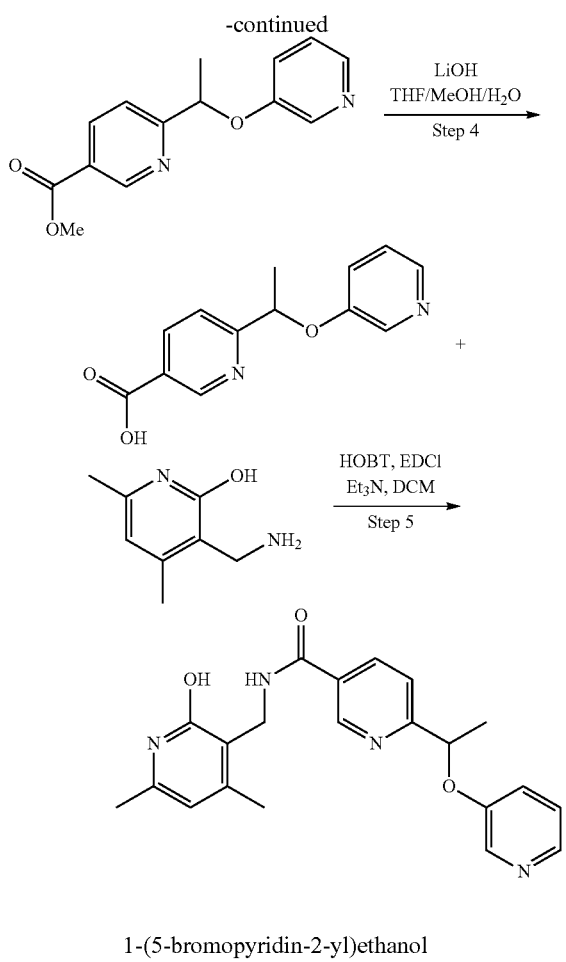

1-(5-bromopyridin-2-yl)ethanol

To a solution of 1-(5-bromopyridin-2-yl)ethanone (5 g, 25 mmol) in anhydrous ethanol (100 mL) was added sodium borohydride (2.85 g, 75 mmol) at room temperature. After 2 hours, water (10 mL) was added to quench the reaction at 0° C. and then saturated hydrochloric acid aqueous (10 mL) was added the mixture to adjust pH to 7. The mixture was extracted with ethyl acetate (50 mL). The crude product was purified by column chromatography (petroleum ether/ethyl acetate=1:1) to give 1-(5-bromopyridin-2-yl)ethanol (3 g, 60%).

5-bromo-2-(1-(pyridin-3-yloxy)ethyl)pyridine

A solution of 1-(5-bromopyridin-2-yl)ethanol (600 mg, 3.00 mmol), pyridin-3-ol (283 mg, 2.98 mmol) and triphenyl phosphine (1.54 g, 5.88 mmol) was stirred in anhydrous tetrahydrofuran (20 mL) under nitrogen atmosphere. After stirring for 1 hour, the mixture was cooled to 0° C. Diisopropyl azodicarboxylate (658 mg, 3.26 mmol) was added dropwise and the reaction mixture was stirred at room temperature for 18 hours. Then the solvent was evaporated and the residue was purified by column chromatography (silica gel, pure ether) to 5-bromo-2-(1-(pyridin-3-yloxy)ethyl)pyridine (744 mg, 89%). $^1$H NMR (300 MHz, CD$_3$OD): δ 8.63-8.62 (m, 1H), 8.21-8.19 (m, 1H), 8.08-8.06 (m, 1H), 7.98-7.94 (m, 1H), 7.45 (d, J=5.1 Hz, 1H), 7.33-7.28 (m, 2H), 5.51 (q, J=6.3 Hz, 1H), 1.68 (d, J=6.3 Hz, 3H).

Methyl 6-(1-(pyridin-3-yloxy)ethyl)nicotinate

To a mixture of 5-bromo-2-(1-(pyridin-3-yloxy)ethyl)pyridine (900 mg, 3.23 mmol) in methanol (30 mL) were added palladium acetate (146 mg, 0.65 mmol), 1,3-bis(diphenylphosphino) propane (268 mg, 0.65 mmol) and triethylamine (130 mg, 1.3 mmol). And the reaction mixture was heated to 100° C. under carbon monoxide atmosphere (20 atm) for 12 hours. The mixture was cooled to room temperature and concentrated to give a residue. And then the residue was purified by prep-TLC (silica gel, petroleum ether/ethyl acetate=30:1) to give methyl 6-(1-(pyridin-3-yloxy)ethyl)nicotinate as a light yellow solid (600 mg, 72%). $^1$H NMR (300 MHz, CD$_3$OD): δ 9.10 (s, 1H), 8.37-8.07 (m, 3H), 7.64 (d, J=8.1 Hz, 1H), 7.33-7.28 (m, 2H), 5.60 (q, J=6.3 Hz, 1H), 3.93 (s, 3H), 1.70 (d, J=6.3 Hz, 3H).

6-(1-(pyridin-3-yloxy)ethyl)nicotinic acid

A mixture of methyl 6-(1-(pyridin-3-yloxy)ethyl)nicotinate (600 mg, 2.33 mmol), lithium hydroxide monohydrate (420 mg, 10 mmol), tetrahydrofuran (6 mL), methanol (2 mL) and water (2 mL) was stirred at 20° C. for 4 hours. The mixture was acidified to pH=1 with concentrated hydrochloric acid and then extracted with dichloromethane (10 mL×3). The combined organic phase was separated, dried by sodium sulfate and then filtered. The filtrate was concentrated in vacuo to give 6-(1-(pyridin-3-yloxy)ethyl)nicotinic acid (550 mg, 97%).

N-((2-hydroxy-4,6-dimethylpyridin-3-yl)methyl)-6-(1-(pyridin-3-yloxy)ethyl)nicotinamide (Compound-78)

To a solution of 6-(1-(Pridin-3-yloxy)ethyl)nicotinic acid (150 mg, 0.61 mol) was dissolved in dichloromethane (20 mL), H-benzo[d][1,2,3]triazol-1-ol (124 mg, 0.92 mmol), 1-(3-dmethylaminopropyl)-3-ethylcarbodiimide hydrochloride (176 mg, 0.92 mmol) and triethylamine (3 mL, 1.84 mmol) were added. After stirring at room temperature for 10 minutes, 3-(aminomethyl)-4,6-dimethylpyridin-2-ol (93 mg, 0.61 mmol) was added. The mixture was stirred at room temperature for 18 hours. Once the start material was consumed, water (30 mL) was added. The mixture was extracted with dichloromethane (40 mL). The organic layer was separated and concentrated to give a residue. The residue was purified by column chromatography (silica gel, dichloromethane/methanol=15/1) to give N-((2-hydroxy-4,6-dimethylpyridin-3-yl)methyl)-6-(1-(pyridin-3-yloxy)ethyl)nicotinamide (50 mg, 21.5%).

LRMS (M+H$^+$) m/z: calcd 378.17. found 378. HPLC purity (214 nm): 94%. $^1$H NMR (300 MHz, CD$_3$OD): δ 8.93 (d, J=1.2 Hz, 1H), 8.20-8.15 (m, 3H), 7.57 (d, J=8.1 Hz, 1H), 7.31-7.27 (m, 2H), 6.09 (s, 1H), 5.56 (q, J=6.3 Hz, 1H), 4.48 (s, 2H), 2.34 (s, 3H), 2.24 (s, 3H), 1.69 (d, J=6.6 Hz, 3H).

Example 66

Synthesis of N-((2-hydroxy-4,6-dimethylpyridin-3-yl)methyl)-2-phenoxypyrimidine-5-carboxamide (Compound I-79)

This synthesis involved 3 steps.

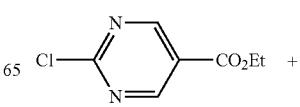

-continued

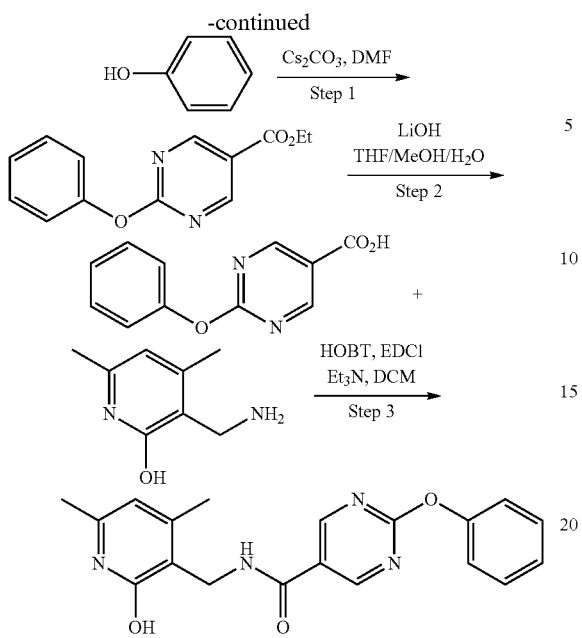

Ethyl 2-phenoxypyrimidine-5-carboxylate

To a solution of ethyl 2-chloropyrimidine-5-carboxylate (0.5 g, 2.7 mmol) in N,N-dimethylformamide (6.0 mL) was added cesium carbonate (676 mg, 2.1 mmol) and phenol (205 mg, 2.18 mmol). The mixture was stirred at 100° C. for 24 hours. The mixture was concentrated in vacuo. To the residue, was added water (50 mL) and extracted with dichloromethane (2*50 mL). The combined organic phase was separated, dried over sodium sulphate, filtered and concentrated to give a residue. The residue was purified by column chromatography (silica gel, petroleum ether/ethyl acetate=20/1) to give the product ethyl 2-phenoxypyrimidine-5-carboxylate (472 mg, 81%) as colorless oil. $^1$H NMR (300 MHz, CDCl$_3$): δ 8.55 (s, 2H), 7.43-7.06 (m, 5H), 4.29 (q, J=8.9 Hz, 2H), 1.31 (t, J=8.9 Hz, 3H).

2-phenoxypyrimidine-5-carboxylic acid

To a solution of ethyl 2-phenoxypyrimidine-5-carboxylate (400 mg, 1.6 mmol) in mixed solution of tetrahydrofuran/methanol/water=3:1:1 (4 mL) was added lithium hydroxide monohydrate (200 mg, 8.4 mmol). The mixture was stirred at room temperature for 2 hours. The suspension was concentrated in vacuo. To the residue, was added water (50 mL) and extracted with dichloromethane (2*50 mL). The combined organic phase was separated, dried by sodium sulfate, filtered and concentrated to give a residue. The residue was purified by column chromatography (silica gel, petroleum ether/ethyl acetate=5/1) to give the product 2-phenoxypyrimidine-5-carboxylic acid (300 mg, 79%) as pale solid.

N-((2-hydroxy-4,6-dimethylpyridin-3-yl)methyl)-2-phenoxypyrimidine-5-carboxamide (Compound I-79)

A solution of 2-phenoxypyrimidine-5-carboxylic acid (300 mg, 1.4 mmol) in dichloromethane (15.0 mL) was added N-hydroxybenzotriazole (270 mg, 2 mmol), 1-(3-dimethylaminopropyl)-3-ethylcarbodiimide hydrochloride (384 mg, 2 mmol), triethylamine (202 mg, 2 mmol). Then the mixture was stirred for 30 minutes, 3-(aminomethyl)-4,6-dimethylpyridin-2-ol (270 mg, 2 mmol) was added and the mixture was stirred at room temperature 24 hours. The mixture was washed with water (50 mL), and extracted with dichloromethane (2*50 mL). The combined organic phase was separated, dried over sodium sulphate, filtered and concentrated to give a residue. The residue was purified by column chromatography (silica gel, methanol/dichloromethane=1:20, 1% NH$_3$) to afford N-((2-hydroxy-4,6-dimethylpyridin-3-yl)methyl)-2-phenoxypyrimidine-5-carboxamide (200 mg, 46%) as white solid. LRMS (M+H$^+$) m/z: calcd 350.14. found 350. HPLC purity (214 nm): 100%. $^1$H NMR (300 MHz, CD$_3$OD): δ 8.93 (s, 2H), 7.46-7.16 (m, 5H), 6.10 (s, 1H), 4.48 (s, 2H), 2.35 (s, 3H), 2.24 (s, 3H).

Example 67

Synthesis of N-((2-hydroxy-4,6-dimethylpyridin-3-yl)methyl)-2-methyl-4-(piperidin-1-ylmethyl)benzamide (Compound I-80)

This synthesis involved 6 steps.

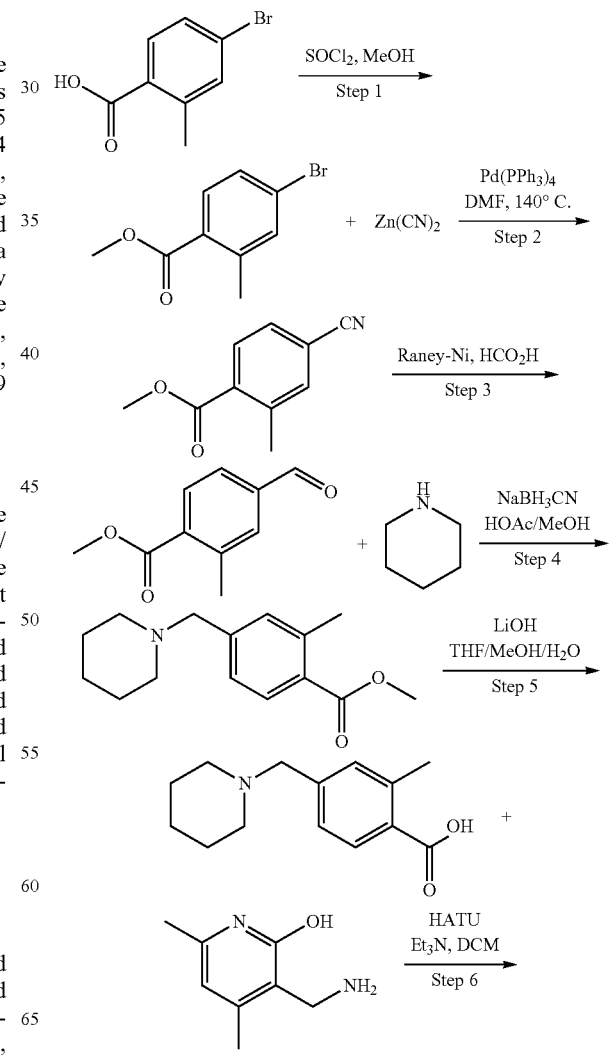

-continued

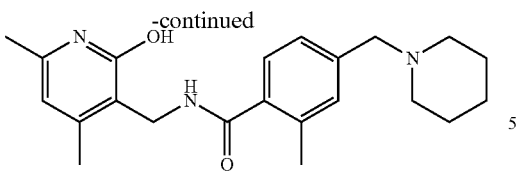

Methyl 4-bromo-2-methylbenzoate

To 4-bromo-2-methylbenzoic acid (1 g, 4.7 mol), thionyl chloride (40 mL) was added. The mixture was stirred at 80° C. for 2 hours. After cooling the reaction mixture to room temperature, the mixture was concentrated to dryness. Methanol (40 mL) was added and then the mixture was concentrated in vacuo to give methyl 4-bromo-2-methylbenzoate as a yellow oil (800 mg, 78%).

Methyl 4-cyano-2-methylbenzoate

A mixture of methyl 4-bromo-2-methylbenzoate (1 g, 4.4 mmol), zinc cyanide (0.7 g, 6.0 mmol) and tetrakis(triphenylphosphine)palladium(0) (100 mg, 0.086 mmol) in N,N-dimethylformamide was heated to 140° C. under nitrogen atmosphere. And then the mixture stirred under reflux condition for 12 hours. The mixture was cooled to room temperature, and partitioned between dichloromethane (20 mL*3) and brine (60 mL). The organic layer was concentrated to dryness and the residue was purified by column chromatography (silica gel, petroleum ether/ethyl acetate=15:1) to give methyl 4-cyano-2-methylbenzoate as a white solid (200 mg, 26%). LRMS (M+H$^+$) m/z: calcd 175.06. found 175. $^1$H NMR (300 MHz, CDCl$_3$): δ 7.97 (d, J=8.7 Hz, 1H), 7.57-7.53 (m, 2H), 3.93 (s, 3H), 2.62 (s, 3H).

Methyl 4-formyl-2-methylbenzoate

Raney-Ni (3.0 mL, washed with ethanol for 3 times) was added to a solution of 4-cyano-2-methylbenzoate (0.93 g, 5.3 mmol) in ethanol (20 mL). Then formic acid (10 mL, 75%) was added to the mixture. The mixture was stirred at 110° C. for 2 hours. After filtration, the mixture was concentrated. The residue was purified by column chromatography (silica gel, petroleum ether/ethyl acetate=20:1) to gave product methyl 4-formyl-2-methylbenzoate as a yellow oil (620 mg, 65%).

Methyl 2-methyl-4-(piperidin-1-ylmethyl)benzoate

To a solution of methyl 4-formyl-2-methylbenzoate (300 mg, 1.7 mmol) and piperidine (92 mg, 1.1 mmol) in methanol (50 mL) was added acetic acid (1 drop) followed by sodium cyanoborohydride (221 mg, 3.5 mmol). The mixture was stirred at room temperature for 24 hours. The mixture was filtered, acidified with concentrated hydrochloride acid (1 mL) and concentrated in vacuo. To the residue, water (50 mL) was added. The mixture was extracted with dichloromethane (50 mL). The combined organic phase was separated, dried by sodium sulfate, filtered and concentrated to give a residue. The residue was purified by column chromatography (silica gel, petroleum ether/ethyl acetate=4:1, 1% NH$_3$) to give methyl 2-methyl-4-(piperidin-1-ylmethyl)benzoate as a yellow oil (200 mg, 60%). LRMS (M+H$^+$) m/z: calcd 247.16. found 247. $^1$H NMR (300 MHz, CDCl$_3$): δ 7.73 (d, J=8.7 Hz, 1H), 7.52-7.50 (m, 2H), 3.91 (s, 3H), 3.62 (s, 2H), 2.52 (s, 3H), 2.32-2.24 (m, 4H), 1.47-1.44 (m, 6H).

2-methyl-4-(piperidin-1-ylmethyl)benzoic acid

To a solution of methyl 2-methyl-4-(piperidin-1-ylmethyl) benzoate (1.8 g, 7.3 mmol) in the mixture solution of tetrahydrofuran:methanol:water=3:1:1 (20 mL) was added lithium hydroxide monohydrate (1 g, 42 mmol). The mixture was stirred at room temperature for 2 hours. The suspension was concentrated in vacuo and quenched with hydrochloride acid aqueous (1N, 5 mL). To the residue, water (50 mL) was added. The mixture was extracted with dichloromethane (50 mL). The combined organic phase was separated, dried over sodium sulfate, filtered and concentrated to give a residue. The residue was purified by column chromatography (silica gel, methanol/dichloromethane=1:15) to give the product 2-methyl-4-(piperidin-1-ylmethyl)benzoic acid (360 mg, 21%) as pale solid.

LRMS (M+H$^+$) m/z: calcd 233.14. found 233.

N-((2-hydroxy-4,6-dimethylpyridin-3-yl)methyl)-2-methyl-4-(piperidin-1-yl methyl)benzamide (Compound I-80)

A solution of 2-methyl-4-(piperidin-1-ylmethyl)benzoic acid (100 mg, 0.43 mmol) in dichloromethane (50 mL) was added 2-(7-aza-1H-benzotriazole-1-yl)-1,1,3,3-tetramethyluronium hexafluorophosphate (35 mg, 0.1 mmol), triethylamine (32 mg, 0.3 mmol). The mixture was stirred for 30 minutes. Then 3-(aminomethyl)-4,6-dimethylpyridin-2-ol (27 mg, 0.2 mmol) was added and the mixture was stirred at room temperature for 12 hours. The mixture was washed with water (50 mL), dried over sodium sulfate, filtered and concentrated to give a residue. The residue was purified by column chromatography (silica gel, dichloromethane/methanol=20:1) to afford N-((2-hydroxy-4,6-dimethylpyridin-3-yl)methyl)-2-methyl-4-(piperidin-1-ylmethyl)benzamide as white solid (35 mg, 19%). LRMS (M+H$^+$) m/z: calcd 367.23. found 367. HPLC purity (214 nm): 96%. $^1$H NMR (300 MHz, CD$_3$OD): δ 7.54-7.46 (m, 3H), 6.26 (s, 1H), 4.62 (s, 2H), 4.17 (s, 2H), 3.10 (s, 4H), 2.54 (s, 3H), 2.53 (s, 3H), 2.39 (s, 3H), 1.93-1.89 (m, 4H), 1.77-1.75 (m, 2H).

Example 68

Synthesis of N-((2-hydroxy-4,6-dimethylpyridin-3-yl)methyl)-4-(1-(tetrahydrofuran-3-yloxy)ethyl)benzamide (Compound I-82)

This synthesis involved 4 steps.

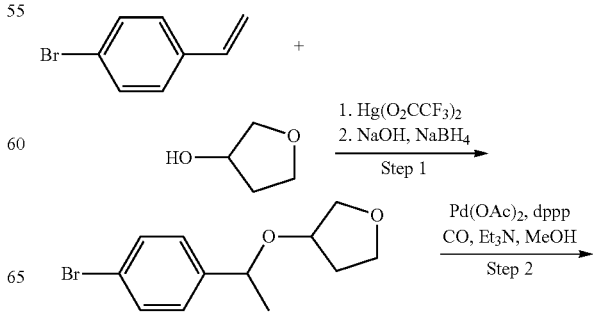

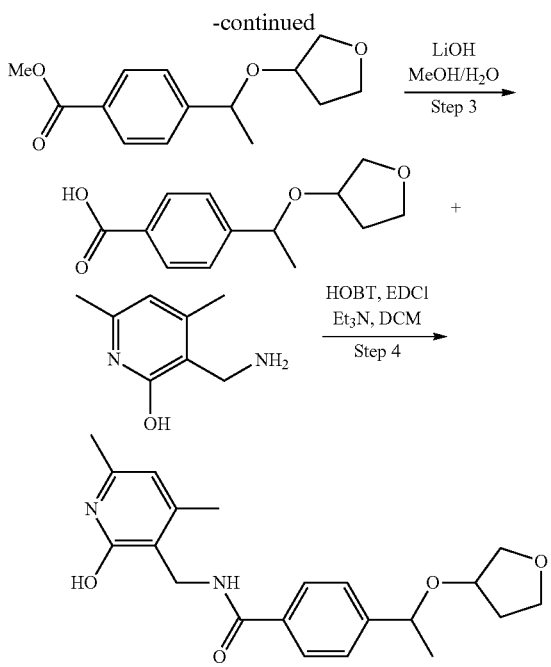

3-(1-(4-bromophenyl)ethoxy)-tetrahydrofuran

To the solution of 3-(1-(4-bromophenyl)ethoxy)-tetrahydrofuran (410 mg, 1.52 mmol) in methanol (20 mL) was added 1,3-bis(diphenylphosphino) propane (125 mg, 0.3 mmol), palladium acetate (67.3 mg, 0.3 mmol), and triethylamine (767 mg, 7.6 mmol), the mixture was stirred at 90° C. for 12 hours under an atmosphere of carbon monoxide in sealed tube. Then the mixture was concentrated and purified by column chromatography (silica gel, dichloromethane/methanol=20:1) to give methyl-4-(1-(tetrahydrofuran-3-yloxy)ethyl)benzoate (371 mg, 97.6%) as oil 4-(1-(tetrahydrofuran-3-yloxy)ethyl)benzoic acid To the solution of methyl 4-(1-(tetrahydrofuran-3-yloxy)ethyl)benzoate (371 mg, 1.48 mmol) in methanol (15 mL) and water (5 mL) was added lithium hydroxide hydrate (100 mg, 2.4 mmol) were add ed. The mixture was stirred at room temperature for 12 hours. Then the reaction mixture was acidified by hydrochloric acid aqueous solution (1 N) to adjust pH=6 and extracted with dichloro methane (10 mL×3). The organic layers were combined and concentrated to give 4-(1-(tetrahydrofuran-3-yloxy)ethyl)benzoic acid (311 mg, 89%)

N-((2-hydroxy-4,6-dimethylpyridin-3-yl)methyl)-4-(1-(tetrahydrofuran-3-yloxy)ethyl)benzamide A mixture of 4-(1-(tetrahydrofuran-3-yloxy)ethyl)benzoic acid (311 mg, 1.32 mmol), 1-ethyl-3-(3-dimethylaminopropyl)carbodiimide hydrochloride (380 mg, 1.98 mmol), N-hydroxybenzotriazole (267.3 mg, 1.98 mmol) and triethylamine (400 mg, 3.96 mmol) in dichloromethane (50 mL) was stirred for 30 minutes at room temperature. Then to the mixture, 3-(aminomethyl)-4,6-dimethylpyridin-2-ol (200.64 mg, 1.32 mmol) was added. The resultant mixture was stirred at room temperature for 12 hours. Then the mixture was washed with water (30 mL×3). The organic layer was concentrated to give a residue and the residue was purified by column chromatography (silica gel, dichloromethane/methanol=20:1) to give N-((2-hydroxy-4,6-dimethylpyridin-3-yl)methyl)-4-(1-(m-tolyloxy)ethyl)benzamide (Compound I-82) (452 mg, 92%). LRMS (M+H$^+$) m/z: calcd 370. found 370. $^1$H NMR (300 MHz, CD$_3$OD): a 7.78 (d, J=8.4 Hz, 2H), 7.42-7.41 (m, 2H), 6.11 (s, 1H), 4.61-4.58 (m, 1H), 4.49 (s, 2H), 4.07-4.04 (m, 1H), 3.87-3.62 (m, 4H), 2.37 (s, 3H), 2.24 (s, 3H), 1.98-1.87 (m, 2H), 1.40-1.38 (m, 3H).

Example 69

Synthesis of N-((2-hydroxy-4,6-dimethylpyridin-3-yl)methyl)-4-(tetrahydrofuran-2-yl)benzamide (Compound I-84)

This synthesis involved 4 steps.

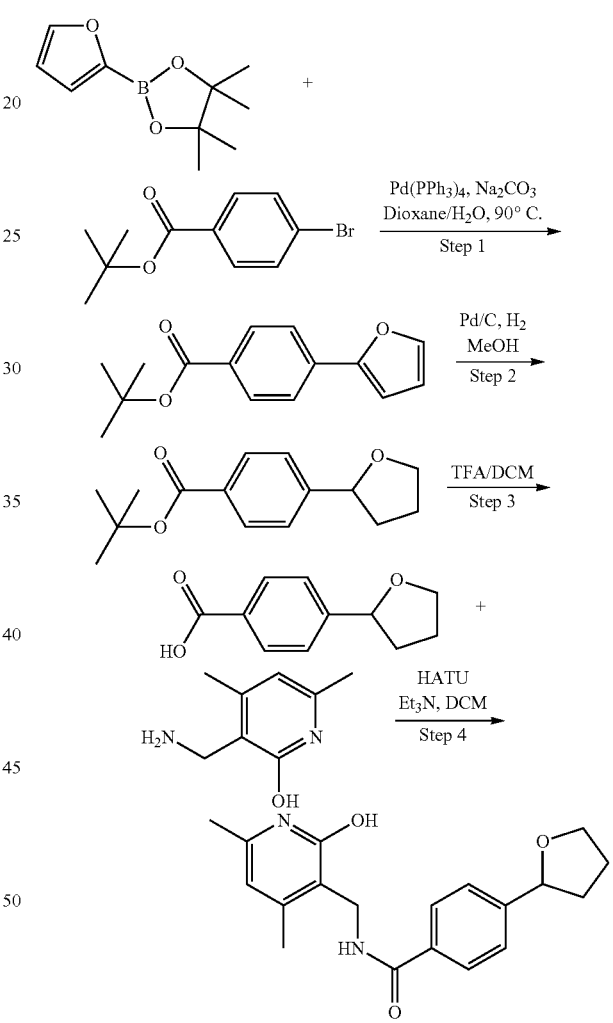

Tert-butyl 4-(furan-2-yl)benzoate

A mixture of 2-(furan-2-yl)-4,4,5,5-tetramethyl-1,3-dioxolane (500 mg, 2.6 mmol), tert-butyl 4-bromobenzoate (512 mg, 2 mmol) and sodium carbonate (636 mg, 6 mmol), tetra (triphenylphosphine) palladium (115 mg, 0.1 mmol) in mixed solution of 1,4-dioxane (20 ml) and water (4 ml) was stirred for 15 hours at 90° C. under nitrogen atmosphere. After cooling to room temperature, the reaction mixture was concentrated to give a residue. The residue was purified by column chromatography (silica gel, petroleum ether/ethyl acetate=10:1) to give tert-butyl 4-(furan-2-yl)benzoate (400 mg, 82%) as a yellow oil. LRMS (M+H$^+$) m/z: calcd 244.11. found 244. $^1$H NMR (300 MHz, CD$_3$OD): δ 7.99-7.96 (m, 2H), 7.78-7.75 (m, 2H), 7.63-7.62 (m, 1H), 6.94-6.93 (m, 1H), 6.57-6.56 (m, 1H), 1.61 (s, 9H).

Tert-butyl 4-(tetrahydrofuran-2-yl)benzoate

To a solution of tert-butyl 4-(furan-2-yl)benzoate (400 mg, 1.64 mmol) in methanol (20 mL) was added palladium on carbon (10%, 100 mg). After stirring for 24 hours at room temperature under hydrogen atmosphere, the mixture was filtered. And the filtrate was concentrated in vacuo to give tert-butyl 4-(tetrahydrofuran-2-yl)benzoate (350 mg, 86%) as a white solid. LRMS (M+H$^+$) m/z: calcd 248.14. found 248. $^1$H NMR (300 MHz, CD$_3$OD): δ 7.94-7.85 (m, 2H), 7.44-7.28 (m, 2H), 4.95-4.93 (m, 1H), 3.60-3.56 (m, 2H), 2.73-2.68 (m, 2H), 1.77-1.73 (m, 2H), 1.68 (s, 9H).

4-(tetrahydrofuran-2-yl)benzoic acid

To a solution of tert-butyl 4-(tetrahydrofuran-2-yl)benzoate (350 mg, 1.41 mmol) in dichloromethane (10 mL) was added 2,2,2-trifluoroacetic acid (2 mL). The resulting mixture was stirred at room temperature for 0.5 hours. The mixture was concentrated to give 4-(tetrahydrofuran-2-yl)benzoic acid (200 mg, 74%) as a white solid.
LRMS (M+H$^+$) m/z: calcd 192.08. found 192.

N-((2-hydroxy-4,6-dimethylpyridin-3-yl)methyl)-4-(tetrahydrofuran-2-yl)benzamide (Compound I-84)

To a solution of 4-(tetrahydrofuran-2-yl)benzoic acid (95 mg, 0.5 mmol) in dichloromethane (20 mL) were added o-(7-azabenzotriazol-1-yl)-N,N,N',N'-tetramethyluronium hexafluorophosphate (380 mg, 1 mmol) and triethylamine (202 mg, 2 mmol). The mixture was stirred for 0.5 hour. Then 3-(aminomethyl)-4,6-dimethylpyridin-2-ol (120 mg, 0.8 mmol) was added and the mixture was stirred at room temperature for 4 hours. The mixture was washed with water (50 mL). The organic phase was separated and concentrated to give a residue. The residue was purified through column chromatography (silica gel, dichloromethane/methanol=20:1) and to afford N-((2-hydroxy-4,6-dimethylpyridin-3-yl)methyl)-4-(tetrahydrofuran-2-yl)benzamide (35 mg, 21%) as a white solid. LRMS (M+H$^+$) m/z: calcd 326.16. found 326.
HPLC purity (214 nm): 95%. $^1$H NMR (300 MHz, CD$_3$OD): δ 7.76 (d, J=8.1 Hz, 2H), 7.41 (d, J=8.1 Hz, 2H), 6.11 (s, 1H), 4.94-4.91 (m, 1H), 4.49 (s, 2H), 4.13-4.06 (m, 1H), 3.97-3.89 (m, 1H), 2.36 (s, 3H), 2.24 (s, 3H), 2.07-1.98 (m, 2H), 1.81-1.77 (m, 2H).

Example 70

Synthesis of compound 4-(1-(cyclohexyloxy)ethyl)-N-((2-hydroxy-4,6-dimethylpyridin-3-yl)methyl)benzamide (Compound I-85)

This synthesis involved 3 steps.

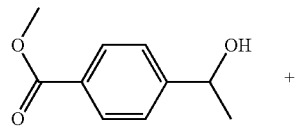

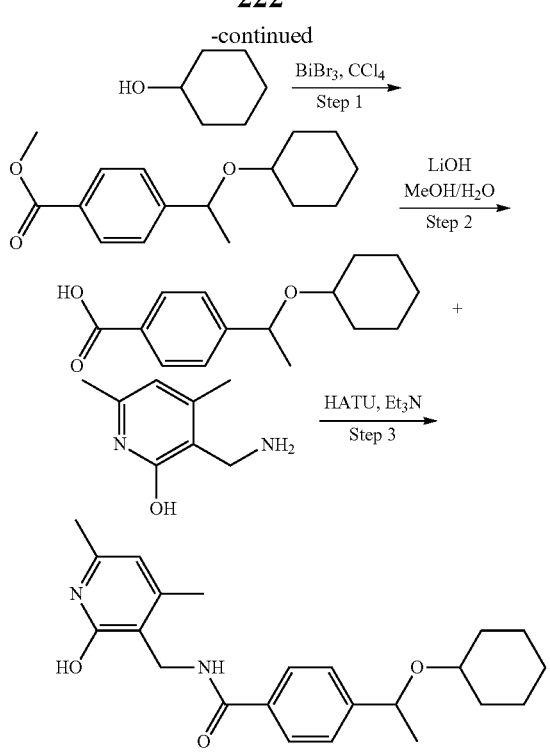

Synthesis of methyl 4-(1-(cyclohexyloxy)ethyl)benzoate

To the solution of cyclohexanol (167 mg, 1.67 mmol) in carbon tetrachloride (50 mL) was added bismuth (III) bromide (744.4 mg, 1.67 mmol), the mixture was stirred for 30 minutes at room temperature, the methyl 4-(1-hydroxyethyl)benzoate (300 mg, 1.67 mmol) was added, the mixture was stirred at room temperature for 12 hours. Then the mixture was concentrated and purified by column chromatography (silica gel, Petroleum ether/ethyl acetate=20:1) to give methyl 4-(1-(cyclohexyloxy)ethyl)benzoate (60 mg, 14%) as oil.

4-(1-(cyclohexyloxy)ethyl)benzoic acid

To the solution of methyl 4-(1-(cyclohexyloxy)ethyl)benzoate (60 mg, 0.23 mmol) in methanol and water (50 mL/10 mL) was added lithium hydroxide (100 mg, 4.2 mmol), the solution was stirred at room temperature for 12 hours. Then the solution was acidified by hydrogen chloride (1 N/mol) pH to 6, extracted with dichloromethane (80 mL*3), evaporated the solvent to give 4-(1-(cyclohexyl oxy)ethyl)benzoic acid (47 mg 82%).

4-(1-(cyclohexyloxy)ethyl)-N-((2-hydroxy-4,6-dimethylpyridin-3-yl)methyl)benzamide (Compound I-85)

To the solution of 4-(1-(cyclohexyloxy)ethyl)benzoic acid (62 mg, 0.25 mmol) in dichloromethane (80 mL) was added o-(7-Azabenzotriazol-1-yl)-N,N,N',N'-tetramethyluronium hexafluorophosphate (143 mg, 0.38 mmol) and triethylamine (76 mg, 0.75 mmol). then the 3-(aminomethyl)-4,6-dimethylpyridin-2-ol (131 mg, 0.86 mmol) was added, the solution was stirred at room temperature for 12 hours, then washed with water (50 mL*3), the organic layer was evaporate ed and purified by column chromatography (silica gel, dichloromethane/methanol=20:1) to give 4-(1-(cyclohexyloxy)ethyl)-N-((2-hydroxy-4,6-dimethylpyridin-3-yl)methyl)benzamide (57 mg, 60%). LRMS (M+H$^+$) m/z: calcd: 382.23. found 382; $^1$H-NMR (300 MHz, CD$_3$OD) δ 7.76 (d, J=8.4 Hz, 2H), 7.40 (d, J=8.4 Hz, 2H), 6.11 (s, 1H), 4.69-4.67 (m, 1H), 4.49 (s, 2H), 3.20-3.14 (m, 1H), 2.37 (s, 3H), 2.24 (s, 3H), 1.69 (m. 1H), 1.51-1.49 (m, 3H), 1.38-1.36 (m, 1H), 1.29-1.20 (m, 8H).

Example 71

Synthesis of 4-cyclopentyl-N-((2-hydroxy-4,6-dimethylpyridin-3-yl)methyl)benzamide (Compound I-86)

This synthesis involved 4 steps.

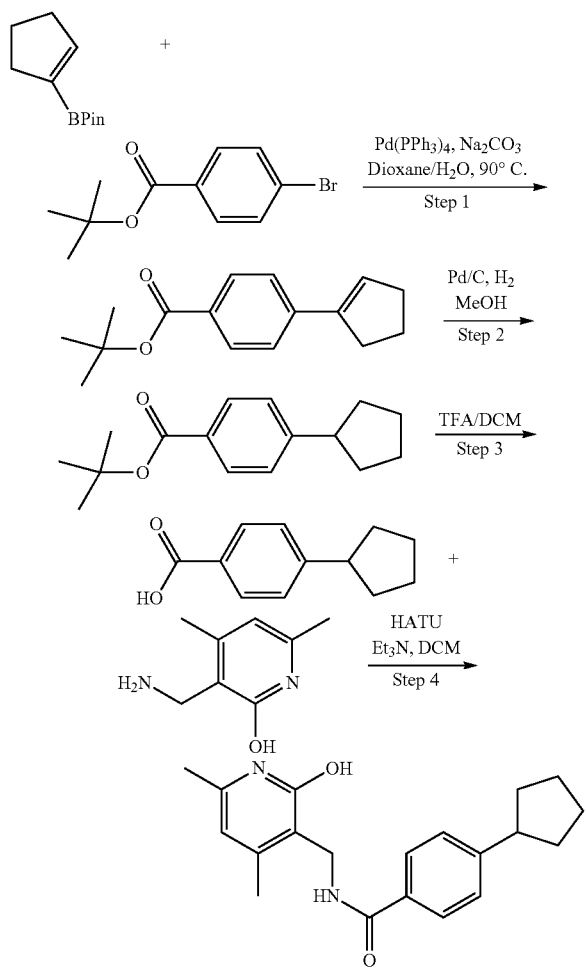

Tert-butyl 4-cyclopentenylbenzoate

A mixture of 2-cyclopentenyl-4,4,5,5-tetramethyl-1,3,2-dioxaborolane (500 mg, 2.6 mmol), tert-butyl 4-bromobenzoate (512 mg, 2 mmol), sodium carbonate (636 mg, 6 mmol) and tetra(triphenylphosphine) palladium (115 mg, 0.1 mmol) in 1,4-dioxane (20 mL) and water (4 mL) was stirred for 15 hours at 90° C. under nitrogen atmosphere. After cooling to room temperature, the reaction mixture was concentrated to give a residue. The residue was purified by column chromatography (silica gel, petroleum ether/ethyl acetate=10:1) to give tert-butyl 4-cyclopentenylbenzoate (400 mg, 82%) as a yellow oil. LRMS (M+H$^+$) m/z: calcd 244.15. found 244. $^1$H NMR (300 MHz, CD$_3$OD): δ 7.94-7.91 (m, 2H), 7.58-7.54 (m, 2H), 6.43-6.42 (m, 1H), 2.78-2.76 (m, 2H), 2.61-2.59 (m, 2H), 2.11-2.08 (m, 2H), 1.64 (s, 9H).

Tert-butyl 4-cyclopentylbenzoate

To a solution of tert-butyl 4-cyclopentenylbenzoate (400 mg, 1.64 mmol) in methanol (20 mL) was added palladium on carbon (10%, 100 mg). The mixture was stirred for 24 hours at room temperature under hydrogen atmosphere. The mixture was filtered and concentrated in vacuo to give tert-butyl 4-cyclopentylbenzoate (350 mg, 86%) as a white solid. LRMS (M+H$^+$) m/z: calcd 246.16. found 246

4-cyclopentylbenzoic acid

To a solution of tert-butyl 4-cyclopentylbenzoate (350 mg, 1.42 mmol) in dichloromethane (10 mL) was added 2,2,2-trifluoroacetic acid (2 mL). After stirring at room temperature for 0.5 hour, the mixture was concentrated to give 4-cyclopentylbenzoic acid (200 mg, 74%) as a white solid. LRMS (M+H$^+$) m/z: calcd 190.10. found 190. $^1$H NMR (300 MHz, CD$_3$OD): δ 12.78 (br, 1H), 7.86 (d, J=8.1 Hz, 2H), 7.37 (d, J=8.1 Hz, 2H), 3.10-3.01 (m, 1H), 2.05-2.01 (m, 2H), 1.78-1.65 (m, 6H).

4-cyclopentyl-N-((2-hydroxy-4,6-dimethylpyridin-3-yl)methyl)benzamide (Compound I-86)

To a solution of 4-cyclopentylbenzoic acid (95 mg, 0.5 mmol) in dichloromethane (20 mL) were added o-(7-azabenzotriazol-1-yl)-N,N,N',N'-tetramethyluronium hexafluorophosphate (380 mg, 1 mmol) and triethylamine (202 mg, 2 mmol). The mixture was stirred for 0.5 hour. Then 3-(aminomethyl)-4,6-dimethylpyridin-2-ol (120 mg, 0.8 mmol) was added. After stirring at room temperature for 4 hours, the mixture was washed with water (50 mL). Organic phase was separated and concentrated to give a residue. The residue was purified by column chromatography (silica gel, dichloromethane/methanol=20:1) and to afford 4-cyclopentyl-N-((2-hydroxy-4,6-dimethylpyridin-3-yl)methyl)benzamide (35 mg, 22%) as white solid. LRMS (M+H$^+$) m/z: calcd 324.18. found 324. HPLC purity (214 nm): 100%. $^1$H NMR (300 MHz, CD$_3$OD): δ 7.71 (d, J=8.1 Hz, 2H), 7.32 (d, J=8.1 Hz, 2H), 6.10 (s, 1H), 4.48 (s, 2H), 3.08-3.02 (m, 1H), 2.36 (s, 3H), 2.24 (s, 3H), 2.10-2.05 (m, 2H), 1.84-1.62 (m, 6H).

Example 72

Synthesis of N-((2-hydroxy-4,6-dimethylpyridin-3-yl)methyl)-2-methyl-4-(1-(piperidin-1-yl)ethyl)benzamide (Compound I-87)

This synthesis involved 6 steps.

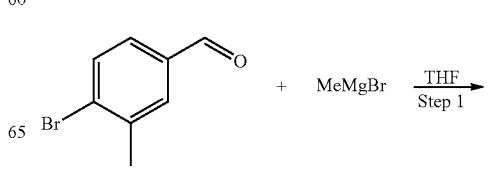

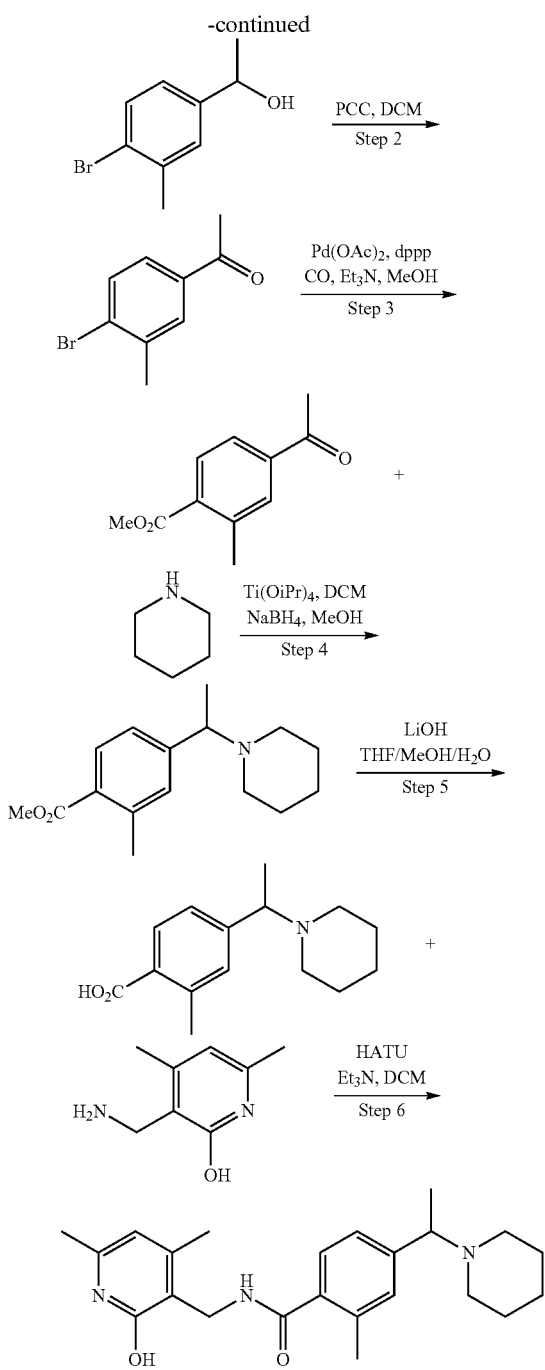

1-(4-bromo-3-methylphenyl)ethanone 1-(4-bromo-3-methylphenyl)ethanol (2.14 g, 9.9 mmol) and pyridinium chlorochromate (2.62 g, 12 mmol) were added to a solution of dichloromethane (30 mL) under nitrogen atmosphere. And the reaction was stirred at room temperature for 12 hours. The mixture was partitioned between dichloromethane (3*20 mL) and brine (20 mL). The organic layer was concentrated to dryness and the residue was purified by column chromatography (silica gel, petroleum ether/ethyl acetate=30:1) to give 1-(4-bromo-3-methylphenyl) ethanone (2.08 g, 99%) as a colorless oil. LRMS (M+H$^+$) m/z: calcd 211.98. found 211. $^1$H NMR (300 MHz, CDCl$_3$): δ 7.81 (s, 1H), 7.62-7.61 (m, 2H), 2.58 (s, 3H), 2.46 (s, 3H).

Methyl 4-acetyl-2-methylbenzoate

To a reversible vial was added the solution of 1-(4-bromo-3-methylphenyl)ethanone (2.1 g, 9.9 mmol), triethylamine (5.0 g, 49 mmol), palladium(II) acetate (116 mg, 0.3 mmol) and 1,3-bis(diphenylphosphino) propane (480 mg, 1 mmol) in methanol (36 mL). Then the reaction mixture was charged with carbon monoxide. The mixture was stirred under carbon monoxide atmosphere (15 atm) at 110° C. for 12 hours. The suspension was concentrated in vacuo. To the residue, water was added (50 mL) and extracted with dichloromethane (2*50 mL). The combined organic phase was dried over sodium sulfate, filtered and concentrated to give a residue. The residue was purified by column chromatography (silica gel, petroleum ether/ethyl acetate=20:1) to give methyl 4-acetyl-2-methylbenzoate as colorless oil (1.78 g, 92%). $^1$H NMR (300 MHz, CDCl$_3$): δ 7.94 (s, 1H), 7.82-7.81 (m, 2H), 3.92 (s, 3H), 2.64 (s, 3H), 2.62 (s, 3H).

Methyl 2-methyl-4-(1-(piperidin-1-yl)ethyl)benzoate

To a solution of methyl 4-acetyl-2-methylbenzoate (0.4 g, 2 mmol) and titanium tetraisopropanolate (2 mL) in dichloromethane (5 mL) was stirred at 50° C. Acetic acid (1 drop) was added followed by sodium borohydride (133 mg, 3.5 mmol) and methanol (5 mL). The mixture was stirred at 50° C. for 24 hours, and then was stirred at 25° C. for 2 hours, then filtered, acidified with concentrated hydrochloride acid (2 mL) and concentrated to give a residue. The residue was taken up with water (50 mL) and the mixture was extracted with dichloromethane (2*50 mL). The combined organic phase was separated, dried over sodium sulfate, concentrated and purified by column chromatography (silica gel, petroleum ether/ethyl acetate=4:1, 1% NH$_3$) to give methyl 2-methyl-4-(1-(piperidin-1-yl)ethyl)benzoate (283 mg, 60%) as a yellow oil. LRMS (M+H$^+$) m/z: calcd 261.17. found 261.

2-methyl-4-(1-(piperidin-1-yl)ethyl)benzoic acid

To a solution of methyl 2-methyl-4-(1-(piperidin-1-yl) ethyl)benzoate (283 mg, 1.1 mmol) in the mixture solution of tetrahydrofuran:methanol:water=3:1:1 (10 mL) was added lithium hydroxide (100 mg, 4.2 mmol). The mixture was stirred at room temperature for 2 hours. The suspension was concentrated in vacuo and quenched with hydrochloride acid aqueous (1N, 5 mL). To the residue was added water (50 mL). The mixture was extracted with dichloromethane (2*50 mL). The combined organic phase was separated, dried over sodium sulfate, filtered and concentrated. The residue was purified by column chromatography (silica gel, petroleum

1-(4-bromo-3-methylphenyl)ethanol

A solution of 4-bromo-3-methylbenzaldehyde (4 g, 20 mmol) in tetrahydrofuran (40 mL) was cooled to 0° C. then methylmagnesium bromide (20 mL, 1N in tetrahydrofuran) was dropped and the mixture was stirred at 0° C. to room temperature for 2 hours. Ammonium chloride aqueous (40 mL) was added and the mixture was extracted with dichloromethane (3*20 mL), dried over sodium sulfate, filtered and concentrated to give a residue. The residue was purified by column chromatography (silica gel, petroleum ether/ethyl acetate=20:1) to give 1-(4-bromo-3-methylphenyl)ethanol as a colorless oil (4.0 g, 93%).

ether/ethyl acetate=1:1) to give the product 2-methyl-4-(1-(piperidin-1-yl)ethyl)benzoic acid as pale solid (247 mg, 89%).

N-((2-hydroxy-4,6-dimethylpyridin-3-yl)methyl)-2-methyl-4-(1-(piperidin-1-yl)ethyl)benzamide (Compound I-87)

A solution of 2-methyl-4-(1-(piperidin-1-yl)ethyl)benzoic acid (100 mg, 0.40 mmol) in dichloromethane (50 mL) was added 2-(7-aza-1H-benzotriazole-1-yl)-1,1,3,3-tetramethyluronium hexafluorophosphate (35 mg, 0.1 mmol) and triethylamine (32 mg, 0.3 mmol). The mixture was stirred for 30 minutes. Then 3-(aminomethyl)-4,6-dimethylpyridin-2-ol (27 mg, 0.2 mmol) was added and the mixture was stirred at room temperature for 12 hours. The mixture was washed with water (50 mL), dried over sodium sulfate, filtered and concentrated. The residue was purified by preparative-TLC (silica gel, methanol/dichloromethane=1:15, 1% $NH_4OH$) to afford N-((2-hydroxy-4,6-dimethylpyridin-3-yl)methyl)-2-methyl-4-(piperidin-1-ylmethyl)benzamide as a white solid (35 mg, 23%). LRMS (M+H$^+$) m/z: calcd 381.51. found 381. HPLC purity (214 nm): 93%. $^1$H NMR (300 MHz, $CD_3OD$): δ 7.42-7.32 (m, 3H), 6.11 (s, 1H), 4.85 (s, 2H), 4.79-4.72 (m, 1H), 2.94-2.79 (m, 4H), 2.40 (s, 3H), 2.34 (s, 3H), 2.24 (s, 3H), 1.83-1.63 (m, 9H).

Example 73

Synthesis of N-((2-hydroxy-4,6-dimethylpyridin-3-yl)methyl)-4-(1-(2-oxopiperidin-1-yl)ethyl)benzamide (Compound I-88)

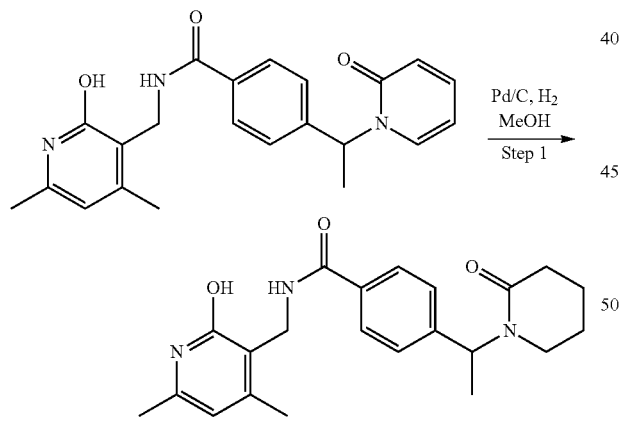

To a solution of N-((2-hydroxy-4,6-dimethylpyridin-3-yl)methyl)-4-(1-(2-oxopyridin-1(2H)-yl)ethyl)benzamide (30 mg, 0.08 mmol) in methanol was added palladium on carbon (30 mg). The mixture was stirred at room temperature for 12 hours under hydrogen atmosphere. Then the mixture was filtered and the filtrate was concentrated to give N-((2-hydroxy-4,6-dimethylpyridin-3-yl)methyl)-4-(1-(2-oxopiperidin-1-yl)ethyl)benzamide (21 mg, 67%). LRMS (M+H) m/z: calcd 381.19. found 381. HPLC purity (214 nm): 95%. $^1$H NMR (300 MHz, $CD_3OD$): δ 7.78 (d, J=8.1 Hz, 2H), 7.36 (d, J=8.1 Hz, 2H), 6.10 (s, 1H), 6.00 (q, J=6.9 Hz, 1H), 4.49 (s, 2H), 3.23-3.19 (m, 1H), 2.83-2.79 (m, 1H), 2.46-2.42 (m, 2H), 2.36 (s, 3H), 2.24 (s, 3H), 1.81-1.63 (m, 4H), 1.54 (d, J=6.9 Hz, 3H).

Example 74

Synthesis of N-((4,6-dimethyl-2-oxo-1,2-dihydropyridin-3-yl)methyl)-4-((4-(2-hydroxyethyl)piperazin-1-yl)methyl)benzamide (Compound I-89)

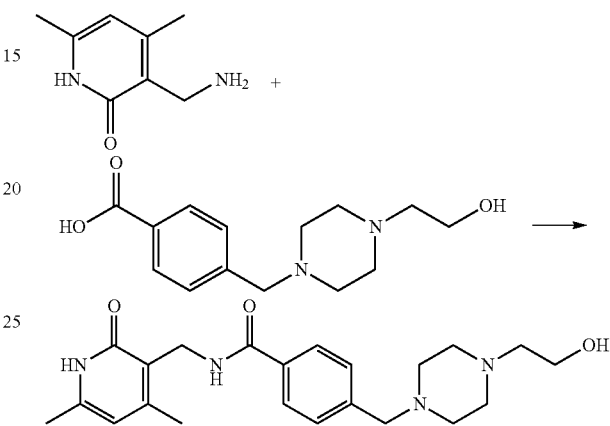

A mixture of 3-(aminomethyl)-4,6-dimethylpyridin-2(1H)-one (70 mg, 0.46 mmol), 4-((4-(2-hydroxyethyl)piperazin-1-yl)methyl)benzoic acid (122 mg, 0.46 mmol), o-(7-azabenzotriazole-1-yl)-N,N,N',N'-tetramethyluronium hexafluorophosphate (210 mg, 0.55 mmol) and triethylamine (70 mg, 0.69 mmol) in anhydrous dichloromethane (5 mL) was stirred at room temperature for 15 hours. Then the mixture was filtered and the solid was washed with water (10 mL), methanol (10 mL) and dichloromethane (10 mL) in turns to give N-((4,6-dimethyl-2-oxo-1,2-dihydropyridin-3-yl)methyl)-4-((4-(2-hydroxyethyl)piperazin-1-yl)methyl)benzamide as white solid (30 mg, 16.4%). LRMS (M+H$^+$) m/z: calcd 398.23. found 398. HPLC purity (214 nm): 89%.

Example 75

Synthesis of compound N-((2-hydroxy-4,6-dimethylpyridin-3-yl)methyl)-4-(1-(tetrahydro-2H-pyran-4-yloxy)ethyl)benzamide (Compound I-144)

This synthesis involved 4 steps.

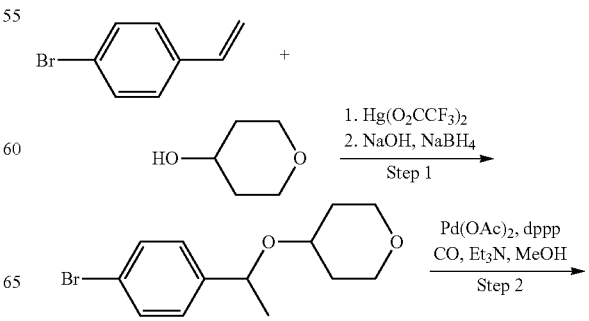

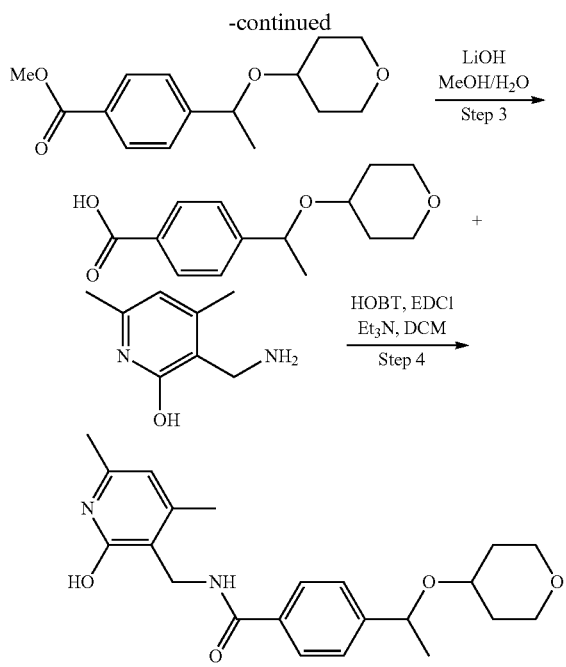

4-(1-(4-bromophenyl)ethoxy)-tetrahydro-2H-pyran

To the solution of 1-bromo-4-vinylbenzene (500 mg, 2.75 mmol) in tetrahydro-2H-pyran-4-ol (20 mL) was added mercuric trifluoroacetate (1.18 g, 2.75 mmol), the mixture was stirred for 1 hour at room temperature, then at 0° C. 3 mol/L sodium hydroxide (20 mL) was added with vigorous stirring, after 2 minute, sodium borohydride (0.5 mol/L) in sodium hydroxide (20 ml, 3 mol/L) was added. After 12 hours, the mixture was extracted with ethyl acetate (50 mL*3). The organics were washed with water (5×20 mL) and dried with sodium sulfate, the solvent was removed and purified by column chromatography (silica gel, dichloromethane/methanol=20:1). to give 3-(1-(4-bromo phenyl)ethoxy)-tetrahydrofuran (461 mg, 59%) as oil.

Methyl 4-(1-(tetrahydro-2H-pyran-4-yloxy)ethyl)benzoate

To the solution of 3-(1-(4-bromophenyl)ethoxy)-tetrahydrofuran (461 mg, 1.62 mmol) in methanol (20 mL) was added 1,3-bis(diphenylphosphino) propane (125 mg, 0.3 mmol), Palladium acetate (67.3 mg, 0.3 mmol), and triethylamine (767 mg, 7.6 mmol), the mixture was stirred at 90° C. for 12 hours under an atmosphere of carbon monoxide in sealed tube. Then the mixture was concentrate ed and purified by column chromatography (silica gel, dichloromethane/methanol=20:1) to give methyl 4-(1-(tetrahydrofuran-3-yloxy)ethyl)benzoate (379 mg, 88.6%) as oil 4-(1-(tetrahydro-2H-pyran-4-yloxy)ethyl)benzoic acid To the solution of methyl 4-(1-(tetrahydro-2H-pyran-4-yloxy)ethyl)benzoate (379 mg, 1.44 mmol) in methanol (15 mL) and water (5 mL) was added lithium hydroxide hydrate (100 mg, 2.4 mmol) were added. The mixture was stirred at room temperature for 12 hours. Then the reaction mixture was acidified by hydrochloric acid aqueous solution (1 N) to adjust pH=6 and extracted with dichloromethane (10 mL*3). The organic layers were combined and concentrated to give 4-(1-(tetrahydro-2H-pyran-4-yloxy)ethyl)benzoic acid (326 mg, 91%)

N-((2-hydroxy-4,6-dimethylpyridin-3-yl)methyl)-4-(1-(tetrahydrofuran-3-yloxy)ethyl)benzamide (Compound I-144)

A mixture of 4-(1-(tetrahydro-2H-pyran-4-yloxy)ethyl)benzoic acid (326 mg, 1.3 mmol), 1-ethyl-3-(3-dimethylaminopropyl)carbodiimide hydrochloride (380 mg, 1.98 mmol), N-hydroxybenzotriazole (267.3 mg, 1.98 mmol) and triethylamine (400 mg, 3.96 mmol) in dichloromethane (50 mL) was stirred for 30 minutes at room temperature. Then to the mixture, 3-(aminomethyl)-4,6-dimethylpyridin-2-ol (200.64 mg, 1.32 mmol) was added. The resultant mixture was stirred at room temperature for 12 hours. Then the mixture was washed with water (30 mL×3). The organic layer was concentrated to give a residue and the residue was purified by column chromatography (silica gel, dichloromethane/methanol=20:1) to give N-((2-hydroxy-4,6-dimethylpyridin-3-yl)methyl)-4-(1-(m-tolyloxy)ethyl)benzamide (411 mg, 82%). LRMS (M+H+) m/z: calcd 384.2. found 384.

¹H.NMR (300 MHz, CD₃OD): δ 7.77 (d, J=8.4 Hz, 2H), 7.419 (d, J=8.1 Hz, 2H), 6.11 (s, 1H), 4.71 (q, J=6.6 Hz), 4.49 (s, 2H), 3.92-3.81 (m, 2H), 3.43-3.37 (m, 3H), 2.37 (s, 3H), 2.24 (s, 3H), 1.94-1.92 (m, 1H), 1.68-1.67 (m, 1H), 1.58-1.51 (m, 2H), 1.39 (d, J=6.3 Hz, 3H).

Example 76

Synthesis of N-((2-hydroxy-4,6-dimethylpyridin-3-yl)methyl)-4-(1-phenoxypropan-2-yl)benzamide (compound I-146)

This synthesis involved 8 steps.

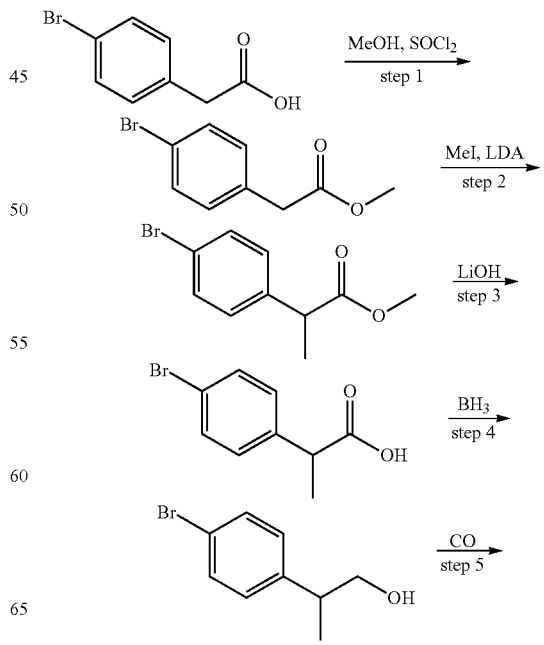

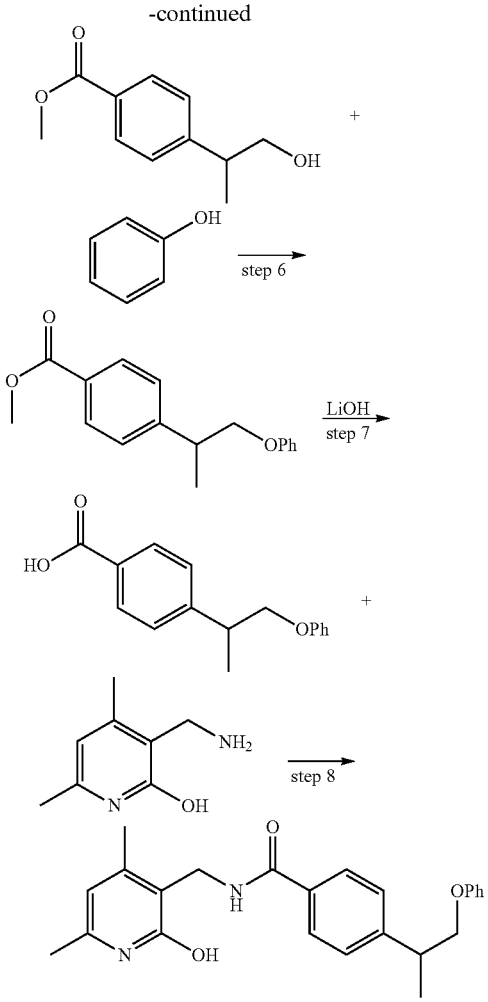

Methyl 2-(4-bromophenyl)acetate

To a solution of 2-(4-bromophenyl)acetic acid (10 g, 47 mmol) in methanol (100 mL) was dropwise thionyl chloride (0.2 mL) at room temperature. The mixture solution was heated to reflux for 3 hours. Then removed the solvent to dry to gave methyl 2-(4-bromophenyl)acetate as a colorless oil (10 g, 94%). $^1$H NMR (300 MHz, CDCl$_3$): δ 7.45 (d, J=9 Hz, 2H), 7.15 (d, J=9 Hz, 2H), 3.70 (s, 3H), 3.58 (s, 2H).

Methyl 2-(4-bromophenyl)propanoate

To a solution of lithium diisopropylamide (2 mol/L, 22 mL, 44 mmol) in tetrahydrofuran (80 mL) was dropwise a solution of methyl 2-(4-bromophenyl)acetate (10 g, 44 mmol) in tetrahydrofuran (20 mL) at −78° C. The mixture solution was stirred for 0.5 hour at that temperature, then iodomethane (8 g, 56 mmol) was added. The mixture was stirred for 10 minutes at −78° C., then was removed from the cooling bath and stirred for 0.5 hour. The reaction was quenched with sat. ammonium chloride, then diluted with ethyl acetate, washed with water, The organic layer concentrated to dry, purified by column chromatography (silica-gel, petroleum:ethyl acetate=20:1) to give methyl 2-(4-bromophenyl)propanoate as a colorless oil (10 g, 91%). $^1$H NMR (300 MHz, CDCl$_3$): δ 7.44 (d, J=9 Hz, 2H), 7.17 (d, J=9 Hz, 2H), 3.65-3.70 (m, 4H), 1.48 (d, J=6 Hz, 3H).

2-(4-bromophenyl)propanoic acid

To a solution of methyl 2-(4-bromophenyl)propanoate (2 g, 8.2 mmol) in tetrahydrofuran (30 mL) and water (20 mL) was added (1.2 g, 41 mmol) at room temperature, the mixture solution was stirred for 3 hours, then diluting with ethyl acetate (100 mL), and acidified with hydrochoric acid (6 M) to ph=3. The organic layer was dried over sodium sulfate, and concentrated to dry. The result residue 2-(4-bromophenyl)propanoic acid (2 g) was used directly for the next step without purification.

2-(4-bromophenyl)propan-1-ol

To a solution of 2-(4-bromophenyl)propanoic acid (2 g, crude) in tetrahydrofuran (50 mL) was added a solution of borane in tetrahydrofuran (1 mmol/L, 13 mL, 13 mmol) at 0° C. The mixture solution was stirred for 3 hours at 0° C., then worm to room temperature, and quenched by water. The solvent was removed, purified by column chromatography (silica-gel, petroleum:ethyl acetate=5:1) to give 2-(4-bromophenyl)propan-1-ol as a colorless oil (1.8 g, 96%). $^1$H NMR (300 MHz, CDCl$_3$): δ 1.7.38-7.46 (m, 2H), 7.10-7.13 (m, 2H), 3.72-3.78 (m, 2H), 2.84-2.98 (m, 1H), 1.23-1.27 (m, 3H).

Methyl 4-(1-hydroxypropan-2-yl)benzoate

A suspension solution of 2-(4-bromophenyl)propan-1-ol (1.8 g, 8.4 mmol), 1,3-Bis(diphenylphosphino)propane (500 mg), palladium acetate (500 mg) and triethylamine (2 mL) in methanol (100 mL) was filled carbon monoxide gas in a seal tube. The reaction was heated to 100° C. for 30 hours. The mixture solution was concentrated to dry. The residue was purified by column chromatography (silica-gel, petroleum/ethyl acetate=8:1) to give 4-(1-hydroxypropan-2-yl)benzoate as a colorless oil (0.8 g, 50%). $^1$H NMR (300 MHz, CDCl$_3$): δ 7.97-8.00 (m, 2H), 7.30-7.32 (m, 2H), 3.90 (s, 3H), 3.69-3.74 (m, 2H), 2.98-3.03 (m, 1H), 1.30 (t, J=2 Hz, 3H).

Methyl 4-(1-phenoxypropan-2-yl)benzoate

To a solution of 4-(1-hydroxypropan-2-yl)benzoate (100 mg, 0.52 mmol), phenol (78 mg, 0.8 mmol), triphenylphosphine (216 mg, 0.8 mmol) in tetrahydrofuran (30 mL) was added diisopropyl azodicarboxylate (166 mg, 0.8 mmol) at room temperature. The mixture solution was stirred for 18 hours. Then tetrahydrofuran was removed in vacuo. The residue was purified by column chromatography (silica-gel, petroleum/ethyl acetate=6:1) to give methyl 4-(1-phenoxypropan-2-yl)benzoate as a colorless oil (100 mg, 71%). $^1$H NMR (300 MHz, CDCl$_3$): δ 7.98 (d, J=9 Hz, 2H), 7.37 (d, J=9 Hz, 2H), 7.23-7.29 (m, 2H), 6.85-6.95 (m, 3H), 3.98-4.11 (m, 2H), 3.91 (s, 3H), 3.27-3.34 (m, 1H), 1.43 (d, J=6 Hz, 2H).

4-(1-phenoxypropan-2-yl)benzoic acid

A suspension solution of methyl 4-(1-phenoxypropan-2-yl)benzoate (0.1 g, 0.4 mmol) and lithium hydroxide (48 mg, 2 mmol) in tetrahydrofuran (20 mL) and water (10 mL) was stirred at room temperature for 2 hours. The mixture solution was diluting with ethyl acetate (50 mL), and acidified with hydrochloric acid to PH<4. The organic layer was separated, dried over sodium sulfate, and concentrated to dry. The residue 4-(1-phenoxypropan-2-yl)benzoic acid (60 mg, 65%) was used directly for the next step without purification.

4-(1-phenoxypropan-2-yl)-N-((2,4,6-trimethylpyridin-3-yl)methyl)benzamide

A mixture solution of 4-(1-phenoxypropan-2-yl)benzoic acid (60 mg, 0.2 mmol), 3-(aminomethyl)-4,6-dimethylpyridin-2-ol (37 mg, 0.2 mmol), 1-Hydroxybenzotriazole (30 mg, 0.2 mmol), 1-(3-Dimethylaminopropyl)-3-ethylcarbodiimide hydrochloride (40 mg, 0.2 mmol) and triethylamine (0.1 mL) in dichloromethane (50 mL) was stirred at room temperature for 18 hours. The mixture solution was diluting with ethyl acetate (50 mL), washed with water (20 mL). The organic layer was concentrated to dry. The residue was purified by column chromatography (silica-gel, dichloromethane/methanol=30:1) to give 4-(1-phenoxypropan-2-yl)-N-((2,4,6-trimethylpyridin-3-yl)methyl)benzamide as a yellow solid (60 mg, 64%). LRMS (M+H$^+$) m/z: calcd 391.19. found 391. HPLC Purity (214 nm): 95%. $^1$H NMR (300 MHz, CDCl$_3$): δ 7.70-7.78 (m, 3H), 7.21-7.31 (m, 4H), 6.82-6.94 (m, 3H), 5.91 (s, 1H), 4.54-4.56 (m, 2H), 3.93-4.07 (m, 2H), 3.24-3.28 (m, 1H), 2.38 (s, 3H), 2.25 (s, 3H), 1.39 (d, J=6 Hz, 3H).

Example 77

Synthesis of (S)-4-(1-(3-(2-aminopyrimidin-5-yl)phenoxy)ethyl)-N-((2-hydroxy-4,6-dimethylpyridin-3-yl)methyl)benzamide (Compound 181)

This synthesis involved 3 steps.

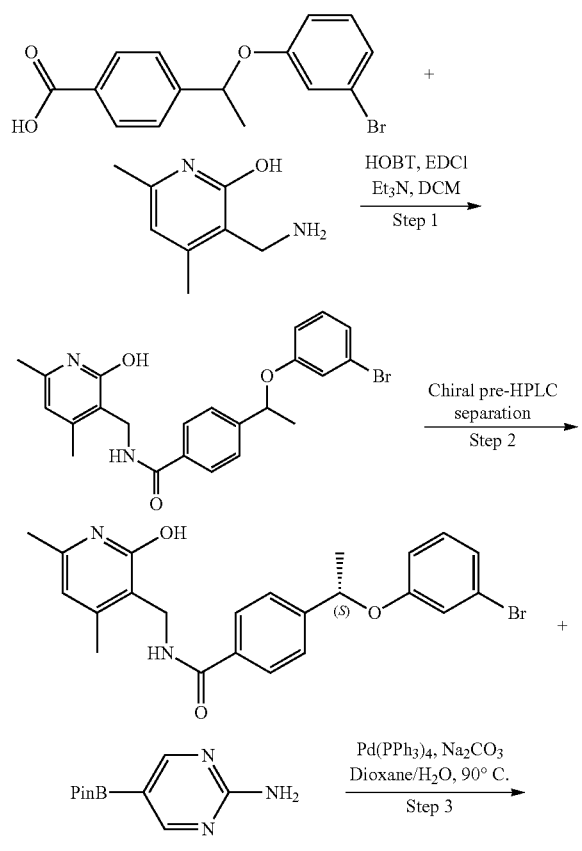

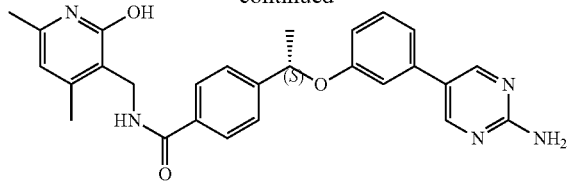

4-(1-(3-bromophenoxy)ethyl)-N-((2-hydroxy-4,6-dimethylpyridin-3-yl)methyl)benzamide To a solution of 4-(1-(3-bromophenoxy)ethyl)benzoic acid (0.9 g, 2.8 mmol), 1-ethyl-(3-dimethylaminopropyl)carbodiimide hydrochloride (0.77 g, 4.0 mmol) and 1-hydroxybenzotriazole (0.54 g, 4.0 mmol) in dichloromethane (20 mL) was added triethylamine (0.8 g, 8.0 mmol). The reaction mixture was stirred for 15 minutes at room temperature, then 3-(aminomethyl)-4,6-dimethylpyridin-2-ol (0.76 g, 5 mmol) was added. The reaction mixture was stirred at room temperature for 12 hours. After the reaction, the mixture was washed with water (20 mL), concentrated and purified by column chromatography (silica gel: dichloromethane: methanol=20:1) to give pure product 4-(1-(3-bromophenoxy)ethyl)-N-((2-hydroxy-4,6-dimethylpyridin-3-yl)methyl)benzamide (1.2 g, 93%) as a white solid.

(S)-4-(1-(3-bromophenoxy)ethyl)-N-((2-hydroxy-4,6-dimethylpyridin-3-yl)methyl)benzamide (1-(3-bromophenoxy)ethyl)-N-((2-hydroxy-4,6-dimethylpyridin-3-yl)methyl)benzamide (1.2 g, 2.6 mmol) was separated by chiral HPLC (Daicel AD-H (250 mm×20 mm×5 μm), hexane/ethanol (0.2 diethylamine)=30:70, flow rate: 13 mL/min), then (S)-4-(1-(3-bromophenoxy)ethyl)-N-((2-hydroxy-4,6-dimethylpyridin-3-yl)methyl)benzamide (0.5 g, 89%) were obtained.

(S)-4-(1-(3-(2-aminopyrimidin-5-yl)phenoxy)ethyl)-N-((2-hydroxy-4,6-dimethylpyridin-3-yl)methyl)benzamide (Compound 181)

To a solution of (S)-4-(1-(3-bromophenoxy)ethyl)-N-((2-hydroxy-4,6-dimethylpyridin-3-yl)methyl)benzamide (0.20 g, 0.44 mmol), 5-(4,4,5,5-tetramethyl-1,3,2-dioxaborolan-2-yl)pyrimidin-2-amine (0.13 g, 0.59 mmol), tetrakis(triphenylphosphine) palladium(0) (0.05 g, 0.04 mmol) in 1,4-dioxane (10 mL) and water (1.0 mL) was added sodium carbonate (0.14 g, 1.0 mmol). The reaction mixture was stirred at 90° C. for 12 hours. After the reaction, the mixture was poured to the water (100 mL) and the product was extracted by dichloromethane (100 mL), concentrated and purified by column chromatography (silica gel:dichloromethane:methanol=12:1 with 1% ammonia aqueous solution) to give pure product (S)-4-(1-(3-(2-aminopyrimidin-5-yl)phenoxy)ethyl)-N-((2-hydroxy-4,6-dimethylpyridin-3-yl)methyl)benzamide (0.12 g, 60%) as a white solid. LR MS (M+H$^+$): calcd for: 469.21. found 469.

HPLC Purity (214 nm) 96%. $^1$H NMR (300 MHz, DMSO-d$_6$): δ 11.44 (s, 1H), 8.47 (s, 2H), 8.29 (t, J=4.8 Hz, 1H), 7.77 (d, J=8.4 Hz, 2H), 7.46 (d, J=8.4 Hz, 2H), 7.24-7.06 (m, 3H), 6.85-6.76 (m, 3H), 5.82 (s, 1H), 5.65 (q, J=6.6 Hz, 1H), 4.25 (d, J=4.8 Hz, 2H), 2.13 (s, 3H), 2.09 (s, 3H), 1.55 (d, J=6.6 Hz, 3H).

Example 78

Synthesis of compound (R)— or (S)—N-((2-hydroxy-4,6-dimethylpyridin-3-yl)methyl)-2-methyl-4-(1-phenylethyl)benzamide (Compound I-185) and (S)— or (R)—N-((2-hydroxy-4,6-dimethylpyridin-3-yl)methyl)-2-methyl-4-(1-phenylethyl)benzamide (Compound I-186)

This synthesis involved 6 steps.

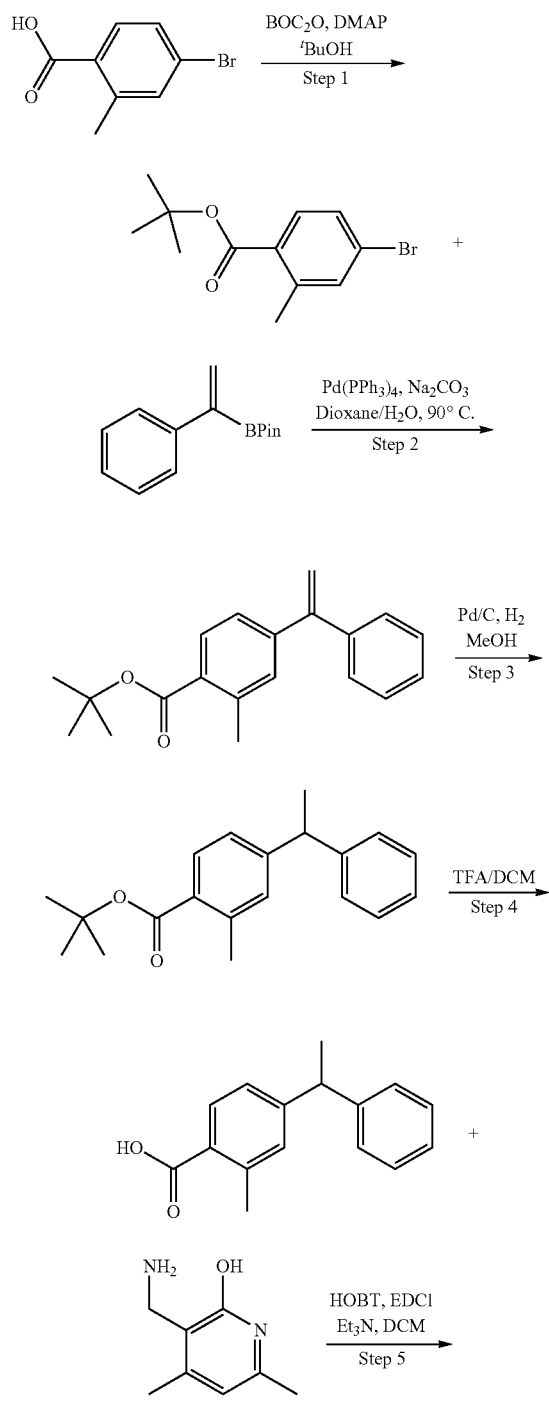

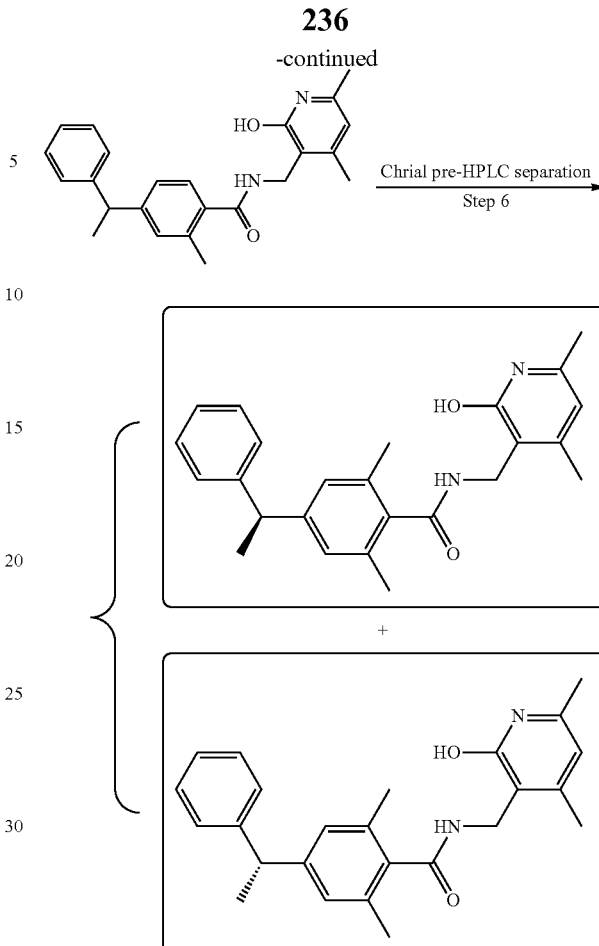

Tert-butyl 4-bromo-2-methylbenzoate

A solution of 4-dimethylamiopryidine (0.012 mol, 1.5 g) in 20 mL of tert-butanol was added to solution of 4-bromo-2-methylbenzoic acid (5 g, 0.023 mol) and di-tert-butyl dicarbonate (10.13 g, 0.046 mol) in 30 mL of tert-butanol. The mixture was stirred at room temperature for 18 hours. The mixture was concentrated and subjected to column chromatography (silica gel, petroleum ether/ethyl acetate=20:1) to give tert-butyl 4-bromo-2-methylbenzoate (6 g, 98%).

Tert-butyl 2-methyl-4-(1-phenylvinyl)benzoate

To a solution of tert-butyl 4-bromo-2-methylbenzoate (2 g, 7 mmol) in dioxane/water (50 mL, 4:1) was added styrylboronic acid pinacol ester (1.64 g, 7 mmol), tetrakis(triphenylphosphine)palladium (0.7 mmol, 0.904 g), sodium carbonate (21 mmol, 2.3 g). The mixture was stirred at 90° C. under nitrogen gas atmosphere for 18 hours. LC-MS showed the start material has been consumed. Then evaporated the solvent and purified by column chromatography (silica gel, petroleum ether/ethyl acetate=30:1) to give tert-butyl 2-methyl-4-(1-phenylvinyl)benzoate (1.8 g, 91%).

$^1$H-NMR (300 MHz, CD$_3$OD) δ 7.80 (d, J=8.1 Hz, 1H), 7.32-7.19 (m, 5H), 7.18 (s, 2H), 5.49 (t, J=3.3 Hz, 2H), 2.56 (s, 3H), 1.60 (s, 9H).

Tert-butyl 2-methyl-4-(1-phenylethyl)benzoate

The tert-butyl 2-methyl-4-(1-phenylvinyl)benzoate (1.8 g, 6.1 mmol), palladium 10% on carbon (0.61 mmol, 700 mg) and 30 mL menthol was stirred at room temperature under the atmosphere of hydrogen (4 atmosphere) for 24 hours. Then mixture was filtered, the filtrate was concentrated to give tert-butyl 2-methyl-4-(1-phenylethyl)benzoate (1.6 g, 90%) product. $^1$H-NMR (300 MHz, CD$_3$OD) δ 7.67 (d, J=8.1 Hz, 1H), 7.24-7.08 (m, 7H), 4.02 (m, 1H), 2.48 (s, 3H), 1.59-1.61 (s, 9H).

2-methyl-4-(1-phenylethyl)benzoic acid

To a solution of tert-butyl 2-methyl-4-(1-phenylethyl)benzoate (1.6 g, 5.4 mmol) in dichloromethane 9 mL, and 3 mL trifluoroacetic acid was added. The mixture was stirred 0.5 hour. Thin layer chromatography showed full conversion. The reaction mixture was concentrated to give 2-methyl-4-(1-phenylethyl)benzoic acid (1 g, 90%).

N-((2-hydroxy-4,6-dimethylpyridin-3-yl)methyl)-4-(1-phenylethyl)benzamide 2-methyl-4-(1-phenylethyl)benzoic acid (150 mg, 0.6 mmol) was dissolved in 20 mL dichloromethane, and then N-hydroxybenzotriazole (0.9 mmol, 100 mg), 1-(3-Dimethylaminopropyl)-3-ethylcarbodiimide hydrochloride (0.9 mmol, 200 mg), triethylamine (10.48 mmol, 3 mL) was added to the mixture. After the mixture was stirred at room temperature for 10 minute, 3-(aminomethyl)-4,6-dimethylpyridin-2-ol (0.6 mmol, 90 mg) was added. The mixture was stirred at room temperature for 18 hours. Then washed with water (30 mL), extracted with dichloromethane (40 mL). The organic layer were concentrated and subjected to column chromatography (silica gel, dichloromethane/menthol=15/1) to give N-((2-hydroxy-4,6-dimethylpyridin-3-yl)methyl)-4-(1-phenylethyl)benzamide (150 mg, 90%). $^1$H NMR (300 MHz, CD$_3$OD): δ 7.25-7.05 (m, 8H), 6.08 (s, 1H), 4.44 (s, 2H), 4.09 (m, 1H), 2.35 (s, 3H), 2.31 (s, 3H), 2.23 (s, 3H) 1.59 (d, J=8.4 Hz, 3H); LRMS (M+H$^+$) m/z: calcd 374.20. found 374.

(R)— or (S)—N-((2-hydroxy-4,6-dimethylpyridin-3-yl)methyl)-2-methyl-4-(1-phenylethyl)benzamide (Compound I-185) and (S)— or (R)—N-((2-hydroxy-4,6-dimethylpyridin-3-yl)methyl)-2-methyl-4-(1-phenylethyl)benzamide (Compound I-186)

N-((2-hydroxy-4,6-dimethylpyridin-3-yl)methyl)-4-(1-phenylethyl)benzamide was separated by chiral HPLC (condition: Daicel AD-H (250 mm×20 mm×5 m), hexane/ethanol (0.2 diethylamine)=30:70, flow rate: 13 mL/min). Then (R)—N-((2-hydroxy-4,6-dimethylpyridin-3-yl)methyl)-4-(1-phenylethyl)benzamide (60 mg, 56%) and (S)—N-((2-hydroxy-4,6-dimethylpyridin-3-yl)methyl)-4-(1-phenylethyl)benzamide (70 mg, 58%) were obtained. The retention times for the two enantiomers were 5.26 minute and 6.59 minute in chiral prep-HPLC chromatography.

LRMS (M+H$^+$) m/z: calcd 407.19. found 407. HPLC Purity (214 nm): 99%. $^1$H NMR (300 MHz, CD$_3$OD): δ 7.25-7.05 (m, 8H), 6.08 (s, 1H), 4.44 (s, 2H), 4.09 (m, 1H), 2.35 (s, 3H), 2.31 (s, 3H), 2.23 (s, 3H) 1.59 (d, J=8.4 Hz, 3H). Although the separated enantiomers were not optically characterized, for convenience sake the (R) enantiomer was designated Compound I-185 and the (S) enantiomer designated Compound I-186.

Example 79

Synthesis of (R)— or (S)-3-fluoro-N-((2-hydroxy-4,6-dimethylpyridin-3-yl)methyl)-4-(1-phenoxyethyl)benzamide (Compound I-160) and (S)- or (R)-3-fluoro-N-((2-hydroxy-4,6-dimethylpyridin-3-yl)methyl)-4-(1-phenoxyethyl)benzamide (I-161)

This synthesis involved 6 steps.

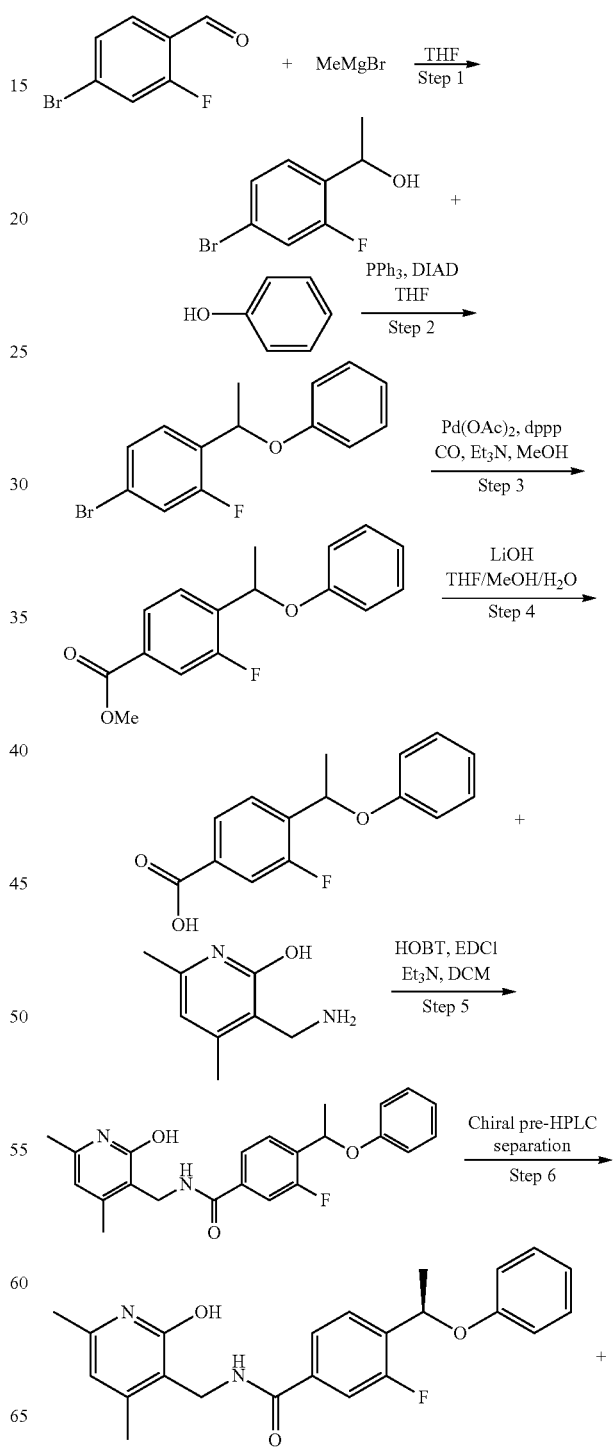

-continued

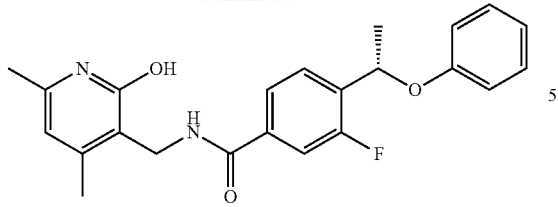

1-(4-bromo-2-fluorophenyl)ethanol

To a solution of 4-bromo-2-fluorobenzaldehyde (2.01 g, 9.9 mmol) in tetrahydrofuran (20 mL) was dropped methylmagnesium bromide (10 mmol, 1N in tetrahydrofuran) and the mixture was stirred at room temperature for 30 minutes. TLC showed all starting material was consumed, then the mixture was quenched with aqueous ammonium chloride (1N, 5 mL). To the mixture, water (50 mL) was added and extracted with dichloromethane (2*50 mL). The combined organic phase was separated, dried over sodium sulfate, filtered and concentrated. The residue was purified by column chromatography (silica gel, petroleum ether/ethyl acetate=20:1) to give the product 1-(4-bromo-2-fluorophenyl)ethanol as colorless oil (2.0 g, 92%). $^1$H NMR (300 MHz, CDCl$_3$): δ 7.40-7.19 (m, 3H), 5.16 (q, J=6.3 Hz, 1H), 1.76 (s, 1H), 1.49 (d, J=6.3 Hz, 3H).

4-bromo-2-fluoro-1-(1-phenoxyethyl)benzene

To a solution of 1-(4-bromo-2-fluorophenyl)ethanol (0.5 g, 2.3 mmol) in tetrahydrofuran (20 mL) was added triphenylphosphine (0.78 g, 3 mmol) and phenol (284 mg, 3 mmol). The mixture was stirred at room temperature for 30 minutes then diisopropyl azodicarboxylate (0.6 g, 3 mmol) was added and the mixture was stirred at room temperature for 12 hours. The mixture was concentrated in vacuo. To the residue, water (50 mL) was added, extracted with dichloromethane (2*50 mL). The combined organic phase was separated, dried over sodium sulfate, filtered and concentrated to give a residue. The residue was purified by column chromatography (silica gel, petroleum ether/ethyl acetate=100:1) to give 4-bromo-2-fluoro-1-(1-phenoxyethyl)benzene (600 mg, 88%) as colorless oil. $^1$H NMR (300 MHz, CDCl$_3$): δ 7.34-7.18 (m, 5H), 6.93-6.81 (m, 3H), 5.57 (q, J=6.3 Hz, 1H), 1.63 (d, J=6.3 Hz, 3H).

Methyl 3-fluoro-4-(1-phenoxyethyl)benzoate

To a reversible vial was added 4-bromo-2-fluoro-1-(1-phenoxyethyl)benzene (600 mg, 2 mmol) in methanol (16 mL) was added triethylamine (909 mg, 9 mmol), palladium diacetate (116 mg, 0.5 mmol) and 1,3-bis(diphenylphosphino)propane (480 mg, 1.16 mmol). Then the reaction mixture was charged with carbon monoxide. The mixture was reacted under carbon oxide atmosphere (15 atm) at 110° C. for 12 hours. The suspension was concentrated in vacuo. To the residue, water was added (50 mL), extracted with dichloromethane (2*50 mL). The combined organic phase was separated, dried over sodium sulfate, filtered and concentrated to give a residue. The residue was purified by column chromatography (silica gel, petroleum ether/ethyl acetate=40:1) to give methyl 3-fluoro-4-(1-phenoxyethyl) benzoate as colorless oil (0.40 g, 72%). $^1$H NMR (300 MHz, CDCl$_3$): δ 7.77-7.68 (m, 2H), 7.50 (t, J=7.8 Hz, 1H), 7.23-7.16 (m, 2H), 6.91-6.80 (m, 3H), 5.64 (q, J=6.3 Hz, 1H), 3.90 (s, 3H), 1.64 (d, J=6.3 Hz, 3H).

3-fluoro-4-(1-phenoxyethyl)benzoic acid

To a solution of methyl 3-fluoro-4-(1-phenoxyethyl)benzoate (400 mg, 1.5 mmol) in mixed solution of tetrahydrofuran/methanol/water=3:1:1 (4 mL) was added lithium hydroxide (200 mg, 8.4 mmol). The mixture was stirred at room temperature for 2 hours. The suspension was concentrated in vacuo and quenched with hydrochloride acid aqueous (1N, 5 mL). To the residue, water (50 mL) was added and extracted with dichloromethane (2*50 mL). The combined organic phase was separated, dried over sodium sulfate, filtered and concentrated to give a residue. The residue was purified by column chromatography (silica gel, petroleum ether/ethyl acetate=5:1) to give 3-fluoro-4-(1-phenoxyethyl)benzoic acid as pale solid (300 mg, 82%).

3-fluoro-N-((2-hydroxy-4,6-dimethylpyridin-3-yl)methyl)-4-(1-phenoxyethyl)benzamide A solution of 3-fluoro-4-(1-phenoxyethyl)benzoic acid (300 mg, 1.2 mmol) in dichloromethane (15.0 mL) was added N-hydroxybenzotriazole (270 mg, 2 mmol), 1-(3-dimethylaminopropyl)-3-ethylcarbodiimide hydrochloride (384 mg, 2 mmol), triethylamine (202 mg, 2 mmol). The mixture was stirred for 30 minutes. Then 3-(aminomethyl)-4,6-dimethylpyridin-2-ol (270 mg, 1.8 mmol) was added and the mixture was stirred at room temperature for 12 hours. To the mixture, water (50 mL) was added. The mixture was then extracted with dichloromethane (2*50 mL). The combined organic phase was separated, dried over sodium sulfate, filtered and concentrated to give a residue. The residue was purified by preparative-TLC (silica gel, methanol/dichloromethane=1:20, 1% NH$_3$) to give 3-fluoro-N-((2-hydroxy-4,6-dimethylpyridin-3-yl)methyl)-4-(1-phenoxyethyl)benzamide as white solid (217 mg, 46%). LRMS (M+H$^+$) m/z: calcd 394.17. found 394. HPLC purity (214 nm): 96%. $^1$H NMR (300 MHz, CD$_3$OD): δ 7.57-7.49 (m, 3H), 7.16 (t, J=8.4 Hz, 2H), 6.85-6.82 (m, 3H), 6.09 (s, 1H), 5.68 (q, J=6.6 Hz, 1H), 4.45 (s, 2H), 2.34 (s, 3H), 2.23 (s, 3H), 1.62 (d, J=8.4 Hz, 3H).

(R)— or (S)-3-fluoro-N-((2-hydroxy-4,6-dimethylpyridin-3-yl)methyl)-4-(1-phenoxyethyl)benzamide (Compound I-160) and (S)— or (R)-3-fluoro-N-((2-hydroxy-4,6-dimethylpyridin-3-yl)methyl)-4-(1-phenoxyethyl)benzamide (I-161)

3-Fluoro-N-((2-hydroxy-4,6-dimethylpyridin-3-yl)methyl)-4-(1-phenoxyethyl)benzamide was separated by chiral prep-HPLC (Daicel AD-H (250 mm×20 mm×5 um), hexane: ethanol (0.2% diethylamine)=50: 50, flow rate: 13 mL/min), then (R or S) 3-fluoro-N-((2-hydroxy-4,6-dimethylpyridin-3-yl)methyl)-4-(1-phenoxyethyl)benzamide (58 mg, 54%) and (S or R). 3-fluoro-N-((2-hydroxy-4,6-dimethylpyridin-3-yl)methyl)-4-(1-phenoxyethyl)benzamide (58 mg, 54%) was obtained. The retention times for the two enantiomers were 5.973 minutes and 7.549 minutes in chiral HPLC chromatography. LRMS (M+H$^+$) m/z: calcd 394.17. found 394. HPLC purity (214 nm): 100%. $^1$H NMR (300 MHz, CD$_3$OD): δ 7.57-7.49 (m, 3H), 7.16 (t, J=8.4 Hz, 2H), 6.85-6.82 (m, 3H), 6.09 (s, 1H), 5.68 (q, J=6.6 Hz, 1H), 4.45 (s, 2H), 2.34 (s, 3H), 2.23 (s, 3H), 1.62 (d, J=8.4 Hz, 3H). Although the separated enantiomers were not optically characterized, for convenience sake, the (R)-enantiomer was designated as Compound I-160 and the (S)-enantiomer as Compound I-161.

Example 80

Synthesis of compound (R) 4H-[1,2,4]triazolo[4,3-a][1,5]benzodiazepine, 5,6-dihydro-1,4-dimethyl-8-(6-aminopyridin-3-yl)-6-(4-chlorophenyl) (Compound 174)

This synthesis involved 3 steps.

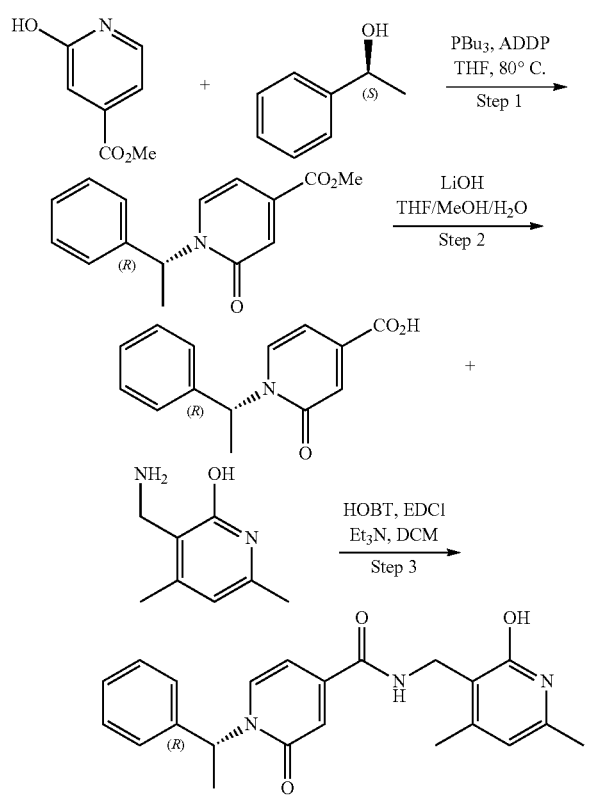

(R)-methyl 2-oxo-1-(1-phenylethyl)-1,2-dihydropyridine-4-carboxylate

To a solution of methyl 2-hydroxyisonicotinate (459 mg, 3 mmol) and (S)-1-phenylethanol (366 mg, 3 mmol) in tetrahydrofuran (30 mL) was added dropwise a solution of tributylphosphine (909 mg, 4.5 mmol) in tetrahydrofuran (10 mL). The reaction solution was stirred at 0° C. for 0.5 hours. To the above solution was added 1,1'-(Azodicarbonyl)-dipiperidine (1134 mg, 4.5 mmol). The reaction mixture was stirred at 0° C. for 0.5 hours. The reaction mixture was concentrated in vacuo. The residue was purified by column chromatography (silica gel, petroleum ether/ethyl acetate=1:1) to give (R)-methyl 2-oxo-1-(1-phenylethyl)-1,2-dihydropyridine-4-carboxylate as a white solid (451 mg, 58%).

(R)-2-oxo-1-(1-phenylethyl)-1,2-dihydropyridine-4-carboxylic acid

A mixture of (R)-methyl 2-oxo-1-(1-phenylethyl)-1,2-dihydropyridine-4-carboxylate (451 mg, 1.75 mmol), lithium hydroxide monohydrate (369 mg, 8.77 mmol), water (4 mL) and methanol (4 mL) in tetrahydrofuran (12 mL) was stirred at 20° C. for 12 hours. The reaction mixture was concentrated. The residue was acidified with concentrated hydrochloride solution to pH=2. The mixture was extracted with ethyl acetate (20 mL×2). The organic phase was dried over sodium sulfate and filtered. The filtrate was concentrated. The residue was purified by column chromatography (silica gel, petroleum ether/ethyl acetate=1:2) to give (R)-2-oxo-1-(1-phenylethyl)-1,2-dihydropyridine-4-carboxylic acid as a white solid (336 mg, 80%). LRMS (M+H$^+$) m/z: calcd 243.13. found 243.

(R)—N-((2-hydroxy-4,6-dimethylpyridin-3-yl)methyl)-2-oxo-1-(1-phenylethyl)-1,2-dihydropyridine-4-carboxamide (Compound 174)

To a solution of (R)-2-oxo-1-(1-phenylethyl)-1,2-dihydropyridine-4-carboxylic acid (336 mg, 1.4 mmol), 1-hydroxybenzotriozole (373 mg, 2.8 mmol), 1-(3-Dimethylaminopropyl)-3-ethylcarbodiimide hydrochloride (531 mg, 2.8 mmol), triethylamine (1.0 mL) in dichloromethane (30 mL) was added 3-(aminomethyl)-4,6-dimethylpyridin-2-ol (210 mg, 1.4 mmol). The reaction mixture was stirred at 0° C. for 13 hours. The mixture was washed with water (20 mL×2). The organic phase was dried over sodium sulfate and filtered. The filtrate was concentrated. The residue was purified by column chromatography (silica gel, dichloromethane/methanol=10:1) to give (R)—N-((2-hydroxy-4,6-dimethylpyridin-3-yl)methyl)-2-oxo-1-(1-phenylethyl)-1,2-dihydropyridine-4-carboxamide as a white solid (360 mg, 68%). LRMS (M+H$^+$) m/z: calcd 377.17. found 377. HPLC Purity (214 nm): 100%. $^1$H NMR (300 MHz, d$^6$-DMSO): δ 11.44 (s, 1H), 8.53 (t, J=4.8 Hz, 1H), 7.66 (d, J=3.3 Hz, 1H), 7.38-7.26 (m, 5H), 6.78 (s, 1H), 6.51 (dd, J=1.8 Hz, J$_2$=6.9 Hz, 1H), 6.13 (q, J=7.2 Hz, 1H), 5.84 (s, 1H), 4.22 (d, J=4.8 Hz, 2H), 2.13 (s, 3H), 2.10 (s, 3H), 1.68 (d, J=7.2 Hz, 3H).

(S)-4H-[1,2,4]triazolo[4,3-a][1,5]benzodiazepine, 5,6-dihydro-1,4-dimethyl-8-(6-aminopyridin-3-yl)-6-(4-chlorophenyl) (Compound 175) was similarly prepared using the appropriate chiral reagents.

Example 81

Synthesis of compound (R)— or (S)-2-fluoro-N-((2-hydroxy-4,6-dimethylpyridin-3-yl)methyl)-4-(1-phenoxyethyl)benzamide (Compound I-187) and (S)- or (R)-2-fluoro-N-((2-hydroxy-4,6-dimethylpyridin-3-yl)methyl)-4-(1-phenoxyethyl)benzamide (Compound I-188)

This synthesis involved 6 steps.

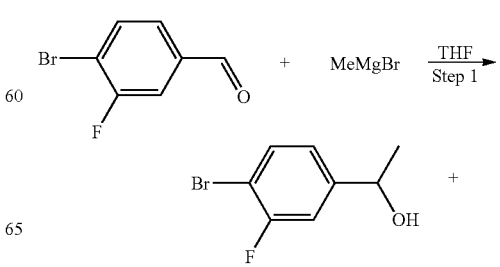

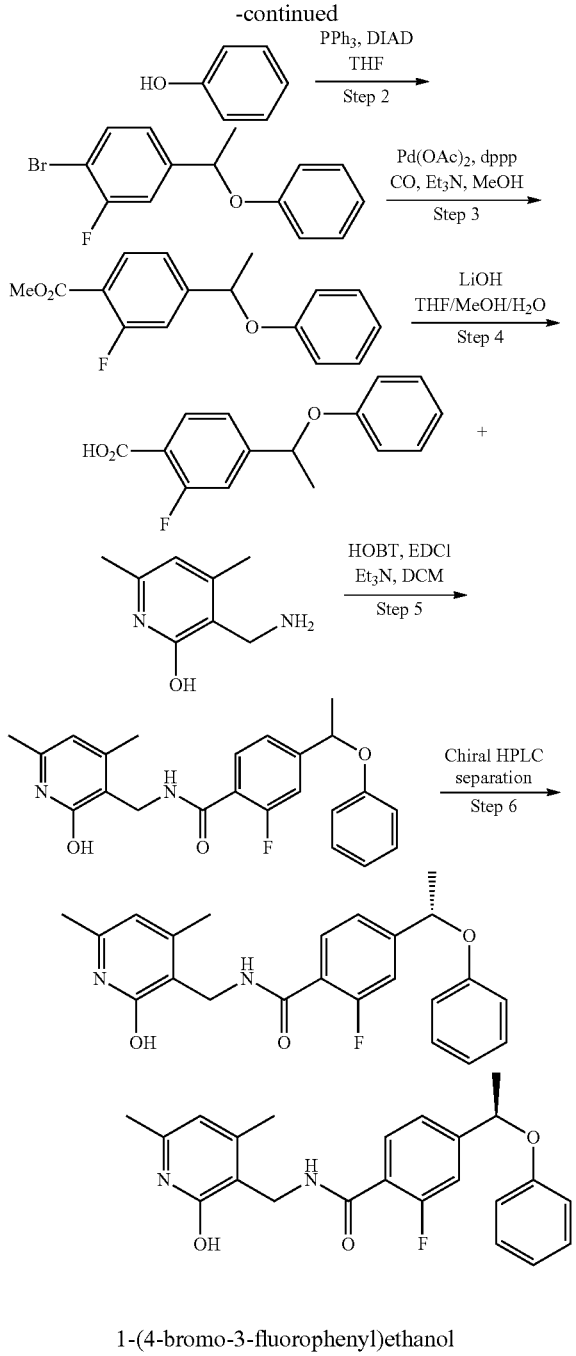

1-(4-bromo-3-fluorophenyl)ethanol

To a solution of 4-bromo-3-fluorobenzaldehyde (5 g, 24.75 mmol) in anhydrous tetrahydrofuran (100 mL) was added methyl magnesium bromide (3 M solution in tetrahydrofuran, 8.21 mL) at −45° C. under the atmosphere of nitrogen then stirred at room temperature. After 2 hours, LC-MS showed the desired product has received. The aqueous of ammonium chloride (15 mL) was added to quench the reaction, and extracted with ethyl acetate (50 mL), combined and concentrated the organic layers. The crude product was purified by column chromatography (petroleum ether/ethyl acetate=1:1) to give 1-(4-bromo-3-fluorophenyl)ethanol (4 g, 78%). LCMS (M+H$^+$) m/z: calcd 217.97. found 218. $^1$H NMR (300 MHz, CD$_3$OD): δ 7.92-7.87 (m, 1H), 7.23-7.19 (m, 1H), 7.07-7.10 (m, 1H), 4.80 (d, J=6.3 Hz, 1H), 1.41 (t, J=2.7 Hz, 3H).

1-bromo-2-fluoro-4-(1-phenoxyethyl)benzene

A solution of 1-(4-bromo-3-fluorophenyl)ethanol (1 g, 4.58 mmol), phenol (474 mg, 4.58 mmol), and triphenyl phosphine (2.4 g, 6.88 mmol) was stirred in dry tetrahydrofuran (40 mL) under nitrogen atmosphere. After 1 h, the mixture was cooled to 0° C. Diisopropyl azodicarboxylate (2.3 g, 6.88 mmol) was added with drop-wise method and the reaction was stirred at room temperature for 18 hours. The solvent was evaporated and the residue was purified by column chromatography (silica gel, petroleum ether) to get 1-bromo-2-fluoro-4-(1-phenoxyethyl)benzene (900 mg, 89%).

Methyl 2-fluoro-4-(1-phenoxyethyl)benzoate

To a mixture of 1-bromo-2-fluoro-4-(1-phenoxyethyl)benzene (900 mg, 3.23 mmol) in menthol (30 mL) was added palladium acetate (170 mg, 0.65 mmol), 1,3-bis(diphenylphosphino) propane (242 mg, 0.65 mmol) and triethylamine (1.3 mg, 3 mmol). The reaction mixture was stirred and heated to 100° C. under carbon monoxide atmosphere in a pressure reactor for 18 hours. The mixture was cooled to room temperature and filtered, the organic was evaporated to dryness, and then the residue was purified by column chromatography (silica gel, petroleum ether/ethyl acetate=10/1) to give methyl 2-fluoro-4-(1-phenoxyethyl)benzoate (600 mg, 69%). $^1$H NMR (300 MHz, CDCl$_3$) δ 7.88 (t, J=7.5 Hz, 1H), 7.25-7.14 (m, 4H), 6.92-6.80 (m, 3H), 5.30 (d, J=6.6 Hz 1H), 3.90 (s, 3H), 1.62 (d, J=6.6 Hz, 3H).

2-fluoro-4-(1-phenoxyethyl)benzoic acid

To a solution of Lithium hydroxide (420 mg, 10.2 mmol) in tetrahydrofuran, menthol and water (20 mL, 3:1:1, V/V) was added methyl 2-fluoro-4-(1-phenoxyethyl)benzoate (600 mg, 2.42 mmol). The reaction mixture was stirred at room temperature for 1 h. The mixture was quench with 10% hydrochloric acid (aqueous), extracted with dichloromethane and menthol (30 mL, 10:1), the combine organic layer was dried with anhydrous sodium sulfate, filtered and evaporated to give product 2-fluoro-4-(1-phenoxyethyl)benzoic acid (450 mg, 82%). LCMS (M+H$^+$) m/z: calcd 260.08. found 260.

2-fluoro-N-((2-hydroxy-4,6-dimethylpyridin-3-yl)methyl)-4-(1-phenoxyethyl)benzamide The 2-fluoro-4-(1-phenoxyethyl)benzoic acid (150 mg, 0.514 mmol), 2-(7-Aza-1H-benzotriazole-1-yl)-1,1,3,3-tetramethyluroniumhexafluorophosphate (353 mg, 0.84 mmol) was dissolved in 20 mL dichloromethane, and then added triethylamine (2 mL). After the mixture was stirred at room temperature for 10 minute, 3-(aminomethyl)-4,6-dimethylpyridin-2-ol (0.514 mmol, 96 mg) was added. The mixture was stirred at room temperature for 12 hours then washed with water (10 mL), extracted with dichloromethane (20 mL). The organic layer were concentrated and s purified by column chromatography (silica gel, dichloromethane/methanol=20:1) to give 2-fluoro-N-((2-hydroxy-4,6-dimethylpyridin-3-yl) methyl)-4-(1-phenoxyethyl)benzamide (70 mg, 47%). LCMS (M+H$^+$) m/z: calcd 394.17. found 394. $^1$H NMR (300 MHz, CD$_3$OD) δ 7.69 (t, J=6.1 Hz, 1H), 7.28-7.13 (m, 4H), 6.86-6.81 (m, 3H), 6.06 (s, 1H), 5.43-5.41 (m, 1H), 4.47 (s, 2H), 2.34 (s, 3H), 2.22 (s, 3H). 1.57 (d, J=6.6 Hz, 3H).

(R)— or (S)-2-fluoro-N-((2-hydroxy-4,6-dimethylpyridin-3-yl)methyl)-4-(1-phenoxyethyl)benzamide (Compound I-187) and (S)— or (R)-2-fluoro-N-((2-hydroxy-4,6-dimethylpyridin-3-yl)methyl)-4-(1-phenoxyethyl)benzamide (Compound I-188)

2-fluoro-N-((2-hydroxy-4,6-dimethylpyridin-3-yl)methyl)-4-(1-phenoxyethyl)benzamide (70 mg, 0.17 mmol) was separated by chiral HPLC (Daicel AD-H (250 mm×20 mm×5 µm), hexane/ethanol (0.2 diethylamine)=30:70, flow rate: 13 mL/min), then (R or S) 2-fluoro-N-((2-hydroxy-4,6-dimethylpyridin-3-yl)methyl)-4-(1-phenoxyethyl)benzamide (30 mg, 56%) and (S or R) 2-fluoro-N-((2-hydroxy-4,6-dimethylpyridin-3-yl)methyl)-4-(1-phenoxyethyl)benzamide (25 mg, 58%) were obtained. The retention times were 13.06 minute and 9.83 minute for the two enantiomers in chiral prep-HPLC chromatography. LCMS (M+H$^+$) m/z: calcd 394.17. found 394. HPLC Purity (214 nm): 100%. $^1$H NMR (300 MHz, CD$_3$OD) δ 7.69 (t, J=6.1 Hz, 1H), 7.28-7.13 (m, 4H), 6.86-6.81 (m, 3H), 6.06 (s, 1H), 5.43-5.41 (m, 1H), 4.47 (s, 2H), 2.34 (s, 3H), 2.22 (s, 3H), 1.57 (d, J=6.6 Hz, 3H). Although the separated enantiomers were not optically characterized, for convenience sake the (R) enantiomer was designated Compound I-187 and the (S)-enantiomer was designated as Compound I-188.

Example 82

Synthesis of (R)— or (S)-4-(1-(4-cyanophenoxy)ethyl)-N-((2-hydroxy-4,6-dimethylpyridin-3-yl)methyl)benzamide (Compound 176) and (S)— or (R)-4-(1-(4-cyanophenoxy)ethyl)-N-((2-hydroxy-4,6-dimethylpyridin-3-yl)methyl)benzamide (Compound 177)

The synthesis involved 4 steps.

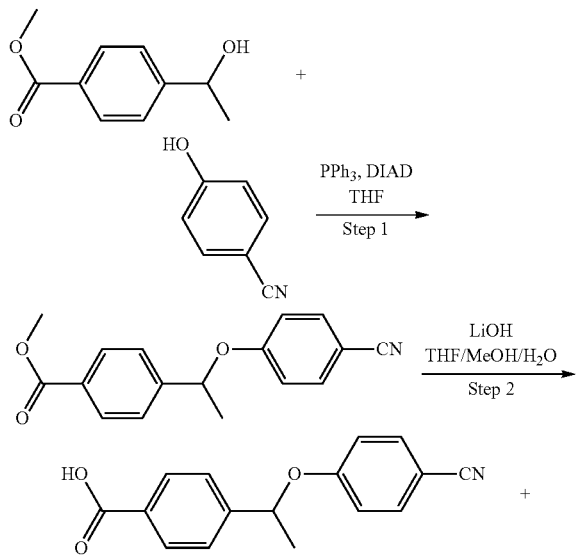

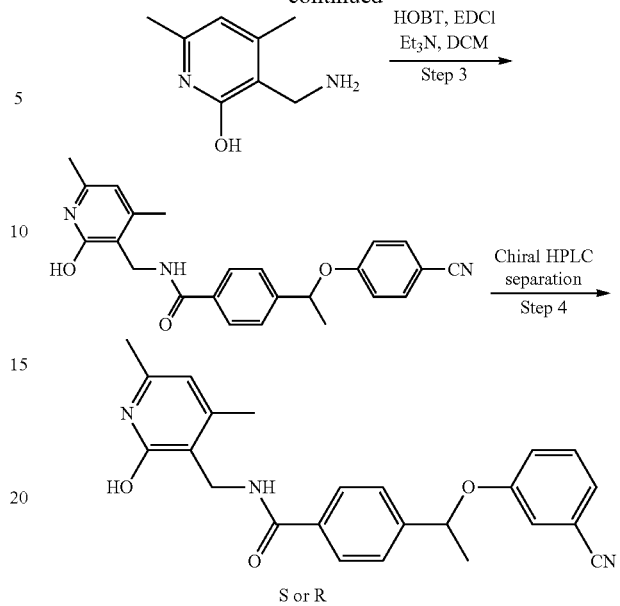

Methyl 4-(1-(4-cyanophenoxy)ethyl)benzoate

Methyl 4-(1-hydroxyethyl)benzoate (540 mg, 3 mmol), 3-hydroxybenzonitrile (360 mg, 3 mmol), triphenylphosphine (1.04 mg, 4 mmol), azodicarboxylic acid diisopropyl ester (800 mg, 4 mmol) in tetrahydrofuran (130 mL) were stirred at 20° C. for 12 hours. Water was added and the mixture was extracted with ethyl acetate (150 mL×3), the combined organic phase was dried by sodium sulfate, then filtered. The filtrate was evaporated in vacuum and the residue was purified by column chromatography (silica gel, petroleum ether/ethyl acetate=3:1) to give methyl 4-(1-(4-cyanophenoxy)ethyl)benzoate (370 mg, 45%) as colorless oil. LRMS (M+H$^+$) m/z: calcd 281.11. found 281.

4-(1-(4-cyanophenoxy)ethyl)benzoic acid

A mixture of methyl 4-(1-(4-cyanophenoxy)ethyl)benzoate (370 mg, 1.3 mmol), lithium hydroxide monohydrate (571 mg, 13.6 mmol), tetrahydrofuran (45 mL), methanol (15 mL) and water (15 mL) was stirred at 20° C. for 4 hours. The mixture was neutralized to pH=1 with concentrated hydrochloric acid and then extracted with ethyl acetate (55 mL×3). The combined organic phase was dried by sodium sulfate, then filtered. The filtrate was evaporated in vacuo to give 4-(1-(4-cyanophenoxy)ethyl)benzoic acid (310 mg, 74%) as a white solid. LRMS (M+H$^+$) m/z: cald 267.09. found 267.

4-(1-(4-cyanophenoxy)ethyl)-N-((2-hydroxy-4,6-dimethylpyridin-3-yl)methyl)benzamide A mixture of 4-(1-(4-cyanophenoxy)ethyl)benzoic acid (260 mg, 1 mmol), 1-Ethyl-3-(3-dimethylaminopropyl)carbodiimide (382 mg, 2 mmol), 1-Hydroxybenzotriazole (270 mg, 2 mmol), triethylamine (0.4 mL) in dichloromethane (55 mL) were stirred at 25° C. for 0.5 hour. Then 3-(aminomethyl)-4,6-dimethylpyridin-2-ol (152 mg, 1 mmol) was added to the above mixture. The mixture was stirred at 25° C. for 12 hours. To the mixture, water (10 mL) was added and the mixture was extracted with dichloromethane (50 mL×3). The combined organic phase was dried by sodium sulfate and then filtered. The filtrate was evaporated in vacuo. The residue was purified by column chromatography (silica gel, dichloromethane/methanol=20:1) to give 4-(1-(4-cyanophenoxy)ethyl)-N-((2-hydroxy-4,6-dimethylpyridin-3-yl)methyl)benzamide (150 mg, 48%) as a white solid. LRMS (M+H⁺) m/z: cald. 401.17. found 401.

(R)— or (S)-4-(1-(4-cyanophenoxy)ethyl)-N-((2-hydroxy-4,6-dimethylpyridin-3-yl)methyl)benzamide (Compound 176) and (S)— or (R)-4-(1-(4-cyanophenoxy)ethyl)-N-((2-hydroxy-4,6-dimethylpyridin-3-yl)methyl)benzamide (Compound 177)

4-(1-(4-cyanophenoxy)ethyl)-N-((2-hydroxy-4,6-dimethylpyridin-3-yl)methyl)benzamide (150 mg, 0.38 mmol) was separated by chiral HPLC (Daicel AD-H (250 mm×20 mm×5 μm), hexane/ethanol (0.2 diethylamine)=35:65, flow rate: 13 mL/min), then (R or S) 4-(1-(4-cyanophenoxy)ethyl)-N-((2-hydroxy-4,6-dimethylpyridin-3-yl)methyl)benzamide (60 mg, 40%) and (S or R) 4-(1-(4-cyanophenoxy)ethyl)-N-((2-hydroxy-4,6-dimethylpyridin-3-yl)methyl)benzamide (65 mg, 44%) were obtained. LRMS (M+H⁺) m/z: calcd 401.17. found 401. HPLC Purity (214 nm): 100%. $^1$H NMR (300 MHz, d$^6$-DMSO): δ 11.47 (s, 1H), 8.33-8.31 (m, 1H), 7.80 (d, J=8.1 Hz, 2H), 7.68 (d, J=7.8 Hz, 2H), 7.44 (d, J=8.1 Hz, 2H), 7.05 (d, J=8.1 Hz, 2H), 5.85 (s, 1H), 5.70 (q, J=6.6 Hz, 1H), 4.28 (d, J=4.8 Hz, 2H), 2.12 (d, J=14.1 Hz, 6H), 1.57 (d, J=6.6 Hz, 3H). Although the separated enantiomers were not optically characterized, for convenience sake the (R) enantiomer was designated Compound I-176 and the (S)-enantiomer was designated as Compound I-177.

Example 83

Synthesis of N-((2-hydroxy-4-methoxy-6-methylpyridin-3-yl)methyl)-4-phenoxybenzamide (Compound I-195)

This synthesis involved 6 steps.

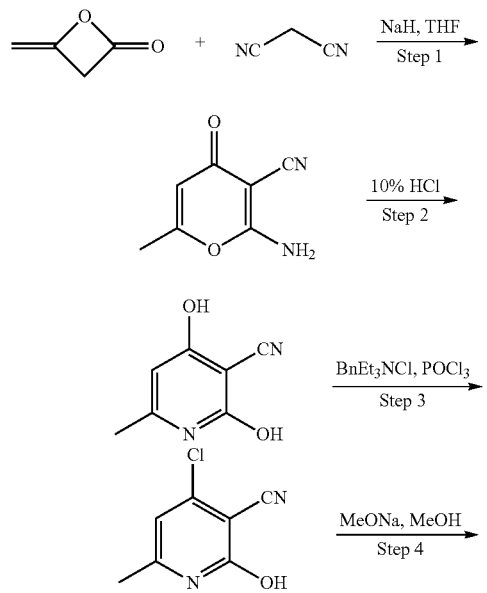

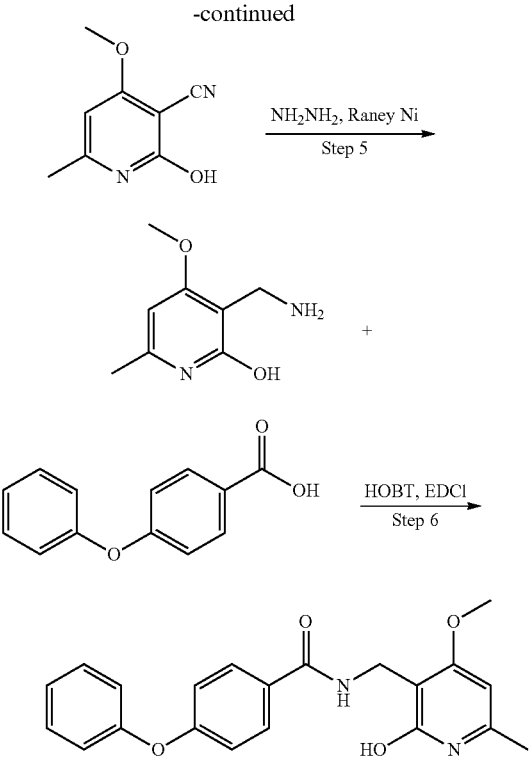

2-amino-6-methyl-4-oxo-4H-pyran-3-carbonitrile

To a solution of malononitrile (3.3 g, 50 mmol) in 100 mL of anhydrous tetrahydrofuran was added sodium hydride (60%, 2.2 g, 55 mmol) at −10° C. The resulting reaction mixture was stirred for 2 hours. Then diketene (4.2 g, 50 mmol) was added dropwise to the solution. The reaction mixture was allowed to warmed to room temperature and continued to stir for 30 minutes. The mixture was neutralized with diluted hydrochloric acid, and then concentrated in vacuo to give crude 2-amino-6-methyl-4-oxo-4H-pyran-3-carbonitrile as red solid, which was used in the next step without further purification.

2,4-dihydroxy-6-methylnicotinonitrile

A suspension of 2-amino-6-methyl-4-oxo-4H-pyran-3-carbonitrile (6.0 g, 40 mmol) in 10% HCl (60 mL) was heated under reflux for 4 hours. The precipitate was collected by filtration and washed with water, and then recrystallized from methanol to give 2,4-dihydroxy-6-methylnicotinonitrile (5.0 g, 80%) as a brown solid. $^1$H NMR (300 MHz, CD$_3$OD): δ 12.44-12.46 (m, 1H), 11.69 (s, 1H), 5.85 (s, 1H), 2.15 (s, 3H).

4-chloro-2-hydroxy-6-methylnicotinonitrile

To a solution of 2,4-dihydroxy-6-methylnicotinonitrile (1.5 g, 10 mmol) in acetonitrile (50 mL) were added benzyltriethylammonium chloride (9.1 g, 40 mmol) and phosphoryl chloride (6.13 g, 40 mmol). The reaction mixture was heated to 40° C. for 4 hours at the same temperature. LC-MS showed that 2,4-dihydroxy-6-methylnicotinonitrile was consumed completely. The solvent was removed by rotary evaporation. To the residue was added dichloromethane (100 mL) and water (50 mL). The organic phase was separated, and it was washed with brine (50 mL) once, dried over anhydrous magnesium sulfate, filtered, and concentrated under reduced pressure to give crude product, which was purified by silica gel column chromatography with dichloromethane/methanol=10:1 to afford 4-chloro-2-hydroxy-6-methylnicotinonitrile (800 mg, 24%) as a brown solid.

2-hydroxy-4-methoxy-6-methylnicotinonitrile

To a pressure vessel were added 4-chloro-2-hydroxy-6-methylnicotinonitrile (337 mg, 2.0 mmol), sodium methanolate (540 mg, 10.0 mmol), methanol (15 mL), and magnetic stirrer. The pressure vessel was sealed, and it was stirred at 100° C. for 16 hours. After being cooled to room temperature, the vessel was opened, and the reaction solution was transferred to an eggplant-shaped bottle. The solvent was removed by rotary evaporation. To the residue was added water (10 mL) and ethyl acetate (50 mL). The layers were separated. The organic phase was concentrated in vacuo to provide crude product which was purified by silica gel column chromatography with dichloromethane/methanol=10:1 to afford 2-hydroxy-4-methoxy-6-methylnicotinonitrile (70 mg, 21%) as a brown solid.

3-(aminomethyl)-4-methoxy-6-methylpyridin-2-ol 2-hydroxy-4-methoxy-6-methylnicotinonitrile (70 mg, 0.43 mmol) was dissolved in ethanol (10 mL) and was warmed to 55° C. before it was treated with Raney nickel (0.5 mL slurry in water) followed by addition of hydrazine monohydrate (2 mL). The resulting mixture was allowed to stir at 55° C. for 2 hours. The cooled reaction mixture was filtered through diatomaceous earth, rinsed with methanol. The filtrate was concentrated in vacuo to provide crude product which was purified by silica gel column chromatography with dichloromethane/methanol=10:1 to afford 3-(aminomethyl)-4-methoxy-6-methylpyridin-2-ol (40 mg, 56% yield) as a yellow solid. $^1$H NMR (300 MHz, DMSO-d$^6$): δ 6.04 (s, 1H), 4.87 (br s, 3H), 3.77 (s, 3H), 3.42 (s, 2H), 2.15 (s, 3H).

N-((2-hydroxy-4-methoxy-6-methylpyridin-3-yl)methyl)-4-phenoxybenzamide (Compound I-195)

To a solution of 4-phenoxybenzoic acid (60 mg, 0.28 mmol) in dichloromethane (15 mL) were added 1-Hydroxybenzotriazole (49 mg, 0.36 mmol), 1-(3-Dimethylaminopropyl)-3-ethylcarbodiimide hydrochloride (69 mg, 0.36 mmol) and triethylamine (73 mg, 0.72 mmol). The resulting solution was stirred at room temperature for 30 minutes. Then 3-(aminomethyl)-4-methoxy-6-methylpyridin-2-ol (40 mg, 0.24 mmol) was added to the solution, and it was stirred at room temperature for 16 hours. Water (20 mL) was added to the mixture. It was extracted with dichloromethane (50 mL). The organic layer was concentrated in vacuo to provide crude product which was purified by silica gel column chromatography dichloromethane/methanol=10:1 to afford N-((2-hydroxy-4-methoxy-6-methylpyridin-3-yl)methyl)-4-phenoxybenzamide (32 mg, 37%) as a white solid.

LRMS (M+H$^+$) m/z: calcd 365.14. found 365. HPLC Purity (214 nm): 100%. $^1$H NMR (300 MHz, CD$_3$OD): δ 7.76-7.79 (d, J=9 Hz, 2H), 7.37-7.42 (m, 2H), 7.15-7.20 (m, 1H), 6.95-7.05 (m, 4H), 6.26 (s, 1H), 4.46 (m, 2H), 3.91 (s, 3H), 2.32 (s, 3H).

Example 84

Synthesis of compound N-((2-hydroxy-4,6-dimethylpyridin-3-yl)methyl)-4-(1-(tetrahydrofuran-3-yl oxy)ethyl)benzamide (Compound I-184) and its Enantiomers This synthesis involved 5 steps.

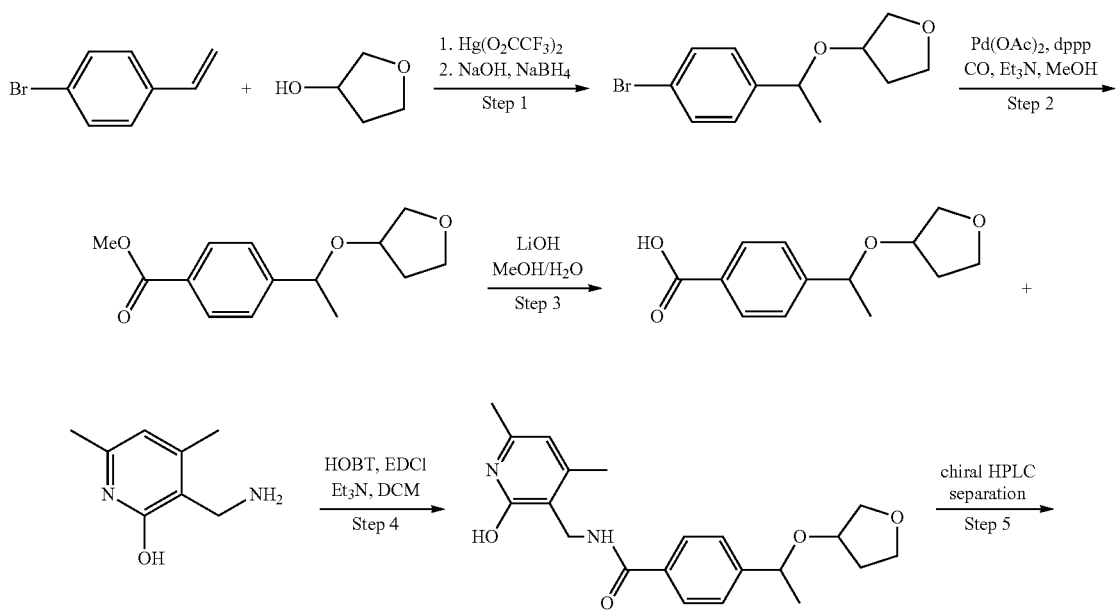

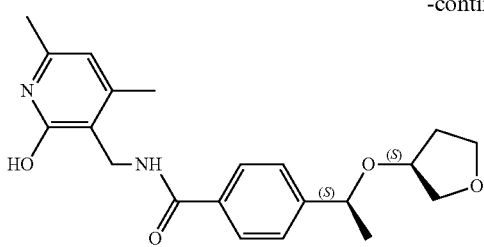
+
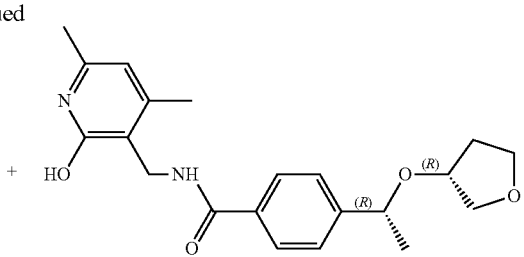

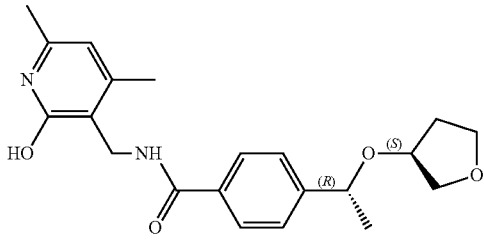
+
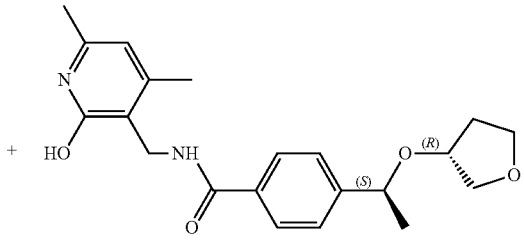

3-(1-(4-bromophenyl)ethoxy)-tetrahydrofuran

To the solution of 3-(1-(4-bromophenyl)ethoxy)-tetrahydrofuran (410 mg, 1.52 mmol) in methanol (20 mL) was added 1,3-bis(diphenylphosphino) propane (125 mg, 0.3 mmol), palladium acetate (67.3 mg, 0.3 mmol), and triethylamine (767 mg, 7.6 mmol), the mixture was stirred at 90° C. for 12 hours under an atmosphere of carbon monoxide in sealed tube. Then the mixture was concentrated and purified by column chromatography (silica gel, dichloromethane/methanol=20:1) to give methyl-4-(1-(tetrahydrofuran-3-yloxy)ethyl)benzoate (371 mg, 97.6%) as oil

4-(1-(tetrahydrofuran-3-yloxy)ethyl)benzoic acid

To the solution of methyl 4-(1-(tetrahydrofuran-3-yloxy)ethyl)benzoate (371 mg, 1.48 mmol) in methanol (15 mL) and water (5 mL) was added lithium hydroxide hydrate (100 mg, 2.4 mmol) were add ed. The mixture was stirred at room temperature for 12 hours. Then the reaction mixture was acidified by hydrochloric acid aqueous solution (1 N) to adjust pH=6 and extracted with dichloro methane (10 mL×3). The organic layers were combined and concentrated to give 4-(1-(tetrahydrofuran-3-yloxy)ethyl)benzoic acid (311 mg, 89%)

N-((2-hydroxy-4,6-dimethylpyridin-3-yl)methyl)-4-(1-(tetrahydrofuran-3-yloxy)ethyl)benzamide (Compound I-184)

A mixture of 4-(1-(tetrahydrofuran-3-yloxy)ethyl)benzoic acid (311 mg, 1.32 mmol), 1-ethyl-3-(3-dimethylaminopropyl)carbodiimide hydrochloride (380 mg, 1.98 mmol), N-hydroxybenzotriazole (267.3 mg, 1.98 mmol) and triethylamine (400 mg, 3.96 mmol) in dichloromethane (50 mL) was stirred for 30 minutes at room temperature. Then to the mixture, 3-(aminomethyl)-4,6-dimethylpyridin-2-ol (200.64 mg, 1.32 mmol) was added. The resultant mixture was stirred at room temperature for 12 hours. Then the mixture was washed with water (30 mL×3). The organic layer was concentrated to give a residue and the residue was purified by column chromatography (silica gel, dichloromethane/methanol=20:1) to give N-((2-hydroxy-4,6-dimethylpyridin-3-yl)methyl)-4-(1-(m-tolyloxy)ethyl)benzamide (452 mg, 92%). LRMS (M+H$^+$) m/z: calcd 370. found 370. $^1$H NMR (300 MHz, CD$_3$OD): δ 7.78 (d, J=8.4 Hz, 2H), 7.42-7.41 (m, 2H), 6.11 (s, 1H), 4.61-4.58 (m, 1H), 4.49 (s, 2H), 4.07-4.04 (m, 1H), 3.87-3.62 (m, 4H), 2.37 (s, 3H), 2.24 (s, 3H), 1.98-1.87 (m, 2H), 1.40-1.38 (m, 3H)

Enantiomers of N-((2-hydroxy-4,6-dimethylpyridin-3-yl)methyl)-4-(1-(tetrahydrofuran-3-yloxy)ethyl)benzamide N-((2-hydroxy-4,6-dimethylpyridin-3-yl)methyl)-4-(1-(tetrahydrofuran-3-yloxy)ethyl)benzamide (157 m g, 0.42 mmol) was separated into four enantiomers by chiral prep-HPLC (Daicel OJ-H (200 mm×20 mm×5 um), hexane: ethanol (0.2% DEA)=80:20, flow rate: 20 mL/min). The retention times were 11.030 minutes (21 mg, 13%), 12.126 minutes (27 mg, 17%), 8.011 minutes (14 mg, 9%) and 11.054 (11 mg, 7%) minutes respectively in chiral HPLC chromatography. LRMS (M+H$^+$) m/z: calcd 370.19. found 370. $^1$H NMR (300 MHz, d$_4$-CD$_3$OD): δ 7.78 (d, J=8.4 Hz, 2H), 7.42-7.41 (m, 2H), 6.11 (s, 1H), 4.61-4.58 (m, 1H), 4.49 (s, 2H), 4.07-4.04 (m, 1H), 3.87-3.62 (m, 4H), 2.37 (s, 3H), 2.24 (s, 3H), 1.98-1.87 (m, 2H), 1.40-1.38 (m, 3H). Each of the enantiomers is a compound of Formula I and part of the present invention. Although the separated enantiomers were not optically characterized, for convenience sake the (R, R) enantiomer was designated Compound I-203; the (S,S) enantiomer was designated Compound I-204; the (R, S) enantiomer was designated Compound I-205; and the (S,R) enantiomer was designated Compound I-206.

Example 85

Synthesis of 3-(3-cyanophenoxy)-N-((2-hydroxy-4,6-dimethylpyridin-3-yl)methyl)benzamide (Compound I-164)

This synthesis involved 4 steps.

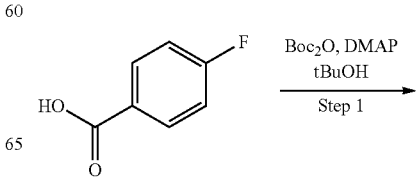

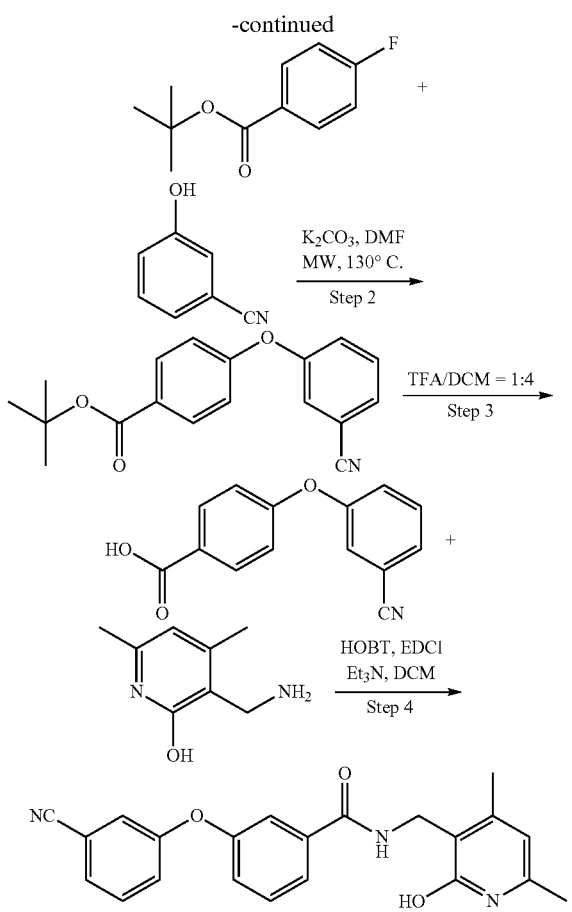

Tert-butyl 4-fluorobenzoate

To the solution of 4-fluorobenzoic acid (10 g, 0.07 mol) in tert-Butanol (200 ml) was added 4-di methylaminopyridine (4.36 g, 35.7 mmol), then Pyrocarbonic acid di-tert-butyl ester (31.1 g, 0.14 mol) was added at 0° C., the solution was stirred for 4 h at room temperature, then water (200 ml) was added and extracted with dichloromethane, evaporated the solvent purified by column chromatography (silica gel, Petroleum ether/ethyl acetate=20:1) to give tert-butyl 4-fluorobenzoate (10.2 g, 74%) H-NMR (300 MHz, CD$_3$OD) $^1$H-NMR (300 MHz, CD$_3$OD) δ 7.98 (m, 2H), 7.15 (m, 2H), 1.59 (s, 9H)

Tert-butyl 4-(3-cyanophenoxy)benzoate

To the solution of tert-butyl 4-fluorobenzoate (500 mg, 2.55 mmol) and 3-hydroxybenzonitrile (306 mg, 2.55 mmol) in N,N-dimethylformamide (80 mL) was added potassium carbonate (528 mg, 3.8 mmol), the mixture was stirred at 130° C. for 1 hour under microwave. Then evaporated the solvent purified by column chromatography (silica gel, Petroleum ether/ethyl acetate=10:1) to give tert-butyl-4-(3-cyanophenoxy)benzoate (185 mg, 57%), as oil, $^1$H-NMR (300 MHz, CD$_3$OD) δ 8.00 (m, 2H), 7.56 (m, 2H), 7.43 (m, 2H), 7.05 (m, 2H), 1.59 (s, 9H).

4-(3-cyanophenoxy)benzoic acid

To the solution of tert-butyl 4-(3-cyanophenoxy)benzoate (178 mg, 0.6 mmol) in dichloromethane 50 ml) was added trifluoroacetic acid (12.5 ml) the solution was stirred at room temperature for 12 hours, water (50 mL) was added and washed 3 times, the organic layer was evaporated and purified by column chromatography (silica gel, Petroleum ether/ethyl acetate=10:1) to give 4-(3-cyanophenoxy)benzoic acid (40 mg, 28%)

3-(3-cyanophenoxy)-N-((2-hydroxy-4,6-dimethylpyridin-3-yl)methyl)benzamide

A solution of 4-(3-cyanophenoxy)benzoic acid (40 mg, 0.17 mmol) in dichloromethane (20 mL) was added 1-ethyl-3-(3-dimethylaminopropyl)carbodiimide hydrochloride (48 mg, 0.25 mmol), N-hydroxy benzotriazole (34 mg, 0.25 mmol) and triethylamine (34 mg, 0.33 mmol), stirred for 30 min. Then 3-(aminomethyl)-4,6-dimethylpyridin-2-ol (26 mg, 0.17 mmol) was added and the mixture was stirred at room temperature for 12 hours. The mixture was washed with water (50 mL), dried over sodium sulfate, concentrated. The residue was purified by column chromatography (silica gel, dichloromethane/methanol=20:1) to give 3-(3-cyanophenoxy)-N-((2-hydroxy-4,6-dimethylpyridin-3-yl)methyl)benzamide (21 mg, 58%)

LRMS (M+H$^+$) m/z: calcd: 373. found 373; $^1$H-NMR (300 MHz, DMSO) δ 11.49 (s, 1H), 8.35 (s, 1H), 7.89 (m, 2H), 7.59 (m, 2H), 7.40 (m, 1H), 7.08 (m, 2H), 5.85 (s, 1H), 2.28 (s, 2H), 3.14 (m, 6H).

Example 86

Synthesis of compound N-((2-hydroxy-4,6-dimethylpyridin-3-yl)methyl)-4-(1-(pyrimidin-4-yloxy)ethyl)benzamide (Compound I-155)

This synthesis involved 4 steps.

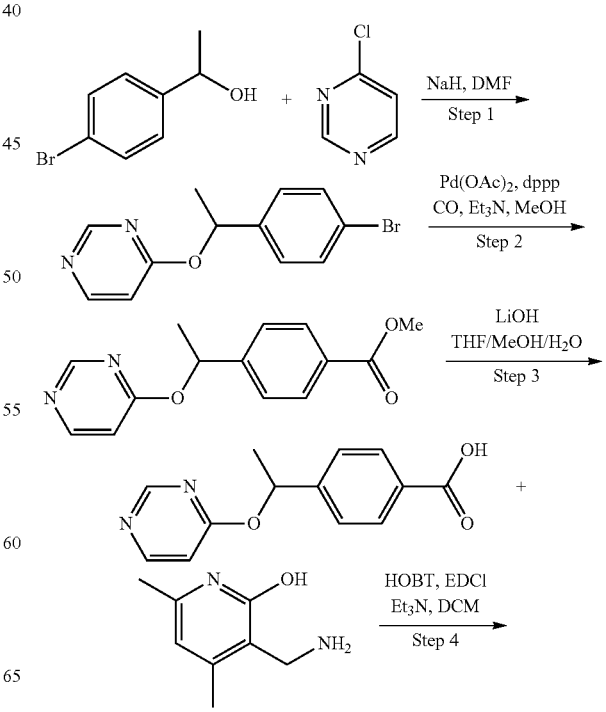

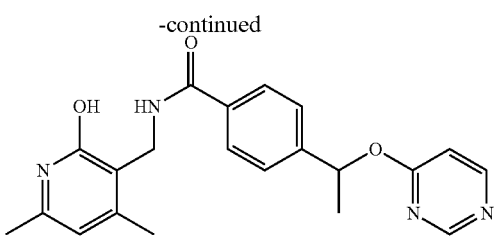

4-(1-(4-bromophenyl)ethoxy)pyrimidine

To a solution of 1-(4-bromophenyl)ethanol (1 g, 5 mmol) in 20 mL of anhydrous N,N-dimethylformamide was added sodium hydride (0.36 g, 15 mmol) at room temperature and then stirred for 1 hour, 4-chloropyrimidine hydrochloride (1 g, 6 mmol) was added, and then heated at 100° C. for 12 hours. The reaction mixture was concentrated, the residue was purified by chromatography with petroleum/ethyl acetate=1:1 to afford 4-(1-(4-bromophenyl)ethoxy)pyrimidine (1.2 g, 86% yield). LRMS (M+H+) m/z: calcd for 278.01. found 278. $^1$H NMR (300 MHz, CD$_3$OD) δ 8.65 (s, 1H), 8.42 (d, J=6.0 Hz, 1H), 7.48 (d, J=8.4 Hz, 2H), 7.35 (d, J=8.4 Hz, 2H), 6.92 (dd, J=6.0 and 1.2 Hz, 1H), 6.26 (q, J=6.6 Hz, 1H), 1.64 (d, J=6.6 Hz, 3H).

Methyl 4-(1-(pyrimidin-4-yloxy)ethyl)benzoate

To a solution of 4-(1-(4-bromophenyl)ethoxy)pyrimidine (0.7 g, 2.5 mmol) in methanol (30 mL) was added palladium acetate (55 mg, 0.25 mmol), 1,3-bis(diphenylphosphino)propane (140 mg, 0.3 mmol) and triethylamine (2 mL, 13 mmol) and then stirred at 100° C. under 15 atm carbon monoxide atmosphere for 16 hours. The reaction mixture was concentrated, the residue was purified by chromatography with petroleum/ethyl acetate=1:1 to give methyl 4-(1-(pyrimidin-4-yloxy)ethyl)benzoate (0.6 g, 93% yield). LRMS (M+H$^+$) m/z: calcd for 258.10. found 258.

$^1$H NMR (CD$_3$OD, 300 MHz) δ 8.64 (s, 1H), 8.43 (d, J=5.7 Hz, 1H), 7.98 (d, J=8.4 Hz, 2H), 7.50 (d, J=8.4 Hz, 2H), 6.94 (dd, J=6.0 and 1.2 Hz, 1H), 6.34 (q, J=6.6 Hz, 1H), 3.89 (s, 3H), 1.66 (d, J=6.6 Hz, 3H).

4-(1-(pyrimidin-4-yloxy)ethyl)benzoic acid

To a solution of methyl 4-(1-(pyrimidin-4-yloxy)ethyl)benzoate (0.26 g, 1 mmol) in methanol (5 mL) and tetrahydrofuran (15 mL) was added lithium hydroxide (120 mg, 5 mmol) in water (5 mL), then stirred at room temperature for 5 hours. The reaction mixture was concentrated, the residue was acidified with 6 N hydrochloric acid, by filtration the solid was collected to give-4-(1-(pyrimidin-4-yloxy)ethyl) benzoic acid (0.19 g, 78% yield). LRMS (M+H+) m/z: calcd for 244.08. found 244.

N-((2-hydroxy-4,6-dimethylpyridin-3-yl)methyl)-4-(1-(pyrimidin-4-yloxy)ethyl)benzamide (Compound I-155)

To a solution of 4-(1-(pyrimidin-4-yloxy)ethyl)benzoic acid (0.1 g, 0.4 mmol) in anhydrous dichloromethane (20 mL) was added 1H-benzo[d][1,2,3]triazol-1-ol (85 mg, 0.6 mmol), 1-(3-Dimethylaminopropyl)-3-ethylcarbodiimide hydrochloride (120 mg, 0.6 mmol) and triethylamine (0.2 mL, 1.2 mmol), and stirred at room temperature for 0.5 hour, 3-(aminomethyl)-4,6-dimethylpyridin-2-ol (90 mg, 0.6 mmol) was added and stirred for 3 hours. To the reaction mixture was added water (20 mL), extracted with dichloromethane (20 mL) two times, combined and concentrated the organic layers, the residue was purified by column chromatography with dichloromethane/methanol=15:1 to afford N-((2-hydroxy-4,6-dimethylpyridin-3-yl)methyl)-4-(1-(pyrimidin-4-yloxy)ethyl)benzamide (60 mg, 40% yield). LRMS (M+H+) m/z: calcd for 378.17. found 378. HPLC purity (214 nm): 98%. $^1$H NMR (CD$_3$OD, 300 MHz) δ 8.67 (s, 1H), 8.46 (d, J=6.0 Hz, 1H), 7.81 (d, J=8.1 Hz, 2H), 7.53 (d, J=8.4 Hz, 2H), 6.98 (dd, J=6.0 and 1.2 Hz, 1H), 6.36 (q, J=6.6 Hz, 1H), 6.15 (s, 1H), 4.52 (s, 2H), 2.39 (s, 3H), 2.28 (s, 3H), 1.69 (d, J=8.7 Hz, 3H).

Example 87

Synthesis of compound 3-(4-cyanophenoxy)-N-((2-hydroxy-4,6-dimethylpyridin-3-yl)methyl)benzamide (Compound I-167)

This synthesis involved 3 steps.

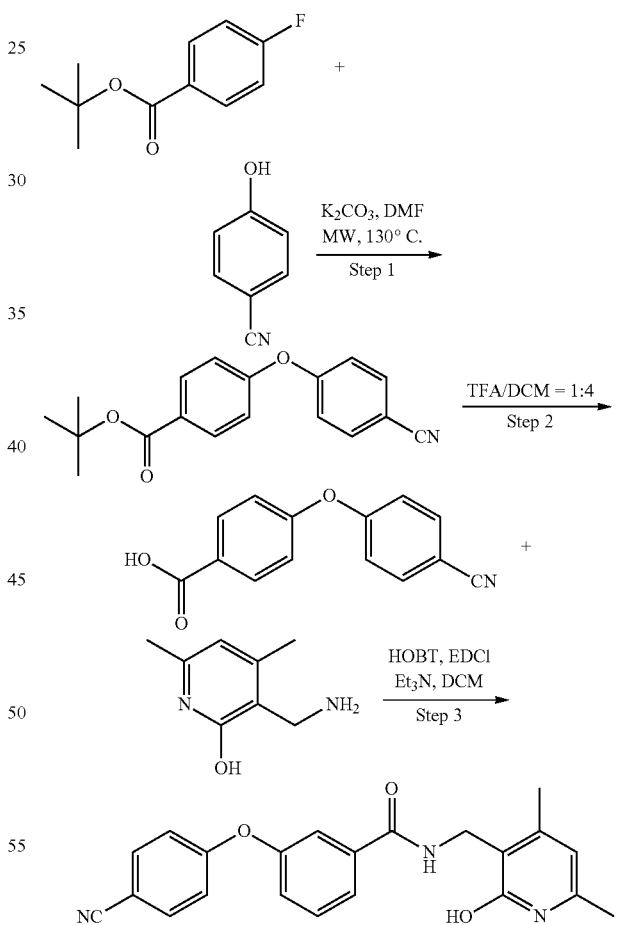

Tert-butyl 4-(4-cyanophenoxy)benzoate

To a solution of tert-butyl 4-fluorobenzoate (392 mg, 2 mmol) in dimethyl formamide (20 mL) was added 4-hydroxybenzonitrile (240 mg, 2 mmol) and potassium carbonate (552 mg, 4 mmol), the mixture was heated to 130° C. for 0.5 hour by microwave (pressure: 3.2 bar, equipment power:

150 W). The solvent was evaporated in vacuo and purified by column chromatography (silica gel, dichloromethane/methanol=20:1) to give tert-butyl 4-(4-cyanophenoxy)benzoate (80 mg, 14%). LRMS (M+H⁺) m/z: calcd 295.12. found 295.

4-(4-cyanophenoxy)benzoic acid

The solution of tert-butyl 4-(4-cyanophenoxy)benzoate (80 mg, 0.27 mmol) in dichloromethane: trifluoroacetic acid (4:1, 3 mL) was stirred overnight at room temperature. The solvent was evaporated in vacuo to give 4-(4-cyanophenoxy)benzoic acid (45 mg, 70%). LRMS (M+H⁺) m/z: calcd 239.06. found 239.

3-(4-cyanophenoxy)-N-((2-hydroxy-4,6-dimethylpyridin-3-yl)methyl)benzamide (Compound I-167)

4-(4-cyanophenoxy)benzoic acid (45 mg, 0.19 mmol), 1-(3-Dimethylaminopropyl)-3-ethylcarbodiimide hydrochloride (47 mg, 0.25 mmol), 1-Hydroxybenzotriazole (33 mg, 0.25 mmol), triethylamine (00.1 mL) in dichloromethane (5 mL) were stirred at 25° C. for 0.5 hour. Then 3-(aminomethyl)-4,6-dimethylpyridin-2-ol (50 mg, 0.33 mmol) was added to the above mixture. The mixture was stirred at 25° C. overnight and purified by column chromatography (silica gel, dichloromethane/methanol=12:1) to give 3-(4-cyanophenoxy)-N-((2-hydroxy-4,6-dimethylpyridin-3-yl)methyl)benzamide as a white solid (17 mg, 25%). LRMS (M+H⁺) m/z: 373.14. found 373. HPLC Purity (214 nm): 94%. ¹H NMR (300 MHz, DMSO): δ 11.47 (s, 1H), 8.38 (s, 1H), 7.94-7.84 (m, 4H), 7.17-7.13 (m, 4H), 5.85 (s, 1H), 4.29 (d, J=4.5 Hz, 2H), 2.17-2.09 (m, 6H).

Example 88

Synthesis of compound (R)— or (S)—N-((2-hydroxy-4,6-dimethylpyridin-3-yl)methyl)-2-methyl-4-(1-phenylethyl)benzamide (Compound I-172) and (S)— or (R)—N-((2-hydroxy-4,6-dimethylpyridin-3-yl)methyl)-2-methyl-4-(1-phenylethyl)benzamide (Compound I-173)

This synthesis involved 6 steps.

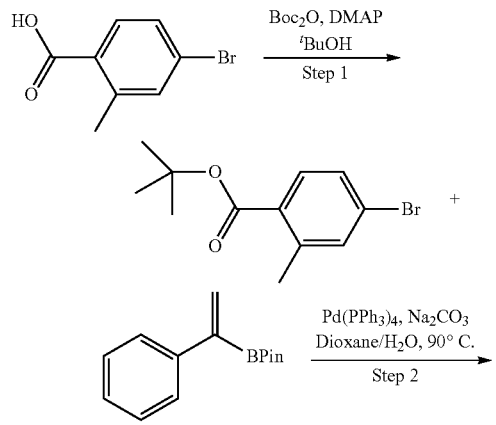

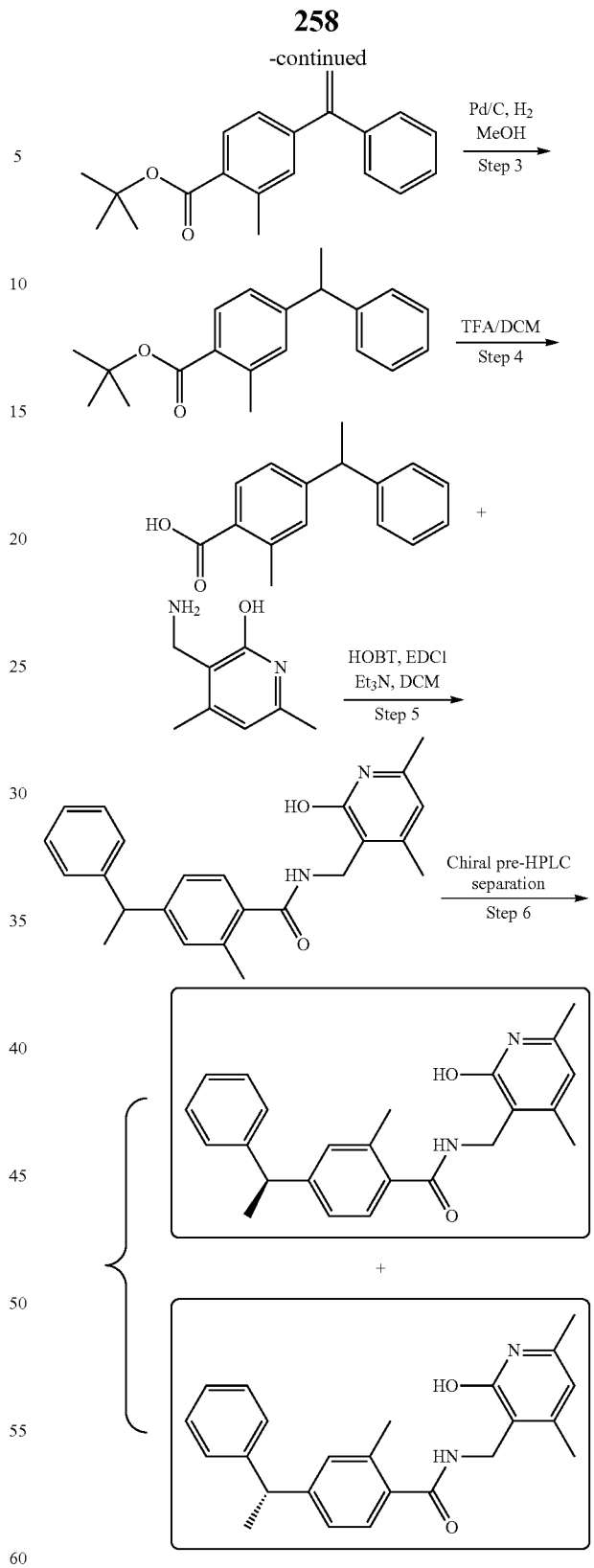

Tert-butyl 4-bromo-2-methylbenzoate

A solution of 4-dimethylamiopryidine (0.012 mol, 1.5 g) in 20 mL of tert-butanol was added to solution of 4-bromo-2-methylbenzoic acid (5 g, 0.023 mol) and di-tert-butyl dicarbonate (10.13 g, 0.046 mol) in 30 mL of tert-butanol. The mixture was stirred at room temperature for 18 hours. The mixture was concentrated and subjected to column chromatography (silica gel, petroleum ether/ethyl acetate=20:1) to give tert-butyl 4-bromo-2-methylbenzoate (6 g, 98%).

Tert-butyl 2-methyl-4-(1-phenylvinyl)benzoate

To a solution of tert-butyl 4-bromo-2-methylbenzoate (2 g, 7 mmol) in dioxane/water (50 mL, 4:1) was added styrylboronic acid pinacol ester (1.64 g, 7 mmol), tetrakis(triphenylphosphine)palladium (0.7 mmol, 0.904 g), sodium carbonate (21 mmol, 2.3 g). The mixture was stirred at 90° C. under nitrogen gas atmosphere for 18 hours. LC-MS showed the start material has been consumed. Then evaporated the solvent and purified by column chromatography (silica gel, petroleum ether/ethyl acetate=30:1) to give tert-butyl 2-methyl-4-(1-phenylvinyl)benzoate (1.8 g, 91%).

$^1$H-NMR (300 MHz, CD$_3$OD) δ 7.80 (d, J=8.1 Hz, 1H), 7.32-7.19 (m, 5H), 7.18 (s, 2H), 5.49 (t, J=3.3 Hz, 2H), 2.56 (s, 3H), 1.60 (s, 9H).

Tert-butyl 2-methyl-4-(1-phenylethyl)benzoate

The tert-butyl 2-methyl-4-(1-phenylvinyl)benzoate (1.8 g, 6.1 mmol), palladium 10% on carbon (0.61 mmol, 700 mg) and 30 mL menthol was stirred at room temperature under the atmosphere of hydrogen (4 atmosphere) for 24 hours. Then mixture was filtered, the filtrate was concentrated to give tert-butyl 2-methyl-4-(1-phenylethyl)benzoate (1.6 g, 90%) product. $^1$H-NMR (300 MHz, CD$_3$OD) δ 7.67 (d, J=8.1 Hz, 1H), 7.24-7.08 (m, 7H), 4.02 (m, 1H), 2.48 (s, 3H), 1.59-1.61 (s, 9H).

2-methyl-4-(1-phenylethyl)benzoic acid

To a solution of tert-butyl 2-methyl-4-(1-phenylethyl)benzoate (1.6 g, 5.4 mmol) in dichloromethane 9 mL, and 3 mL trifluoroacetic acid was added. The mixture was stirred 0.5 hour. Thin layer chromatography showed full conversion. The reaction mixture was concentrated to give 2-methyl-4-(1-phenylethyl)benzoic acid (1 g, 90%).

N-((2-hydroxy-4,6-dimethylpyridin-3-yl)methyl)-4-(1-phenylethyl)benzamide 2-methyl-4-(1-phenylethyl)benzoic acid (150 mg, 0.6 mmol) was dissolved in 20 mL dichloromethane, and then N-hydroxybenzotriazole (0.9 mmol, 100 mg), 1-(3-Dimethylaminopropyl)-3-ethylcarbodiimide hydrochloride (0.9 mmol, 200 mg), triethylamine (10.48 mmol, 3 mL) was added to the mixture. After the mixture was stirred at room temperature for 10 minute, 3-(aminomethyl)-4,6-dimethylpyridin-2-ol (0.6 mmol, 90 mg) was added. The mixture was stirred at room temperature for 18 hours. Then washed with water (30 mL), extracted with dichloromethane (40 mL). The organic layer were concentrated and subjected to column chromatography (silica gel, dichloromethane/menthol=15/1) to give N-((2-hydroxy-4,6-dimethylpyridin-3-yl)methyl)-4-(1-phenylethyl)benzamide (150 mg, 90%).

$^1$H NMR (300 MHz, CD$_3$OD): δ 7.25-7.05 (m, 8H), 6.08 (s, 1H), 4.44 (s, 2H), 4.09 (m, 1H), 2.35 (s, 3H), 2.31 (s, 3H), 2.23 (s, 3H) 1.59 (d, J=8.4 Hz, 3H); LRMS (M+H$^+$) m/z: calcd 374.20. found 374.

(R)— or (S)—N-((2-hydroxy-4,6-dimethylpyridin-3-yl)methyl)-2-methyl-4-(1-phenylethyl)benzamide (Compound I-172) and (S)— or (R)—N-((2-hydroxy-4,6-dimethylpyridin-3-yl)methyl)-2-methyl-4-(1-phenylethyl)benzamide (Compound I-173)

N-((2-hydroxy-4,6-dimethylpyridin-3-yl)methyl)-4-(1-phenylethyl)benzamide was separated by chiral HPLC (condition: Daicel AD-H (250 mm×20 mm×5 µm), hexane/ethanol (0.2 diethylamine)=30:70, flow rate: 13 mL/min). Then (R or S)N-((2-hydroxy-4,6-dimethylpyridin-3-yl)methyl)-4-(1-phenylethyl)benzamide (60 mg, 56%) and (S or R)N-((2-hydroxy-4,6-dimethylpyridin-3-yl)methyl)-4-(1-phenylethyl)benzamide (70 mg, 58%) were obtained. The retention times were 5.26 minute and 6.59 minute respectively in chiral prep-HPLC chromatography. LRMS (M+H$^+$) m/z: calcd 407.19. found 407. HPLC Purity (214 nm): 99%. $^1$H NMR (300 MHz, CD$_3$OD): δ 7.25-7.05 (m, 8H), 6.08 (s, 1H), 4.44 (s, 2H), 4.09 (m, 1H), 2.35 (s, 3H), 2.31 (s, 3H), 2.23 (s, 3H) 1.59 (d, J=8.4 Hz, 3H). Although the separated enantiomers were not optically characterized, for convenience sake the (R) enantiomer was designated Compound I-172 and the (S) enantiomer designated Compound I-173.

Example 89

Synthesis of N-((2-hydroxy-4,6-dimethylpyridin-3-yl)methyl)-4-(1-phenoxypropan-2-yl)benzamide (Compound I-116)

This synthesis involved 8 steps.

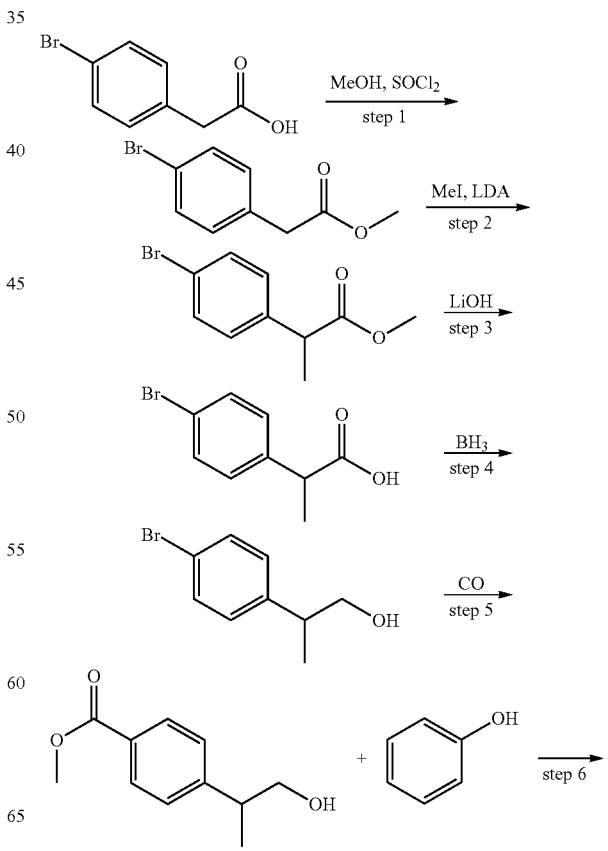

-continued

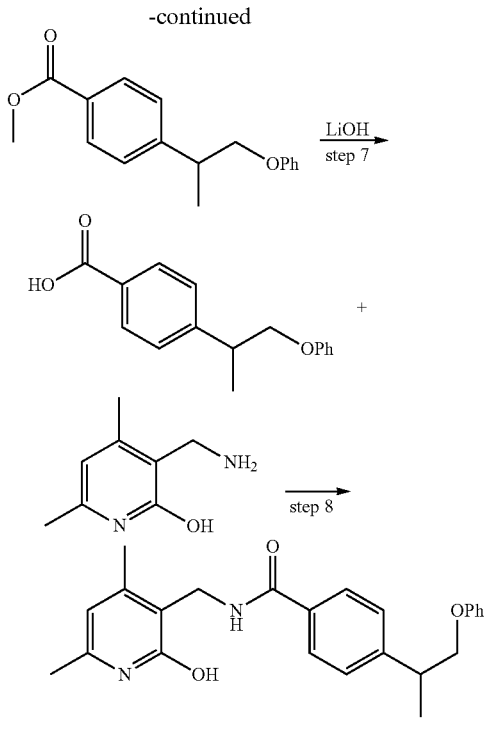

Methyl 2-(4-bromophenyl)acetate

To a solution of 2-(4-bromophenyl)acetic acid (10 g, 47 mmol) in methanol (100 mL) was dropwise thionyl chloride (0.2 mL) at room temperature. The mixture solution was heated to reflux for 3 hours. Then removed the solvent to dry to gave methyl 2-(4-bromophenyl)acetate as a colorless oil (10 g, 94%). $^1$H NMR (300 MHz, CDCl$_3$): δ 7.45 (d, J=9 Hz, 2H), 7.15 (d, J=9 Hz, 2H), 3.70 (s, 3H), 3.58 (s, 2H).

Methyl 2-(4-bromophenyl)propanoate

To a solution of lithium diisopropylamide (2 mol/L, 22 mL, 44 mmol) in tetrahydrofuran (80 mL) was dropwise a solution of methyl 2-(4-bromophenyl)acetate (10 g, 44 mmol) in tetrahydrofuran (20 mL) at −78° C. The mixture solution was stirred for 0.5 hour at that temperature, then iodomethane (8 g, 56 mmol) was added. The mixture was stirred for 10 minutes at −78° C., then was removed from the cooling bath and stirred for 0.5 hour. The reaction was quenched with sat. ammonium chloride, then diluted with ethyl acetate, washed with water, The organic layer concentrated to dry, purified by column chromatography (silica-gel, petroleum:ethyl acetate=20:1) to give methyl 2-(4-bromophenyl)propanoate as a colorless oil (10 g, 91%). $^1$H NMR (300 MHz, CDCl$_3$): δ 7.44 (d, J=9 Hz, 2H), 7.17 (d, J=9 Hz, 2H), 3.65-3.70 (m, 4H), 1.48 (d, J=6 Hz, 3H).

2-(4-bromophenyl)propanoic acid

To a solution of methyl 2-(4-bromophenyl)propanoate (2 g, 8.2 mmol) in tetrahydrofuran (30 mL) and water (20 mL) was added (1.2 g, 41 mmol) at room temperature, the mixture solution was stirred for 3 hours, then diluting with ethyl acetate (100 mL), and acidified with hydrochoric acid (6 M) to ph=3. The organic layer was dried over sodium sulfate, and concentrated to dry. The result residue 2-(4-bromophenyl) propanoic acid (2 g) was used directly for the next step without purification.

2-(4-bromophenyl)propan-1-ol

To a solution of 2-(4-bromophenyl)propanoic acid (2 g, crude) in tetrahydrofuran (50 mL) was added a solution of borane in tetrahydrofuran (1 mmol/L, 13 mL, 13 mmol) at 0° C. The mixture solution was stirred for 3 hours at 0° C., then worm to room temperature, and quenched by water. The solvent was removed, purified by column chromatography (silica-gel, petroleum:ethyl acetate=5:1) to give 2-(4-bromophenyl)propan-1-ol as a colorless oil (1.8 g, 96%). $^1$H NMR (300 MHz, CDCl$_3$): δ 1.7.38-7.46 (m, 2H), 7.10-7.13 (m, 2H), 3.72-3.78 (m, 2H), 2.84-2.98 (m, 1H), 1.23-1.27 (m, 3H).

Methyl 4-(1-hydroxypropan-2-yl)benzoate

A suspension solution of 2-(4-bromophenyl)propan-1-ol (1.8 g, 8.4 mmol), 1,3-Bis(diphenylphosphino)propane (500 mg), palladium acetate (500 mg) and triethylamine (2 mL) in methanol (100 mL) was filled carbon monoxide gas in a seal tube. The reaction was heated to 100° C. for 30 hours. The mixture solution was concentrated to dry. The residue was purified by column chromatography (silica-gel, petroleum/ethyl acetate=8:1) to give 4-(1-hydroxypropan-2-yl)benzoate as a colorless oil (0.8 g, 50%). $^1$H NMR (300 MHz, CDCl$_3$): δ 7.97-8.00 (m, 2H), 7.30-7.32 (m, 2H), 3.90 (s, 3H), 3.69-3.74 (m, 2H), 2.98-3.03 (m, 1H), 1.30 (t, J=2 Hz, 3H).

Methyl 4-(1-phenoxypropan-2-yl)benzoate

To a solution of 4-(1-hydroxypropan-2-yl)benzoate (100 mg, 0.52 mmol), phenol (78 mg, 0.8 mmol), triphenylphosphine (216 mg, 0.8 mmol) in tetrahydrofuran (30 mL) was added diisopropyl azodicarboxylate (166 mg, 0.8 mmol) at room temperature. The mixture solution was stirred for 18 hours. Then tetrahydrofuran was removed in vacuo. The residue was purified by column chromatography (silica-gel, petroleum/ethyl acetate=6:1) to give methyl 4-(1-phenoxypropan-2-yl)benzoate as a colorless oil (100 mg, 71%). $^1$H NMR (300 MHz, CDCl$_3$): δ 7.98 (d, J=9 Hz, 2H), 7.37 (d, J=9 Hz, 2H), 7.23-7.29 (m, 2H), 6.85-6.95 (m, 3H), 3.98-4.11 (m, 2H), 3.91 (s, 3H), 3.27-3.34 (m, 1H), 1.43 (d, J=6 Hz, 2H).

4-(1-phenoxypropan-2-yl)benzoic acid

A suspension solution of methyl 4-(1-phenoxypropan-2-yl)benzoate (0.1 g, 0.4 mmol) and lithium hydroxide (48 mg, 2 mmol) in tetrahydrofuran (20 mL) and water (10 mL) was stirred at room temperature for 2 hours. The mixture solution was diluting with ethyl acetate (50 mL), and acidified with hydrochloric acid to PH<4. The organic layer was separated, dried over sodium sulfate, and concentrated to dry. The residue 4-(1-phenoxypropan-2-yl)benzoic acid (60 mg, 65%) was used directly for the next step without purification.

4-(1-phenoxypropan-2-yl)-N-((2,4,6-trimethylpyridin-3-yl)methyl)benzamide (Compound I-116)

A mixture solution of 4-(1-phenoxypropan-2-yl)benzoic acid (60 mg, 0.2 mmol), 3-(aminomethyl)-4,6-dimethylpyridin-2-ol (37 mg, 0.2 mmol), 1-Hydroxybenzotriazole (30 mg, 0.2 mmol), 1-(3-Dimethylaminopropyl)-3-ethylcarbodiimide hydrochloride (40 mg, 0.2 mmol) and triethylamine (0.1 mL) in dichloromethane (50 mL) was stirred at room temperature for 18 hours. The mixture solution was diluting with ethyl acetate (50 mL), washed with water (20 mL). The organic layer was concentrated to dry. The residue was purified by column chromatography (silica-gel, dichloromethane/methanol=30:1) to give 4-(1-phenoxypropan-2-yl)-N-((2,4,6-trimethylpyridin-3-yl)methyl)benzamide as a yellow solid (60 mg, 64%). LRMS (M+H$^+$) m/z: calcd 391.19. found 391.

HPLC Purity (214 nm): 95%. $^1$H NMR (300 MHz, CDCl$_3$): δ 7.70-7.78 (m, 3H), 7.21-7.31 (m, 4H), 6.82-6.94 (m, 3H), 5.91 (s, 1H), 4.54-4.56 (m, 2H), 3.93-4.07 (m, 2H), 3.24-3.28 (m, 1H), 2.38 (s, 3H), 2.25 (s, 3H), 1.39 (d, J=6 Hz, 3H).

Example 90

Synthesis of (R)— or (S)-4-(1-(2,4-difluorophenoxy)ethyl)-N-((2-hydroxy-4,6-dimethylpyridin-3-yl)methyl)benzamide (Compound I-171) and (S)— or (R)-4-(1-(2,4-difluorophenoxy)ethyl)-N-((2-hydroxy-4,6-dimethylpyridin-3-yl)methyl)benzamide (Compound I-191)

This synthesis involved 4 steps.

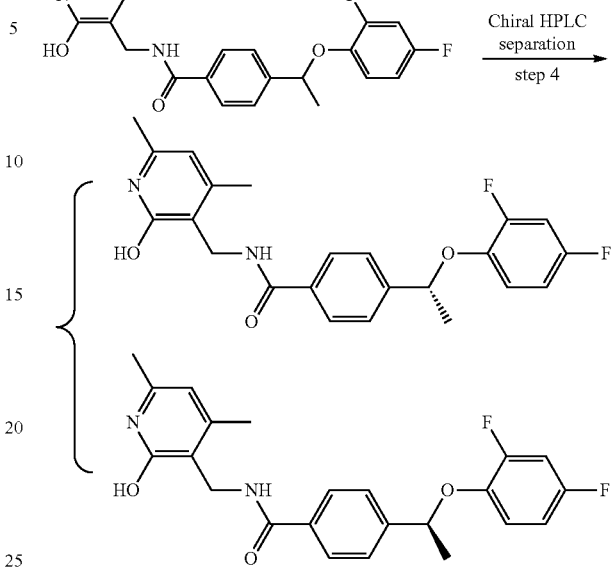

Methyl 4-(1-(2,4-difluorophenoxy)ethyl)benzoate

To the solution of 4-(1-hydroxyethyl)benzoate (300 mg. 1.67 mmol) in tetrahydrofuran (80 mL) was added triphenylphosphine (570 mg, 2.2 mmol) and 2,4-difluorophenol (159 mg, 1.67 mmol), the mixture was stirred for 30 minutes at room temperature, then diisopropylazodicarboxylate (568.3 mg, 2.2 mmol) was added dropwise to the solution at 0° C. The mixture was stirred at room temperature for 12 hours. Then the mixture was concentrated and the residue was purified by column chromatography (silica gel, Petroleum ether/ethyl acetate=20:1) to give methyl 4-(1-(2,4-difluorophenoxy)ethyl)benzoate (151 mg, 33%) as oil. $^1$H-NMR (300 MHz, CD$_3$OD) δ 8.03 (d, J=8.1 Hz, 2H), 7.460 (d, J=8.1 Hz, 2H), 6.86-6.72 (m, 3H), 5.29 (q, 1H), 3.91 (s, 3H), 1.67 (d, J=6.3 Hz, 2H).

4-(1-(2,4-difluorophenoxy)ethyl)benzoic acid

To the solution of methyl 4-(1-(2,4-difluorophenoxy)ethyl)benzoate (151 mg, 0.54 mmol) in meth anol/water (50 mL) was added lithium hydroxide (50 mg, 2.1 mmol), the solution was stirred at room temperature for 12 hours. Then the solution was acidified by hydrogen chloride (1 N/mol) pH to 6, extracted with dichloromethane (50 mL*3), evaporated the solvent and the residue was purified by column chromatography (silica gel, Petroleum ether/ethyl acetate=5:1) to give 4-(1-(2,4-difluorophenoxy)ethyl)benzoic acid (127 mg, 88%)

4-(1-(2,4-difluorophenoxy)ethyl)-N-((2-hydroxy-4,6-dimethylpyridin-3-yl)methy l)benzamide To a solution of 4-(1-(2,4-difluorophenoxy)ethyl)benzoic acid (127 mg, 0.5 mmol) in dichloromethane (80 mL) was added N-hydroxybenzotriazole (101.25 mg, 0.75 mmol), 1-ethyl-3-(3-dimethylaminopropyl)carbodiimide hydrochloride (144 mg, 0.75 mmol) and triethylamine (151 mg, 1.5 mm ol). then the 3-(aminomethyl)-4,6-dimethylpyridin-2-ol (76 mg, 0.5 mmol) was added, the solution was stirred at room temperature for 12 hours, water was added and washed 3 times, the organic layer was evaporated and the residue was purified by column chromatography (silica gel, dichloromethane/methanol=20:1) to give 4-(1-(2,4-difluorophenoxy)ethyl)-N-((2-hydroxy-4,6-dimethylpyridin-3-yl)methyl)benzamide (78 mg, 38%).

(R)— or (S)-4-(1-(2,4-difluorophenoxy)ethyl)-N-((2-hydroxy-4,6-dimethylpyridin-3-yl)methyl)benzamide (Compound I-171) and (S)— or (R)-4-(1-(2,4-difluorophenoxy)ethyl)-N-((2-hydroxy-4,6-dimethylpyridin-3-yl)methyl)benzamide (Compound 191)

4-(1-(2,4-difluorophenoxy)ethyl)-N-((2-hydroxy-4,6-dimethylpyridin-3-yl)methyl)benzamide (78 mg, 0.19 mmol) was separated by chiral prep-HPLC (Daicel AD-H (200 mm×20 mm×5 um), hexane: ethanol (0.2% DEA)=80:20, flow rate: 20 mL/min), then (R or S) 4-(1-(2,4-difluorophenoxy)ethyl)-N-((2-hydroxy-4,6-dimethylpyridin-3-yl)methyl)benzamide (24 mg, 31%) and (S or R) 4-(1-(2,4-difluorophenoxy)ethyl)-N-((2-hydroxy-4,6-dimethylpyridin-3-yl)methyl)benzamide (27 mg, 33%) was obtained. The retention times were 15.172 minutes and 24.793 minutes separately in Chiral HPLC chromatography. LRMS (M+H+) m/z: cald. 412.16. found 412. $^1$H NMR (300 MHz, $d_4$-CD$_3$OD): δ 7.75 (d, J=8.1 Hz, 2H), 7.45 (d, J=8.1 Hz, 2H), 6.94-6.88 (m, 2H), 6.70-6.68 (m, 1H), 6.08 (s, 1H), 5.44 (q, 1H), 4.47 (s, 2H), 2.34 (s, 3H), 2.23 (s, 3H), 1.61 (d, J=6.3 Hz, 3H). Although the separated enantiomers were not optically characterized, for convenience sake the (R) enantiomer was designated Compound I-171 and the (S) enantiomer was designated Compound I-191.

Example 91

Synthesis of N-((2-oxo-2,5,6,7-tetrahydro-1H-cyclopenta[b]pyridin-3-yl)methyl)-4-phenoxybenzamide (Compound I-178)

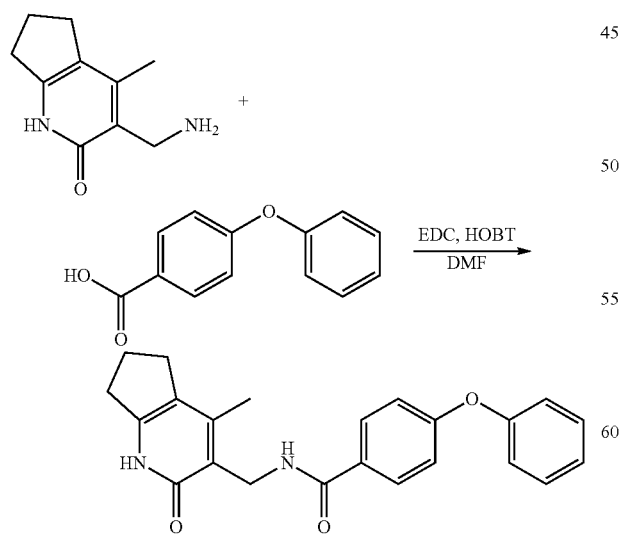

In a pyrex vial 3-(aminomethyl)-4-methyl-6,7-dihydro-1H-cyclopenta[b]pyridin-2(5H)-one (35 mg, 0.21 mmol), 4-phenoxybenzoic acid (50 mg, 0.23 mmol), HOBT (36 mg, 0.23 mmol) and DMF (1.5 mL) were cooled to 0° C. EDC (45 mg, 0.23 mmol) was then added in one portion and the cold bath was removed. The reaction was mixed at ambient temperature overnight then diluted with MeOH (2 mL) and water (1 mL), filtered through a PTFE screen and purified by reverse-phase HPLC 10-95% gradient of MeCN in water (0.1% TFA). The product fractions were lyophilized to produce N-((2-oxo-2,5,6,7-tetrahydro-1H-cyclopenta[b]pyridin-3-yl)methyl)-4-phenoxybenzamide as a white solid (43 mg, 56%). $^1$H NMR (400 MHz, DMSO-$d_6$) δ 8.70 (t, J=5.71 Hz, 1H), 7.87-7.96 (m, 2H), 7.38-7.47 (m, 2H), 7.15-7.23 (m, 2H), 7.05-7.11 (m, 2H), 6.99-7.05 (m, 2H), 4.19 (d, J=5.61 Hz, 2H), 2.69 (t, J=7.48 Hz, 2H), 2.58 (t, J=7.17 Hz, 2H), 1.98 (quin, J=7.43 Hz, 1H). LRMS (M+H$^+$) m/z: calcd 361.15. found 361.2.

Example 92

Synthesis of N-((2-hydroxy-4,6-dimethylpyridin-3-yl)methyl)-6-(1-phenoxyethyl)pyridazine-3-carboxamide (Compound I-182)

This synthesis involved 6 steps.

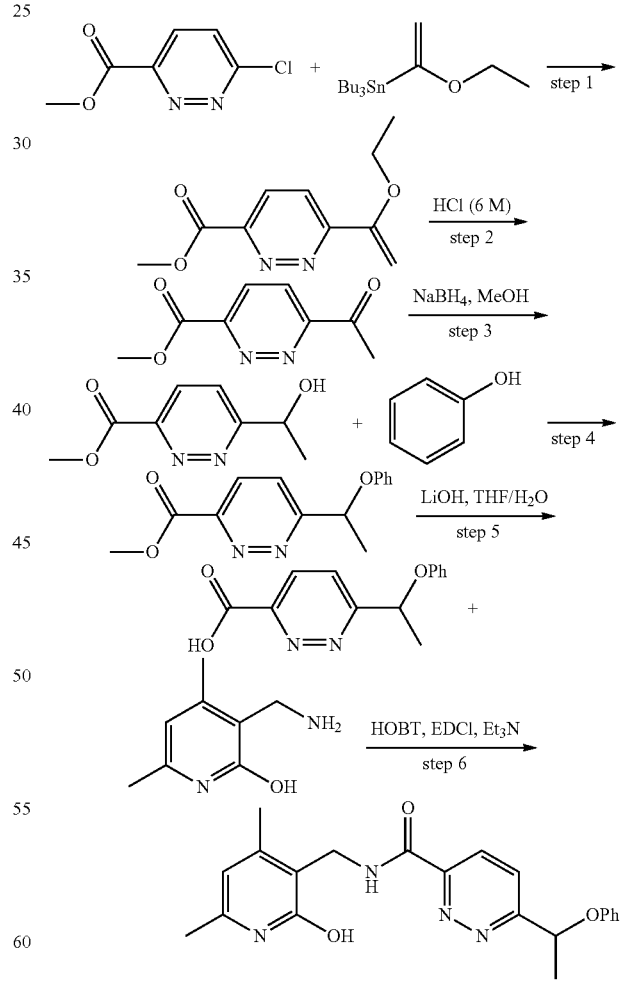

Methyl 6-(1-ethoxyvinyl)pyridazine-3-carboxylate

A solution of methyl 6-chloropyridazine-3-carboxylate (1.5 g, 8.7 mmol), ethoxyvinyl tin (3.2 g, 8.7 mmol), transbis(triphenyl-phosphine)palladium (200 mg) and N,N-dimethylformamide (50 mL) were combined. The mixture solution was heated to 80° C. for 10 hours under nitrogen gas protected. N,N-dimethylformamide was concentrated to dry in vacuo. The residue was purified by column chromatography (silica-gel, petroleum/ethyl acetate=4:1) to give methyl 6-(1-ethoxyvinyl)pyridazine-3-carboxylate as a white solid (1.3 g, 72%). $^1$H NMR (300 MHz, CDCl$_3$): δ 8.22 (d, J=9 Hz, 1H), 7.98 (d, J=9 Hz, 1H), 4.98 (d, J=2.4 Hz, 1H), 4.68 (d, J=Methyl 6-acetylpyridazine-3-carboxylate. A solution of methyl 6-(1-ethoxyvinyl)pyridazine-3-carboxylate (1.3 g, 7.2 mmol) in hydrochloric acid (6 mol/L, 20 mL) was stirred at room temperature for 4 hours. The mixture solution was neutralized with potassium carbonate, extracted with ethyl acetate (100 mL). The organic layer was concentrated to dry to give methyl 6-acetylpyridazine-3-carboxylate as a white solid (0.9, 81%). $^1$H NMR (300 MHz, CDCl$_3$): δ 8.36-8.40 (m, 1H), 8.36-8.40 (m, 1H), 4.00 (s, 3H), 2.82 (s, 3H).

Methyl 6-(1-hydroxyethyl)pyridazine-3-carboxylate

To a solution of methyl 6-acetylpyridazine-3-carboxylate (0.8 g, 4.4 mmol) in methanol (30 mL) was added sodium borohydride (340 mg, 8.8 mmol) at −70° C. under nitrogen gas protected. The mixture solution was stirred for 3 hours at −70° C., then poured into ethyl acetate (50 mL) and water (50 mL). Separated organic layer was dried over sodium sulfate and concentrated to dry. The residue was purified by column chromatography (silica-gel, petroleum/ethyl acetate=5:) to give methyl 6-(1-hydroxyethyl)pyridazine-3-carboxylate as a white solid (200 mg, 25%). $^1$H NMR (300 MHz, CDCl$_3$): δ 8.22 (d, J=9 Hz, 1H), 7.93 (d, J=9 Hz, 1H), 5.07 (m, 1H), 3.96 (s, 3H), 1.46 (d, J=6 Hz, 3H).

Methyl 6-(1-phenoxyethyl)pyridazine-3-carboxylate

To a solution of methyl 6-(1-hydroxyethyl)pyridazine-3-carboxylate (100 mg, 0.55 mmol), phenol (78 mg, 0.8 mmol), triphenylphosphine (216 mg, 0.8 mmol) in tetrahydrofuran (30 mL) was added diisopropyl azodicarboxylate (166 mg, 0.8 mmol) at room temperature. The mixture solution was stirred for 18 hours. Then tetrahydrofuran was removed in vacuo. The residue was purified by column chromatography (silica-gel, petroleum/ethyl acetate=5:1) to give methyl 6-(1-phenoxyethyl)pyridazine-3-carboxylate as a colorless oil (100 mg, 70%). $^1$H NMR (300 MHz, DMSO-d$_6$): δ 8.20 (d, J=9 Hz, 1H), 7.93 (d, J=9 Hz, 1H), 7.20-7.25 (m, 2H), 6.87-6.94 (m, 3H), 5.87-5.90 (m, 1H), 3.94 (s, 3H), 1.68 (d, J=6 Hz, 3H).

6-(1-phenoxyethyl)pyridazine-3-carboxylic acid

A suspension solution of methyl 6-(1-phenoxyethyl)pyridazine-3-carboxylate (0.1 g, 0.4 mmol) and lithium hydroxide (48 mg, 2 mmol) in tetrahydrofuran (20 mL) and water (10 mL) was stirred at room temperature for 2 hours. The mixture solution was diluting with ethyl acetate (50 mL), and acidified with hydrochloric acid to PH<5. The organic layer was separated, dried over sodium sulfate, and concentrated to give 6-(1-phenoxyethyl)pyridazine-3-carboxylic acid (60 mg, 65%) which was used directly for the next step without purification.

N-((2-hydroxy-4,6-dimethylpyridin-3-yl)methyl)-6-(1-phenoxyethyl)pyridazine-3-carboxamide (Compound I-182)

A mixture solution of 6-(1-phenoxyethyl)pyridazine-3-carboxylic acid (60 mg, 0.2 mmol), 3-(aminomethyl)-4,6-dimethylpyridin-2-ol (37 mg, 0.2 mmol), 1-Hydroxybenzotriazole (30 mg, 0.2 mmol), 1-(3-Dimethylaminopropyl)-3-ethylcarbodiimide hydrochloride (40 mg, 0.2 mmol) and triethylamine (0.1 mL) in dichloromethane (50 mL) was stirred at room temperature for 18 hours. The mixture solution was diluting with ethyl acetate (50 mL), washed with water (20 mL). The organic layer was concentrated, the residue was purified by column chromatography (silica-gel, dichloromethane/methanol=30:1) to give N-((2-hydroxy-4,6-dimethylpyridin-3-yl)methyl)-6-(1-phenoxyethyl)pyridazine-3-carboxamide as a yellow solid (60 mg, 64%). LRMS (M+H$^+$) m/z: calcd 379.17. found 379. HPLC Purity (214 nm): 95%. $^1$H NMR (300 MHz, CDCl$_3$): δ 9.06 (s, 1H), 8.20 (d, J=9 Hz, 1H), 7.73 (d, J=9 Hz, 1H), 7.15-7.25 (m, 2H), 6.82-6.91 (m, 3H), 5.96 (s, 1H), 5.76-5.78 (m, 1H), 4.63 (d, J=6 Hz, 2H), 2.36 (s, 6H), 1.70 (d, J=6 Hz, 3H).

Example 93

Synthesis of 4-(2-hydroxy-1-phenoxyethyl)-N-((2-hydroxy-4,6-dimethylpyridin-3-yl)methyl)benzamide (Compound I-183)

This synthesis involved 8 steps.

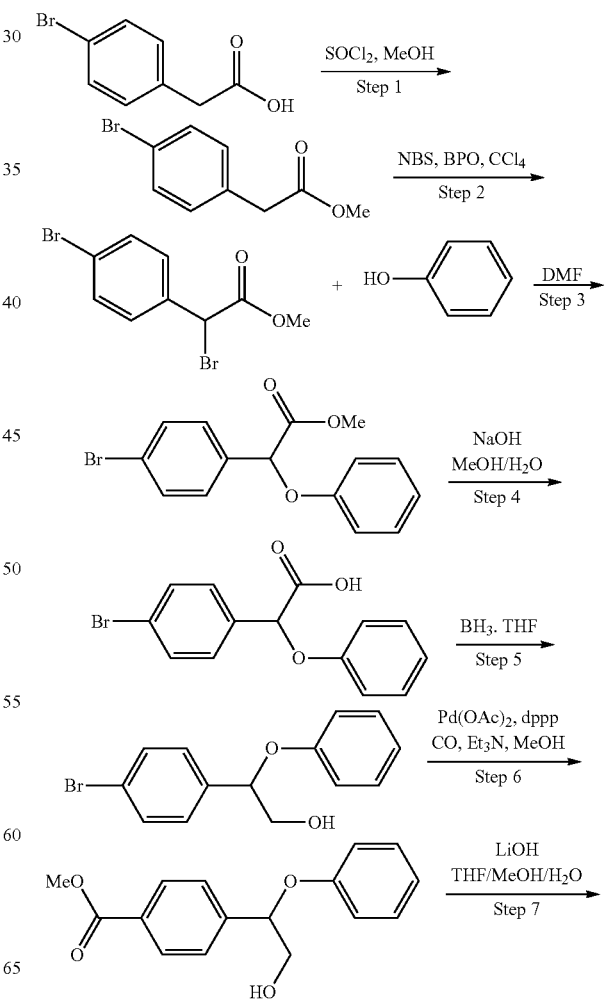

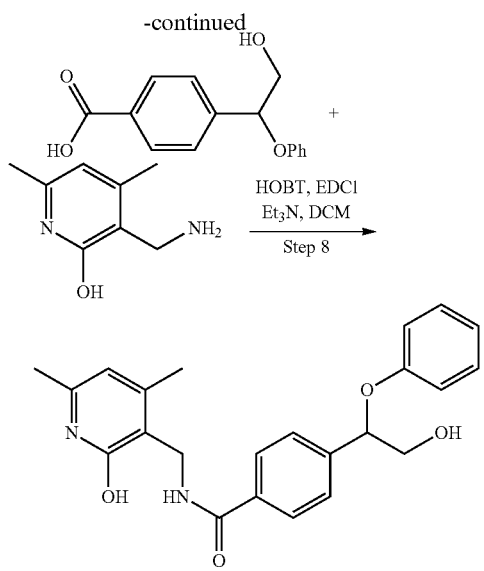

Methyl 2-(4-bromophenyl)acetate

To a solution of 2-(4-bromophenyl)acetic acid (10 g, 46.7 mmol) in menthol was added thionyl chloride (8.34 g, 70.07 mmol) dropwise. The mixture was then stirred at room temperature for 18 hours. The reaction mixture was concentrated, and obtained methyl 2-(4-bromophenyl)acetate (10.5 g, 99.8%).

Methyl 2-bromo-2-(4-bromophenyl)acetate

To a solution of methyl 2-(4-bromophenyl)acetate (9 g, 39.5 mmol) in carbon tetrachloride was added N-bromosuccinimide (7.1 g, 40 mmol), benzoyl peroxide (1.2 g, 6.7 mmol). The mixture was heated to reflux, and then stirred at the 77° C. for 4 hours. Thin layer chromatography showed full conversion. Then the mixture was concentrated under vacuum. The residue was purified by column chromatography (silica gel, petroleum ether/ethyl acetate=20/1) to give methyl 2-bromo-2-(4-bromophenyl)acetate (12 g, 91%). $^1$H NMR (300 MHz, CDCl$_3$) δ 7.68-7.65 (m, 2H), 7.52-7.49 (m, 2H), 5.35-5.31 (m, 1H), 3.89 (s, 3H).

Methyl 2-(4-bromophenyl)-2-phenoxyacetate

To a solution of methyl 2-bromo-2-(4-bromophenyl)acetate (9 g, 29.3 mmol) in N,N-dimethylformamide was added phenol (5.5 g, 60 mmol), cesium carbonate (9.5 g, 30 mmol), tetrabutylammonium iodide (1.08 g, 2.93 mmol). The mixture was stirred at 40° C. for 15 hours. Thin layer chromatography showed the start material was consumed completely. Then the mixture was concentrated under vacuum and purified by column chromatography (silica gel, petroleum ether/ethyl acetate=25:1) to give methyl 2-(4-bromophenyl)-2-phenoxyacetate (6 g, 61%).

2-(4-bromophenyl)-2-phenoxyacetic acid

To a solution of lithium hydroxide (3.5 g, 0.042 mmol) in tetrahydrofuran, menthol and water (120 mL, 3:1:1) was added methyl 2-(4-bromophenyl)-2-phenoxyacetate (6.8 g, 0.021 mol). The reaction mixture was stirred at room temperature for 1 hour. The mixture was quench with 10% hydrochloric acid (aqueous, 5 mL), extracted with dichloromethane and menthol (10:1), the combine organic layer was dried with anhydrous sodium sulfate, filtered and evaporated to give 2-(4-bromophenyl)-2-phenoxyacetic acid (6 g, 80%). $^1$H NMR (300 MHz, DMSO-d$_6$): δ 7.68-7.65 (m, 5H), 7.52-7.49 (m, 2H), 6.88-6.86 (m, 2H), 5.35-5.31 (m, 1H).

2-(4-bromophenyl)-2-phenoxyethanol

To a solution of 2-(4-bromophenyl)-2-phenoxyacetic acid (6 g, 19.6 mmol) in anhydrous tetrahydrofuran (100 mL) was added borane-tetrahydrofuran complex (1 M, 40 mL) at −5° C. The solution was stirred at room temperature for 15 hours. After 2 hours, LC-MS showed the desired product was obtained. Water:acetic acid (1:1, 50 mL) was added at 0° C. to quench the reaction, the mixture was added 10 mL saturated sodium bicarbonate to adjust pH=7, extracted with ethyl acetate (100 mL). Then combined and concentrated the organic layers. The crude product was purified by column chromatography (silica gel, dichloromethane/menthol=40:1) to give 2-(4-bromophenyl)-2-phenoxyethanol (5 g, 80%). LCMS (M+H$^+$) m/z: calcd 292.06. found 292.

Methyl 4-(2-hydroxy-1-phenoxyethyl)benzoate

To a mixture of 2-(4-bromophenyl)-2-phenoxyethanol (500 mg, 1.73 mmol) in methanol (20 mL) was added palladium acetate (100 mg, 0.35 mmol), 1,3-bis(diphenylphosphino) propane (130 mg, 0.35 mmol) and triethylamine (1.3 g, 3 mmol). And the reaction mixture was stirred and heated to 100° C. under carbon monoxide atmosphere in a pressure reactor for 24 hours. The mixture was cooled to room temperature and filtered, the organic was evaporated to dryness, and then the residue was purified by column chromatography (silica gel, petroleum ether/ethyl acetate=4/1) to give methyl 4-(2-hydroxy-1-phenoxyethyl)benzoate (400 mg, 76%). $^1$H NMR (300 MHz, CD$_3$OD) δ 7.96 (d, J=8.4 Hz, 2H), 7.50 (d, J=8.4 Hz, 2H), 7.14 (t, J=3.3 Hz, 2H), 6.88-6.86 (m, 3H) 5.35-5.31 (m, 1H), 3.87-3.79 (m, 5H).

4-(2-hydroxy-1-phenoxyethyl)benzoic acid

To a solution of lithium hydroxide (400 mg, 10.2 mmol) in tetrahydrofuran, menthol and water (20 mL, 3:1:1, V/V) was added methyl 4-(2-hydroxy-1-phenoxyethyl)benzoate (400 mg, 1.47 mmol). The reaction mixture was stirred at room temperature for 1 hour. The mixture was quenched with 10% HCl (aqueous, 5 mL), extracted with dichloromethane and menthol (60 mL, 10:1), the combine organic layer was dried with anhydrous sodium sulfate, filtered and evaporated to give 4-(2-hydroxy-1-phenoxyethyl)benzoic acid (300 mg, 70%). LCMS (M+H$^+$) m/z: calcd 258.09. found 258

4-(2-hydroxy-11-phenoxyethyl)-N-((2-hydroxy-4,6-dimethylpyridin-3-yl)methyl)benzamide The 4-(2-hydroxy-1-phenoxyethyl)benzoic acid (100 mg, 0.3870 mmol), was dissolved into dichloromethane (20 mL), and then N-hydroxybenzotriazole (0.5814 mmol, 80 mg), 1-(3-Dimethylaminopropyl)-3-ethylcarbodiimide hydrochloride (0.5814 mmol, 112 mg), triethylamine (1.69 mmol, 2 mL) was added to the mixture. After the mixture was stirred at room temperature for 10 minutes, 3-(aminomethyl)-4,6-dimethylpyridin-2-ol (0.387 mol, 58 mg) was added. The mixture was stirred at room temperature for 18 hours. Then washed with water (20 mL), extracted with dichloromethane (20 mL). The organic layer were concentrated and subjected to column chromatography (silica gel, dichloromethane/menthol=15:1) to give 4-(2-hydroxy-1-phenoxyethyl)-N-((2-hydroxy-4,6-dimethylpyridin-3-yl)methyl)benzamide (30 mg, 15%).

LCMS (M+H⁺) m/z: calcd 392.17. found 392. HPLC purity (214 nm): 97%. $^1$H NMR (300 MHz, CD$_3$OD) δ 7.74 (d, J=8.1 Hz, 2H), 7.45 (d, J=8.1 Hz, 2H), 7.16-7.13 (m, 2H), 7.16-7.11 (m, 3H), 6.08 (s, 1H), 5.32-5.29 (m, 1H), 4.46 (s, 2H), 3.81-3.79 (m, 2H), 2.33 (s, 3H), 2.22 (s, 3H).

Example 94

Synthesis of N-((4-amino-2-hydroxy-6-methylpyridin-3-yl)methyl)-4-phenoxybenzamide (Compound I-196)

This synthesis involved 6 steps.

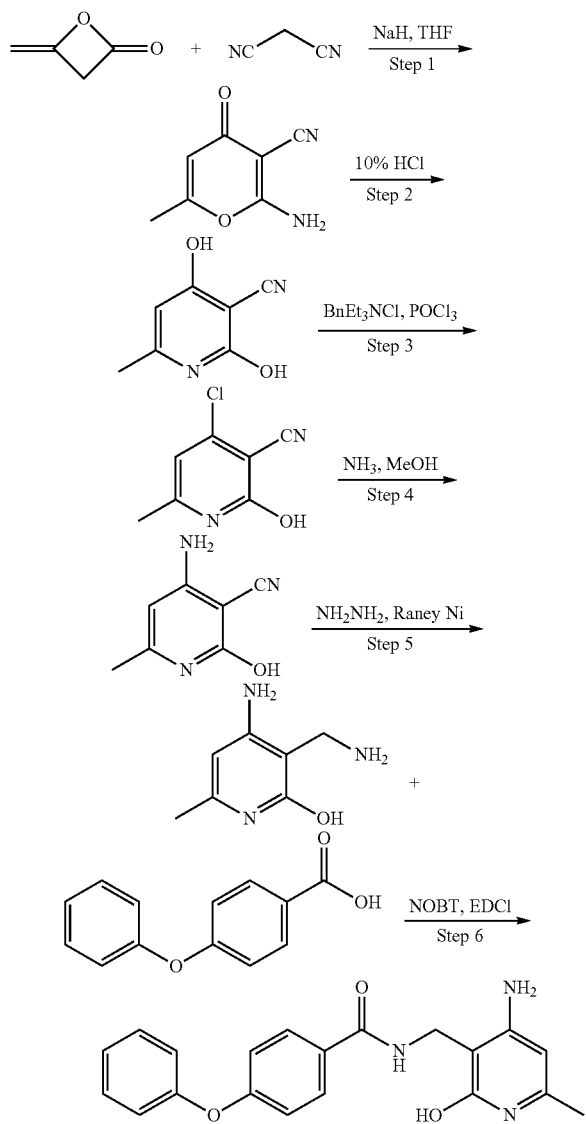

2-amino-6-methyl-4-oxo-4H-pyran-3-carbonitrile

To a solution of malononitrile (3.3 g, 50 mmol) in anhydrous tetrahydrofuran (100 mL) was added sodium hydride (60%, 2.2 g, 55 mmol) at −10° C. The resulting reaction mixture was stirred for 2 hours. Then diketene (4.2 g, 50 mmol) was added dropwise to the solution. The reaction mixture was allowed to warmed to room temperature and continued to stir for 30 minutes. The mixture was neutralized with hydrochloric acid, and then concentrated in vacuo to give crude product as red solid, which was used in the next step without further purification.

2,4-dihydroxy-6-methylnicotinonitrile

A suspension of 2-amino-6-methyl-4-oxo-4H-pyran-3-carbonitrile (6.0 g, 40 mmol) in 10% hydrochloric acid (60 mL) was heated under reflux for 4 hours. The precipitate was collected by filtration and washed with water, and then recrystallized from methanol to give 2,4-dihydroxy-6-methylnicotinonitrile (5.0 g, 80%) as a brown solid. $^1$H NMR (300 MHz, CD$_3$OD): δ 12.44-12.46 (m, 1H), 11.69 (s, 1H), 5.85 (s, 1H), 2.15 (s, 3H).

4-chloro-2-hydroxy-6-methylnicotinonitrile

To a solution of 2,4-dihydroxy-6-methylnicotinonitrile (1.5 g, 10 mmol) in acetonitrile (50 mL) were added benzyltriethylammonium chloride (9.1 g, 40 mmol) and phosphoryl chloride (6.13 g, 40 mmol). The reaction mixture was heated to 40° C. for 4 hours. The solvent was removed by rotary evaporation, to the residue was added dichloromethane (100 mL) and water (50 mL), the organic phase was separated, and washed with brine (50 mL) once, dried by anhydrous magnesium sulfate, filtered and concentrated under reduced pressure to give crude product which was purified by silica gel column chromatography with dichloromethane/methanol=10:1 to afford 4-chloro-2-hydroxy-6-methylnicotinonitrile (800 mg, 24% yield) as a brown solid.

4-amino-2-hydroxy-6-methylnicotinonitrile

To a pressure vessel were added 4-chloro-2-hydroxy-6-methylnicotinonitrile (600 mg, 3.6 mmol), ammonia methanol solution (7 mol/L, 15 mL) and magnetic stirrer. The pressure vessel was sealed, and stirred at 100° C. for 16 hours. After being cooled to room temperature, the solvent and excess ammonia were removed by rotary evaporation. The residue was purified by silica gel column chromatography with dichloromethane/methanol=10:1 to afford 4-amino-2-hydroxy-6-methylnicotinonitrile (350 mg, 66% yield) as a brown solid.

4-amino-3-(aminomethyl)-6-methylpyridin-2-ol 4-amino-2-hydroxy-6-methylnicotinonitrile (350 mg, 2.4 mmol) was dissolved in ethanol (15 mL) and warmed to 50° C. before it was treated with raney nickel (1 ml slurry in water) followed by addition of hydrazine monohydrate (2 ml). The resulting mixture was allowed to stir at 50° C. for 2 hours. The cooled reaction mixture was filtered through celite, rinsed with methanol. The filtrate was concentrated in vacuo to provide crude product which was purified by silica gel column chromatography with dichloromethane/methanol=10:1 to afford 4-amino-3-(aminomethyl)-6-methylpyridin-2-ol (200 mg, 56% yield) as a yellow solid.

N-((4-amino-2-hydroxy-6-methylpyridin-3-yl)methyl)-4-phenoxybenzamide (Compound I-196)

To a solution of 4-phenoxybenzoic acid (196 mg, 0.91 mmol) in dichloromethane (15 mL) were added 1-hydroxybenzotriazole (177 mg, 1.3 mmol), 1-(3-Dimethylaminopropyl)-3-ethylcarbodiimide hydrochloride (251 mg, 1.3 mmol) and triethylamine (265 mg, 2.6 mmol). The resulting solution was stirred at room temperature for 30 minutes. Then 4-amino-3-(aminomethyl)-6-methylpyridin-2-ol (200 mg, 1.3 mmol) was added to the solution, and it was stirred at room temperature for 16 hours. Water (20 ml) was added to the mixture. It was extracted with dichloromethane (50 ml). The organic layer was concentrated in vacuo to provide crude product which was purified by silica gel column chromatography with dichloromethane/methanol=10:1 to afford N-((4-amino-2-hydroxy-6-methylpyridin-3-yl)methyl)-4-phenoxybenzamide (180 mg, 57% yield) as a white solid. LRMS (M+H$^+$) m/z: calcd 350.14. found 350. HPLC Purity (214 nm): 97%. $^1$H NMR (300 MHz, CDCl$_3$): δ 10.71 (d, J=2.4 Hz, 1H), 7.76-7.79 (d, J=8.7 Hz, 2H), 7.32-7.38 (m, 2H), 7.12-7.17 (m, 1H), 6.94-7.02 (m, 4H), 5.64-5.65 (br, 1H), 5.51 (s, 1H), 4.47-4.49 (d, J=6.6 Hz, 2H), 3.48 (s, 2H), 2.16 (s, 3H).

Example 95

Synthesis of N-((2-hydroxy-6-methyl-4-(methylamino)pyridin-3-yl)methyl)-4-phenoxybenzamide (Compound I-194)

This synthesis involved 6 steps.

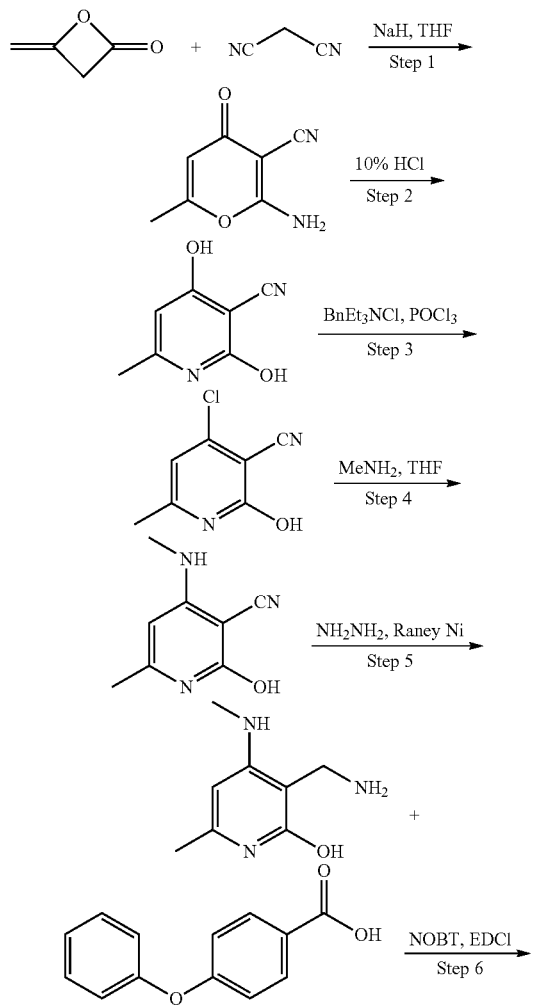

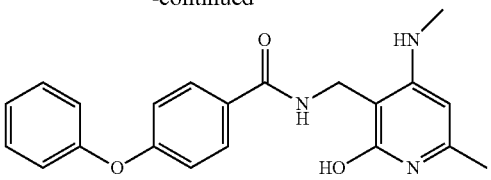

2-amino-6-methyl-4-oxo-4H-pyran-3-carbonitrile

To a solution of malononitrile (3.3 g, 50 mmol) in 100 ml of anhydrous tetrahydrofuran was added sodium hydride (60%, 2.2 g, 55 mmol) at –10° C. The resulting reaction mixture was stirred for 2 hours. Then diketene (4.2 g, 50 mmol) was added dropwise to the solution. The reaction mixture was allowed to warm to room temperature and continued to stir for 30 minutes. The mixture was neutralized with hydrochloric acid, and then concentrated to give crude product as red solid, which was used in the next step without further purification.

2,4-dihydroxy-6-methylnicotinonitrile

A suspension of 2-amino-6-methyl-4-oxo-4H-pyran-3-carbonitrile (6.0 g, 40 mmol) in 10% HCl (60 ml) was heated under reflux for 4 hours. The precipitate was collected by filtration and washed with water, and then recrystallized from methanol to give 2,4-dihydroxy-6-methylnicotinonitrile (5.0 g, 80%) as a brown solid. $^1$H NMR (300 MHz, CD$_3$OD): δ 12.44-12.46 (m, 1H), 11.69 (s, 1H), 5.85 (s, 1H), 2.15 (s, 3H).

4-chloro-2-hydroxy-6-methylnicotinonitrile

To a solution of 2,4-dihydroxy-6-methylnicotinonitrile (1.5 g, 10 mmol) in acetonitrile (50 mL) were added benzyltriethylammonium chloride (9.1 g, 40 mmol) and phosphoryl chloride (6.13 g, 40 mmol). The reaction mixture was heated to 40° C. for 4 hours at the same temperature. LC-MS showed that 2,4-dihydroxy-6-methylnicotinonitrile was consumed completely. The solvent was removed by rotary evaporation. To the residue was added dichloromethane (100 ml) and water (50 ml). The organic phase was separated, and it was washed with brine (50 ml) once, dried over anhydrous magnesium sulfate, filtered, and concentrated under reduced pressure to give crude product which was purified by silica gel column chromatography with dichloromethane/methanol=10:1 to afford 4-chloro-2-hydroxy-6-methylnicotinonitrile (800 mg, 24% yield) as a brown solid.

2-hydroxy-6-methyl-4-(methylamino)nicotinonitrile

To a pressure vessel were added 4-chloro-2-hydroxy-6-methylnicotinonitrile (337 mg, 2.0 mmol), methylamine tetrahydrofuran solution (2 mol/L, 15 mL), and magnetic stirrer. The pressure vessel was sealed, and it was stirred at 90° C. for 2 hours. After being cooled to room temperature, the vessel was opened, and the reaction solution was transferred to an eggplant-shaped bottle. The solvent and excess methylamine were removed by rotary evaporation. The residue was purified by silica gel column chromatography with dichloromethane/methanol=10:1 to afford 2-hydroxy-6-methyl-4-(methylamino)nicotinonitrile (200 mg, 61% yield) as a brown solid. $^1$H NMR (300 MHz, methanol-d$_4$): δ 5.89 (s, 1H), 3.56 (d, J=10.8 Hz, 3H), 2.94 (s, 1H), 2.55 (s, 1H), 2.24 (s, 1H).

3-(aminomethyl)-6-methyl-4-(methylamino)pyridin-2-ol 2-hydroxy-6-methyl-4-(methylamino)nicotinonitrile (163 mg, 1.0 mmol) was dissolved in ethanol (10 mL) and was warmed to 55° C. before it was treated with Raney nickel (0.5 mL slurry in water) followed by addition of hydrazine monohydrate (2 mL). The resulting mixture was allowed to stir at 55° C. for 2 hours. The cooled reaction mixture was filtered through celite, rinsed with methanol. The filtrate was concentrated in vacuo to provide crude product which was purified by silica gel column chromatography with dichloromethane/methanol=10:1 to afford 3-(aminomethyl)-6-methyl-4-(methylamino)pyridin-2-ol (60 mg, 36% yield) as a brown solid.

N-((2-hydroxy-6-methyl-4-(methylamino)pyridin-3-yl)methyl)-4-phenoxybenzamide (Compound I-194)

To a solution of 4-phenoxybenzoic acid (54 mg, 0.25 mmol) in dichloromethane (15 mL) were added 1-Hydroxybenzotriazole (49 mg, 0.36 mmol), 1-(3-Dimethylaminopropyl)-3-ethylcarbodiimide hydrochloride (69 mg, 0.36 mmol) and triethylamine (73 mg, 0.72 mmol). The resulting solution was stirred at room temperature for 30 minutes. Then 3-(aminomethyl)-6-methyl-4-(methylamino) pyridin-2-ol (60 mg, 0.36 mmol) was added to the solution, and it was stirred at room temperature for 16 hours. Water (20 mL) was added to the mixture. It was extracted with dichloromethane (50 mL). The organic layer was concentrated to provide crude product which was purified by silica gel column chromatography with dichloromethane/methanol=10:1 to afford N-((2-hydroxy-6-methyl-4-(methylamino)pyridin-3-yl)methyl)-4-phenoxybenzamide (10 mg, 11% yield) as a white solid. LRMS (M+H$^+$) m/z: calcd 364.16. found 364. HPLC Purity (214 nm): 98%. $^1$H NMR (300 MHz, CD$_3$OD): δ 7.78-7.81 (d, J=8.7 Hz, 2H), 7.37-7.43 (m, 2H), 7.20 (d, J=7.5 Hz, 1H), 6.97-7.06 (m, 4H), 5.90 (s, 1H), 4.40 (s, 2H), 2.90 (s, 3H), 2.23 (s, 3H).

Example 96

Synthesis of 3-chloro-N-((2-hydroxy-4,6-dimethylpyridin-3-yl)methyl)-4-(1-phenoxyethyl)benzamide (Compound I-180) and its Enantiomers (Compounds I-189 and I-190)

This synthesis involved 8 steps.

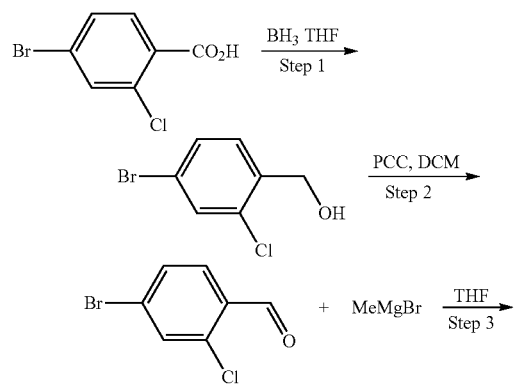

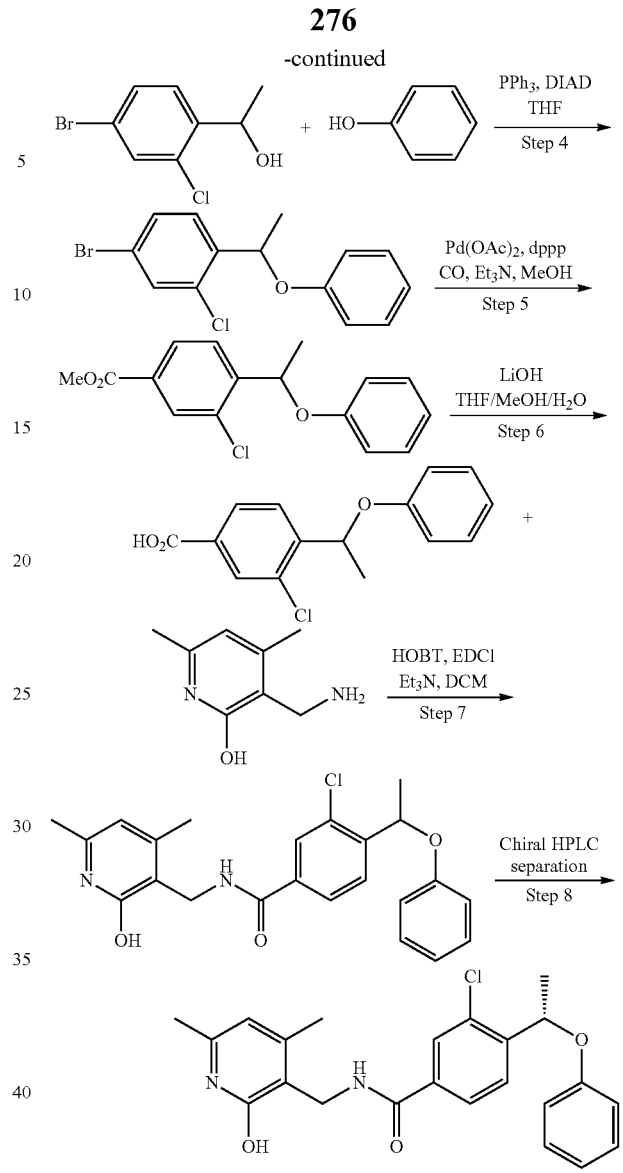

4-bromo-2-chlorophenyl)methanol

A solution of BH$_3$ (34 mL, 1M in tetrahydrofuran) was added dropwise to the solution of 4-bromo-3-chlorobenzoic acid (2.5 g, 11.4 mmol) in tetrahydrofuran at 0° C. The mixture was stirred at 40° C. overnight. Acetic acid (5 mL) was added dropwise to the reaction mixture. The mixture was concentrated to give a residue. The residue was purified by column chromatography (silica gel, petroleum ethe/ethyl acetate=1:1) to give (4-bromo-2-chlorophenyl)methanol as a white solid (4.47 g, 91%). $^1$H NMR (300 MHz, d$^6$-DMSO): 7.69 (d, J=8.1, 1H), δ 7.53 (d, J=0.9, 1H), 7.19 (dd, J$_1$=8.1, 1H J$_2$=0.9, 1H), 5.38 (s, 1H), δ 4.48 (s, 2H).

4-bromo-2-chlorobenzaldehyde

A mixture of (4-bromo-3-chlorophenyl)methanol (2.0 g, 9.0 mmol), pyridinium chlorochromate (2912 mg, 13.5 mmol) in dichloromethane (50 mL0 was stirred at 25° C. for 3 hours. The mixture was concentrated to give a residue. The residue was purified by column chromatography (silica gel, petroleum ethe/ethyl acetate=1:1) to give (4-bromo-2-chlorophenyl)methanol as a white solid (4.12 g g, 81%). $^1$H NMR (300 MHz, d$^6$-DMSO): δ 9.96 (s, 1H), 7.69 (d, J=8.1, 1H), 7.53 (d, J=0.9, 1H), 7.19 (dd, J$_1$=8.1, 1H J$_2$=0.9, 1H).

1-(4-bromo-2-chlorophenyl)ethanol

A solution of methylmagnesium bromide (4.8 mL, 3M, 14.4 mmol) was added dropwise to the solution of (4-bromo-2-chlorophenyl)methanol (1.52 g, 7.0 mmol) in tetrahydrofuran at −40° C. Then the mixture was stirred at 25° C. for 3 hrs. Saturated ammonium chloride solution (10 mL) was added to the mixture. The mixture was concentrated to give a residue. The residue was purified by column chromatography (silica gel, petroleum ether/ethyl acetate=1:1) to give 1-(4-bromo-2-chlorophenyl)ethanol as a white solid (1.32 g, 81%). $^1$H NMR (300 MHz, d$^6$-DMSO): 7.69 (d, J=8.1, 1H), δ 7.53 (d, J=0.9, 1H), 7.19 (dd, J$_1$=8.1, 1H J$_2$=0.9, 1H), 5.38 (d, J=3.6, 1H), δ 4.70 (m, 1H), 1.30 (d, J=6.6, 3H).

4-bromo-2-chloro-1-(1-phenoxyethyl)benzene

A solution of 1-(4-bromo-2-chlorophenyl)ethanol (1.32 g, 5.6 mmol), phenol (525 mg, 5.6 mmol) and triphenylphosphine (2198 mg, 8.4 mmol) in tetrahydrofuran (30 mL) was stirred at room temperature for 0.5 hour. Diisopropyl azodicarboxylate (1695 mg, 8.4 mmol) was dropwise to the reaction mixture and was stirred at room temperature for 12 hours. The mixture was concentrated to give a residue. The residue was purified by column chromatography (silica gel, petroleum ethe/ethyl acetate=5:1) to give 4-bromo-2-chloro-1-(1-phenoxyethyl)benzene as a colorless oil (882 mg 54%).

$^1$H NMR (300 MHz, CDCl$_3$): 7.37 (d, J=8.1, 1H), δ 7.27-7.20 (m, 3H), 6.92-6.82 (m, 3H), 5.30 (q, J=6.6, 1H), 1.62 (d, J=6.6, 3H).

Methyl 3-chloro-4-(1-phenoxyethyl)benzoate

A mixture of 4-bromo-2-chloro-1-(1-phenoxyethyl)benzene (882 mg, 3.0 mmol), palladium acetate (137 mg, 0.6 mmol), 1,3-bis(diphenylphosphino)propane (376 mg, 0.9 mmol), triethylamine (2.1 mL) in methanol (30 mL) was stirred at 100° C. under carbon monoxide (20 atms) for 12 hours. The mixture was concentrated to give a residue. The residue was purified by column chromatography (silica gel, petroleum ether/ethyl acetate=5:1) to give methyl 3-chloro-4-(1-phenoxyethyl)benzoate (750 mg, 90%). $^1$H NMR (300 MHz, CDCl$_3$): 7.37 (d, J=8.1, 1H), δ 7.27-7.20 (m, 3H), 6.92-6.82 (m, 3H), 5.30 (q, J=6.6, 1H), 3.92 (s, 3H), 1.62 (d, J=6.6, 3H).

3-chloro-4-(1-phenoxyethyl)benzoic acid

A mixture of methyl 3-chloro-4-(1-phenoxyethyl)benzoate (750 mg, 2.7 mmol), lithium hydroxide monohydrate (571 mg, 13.6 mmol), water (5 mL) and methanol (5 mL) in tetrahydrofuran (15 mL) was stirred at 20° C. for 5 hours. The reaction mixture was concentrated. The residue was acidified to pH=2 with concentrated hydrochloride solution. The mixture was extracted with ethyl acetate (20 mL×2). The organic phase was dried over sodium sulfate and filtered. The filtrate was concentrated. The residue was purified by column chromatography (silica gel, petroleum ether/ethyl acetate=2:1) to give 3-chloro-4-(1-phenoxyethyl)benzoic acid as a white solid (500 mg, 71%). LRMS (M+H$^+$) m/z: 276.06. found 276.

3-chloro-N-((2-hydroxy-4,6-dimethylpyridin-3-yl)methyl)-4-(1-phenoxyethyl)benzamide (Compound I-180)

To a solution of 3-chloro-4-(1-phenoxyethyl)benzoic acid (262 mg, 1.0 mmol), 1-hydroxybenzotriozole (202 mg, 1.5 mmol), 1-(3-Dimethylaminopropyl)-3-ethylcarbodiimide hydrochloride (288 mg, 1.5 mmol) triethylamine (0.4 mL) in dichloromethane (15 mL) was added 3-(aminomethyl)-4,6-dimethylpyridin-2-ol (152 mg, 1.0 mmol). The reaction mixture was stirred at 20° C. for 13 hours. The mixture was washed with water (20 mL×2). The organic phase was dried over sodium sulfate and filtered. The filtrate was concentrated. The residue was purified by column chromatography (silica gel, dichloromethane/methanol=10:1) to give 3-chloro-N-((2-hydroxy-4,6-dimethylpyridin-3-yl)methyl)-4-(1-phenoxyethyl)benzamide as a white solid (360 mg, 88%). LRMS (M+H$^+$) m/z: 410.14. found 410. HPLC Purity (214 nm): 99%. $^1$H NMR (300 MHz, d$^6$-DMSO): δ 11.46 (s, 1H), δ 8.33 (d, J=5.1, 1H), 7.47 (s, 1H), 7.34 (m, 2H), 67.20 (m, 2H), 6.88 (m, 3H), 5.84 (s, 1H), δ 5.54 (q, J=6, 1H), 4.25 (d, J=4.5, 2H), 2.17 (s, 3H), 2.13 (s, 3H), 3.06 (d, J=6, 3H).

(R)— or (S)-3-chloro-N-((2-hydroxy-4,6-dimethylpyridin-3-yl)methyl)-4-(1-phenoxyethyl)benzamide (Compound I-206) and (S)— or (R)-3-chloro-N-((2-hydroxy-4,6-dimethylpyridin-3-yl)methyl)-4-(1-phenoxyethyl)benzamide (Compound I-207)

3-chloro-N-((2-hydroxy-4,6-dimethylpyridin-3-yl)methyl)-4-(1-phenoxyethyl)benzamide (150 mg, 0.36 mmol) was separated by chiral HPLC (Daicel AD-H (250 mm×20 mm×5 μm), hexane/ethanol (0.2 diethylamine)=30:70, flow rate: 13 mL/min), then (R or S) 3-chloro-N-((2-hydroxy-4,6-dimethylpyridin-3-yl)methyl)-4-(1-phenoxyethyl)benzamide (40 mg, 27%) and (S or R) 3-chloro-N-((2-hydroxy-4,6-dimethylpyridin-3-yl)methyl)-4-(1-phenoxyethyl)benzamide (50 mg, 33%) were obtained. The retention times were 17.275 minute and 20.835 minute respectively in chiral prep-HPLC chromatography. LRMS (M+H$^+$) m/z: calcd 378.21. found 378. LRMS (M+H$^+$) m/z: 410.14. found 410. HPLC Purity (214 nm): ee=100% (both for R and S). $^1$H NMR (300 MHz, DMSO-d$_6$): 11.46 (s, 1H), δ 8.33 (d, J=5.1, 1H), 7.47 (s, 1H), 7.34 (m, 2H), δ7.20 (m, 2H), 6.88 (m, 3H), 5.84 (s, 1H), δ 5.54 (q, J=6, 1H), 4.25 (d, J=4.5, 2H), 2.17 (s, 3H), δ2.13 (s, 3H), 3.06 (d, J=6, 3H). For convenience sake the (R)-enantiomer was designated Compound I-189 and the (S)-enantiomer was designated I-190

Example 97

Synthesis of Racemic N-((2-hydroxy-4-methoxy-6-methylpyridin-3-yl)methyl)-2-oxo-1-(1-phenylethyl)-1,2-dihydropyridine-4-carboxamide (Compound I-197) and its Enantiomers (Compounds I-198 and I-199)

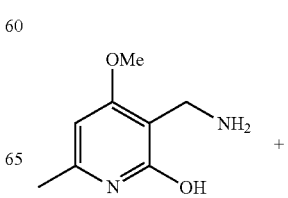

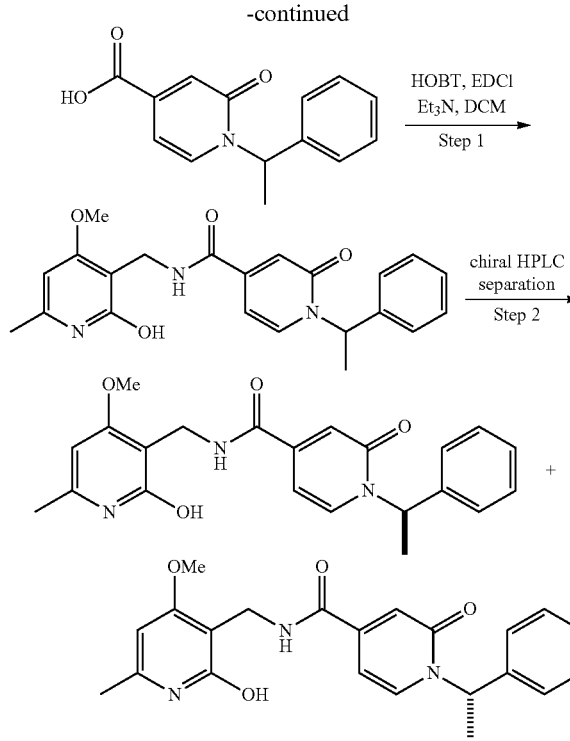

N-((2-hydroxy-4-methoxy-6-methylpyridin-3-yl)methyl)-2-oxo-1-(1-phenylethyl)-1,2-dihydropyridine-4-carboxamide (Compound I-197)

To a solution of 2-oxo-1-(1-phenylethyl)-1,2-dihydropyridine-4-carboxylic acid (97 mg, 0.40 mmol) in dichloromethane (15 mL) were added 1-Hydroxybenzotriazole (73 mg, 0.54 mmol), 1-(3-Dimethylaminopropyl)-3-ethylcarbodiimide hydrochloride (104 mg, 0.54 mmol) and triethylamine (111 mg, 1.1 mmol). The resultant solution was stirred at room temperature for 30 minutes. Then 3-(aminomethyl)-4-methoxy-6-methylpyridin-2-ol (60 mg, 0.36 mmol) was added to the solution, and it was stirred at room temperature for 16 hours. Water (20 mL) was added to the mixture. It was extracted with dichloromethane (50 mL). The organic layer was concentrated in vacuo to provide crude product which was purified by silica gel column chromatography with dichloromethane/methanol=10:1 to afford N-((2-hydroxy-4-methoxy-6-methylpyridin-3-yl)methyl)-2-oxo-1-(1-phenylethyl)-1,2-dihydro pyridine-4-carboxamide (40 mg, 28% yield) as a white solid. $^1$H NMR (300 MHz, CD$_3$OD): δ 7.56 (d, J=7.2 Hz, 1H), 7.31-7.39 (m, 5H), 6.86 (d, J=1.8 Hz, 1H), 6.60 (br, 1H), 6.25-6.30 (m, 2H), 4.41 (s, 2H), 3.91 (s, 3H), 2.31 (s, 3H), 1.76 (d, J=7.2 Hz, 3H).

(R)N-((2-hydroxy-4-methoxy-6-methylpyridin-3-yl)methyl)-2-oxo-1-(1-phenylethyl)-1,2-dihydropyridine-4-carboxamide (Compound I-198) and (S)N-((2-hydroxy-4-methoxy-6-methylpyridin-3-yl)methyl)-2-oxo-1-(1-phenylethyl)-1,2-dihydropyridine-4-carboxamide (Compound I-199)

N-((2-hydroxy-4-methoxy-6-methylpyridin-3-yl)methyl)-2-oxo-1-(1-phenylethyl)-1,2-dihydropyridine-4-carboxamide was separated by chiral HPLC (Daicel AD-H (250 mm*20 mm*5 um), hexane: ethanol (0.2% DEA)=50:50, flow rate: 13 ml/min), then (R or S) N-((2-hydroxy-4-methoxy-6-methylpyridin-3-yl)methyl)-2-oxo-1-(1-phenylethyl)-1,2-dihydropyridine-4-carboxamide and (S or R)N-((2-hydroxy-4-methoxy-6-methylpyridin-3-yl)methyl)-2-oxo-1-(1-phenylethyl)-1,2-dihydropyridine-4-carbox amide were obtained. The retention times were 8.55 minute and 12.73 minute respectively in chiral prep-HPLC chromatography. LRMS (M+H$^+$) m/z: calcd 394.17. found 394. HPLC Purity (214 nm): 99%, 97% respectively. $^1$H NMR (300 MHz, CD$_3$OD): δ 7.56 (d, J=7.2 Hz, 1H), 7.31-7.39 (m, 5H), 6.86 (d, J=1.8 Hz, 1H), 6.60 (br, 1H), 6.25-6.30 (m, 2H), 4.41 (s, 2H), 3.91 (s, 3H), 2.31 (s, 3H), 1.76 (d, J=7.2 Hz, 3H). Although the separated enantiomers were not optically characterized, for convenience sake the (R) enantiomer was designated Compound I-198 and the (S) enantiomer was designated Compound I-199.

Example 98

Synthesis of 1N-((4,6-dimethyl-2-oxo-1,2-dihydropyridin-3-yl)methyl)-3,5-dimethyl-2-oxo-1-(1-phenylethyl)-1,2-dihydropyridine-4-carboxamide (Compound I-200) and its Enantiomers (Compounds I-201 and I-202)

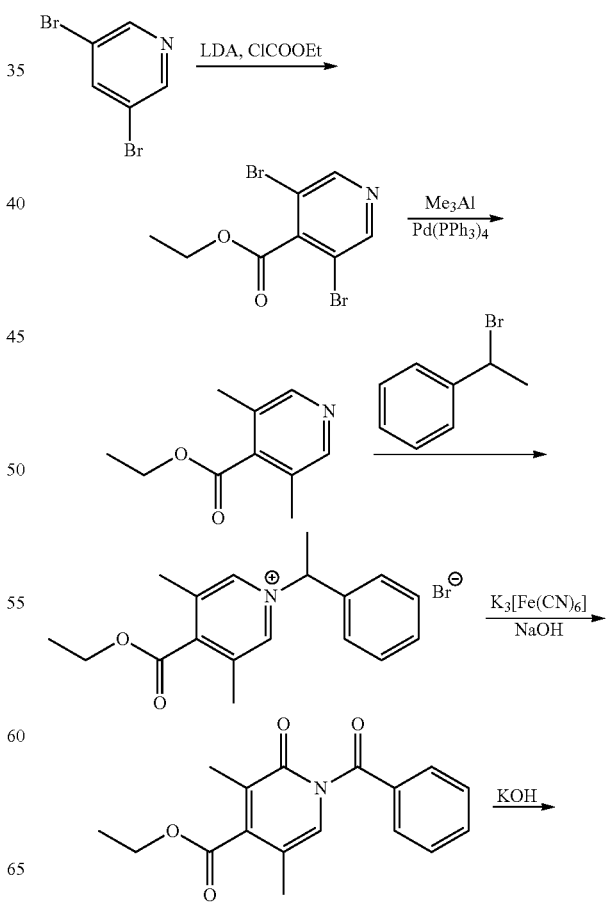

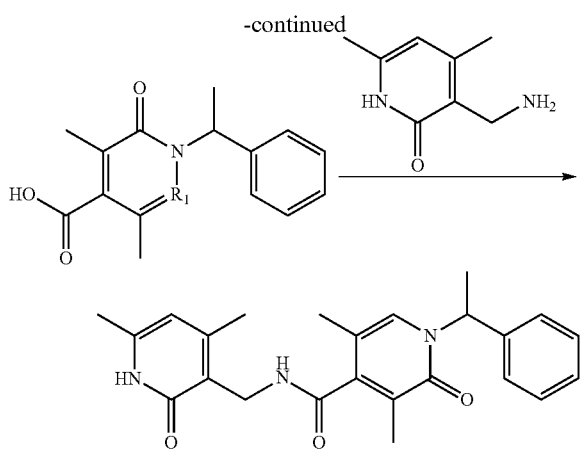

Ethyl 3,5-dibromoisonicotinate

To a solution of 3,5-dibromopyridine (5 g, 21.11 mmol) in THF was added LDA (2 M in THF, 12.66 ml, 25.33 mmol) at −78° C. The mixture was stirred at −78° C. for 45 min. Then ethyl carbonochloridate (2.29 g, 21.11 mmol) was added and the mixture stirred at −78° C. for 1 hours. After reaction completed, the reaction was quenched by addition of 5 mL of saturated NH$_4$Cl and extracted with EtOAc. The extractions were combined, washed with H$_2$O, dried over Na$_2$SO$_4$ and concentrated under vacuum. The residue was purified by flash column (Eluent: PE/EtOAc=10:1), to give ethyl 3,5-dibromoisonicotinate as a yellow solid. (1.9 g, yield 29%) LCMS (M+H$^+$) m/z: calcd 306.8. found 309.7.

Ethyl 3,5-dimethylisonicotinate

To a solution of ethyl 2-methyl-1H-indole-3-carboxylate (2 g, 6.15 mmol), Pd(PPh$_3$)-4(0.36 g, 0.31 mmol) in dioxane (20 mL) was added Me$_3$Al (2 M in THF, 7.69 ml, 15.37 mmol) under N$_2$. The mixture was stirred at reflux overnight. After the complete of the reaction, the reaction was quenched by addition of 5 mL of water and extracted with EtOAc. The extractions were combined, washed with H$_2$O, dried over Na$_2$SO$_4$, and concentrated under vacuum. The residue was purified by flash column (Eluent: PE/EtOAc=15:1) to give ethyl 3,5-dimethylisonicotinate as a yellow solid. (0.9 g, yield 78%). LRMS (M+H$^+$) m/z: calcd 180.2. found 179.01.

4-(ethoxycarbonyl)-3,5-dimethyl-1-(1-phenylethyl)pyridin-1-ium bromide 1-(bromoethyl)benzene (1.3 g, 7.03 mmol) was added to ethyl 3,5-dimethylisonicotinate (0.7 g, 3.91 mmol) in dioxane (20 mL) and the resultant mixture was stirred at reflux overnight. The resulting solution was used to the next step without further purification.

Ethyl 1-benzoyl-3,5-dimethyl-2-oxo-1,2-dihydropyridine-4-carboxylate

To the solution of 4-(ethoxycarbonyl)-3,5-dimethyl-1-(1-phenylethyl)pyridin-1-ium bromide (3.91 mmol) was added portionwise the mixture of potassium ferricyanide (2.57 g, 7.81 mmol) and sodium hydroxide (0.94 g, 23.44 mmol) in H$_2$O (5 ml) for 2 h at room temperature. The solution was concentrated under vacuum, diluted with water and extracted with ethyl acetate. The organic layers were combined, dried over Na$_2$SO$_4$ and concentrated to give a residue. The residue was used to the next step without further purification.

3,5-dimethyl-2-oxo-1-(1-phenylethyl)-1,2-dihydropyridine-4-carboxylic acid

To the solution of ethyl 1-benzoyl-3,5-dimethyl-2-oxo-1,2-dihydropyridine-4-carboxylate (1.06 g, 3.54 mmol) in methanol/H$_2$O (40 mL, 1:1) was added KOH (0.79 g, 14.16 mmol). The mixture was refluxed overnight. Then the mixture was concentrated under vacuum, diluted with water (5 mL) and acidified with 1 N HCl to pH=2. The mixture was extracted with ethyl acetate. The extractions were combined, dried over Na$_2$SO$_4$, and concentrated to give a residue 3,5-dimethyl-2-oxo-1-(1-phenylethyl)-1,2-dihydropyridine-4-carboxylic acid as a white solid. (70 mg, yield 7.3%) LRMS (M+H$^+$) m/z: calcd 271.31. found 272.1. The residue was used in the next step.

N-((4,6-dimethyl-2-oxo-1,2-dihydropyridin-3-yl)methyl)-3,5-dimethyl-2-oxo-1-(1-phenylethyl)-1,2-dihydropyridine-4-carboxamide (Compound I-200)

To a solution of 3,5-dimethyl-2-oxo-1-(1-phenylethyl)-1,2-dihydropyridine-4-carboxylic acid (0.07 g, 0.26 mmol) in dichloromethane (10 mL) was added EDCI (0.06 g, 0.39 mmol), HOBt (0.05 g, 0.38 mmol) and triethylamine (0.078 g, 0.77 mmol). After stirred for 30 min, 3-(aminomethyl)-4,6-dimethyl pyridin-2(1H)-one (0.058 g, 0.39 mmol) was added and the reaction mixture was stirred at room temperature for 3 hours. The solution was concentrated under vacuum. The residue was diluted with water (20 mL) and extracted with ethyl acetate (20 mL). The extractions were combined, washed with H$_2$O, dried over Na$_2$SO$_4$, and concentrated under vacuum. The residue was purified by prep. HPLC (Condition: Column: YMC C18 150*30 mm*5 um; Mobile phase A: water with 0.05% ammonia solution Mobile phase B: MeCN; column temperature: 30° C.; Gradient: A/B, 35-65%) to give N-((4,6-dimethyl-2-oxo-1,2-dihydropyridin-3-yl)methyl)-3,5-dimethyl-2-oxo-1-(1-phenylethyl)-1,2-dihydropyridine-4-carboxamide as yellow solid. (7.5 mg, yield 7.1%)

LCMS (M+H$^+$) m/z: calcd 405.21. found 406. $^1$H NMR (400 MHz, CDCl$_3$-d$_4$) δ 7.29-7.26 (m, 2H), 7.25-7.19 (m, 2H), 6.99 (t, 1H), 6.66 (s, 1H), 6.39-6.33 (dd, 1H), 5.86 (s, 1H), 4.43-4.42 (d, 2H), 2.3 (s, 3H), 2.12 (s, 3H), 2.00 (s, 3H) 1.79 (s, 3 H), 1.60-1.59 (d, 3H).

(S)— or (R)—N-((4,6-dimethyl-2-oxo-1,2-dihydropyridin-3-yl)methyl)-3,5-dimethyl-2-oxo-1-(1-phenylethyl)-1,2-dihydropyridine-4-carboxamide (Compound I-202) and (R)— or (S)—N-((4,6-dim ethyl-2-oxo-1,2-dihydropyridin-3-yl)methyl)-3,5-dimethyl-2-oxo-1-(1-phenylethyl)-1,2-dihydropyridine-4-carboxamide (Compound I-201)

N-((4,6-dimethyl-2-oxo-1,2-dihydropyridin-3-yl)methyl)-3,5-dimethyl-2-oxo-1-(1-phenylethyl)-1,2-dihydropyridine-4-carboxamide (70 mg) were separated by SFC (Condition: Column: AS (250*30 mm, 5 um), eluent: CO$_2$:EtOH: NH$_3$.H$_2$O=78:22:0.1, flow rate: 50 ml/min, column temperature: 38° C., wavelength: 220 nm) to give 15.6 mg and 14.8 mg of two enantiomers. The LCMS and HNMR of two enantiomers were the same as the racemic compound. Although the separated enantiomers were not optically characterized, for convenience sake the (R) enantiomer was designated Compound I-201 and the (S) enantiomer was designated Compound I-202.

Example 99

IC$_{50}$ measurements for Inhibitors using EZH2

EZH2 Assay: Assays were carried out by mixing rPRC2 together with biotinylated oligonucleosome substrates in the presence of the radio-labeled enzyme co-factor, S-adenosyl-L-methionine ($^3$H SAM) (Perkin Elmer) and monitoring the enzymatically mediated transfer of tritiated methyl groups from $^3$H SAM to histone lysine residues. The amount of resulting tritiated methyl histone product was measured by first capturing the biotinylated oligonucleosomes in streptavidin (SAV) coated FlashPlates (Perkin Elmer), followed by a wash step to remove un-reacted $^3$H SAM, and then counting on a TopCount NXT 384 well plate scintillation counter (Perkin Elmer). The final assay conditions for EZH2 were as follows: 50 mM Tris Buffer pH 8.5, 1 mM DTT, 69 µM Brij-35 detergent, 5.0 mM MgCl$_2$, 0.1 mg/mL BSA, 0.2 µM $^3$H SAM, 0.2 µM biotinylated oligonucleosomes, 3.6 µM H3K27me3 peptide and 2 nM EZH2.

Compound IC$_{50}$ measurements were obtained as follows: Compounds were first dissolved in 100% DMSO as 10 mM stock solutions. Ten point dose response curves were generated by dispensing varying amounts of the 10 mM compound solution in 10 wells of the 384 well plate (Echo; Labcyte), pure DMSO was then used to backfill the wells to insure all wells have the same amount of DMSO. A 12.5 µL volume of the HMT enzyme, H3K27me3 peptide and oligonucleosome substrate in assay buffer was added to each well of the assay plate using a Multidrop Combi (ThermoFisher). Compounds were pre-incubated with the enzyme for 20 min, followed by initiation of the methyltransferase reaction by addition of 12.5 µL of 3H SAM in assay buffer (final volume=25 µL). The final concentrations of compounds ranged from a top default concentration of 80 µM down to 0.16 µM in ten 2-fold dilution steps. Reactions were carried out for 60 minutes and quenched with 20 µL per well of 1.96 mM SAH, 50 mM Tris PH 8.5, 200 mM EDTA. Stopped reactions were transferred to SAV coated Flashplates (Perkin Elmer), incubated for 120 min, washed with a plate washer, and then read on the TopCount NXT (1.0 min/well) to measure the amount of methyl histone product formed during the reaction. The amount of methyl histone product was compared with the amount of product formed in the 0% and 100% inhibition control wells allowing the calculation of % Inhibition in the presence of the individual compounds at various concentrations. IC$_{50}$'s were computed using a 4 parameter fit non-linear curve fitting software package (XLFIT, part of the database package, ActivityBase (IDBS)) where the four parameters were IC$_{50}$, Hill slope, pre-transitional baseline (0% INH), and post-transitional baseline (100% INH); with the latter two parameters being fixed to zero and 100%, respectively, by default.

Assay for Y641N EZH2 was performed as above using reconstituted H3K27Me$_2$ oligonucleosomes as substrate.

Table 2 shows the activity of selected compounds of this invention in the EZH2 and Y641N EZH2 activity inhibition assay. IC$_{50}$ values are reported as follows: "A" indicates an IC$_{50}$ value of less than 1 µM; "B" indicates an IC$_{50}$ value of 1 µM to 10 µM; and "C" indicates an IC$_{50}$ value of greater than 10 µM and less than 50 µM for each enzyme; "D" indicates an IC$_{50}$ value of greater than 50 µM for each enzyme; "*" indicates that no inhibition was observed at the highest concentration of compound tested; and "NT" means the compound was not tested for the indicated enzyme and was one of the isolated enantiomers. Rows that list multiple compounds designated with a "†" represent the testing of separated enantiomers that had not been optically characterized. The assay result for each separate enantiomer is indicated.

TABLE 2

IC50 Values for Compounds of Formula I against EZH2 and Y641N EZH2 Mutant Enzymes.

| Cmpd No. | EZH2 IC50 | Y641N EZH2 IC50 |
|---|---|---|
| I-1 | B | C |
| I-2 | B | C |
| I-3 | A | B |
| I-4 | B | NT |
| I-5 | B | NT |
| I-6 | B | NT |
| I-7 | B | NT |
| I-8 | B | B |
| I-9 | A | B |
| I-10 | B | B |
| I-11 | B | B |
| I-12 | B | C |
| I-13 | A | B |
| I-14 | D | * |
| I-15 | D | * |
| I-16 | B | C |
| I-17 | B | D |
| I-18 | C | * |
| I-19 | B | C |
| I-20 | B | D |
| I-21 | B | C |
| I-22 | A | B |
| I-23 | A | A |
| I-24 | C | D |
| I-25 | B | C |
| I-26 | C | * |
| I-27 | A | B |
| I-28 | B | C |
| I-29 | C | * |
| I-30 | C | * |
| I-31 | A | A |
| I-32 | A | B |
| I-33 | A | A |
| I-34 | A | B |
| I-35 | A | B |
| I-36 | C | * |
| I-37 | B | B |
| I-38 | A | B |
| I-39 | A | A |
| I-40 | B | C |
| I-41 | A | A |
| I-42 | A | A |
| I-43 | C | D |
| I-44 | A | A |
| I-45 | D | * |
| I-46 | A | A |
| I-47 | D | C |
| I-48 | B | * |
| I-49 | C | C |
| I-50 | B | * |
| I-51 | B | * |
| I-52 | C | C |
| I-53 | C | C |
| I-54 | A | B |
| I-55 | A | A |
| I-56 | B | * |
| I-57/I-58† | * | * |
|  | A | A |
| I-59 | B | B |
| I-60 | A | B |
| I-61 | A | B |
| I-62 | A | B |
| I-63 | A | A |
| I-64 | B | * |
| I-65 | C | * |

TABLE 2-continued

IC50 Values for Compounds of Formula I against EZH2 and Y641N EZH2 Mutant Enzymes.

| Cmpd No. | EZH2 IC50 | Y641N EZH2 IC50 |
| --- | --- | --- |
| I-66 | A | A |
| I-67/I-68† | B | * |
|  | A | A |
| I-69 | A | A |
| I-70/I-71† | A | B |
|  | A | A |
| I-72/I-73† | C | B |
|  | A | B |
| I-74/I-75† | C | B |
|  | A | A |
| I-76 | C | * |
| I-77 | B | B |
| I-78 | B | * |
| I-79 | C | * |
| I-80 | B | C |
| I-81 | B | C |
| I-82 | B | C |
| I-83 | A | B |
| I-84 | B | C |
| I-85 | A | B |
| I-86 | A | B |
| I-87 | B | B |
| I-88 | B | * |
| I-89 | B | * |
| I-116 | A | * |
| I-155 | A | B |
| I-156 | * | * |
| I-157 | * | * |
| I-158 | * | * |
| I-159 | * | * |
| I-160 | * | * |
| I-161 | A | A |
| I-162 | B | * |
| I-163 | A | A |
| I-164 | A | B |
| I-167 | A | B |
| I-168 | B | * |
| I-169 | A | A |
| I-170 | * | * |
| I-171/I-191 | B | * |
|  | A | A |
| I-172/I-173† | A | A |
|  | B | B |
| I-174/I-175† | * | * |
|  | A | A |
| I-176/I-177† | B | B |
|  | A | B |
| I-178 | C | C |
| I-179 | D | * |
| I-181 | A | A |
| I-182 | B | * |
| I-183 | B | * |
| I-184 | A | B |
| I-185/I-186† | B | * |
|  | A | A |
| I-187/I-188† | * | * |
|  | A | A |
| I-189/I-190† | * | * |
|  | A | A |
| I-192 | A | B |
| I-193 | * | * |
| I-194 | A | * |
| I-195 | A | B |
| I-196 | B | * |
| I-198/I-199† | * | * |
|  | A | A |
| I-200 | A | B |
| I-201/I-202† | A | A |
|  | B | * |
| I-203/I-204/I-205/I-206† | A | B |
|  | A | B |
|  | * | * |
|  | * | * |

We claim:

1. A compound of Formula II:

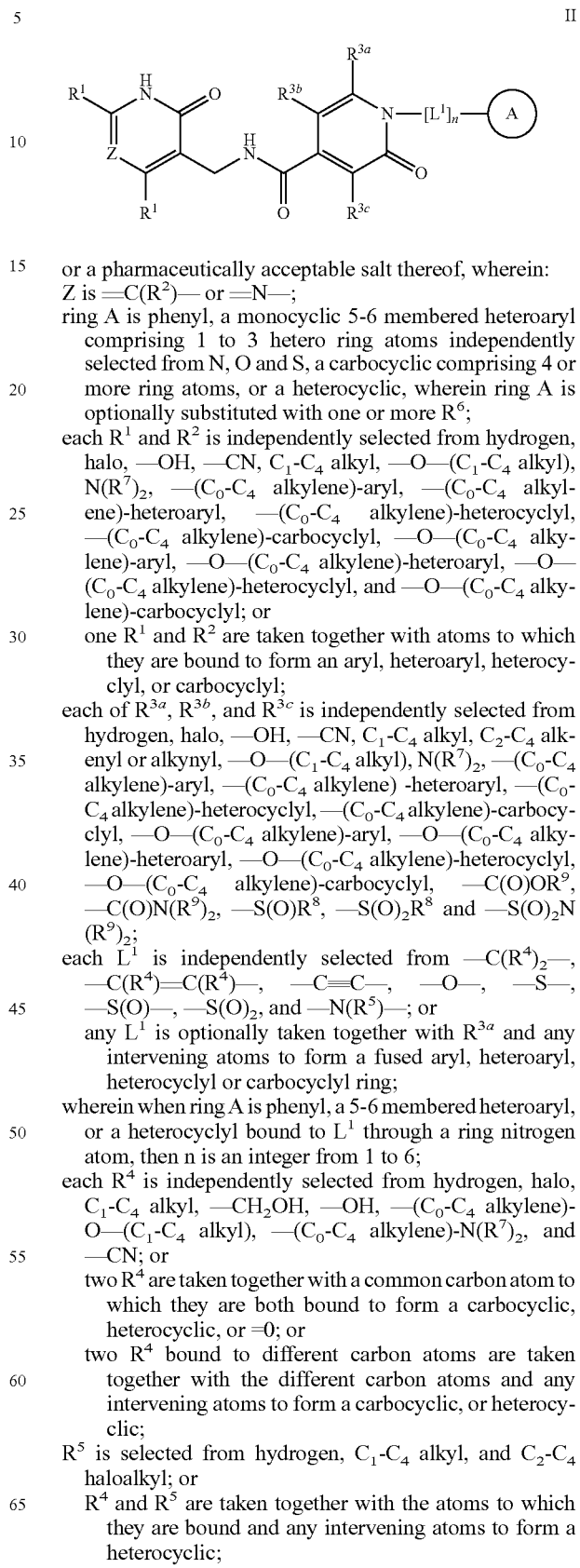

II or a pharmaceutically acceptable salt thereof, wherein:

Z is $=C(R^2)-$ or $=N-$;

ring A is phenyl, a monocyclic 5-6 membered heteroaryl comprising 1 to 3 hetero ring atoms independently selected from N, O and S, a carbocyclic comprising 4 or more ring atoms, or a heterocyclic, wherein ring A is optionally substituted with one or more $R^6$;

each $R^1$ and $R^2$ is independently selected from hydrogen, halo, —OH, —CN, $C_1$-$C_4$ alkyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, and —O—($C_0$-$C_4$ alkylene)-carbocyclyl; or one $R^1$ and $R^2$ are taken together with atoms to which they are bound to form an aryl, heteroaryl, heterocyclyl, or carbocyclyl;

each of $R^{3a}$, $R^{3b}$, and $R^{3c}$ is independently selected from hydrogen, halo, —OH, —CN, $C_1$-$C_4$ alkyl, $C_2$-$C_4$ alkenyl or alkynyl, —O—($C_1$-$C_4$ alkyl), $N(R^7)_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)O$R^9$, —C(O)N($R^9$)$_2$, —S(O)$R^8$, —S(O)$_2R^8$ and —S(O)$_2$N($R^9$)$_2$;

each $L^1$ is independently selected from —C($R^4$)$_2$—, —C($R^4$)=C($R^4$)—, —C≡C—, —O—, —S—, —S(O)—, —S(O)$_2$, and —N($R^5$)—; or any $L^1$ is optionally taken together with $R^{3a}$ and any intervening atoms to form a fused aryl, heteroaryl, heterocyclyl or carbocyclyl ring;

wherein when ring A is phenyl, a 5-6 membered heteroaryl, or a heterocyclyl bound to $L^1$ through a ring nitrogen atom, then n is an integer from 1 to 6;

each $R^4$ is independently selected from hydrogen, halo, $C_1$-$C_4$ alkyl, —CH$_2$OH, —OH, —($C_0$-$C_4$ alkylene)-O—($C_1$-$C_4$ alkyl), —($C_0$-$C_4$ alkylene)-N($R^7$)$_2$, and —CN; or two $R^4$ are taken together with a common carbon atom to which they are both bound to form a carbocyclic, heterocyclic, or =O; or two $R^4$ bound to different carbon atoms are taken together with the different carbon atoms and any intervening atoms to form a carbocyclic, or heterocyclic;

$R^5$ is selected from hydrogen, $C_1$-$C_4$ alkyl, and $C_2$-$C_4$ haloalkyl; or $R^4$ and $R^5$ are taken together with the atoms to which they are bound and any intervening atoms to form a heterocyclic;

each R⁶ is independently selected from halo, —CN, =O, —(C₁-C₄ alkylene)-O—R⁸, —(C₀-C₄ alkylene)-O—(C₀-C₄ alkylene)-R⁹, —(C₀-C₄ alkylene)-N(R⁷)₂, —(C₀-C₄ alkylene)-R⁸, —(C₀-C₄ alkylene)-C(O)—O—R⁹, —(C₀-C₄ alkylene)-O—C(O)—R⁹, —(C₀-C₄ alkylene)-C(O)—N(R⁹)₂, —(C₀-C₄ alkylene)-S(O)—R⁸, —(C₀-C₄ alkylene)-S(O)₂—R⁸ and —(C₀-C₄ alkylene)-S(O)₂—N(R⁹)₂; or
- two R⁶ bound to adjacent atoms in ring A are taken together with the atoms to which they are bound to form a monocyclic aryl, heteroaryl, heterocyclyl, or carbocyclyl;

each R⁷ is independently selected from hydrogen, —(C₀-C₄ alkylene)-R⁹, —(C₂-C₄ alkylene)-O—R⁸, C₂-C₄ haloalkyl, —S(O)₂—R⁸, —C(=O)—R⁸, —C(=O)—N(R⁹)(R⁹), —(C₂-C₄ alkylene)-O—C(=O)—R⁸ and —(C₀-C₄ alkylene)-C(=O)—O—R⁹; or
- two R⁷ are taken together with the nitrogen atom to which they are commonly bound to form an optionally substituted heterocyclyl or heteroaryl;

R⁸ is selected from C₁-C₄ alkyl, aryl, heteroaryl, carbocyclyl and heterocyclyl;
each R⁹ is independently selected from hydrogen and R⁸;
═══ represents a single or double bond;
n is 0 or an integer from 1 to 6;
wherein any portion of the compound designated as alkyl, alkylene, alkenyl, alkynyl, aryl, heteroaryl, heterocyclyl or carbocyclyl is optionally substituted; and each ring of any aryl, heteroaryl, heterocyclyl or carbocyclyl has not more than three substituents per ring.

2. The compound of claim 1, wherein Z is =CH—.

3. The compound of claim 1, wherein each R¹ is independently selected from hydrogen and —CH₃.

4. The compound of claim 3, wherein each R¹ is —CH₃.

5. The compound of claim 1, wherein one R¹ is —CH₃ and the other R¹ is selected from —OCH₃ and —NHCH₃.

6. The compound of claim 1, wherein -[L¹]ₙ- is selected from —O—, —S(O)—, —S(O)₂—, —C(R⁴)₂—, —N(R⁷)—, —C(R⁴)₂—C(R⁴)₂—, —C(R⁴)₂—O-†, —C(R⁴)₂—C(R⁴)₂—O-†, —C(R⁴)₂—N(R⁷)-† and —O—C(R⁴)₂-†, wherein † represents the portion of -[L¹]ₙ- bound to ring A.

7. The compound of claim 6, wherein -[L¹]ₙ- is selected from —O—, —S(O)—, —S(O)₂—, —CH₂—, —CH₂—O-†, —CH(CH₃)—O-†, —N(CH₃)-†, —N(CH₂CH₃)-†, —N(CH(CH₃)₂)-†, —N(CH₂CH(CH₃)₂)-†, —NH-†, —CH₂—N(CH₃)-†, —CH₂—NH-†, —CH(OH)—, —C(CH₃)—, —O—CH₂-†, —CH₂—CH₂—, —CH(CH₃)—CH₂-†, —CH(CH₃)—CH₂—O-†, —C((CH₃)₂)—, —C(CH₃)(OCH₃)—, —CH(OCH₃)—, —CH(CH₂OH)—, —C(CH₃)(OH)—, —CH(CH₂CH₃)—O-†, —CH(CH(CH₃)₂)—O-† and —CH(CH₂OCH₃)—.

8. The compound of claim 7, wherein -[L¹]ₙ— is selected from —O—, —S(O)—, —S(O)₂—, —CH₂—O-†, —CH(CH₃)—O-†, —N(CH₃)-†, —NH-†, —CH(OCH₃)—, —CH₂—N(CH₃)-†, —CH₂—NH-†, —CH(OH)—, —C(CH₃)—, —CH₂—, —CH₂—CH₂—, —C(CH₃)(OH)—, —CH(CH₂CH₃)—O-†, —CH(CH(CH₃)₂)—O-† and —O—CH₂-†.

9. The compound of claim 1, wherein each R^{3a}, R^{3b}, and R^{3c} is independently selected from hydrogen, halo, C₁-C₄ alkyl and —O—(C₁-C₄ alkyl).

10. The compound of claim 9, wherein each R^{3a}, R^{3b}, and R^{3c} is independently selected from hydrogen, fluoro, chloro, —CH₃ and —OCH₃.

11. The compound of claim 1, having structural Formula I-i:

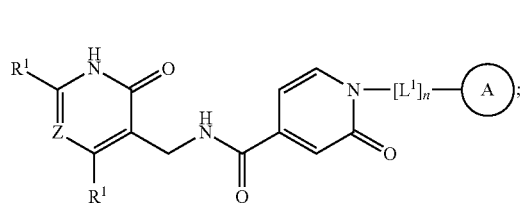

or a pharmaceutically acceptable salt thereof.

12. The compound of claim 11, wherein -[L¹]ₙ- is selected from —CH(CH₃)—CH₂-† and —CH(CH₃)-†; and ring A is phenyl optionally substituted with one or more R⁶.

13. The compound of claim 1, wherein ring A is selected from phenyl, cyclopentyl, cyclohexyl, pyrimindin-2-yl, 2,3-dihydrobenzofuran-2-yl, pyridin-2-yl, pyridin-4-yl, piperidin-1-yl, piperidin-4-yl, pyrrolidin-3-yl, pyrrolidin-2-yl, tetrahydrofuran-3-yl, tetrahydrofuran-2-yl, 3-oxopiperazin-1-yl, morpholin-4-yl, morpholin-2-yl, tetrahydro-2H-pyran-4-yl, and tetrahydro-2H-pyran-3-yl, wherein ring A is optionally substituted with one or more R⁶.

14. The compound of claim 13, wherein each R⁶ is independently selected from =O, halo, —CN, C₁-C₄ alkyl, C₁-C₄ haloalkyl, —O—(C₁-C₄ alkyl), optionally substituted heterocyclyl, and optionally substituted heteroaryl.

15. The compound of claim 14, wherein ring A is selected from cyclopentyl, cyclohexyl, tetrahydrofuran-3-yl, tetrahydrofuran-2-yl, piperidin-1-yl, phenyl, pyrimidinyl, 2,3-dihydrobenzofuran-2-yl, pyridinyl, or 2-oxo-1H-pyridin-1-yl, wherein ring A is optionally substituted with up to two R⁶ independently selected from —CN, —CH₂CH₃, —CH₃, —OCH₃, =O, fluoro, pyridinyl, pyridazinyl, 1H-pyrazolyl, 1H-pyrrolyl, and pyrimidinyl.

16. The compound of claim 14, wherein each R⁶ is independently selected from fluoro, —CH₃, —CH₂CH₃, —CF₃, —OCH₃, —CN, pyridin-4-yl, 1H-pyrrol-4-yl, pyridazin-4-yl, pyrimidin-4-yl, and 6-aminopyridin-3-yl.

17. A pharmaceutical composition comprising:
a) a compound of Formula II:

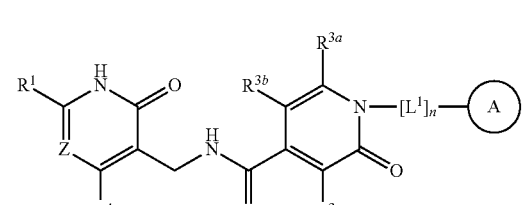

or a pharmaceutically acceptable salt thereof, wherein:
Z is =C(R²)— or =N—;
ring A is phenyl, a monocyclic 5-6 membered heteroaryl comprising 1 to 3 hetero ring atoms independently selected from N, O and S, a carbocyclic comprising 4 or more ring atoms, or a heterocyclic, wherein ring A is optionally substituted with one or more R⁶;
each R¹ and R² is independently selected from hydrogen, halo, —OH, —CN, C₁-C₄ alkyl, —O—(C₁-C₄ alkyl), N(R⁷)₂, —(C₀-C₄ alkylene)-aryl, —(C₀-C₄ alkylene)-heteroaryl, —(C₀-C₄ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, and —O—($C_0$-$C_4$ alkylene)-carbocyclyl; or
  one $R^1$ and $R^2$ are taken together with atoms to which they are bound to form an aryl, heteroaryl, heterocyclyl, or carbocyclyl;
each of $R^{3a}$, $R^{3b}$ and $R^{3c}$ is independently selected from hydrogen, halo, —OH, —CN, $C_1$-$C_4$ alkyl, $C_2$-$C_4$ alkenyl or alkynyl, —O—($C_1$-$C_4$ alkyl), N($R^7$)$_2$, —($C_0$-$C_4$ alkylene)-aryl, —($C_0$-$C_4$ alkylene)-heteroaryl, —($C_0$-$C_4$ alkylene)-heterocyclyl, —($C_0$-$C_4$ alkylene)-carbocyclyl, —O—($C_0$-$C_4$ alkylene)-aryl, —O—($C_0$-$C_4$ alkylene)-heteroaryl, —O—($C_0$-$C_4$ alkylene)-heterocyclyl, —O—($C_0$-$C_4$ alkylene)-carbocyclyl, —C(O)O$R^9$, —C(O)N($R^9$)$_2$, —S(O)$R^8$, —S(O)$_2R^8$ and —S(O)$_2$N($R^9$)$_2$;
each $L^1$ is independently selected from —C($R^4$)$_2$—, —C($R^4$)=C($R^4$)—, —C≡C—, —O—, —S—, —S(O)—, —S(O)$_2$, and —N($R^5$)—; or
  any $L^1$ is optionally taken together with $R^{3a}$ and any intervening atoms to form a fused aryl, heteroaryl, heterocyclyl or carbocyclyl ring;
wherein when ring A is phenyl, a 5-6 membered heteroaryl, or a heterocyclyl bound to $L^1$ through a ring nitrogen atom, then n is an integer from 1 to 6;
each $R^4$ is independently selected from hydrogen, halo, $C_1$-$C_4$ alkyl, —CH$_2$OH, —OH, —($C_0$-$C_4$ alkylene)-O—($C_1$-$C_4$ alkyl), —($C_0$-$C_4$ alkylene)-N($R^7$)$_2$, and —CN; or
  two $R^4$ are taken together with a common carbon atom to which they are both bound to form a carbocyclic, heterocyclic, or =O; or
  two $R^4$ bound to different carbon atoms are taken together with the different carbon atoms and any intervening atoms to form a carbocyclic, or heterocyclic;

$R^5$ is selected from hydrogen, $C_1$-$C_4$ alkyl, and $C_2$-$C_4$ haloalkyl; or
  $R^4$ and $R^5$ are taken together with the atoms to which they are bound and any intervening atoms to form a heterocyclic;
each $R^6$ is independently selected from halo, —CN, =O, —($C_1$-$C_4$ alkylene)-O—$R^8$, —($C_0$-$C_4$ alkylene)-O—($C_0$-$C_4$ alkylene)-$R^9$, —($C_0$-$C_4$ alkylene)-N($R^7$)$_2$, —($C_0$-$C_4$ alkylene)-$R^8$, —($C_0$-$C_4$ alkylene)-C(O)—O—$R^9$, —($C_0$-$C_4$ alkylene)-O—C(O)—$R^9$, —($C_0$-$C_4$ alkylene)-C(O)—N($R^9$)$_2$, —($C_0$-$C_4$ alkylene)-S(O)—$R^8$, —($C_0$-$C_4$ alkylene)-S(O)$_2$—$R^8$ and —($C_0$-$C_4$ alkylene)-S(O)$_2$—N($R^9$)$_2$; or
  two $R^6$ bound to adjacent atoms in ring A are taken together with the atoms to which they are bound to form a monocyclic aryl, heteroaryl, heterocyclyl, or carbocyclyl;
each $R^7$ is independently selected from hydrogen, —($C_0$-$C_4$ alkylene)-$R^9$, —($C_2$-$C_4$ alkylene)-O—$R^8$, $C_2$-$C_4$ haloalkyl, —S(O)2-$R^8$, —C(=O)—$R^8$, —C(=O)—N($R^9$)($R^9$), —($C_2$-$C_4$ alkylene)-O—C(=O)—$R^8$ and —($C_0$-$C_4$ alkylene)-C(=O)—O—$R^9$; or
  two $R^7$ are taken together with the nitrogen atom to which they are commonly bound to form an optionally substituted heterocyclyl or heteroaryl;
$R^8$ is selected from $C_1$-$C_4$ alkyl, aryl, heteroaryl, carbocyclyl and heterocyclyl;
each $R^9$ is independently selected from hydrogen and $R^8$;
n is 0 or an integer from 1 to 6;
wherein any portion of the compound designated as alkyl, alkylene, alkenyl, alkynyl, aryl, heteroaryl, heterocyclyl or carbocyclyl is optionally substituted; and each ring of any aryl, heteroaryl, heterocyclyl or carbocyclyl has not more than three substituents per ring; and
b) a pharmaceutically acceptable carrier.

* * * * *